(12) United States Patent
Makarov et al.

(10) Patent No.: US 8,440,404 B2
(45) Date of Patent: *May 14, 2013

(54) METHODS AND COMPOSITIONS FOR GENERATING AND AMPLIFYING DNA LIBRARIES FOR SENSITIVE DETECTION AND ANALYSIS OF DNA METHYLATION

(75) Inventors: Vladimir L. Makarov, Ann Arbor, MI (US); Emmanuel Kamberov, Ann Arbor, MI (US); Tong Sun, Novi, MI (US); Jonathon H. Pinter, Ypsilanti, MI (US); Brendan J. Tarrier, Whitmore Lake, MI (US); Eric E. Bruening, Chelsea, MI (US); Takao Kurihara, Ann Arbor, MI (US); Tim Tesmer, Whittaker, MI (US); Joseph M'Mwirichia, Ypsilanti, MI (US)

(73) Assignee: Rubicon Genomics, Ann Arbor, MI (US)

( * ) Notice: Subject to any disclaimer, the term of this patent is extended or adjusted under 35 U.S.C. 154(b) by 854 days.

This patent is subject to a terminal disclaimer.

(21) Appl. No.: 11/071,864

(22) Filed: Mar. 3, 2005

(65) Prior Publication Data
US 2005/0202490 A1   Sep. 15, 2005

Related U.S. Application Data

(60) Provisional application No. 60/551,941, filed on Mar. 8, 2004.

(51) Int. Cl.
*C12Q 1/68* (2006.01)
*C12P 19/34* (2006.01)

(52) U.S. Cl.
USPC ......... 435/6.11; 435/6.1; 435/6.12; 435/91.1; 435/91.2

(58) Field of Classification Search ............................ None
See application file for complete search history.

(56) References Cited

U.S. PATENT DOCUMENTS

| | | |
|---|---|---|
| 5,043,272 A | 8/1991 | Hartley |
| 5,104,792 A | 4/1992 | Silver et al. |
| 5,106,727 A | 4/1992 | Hartley et al. |
| 5,405,760 A | 4/1995 | Raleigh et al. |
| 5,514,545 A | 5/1996 | Eberwine |
| 5,714,318 A | 2/1998 | Sagner et al. |
| 5,731,171 A | 3/1998 | Bohlander |
| 5,759,821 A | 6/1998 | Teasdale |
| 5,759,822 A | 6/1998 | Chenchik et al. |
| 5,814,444 A | 9/1998 | Rabinovitch |
| 5,871,920 A | 2/1999 | Page et al. |
| 5,932,451 A | 8/1999 | Wang et al. |
| 5,948,649 A | 9/1999 | Stewart et al. |
| 5,968,743 A | 10/1999 | Matsunaga et al. |
| 5,994,058 A | 11/1999 | Senapathy |
| 6,045,994 A | 4/2000 | Zabeau et al. |
| 6,060,245 A | 5/2000 | Sorge et al. |
| 6,107,023 A | 8/2000 | Reyes et al. |
| 6,114,149 A | 9/2000 | Fry et al. |
| 6,124,120 A | 9/2000 | Lizardi |
| 6,214,556 B1 | 4/2001 | Olek et al. |
| 6,280,949 B1 | 8/2001 | Lizardi |
| 6,300,071 B1 | 10/2001 | Vuylsteke et al. |
| 6,365,375 B1 | 4/2002 | Dietmaier et al. |
| 6,379,932 B1 | 4/2002 | Arnold et al. |
| 6,383,754 B1 | 5/2002 | Kaufman et al. |
| 6,509,160 B1 | 1/2003 | Sapolsky et al. |
| 6,521,428 B1 | 2/2003 | Senapathy |
| 6,537,757 B1 | 3/2003 | Langmore et al. |
| 6,605,432 B1 | 8/2003 | Huang |
| 6,621,782 B1 | 9/2003 | Nakane et al. |
| 6,632,611 B2 | 10/2003 | Su et al. |
| 6,638,722 B2 | 10/2003 | Ji et al. |
| 6,677,121 B2 | 1/2004 | Lizardi et al. |
| 6,692,918 B2 | 2/2004 | Kurn |

(Continued)

FOREIGN PATENT DOCUMENTS

| | | |
|---|---|---|
| EP | 0466520 | 1/1992 |
| EP | 0684315 A1 | 11/1995 |

(Continued)

OTHER PUBLICATIONS

Gonzalgo et al. Identification and characterization of differentially methylated regions of genomic DNA by methylation-sensitive arbitrarily primed PCR. Cancer Research, vol. 57, pp. 594-599, Feb. 1997.*

(Continued)

*Primary Examiner* — Jennifer Dunston
(74) *Attorney, Agent, or Firm* — Parker Highlander PLLC

(57) ABSTRACT

The present invention regards a variety of methods and compositions for obtaining epigenetic information, such as DNA methylation patterns, through the preparation, amplification and analysis of Methylome libraries. In particular, the method employs preparation of a DNA molecule by digesting the DNA molecule with at least one methylation-sensitive restriction enzyme; incorporating a nucleic acid molecule into at least some of the digested DNA molecules by either (1) incorporating at least one primer from a plurality of primers that have a 5' constant sequence and a 3' variable sequence, wherein the primers are substantially non-self-complementary and substantially non-complementary to other primers in the plurality; or (2) incorporating an oligonucleotide having an inverted repeat and a loop under conditions wherein the oligonucleotide becomes blunt-end ligated to one strand of the digested DNA molecule, followed by polymerization from a 3' hydroxyl group present in a nick in the oligonucleotide-linked molecule; and amplifying one or more of the DNA molecules.

37 Claims, 88 Drawing Sheets

U.S. PATENT DOCUMENTS

| | | | |
|---|---|---|---|
| 6,762,022 B2 | 7/2004 | Makarov et al. | |
| 6,773,886 B2 | 8/2004 | Kaufman et al. | |
| 6,794,141 B2 | 9/2004 | Erlander et al. | |
| 6,808,888 B2 | 10/2004 | Zhang et al. | |
| 6,825,010 B2 | 11/2004 | Spier et al. | |
| 7,655,791 B2* | 2/2010 | Makarov et al. | 536/25.4 |
| 7,718,403 B2* | 5/2010 | Kamberov et al. | 435/91.2 |
| 2001/0021518 A1 | 9/2001 | Goudsmit et al. | |
| 2001/0046669 A1 | 11/2001 | McCobmie et al. | |
| 2002/0058250 A1 | 5/2002 | Firth | |
| 2003/0013671 A1 | 1/2003 | Mineno et al. | |
| 2003/0099997 A1 | 5/2003 | Bestor | |
| 2003/0129602 A1 | 7/2003 | Huang | |
| 2003/0143599 A1 | 7/2003 | Makarov et al. | |
| 2003/0165885 A1 | 9/2003 | Arnold et al. | |
| 2003/0186237 A1 | 10/2003 | Ginsberg et al. | |
| 2003/0232371 A1 | 12/2003 | Bestor | |
| 2004/0043416 A1 | 3/2004 | Ji et al. | |
| 2004/0063144 A1 | 4/2004 | Lizardi | |
| 2004/0209298 A1 | 10/2004 | Kamberov et al. | |
| 2004/0209299 A1 | 10/2004 | Pinter et al. | |

FOREIGN PATENT DOCUMENTS

| | | | |
|---|---|---|---|
| EP | 0976835 | | 2/2000 |
| EP | 1275738 | | 1/2003 |
| JP | 8173164 | | 7/1996 |
| WO | WO-93/24654 | A1 | 12/1993 |
| WO | WO 96/01327 | | 1/1996 |
| WO | WO-96/15264 | | 5/1996 |
| WO | WO-97/30062 | | 8/1997 |
| WO | WO-98/02575 | | 1/1998 |
| WO | WO-98/15652 | A1 | 4/1998 |
| WO | WO 98/23777 | * | 6/1998 |
| WO | WO-99/28498 | | 6/1999 |
| WO | WO-00/17390 | | 3/2000 |
| WO | WO-01/09384 | | 2/2001 |
| WO | WO-01/51661 | | 7/2001 |
| WO | WO-02/06533 | | 1/2002 |
| WO | WO-02/20571 | | 3/2002 |
| WO | WO-02/060318 | | 8/2002 |
| WO | WO-02/072772 | | 9/2002 |
| WO | WO-02/101022 | | 12/2002 |
| WO | WO-02/103054 | | 12/2002 |
| WO | WO-03/012118 | | 2/2003 |
| WO | WO-03/016546 | | 2/2003 |
| WO | WO-03/025215 | | 3/2003 |
| WO | WO-03/027259 | | 4/2003 |
| WO | WO-03/035860 | | 5/2003 |
| WO | WO-03/050242 | | 6/2003 |
| WO | WO-03/087774 | | 10/2003 |

OTHER PUBLICATIONS

Burman et al. Hypomethylation of an expanded FMR1 allele is not associated with a global DNA methylation defect. American Journal of Human Genetics, vol. 65, pp. 1375-1386, 1999.*

Olek et al. A modified and improved method for biosulphite based cytosine methylation analysis. Nucleic Acids Research, vol. 24, No. 24, pp. 5064-5066, 1996.*

Adam et al., "Cross-linking of the p55 Tumor Necrosis Factor Receptor cytoplasmic Domain by a dimeric Ligand Induces Nuclear Factor-kB and Mediates Cell Death," J. Biol. Chem., 270(29): 17482-17487, 1995.

Bohlander et al., "A Method for the Rapid Sequence-Independent Amplification of Microdissected Chromosomal Materiarl,"Genomics, 13:1322-1324, 1992.

Champoux, "DNA Topoisomerases: Structure, Function, and Mechanism," Annu. Rev. Biochem., 70: 369-413, 2001.

Chang et al., "PCR amplification of chromosome-specific DNA isolated from flow cytometry-sorted chromosomes," Genomics, 12(2): 307-312, 1992.

Chen et al., "Methylation Target Array for Rapid Analysis of CpG Island Hypermethylation in Multiple Tissue Genomes," Am. J. Pathol., 163(1): 37-45, 2003.

DeRisi Laboratory, Dept. of Biochemistry and Biophysics, Univ. of California at San Francisco, "Random DNA Amplification. Directions for amplifying products for printing on arrays," 2001.

Grothues et al., "PCR amplification of megabase DNA with tagged random primers (T-PCR)," Nucleic Acids Res., 21(5):1321-1322, 1993.

Guan et al., "Generation of band-specific painting probes from a single microdissected chromosome," Human Mol. Genet., 2(8): 1117-1121, 1993.

Guilfoyle et al., "Ligation-mediated PCR amplification of specific fragments from a Class-II restriction endonuclease total digest," Nucleic Acids Res., 25(9):1854-1858, 1997.

Hadano et al., "Laser microdissection and single unique primer PCR allow generation of regional chromosome DNA clones from a single human chromosome," Genomics, 11:364:373, 1991.

Invitrogen Corporation, Carlsbad, California 92008, TOPO TA Cloning. Version P 051302 / 25-0184, pp. 1-26, 1999-2002.

Kao et al "Chromosome microdissection and clonin. In human genome and genetic disease analysis," Proc. Natl. Acad. Sci. USA, 88:1844-1848, 1991.

Kempf et al., "Improved stimulation of human dendritic cells by receptor engagement with surface-modified microparticles," J Drug Target, 11(1): 11-8, 2003.

Kikuchi et al., "Expression profiles of non-small cell lung cancers on cDNA microarrays:Identification of genes for prediction of lymph-node metastasis and sensitivity to anti-cancer drugs," Oncogene, 22(14): 2192-2205, 2003.

Kinzler et al., "Whole genome PCR: application to the identification of sequences bound by gene regulatory proteins," Nucleic Acids Research, 17(10): 3645-3653, 1989.

Kittler et al., "A Whole Genome Amplification Method to Generate Long Fragments from Low Quantities of Genomics DNA", Anal. Biochem., 300: 237-244, 2002.

Klein et al., "Comparative genomic hybridization, loss of heterozygosity, and DNA sequence analysis of single cells," Proc. Natl. Acad. Sci. USA, 96: 4494-4499, 1999.

Ko et al. "Unbiased amplification of highly complex mixture of DNA fragments by 'Ione linker'-tagged PCR," Nucleic Acids Res., 18: 4293-4294, 1990.

Lisitsyn et al., "Cloning the differences between two complex genomes," Science, 259: 946-951, 1993.

Lucito et al., "Genetic analysis using genomic representations," Proc. Natl. Acad. Sci. USA, 95: 4487-4492, 1998.

Makrigiorgos et al., "A PCR-based amplification method retaining the quantitative difference between two complex genomes," Nature Biotechnology, 20(9): 936-939, 2002.

Melief et al., "Effective theraputic anticancer vaccines based on precision guiding of cytolytic T lymphocytes," Immunol Rev., 188: 177-82, 2002.

Miyashita, K., et al., "A mouse chromosome 11 library generated from sorted chromosomes using linker-adapter polymerase chain reaction," Cytogenet. Cell Genet., 66(1): 54-57, 1994.

Perou et al., "Molecular Portraits of Human Breast Tumors," Nature, 406(6797): 747-52, 2000.

Phillips et al., "Antisense RNA Amplification: A Linear Amplification Method for Analyzing the mRNA Population from Single Living Cells," Methods: Acompanion to Methods in Enzymology 10, Article No. 0104, 283-288, 1996.

Sato et al., "Combination of monocyte-derived dendritic cells and activated T cells which express CD40 ligand: a new approach to cancer immunotherapy," Cancer Immunol Immunother, 53(1): 53-61, 2004.

Saunders et al., "PCR amplification of DNA microdissected from a single polytene chromosome band: A comparison with conventional microcloning," Nucleic Acids Res., 17: 9027-9037, 1989.

Schmidt et al., "CapSelect: A highly sensitive method for 5' CAP-dependant enrichment of full-length cDNA in PCR-mediated analysis of mRNAs," Nucleic Acids Research, 27(21), e31, 1999.

Sharrrocks, Andrew D., et al., "The Design of Primers for PCR", PCR Technology Current Innovations, Chapter 2, 5-11, 1994.

Siebert et al., "An improved PCR method for walking in uncloned genomic DNA," Nucleic Acids Res., 23: 1087-1088, 1995.

Smith, "Ligation-mediated PCR of restriction fragments from large DNA molecules," PCR Methods Appl., 2(1):21-7, 1992.

Smith et al., "Single primer amplification (SPA) of cDNA for microarray expression analysis," *Nucleic Acids Research*, 31(3): e9, 2003.

Studier et al., "Relationships among Different Strains of T7 and among T7-Related Bacteriophages," *Virology*, 95(1): 70-84, 1979.

Tanabe et al., "Evaluation of a Whole-Genome Amplification Method Based on Adaptor-Ligation PCR of Randomly Sheared Genomic DNA," *Genes, Chromosomes & Cancer*, 38: 168-176, 2003.

Telenius et al., "Degenerate Oligonucleotide-Primed PCR: General Amplification of Target DNA by a Single Degenerate Primer," *Genomics*, 13: 718-725, 1992.

VanDevanter et al., "Pure chromosome-specific PCR libraries from single sorted chromosome," *Proc. Natl. Acad. Sci. USA*, 91: 5858-5862, 1994.

Vooijs et al., "Libraries for each human chromosome, constructed from sorter-enriched chromosomes by using linker-adaptor PCR," *Am. J. Hum. Genet.*, 52(3): 586-597, 1993.

Wold, "Replication Protien A: A Heterotrimeric, Single-Stranded DNA-Binding Protein Required for Eukaryotic DNA Metabolism," *Annu. Rev. Biochem.*, 66: 61-92, 1997.

Wong et al., "Use of tagged random hexamer amplification (TRHA) to clone and sequence minute quantities of DNA-application to a 180 kb plasmid isolated from sphingmonas F199," *Nucleic Acids Research,*, 24(19): 3778-3783, 1996.

Yan et al., "Dissecting Complex Epigenetic Alterations in Breast Cancer Using CpG Island Microarrays," *Cancer Res.*, 61: 8375-8380, 2001.

Zhang et al., "Whole genome amplification from a single cell: Implications for genetic analysis," *Proc. Natl. Acad.*, 89(13): 5847-5851, 1992.

Zheleznaya et al., "PCR Fragmentation of DNA," *Biochemistry*, 64(4): 373-8, 1999.

Badal et al., "CpG Methylation of Human Papillomavirus Type 16 DNA in Cervical Cancer Cell Lines and in Clinical Specimens: Genomic Hypomethylation Correlates with Carcinogenic Progression," *Journal of Virology*, 77(11): 6227-6234, 2003.

Baldini et al., "Chromosomal assignment of human YAC clones by fluorescence in situ hybridization: use of single-yeast-colony PCR and multiple labeling," *Genomics*, 14: 181-184, 1992.

Barbaux et al., "Use of degenerate oligonucleotide primed PCR (DOP-PCR) for the genotyping of low-concentration DNA samples," *J Mol Med*, 79:329-332, 2001.

Beekman et al., "A powerful and rapid approach to human genome scanning using small quantities of genomic DNA," *Genet. Res. Camb.*, 77:129-134, 2001.

Breen et al., "YAC mapping by FISH using Alu-PCR-generated probes," *Genomics*, 13: 726-730, 1992.

Buchanan et al., "Long DOP-PCR of rare archival anthropological samples," *Hum. Biol.*, 72(6): 911-25, 2000.

Campbell et al., "The effect of divalent cations on the mode of action DNase 1. The initial reaction products produced from covalently closed circular DNA," *J. Biol. Chem.*, 255: 3726-3735, 1980.

Cheng et al., "Degenerate oligonucleotide primed-polymerase chain reaction and capillary electrophoretic analysis of human DNA on microchip-based devices," *Anal. Biochem.*, 257(2): 101-6, 1998.

Cheung et al., "Whole genome amplification using a degenerate oligonucleotide primer allows hundreds of genotypes to be performed on less than one nanogram of genomic DNA," *Proc. Natl. Acad. Sci. USA*, 93: 14676-14679, 1996.

Chotai et al., "A rapid, PCR based test for differential molecular diagnosis of Prader-Willi and Angelman syndromes," *J. Med. Genet.*, 35: 472-475, 1998.

Dean et al., "Comprehensive human genome amplification using multiple displacement amplification," *PNAS*, 99(8): 5261-5266, 2002.

Frigola et al., "Methylome profiling of cancer cells by amplification of inter-methylated sites (AIMS)," *Nucleic Acids Res.*, 30(7): e28, 2002.

Fu et al., "Sequencing Double-Stranded DNA by Strand Displacement," *Nucleic Acids Research*, 25(3): 677-679, 1997.

Hawkins et al., "Whole genome amplification—applications and advances," Current Opinion in Biotechnology, 13: 65-67, 2002.

Huang et al., "Methylation profiling of CpG islands in human breast cancer cells," *Human Molecular Genetics*, 8(3): 459-470, 1999.

Igloi, "Substrate properties of fluorescent ribonucleotides in the terminal transferase-catalyzed labeling of DNA sequencing primers," *Biotechniques*, 21: 1084-1092, 1996.

Jones et al., "Amplification of 4-9-kb Human Genomic DNA Flanking a Known Site Using a Panhandle PCR Variant," *BioTechniques*, 23: 132-138, 1997.

Kaiser et al., "Specific-primer-directed DNA sequencing using automated fluorescent detection," *Nucleic Acids Res.*, 17: 6087-6102, 1989.

Kilger et al., "Direct DNA sequence determination from total genomic DNA," *Nucleic Acids Research*, 25(10): 2032-2034, 1997.

Kusov et al., "A new G-tailing method for the determination of the poly(A) tail length applied to hepatitis A virus RNA," *Nucleic Acids Research* 29(12): e57, 2001.

Kuukasjarvi et al., "Optimizing DOP-PCR for Universal Amplificatino of Small DNA Samples in Comparative Genomic Hybridization," *Genes, Chromosomes & Cancer*, 18: 94-101, 1997.

Lengauer et al., "Fluorescence in situ hybridization of YAC clones after Alu-PCR amplification," *Genomics*, 13: 826-828, 1992.

Ludecke et al., "Cloning defined regions of the human genome by microdissection of banded chromosomes and enzymatic amplification," *Nature*, 338(6213): 348-50, 1989.

McGrath et al., "Sequence analysis of DNA randomly amplified from the *Saccharomyces cerevisiae* genome," *Molecular and Cellular Probes,*, 12: 397-405, 1998.

Mullis et al., "Specific enzymatic amplification of DNA in vitro: the polymerase chain reaction," Cold Spring Harbor Symp., 263-273, 1986.

Nelson et al., "Alu-primed polymerase chain reaction for regional assignment of 110 yeast artificial chromosome clones from the human X chromosome: identification of clones associated with a disease locus," *PNAS*, 88: 6157-6161, 1991.

Nishigaki et al., "Whole genome sequence-enabled prediction of sequences performed for random PCR products of *Escherichia coli*," *Nucleic Acids Research* 28(9): 1879-1884, 2000.

PCT International Preliminary Examination Report, PCT NL01 00020, dated Mar. 25, 2003.

PCT International Search, PCT-NL01 00020, dated Jul. 18, 2002.

Pfeifer, "Chromatin structure analysis by ligation-mediated and terminal transferase-mediated polymerase chain reaction," *Methods Enzymol.*, 304: 548-571, 1999.

Reyes et al., "Sequence-independent, single-primer amplification (SISPA) of complex DNA populations," *Molecular and Cellular Probes* 5: 473-481, 1991.

Rose et al., "Consensus-degenerate hybrid oligonucleotide primers for amplification of distantly related sequences," *Nucleic Acids Research*, 26(7): 1628-1635, 1998.

Sanchez-Cespedes et al., "Degenerate oligonucleotide-primed PCR (DOP-PCR): evaluation of its reliability for screening of genetic alterations in neoplasia," *Biotechniques*, 25(6): 1036-8, 1998.

Schiefermayr et al., "Degradation of DNA sequencing primers by a terminal transferase-associated exonuclease," *Anal. Biochem.*, 230: 180-182, 1995.

Shyamala et al., "Genome walking by single-specific-primer polymerase chain reaction: SSP-PCR," *Gene*, 84: 1-8, 1989.

Smith et al., "Automated differential display using a flourescently labeled universal primer," *Biotechniques*, 23(2): 274-279, 1997.

Snabes et al., "Preimplantation single-cell analysis of multiple genetic loci by whole-genome amplification," *Proc. Natl. Acad. Sci. USA*, 91:6181-6185, 1994.

Strichman-Almashanu et al., "A Genome-Wide Screen for Normally Methylated Human CpG Islands That Can Identify Novel Imprinted Genes," *Genome Research*, 12(4): 543-54, 2002.

Sutcliffe et al., "PCR amplification and analysis of yeast artificial chromosomes," *Genomics*, 13: 1303-1306, 1992.

Toyota et al., "Methylated CpG Island Amplification for Methylation Analysis and Cloning Differentially Methylated Sequences," *Methods in Molecular Biology*, 200: 101-10, 2002.

Wells et al., "Comprehensive chromosomal analysis of human preimplantation embryos using whole genome amplification and single cell comparative genomic hybridization," *Molecular Human Reproduction*, 6(11): 1055-1062, 2000.

Wells et al., "Detailed chromosomal and molecular genetic analysis of single cells by whole genome amplification and comparative genomic hybridisation," *Nucleic Acids Research*, 27(4): 1214-1218, 1999.

Wesley et al., "Cloning regions of the *Drosophila* genome by microdissection of polytene chromosome DNA and PCR with non-specific primer," *Nucleic Acids Res.*, 18(3): 599-603, 1990.

Yan et al., "Dissecting Complex Epigenetic Alterations in Breast Cancer Using CpG Island Microarrays," *Cancer Research*, 61: 8375-8380, 2001.

Zheleznaya et al., "PCR Fragmentation of DNA," *Biochemistry* (Moscow), 64(4): 373-8, 1999.

Agarwal and Perl, "PCR amplification of highly GC-rich DNA template after denaturation by NaOH," *Nucleic Acids Research*, 21:5283-4, 1993.

Cusi et al., "PCR amplification of GC-rich templates containing palindromic sequences using initial alkali denaturation," *BioTechniques*, 12:502-4, 1992.

Office Action, issued in related U.S. Appl. No. 11/367,046, mail date Feb. 8, 2008.

Office Action issued in European Patent Application 05724509.4, dated Mar. 20, 2012.

Bachmann et al., "Successful amplification of extremely GC-rich promoter regions using a novel 'slowdown PCR' technique," *Pharmacogenetics*, 13(12): 759-766, 2003.

Bellizi et al., "A procedure for cloning genomic DNA fragments with increasing thermoresistance," *International Journal of Genes and Genomes*, 219: 63-71, 1998.

Extended European Search Report issued in Application No 10012393.4, dated Jan. 24, 2011.

Shiraishi et al., "Preferential isolation of DNA fragments associated with CpG islands," *Proc. Natl. Acad. Sci.*, 92:4229-4233, 1995.

Extended European Search Report issued in Application No. 11000322.5, dated Sep. 26, 2011.

\* cited by examiner

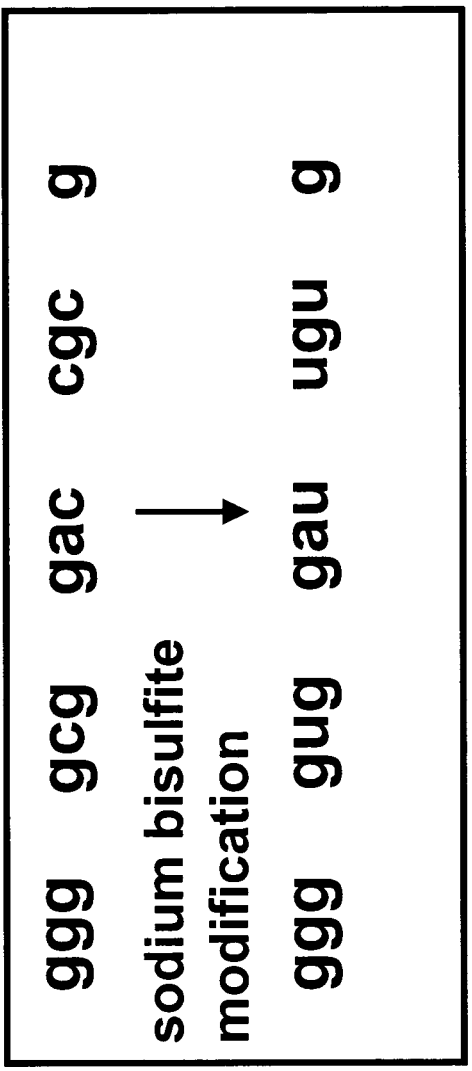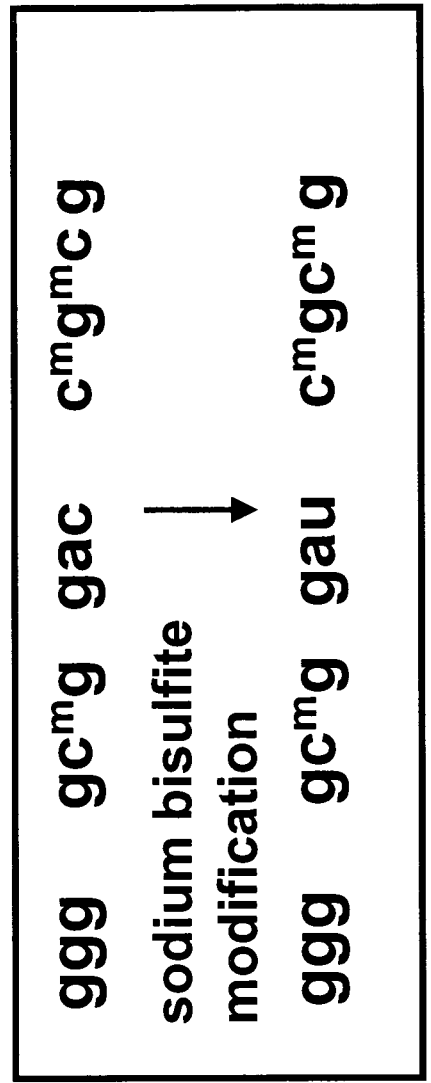
FIG. 3

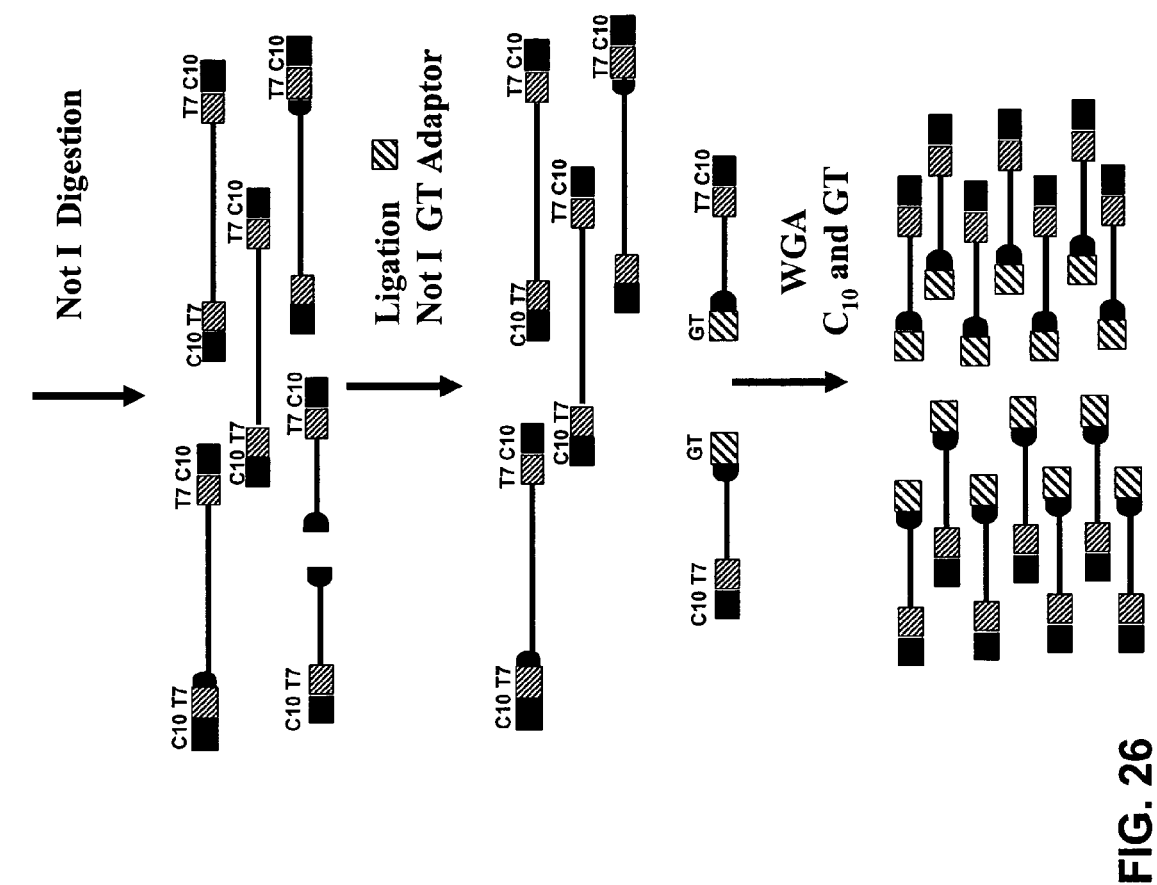
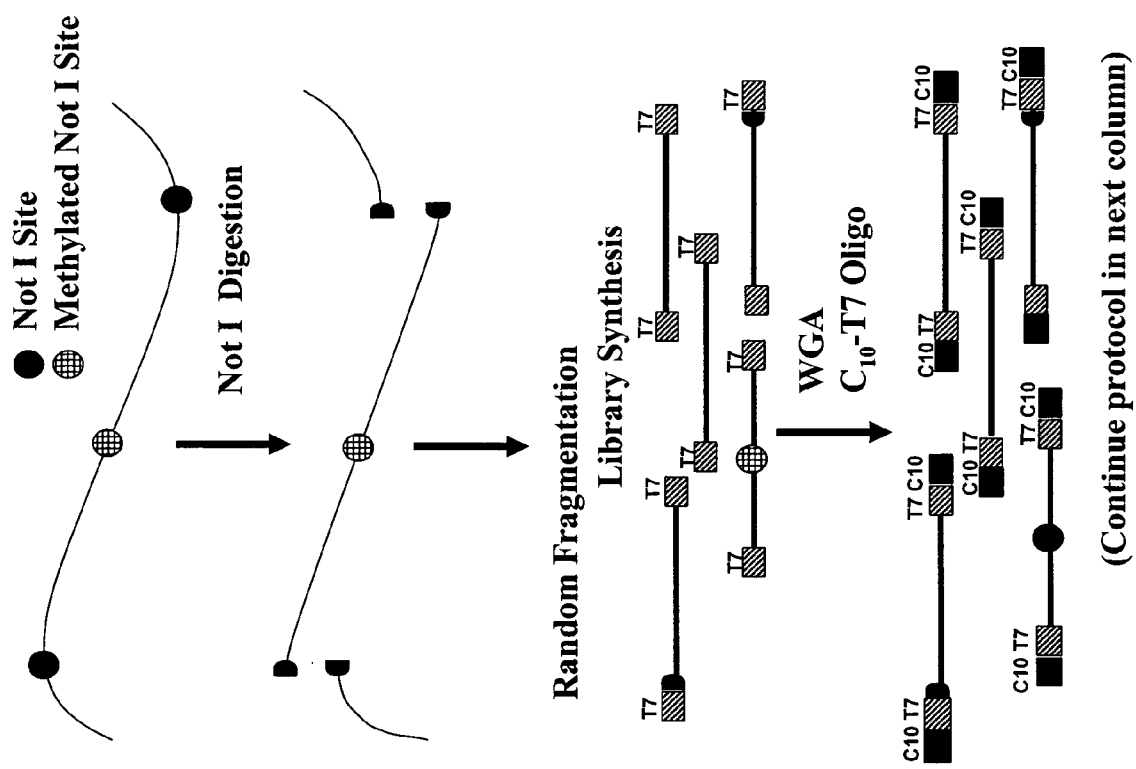
FIG. 26

Blunt End T7 Adaptor

5'-GTAATACGACTCACTATAGG-3'
3'-xTGACGTGATATCC-5'

3' Overhang T7 Adaptor

5'-GTAATACGACTCACTATAGGN-3'
3'-xTGACGTGATATCC-5'

5' Overhang T7 Adaptor

5'-GTAATACGACTCACTATAGG-3'
3'-xTGACGTGATATCCN-5'

Not I GT Adaptor

5'-TGTGTTGGGTGTGTTT-3'
3'-xCCCACACAAACCGG-5'

FIG. 32

FIG. 33D

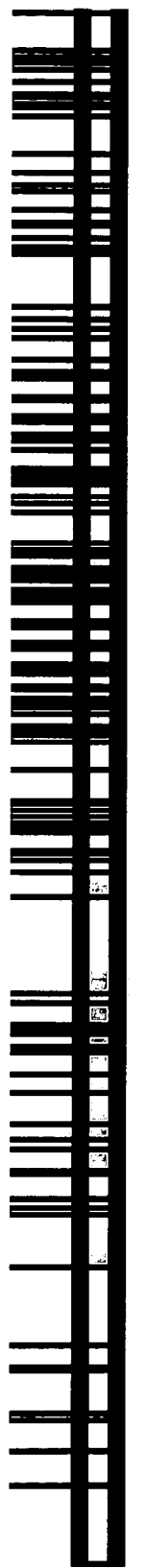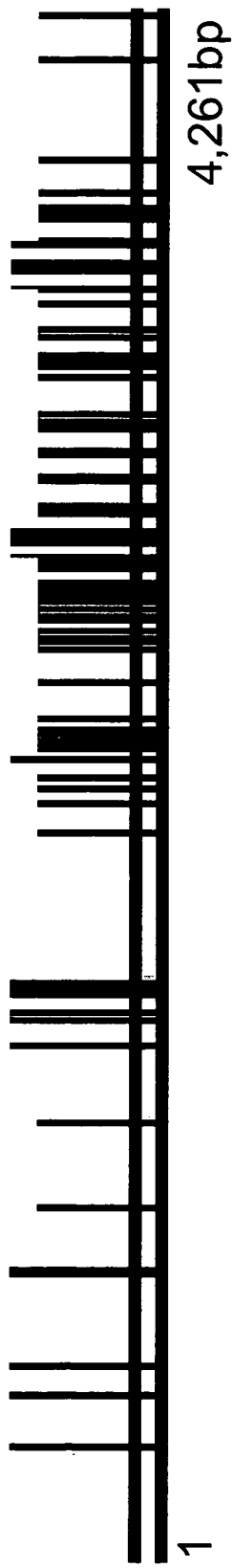
FIG. 33E

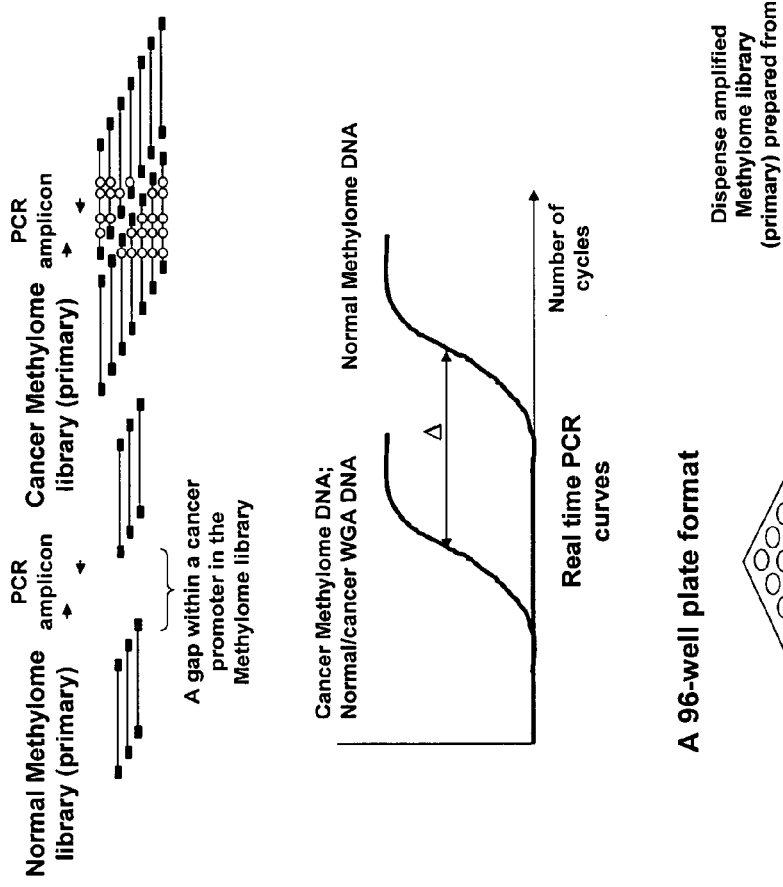
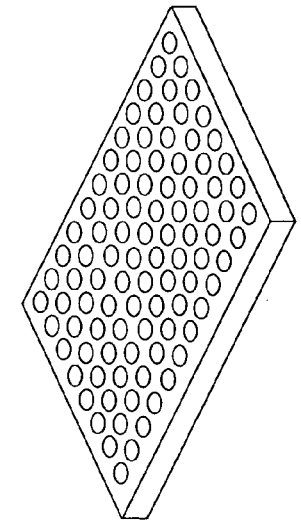
FIG. 34

C-U = Non-Digested Cancer DNA
N-U = Non-Digested Normal DNA
C-C = Digested Cancer DNA
N-C = Digested Normal DNA C-U = Non-Digested Cancer DNA
N-U = Non-Digested Normal DNA
C-C = Digested Cancer DNA
N-C = Digested Normal DNA Secondary library protocol for preparation of Methylome library enriched in CpG islands for genome-wide micro-array methylation markers discovery and diagnostic applications

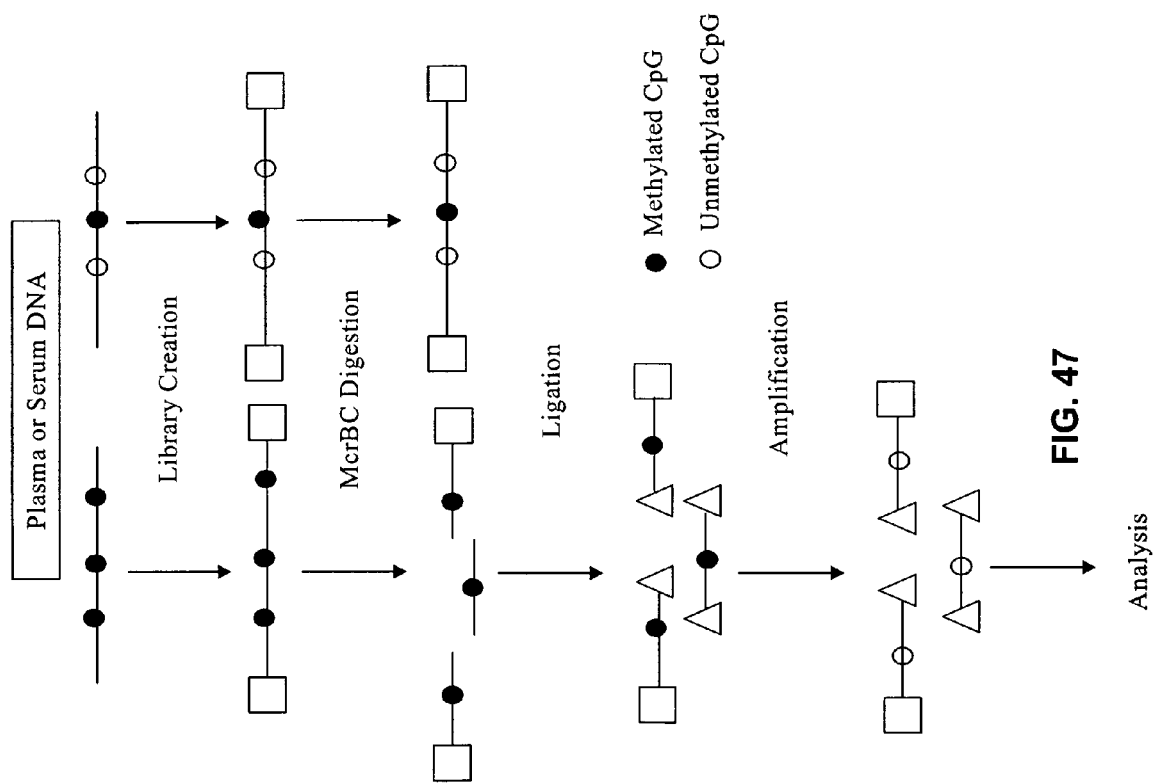

5' T7N Overhang Adaptors

N2T7

(SEQ ID NO:17)
5'-GTAATACGACTCACTATAGG-3'
3'-/3AmMC7/TGAGTGATATCCNN-5'
(SEQ ID NO:55)

N3T7

(SEQ ID NO:17)
5'-GTAATACGACTCACTATAGG-3'
3'-/3AmMC7/TGAGTGATATCCNNN-5'
(SEQ ID NO:56)

N4T7

(SEQ ID NO:17)
5'-GTAATACGACTCACTATAGG-3'
3'-/3AmMC7/TGAGTGATATCCNNNN-5'
(SEQ ID NO:57)

N5T7

(SEQ ID NO:17)
5'-GTAATACGACTCACTATAGG-3'
3'-/3AmMC7/TGAGTGATATCCNNNNN-5'
(SEQ ID NO:58)

3' T7N Overhang Adaptors

T7N2

(SEQ ID NO:202)
5'-GTAATACGACTCACTATAGGNN-3'
3'-/3AmMC7/TGAGTGATATCC-5'
(SEQ ID NO:34)

T7N3

(SEQ ID NO:203)
5'-GTAATACGACTCACTATAGGNNN-3'
3'-/3AmMC7/TGAGTGATATCC-5'
(SEQ ID NO:34)

T7N4

(SEQ ID NO:204)
5'-GTAATACGACTCACTATAGGNNNN-3'
3'-/3AmMC7/TGAGTGATATCC-5'
(SEQ ID NO:34)

T7N5

(SEQ ID NO:205)
5'-GTAATACGACTCACTATAGGNNNNN-3'
3'-/3AmMC7/TGAGTGATATCC-5'
(SEQ ID NO:34)

FIG. 48

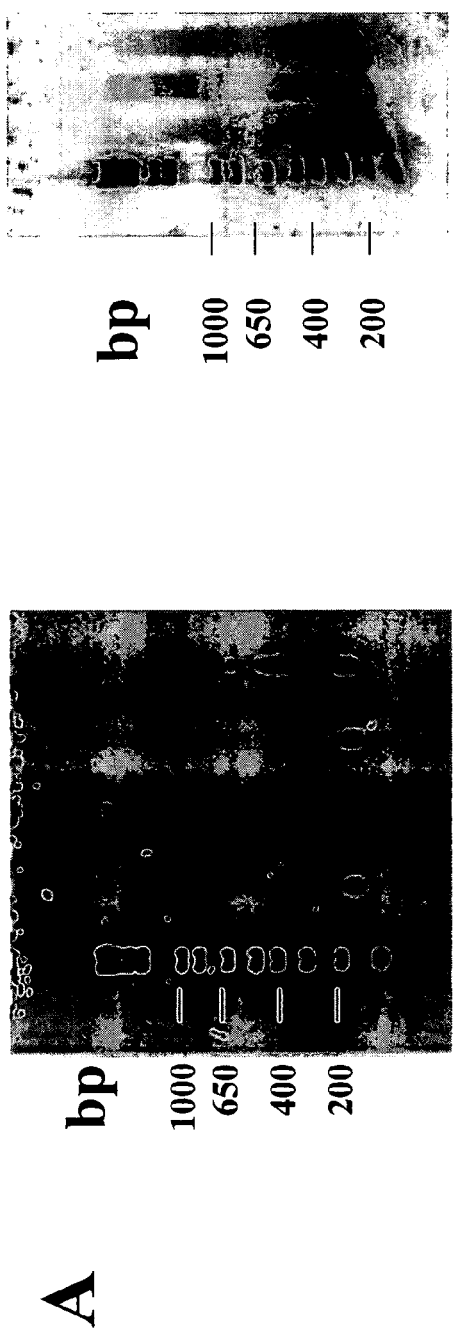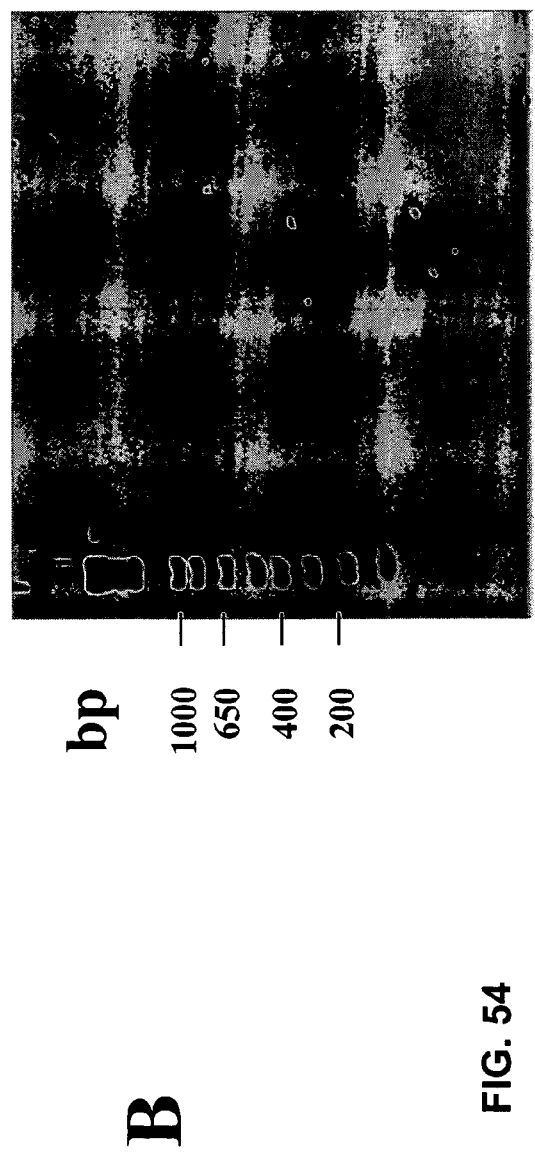
FIG. 54

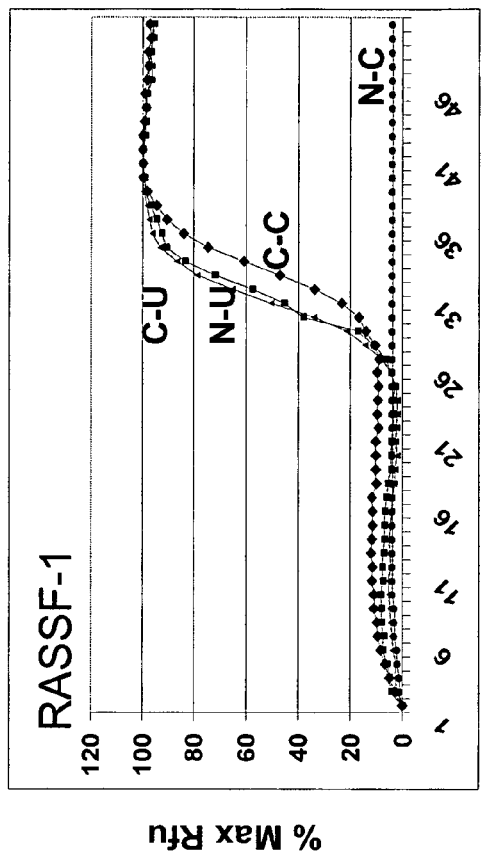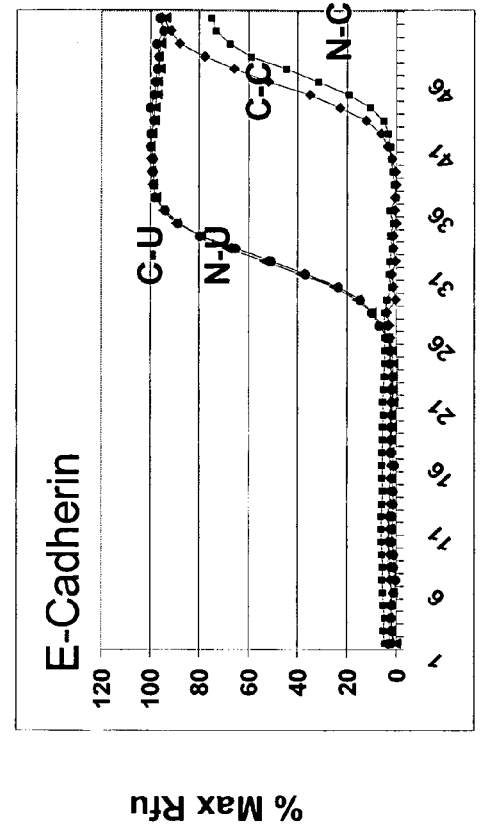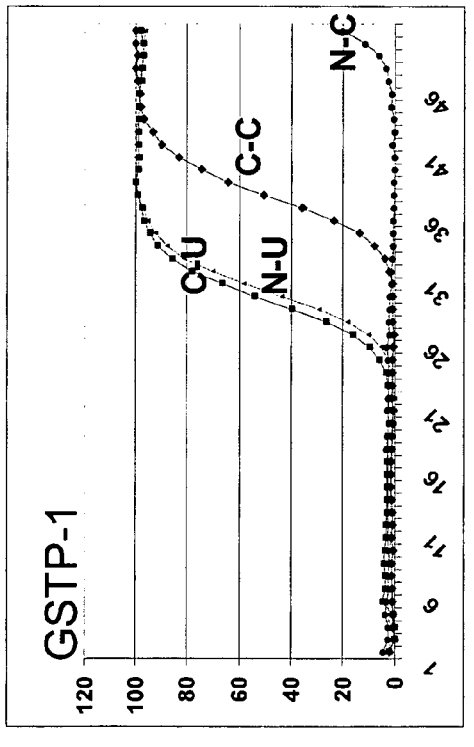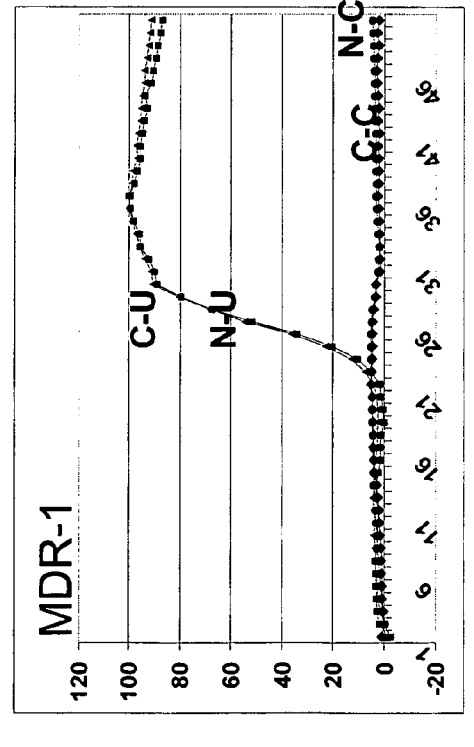
FIG. 55

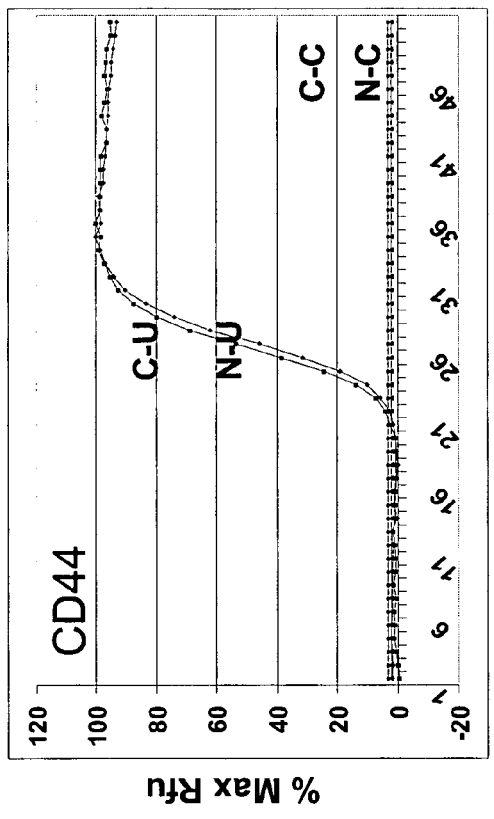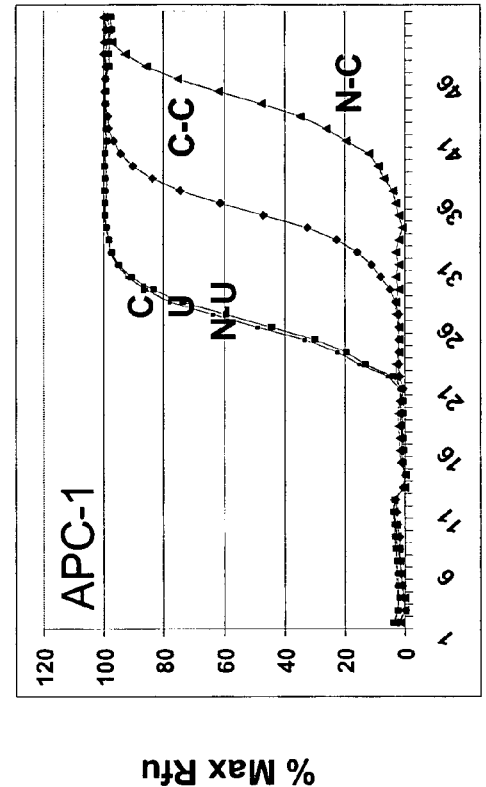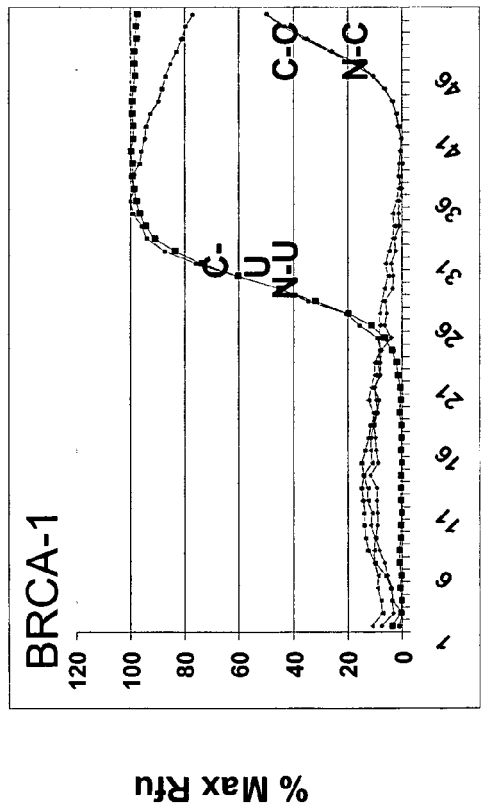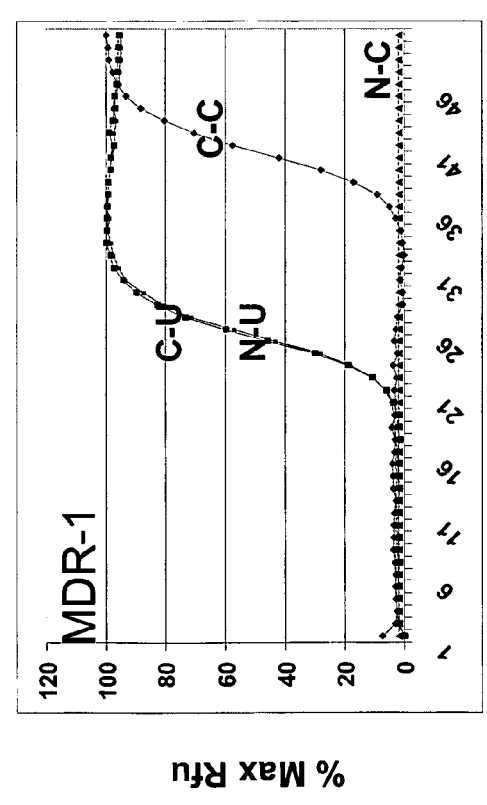
FIG. 56

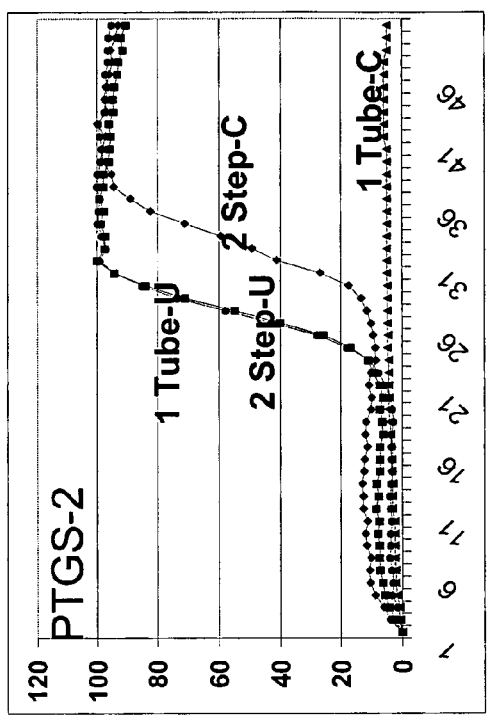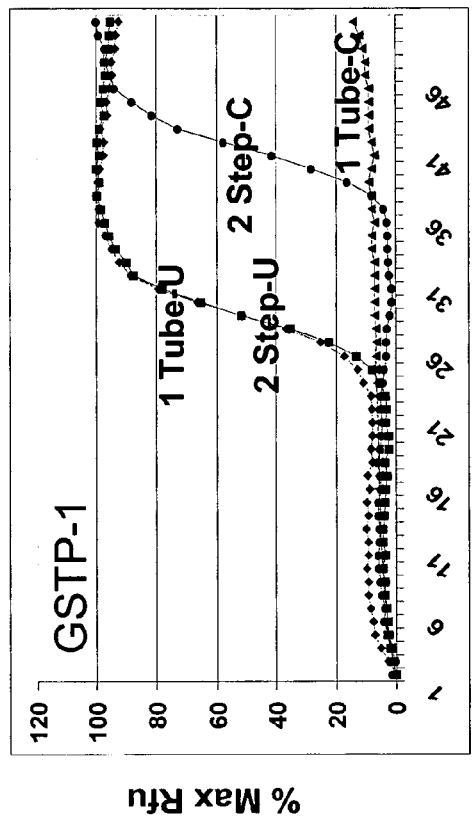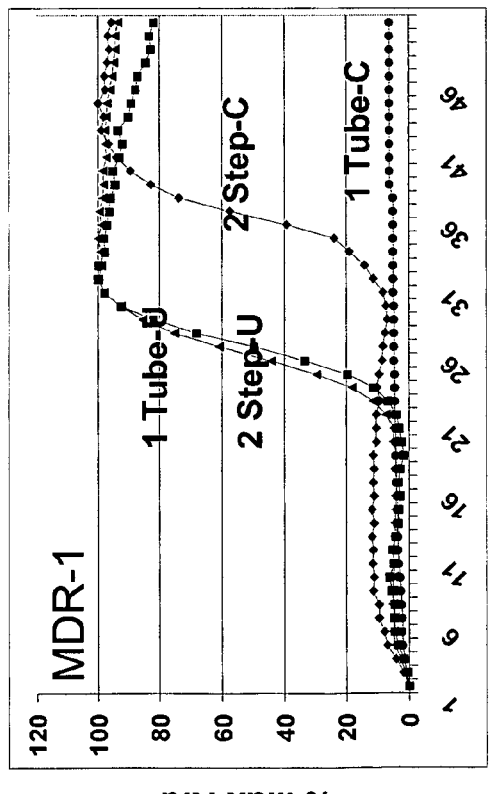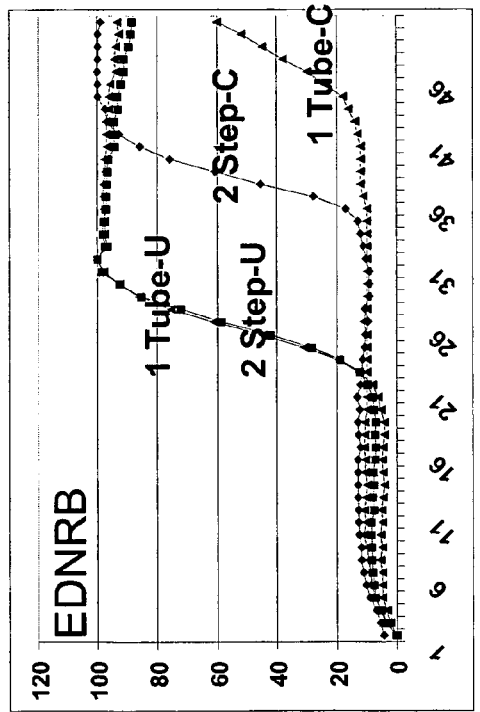
FIG. 57

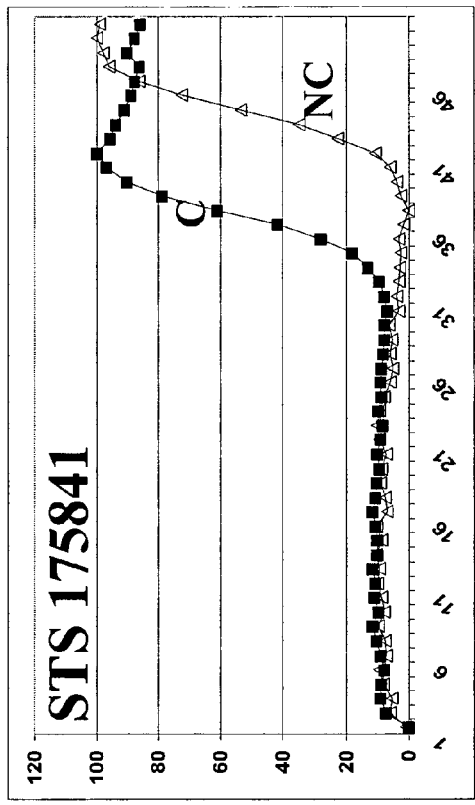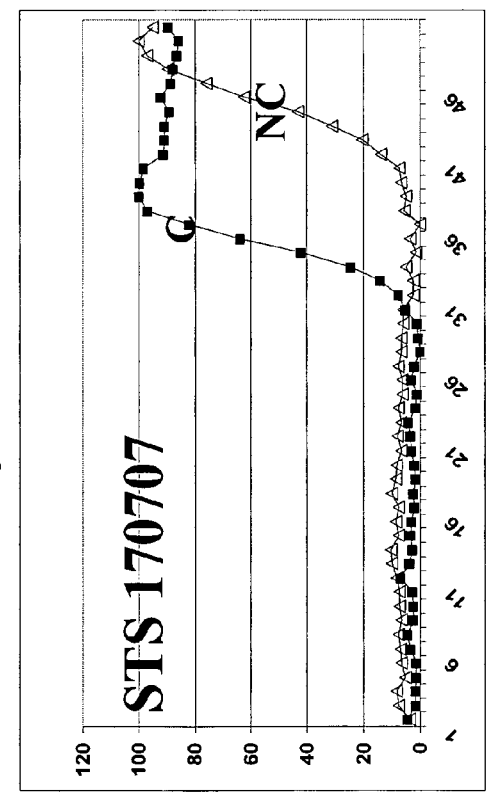
FIG. 60B

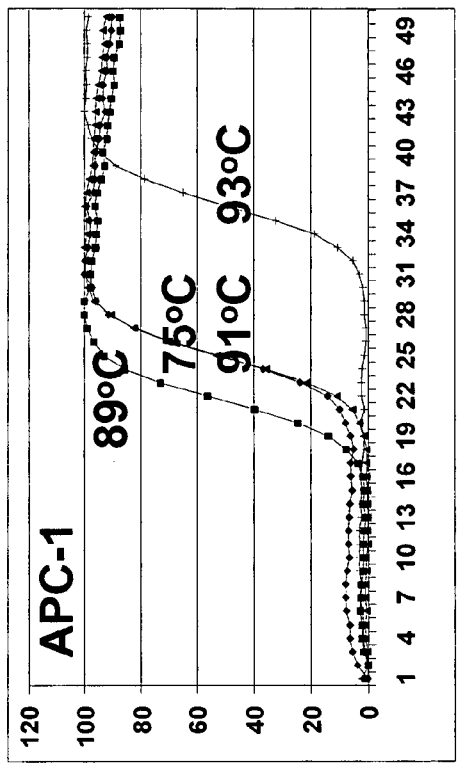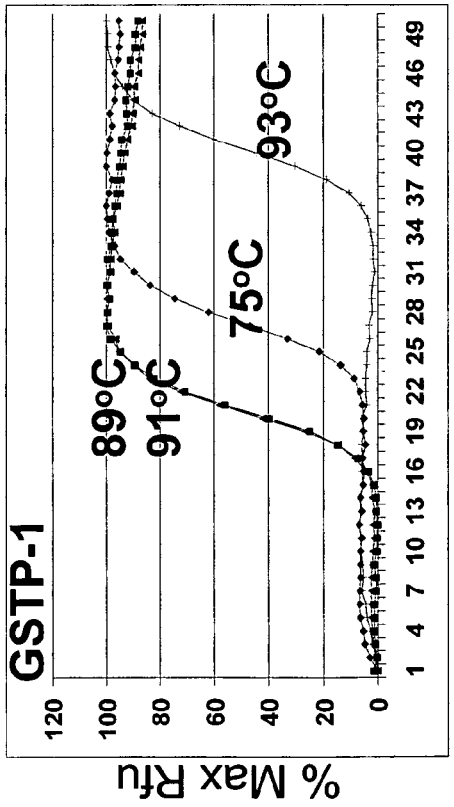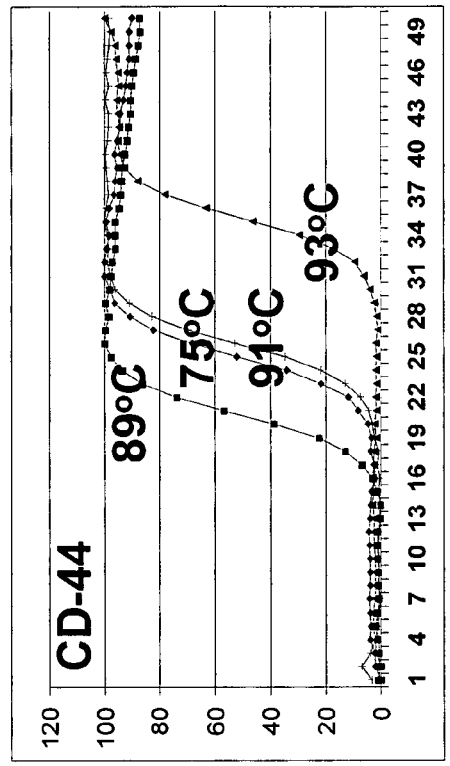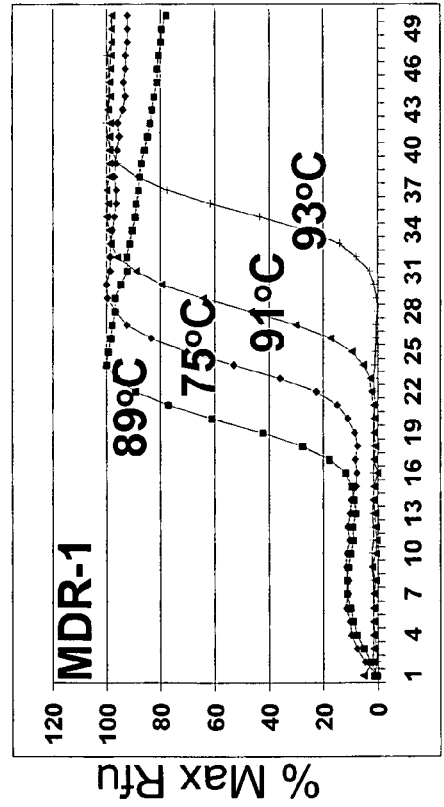
FIG. 62A

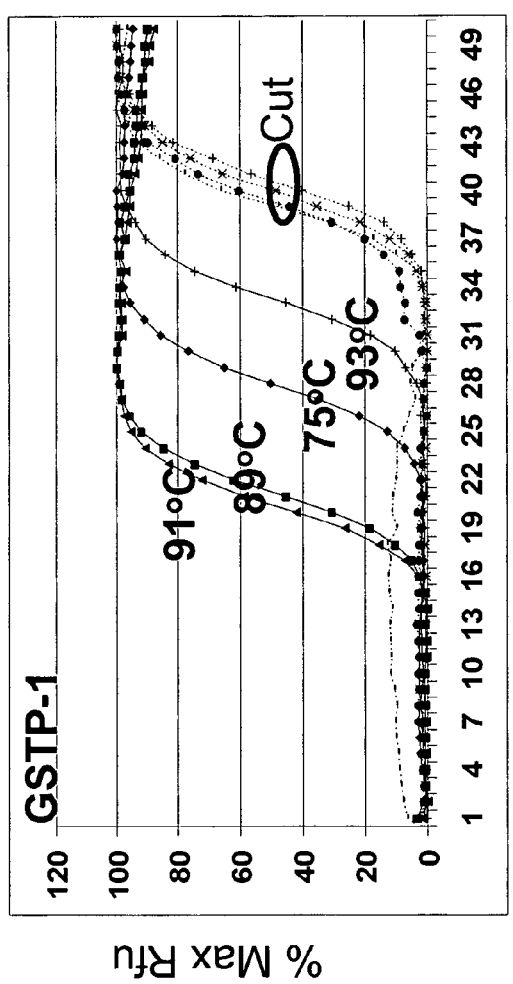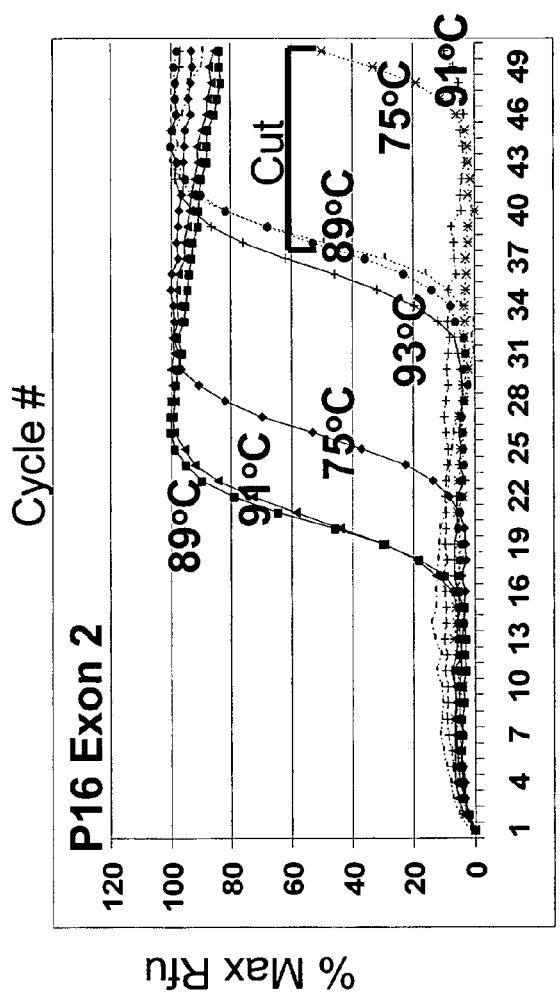
FIG. 62B

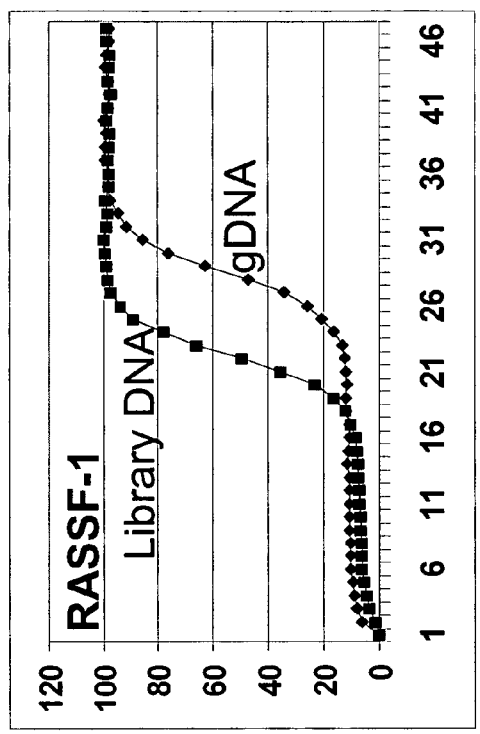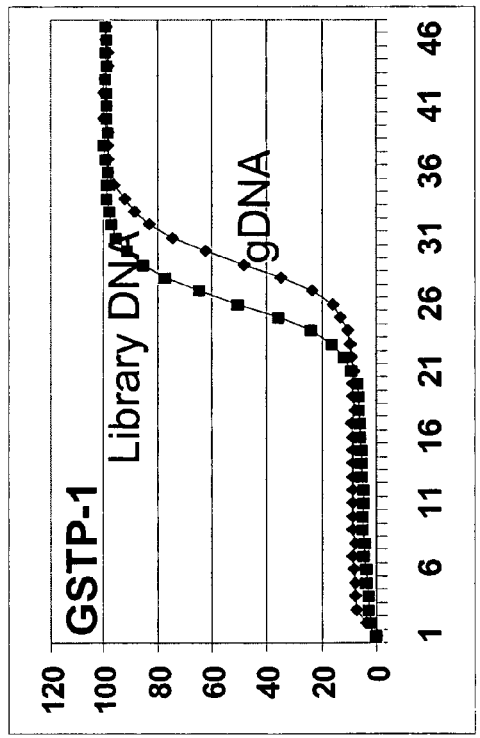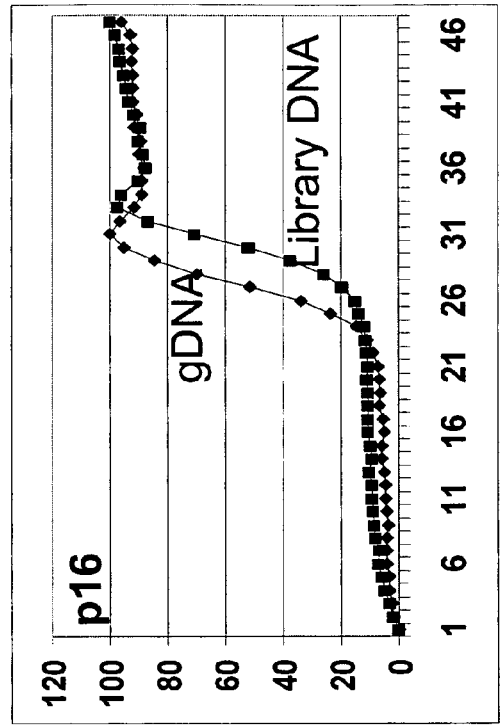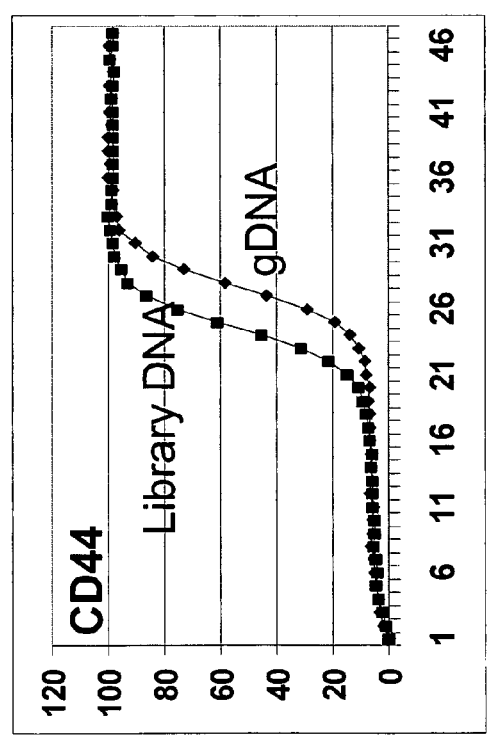
FIG. 66

DP-WGA – degenerate primer mediated whole genome amplification;
LM-WGA – ligation-mediated whole genome amplification

METHODS AND COMPOSITIONS FOR GENERATING AND AMPLIFYING DNA LIBRARIES FOR SENSITIVE DETECTION AND ANALYSIS OF DNA METHYLATION

The present invention claims priority to U.S. Provisional Patent Application 60/551,941, filed Mar. 8, 2004, which is incorporated by reference herein in its entirety.

FIELD OF THE INVENTION

The present invention is directed to the fields of genomics, molecular biology, the epigenetic control of gene expression, and molecular diagnostics. In some embodiments, the present invention relates to methods for amplification and identification of DNA fragments surrounding methylation sites. In other embodiments, the present invention relates to methods for amplifying and identifying sites that are hypomethylated. In some embodiments, the present invention relates to methods for the analysis of methylation of cytosine within the CpG dinucleotide in eukaryotic genomes and its implication in developmental biology, gene imprinting, and cancer diagnostics.

BACKGROUND OF THE INVENTION

Cytosine methylation occurs after DNA synthesis by enzymatic transfer of a methyl group from an S-adenosylmethionine donor to the carbon-5 position of cytosine. The enzymatic reaction is performed by one of a family of enzymes known as DNA methyltransferases. The predominant sequence recognition motif for mammalian DNA methyltransferases is 5'-CpG-3', although non-CpG methylation has also been reported. Due to the high rate of methyl cytosine to thymine transition mutations, the CpG dinucleotide is severely underrepresented and unequally distributed across the human genome. Vast stretches of DNA are depleted of CpGs, and these are interspersed by CpG clusters known as CpG islands. About 50-60% of known genes contain CpG islands in their promoter regions, and they are maintained in a largely unmethylated state except in the cases of normal developmental gene expression control, gene imprinting, X chromosome silencing, ageing, or aberrant methylation in cancer and some other pathological conditions. The patterns of DNA methylation are a critical point of interest for genomic studies of cancer, disease, and ageing. Methylation of DNA has been investigated in terms of cellular methylation patterns, global methylation patterns, and site-specific methylation patterns. The goal of methylation analysis is to develop discovery tools that increase our understanding of the mechanisms of cancer progression, and diagnostic tools that allow the early detection, diagnosis, and treatment of cancers and other diseases. In recent years it has become apparent that the transcriptional silencing associated with 5-methylcytosine is important in mammalian development, genome imprinting, X chromosome inactivation, mental health, and cancer, as well as for protection against intragenomic parasites.
Methylation in Cancer
Epigenetics is the study of inherited changes in DNA structure that affect expression of genes that are not due to a change in the DNA sequence. One major focus of epigenetic studies is the role of methylation in silencing gene expression. Both increased methylation (hypermethylation) and loss of methylation (hypomethylation) have been implicated in the development and progression of cancer and other diseases. Hypermethylation of gene promoter and upstream coding regions results in decreased expression of the corresponding genes. It has been proposed that hypermethylation is used as a cellular mechanism to not only decrease expression of genes not being utilized by the cell, but also to silence transposons and other viral and bacterial genes that have been incorporated into the genome. Genomic regions that are actively expressed within cells are often found to be hypomethylated in the promoter and upstream coding regions. In contrast, downstream regions are typically kept hypermethylated in actively transcribed genes, but become hypomethylated in cancer (Jones and Baylin, 2002; Baylin and Herman, 2000). Thus, there appears to be a cellular balance between silencing of genes by hypermethylation and hypomethylation of promoter and upstream coding regions of genes that are actively being expressed.

Hypermethylation of tumor suppressor genes has been correlated with the development of many forms of cancer (Jain, 2003). The genes most commonly being hypermethylated in various cancers include: 14-3-3 sigma, ABL1 (P1), ABO, APC, AR (Androgen Receptor), BLT1 (Leukotriene B4 Receptor), BRCA1, CALCA (Calcitonin), CASP8 (CASPASE 8), Caveolin 1, CD44, CDH1 (E-Cadherin), CFTR, GNAL, COX2, CSPG2 (Versican), CX26 (Connexin 26), Cyclin A1, DAPK1, DBCCR1, DCIS-1, Endothelin Receptor B, EPHA3, EPO (Erythropoietin), ER (Estrogen Receptor), FHIT, GALNR2, GATA-3, COL9A1, GPC3 (Glypican 3), GST-pi, GTP-binding protein (olfactory subunit), H19, H-Cadherin (CDH13), HIC1, hMLH1, HOXA5, IGF2 (Insulin-Like Growth Factor II), IGFBP7, IRF7, KAI1, LKB1, LRP-2 (Megalin), MDGI (Mammary-derived growth inhibitor), MDR1, MDR3 (PGY3), MGMT (O6 methyl guanine methyl transferase), MINT, MT1a (metallothionein 1), MUC2, MYOD1, N33, NEP (Neutral Endopeptidase 24.1)/CALLA, NF-L (light-neurofilament-encoding gene), NIS (Sodium-Iodide Symporter gene), OCT-6, P14/ARF, P15 (CDKN2B), P16 (CDKN2A), P27KIP1, p57 KIP2, p73, PAX6, PgR (Progesterone Receptor), RAR-Beta2, RASSF1, RB1 (Retinoblastoma), RPA2 (replication protein A2), SIM2, TERT, TESTIN, TGFBR1, THBS1 (Thrombospondin-1), TIMP3, TLS3 (T-Plastin), TMEFF2, Urokinase (uPA), VHL (Von-Hippell Lindau), WT1, and ZO2 (Zona Occludens 2).

While a small list of commonly hypermethylated sites are being routinely screened as potential sites of interest in many cancers, there is a current lack of methodologies for discovering new sites of interest that may play critical roles in the development and/or progression of cancer. There is also a lack of rapid and accurate methodologies for determining the methylation status of specific genes for use as diagnostic, treatment, and prognostic tools for cancer patients.

Hypomethylation has also been implicated as a mechanism responsible for tumor progression (Dunn, 2003). Several genes have been characterized as being hypomethylated in colon carcinoma and/or leukemia, including growth hormone, c-myc, gamma globulin, gamma crystallin, alpha and beta chorionic gonadotropin, insulin, proopiomelanocortin, platelet derived growth factor, c-ha-ras, c-fos, bcl-2, erb-A1, and ornithine decarboxylase. The majority of these genes are involved in growth and cell cycle regulation and it has been proposed that the loss of methylation in these genes contributes to unchecked cell proliferation in these and other cancer types.

While both hypermethylation and hypomethylation have been implicated in the development and progression of several cancers, their specific roles have not been fully elucidated. For instance, does hypermethylation of tumor suppressor genes lead to hypomethylation of cell cycle regulatory genes leading to unchecked cellular proliferation? In order to answer these and other important questions, rapid, accurate, and sensitive technologies for the analysis of DNA methylation patterns within normal and cancer cells are required.

Genome-Wide DNA Methylation Patterns

The analysis of global levels of DNA methylation has proven useful in the study of cancer, disease, and ageing. Changes in global methylation levels have been directly correlated with the development of several types of cancer, including: lung, colon, hepatic, breast, and leukemia (Fruhwald and Plass, 2002). The measurement of global methylation levels has been accomplished by several distinct technologies: Southern blotting, High Pressure Liquid Chromatography (HPLC), High Performance Capillary Electrophoresis (HPCE), MALDI mass spectrometry, and Chemical or Enzymatic incorporation of radio-labeled methyl groups (Fraga and Esteller, 2002).

Southern blotting techniques involve traditional, two-dimensional gel electrophoresis of DNA digested with a non-methylation sensitive restriction endonuclease (first dimension), followed by a methylation sensitive restriction endonuclease (Fanning et al., 1985). This procedure allows the differential resolution of banding patterns between two samples to compare relative methylation patterns. HPLC and HPCE methods both require the breakdown of DNA into the individual nucleotides which are then separated using either chromatography (HPLC) or electrophoresis (HPCE). For HPLC, the resulting methylcytosine and cytosine peaks can be resolved and quantified by comparison to known standards (Tawa et al., 1994; Ramsahoye, 2002). Although peaks can be identified for HPCE, there are no current quantification protocols for quantifying methylcytosine at this time (Fraga et al., 2000). Both of these methods are hampered by the requirement for a large amount of starting material, 2.5 g for HPLC and 1 µg for HPCE. Furthermore, these methods also require specialized, expensive equipment.

Recently, additional variations on the basic HPLC analysis method have been developed. These methods have combined HPLC techniques with primer extension and ion pair reverse phase (IP RP) HPLC (Matin et al., 2002), or electrospray ionization mass spectrometry (Friso et al., 2002). Both of these methods have sought to improve on the accuracy and sensitivity of the previous HPLC technique. The IR RP HPLC method combines bisulfite conversion of DNA with a primer extension reaction, followed by analysis of resulting products by HPLC.

The technique of matrix-assisted laser desorption/ionization (MALDI) mass spectrometry has also been utilized for the accurate quantification of methylation in cancer samples (Tost et al., 2003).

Enzymatic and chemical labeling of methylcytosine residues have also been used in order to quantify global methylation levels. The enzymatic methods involve the addition of a radio-labeled methyl group to cytosine, resulting in an inverse correlation between incorporated label and the amount of methylation in the sample (Duthie et al., 2000). A chemical method for labeling has also been developed based on fluorescent labeling of adenine and cytosine residues by chloracetaldehyde (Oakeley et al., 1999). This method relies on bisulfite conversion of non-methylated cytosines to uracil in order to allow the fluorescent labeling of only methylcytosine.

To study global methylation, Pogribny et al. (1999) have developed an assay based on the use of methylation-sensitive restriction endonucleases HpaII, AciI, and BssHII that leave 5' guanine overhangs after DNA cleavage, with subsequent single radiolabeled nucleotide extension. The selective use of these enzymes was applied to screen for alterations of genome-wide methylation and CpG islands methylation, respectively. The extent of radioactive label incorporation was found to be proportional to the number of unmethylated (cleaved) CpG sites.

In Situ Analysis of DNA Methylation

Another method for investigating genome wide levels of methylation involves methylcytosine specific antibodies (Miller et al., 1974). This method also allows further investigations into levels of methylation on different chromosomes and even different parts of a single chromosome (Barbin et al., 1994). Furthermore, in situ hybridization can be utilized to analyze the differential methylation patterns of adjacent cells in tissue sections.

Site-Specific DNA Methylation Analysis

Analysis of site-specific methylation patterns can be divided into two distinct groups, bisulfite conversion methods and non-bisulfite based methods. The bisulfite conversion method relies on treatment of DNA samples with sodium bisulfite which converts unmethylated cytosine to uracil, while methylated cytosines are maintained (Furuichi et al., 1970). This conversion results in a change in the sequence of the original DNA. Analysis of the sequence of the resulting DNA allows the determination of which cytosines in the DNA were methylated. There are several methodologies utilized for the analysis of bisulfite converted DNA including sequencing, methylation-specific PCR, COBRA (COmbined Bisulfite Restriction Analysis), methylation-sensitive single nucleotide primer extension, and methylation-sensitive single-strand conformation analysis.

The major drawback to bisulfite conversion of DNA is that it results in up to 96% degradation of the DNA sample (Grunau et al., 2001). The harsh effect of bisulfite treatment, in combination with the need to convert all methylated cytosines, requires a substantial amount of input DNA in order to obtain enough usable DNA following conversion. Furthermore, the high levels of degradation complicate the detection of differences in methylation patterns in DNA samples from mixed cell populations, for example cancer cells in a background of normal cells. Changing the incubation conditions in order to minimize DNA degradation can result in incomplete conversion and the identification of false positives.

Bisulfite DNA Conversion Methods for Methylation Analysis

The most direct method for analysis of bisulfite converted DNA is direct sequencing (Frommer et al., 1992). Amplification of fragments of interest followed by sequencing will quickly and accurately identify all cytosines that were methylated, as all non-methylated cytosines will have been converted to Uracil. One drawback to direct sequencing is the necessity to design amplification and sequencing primers that are based on all of the possible sequences depending on the level of methylation. The conversion of cytosine to uracil will alter the priming sequences along with the target sequences. Furthermore, sequencing is a labor intensive and time-consuming activity if one is investigating large numbers of sequences and/or large numbers of samples.

Methylation-Specific PCR (MS-PCR) is the most commonly used technique for analysis of methylation. MS-PCR is utilized to determine the methylation status of specific cytosines following conversion of unmethylated cytosines to uracil by bisulfite conversion (Herman et al., 1996). The methylation status of specific cytosines can be determined by utilizing primers that are specific for the cytosine of interest. The differences in sequences following conversion allow different primer sets to determine whether the initial sequence was methylated. Melting curve Methylation Specific PCR (McMS-PCR) replaced sequence analysis of the resulting PCR products, with the more efficient process of melt curve analysis (Akey et al., 2002; Guldberg et al., 2002). Differences in the melting temperature of the products are due to the sequence differences resulting from bisulfite conversion of methylated versus unmethylated DNA samples. Another method for analyzing MS-PCR products using melting characteristics involves the use of denaturing high-performance liquid chromatography (Baumer, 2002). In this method, MS-PCR is carried out under conditions that will amplify both alleles (converted and unconverted cytosines). The products of MS-PCR are analyzed by HPLC under denaturing conditions, allowing the resolution of different products based on sequence differences due to bisulfite conversion.

One version of MS-PCR, called MethyLight (Eads et al., 2000), involves the use of fluorescence-based real-time quantitative PCR to allow both detection and quantitation of the converted products in one step. The major drawback of these techniques is the necessity to design primers specific for each methylation site that are based on the different converted sequence possibilities. An additional modification to the MethyLight protocol involves using an additional fluorescent probe directed against unconverted DNA. This protocol, ConLight-MSP, was developed to address the issue of overestimation of methylation due to incomplete conversion of DNA by bisulfite (Rand et al., 2002). A second method aimed at addressing the problem of incomplete bisulfite conversion is bisulfite conversion-specific Methylation-Specific PCR (BS-MSP) (Sasaki et al., 2003). In this technique, two rounds of PCR are carried out following bisulfite conversion of DNA. In the first round, primers are utilized that do not contain CpG's, but do contain cytosines at the 3' position. Thus, only fully converted DNA will be amplified in the first round of amplification. A second, traditional MSP amplification is subsequently carried out to amplify the CpG's of interest. This will result in a lower level of background amplification of sites with incomplete conversion of DNA, and a more accurate determination of the level of methylation in the sample.

Other methods for site-specific methylation analysis include COBRA, Methylation-sensitive single nucleotide primer extension (MS-SNuPE), and methylation-sensitive single-strand conformation analysis (MS-SSCA). COBRA combines the techniques of bisulfite conversion with methylation-sensitive restriction endonuclease analysis (described below) to enable highly specific, highly sensitive quantitation of methylation sites contained within recognition sites for methylation-sensitive restriction enzymes (Xiong and Laird, 1997). Melting curve combined bisulfite restriction analysis (McCOBRA) was developed to allow analysis of bisulfite converted DNA without gel electrophoresis (Akey et al., 2002). In this procedure, bisulfite converted DNA is amplified by PCR with specific primer pairs surrounding a potential methylation site. The resulting PCR products are digested with a restriction site that will only recognize and cut DNA that was originally methylated. Melt curve analysis will yield two peaks, based on the size difference of the cut versus uncut DNA, and allow the determination of the methylation status of that site in the original DNA. Another variation of COBRA, termed Pyro-sequencing methylation analysis (PyroMethA) involves the use of the Pyrosequencing reaction to determine methylation status in place of the restriction analysis used in COBRA (Collela et al., 2003; Tost et al., 2003). MS-SNuPE combines MS-PCR amplification of bisulfite converted DNA with single nucleotide extension of MS-PCR products to incorporate radio-labeled C (methylated) or T (unmethylated) that can be detected using a phosphoimager (Gonzalgo and Jones, 1997). The ratio of C/T incorporation will indicate the level of methylation at a particular site. Finally, MS-SSCA utilizes bisulfite converted DNA with single-stranded conformational polymorphism (SSCP) analysis to detect sequence differences through changes in the migration of the molecules during electrophoresis (Burri and Chaubert, 1999; Suzuki et al., 2000).

Another method for analyzing the methylation status of specific sites was created based on changes in restriction endonuclease recognition sites following bisulfite conversion of DNA (Sadri and Hornsby, 1996). In this procedure, DNA is bisulfite converted and a specific region of interest is amplified by PCR. Following amplification, the resulting products are digested with either a restriction endonuclease that will only cleave the sequence generated by conversion of an unmethylated CpG, or a restriction endonuclease that will cleave the same site only if it was originally methylated and not converted by bisulfite treatment. Comparison of the products of digestion will indicate the methylation status of the site of interest and, potentially, relative levels of methylation of the site from a mixed population of cells. This method improves on normal MSP by not relying on differences in PCR amplification between converted and non-converted DNA. However, this method is also susceptible to incomplete conversion of the starting DNA. Furthermore, this method is dependent on bisulfite conversion resulting in a different restriction endonuclease recognition site being created by bisulfite conversion. The authors estimated that approximately 25% of CpG sites would be able to be analyzed by this method, leaving the majority of CpG sites unanalyzed. A newly developed technique, HeavyMethyl, utilizes real-time PCR analysis of unconverted DNA (Cottrell et al., 2004). Specificity for methylated sites is achieved by using a methylation sensitive oligonucleotide blocker. This blocker will only bind to unmethylated DNA, blocking annealing of the primer and preventing amplification. Methylated sequences will not bind the blocker and will be primed and extended, resulting in cleavage of the probe and fluorescent detection. The advantages of this system include lowered background, higher specificity of signal, and decreased requirement for starting material due to the lack of a bisulfite conversion step. However, development of each assay will require the design and optimization of 5 oligonucleotides: 2 primers, 2 blocking nucleotides, and a probe. This requirement will greatly increase the difficulty and cost of developing site-specific assays. Furthermore, small samples of DNA will only yield enough material for a few assays and will not allow analysis of large numbers of potential methylation sites.

All of the aforementioned methods that can be used to analyze bisulfite-converted DNA require several nanograms of converted DNA per assay and are thus impractical for genomewide methylation analysis. To allow genomewide methylation analysis by these methods, techniques must utilized that can efficiently amplify small quantities of converted DNA.

Non-Bisulfite Based Methods of Methylation Analysis

Non-bisulfite based methods for analysis of DNA methylation rely on the use of methylation-sensitive and methylation-insensitive restriction endonucleases (Cedar et al., 1979). Following digestion of sample DNA with either methylation-sensitive or methylation-insensitive restriction enzymes (ex. MspI and HpaII), the DNA can be analyzed by methods such as Southern Blotting and PCR. Southern blot analysis involves electrophoretic separation of the resulting DNA fragments and hybridization with a labeled probe adjacent to the CpG of interest. If the hybridization signal from the methylation-sensitive and methylation-insensitive digested DNA samples results in different size bands, than the site of interest was methylated. In contrast, PCR analysis involves amplification across the CpG of interest. The expected band will only be observed in the methylation-sensitive digested sample if the site of interest is methylated. The disadvantages of the Southern blotting assay is that specific probes must be developed for every site of interest and large amounts of starting DNA (ex: 10 µg) are required. The PCR assay requires much lower amounts of DNA for each site of interest (ex: 1-10 ng), but necessitate the design and testing of specific primer pairs for every site of interest. Furthermore, although each individual assay requires only nanogram quantities of DNA, analysis of hundreds or even thousands of potential methylation sites still involves µg quantities of DNA. The overall limitation of these technologies is their dependence on the presence of a methylation-sensitive restriction site present at the CpG of interest. Thus, although these assays are relatively quick and simple, they cannot be used to test all potential methylation sites. Furthermore, these methods can only be used for analysis of sites that have been previously identified and have had detection assays designed for them, and they do not allow for the discovery of new sites of interest.

Ligation-mediated PCR (LM-PCR) was developed to increase the sensitivity of methylation analysis by restriction endonuclease digestion (Steigerwald et al., 1990). In this method, the methylation status of specific sites is determined DNA is digested with a methylation-sensitive restriction endonuclease that will cleave a site of interest, along with a methylation-sensitive restriction endonuclease that will cut in fairly close proximity to the methylated site of interest. Following digestion, a primer extension reaction is performed using a previously characterized primer that is upstream from both digestion sites. A linker sequence is ligated to the resulting end of the extended sequence. A second primer extension step is performed using a primer based on the linker sequence, and PCR amplification is performed using the linker sequence and a nested primer downstream from the primer used in the primary primer extension reaction. The products of amplification are analyzed by gel electrophoresis. Two potential bands are produced by this method: a full length amplimer indicating methylation of the target sequence, and a shorter amplicon indicating a lack of methylation. A mixture of both products indicates that partial methylation existed in the sample, and an estimation of the amount of methylation can be determined by comparison of the ratio of the two products. This method greatly improved on the sensitivity of PCR-based methods of analysis, but is greatly hindered by the necessity of creating 2 primers for each loci of interest, and the requirement for analyzing 1 specific site per reaction.

The technique of Differential Methylation Hybridization (DMH) has been utilized to screen CpG island arrays to determine methylation status of a large number of sites at a time (Huang et al., 1999). In this procedure, DNA is digested with a frequent cutting restriction endonuclease to generate small DNA fragments. Linkers are ligated to the products of digestion and repetitive DNA is subtracted. The resulting molecules are digested with a methylation-sensitive restriction endonuclease. PCR of the digestion products with a primer complementary to the linkers results in amplification of all molecules that contain either methylated restriction sites or no restriction sites. The products of amplification are then hybridized to a CpG island array consisting of clones containing multiple restriction endonuclease sites for the enzyme used to digest the DNA. Hybridization to a clone indicates that the site was methylated in the starting DNA. This method requires the generation of a large number of clones for creation of the array and is limited by the ability to amplify the products of the original digestion. Many fragments will be either too large to be amplified, or be so small as to result in suppression of amplification or poor hybridization to the array. Furthermore, there will be a high level of background of products that do not contain methylation sites of interest that will affect the signal to noise ratio of the array hybridization.

Yan et al., (2001) and Chen et al., (2003) have developed a closely related method referred to as Methylation Target Arrays (MTA), derived from the concept of tissue microarray, for simultaneous analysis of DNA hypermethylation in multiple samples. In MTA, target DNA is digested with four-base restriction endonucleases, such as MseI, BfaI, NlaIII, or Tsp509I, known to restrict DNA into short fragments, but to retain CpG islands relatively intact. The GC-rich fragments are then isolated through an affinity column containing methyl-binding MeCP2 protein. Linkers are ligated to the overhangs of the CpG island fragments and are digested with methylation-sensitive restriction enzymes, BstUI and HpaII. Finally, the fragments are amplified with flanking primers. CpG sites that are methylated are protected from cleavage and are amplified in the process, whereas non-methylated CpG islands are lost to restriction. Initially, a microarray containing 7,776 short GC-rich tags tethered to glass slide surfaces was used to study 17 paired tissues of breast tumors and normal controls. Amplicons, representing differential pools of methylated DNA fragments between tumors and normal controls, were co-hybridized to the microarray panel. Hypermethylation of multiple CpG island loci was then detected in a two-color fluorescence system. Hierarchical clustering segregated these tumors based on their methylation profiles and identified a group of CpG island loci that corresponds to the hormone-receptor status of breast cancer. A panel of 468 MTA amplicons, representing the whole repertoire of methylated CpG islands in 93 breast tumors, 20 normal breast tissues, and 4 breast cancer cell lines, were arrayed on a nylon membrane for probe hybridization. Hybridization was performed with PCR-generated probes for 10 promoters, labeled with $^{32}$P-dCTP. Positive hybridization signals detected in tumor amplicons, but not in normal amplicons, were indicative of aberrant hypermethylation in tumor samples. This was attributed to aberrant sites that were protected from methylation-sensitive restriction digestion and were amplified by PCR in tumor samples, while the same sites were restriction digested and could not be amplified in normal samples. Hypermethylation frequencies of the 10 genes GPC3, RASSF1A, 3OST3B, HOXA5, uPA, WT1, BRCA1, DAPK1, and KL were tested in breast tumors and cancer cell lines.

The aforementioned DMH and MTA technologies are described in U.S. Pat. No. 6,605,432, PCT WO03/087774A2, and U.S. Patent Application US20030129602A1 by Huang (see bellow). Drawbacks of these methods are the lack of complete coverage of all regions of the genome during the initial restriction digest, generation of false positive results due to incomplete cleavage by a methylation-sensitive restriction enzyme, inability to analyse nicked, degraded, or partially double-stranded DNA from body fluids, as well as lack of quantitation and relatively low sensitivity. Thus, these techniques are limited to applications in which large quantities of DNA are readily available and methylated DNA represents high percentage of the total DNA. Therefore, a sensitive diagnostic method that is capable of amplifying all regions of the genome and detect methylation when using samples containing only small fraction of methylated DNA in a vast majority of non-methylated DNA is still needed.

Several techniques have been developed in order to identify unknown methylation hotspots, including restriction landmark genomic scanning (RLGS), methylation-sensitive representational difference analysis (MS-RDA), methylated CpG island amplification-representational difference analysis (MCA-RDA), methylation-sensitive arbitrarily primed PCR (MS-AP-PCR), methylation-spanning linker libraries (MSLL), differential methylation hybridization (DMH, see above), methylation-sensitive amplification polymorphism (MSAP), affinity capture of CpG islands, and CpG island microarray analysis (see above).

RLGS involves the digestion of high molecular weight DNA by a methylation sensitive restriction endonuclease, such as NotI, that targets CpG islands (Hayashizaki et al., 1993). The products of digestion are differentiated by two dimensional gel electrophoresis involving $2^{nd}$ and $3^{rd}$ digestions with non-methylation sensitive restriction endonucleases (Rush and Plass, 2002). The pattern of banding between two samples can be compared to determine changes in methylation status. Subsequently, these techniques have been expanded to include cloning of specific bands from the 2-D gel in order to identify methylated sequences. Recently, computer based RLGS systems have been developed to predict banding patterns based on digestion of genomic DNA with methylation-sensitive restriction endonucleases (Masuyama et al., 2003; Rouillard et al., 2001; Akiyoshi et al., 2000). The drawbacks of these techniques include a requirement for a large amount of starting material, the difficulty of resolving complex samples containing cells with different methylation patterns, and the large amount of work necessary to identify all of the bands of interest. Furthermore, although this technique is reproducible, sequence variations between samples can result in gain or loss of cleavage sites, resulting in changes in the banding pattern that are not related to changes in methylation.

Methylation-sensitive representational difference analysis (MS-RDA) was developed to determine differences in methylation status between control and cancer samples to allow the identification of methylated regions in cancer (Ushihima et al., 1997; Kaneda et al., 2003). In this method, two DNA samples (Tester and Driver) are digested with a methylation-sensitive restriction endonuclease. The resulting products from each sample have an adaptor ligated to them and are amplified by PCR. Following amplification, the adaptors are removed and a second adaptor is ligated to the 5' end of the tester sample. The two samples are mixed, with the driver in large excess compared to the tester. Denaturing and annealing steps result in the production of mostly driver/driver or driver/tester molecules for sites that were methylated in the driver and the tester DNA, and tester/tester molecules for sites that were methylated in only the tester DNA sample. The resulting 3' ends are filled in, producing molecules with the second adaptor at both ends only in the case of tester/tester hybridization. Amplification of the tester/tester hybrids by PCR using the second adaptor sequence results in isolation of those sites methylated only in the tester sample. The enriched molecules can then be analyzed by a number of techniques known in the art, including PCR, microarray hybridization, and sequencing. Although this protocol has been useful in the identification of specific methylation differences between cancer and normal samples, there are several limitations inherent in this methodology. The limitations of this technology include the requirement for two restriction endonuclease sites within close enough proximity to allow PCR amplification, but not so close as to result in suppression of the resulting products. Furthermore, RDA produces only enrichment of sequences and does not completely select against sites that are methylated as some tester/tester hybrids are formed even in the presence of a large excess of driver.

Another related procedure, methylated CpG island amplification-representational difference analysis (MCA-RDA), was developed to amplify and enrich methylated CpG islands present in the tester DNA (Toyota et al., 1999; Toyota and Issa, 2002). In this method, tester and driver are first digested with a methylation-sensitive restriction endonuclease that results in blunt ends (ex: Sma I). Subsequently the methylated restriction sites are cleaved with a non-methylation-sensitive isoschizomer of the first endonuclease (ex: Xma I) that produces overhanging ends. Adaptors are ligated to the resulting overhanging ends, but not to the blunt ends. The molecules that contain an adaptor at both ends are amplified by PCR and RDA is performed as described above to select for those molecules only present in the tester population. This protocol improves on MS-RDA by amplifying entire CpG islands. However, this method is even more limited than MS-RDA in that appropriate isoschizomers for methylated restriction sites are required to produce the libraries.

The procedure of methylation-sensitive arbitrarily primed PCR (MS-AP-PCR) was developed in order to identify genomic regions with altered patterns of methylation (Gonzalgo et al., 1997). In this method, DNA is digested with methylation sensitive and methylation insensitive restriction endonucleases. Following digestion, arbitrarily primed PCR is performed using short primers under low stringency conditions for a couple of cycles, followed by high-stringency amplification. The products are separated by high-resolution polyacrilimide gel electrophoresis and band differences between control and test samples are isolated and sequenced. The banding patterns observed during electrophoresis are fairly reproducible between reactions due to the fact that a specific primer sequence is utilized for each reaction. Random primed PCR is different in that it utilizes degenerate primers that contain a large number of primer sequences.

The identification of epigenetic boundaries was determined in corn by creating methylation-spanning linker libraries (MSLL) (Yuan et al., 2002). In this method, genomic DNA is digested with a methylation-sensitive restriction endonuclease and ligated into BAC vectors. The resulting libraries were end-sequenced and analyzed for methylated DNA sites. This technique allows the determination of methylated sequences without a priori knowledge, and allows the improved cloning and sequencing of genomic regions that are resistant to shotgun cloning. However, MSLL is a low-throughput technology that is limited by the constraints of sequencing large numbers of clones that will contain many repeats of the same insertion sequences.

Methylation-sensitive amplification polymorphism (MSAP) has been utilized to determine changes in methylation patterns in banana plants (Peraze-Echeverria et al., 2001). In this technique, a double digest is performed on two aliquots of DNA. There is a common methylation insensitive restriction endonucleases utilized in both digestions. The second restriction endonuclease is methylation sensitive in one digest (ex. Hpa II), and a methylation insensitive isoschizomer (ex. Msp I) in the other digest. The resulting products of digestion have adaptors ligated to them and are amplified under various selective conditions. The amplicons are then subjected to gel electrophoresis and detection. Comparisons are made between the samples digested with methylation sensitive and methylation insensitive restriction endonucleases between samples. Changes in the banding patterns are recorded as changes in methylation patterns in different samples. This technique allows the amplification and analysis of specific sites of methylation, but is dependent on the existence of methylation sensitive and methylation insensitive restriction endonuclease isoschizomers.

The Methylation-Dependent Restriction Endonuclease McrBC

McrBC is an *E. coli* protein complex that cleaves DNA based on recognition of RmC sequences that are separated by 40 to 3000 bp (Sutherland et al., 1992; Stewart and Raliegh, 1998). McrBC induced cleavage occurs by DNA translocation following binding of the DNA at the RmC recognition site, resulting in interaction of two McrBC substrates (Dryden et al., 2001). Thus, cleavage by McrBC does not always result in cleavage at the same location between methylation sites and different patterns of cleavage can be observed in DNA with multiple methylation sites at varying distances from each other, depending on the number and density of methylated sites. The requirement of McrBC for the two methylation recognition sites to occur on the same strand (cis) or on opposite strands (trans) is not clear. There has been one report of successful cleavage of both cis methylated DNA and trans methylated DNA (Sutherland et al., 1992), but further clarification of this issue is required.

There is an example of McrBC being used to identify methylated regions of interest (PCT WO 03/035860). This method involves the degradation of two sources of DNA. One sample is degraded with an enzyme such as McrBC, and one sample is degraded with a methylation-sensitive restriction endonuclease. The hybridization of the two samples provides a screen to determine which samples were cut with McrBC. The hybridized products are isolated and the resulting molecules are sequenced to identify the methylated regions of interest. While this protocol is aimed at universal detection of global methylation patterns through use of McrBC, it involves a subtractive procedure and does not allow the amplification of the products following subtraction and isolation.

Other uses for McrBC that have been reported include using McrBC expressing bacterial strains to digest plasmids containing genomic DNA in order to subtract repetitive elements (i.e. heavily methylated) in order to isolate genomic regions of interest from plants (U.S. Patent Application US20010046669). The specific steps involve fragmenting DNA, inserting the DNA fragments into a suitable vector, and then inserting the library DNA into McrBC expressing bacteria. The bacteria will cleave any vector sequences that contain sequences with multiple methylated genomic inserts. Thus, only non-methylated inserts will contain intact plasmids that will grow. The resulting colonies contain molecules from regions of hypomethylation. This method was utilized to increase the cloning of gene-coding regions from plant genomes.

Methylation patterns in simple genomes have been investigated by use of McrBC cleavage (Badal et al., 2003). In this work, the methylation patterns of HPV were investigated in cervical cancer. Viral genomic DNA was digested by McrBC and the resulting fragments underwent bisulfate sequencing. The small size of the HPV genome (7900 bp) allows repetitive sequencing efforts to quickly identify all sequences and methylation sites within the HPV genome. This methodology has limited application to human DNA due to the large size of the human genome. Furthermore, there are no mechanisms for amplifying or selecting molecules based on their methylation status.

Patents and Patent Applications Related to Methylation Detection and Analysis

U.S. Pat. No. 6,214,556 B1 and corresponding PCT WO99/28498 issued to Olek et al. describe a method of methylation analysis in which DNA is fragmented by means of mechanical shearing or digestion with a restriction endonuclease and then treated with sodium bisulfite to convert non-methylated cytosine to uracil. Converted DNA is amplified by two different methods. In the first method, double-stranded adaptor molecules of known sequence are ligated to the DNA fragments before bisulfite conversion and then amplified by polymerization using primers complementary to the adaptor sequences present after the bisulfite treatment. In some versions of the method, the primers used for amplification can also contain one to four bases long 3'-extensions that go into the unknown sequence and that represent different base permutations. In the second method representing a modification of the DOP-PCR technique, primers that contain a constant 5' region and a degenerate 3' region are used to amplify converted DNA fragments or subsets of them. In both methods of amplification two types of sequences are used for amplification. Type one sequences completely lack cytosine or only have cytosine in the context of the CpG dinucleotide, and type two sequences completely lack guanine or only have guanine in the context of the CpG dinucleotide These two types of sequences are used to specifically target strands of DNA that are rich in guanine or rich in cytosine respectively after bisulfite conversion. Overall the quantity of the remaining cytosines on the G-rich strand or the quantity of remaining guanines on the C-rich strand is determined by hybridization or by polymerization. In one version of the method, the target DNA is cleaved with methylation-sensitive restriction enzyme prior to bisulfite conversion for the obvious reason of reducing the amount of non-methylated DNA. The method described above suffers from the inherent drawbacks of all techniques based on bisulfite conversion, namely reduced sensitivity due to significant loss of DNA during the process of bisulfite conversion that compromises the analysis of clinical samples containing only small percentage of methylated DNA in a vast majority of non-methylated DNA, as well as problems implementing the method to assay methylation in clinical settings due to multiple and complex preparation steps.

U.S. Patent Applications 20030099997A1 and 20030232371A1 and corresponding PCT WO 03/035860A1 by Bestor disclose methods for detection of methylated promoters and gene identification based on differential hybridization of a test and control DNA samples, one of which has been treated with a methylation-dependent endonuclease McrBC and the other one by a methylation-sensitive restriction endonuclease (HpaII, HhaI, MaeII, BstU, or AciI). The two samples are modified such as to prevent formation of duplexes between homologous DNA fragments. The samples from the two sources are then denatured and hybridized to form hetero-duplexes. The modification of at least one of the samples is performed in such a way as to facilitate the isolation of the resulting hetero-duplexes that are then analyzed by sequencing and the positions of methylated cytosines are determined. Although this technology can accurately determine the methylation status of a gene promoter and allows for the discovery of new sites of interest, it suffers from limitations such as the requirement for significant amount of starting DNA material, inability to process multiple samples simultaneously, and dependence on the presence of a methylation-sensitive restriction site present at the CpG of interest.

PCT WO 03/027259A2 by Wang describes a method for analysis of the methylation status of test and control DNA samples based on cleavage of the DNA with methylation sensitive restriction enzyme(s), ligation of linkers to the generated overhangs, PCR amplification, and labeling of the fragments receiving ligated linkers, hybridization of the fragments on solid support containing immobilized target DNA sequences, and comparison of the signals produced after hybridization of the test and control samples, thereby detecting the extent of methylation of one or more regions of DNA. This is limited by dependence on the presence of a methylation-sensitive restriction site present at the CpG site(s) of interest and that this procedure can only be used for analysis of sites that have been previously identified. Thus, it does not allow for the discovery of new methylation sites of interest.

PCT WO 03/025215A1 by Carrol et al. describes a method for analysis of DNA methylation patterns by digesting DNA with a methylation-sensitive restriction enzyme followed by amplification with primers annealing to the non-cleaved form of the recognition sequence. The results of the amplification reaction are then compared to an identical reaction run in parallel using the same primers to amplify another aliquot of the DNA sample that has not been cleaved with restriction enzyme. This method is limited to the availability of suitable restriction sites and requires significant amounts of input DNA for analysis of multiple restriction sites. In addition, it depends on the complicated design and empirical testing of primers for each of thousands of potentially methylated sites required for successful profiling, each with very high GC content.

PCT WO 03/080862A1 to Berlin discloses a method and devices for amplification of nucleic acids retaining the methylation pattern of the original template. The method comprises denaturing of genomic DNA, annealing of specific primers in an extension/polymerization reaction with DNA polymerase, and incubation of the resulting double-stranded DNA with a methyltransferase in the presence of a labeled methyl group donor to restore the methylation pattern encoded in the original template. The described steps are repeated several times, resulting in linear amplification that retains the methylation status of the target DNA. Amplified DNA is then digested by a methylation-sensitive restriction enzyme or subjected to bisulfate conversion, and the resulting products are analyzed by methods capable of retrieving the methylation information. While this method can amplify DNA regionally while retaining the methylation information of pre-designed sites, amplification of DNA in linear mode is a slow and inefficient process, as opposed to exponential amplification. Furthermore, the amount of input DNA required for the procedure is still significant. In addition, this method is limited to regions for which prior knowledge of methylation is known. Thus, it cannot be applied for genome-wide screening of methylation patterns.

U.S. Pat. No. 6,300,071B1 issued to Vuylsteke et al. describes a method for detecting DNA methylation using the technique of Amplified Fragment Length Polymorphisms (AFLP). A test and a control DNA sample are digested with one or more specific restriction endonucleases to fragment DNA into series of restriction fragments. The resulting restriction fragments are ligated with one or more double-stranded synthetic oligonucleotide adaptors. A combination of methylation-sensitive and methylation-insensitive restriction enzymes is used to produce amplifiable fragments that originate from either methylated or from non-methylated DNA. A combination of primers that a complementary to specific promoter sequences and primers complementary to adaptor sequences is used for PCR amplification and the resulting fragments are analysed by gel electrophoresis for restriction patterns. This method can be used for simultaneous analysis of methylation at multiple promoters but requires prior knowledge of sequences, empirical testing of multiple primers for compatibility and has limited application for clinical diagnostics.

Patent US 2005/0009059A1 ussued to Shapero et al. provides a method for determining if a cytosine in a target DNA sequence is methylated by the steps of: fragmentation with restriction enzyme, ligation of a double-stranded adaptor with a common priming sequence, conversion of non-methylated cytosines to uracils by treatment with sodium bisulfite, and hybridizing a capture probe comprising a second common sequence, a tag sequence, a recognition sequence for Type IIS restriction enzyme, and a region that is complementary to a region of the target sequence 3' of a cytosine. The capture probe is extended and amplified with first and second common sequence primers to generate double-stranded extended capture probe that is then digested with Type IIS restriction enzyme. The resulting fragments are extended by one base with a labeled nucleotide and analyzed using an array of oligonucleotide probes. As other methods in the art based on conversion with sodium bisulfite the method described in this patent is limited to using only relatively large amounts of input DNA and requires design of complex oligonucleotide probes that are difficult to make compatible in a multiplex reaction.

U.S. Pat. No. 6,605,432, PCT WO03/087774 A2, and U.S. Patent Application US20030129602A1 by Huang describe the previously discussed Differential Methylation Hybridization (DMH) and Methylation Target Arrays (MTA) technologies (see Yan et al., 2001, Chen et al., 2003, and Huang et al., 1999). One to two micrograms of genomic DNA isolated from tumor or control samples are digested overnight with Mse I, a four-base restriction enzyme that cuts frequently in the rest of the genome but less frequently in CpG islands leaving promoter sites relatively intact. Digested products are purified and ligated to double-stranded linker of known sequence. Ligated DNA fragments are then purified and digested overnight with the methylation-sensitive restriction enzyme BstUI. After purification and buffer exchange the samples are digested again overnight with another methylation-sensitive restriction enzyme, HpaI. Samples are amplified by PCR using primer complementary to the known linker sequence. The resulting products are labeled and hybridized to microarrays comprising CpG island clones or other CpG-rich genomic probes.

The methods described in these patents require microgram quantities of DNA and involve multiple steps including 3 overnight digestions and 3 purification steps They also suffer from additional drawbacks such as the lack of complete coverage of all regions of the genome during the initial restriction digest. Regions with low density of cleavage sites will not be amplified and their methylation status could not be determined using this technology. Incomplete cleavage by methylation-sensitive restriction enzyme will produce false positive results. Also, if the DNA source is nicked or degraded or only partially double-stranded as is often the case with DNA in blood circulation or other body fluids, cleavage with restriction enzyme will be inefficient and the method will perform poorly. In addition, the method of detection by microarray hybridization employed in these techniques is not quantitative and has limited dynamic range and low sensitivity. Thus, the methods described in these patents are limited to applications in which large quantities of DNA are readily available and methylated DNA represents high percentage of the total DNA.

The aforementioned methods in the art that employ adaptor ligation to DNA fragments are suitable for high molecular weight DNA samples and for partially degraded DNA but not for circulating, cell-free DNA samples from serum, plasma, and urine, which are heavily degraded and comprised substantially of mono-, di-, and tri-nucleosomal sized fragments shorter than 500 bp. First, a 4-bp recognition sequence restriction enzyme only cleaves on average every 256 base pairs, so methods that rely on such cleavage prior to adaptor ligation will not be applicable to any mononucleosomal sized fragments and to only a minority of dinucleosomal sized fragments. Second, there are no descriptions in the art for converting heavily damaged DNA containing nicks or single-stranded gapped regions into amplifiable molecules that retain methylation information. These limitations of the art preclude effective methylation analysis of DNA from non-invasive clinical sources such as serum, plasma, and urine, since a majority of the DNA may remain in an unamplifiable form. Thus, there exists a need for methods that can amplify substantially all the DNA from such sources to increase the sensitivity of methylation assays and to reduce the quantity of such DNA required for analysis. These novel methods will be of particular importance for diagnostic applications, where methylated markers indicative of a condition may exist only as a minor (<1%) fraction within the samples.

SUMMARY OF THE INVENTION

The present invention relates to novel methods and compositions for determining and analyzing methylation of a DNA molecule by preparing plurality of fragments using restriction enzymes that differentiate between methylated and non-methylated regions, incorporating a known sequence at the end of said DNA fragments, amplifying said DNA fragments and determining the methylation status of one or more regions in the original DNA molecule. In a general aspect of the invention, the methods change the ratio of methylated to non-methylated DNA in a plurality of DNA molecules, such as by eliminating nonmethylated regions and retaining methylated regions, and in further aspects this difference is amplified and/or quantitated. In other words, there may be elimination or substantial reduction of background material, which may be considered the nonmethylated fraction in a plurality of DNA molecules, such that there is a change in the ratio of methylation. Such an enrichment may be at least 1000× compared to the original plurality of DNA molecules, for example.

In particular embodiments, the present invention regards the preparation and amplification of special Methylome DNA libraries and subsequent identification of specific DNA sequences that are either hypermethylated or hypomethylated. In comparison to the whole genome libraries (see, for example, U.S. patent application Ser. Nos. 10/797,333, filed Mar. 8, 2004, published as U.S. Patent Application Publication No.: 2004/0209299 and is now abandoned and 10/795,667, filed Mar. 8, 2004, now U.S. Pat. No. 7,718,403 and incorporated by reference herein in its entirety), the Methylome libraries are characterized by a selective depletion or even complete elimination of sequences corresponding to those originally non-methylated CpG-rich genomic regions, or by a substantial enrichment of the originally methylated CpG-rich genomic regions, or a combination thereof. In some embodiments, the Methylome libraries are created through cleavage with at least one methylation-sensitive restriction enzyme. In specific embodiments, the Methylome libraries are created through cleavage with a mixture of two or more, such as five or more, methylation-sensitive restriction enzymes. In other embodiments, the Methylome libraries are created through cleavage with one or more methylation-specific enzymes, such as the methylation-dependent cleavage enzyme McrBC, for example. In a separate embodiment, the Methylome libraries are created by cleavage with enzyme McrBC and a mixture of methylation-sensitive restriction enzymes. In a particular embodiment, the DNA molecule or molecules is altered differentially, and the alteration may be any kind of alteration, but in exemplary embodiments it comprises cleavage and/or bisulfite conversion.

The DNA molecules of the present invention for which the methods are employed such that a differential characteristic, for example, methylation, is determined may be of any kind, although in a particular embodiment of the invention the DNA molecule is damaged DNA, such as DNA that results from apoptotic degradation, for example. That is, upon apoptosis of a cell, the DNA is released from the cell and, in specific embodiments, ultimately enters the blood or urine, for example. Thus, the DNA may be considered as circulating within the body and may even pass the kidney barrier. The DNA produced by apoptosis may be fragmented in between nucleosomes, such as being digested mononucleosomally (with a fragmented size of about 200 nt), dinucleosomally (with a fragmented size of about 400 nt), and so forth. In fact, subjecting the apoptotic-produced fragmented DNA to gel electrophoresis often produces a banding pattern, as opposed to a smear expected for DNA that is randomly fragmented, for example. In further specific embodiments, the apoptotic-produced fragmented DNA further comprises nicks and/or gaps in the DNA fragments. Thus, in particular the DNA molecules for the methods herein may be referred to as substantially fragmented and/or cell-free DNA, and in specific aspects the majority of the molecules are less than about 1 kb in size. Methods of the present invention may employ relatively non-invasive methods to collect samples, such as by voided urine or intravenous blood collection, for example. Thus, although in particular embodiments the DNA molecules of the present invention are naturally produced in vivo, in alternative embodiments the DNA molecules of the present invention may be artificially fragmented, such as by nucleases, for example.

In particular aspects of the invention, information regarding the methylation status of one or more specific sequences is obtained by analyzing at least part of one or more DNA molecules, which may be referred to as a library, such as a Methylome amplification library. For example, a nucleic acid molecule, such as genomic DNA, is digested with a restriction enzyme that cleaves DNA based on methylated CpG, such as McrBC, or it is digested with one or more, such as a mixture of several restriction enzymes unable to cleave sites having a methylated CpG. The resulting DNA fragments are incorporated into a library and selectively amplified.

In some embodiments, part or all of a particular group of 11 methylation-sensitive restriction endonucleases, specifically, Aci I, Bst UI, Hha I, HinP1, Hpa II, Hpy 99I, Ava I, Bce AI, Bsa HI, Bsi E1, and Hga I, that have 4-5 base pair recognition sites with at least one CpG dinucleotide, and that have the characteristic of being unable to digest recognition sites having a methylated CpG, may be used to selectively cleave unmethylated CpG regions within DNA prior to, or after, in another embodiment, library preparation. The spatial distribution of recognition sites for these particular nucleases in the human genome closely follows the distribution of the CpG dinucleotides, with their density being very high in the CpG-rich regions (CpG islands). As a result, non-methylated CpG-rich regions, such as those of gene promoters in normal cells, are susceptible to enzymatic cleavage and digested to very short fragments. Methylated CpG regions, such as those that become hypermethylated in some gene promoters of cancer cells, resist cleavage and remain intact.

In other embodiments, originally fragmented DNA (cell-free DNA in blood and urine, or enzymatically, chemically and/or mechanically cut DNA) is converted into a double stranded DNA library first and then digested with a mixture of several restriction enzymes unable to digest sites having a methylated CpG, or with a restriction enzyme that digests based on methylated CpG, such as McrBC. Libraries are generated by methods employed to facilitate subsequent amplification, and in some embodiments the amplification is global, whereas in other embodiments the amplification may be targeted.

The use of multiple methylation-sensitive restriction enzymes for DNA or library cleavage is beneficial to the efficient depletion of non-methylated regions from the Methylome library. Incomplete cleavage resulting from sources other than methylation specific cleavage protection may be detrimental to the preparation and analysis of Methylome libraries. Methylome template DNA, such as where the methylated fraction may constitute less then about 0.1% of total DNA, (such as serum and urine DNA from cancer patients, for example), requires efficient cleavage to maximize sensitivity.

In specific embodiments, the invention concerns determining methylation information from a DNA molecule, such as genomic DNA or even a substantially complete genome, by obtaining one or more DNA molecules, cleaving the DNA molecule(s) differentially based on methylation status, generating a library of the cleaved fragments, and analyzing the amplified cleaved fragments.

The generation of Methylome libraries utilized herein may proceed by any method in the art. In specific embodiments, though, the generation of libraries occurs by particular methods. In a first exemplary method, the DNA that is first cleaved by a mixture of multiple restriction enzymes sensitive to methylation is denatured, and is further subjected to a plurality of primers to form a nucleic acid molecule/primer mixture, wherein the primers comprise nucleic acid sequence that is substantially non-self-complementary and substantially non-complementary to other primers in the plurality, wherein the sequence comprises, in a 5' to 3' orientation a constant region and a variable region; and then subjecting the nucleic acid molecule/primer mixture to a DNA polymerase, under conditions wherein the subjecting steps generate a plurality of molecules comprising the constant region at each end.

A skilled artisan recognizes that the characteristics of the library generated by the first exemplary method utilizes sequence that is substantially non-self-complementary and substantially non-complementary to other primers in the plurality and facilitates not only library generation but subsequent amplification steps. A skilled artisan also recognizes that there is an expected depletion of non-methylated CpG-rich DNA regions that were converted to very short size during multiple restriction enzyme cleavage prior to generation of this library. Very short DNA fragments are not efficient substrates for this particular described amplification method and will be lost during library preparation and amplification. There may also be an exclusion of sequence surrounding at least one or a group of several known cleavage sites, such as exclusion of sequence surrounding at least part of at least one promoter, such as a promoter involved in regulation of cell growth, for example tumor suppressors and/or oncogenes. There may also be exclusion of sequence surrounding at least part of at least one CpG island, which may in fact be comprised of at least part of a promoter.

In a specific embodiment, the invention introduces a method of enrichment of methylated sequences within the library. For the above described method, following amplification of the cleaved DNA fragments, there may be generation of a secondary library. For example, the method may further comprise the steps of cleaving the amplified DNA with one of the methylation-sensitive enzymes used in the original library preparation to produce cleaved products; ligating a second adaptor to the ends of the cleaved products; amplifying at least some of the second adaptor-ligated cleaved products; and analyzing the amplified second adaptor-ligated cleaved products. A skilled artisan recognizes that amplification of a secondary library would result in a substantial enrichment for originally methylated CpG-rich DNA regions because only a small fraction of DNA amplicons from the first amplified library would harbor at least two corresponding CpG-containing restriction sites necessary for the generation of a secondary library.

In a second exemplary method of library generation, there may be attachment of an adaptor, the adaptor having a non-blocked 3' end, to the ends of the original or "polished" DNA fragments to produce adaptor-linked fragments, wherein the 5' end of the DNA fragment is attached to the nonblocked 3' end of the adaptor, leaving a nick site between the juxtaposed 3' end of the DNA fragment and the 5' end of the adaptor; and extending the 3' end of the DNA fragment from the nick site incorporating the adaptor sequence into the DNA strand opposite the adaptor-attached DNA strand, followed by library amplification using PCR with a universal primer complementary to at least a portion of the attached adaptor sequence. A skilled artisan recognizes that nuclease cleavage is not required for adaptor attachment and that using a polymerase for "polishing" and a ligase for attachment may result in nicks and/or gaps being repaired within DNA fragments. In this method, cleavage with a mix of multiple restriction endonucleases can be performed; (A) before adaptor attachment, (B) immediately after adaptor attachment, or (C) after adaptor attachment and extension of the 3' end. A skilled artisan recognizes that there is an expected depletion of non-methylated CpG-rich DNA fragments during amplification in cases (B) and (C) resulting from the high probability of cleaving the corresponding amplicons at least once with a mix of multiple restriction enzymes. A skilled artisan recognizes that in case (A) cleavage before the library synthesis may result in very short library amplicons for non-methylated CpG-rich regions that would be lost during amplification by a PCR suppression mechanism.

For this exemplary method, amplification may be followed by cleavage of DNA fragments, thereby selecting a subset of amplicons or secondary library. For example, the method may further comprise the steps of cleaving the amplified library with the same methylation-sensitive enzyme as used in the original library preparation to produce cleaved products; ligating a second adaptor to the ends of the cleaved products; amplifying at least some of the second adaptor-ligated cleaved products; and analyzing the amplified second adaptor-ligated cleaved products. A skilled artisan recognizes that through generation of the libraries by the second method, the cleavage site itself and its integrity is lost, although the adjacent sequences are preserved. A skilled artisan recognizes that amplification of this type of secondary library would result in a substantial enrichment of the originally methylated CpG-rich DNA because only a small fraction of DNA amplicons from the first amplified library would harbor at least two corresponding CpG-containing restriction sites necessary for the generation of a secondary library.

In a third exemplary method of library generation, there may be a one-step multi-enzyme reaction that simultaneously involves DNA, DNA polymerase, DNA ligase, a special hairpin oligonucleotide, a mix of methylation-sensitive restriction enzymes, and a specified enzyme capable of processing a hairpin oligonucleotide before or after its attachment to DNA. The library synthesis reaction proceeds through simultaneous (a) generation of blunt ends at DNA termini and hairpin adaptor; (b) creation of a non-replicable region within the loop of the hairpin oligonucleotide; (c) ligation of the hairpin oligonucleotide to the ends of "polished" DNA fragments to produce adaptor-linked fragments, wherein the 5' end of the DNA fragment is attached to the nonblocked 3' end of the hairpin adaptor, leaving a nick site between the juxtaposed 3' end of the DNA and a 5' end of the adaptor; (d) extension of the 3' end of the DNA fragment from the nick site to the non-replicable region within the hairpin oligonucleotide and; (e) cleavage of DNA fragments and continuously generated library amplicons with several methylation-sensitive restriction endonucleases. The Methylome library synthesis is followed by library amplification using PCR and universal primer. A skilled artisan recognizes that there is an expected depletion of non-methylated CpG-rich DNA fragments due to the high probability of cleaving of amplicons synthesized at the early stage of the one-step reaction. A skilled artisan also recognizes that the very short library amplicons that can be generated later in a single-step process (as a result of multiple cleavage within non-methylated CpG-rich genomic regions and hairpin adaptor ligation) will be lost during amplification by a PCR suppression mechanism. Finally, a skilled artisan recognizes that nuclease cleavage is not required for adaptor attachment and that using a polymerase for "polishing" and a ligase for attachment may result in nicks and/or gaps being repaired within DNA fragments.

In a specific embodiment, the multiple restriction cleavage is performed separately, such as after the one-step adaptor attachment process described above. The Methylome library synthesis is followed by library amplification using PCR and universal primer.

Methylation libraries utilized herein can be further enriched for CpG-rich regions by implementing a thermo-enrichment step before, during, and/or after the Methylome library preparation and amplification. Library thermo-enrichment is based on differential resistance of double stranded DNA molecules with high GC-base content to strand dissociation at high temperature. The enrichment may be coupled with enzymatic selection for double-stranded DNA molecules. A skilled artisan recognizes that fragment selection and library enrichment level may be adjusted for different GC-base composition by controlled incubation of temperature and time and strongly depend on factors such as DNA fragment size, pH, concentration of monovalent and divalent ions, and the presence or absence of effective concentrations of additives that can alter the melting temperature of a double stranded DNA molecule, such as dimethylsulfoxide or formamide, for example. In a specific embodiment, the temperature employed is the temperature that causes denaturation of a specific fraction of the DNA. In further specific embodiments, the temperature is such that about 50% to about 99% of the DNA molecules are denatured.

In one embodiment, Methylome library thermo-enrichment is achieved by first "polishing" DNA fragment ends with, for example, T4 DNA polymerase, then briefly heating blunt end DNA fragments at sub-melting temperature (~90° C.) and then performing adaptor ligation, 3' end extension, multiple methylation-sensitive restriction enzyme cleavage, and PCR amplification. A skilled artisan recognizes that in this case only a small fraction of all DNA fragments can be converted into a library and amplified, specifically, such as only GC-rich DNA fragments that do not undergo complete denaturation upon heating and return to native double strand conformations necessary for efficient adaptor attachment, cleavage, and subsequent 3' end extension.

In another embodiment, Methylome library thermo-enrichment is achieved by heating DNA fragments at sub-melting temperature (~90° C.) after polishing and adaptor ligation, but before the 3' end extension with T4 DNA polymerase and multiple methylation-sensitive restriction enzyme cleavage and PCR amplification. A skilled artisan recognizes that in this case only a small fraction of all DNA fragments can be converted into a library and amplified, specifically, such as only GC-rich DNA fragments that survive heating and retain a double stranded conformation necessary for efficient extension and library synthesis completion.

In another embodiment, Methylome library thermo-enrichment is performed after library synthesis or even after library synthesis and amplification. In this case, heating of libarary amplicons at sub-melting temperature (~90° C.) is followed by incubation with one or more single-strand specific nucleases such as S1 or Mung Bean nuclease, purification of the sample, and re-amplification of the selected amplicon fraction that proved resistant to single strand specific nuclease digestion. A skilled artisan recognizes that in this case only a fraction of the library, specifically the most stable GC-rich molecules, can retain a double stranded structure, survive nuclease (S1 and/or Mung Bean) treatment, and therefore remain competent for re-amplification.

In one embodiment of the invention, bisulfate-treated DNA is further subjected to a plurality of primers to form a nucleic acid molecule/primer mixture, wherein the primers comprise nucleic acid sequence that is substantially non-self-complementary and substantially non-complementary to other primers in the plurality, wherein the sequence comprises, in a 5' to 3' orientation a constant region and a variable region; and then subjecting the bisulfate-converted nucleic acid molecule/primer mixture to a DNA polymerase, under conditions wherein the subjecting steps generate a plurality of molecules comprising the constant region at each end. The synthesized bisulfite-converted DNA library is then amplified by PCR with universal primer and analyzed.

In another specific embodiment, the bisulfite conversion occurs after attaching adaptors to DNA fragments generated by enzymatic fragmentation, such as with nuclease, chemical fragmentation, or by mechanical fragmentation. The adaptor sequences can be designed to be resistant to bisulfite treatment so that amplification of the bisulfite-converted DNA library can be performed using the same primer sequences.

In another embodiment, a promoter-depleted bisulfite-converted DNA library may be synthesized by the attachment of adaptor and by the digestion with multiple methylation-sensitive restriction enzymes, followed by bisulfite conversion and amplification by PCR with universal primer for analysis. A skilled artisan realizes that such a library would be substantially depleted of originally non-methylated CpG-rich promoter DNA regions and can be especially useful for methylation analysis of DNA with low amounts of methylated DNA (such as cell-free blood and urine DNA from individuals with cancer, for example). A skilled artisan realizes that all previously described variations of the adaptor-mediated method (including the one-step hairpin oligonucleotide method) can be applied to create a promoter-depleted bisulfite-converted DNA library.

In particular aspects of the invention, the ends of the cleaved fragments further comprise a particular sequence, structure (such as an overhang), or both that may be generated during library generation. In specific embodiments, the particular sequence, structure, or both may be added following library generation. The particular sequence and/or structure is preferably known, and in some embodiments the ends of the cleaved fragments of the library comprise substantially the same sequence, structure, or both. Furthermore, in amplification steps this particular sequence may be targeted, such as with a complementary primer.

In other embodiments, the library that is generated, including one that may have been amplified, is analyzed such that the one or more characteristics of the original DNA molecule may be identified. For example, the analysis may be of any kind sufficient to gain information, although in specific embodiments it comprises at least sequencing, quantitative real-time polymerase chain reaction, ligation chain reaction, ligation-mediated polymerase chain reaction, probe hybridization, probe amplification, microarray hybridization, restriction enzyme digestion, a combination thereof, or other suitable methods known in the art. In some embodiments concerning analysis of methylation status, substantially every CpG island may be cleaved, as opposed to some other methods in the art wherein cleavage occurs outside CpG islands. In other embodiments, there are gaps in the library, such as from DNA from non-cancerous cells, that represents a non-methylated CpG island (promoter). In the corresponding cancerous DNA, there are substantially no gaps in the particular region representing a methylated CpG island (such as in a promoter).

In other embodiments, libraries are generated from bisulfite-converted DNA for the purpose of sequencing GC-rich regions and repetitive regions of genomic DNA. GC-rich regions and repetitive elements are often difficult to accurately sequence due to the formation of secondary structure and/or due to slippage of the polymerase during polymerization. Thus, bisulfite conversion of GC-rich regions will result in modification of the sequence to remove secondary structures by conversion of C to T. Sequencing of both of strands of the converted DNA will allow the comparison of the obtained converted sequences to determine the original sequence. Similarly, partial bisulfite conversion of repetitive elements will result in changes in the sequence that will minimize secondary structure, thereby improving the sequencing results and allowing determination of the original sequence through comparison of the sequences obtained from each strand. Furthermore, the partial conversion of GC-rich regions and repetitive elements can decrease stretches of homopolymeric cytosines and, therefore, result in improved sequencing of regions that are susceptible to slippage during polymerization.

The information provided by the methods described herein is useful for a variety of applications. For example, the information may be utilized to develop discovery tools that increase our understanding of the mechanisms of disease progression, and/or diagnostic tools that allow the early detection, diagnosis, treatment and/or post-treatment monitoring of disease, such as cancer.

In specific embodiments, the present invention regards a method for analyzing a DNA molecule, comprising obtaining at least one DNA molecule having one or more regions exhibiting differential characteristics; selectively modifying the at least one DNA molecule at the regions exhibiting the one or more characteristics; incorporating at least one known sequence at both ends of the DNA molecule to produce at least one modified molecule; amplifying the at least one modified molecule; and analyzing the amplified molecule. In a specific embodiment, the at least one DNA molecule comprises genomic DNA or is a genome. In another specific embodiment, the differential characteristics comprise epigenetic modification, structure, sequence, association with non-nucleotide factors, or a combination thereof. In a specific embodiment, the epigenetic modification comprises methylation. In particular embodiments, the altering comprises cleaving, and wherein the altered molecule is further defined as comprising fragments. In a specific embodiment, modifying comprises bisulfite conversion. The cleaving step may comprise digestion with a methylation-sensitive enzyme and/or a methylation-specific enzyme. In another specific embodiment, the ends of the cleaved fragments are further defined as having at least one known sequence, at least one known structure, or both. In an additional embodiment, the at least one known sequence, at least one known structure, or both is the same for substantially all of the ends of the cleaved fragments. In a particular embodiment, the amplifying step utilizes a primer complementary to the known sequence, a primer complementary to a desired sequence in the DNA molecule, or both.

In particular aspects of the invention, the incorporating step is further defined as subjecting the cleaved fragments to a plurality of primers to form a nucleic acid molecule/primer mixture, wherein the primers comprise nucleic acid sequence that is substantially non-self-complementary and substantially non-complementary to other primers in the plurality, wherein the sequence comprises in a 5' to 3' orientation a constant region and a variable region; and subjecting the nucleic acid molecule/primer mixture to a DNA polymerase, under conditions wherein the subjecting steps generate a plurality of molecules comprising the constant region at each end. In a specific embodiment, the fragments do not comprise the at least one known cleavage site. In another specific embodiment, the fragments substantially exclude sequence surrounding the at least one known cleavage site. In a specific embodiment, the sequence surrounding the at least one known cleavage site is further defined as comprising at least part of at least one promoter. In an additional embodiment, the sequence surrounding the at least one known cleavage site is further defined as comprising at least part of at least one CpG island. In some embodiments, methods of the present invention further comprise the steps of cleaving the amplified fragments in substantially the same manner as cleavage of the DNA molecule, thereby producing cleaved products; ligating an adaptor to the ends of the cleaved products; amplifying at least some of the adaptor-ligated cleaved products; and analyzing the amplified adaptor-ligated cleaved products. In a specific embodiment, the incorporating step is further defined as attaching a first adaptor having a nonblocked 3' end to the ends of the cleaved fragments to produce adaptor-linked fragments, wherein the 5' end of the cleaved fragment is attached to the nonblocked 3' end of the adaptor, leaving a nick site between the juxtaposed 3' end of the DNA and a 5' end of the first adaptor; and extending the 3' end of the cleaved fragment from the nick site. In a particular embodiment, prior to the attaching step the method further comprises randomly fragmenting the cleaved fragments; and modifying the ends of the cleaved fragments to provide attachable ends. In other embodiments, the method further comprises the steps of cleaving the amplified cleaved fragments in substantially the same manner as cleavage of the at least one DNA molecule, thereby producing cleaved products; ligating a second adaptor to the ends of the cleaved products; amplifying at least some of the second adaptor-ligated cleaved products; and analyzing the amplified second adaptor-ligated cleaved products. In a specific embodiment, cleaving of the at least one DNA molecule and cleaving of the amplified cleaved fragments comprises cleavage with a methylation-sensitive enzyme. In another specific embodiment, the second adaptor comprises one or more known sequences. In another embodiment of the invention, the incorporating step is further defined as subjecting the bisulfite converted molecules to a plurality of primers to form a nucleic acid molecule/primer mixture, wherein the primers comprise nucleic acid sequence that is substantially non-self-complementary and substantially non-complementary to other primers in the plurality, wherein the sequence comprises in a 5' to 3' orientation a constant region and a variable region; and subjecting the nucleic acid molecule/primer mixture to a DNA polymerase, under conditions wherein the subjecting steps generate a plurality of molecules comprising the constant region at each end. In a specific embodiment, the analyzing step comprises sequencing, quantitative real-time polymerase chain reaction, ligation chain reaction, ligation-mediated polymerase chain reaction, probe hybridization, probe amplification, microarray hybridization, restriction enzyme digestion, or a combination thereof.

In an additional embodiment of the present invention, there is a method for determining information from a DNA molecule, comprising obtaining at least one DNA molecule having one or more regions exhibiting differential characteristics; incorporating at least one known sequence at the ends of fragments of the molecule selectively modifying said DNA fragments at said regions according to said one or more characteristics; amplifying the modified fragments; and analyzing the amplified altered fragments. In a specific embodiment, the at least one DNA molecule comprises genomic DNA or is a genome. In a specific embodiment, the differential characteristics comprise epigenetic modification, structure, sequence, association with non-nucleotide factors, or a combination thereof. In a specific embodiment, the differential characteristic comprises epigenetic modification, such as methylation. The altering may comprise cleaving or bisulfite conversion, for example. In specific embodiments, the cleaving step comprises methylation-specific digestion and/or methylation-sensitive digestion. In a specific embodiment, the ends of the fragments are further defined as having at least one known sequence, at least one known structure, or both. In another specific embodiment, the at least one known sequence, at least one known structure, or both is the same for substantially all of the ends of the cleaved fragments. The amplifying step may utilize a primer complementary to the known sequence, a primer complementary to a desired sequence in a fragment, or both. In a specific embodiment, the incorporating step is further defined as randomly fragmenting the cleaved fragments; modifying the ends of the cleaved fragments to provide attachable ends; attaching a first adaptor having a nonblocked 3' end to the ends of the DNA library fragments to produce first adaptor-linked fragments, wherein the 5' end of the library fragment is attached to the nonblocked 3' end of the first adaptor, leaving a nick site between the juxtaposed 3' end of the DNA and a 5' end of the first adaptor; and extending the 3' end of the library fragment from the nick site. In a specific embodiment, the method further comprises the steps of cleaving said amplified cleaved fragments in substantially the same manner as cleavage of the at least one DNA molecule, thereby producing cleaved products; ligating a second adaptor to the ends of the cleaved products; amplifying at least some of the second adaptor-ligated cleaved products; and analyzing the amplified second adaptor-ligated cleaved products. In a specific embodiment, the analyzing step comprises sequencing, quantitative real-time polymerase chain reaction, ligation chain reaction, ligation-mediated polymerase chain reaction, probe hybridization, probe amplification, microarray hybridization, restriction enzyme digestion, or a combination thereof.

In another embodiment, there is a method of determining methylation status of at least one sequence, comprising obtaining at least one DNA molecule; digesting the at least one DNA molecule with a methylation-sensitive restriction enzyme; incorporating sequence at the ends of the DNA fragments with at least one primer from a plurality of primers, said primer comprising a 5' constant sequence and a 3' variable sequence that is substantially non-self-complementary and substantially non-complementary to other primers in the plurality; amplifying one or more DNA fragments utilizing a primer complementary to at least part of the constant sequence; and analyzing at least part of the sequence of at least one amplified DNA fragment. In a specific embodiment, the methylation-sensitive restriction enzyme cleaves at a site comprising a CpG dinucleotide. In a specific embodiment, the methylation sensitive restriction enzyme is BstUI, AciI, HpaII, HhaI, or a mixture thereof. The incorporating step may be further defined as generating single stranded nucleic acid molecules from the DNA fragments; subjecting the single stranded DNA nucleic acid molecules to a plurality of primers to form a single stranded nucleic acid molecule/primer mixture, wherein the primers comprise nucleic acid sequence that is substantially non-self-complementary and substantially non-complementary to other primers in the plurality and wherein the primers comprise a constant nucleic acid sequence and a variable nucleic acid sequence; and subjecting said single stranded nucleic acid molecule/primer mixture to a polymerase, under conditions wherein said subjecting steps generate a plurality of molecules comprising the constant nucleic acid sequence at each end. In a specific embodiment, the polymerase is a strand-displacing polymerase. In another specific embodiment, the amplifying step comprises polymerase chain reaction. In a specific embodiment, the analyzing step comprises sequencing, quantitative real-time polymerase chain reaction, ligation chain reaction, ligation-mediated polymerase chain reaction, probe hybridization, probe amplification, microarray hybridization, or a combination thereof. The method may further comprise the step of comparing at least part of the sequence of the amplified fragment with a control DNA molecule that was not subjected to the digestion step. In a specific embodiment, the method further comprises digesting the amplified DNA fragments with the methylation-sensitive restriction enzyme; attaching an adaptor to at least one digested amplified DNA fragment to produce an adaptor-linked fragment, wherein the 5' end of the digested amplified DNA fragment is attached to the non-blocked 3' end of the adaptor, leaving a nick site between the juxtaposed 3' end of the DNA and a 5' end of the adaptor; extending the 3' end of the digested amplified DNA fragment from the nick site; amplifying the adaptor-linked fragments with a first primer complementary to at least part of the adaptor to produce amplified adaptor-linked fragments; and analyzing the amplified adaptor-linked fragments to determine the methylation status of the original DNA. In a specific embodiment, the adaptor comprises at least one end that is complementary to the ends of the digested amplified DNA fragments. In a specific embodiment, the adaptor comprises at least one blunt end. In another specific embodiment, the adaptor comprises one or known sequences, such as sequences are substantially non-self complementary and do not substantially interact. In a specific embodiment, the amplifying step comprises polymerase chain reaction. In a further specific embodiment, the analyzing step comprises sequencing, quantitative real-time polymerase chain reaction, ligation chain reaction, ligation-mediated polymerase chain reaction, probe hybridization, probe amplification, microarray hybridization, or a combination thereof.

Another embodiment of the invention relates to a method for determining methylation status of a DNA molecule, comprising obtaining at least one DNA molecule; digesting the DNA molecule with a methylation-specific endonuclease; modifying the ends of the DNA fragments to incorporate a label in at least one strand, thereby producing modified DNA fragments immobilizing at least one modified DNA product through the label to produce an immobilized DNA product; analyzing the immobilized DNA product to determine the methylation status of the original DNA molecule. In a specific embodiment, the methylation-specific endonuclease is McrBC. In an additional specific embodiment, the incorporation of label utilizes DNA polymerase or terminal transferase, for example. In a specific embodiment, the label comprises an affinity tag, such as, for example, one that comprises at least one biotin molecule. In a specific embodiment, the method further comprises the step of randomly fragmenting the modified DNA fragments. The fragmenting step may comprise chemical fragmentation by heat, for example. In an additional specific embodiment, the analyzing step comprises sequencing, quantitative real-time polymerase chain reaction, ligation chain reaction, ligation-mediated polymerase chain reaction, probe hybridization, probe amplification, microarray hybridization, or a combination thereof. In further embodiment, the quantitative real-time polymerase chain reaction or ligation-mediated polymerase chain reaction uses a primer complementary to a desired region of the immobilized DNA product. In particular embodiments, the methods of the invention further comprise subjecting the immobilized DNA product to a plurality of primers to form a nucleic acid molecule/primer mixture, wherein the primers comprise nucleic acid sequence that is substantially non-self-complementary and substantially non-complementary to other primers in the plurality, wherein the sequence comprises in a 5' to 3' orientation a constant region and a variable region; subjecting the nucleic acid molecule/primer mixture to a DNA polymerase, under conditions wherein the subjecting steps generate a plurality of molecules comprising the constant region at each end; amplifying at least one of the molecules utilizing a primer comprising at least part of the constant region at both ends; and analyzing at least one of the amplified fragments to determine the methylation status of the original DNA molecule. In a specific embodiment, the nucleic acid molecule is single stranded. In another specific embodiment, the DNA polymerase is a strand-displacing polymerase. The amplifying step may comprise polymerase chain reaction, for example. The analyzing step may comprise sequencing, quantitative real-time polymerase chain reaction, ligation chain reaction, ligation-mediated polymerase chain reaction, probe hybridization, microarray hybridization, or a combination thereof. In a particular aspect of the invention, there is a method for determining the methylation status of a nucleic acid molecule, comprising obtaining at least one nucleic acid molecule; providing sodium bisulfite to the nucleic acid molecules, wherein the unmethylated cytosines in the nucleic acid molecules are converted to uracil, thereby producing bisulfite-converted single-stranded nucleic acid molecules; subjecting the bisulfite-converted single stranded nucleic acid molecules to a plurality of primers having a constant region and a variable region to form a bisulfite-converted single stranded nucleic acid molecule/primer mixture, wherein the primers comprise a first nucleic acid sequence that is substantially non-self-complementary and substantially non-complementary to other primers in the plurality; and a second nucleic acid sequence that is substantially non-self-complementary and substantially non-complementary to other primers in the plurality and wherein the variable region is enriched in a particular nucleotide to specifically target the bisulfite-converted single-stranded nucleic acid molecules; subjecting the bisulfite-converted single stranded nucleic acid molecule/primer mixture to a polymerase, under conditions wherein the subjecting step generates a plurality of molecules comprising the constant region at each end; amplifying a plurality of the molecules comprising the constant region at each end by utilizing a primer complementary to at least part of the constant sequence, thereby producing amplified molecules; and analyzing the amplified molecules to determine the methylation status of the original DNA molecule. In a specific embodiment, the method further comprises the step of randomly fragmented the bisulfite-converted nucleic acid molecules to produce bisulfite-converted single-stranded nucleic acid fragments. In a specific embodiment, the random fragmentation comprises chemical fragmentation, such as by comprising heat, for example. In another specific embodiment, the polymerase is a strand-displacing polymerase. In another specific embodiment, the amplifying step comprises polymerase chain reaction. In an additional specific embodiment, the analyzing step comprises sequencing, quantitative real-time polymerase chain reaction, ligation chain reaction, ligation-mediated polymerase chain reaction, probe hybridization, probe amplification, microarray hybridization, or a combination thereof. In a further specific embodiment, the quantitative real-time polymerase chain reaction or ligation-mediated polymerase chain reaction comprises methylation-specific polymerase chain reaction.

In a particular embodiment of the invention, there is a method of determining the methylation status of at least part of a DNA molecule, comprising the steps of obtaining at least one DNA molecule; digesting the DNA molecule with a methylation-sensitive restriction enzyme to produce DNA fragments; attaching a first adaptor to the ends of the digested fragments to produce first adaptor-linked fragments, wherein said attaching step comprises one or both of the following steps: (a) modifying the ends of the DNA fragments to provide attachable ends; attaching a first adaptor having a known sequence and a nonblocked 3' end to the ends of the modified DNA fragments to produce adaptor-linked fragments, wherein the 5' end of the modified DNA is attached to the nonblocked 3' end of the adaptor, leaving a nick site between the juxtaposed 3' end of the DNA and a 5' end of the adaptor; and extending the 3' end of the modified DNA from the nick site; and (b) subjecting the DNA fragments to a mixture of adaptors comprising one or more type of ends, said ends comprising 3' overhangs; 5' overhangs; or blunt ends; extending the 3' end of the modified DNA fragments from the nick site amplifying the first adaptor-linked fragments with a primer complementary to the first adaptor; and analyzing at least part of the sequence of the amplified first adaptor-linked fragments. In a specific embodiment, the first adaptor further comprises at least one of the following absence of a 5' phosphate group; a 5' overhang of about 7 nucleotides in length; and a 3' blocked nucleotide. In an additional specific embodiment, the method further comprises the step of incorporating a homopolymeric sequence to the ends of the first adaptor-linked fragments. In a specific embodiment, the incorporating step comprises amplifying the first adaptor-linked fragments utilizing a primer comprising a homopolymeric sequence at its 5' end (such as comprising cytosines); or utilizing terminal transferase activity at the 3' ends of the amplified first adaptor-linked fragments, for example.

In an additional specific embodiment, the analyzing step comprises sequencing, quantitative real-time polymerase chain reaction, ligation chain reaction, ligation-mediated polymerase chain reaction, probe hybridization, probe amplification, microarray hybridization, or a combination thereof. In an additional specific embodiment, the analyzing step comprises the comparison of amplified adaptor-linked fragments from methylation-sensitive digested DNA molecules and undigested DNA molecules. In an additional specific embodiment, the method=further comprises the steps of digesting the amplified homopolymeric sequence-comprising adaptor-linked fragments with the methylation-sensitive restriction enzyme; attaching a second adaptor to the ends of the digested amplified homopolymeric sequence-comprising adaptor-linked fragments to produce secondary adaptor-linked fragments; amplifying the secondary adaptor-linked fragments with a first primer complementary to the second adaptor and a second primer complementary to the homopolymeric sequence of the second adaptor-linked fragments; and analyzing at least part of the sequence of the amplified secondary adaptor-linked fragments. In an additional specific embodiment, the ends of the digested amplified homopolymeric sequence-comprising adaptor-linked fragments are modified to produce attachable ends. In another specific embodiment, the second adaptor is comprised of at least one blunt end or the second adaptor is comprised of overhangs complementary to the ends of the digested amplified homopolymeric sequence-comprising adaptor-linked fragments, for example. The analyzing step may comprise quantitative real-time polymerase chain reaction, ligation chain reaction, ligation-mediated polymerase chain reaction, probe hybridization, probe amplification, microarray hybridization, or a combination thereof.

In another aspect of the invention, there is a method of determining the methylation status of at least part of a DNA molecule, comprising the steps of obtaining at least one DNA molecule; digesting the DNA molecule with a methylation-sensitive restriction enzyme to produce DNA fragments; randomly fragmenting the digested DNA fragments; modifying the ends of the digested DNA fragments to produce modified DNA fragments with attachable ends; attaching a first adaptor to the ends of the modified DNA fragments to produce first adaptor-linked fragments, wherein the 5' end of the modified DNA is attached to the nonblocked 3' end of the first adaptor, leaving a nick site between the juxtaposed 3' end of the DNA and a 5' end of the first adaptor; extending the 3' end of the modified DNA fragment from the nick site; amplifying the first adaptor-linked fragments with a primer complementary to at least part of the first adaptor; and analyzing at least part of the sequence of the amplified first adaptor-linked fragments to determine the methylation status of the original DNA molecule. In a specific embodiment, the first adaptor comprises at least one of the following absence of a 5' phosphate group; a 5' overhang of about 7 nucleotides in length; and a 3' blocked nucleotide. In a specific embodiment, the amplifying step comprises polymerase chain reaction. In another specific embodiment, the method further comprises the step of incorporating a homopolymeric sequence to the ends of the amplified first adaptor-linked fragments to produce amplified homopolymeric sequence comprising first adaptor-linked fragments. The incorporating step may comprise amplifying the first adaptor-linked fragments utilizing a primer comprising a homopolymeric sequence at its 5' end, or it may comprise utilizing terminal transferase activity at the 3' ends of the amplified first adaptor-linked fragments, for example. In another specific embodiment, the analyzing step comprises sequencing, quantitative real-time polymerase chain reaction, ligation chain reaction, ligation-mediated polymerase chain reaction, probe hybridization, probe amplification, microarray hybridization, or a combination thereof.

In an additional embodiment, the method further comprises the steps of digesting the amplified homopolymeric sequence-comprising first adaptor-linked fragments with the methylation sensitive restriction enzyme; ligating a second adaptor to the ends of the digested amplified homopolymeric sequence-comprising adaptor-linked fragments to produce second adaptor-linked fragments, wherein the 5' end of the modified DNA is attached to the nonblocked 3' end of the second adaptor, leaving a nick site between the juxtaposed 3' end of the digested amplified homopolymeric sequence-comprising adaptor-linked fragments and a 5' end of the second adaptor; extending the 3' end of the digested amplified homopolymeric sequence-comprising adaptor-linked fragments from the nick site; amplifying the second adaptor-linked fragments with a first primer complementary to at least part of the second adaptor and a second primer complementary to at least part of the homopolymeric sequence; and analyzing at least part of the sequence of the amplified second adaptor-linked fragments to determine the methylation status of the original DNA molecule. In a specific embodiment, the second adaptor comprises at least one end complementary to the ends produced by digesting the amplified homopolymeric sequence-comprising first adaptor-linked fragments. In a specific embodiment, the second adaptor comprises one or more known sequences. In another specific embodiment, the one or more known sequences do not substantially interact. In an additional embodiment, the amplifying step comprises polymerase chain reaction. In a further specific embodiment, the analyzing step comprises sequencing, quantitative real-time polymerase chain reaction, ligation chain reaction, ligation-mediated polymerase chain reaction, probe hybridization, probe amplification, microarray hybridization, or a combination thereof.

In a particular aspect of the invention, there is a method for preparing a DNA molecule, comprising obtaining at least one DNA molecule; digesting the at least one DNA molecule with a methylation-specific endonuclease; attaching an adaptor having a known sequence and a nonblocked 3' end to the ends of the digested fragments to produce adaptor-linked fragments, wherein the 5' end of the digested fragment is attached to the nonblocked 3' end of the adaptor, leaving a nick site between the juxtaposed 3' end of the digested fragment and a 5' end of the adaptor; amplifying at least one adaptor-linked fragment using a primer that is complementary to at least part of the adaptor to produce size-selected adaptor-linked products; and analyzing at least one of the size-selected adaptor-linked products to determine the methylation status of the original DNA. In a specific embodiment, the methylation-specific endonuclease is McrBc. In a further specific embodiment, the adaptor comprises a 1 to about 6 base pair 5' N base overhang. In an additional specific embodiment, the ends of the DNA fragments are modified to provide attachable ends. In a further specific embodiment, the adaptor comprises at least one blunt end and/or the adaptor comprises one or more known sequences. In a specific embodiment, the one or more known sequences are substantially non-interactive. In a specific embodiment, the amplifying of the at least one adaptor-linked fragment comprises size-selective polymerase chain reaction. In a specific embodiment, the size-selective polymerase chain reaction comprises utilization of a short polymerization step, such as one that comprises about 5 seconds to about 20 seconds or that comprises about 10 seconds, for example. In a specific embodiment, the short polymerization step results in amplicons of between about 30 bp and about 200 bp. In an additional specific embodiment, the adaptor-linked DNA fragments are size-fractionated by physical means prior to the amplifying step, the size fractionation comprises filtration, or the fractionation comprises membrane ultrafiltration, for example. In specific embodiments, the digested DNA fragments are size-fractionated by physical means prior to attachment of the adaptor. In particular embodiments, the size fractionation comprises filtration, or membrane ultrafiltration, for example. In a specific embodiment, the amplifying step comprises polymerase chain reaction. In a specific embodiment, the analyzing step comprises sequencing, quantitative real-time polymerase chain reaction, ligation chain reaction, ligation-mediated polymerase chain reaction, probe hybridization, probe amplification, microarray hybridization, or a combination thereof.

In an additional aspect of the invention, there is a method for preparing a DNA molecule, comprising obtaining at least one DNA molecule; digesting the DNA molecule with a methylation-specific endonuclease to produce DNA fragments; attaching an adaptor to the ends of the digested DNA fragments to provide a nick translation initiation site, thereby producing adaptor-linked fragments; and subjecting the adaptor-linked fragments to nick translation to produce nick translate molecules. In a specific embodiment, the methylation-specific endonuclease is McrBC. In a specific embodiment, the adaptors comprise a mixture of primers comprising 1 to about 6 bp 5' N overhangs. In another specific embodiment, the ends of the digested DNA fragments are modified to provide attachable ends. In an additional specific embodiment, the adaptor comprises at least one blunt end and/or the adaptor comprises a label, such as a 5' label and/or an affinity tag, such as one that comprises at least one biotin molecule. The method may further comprise the step of immobilizing the nick translate molecules through the label. In specific embodiments, the immobilizing step further comprises denaturation of the nick translate molecules. In a particular aspect of the invention, the adaptor comprises a constant sequence comprising a 5' affinity tag on one strand, and a 5' phosphate and a 3' blocked group on the second strand. In another specific embodiment, a 3' end of the modified DNA fragment is attached to the 5' phosphorylated end of the adaptor, thereby leaving a nick between the juxtaposed 5' end of the DNA and the 3' end of the adaptor. In an additional specific embodiment, the second strand comprises an internal nick. In a further specific embodiment, a 3' end of the digested DNA fragment is attached to the 5' phosphorylated end of the adaptor, thereby leaving a first nick in the middle of the non-ligated adaptor sequence and a second nick between the juxtaposed 5' end of the DNA and the 3' end of the adaptor. The method may be further defined as determining the methylation status of the DNA molecule, and comprising amplifying at least one of the nick translate molecules to produce amplified nick translate molecules; and analyzing the amplified nick translate molecules. In a specific embodiment, the analyzing step comprises analyzing at least one amplified nick translate molecule for at least one sequence adjacent to a cleavage site of the restriction endonuclease. The analyzing step may comprise sequencing, quantitative real-time polymerase chain reaction, ligation chain reaction, ligation-mediated polymerase chain reaction, probe hybridization, microarray hybridization, or a combination thereof. The analyzing step may comprise comparison of the amplified molecule with a DNA molecule that was not subjected to digestion with the methylation-specific endonuclease. In a particular aspect of the invention, the method is further defined as determining the methylation status of the DNA molecule and comprising subjecting the immobilized denatured molecules to a plurality of primers to form a nucleic acid molecule/primer mixture, wherein the primers comprise a nucleic acid sequence that is substantially non-self-complementary and substantially non-complementary to other primers in the plurality, wherein said sequence comprises in a 5' to 3' orientation a constant region and a variable region; subjecting said single stranded nucleic acid molecule/primer mixture to a polymerase, under conditions wherein the subjecting steps generate a plurality of molecules comprising the known nucleic acid sequence at each end; amplifying at least one of the molecules comprising the constant region at both ends; and analyzing at least one of the amplified fragments to determine the methylation status of the original DNA molecule. The amplifying step may comprise polymerase chain reaction, such as one that utilizes a primer complementary to at least part of the constant region. In a specific embodiment, the analyzing step comprises sequencing, quantitative real-time polymerase chain reaction, ligation chain reaction, ligation-mediated polymerase chain reaction, probe hybridization, probe amplification, microarray hybridization, or a combination thereof.

In a particular embodiment of the invention, there is a method for preparing a DNA molecule, comprising obtaining at least one DNA molecule; digesting the DNA molecule with a methylaton-specific endonuclease; attaching a first adaptor having a first known sequence and a nonblocked 3' end to the ends of the digested DNA fragments to produce adaptor-linked fragments, wherein the 5' end of the digested DNA fragment is attached to the nonblocked 3' end of the adaptor, leaving a nick between the juxtaposed 3' end of the digested DNA fragment and the 5' end of the adaptor; extending the 3' end of the adaptor-linked fragment from the nick site; randomly fragmenting the adaptor-linked fragments to produce fragmented molecules; modifying the ends of the fragmented molecules to provide attachable ends, thereby producing modified fragmented molecules; attaching a second adaptor having a second known sequence and a nonblocked 3' end to the ends of the modified fragmented molecules to produce adaptor-linked modified fragmented molecules, wherein the 5' end of the modified fragmented molecule is attached to the nonblocked 3' end of the second adaptor, leaving a nick site between the juxtaposed 3' end of the modified fragmented molecule and the 5' end of the second adaptor; extending the 3' end of the adaptor-linked modified fragmented molecules from the nick site to produce extended adaptor-linked modified fragmented molecules; amplifying at least one of the extended adaptor-linked modified fragmented molecules; and analyzing the amplified molecules to determine the methylation status of the original DNA molecule. In a specific embodiment, the methylation-specific endonuclease is McrBC. The first adaptor may comprise a mixture of primers comprising 1 to about 6 base pair 5' N base overhangs. In a specific embodiment, the first adaptor comprises at least one blunt end. In another specific embodiment, the second adaptor comprises at least one blunt end. In an additional specific embodiment, the first and second adaptors comprise the same sequence. In an additional specific embodiment, the amplifying step comprises polymerase chain reaction, such as one that comprises a primer directed to at least part of the sequence of the first adaptor, at least part of the sequence of the second adaptor, or a mixture thereof, for example. In a specific embodiment, the analysis comprises sequencing, quantitative real-time polymerase chain reaction, ligation chain reaction, ligation-mediated polymerase chain reaction, probe hybridization, microarray hybridization, or a combination thereof.

In one aspect of the invention, there is a method for determining the methylation status of a DNA molecule, comprising; obtaining at least one DNA molecule; digesting the DNA molecule with a methylation-specific endonuclease; providing an adaptor comprising: a known sequence; and a nonblocked 3' end; attaching the adaptor to the ends of the digested DNA fragments to produce adaptor-linked fragments, wherein the 5' end of the digested DNA fragment is attached to the nonblocked 3' end of the adaptor, leaving a nick site between the juxtaposed 3' end of the digested DNA fragment and a 5' end of the adaptor; extending the 3' end of the modified DNA fragment from the nick site; amplifying at least a portion of the modified DNA fragment to produce at least one amplification product; and analyzing at least one amplification product to determine the methylation status of the original DNA molecule. In a specific embodiment, the methylation-specific endonuclease is McrBC. The adaptor may comprise a mixture of primers comprising 1 to about 6 base pair 5' N overhangs. In a specific embodiment, the ends of the digested DNA fragments are modified to provide attachable ends. In another specific embodiment, the adaptor comprises at least one blunt-end. In a further specific embodiment, the amplification primer comprises a homopolymeric sequence. In an additional specific embodiment, the adaptor comprises homopolymeric sequence of cytosines. In another specific embodiment, the adaptor-attached DNA fragments comprise a homopolymeric sequence added to the 3' end enzymatically, and the homopolymeric sequence may be added by terminal transferase and/or may comprise guanines, for example. In an additional specific embodiment, the amplifying step and/or the analyzing step comprises polymerase chain reaction.

The analyzing step may comprise polymerase chain reaction that utilizes a first primer complementary to the homopolymeric region and a second primer complementary to a desired sequence in the amplified DNA fragment, for example, and the primer may be complementary to the homopolymeric regions comprises cytosines, for example.

In one aspect of the invention, there is a method of determining the methylation status of at least part of at least one DNA molecule, comprising the steps of obtaining the DNA molecule; attaching a first adaptor to the ends of the DNA molecule to produce first adaptor-linked molecules, wherein said first adaptor comprises homopolymeric sequence and said attaching step comprises one or both of the following steps (a) modifying the ends of the DNA molecules to provide attachable ends; attaching a first adaptor having a known sequence and a nonblocked 3' end to the ends of the DNA molecules to produce adaptor-linked molecules, wherein the 5' end of the DNA is attached to the nonblocked 3' end of the adaptor, leaving a nick site between the juxtaposed 3' end of the DNA molecule and a 5' end of the adaptor; or (b) subjecting the DNA molecules to a mixture of adaptors comprising one or more type of ends, said ends comprising 3' overhangs; 5' overhangs; or blunt ends; to produce adaptor-linked molecules, wherein the 5' end of the DNA molecule is attached to the nonblocked 3' end of the adaptor, leaving a nick site between the juxtaposed 3' end of the DNA molecule and a 5' end of the adaptor; extending the ends of the DNA molecule from the nick site; digesting the first adaptor-linked molecules with a methylation specific restriction endonuclease; attaching a second adaptor to the ends of the digested first adaptor-linked DNA fragments to produce second adaptor-linked DNA fragments, wherein the 5' end of the first adaptor-linked DNA fragment is attached to the nonblocked 3' end of the adaptor, leaving a nick site between the juxtaposed 3' end of the first adaptor-linked DNA fragment and a 5' end of the adaptor; amplifying the second adaptor-linked molecules utilizing a primer mixture comprising a first primer that is complementary to at least part of the second adaptor and a second primer that is complementary to at least part of the homopolymeric tail; and analyzing the amplified second adaptor-linked fragments to determine the methylation status of the original DNA molecule. In a specific embodiment, the first adaptor comprises a homopolymeric tail, such as one that comprises cytosines, for example. In a specific embodiment, the first adaptor-linked fragments comprise a homopolymeric sequence that is attached enzymatically. In another specific embodiment, the enzymatic attachment of the homopolymeric sequence comprises terminal transferase activity. In an additional specific embodiment, the homopolymeric sequence comprises guanines. In an additional specific embodiment, the methylation specific endonuclease comprises McrBC. In another specific embodiment, the second adaptor comprises a mixture of 1 to about 6 base pair 5' N base overhangs. The second adaptor may comprise more than one known sequence that is substantially non-self complementary and substantially non interactive, for example. In an additional embodiment, the amplifying step comprises polymerase chain reaction. The analyzing step may comprise sequencing, quantitative real-time polymerase chain reaction, ligation chain reaction, ligation-mediated polymerase chain reaction, probe hybridization, probe amplification, microarray hybridization, or a combination thereof. In a specific embodiment, the DNA molecule is obtained from plasma or serum.

Another embodiment of the invention concerns a method for determining the methylation status of a nucleic acid molecule, comprising obtaining at least one nucleic acid molecule; randomly fragmenting the nucleic acid molecule to produce fragmented molecules; modifying the ends of the DNA fragments to provide attachable ends, thereby producing modified DNA fragments; attaching a first adaptor to the ends of the modified DNA fragments to produce adaptor-linked fragments, wherein the 5' end of the modified DNA fragment is attached to the nonblocked 3' end of the first adaptor, leaving a nick site between the juxtaposed 3' end of the modified DNA fragment and a 5' end of the first adaptor; extending the 3' end of the adaptor-linked fragments from the nick site; providing sodium bisulfate to said adaptor-linked fragments, wherein the unmethylated cytosines in said nucleic acid molecules are converted to uracil, thereby producing bisulfite-converted molecules; amplifying a plurality of the bisulfate-converted molecules utilizing a primer complementary to at least part of the adaptor, thereby producing amplified molecules; and analyzing the amplified molecules to determine the methylation status of the original DNA molecule. In a specific embodiment, the random fragmentation comprises chemical fragmentation, such as comprising heat, and/or the fragmentation comprises mechanical fragmentation. In a specific embodiment, the attached strand of the adaptor sequence does not comprise guanine and all cytosines are methylated. In an alternative embodiment, the attached strand of the adaptor sequence does not comprise cytosine. In a specific embodiment, the extension of the 3' nick site is performed in the presence of guanine, adenine, thymine, and methylated cytosine. In a specific embodiment, the amplifying step comprises polymerase chain reaction. In another specific embodiment, the analyzing step comprises sequencing, quantitative real-time polymerase chain reaction, ligation chain reaction, ligation-mediated polymerase chain reaction, probe hybridization, probe amplification, microarray hybridization, or a combination thereof. In a specific embodiment, the quantitative real-time polymerase chain reaction or ligation-mediated polymerase chain reaction comprises methylation-specific polymerase chain reaction.

In another aspect of the invention, there is a method for preparing a DNA molecule, comprising obtaining at least one DNA molecule; randomly fragmenting the DNA molecule to produce DNA fragments; modifying the ends of the DNA fragments to provide attachable ends, thereby producing modified DNA fragments; attaching an adaptor having a known sequence and a nonblocked 3' end to the ends of the modified DNA fragment to produce adaptor-linked fragments, wherein the 5' end of the modified DNA fragment is attached to the nonblocked 3' end of the adaptor, leaving a nick site between the juxtaposed 3' end of the modified DNA fragment and a 5' end of the adaptor; extending the 3' end of the modified DNA fragment from the nick site; digesting at least some of the amplified adaptor-linked fragments with a methylation-specific endonuclease; amplifying at least one of the adaptor-linked fragments that were not digested by the methylation-specific endonuclease, thereby producing an amplified undigested adaptor-linked fragment, said amplifying using a primer complementary to the adaptor; and analyzing at least one amplified undigested adaptor-linked fragment to determine the methylation status of the original DNA molecule. In a specific embodiment, the random fragmentation comprises chemical fragmentation and/or comprises mechanical fragmentation. In a specific embodiment, the adaptor comprises at least one blunt end. In another specific embodiment, the methylation-specific endonuclease is McrBC. In particular embodiments, the amplification step comprises polymerase chain reaction. In additional particular embodiments, the analyzing step comprises sequencing, quantitative real-time polymerase chain reaction, ligation chain reaction, ligation-mediated polymerase chain reaction, probe hybridization, microarray hybridization, or a combination thereof. In a specific embodiment, the analyzing step comprises comparing at least one digested amplified adaptor-linked fragment with at least one undigested amplified adaptor-linked fragment.

In a specific aspect of the invention, the methods and compositions provided herein regard detection, such as diagnosis, of cancer, prognosis of cancer, differentiation of aggressive vs. non-aggressive cancer, monitoring of progression of cancer and/or the drug effects on cancer, determination of susceptibility to developing cancer in an individual, and/or determining resistance to cancer therapy and/or susceptibility to developing a resistance to cancer therapy. In particular embodiments, at least one sample from an individual suspected of having cancer or that has cancer is subjected to a method of the invention such that a diagnosis, prognosis, or characterization can be made. In a specific embodiment, the methylation status of at least one DNA molecule from an individual suspected of having or developing cancer or from an individual that is known to have cancer but desires additional information of the cancer, such as the tissue that it originates from, whether it has metastasized, and/or the staging of the cancer, is determined. The sample may originate from any tissue or source of the individual, but in particular embodiments it comes from blood, serum, urine, cheek scrapings, nipple aspirate, biopsy, feces, saliva, sweat, or cerobrospinal fluid, for example.

Thus, in specific embodiments, upon determination of a sample wherein it is determined that at least part of the sequence of at least one DNA molecule is hypermethylated, it is indicated that the individual is susceptible to developing cancer or has cancer. In embodiments wherein upon determination it is determined that at least part of the sequence of at least one DNA molecule is hypomethylated, it is indicated that the individual is not susceptible to cancer and/or does not have cancer. The part of the sequence may comprise a CpG island, a promoter, or both, for example.

The cancer for which a sample from an individual is suspected of having or already has may be of any cancer. In specific embodiments, the cancer is lung, breast, head and neck, prostate, brain, liver, pancreatic, ovarian, spleen, skin, bone, thyroid, kidney, throat, cervical, testicular, melanoma, leukemia, esophageal, or colon, for example.

As such, in a particular embodiment of the invention there is a kit housed in a suitable container that comprises one or more compositions of the present invention for diagnosis, prognosis, and/or characterization of cancer from one or more individuals.

The methods of the present invention can be used for the detection and analysis of a broad range of pathological conditions and physiological processes, for example. Clinical applications can include but are not limited to the following: diagnosis and/or prognosis of cancer, immune disorders, toxicity, central nervous system disorders, proliferative disorders, metabolic malfunctions and disorders, infection, inflammation, cardio-vascular disease, developmental abnormalities, pre-natal diagnosis, etc.

In other embodiments of the invention, methods and compositions are utilized for applications, such as for research applications, for example, for the study of normal physiological processes including the following: control of gene expression, gene silencing and imprinting, X chromosome inactivation, growth and development, ageing, and tissue and cell type-specific gene expression.

In particular aspects, the methods described herein provide non-invasive, rapid, sensitive and economical ways to detect methylation. They are easy to automate and apply in a high-throughput setting for disease diagnostics, research, and/or discovery of new methylation markers for cancer and other medical conditions.

In one embodiment of the invention, there is a method of preparing a DNA molecule, comprising (a) providing a DNA molecule; (b) digesting the DNA molecule with at least one methylation-sensitive restriction enzyme; (c) incorporating a nucleic acid molecule (which may be referred to as incorporating nucleic acid sequence) onto ends of the DNA fragments to provide first modified DNA molecules, by one of the following: (1) incorporating at least one primer from a plurality of primers, said primers comprising a 5' constant sequence and a 3' variable sequence that is substantially non-self-complementary and substantially non-complementary to other primers in the plurality; or (2) incorporating an adaptor comprising an inverted repeat and a loop, under conditions wherein the adaptor becomes blunt-end ligated to one strand of the fragment, thereby producing an adaptor-linked fragment comprising a nick having a 3' hydroxyl group, wherein there is polymerization from the 3' hydroxyl group of at least part of the adaptor-linked fragment; and (d) amplifying one or more of the first modified DNA molecules to provide amplified modified DNA molecules.

In specific embodiments of the method, the incorporating step comprises incorporating at least one primer from a plurality of primers, said primers comprising a 5' constant sequence and a 3' variable sequence that is substantially non-self-complementary and substantially non-complementary to other primers in the plurality. In other specific embodiments, the incorporating step comprises incorporating a first adaptor having a nonblocked 3' end to produce first adaptor-linked fragments, wherein the 5' end of the digested fragment is attached to the nonblocked 3' end of the adaptor, leaving a nick site between the juxtaposed 3' end of the fragment and a 5' end of the first adaptor, and extending the 3' end of the fragment from the nick site. In a further specific embodiment, the incorporating step comprises incorporating an adaptor comprising an inverted repeat and a loop, under conditions wherein the adaptor becomes blunt-end ligated to one strand of the fragment, thereby producing an adaptor-linked fragment comprising a nick having a 3' hydroxyl group, wherein there is polymerization from the 3' hydroxyl group of at least part of the adaptor-linked fragment.

In specific embodiments of the invention, the method further comprises analyzing at least part of the sequence of an amplified modified DNA molecule. In further specific embodiments, the DNA molecule that is provided comprises genomic DNA, such as a comprising a genome. The provided DNA molecule may be provided from a body fluid, such as blood, serum, urine, cerebrospinal fluid, nipple aspirate, sweat, or saliva, or from a tissue, such as biopsy, surgical sample, cheek scrapings, or feces. In a particular aspect of the invention, the DNA molecule that is provided is from a sample of an individual that has a medical condition, such as cancer, for example. In another specific embodiment, the methylation-sensitive restriction enzyme has a 4-5 base pair recognition site that comprises at least one CpG dinucleotide, and exemplary embodiments include Aci I, Bst UI, Hha I, HinP1, Hpa II, Hpy 99I, Ava I, Bce AI, Bsa HI, Bsi E1, Hga I, or a mixture thereof.

In one aspect of the invention, the incorporating step may be further defined as generating single stranded nucleic acid molecules from the DNA fragments; subjecting the single stranded nucleic acid molecules to a plurality of primers to form a single stranded nucleic acid molecule/primer mixture, wherein the primers comprise nucleic acid sequence that is substantially non-self-complementary and substantially non-complementary to other primers in the plurality and wherein the primers comprise a constant nucleic acid sequence and a variable nucleic acid sequence; and subjecting said single stranded nucleic acid molecule/primer mixture to a polymerase to generate a plurality of molecules comprising the constant nucleic acid sequence at each end.

In another aspect of the invention, the incorporating step may be further defined as providing in a single incubation the following: at least one DNA fragment; a hairpin adaptor comprising an inverted repeat and a loop; DNA polymerase comprising 3'-5' exonuclease activity; uracil-DNA-glycosylase; DNA ligase; dNTPs; ATP; and a buffer suitable for activity of the polymerase, glycosylase, and ligase. In a specific embodiment, the incubation further comprises a mixture of methylation-sensitive restriction enzymes and wherein said buffer is further suitable for activity of the restriction enzymes. In another specific embodiment, the inverted repeat comprises at least one replication stop, such as one generated in the synthesis of the hairpin adaptor, for example by incorporation of a non-replicable base analog, or the replication stop may be generated by converting deoxyuridine to an abasic site, such as with the enzyme uracil-DNA-glycosylase.

In additional aspects of the invention, the appropriate methods of the invention further comprising digesting the amplified first modified DNA molecules with the at least one methylation-sensitive restriction enzyme; incorporating a nucleic acid molecule onto ends of the amplified first modified fragments to provide second modified DNA molecules, by one of the following: (1) incorporating a second adaptor having a nonblocked 3' end to produce second adaptor-linked fragments, wherein the 5' end of the fragment is attached to the nonblocked 3' end of the second adaptor, leaving a nick site between the juxtaposed 3' end of the fragment and a 5' end of the second adaptor, and extending the 3' end of the molecule from the nick site; or (2) incorporating an adaptor comprising an inverted repeat and a loop, under conditions wherein the adaptor becomes blunt-end ligated to one strand of the fragment, thereby producing an adaptor-linked fragment comprising a nick having a 3' hydroxyl group, wherein there is polymerization from the 3' hydroxyl group of at least part of the adaptor-linked DNA fragment; and amplifying the second modified DNA molecules to provide amplified second modified DNA molecules.

In specific aspects of the invention, methods comprise analyzing the amplified second modified DNA molecules to determine the methylation status of the provided DNA molecule. Methods of the invention may also further comprise the step of heating the second modified DNA molecules and/or the second adaptor-linked fragments, wherein the extension in the second adaptor-linked fragment has not occurred, to a temperature that causes denaturation of a specific fraction of the DNA.

In specific embodiments of the invention, the incorporating step (2) is further defined as providing in a single incubation the following: at least one amplified first modified fragment; a hairpin adaptor comprising an inverted repeat and a loop; DNA polymerase comprising 3'-5' exonuclease activity; uracil-DNA-glycosylase; DNA ligase; dNTPs; ATP; and a buffer suitable for activity of the polymerase, glycosylase, and ligase. In a specific embodiment, the incubation further comprises a mixture of methylation-sensitive restriction enzymes and wherein the buffer is further suitable for activity of the restriction enzymes. In a specific embodiment, the method is further defined as determining the methylation status of at least part of the provided DNA molecule and/or may be further defined as performing the method with a provided molecule from a sample of an individual with a medical condition in comparison to a control. The provided DNA molecule may comprise a promoter, a CpG island, or both, in particular aspects of the invention, and/or it may also be further defined as bisulfite-converted DNA.

In another aspect of the invention, there is a method of preparing a DNA molecule, comprising: (a) providing a DNA molecule; (b) digesting the molecule with one or more methylation-specific restriction enzymes to provide DNA fragments; (c) incorporating a nucleic acid molecule onto the ends of the DNA fragments to provide first modified DNA molecules, by a method comprising: (1) incorporating at least one primer from a plurality of primers, said primer comprising a 5' constant sequence and a 3' variable sequence that is substantially non-self-complementary and substantially non-complementary to other primers in the plurality; (2) incorporating a first adaptor having a nonblocked 3' end to produce first adaptor-linked fragments, wherein the 5' end of the digested fragment is attached to the nonblocked 3' end of the adaptor, leaving a nick site between the juxtaposed 3' end of the fragment and a 5' end of the first adaptor, and extending the 3' end of the fragment from the nick site; or (3) incorporating an adaptor comprising an inverted repeat and a loop, under conditions wherein the adaptor becomes blunt-end ligated to one strand of the fragment, thereby producing an adaptor-linked fragment comprising a nick having a 3' hydroxyl group, wherein there is polymerization from the 3' hydroxyl group of at least part of the adaptor-linked fragment; and (d) amplifying at least one first modified DNA molecule to provide amplified DNA molecules. In a specific aspect, the amplifying step utilizes a primer that is complementary to the incorporated sequence. In another specific aspect, the method further comprises the step of analyzing at least one of the amplified first modified DNA molecules to determine the methylation status of the provided DNA. The methylation-specific endonuclease may be McrBc, in specific aspects.

In an additional embodiment of the invention, there is a method of preparing a DNA molecule, comprising: (a) providing one or more nucleic acid molecules; (b) incorporating a nucleic acid molecule at the ends of the molecules by one or more of the following, wherein the incorporated molecule is resistant to bisulfate conversion, to provide first modified DNA molecules: (1) incorporating sequence by attaching a first adaptor having a nonblocked 3' end to the ends of the molecule to produce first adaptor-linked molecules, wherein the 5' end of the molecule is attached to the nonblocked 3' end of the adaptor, leaving a nick site between the juxtaposed 3' end of the molecule and a 5' end of the first adaptor, and extending the 3' end of the molecule from the nick site; or (2)

incorporating sequence by providing an adaptor comprising an inverted repeat and a loop, under conditions wherein the adaptor becomes blunt-end ligated to one strand of the DNA molecule, thereby producing an adaptor-linked DNA molecule comprising a nick having a 3' hydroxyl group, wherein there is polymerization from the 3' hydroxyl group of at least part of the adaptor-linked DNA molecule; (c) providing sodium bisulfate to said first modified nucleic acid molecules, wherein the unmethylated cytosines in said nucleic acid molecules are converted to uracil, thereby producing bisulfite-converted single-stranded nucleic acid molecules; and (d) amplifying one or more of the bisulfite-converted molecules.

Particular methods of the invention may further comprise the step of analyzing the amplified bisulfite-converted molecules to determine the methylation status of the provided DNA molecule. The method may also be further defined as performing the method with a provided molecule suspected of being from a cancerous sample in comparison to a control. In particular aspects, the method further comprises digesting the nucleic acid molecules, the first modified DNA molecules, or the bisulfite-converted molecules with a methylation-sensitive restriction enzyme. In specific embodiments, the method further comprises analyzing the digested nucleic acid molecules, the digested first modified DNA molecules, or the digested bisulfite-converted molecules to determine the methylation status of the provided nucleic acid molecules.

In an additional aspect of the invention, there is a method of preparing a DNA molecule, comprising the steps of: (1) providing a DNA molecule; (2) altering the molecule in a single incubation to produce adaptor-linked molecules, said incubation comprising two of more of the following: (a) modifying the ends of the DNA molecules to provide attachable ends; (b) repairing nicks and/or gaps within the DNA molecules; (c) attaching a first hairpin adaptor comprising a known sequence and a nonblocked 3' end to the ends of the DNA molecules to produce adaptor-linked molecules, wherein the 5' end of the DNA is attached to the nonblocked 3' end of the adaptor, leaving a nick site between the juxtaposed 3' end of the DNA molecule and a 5' end of the adaptor; and (d) extending the 3' end of the DNA molecules from the nick site; (3) digesting the adaptor-linked DNA molecules with a mixture of methylation-sensitive restriction enzymes that do not cleave within the attached first adaptor; and (4) amplifying the digested first adaptor-linked DNA molecules with a primer complementary to at least a portion of the stem region of the first adaptor to produce amplified adaptor-linked fragments.

The digestion of the DNA molecules with the mixture of methylation-sensitive restriction enzymes may occur during the altering step. The methylation-sensitive restriction enzyme cleaves at a site comprising a CpG dinucleotide, and a mixture of exemplary methylation-specific restriction enzymes includes Aci I, BstU I, Hha I, HinP1 I, HpaII, Hpy99 I, Ava I, Bce AI, Bsa HI, Bsi E1, Hga I, or a mixture of at least two thereof, such as a mixture of three, four, five, six, seven, eight, nine, ten, or eleven. In specific aspects, the attached hairpin adaptor comprises a non-replicable region in its loop. The non-replicable region may be generated during the altering of the DNA molecule, for example. In other embodiments, the non-replicable region comprises at least one abasic site, such as one that is generated from deoxyuridines comprised within the 5' stem and loop region of the first hairpin adaptor.

The altering step may occur in a solution that comprises a DNA polymerase, a ligase, and, optionally, a uracil-DNA glycosylase, wherein said solution is suitable for activity of said polymerase, ligase, and, optionally, a glycosylase. In other embodiments, the altering step occurs in a solution that comprises a DNA polymerase, ligase, optionally a uracil-DNA glycosylase, and optionally a mixture of methylation-specific restriction enzymes, wherein the solution is suitable for activity of said polymerase, ligase, optionally a glycosylase, and optionally restriction enzymes. In a specific embodiment, the 3' end of the DNA molecules is extended from the nick site up to a non-replicable region of the first adaptor.

In particular embodiments, amplifying comprises a first heating step to fragment abasic regions of the first adaptor-linked molecules. The method may further comprise the step wherein sodium bisulfite is provided to the first adaptor-linked molecules, wherein the unmethylated cytosines in the first adaptor-linked molecules are converted to uracil, thereby producing bisulfite-converted molecules. In a specific embodiment, the adaptor is further defined as comprising a 3' stem region, wherein the 3' stem region does not comprise guanine and wherein all cytosines are methylated. The method may further comprise the step of enriching for first-adaptor attached molecules comprising CpG-rich regions, such as by heating. In further aspects of the invention, a subset of first-adaptor attached molecules is denatured.

In some aspects, the method further comprises the step of comparing at least part of the sequence of the amplified adaptor-linked fragment with a control DNA molecule that was not subjected to the digestion step. The method may also further comprise digesting the amplified first adaptor-linked fragments with at least one of the methylation-sensitive restriction enzymes in the mixture; attaching a second adaptor to at least one digested adaptor-linked fragment to produce a second adaptor-linked fragment, wherein the 5' end of the digested amplified DNA fragment is attached to the non-blocked 3' end of the second adaptor, leaving a nick site between the juxtaposed 3' end of the fragment and a 5' end of the second adaptor; extending the 3' end of the digested amplified DNA fragment from the nick site; and amplifying the second adaptor-linked fragments with a primer complementary to at least part of the second adaptor to produce amplified second adaptor-linked fragments.

Analysis of the amplified second adaptor-linked fragments may be performed to determine the methylation status of the provided DNA. In specific embodiments, the second adaptor comprises at least one end that is complementary to the ends of the digested amplified DNA fragments. The second adaptor may comprise at least one blunt end and/or one or more known sequences, such as those wherein the one or more known sequences are substantially non-self complementary and substantially non-complementary to other second adaptors.

In specific embodiments, the DNA molecule is obtained from plasma, serum, or urine.

In other embodiments of the invention, there is a method of detecting a condition in an individual, comprising the steps of: (1) providing at least one DNA molecule from the plasma, serum, or urine of the individual; (2) altering the molecule in a single incubation, said incubation comprising: (a) modifying the ends of the DNA molecules to provide attachable ends; (b) repairing nicks and/or gaps within the DNA molecule; (c) attaching a first hairpin adaptor comprising a stem, a known sequence and a nonblocked 3' end to the ends of the DNA molecules to produce adaptor-linked molecules, wherein the 5' end of the DNA is attached to the nonblocked 3' end of the adaptor, leaving a nick site between the juxtaposed 3' end of the DNA molecule and a 5' end of the adaptor; (d) extending the 3' end of the DNA molecules from the nick site; and (e) digesting the altered DNA molecules with a mixture of methylation-sensitive restriction enzymes that do not cleave within the attached first adaptor; and (3) amplifying the first adaptor-linked DNA molecules with a primer complementary to at least a portion of the stem region of the first adaptor to produce amplified first adaptor-linked fragments.

In particular embodiments, the method further comprises analyzing amplified first adaptor-linked fragments that are representative of said condition, such as those that comprise a characteristic methylation status. In specific embodiments, the condition is cancer and the amplified adaptor-linked fragments comprise methylated promoter regions, such as, for example, regions that comprise at least one CpG islands.

In another embodiment, there is a method of identifying DNA regions associated with a condition, comprising the steps of: (1) obtaining at least one DNA molecule from the plasma, serum, or urine of one or more individuals with the condition and one or more individuals without the condition; (2) altering the molecule in a single incubation, said incubation comprising: (a) modifying the ends of the DNA molecules to provide attachable ends; (b) repairing nicks and/or gaps within the DNA molecules; (c) attaching a first hairpin adaptor comprising a known sequence, a stem, and a non-blocked 3' end to the ends of the DNA molecules to produce adaptor-linked molecules, wherein the 5' end of the DNA is attached to the nonblocked 3' end of the adaptor, leaving a nick site between the juxtaposed 3' end of the DNA molecule and a 5' end of the adaptor; (d) extending the 3' end of the DNA molecules from the nick site; and (e) digesting with a mixture of methylation-sensitive restriction enzymes that do not cleave within the attached first adaptor; (3) amplifying the first adaptor-linked DNA molecules with a primer complementary to at least a portion of the stem region of the first adaptor; and (4) identifying at least one specific amplified first adaptor-linked fragment that is commonly produced from DNA from individuals with said condition but not from DNA from individuals without said condition. The identifying step comprises sequencing, quantitative real-time polymerase chain reaction, ligation chain reaction, ligation-mediated polymerase chain reaction, probe hybridization, probe amplification, microarray hybridization, or a combination thereof, in particular aspects.

In an additional aspect of the invention, there is a kit for single incubation synthesis of a methylome library, said kit housed in a suitable container, comprising: a buffer suitable for activity of a DNA polymerase, ligase, uracil-DNA-glycosylase, and methylation-sensitive restriction enzyme; and one or more of the following: a hairpin adaptor; a DNA polymerase; a ligase; uracil-DNA-glycosylase; at least one methylation-sensitive restriction enzyme. In a specific embodiment, the adaptor is further defined as comprising at least one of the following: absence of a 5' phosphate group; a non-blocked 3' end; and deoxyuridines comprised within the 5' stem and loop region.

In another embodiment, there is a method of preparing a DNA molecule, comprising: (a) providing DNA resulting from apoptotic degradation; (b) digesting the DNA molecule with at least one methylation-sensitive restriction enzyme; (c) incorporating a first adaptor having a nonblocked 3' end to produce first adaptor-linked fragments, wherein the 5' end of the digested fragment is attached to the nonblocked 3' end of the adaptor, leaving a nick site between the juxtaposed 3' end of the fragment and a 5' end of the first adaptor, and extending the 3' end of the fragment from the nick site; or (d) amplifying one or more of the first modified DNA molecules to provide amplified modified DNA molecules.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3 shows a schematic description of the process of sodium bisulfite conversion of DNA. DNA is treated with sodium bisulfite to chemically convert cytosine to uracil. Methylated cytosines are resistant to this chemical reaction and thus are not converted to uracil. Exemplary sequences shown in FIG. 3 include GGGGCGGACCGCG (SEQ ID NO:207), GGGGUGGAUUGUG (SEQ ID NO:208), GGGGC$^m$GGACC$^m$GC$^m$G (SEQ ID NO:209) and GGGGC-$^m$GGAUC$^m$GC$^m$G (SEQ ID NO:210).

In FIG. 5A, YN primers containing 0, 1, 2 or 3 random N bases were used with or without dNTPs. In FIG. 5B, YN primers containing 0, 1, 2 or 3 random N bases and a model template oligonucleotide (exemplary SEQ ID NO: 9) were used. In FIG. 5C, self-priming of YN-primers were tested. Note: Pyrimidine bases do not stain with SYBR Gold.

FIG. 9A demonstrates the effect of dilution of McrBC on library preparation and amplification. DNA was digested with McrBC (0.02-0.10 U) for 1 h after which libraries were created and amplified. A control sample without McrBC cleavage was used for comparison. Dilution of McrBC results in lowered cleavage rates and less DNA molecules competent to form libraries. Digestion with higher amounts of McrBC does not result in earlier amplification of the resulting libraries, suggesting that 0.1 U of McrBC produces maximal digestion. FIG. 9B is a plot of the amount of McrBC used to digest DNA versus the cycle number at 50% Max RFU during amplification. This result indicates a sigmoidal relationship between the amount of McrBC and the effect on number of cycles necessary for amplification of the resulting libraries. FIG. 9C is a bar graph of the amount of McrBC (Units) versus % DNA digested by McrBC. The % McrBC digested DNA was calculated by setting 0.1 U McrBC as 100% and assuming a standard doubling reaction/PCR cycle. Therefore, each cycle shift to the left was converted to a 50% decrease in the digestion efficiency. The graph indicates that 50% digestion occurs after digestion with 0.7 U McrBC for 1 hour.

FIG. 19A shows the requirement for polishing in order to ligate blunt-ended adaptors and amplify McrBC digested DNA. Furthermore, the ability of Klenow Exo– to polish McrBC-cleaved DNA as effectively as Klenow indicates that McrBC cleavage results in 5' overhangs with competent 3' ends. Omitting the polishing step results in amplifications identical to that of the no DNA negative control. FIG. 19B shows amplification of libraries prepared by McrBC cleavage after ligation of an adaptor containing universal T7 promoter sequence and 5' overhangs comprising from 0 to 6 completely random bases. The amplification of non-polished samples ligated to adaptors with 5 or 6 base overhangs was identical to the control polished sample ligated to blunt-end (0 overhang) adaptor, indicating that the 5' overhangs produced by McrBC cleavage are at least 6 bases long. Adaptor with overhangs shorter than 5 bases were much less efficient. This result indicates that a minimum of 5 bases are required to support efficient hybridization and subsequent ligation of adaptors to McrBC overhangs.

FIG. 26 demonstrates preparation of a methylation specific library based on cleavage using the methylation-sensitive restriction enzyme Not I. Briefly, genomic DNA is digested with Not I, randomly fragmented, and subsequently converted to a Not I methylation-specific whole-genome library. The resulting library is amplified using a T7-C$_{10}$ primer (SEQ ID NO:36). The purified product of the first amplification is subsequently digested again with Not I and universal GT adaptors are ligated to the resulting ends. Finally, only those sequences that had a GT adaptor ligated to them are amplified by PCR using K$_U$ and C$_{10}$ universal primers (SEQ ID NO:15 and SEQ ID NO: 38, respectively). Sequences that contain the C$_{10}$ SEQ ID NO: 38 primer sequence at both ends of the molecule are unable to be amplified due to the characteristics of this type of molecule (U.S. application Ser. No. 10/293, 048, filed Nov. 13, 2002, now U.S. Pat. No. 7,655,791, incorporated by reference herein in its entirety).

In FIG. 29A, genomic DNA is digested with the methylation-specific endonuclease McrBC. Hypermethylated regions are digested into pieces not suitable for library generation. Following cleavage, DNA is randomly fragmented by chemical or mechanical means and is converted into libraries by attachment of universal adaptors as described in Example 15. The resulting amplicons, specific to regions of hypomethylation, are amplified and can be analyzed by techniques such as PCR amplification and microarray hybridization, for example. In FIG. 29B, a second method of library preparation is illustrated wherein a poly C adaptor sequence (12-40 bp) is attached to polished ends following McrBC cleavage. The presence of the poly C sequence prevents amplification of DNA amplicons from hypermethylated regions that contain the poly C sequence at both ends (US Patent Application 20030143599). Libraries are created, amplified and analyzed as in FIG. 29A.

FIG. 32 illustrates the structure of the various adaptor sequences used in library preparation. Structures of the blunt-end, 5' overhang, and 3' overhang adaptors used in the initial library construction are provided. Structure of the adaptor for ligation to Not I digested DNA that contains the Not I overhang is provided. Note that the ligation of this adaptor will not result in a functional Not I cleavage site.

FIG. 34 illustrates one exemplary method of analyzing the products produced in FIG. 33. Specifically, quantitative real-time PCR is used with primer pairs that are within the region of interest (i.e. the promoter sequence containing the restriction digest site). The shift in the number of cycles necessary for amplification between normal cells and cancer cells is an indication of methylation in the cancer sample. The products of a single Methylome library amplification can be dispensed into a 96 well plate, allowing the simultaneous determination of the methylation status of 96 promoter regions at the same time.

FIG. 47 demonstrates a method for generating a methylation-specific library from serum and plasma DNA using the methylation specific endonuclease McrBC. The small size (200 bp-3 kb) of DNA extracted from serum and plasma allows the direct attachment of adaptors to these molecules, such as adaptors containing a $C_{10}$ sequence (SEQ ID NO: 38). Digestion of the resulting library with the methylation-specific restriction endonuclease McrBC results in cleavage between two methylated CpGs. Any molecules that contain less than 2 methylated CpGs are not digested. A second adaptor sequence can be ligated to the resulting cleaved fragments. Amplification of the resulting library with a $C_{10}$ oligo (SEQ ID NO: 38) and a primer complementary to the second adaptor results in amplification of only those fragments containing the second adaptor on one or both ends. Amplicons that were not cleaved by McrBC are not amplified due to the presence of the $C_{10}$ sequence (SEQ ID NO: 38) at both ends. The resulting amplified products can be assayed by microarray hybridization, PCR, probe assay, or other methods known in the art, for example, in order to determine which sequences were methylated in the original starting material.

FIG. 48 illustrates exemplary adaptor sequences utilized during ligation. Optimal ligation can be obtained using the 5' T7N adaptors N2T7 and N5 T7 combined with the 3' T7N adaptors T7N2 and T7N5. However, it should be observed that acceptable results are obtained with a variety of combinations of adaptors as long as at least one adaptor containing a 5' N overhang and one adaptor containing a 3' N overhang are utilized together.

FIG. 54A shows analysis of DNA samples isolated from serum and urine by gel electrophoresis on 1.5% agarose. A typical banding pattern characteristic of apoptotic nucleosomal DNA is observed.

FIG. 54B shows analysis of DNA from libraries prepared from urine by gel electrophoresis on 1.5% agarose.

FIGS. 55 and 56 show typical amplification curves of promoter sites for genes implicated in cancer from libraries derived from serum and urine DNA, respectively, for cancer patients and normal healthy controls.

FIG. 57 shows a comparison between libraries prepared with the single tube method to that of a two-step protocol. Digested samples from the single tube protocol had a greatly reduced background as compared to the two-step protocol. This results in significant improvement of the dynamic range and the throughput of the assay.

FIG. 60B shows real-time PCR curves from DNA chemically converted by sodium bisulfite and non-converted DNA using primers that are specific for converted DNA and do not contain CpG dinucleotides in their sequence.

FIGS. 62A and 62B shows that methylome libraries prepared from cell-free urine DNA by ligation of universal adaptor can be enriched for promoter sequences by pre-heating prior to library preparation at temperatures that will selectively denature the fraction of DNA having low average GC content making it incompetent for ligation. Maximal enrichment of promoter sites is achieved by pre-heating at 89° C. to 91° C.

FIG. 66 shows PCR amplification curves of four promoter sites from secondary methylome libraries prepared from LNCaP prostate cancer cell line compared to control fragmented genomic DNA. Methylated promoters are enriched between 16-fold and 128-fold relative to non-amplified genomic DNA, whereas no amplification is detected for the non-methylated p16 promoter (the amplification curve from the methylome library for this promoter corresponds to a false product).

FIG. 68A shows DNA cleavage with multiple methylation-sensitive restriction enzymes followed by the library synthesis, amplification and analysis. FIG. 68B shows DNA cleavage with multiple methylation-sensitive restriction enzymes occurring after library synthesis, and then followed by amplification and analysis; FIG. 68 C illustrates the possibility of utilizing an alternative whole genome amplification method, specifically, the multiple strand displacement WGA technique that does not require a library synthesis step, such that DNA can be amplified directly after the cleavage with multiple methylation-sensitive restriction enzymes; FIG. 68 D shows preparation of the Methylome library using a single-step multiplex enzymatic approach that utilizes a hairpin oligonucleotide with a special base composition and a mixture of 9 enzymes (see FIG. 73 and FIG. 74); FIG. 68 E describes an envisioned process that combines the Methylome library preparation (as described in FIG. 68 D) and isothermal amplification (for example, by transcription using T7 RNA polymerase, assuming that the hairpin oligonucleotide contains a T7 promoter sequence that become attached to DNA ends during the reaction) into a single-reaction multiplex enzymatic process.

FIG. 69B shows that DNA cleavage with multiple methylation-sensitive restriction enzymes occurs after the library synthesis, and is then followed by bisulfite conversion, amplification and analysis; (B') WGA library synthesis using ligation and adaptors directly followed by bisulfite conversion, amplification and analysis. In FIG. 69C, Methylome library synthesis occurs in one step using a hairpin oligo-adaptor and mix of all enzymes involved in the library synthesis, and then followed by bisulfite conversion, amplification and analysis. In FIG. 69D, DNA bisulfite conversion is followed by degenerate primer-mediated whole genome amplification (DP-WGA)

In FIG. 72A, blunt-end DNA after restriction enzyme cleavage is heated, and the GC-rich DNA fraction is selected by the ligation process. In FIG. 72B, degraded DNA is "polished" by proofreading DNA polymerase, heated and the GC-rich DNA fraction is selected by the ligation process. In FIG. 72C, degraded DNA is "polished" by proofreading DNA polymerase, ligated by its 5' end to the adaptor, heated and the GC-rich DNA fraction is selected by the "fill-in' synthesis process. In FIG. 72D, degraded DNA is converted into Methylome library, amplified using primer with 5' phosphate group, heated and the GC-rich DNA fraction is selected by the ligation of new adaptor(s) and re-amplification.

DETAILED DESCRIPTION OF THE INVENTION

Figure 1:
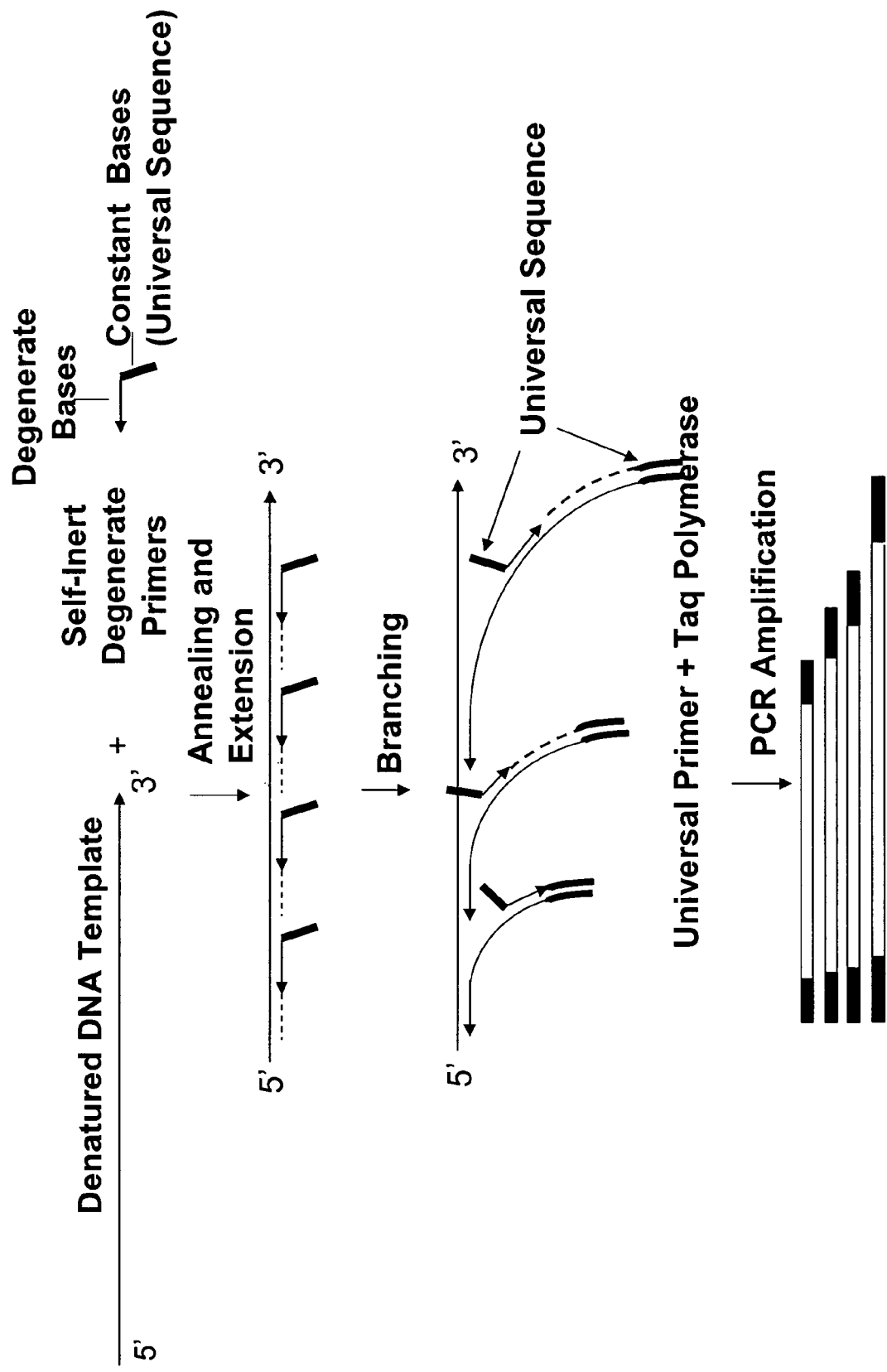
FIG. 1 illustrates a schematic presentation of whole genome amplification by incorporating known sequence with self-inert degenerate primers (see U.S. patent application Ser. No. 10/795,667, filed Mar. 8, 2004, now U.S. Pat. No. 7,718,403 incorporated by reference herein in its entirety) followed by PCR amplification. Dashed lines represent newly synthesized strands. Thicker lines represent the known (universal) sequence.

In keeping with long-standing patent law convention, the words "a" and "an" when used in the present specification in concert with the word comprising, including the claims, denote "one or more."

The practice of the present invention will employ, unless otherwise indicated, conventional techniques of molecular biology, microbiology, recombinant DNA, and so forth which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

The present application is related to the subject matter of U.S. patent application Ser. No. 10/293,048, filed Nov. 13, 2002, now U.S. Pat. No. 7,655,791; U.S. patent application Ser. No. 10/797,333, filed Mar. 8, 2004, published as U.S. Patent Application Publication No.: 2004/0209299 and is now abandoned; U.S. patent application Ser. No. 10/795,667, filed Mar. 8, 2004, now U.S. Pat. No. 7,718,403 all of which are incorporated by reference herein in their entirety.

DEFINITIONS

The term "attachable ends" as used herein refers to DNA ends that are preferably blunt ends or comprise short overhangs on the order of about 1 to about 3 nucleotides, in which an adaptor is able to be attached thereto. A skilled artisan recognizes that the term "attachable ends" comprises ends that are ligatable, such as with ligase, or that are able to have an adaptor attached by non-ligase means, such as by chemical attachment.

The term "base analog" as used herein refers to a compound similar to one of the four DNA nitrogenous bases (adenine, cytosine, guanine, thymine, and uracil) but having a different composition and, as a result, different pairing properties. For example, 5-bromouracil is an analog of thymine but sometimes pairs with guanine, and 2-aminopurine is an analog of adenine but sometimes pairs with cytosine. Another analog, nitroindole, is used as a "universal" base that pairs with all other bases.

The term "backbone analog" as used herein refers to a compound wherein the deoxyribose phosphate backbone of DNA has been modified. The modifications can be made in a number of ways to change nuclease stability or cell membrane permeability of the modified DNA. For example, peptide nucleic acid (PNA) is a new DNA derivative with an amide backbone instead of a deoxyribose phosphate backbone. Other examples in the art include methylphosphonates, for example.

The term "bisulfate-converted DNA" as used herein refers to DNA that has been subjected to sodium bisulfate such that at least some of the unmethylated cytosines in the DNA are converted to uracil.

The term "blocked 3' end" as used herein is defined as a 3' end of DNA lacking a hydroxyl group.

The term "blunt end" as used herein refers to the end of a dsDNA molecule having 5' and 3' ends, wherein the 5' and 3' ends terminate at the same nucleotide position. Thus, the blunt end comprises no 5' or 3' overhang.

The term "polished" as used herein refers to the repair of dsDNA fragment termini which may be enzymatically repaired, wherein the repair constitutes the fill in of recessed 3' ends or the exonuclease activity trimming back of 5' ends to form a "blunt end" compatible with adapter ligation.

The term "CpG island" as used herein is defined as an area of DNA that is enriched in CG dinucleotide sequences (cytosine and guanine nucleotide bases) compared to the average distribution within the genome. The generally accepted CpG island constitutes a region of at least 200-bp of DNA with a G+C content of at least 50% and observed CpG/expected CpG ratio of least 0.6.

The term "DNA immortalization" as used herein is defined as the conversion of a mixture of DNA molecules into a form that allows repetitive, unlimited amplification without loss of representation and/or without size reduction. In a specific embodiment, the mixture of DNA molecules is comprised of multiple DNA sequences.

The term "fill-in reaction" as used herein refers to a DNA synthesis reaction that is initiated at a 3' hydroxyl DNA end and leads to a filling in of the complementary strand. The synthesis reaction comprises at least one polymerase and dNTPs (dATP, dGTP, dCTP and dTTP). In a specific embodiment, the reaction comprises a thermostable DNA polymerase.

The term "genome" as used herein is defined as the collective gene set carried by an individual, cell, or organelle.

The term "hairpin" as used herein refers to a structure formed by an oligonucleotide comprised of 5' and 3' terminal regions that are inverted repeats and a non-self-complementary central region, wherein the self-complementary inverted repeats form a double-stranded stem and the non-self-complementary central region forms a single-stranded loop.

The term "methylation-sensitive restriction endonuclease" as used herein refers to a restriction endonuclease that is unable to cut DNA that has at least one methylated cytosine present in the recognition site. A skilled artisan recognizes that the term "restriction endonuclease" may be used interchangeably in the art with the term "restriction enzyme."

The term "methylation-specific restriction endonuclease" as used herein regards an enzyme that cleaves DNA comprising at least one methylcytosine on at least one strand. In a specific embodiment, the McrBC enzyme is utilized and will not cleave unmethylated DNA. A skilled artisan recognizes that the term "restriction endonuclease" may be used interchangeably in the art with the term "restriction enzyme."

The term "Methylome" as used herein is defined as the collective set of genomic fragments comprising methylated cytosines, or alternatively, a set of genomic fragments that comprise methylated cytosines in the original template DNA.

The term "non-replicable organic chain" as used herein is defined as any link between bases that can not be used as a template for polymerization, and, in specific embodiments, arrests a polymerization/extension process.

The term "non-replicable region" as used herein is defined as any region of an oligonucleotide that can not be used as a template for polymerization, and, in specific embodiments, arrests a polymerization/extension process.

The term "non strand-displacing polymerase" as used herein is defined as a polymerase that extends until it is stopped by the presence of, for example, a downstream primer. In a specific embodiment, the polymerase lacks 5'-3' exonuclease activity.

The term "promoter" as used herein refers to a sequence that regulates the transcription of a particular nucleic acid sequence, which may be referred to as a polynucleotide that encodes a gene product.

The term "random fragmentation" as used herein refers to the fragmentation of a DNA molecule in a non-ordered fashion, such as irrespective of the sequence identity or position of the nucleotide comprising and/or surrounding the break.

The term "random primers" as used herein refers to short oligonucleotides used to prime polymerization comprised of nucleotides, at least the majority of which can be any nucleotide, such as A, C, G, or T.

The term "replication stop" as used herein is defined as any region of an oligonucleotide (which may be comprised as or in an adaptor) that can not be used as a template for polymerization, and, in specific embodiments, arrests a polymerization/extension process.

The term "strand-displacing polymerase" as used herein is defined as a polymerase that will displace downstream fragments as it extends. In a specific embodiment, the polymerase comprises 5'-3' exonuclease activity.

The term "thermophilic DNA polymerase", as used herein refers to a heat-stable DNA polymerase.

A skilled artisan recognizes that there is a conventional single letter code in the art to represent a selection of nucleotides for a particular nucleotide site. For example, R refers to A or G; Y refers to C or T; M refers to A or C; K refers to G or T; S refers to C or G; W refers to A or T; H refers to A or C or T; B refers to C or G or T; V refers to A or C or G; D refers to A or G or T; and N refers to A or C or G or T. Thus, a YN primer comprises at least one, and preferably more, series of dinucleotide sets each comprising a C or a T at the first position and an A, C, G, or T at the second position. These dinucleotide sets may be repeated in the primer (or adaptor).

THE PRESENT INVENTION

A. Amplification of Sodium Bisulfite Converted DNA by Incorporation of Universal Known Sequence with Self-Inert Degenerate Primers In embodiments of the present invention, there is whole genome amplification of DNA comprising incorporation of known sequence followed by a subsequent PCR amplification step using the known sequence. In a specific embodiment, the primers for incorporating the known sequence comprise a degenerate region, and in further specific embodiments, the known sequence and the degenerate region comprise a non-self-complementary nucleic acid sequence. Thus, there is significant reduction in self-hybridization and intermolecular primer hybridization compared to primers containing self-complementary sequences. For amplification of sodium bisulfite-converted DNA, a degenerate primer is mixed with a primer comprising the same known sequence as the degenerate primer but having a homo-polymeric region instead of a degenerate region, herein referred to as a "facilitating primer", and in further specific embodiments, the known sequence and the homo-polymeric region comprise a non-self-complementary nucleic acid sequence. Since sodium bisulfate-converted DNA has a modified base composition and is enriched in adenine and uracil, the homopolymeric region of the primer selectively targeting converted DNA strands comprise either T or A.

Formation of primer dimers is a common problem in existing methods for DNA amplification using random primers. Due to the high complexity of the random primers, and in order to achieve efficient priming for each individual sequence, they have to be applied at very high concentrations.

Thus, the efficiency of annealing to a target DNA template is greatly reduced due to the formation of primer-dimers.

Other problems known in the art when using random primers to amplify DNA are an inability to amplify the genome in its entirety due to locus dropout (loss), generation of short amplification products, and in some cases, the inability to amplify degraded or artificially fragmented DNA.

Figure 2:
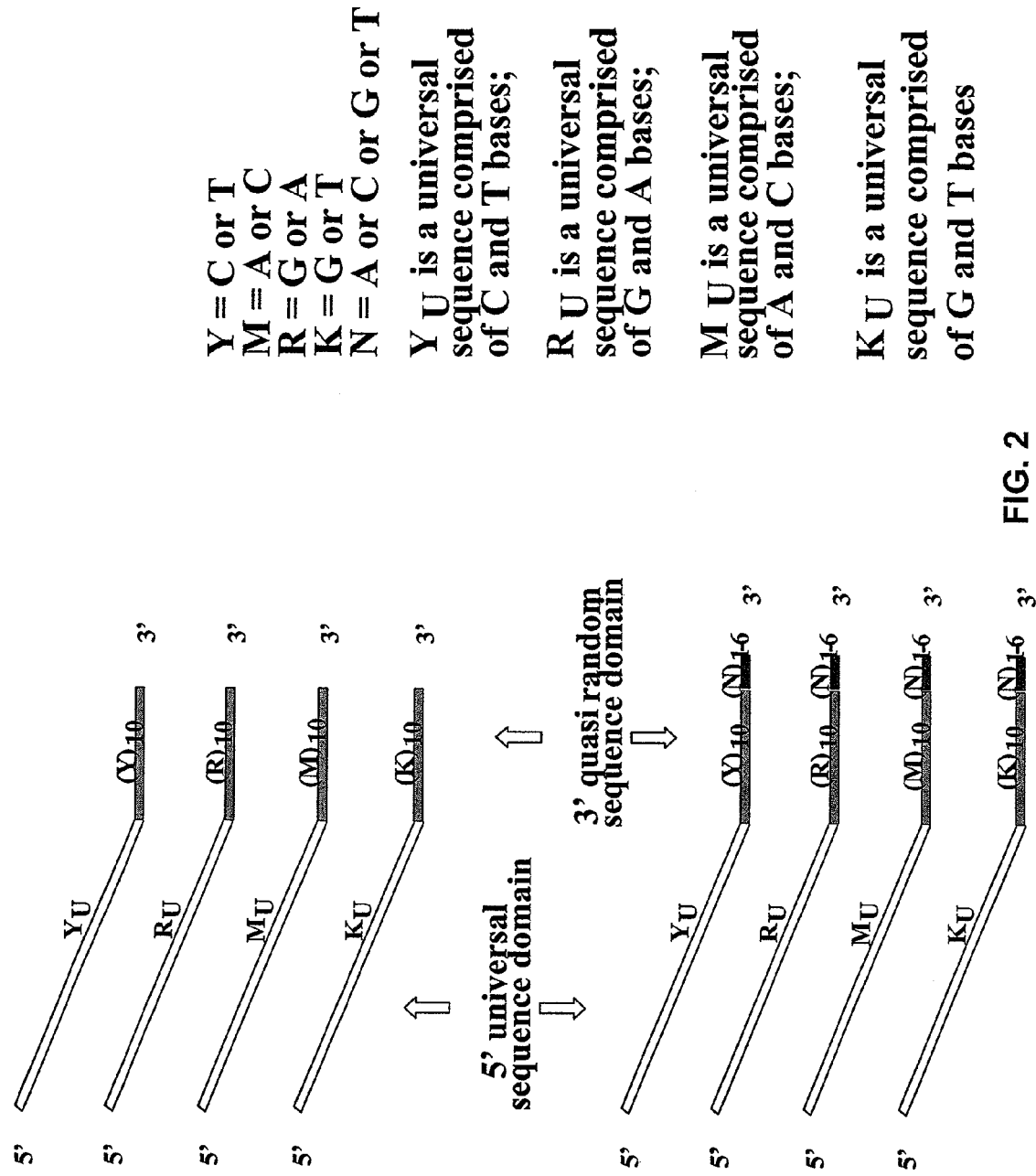
FIG. 2 is a schematic presentation of design of exemplary self-inert degenerate primers with reduced ability to form primer-dimers (see U.S. patent application Ser. No. 10/795, 667, filed Mar. 8, 2004, now U.S. Pat. No. 7,718,403).

In specific embodiments, the invention utilizes an oligonucleotide primer comprising, at least as the majority of its sequence, only two types of nucleotide bases that are not able to participate in stable Watson-Crick pairing with each other, and thus can not self-prime (see U.S. patent application Ser. No. 10/795,667, filed Mar. 8, 2004, now U.S. Pat. No. 7,718,403, for example). The primers comprise a constant known sequence at their 5' end and a degenerate nucleotide sequence located 3' to the constant known sequence. There are four possible two-base combinations known not to participate in Watson-Crick base pairing: C-T, G-A, A-C and G-T. They suggest four different types of degenerate primers that should not form a single Watson-Crick base pair and should not create primer-dimers in the presence of a DNA polymerase and dNTPs. These primers are illustrated in FIG. 2 and are referred to as primers Y, R, M and K, respectively, in accordance with common nomenclature for degenerate nucleotides: Y=C or T, R=G or A, M=A or C and K=G or T.

For example, Y-primers have a 5' known sequence YU comprised of C and T bases and a degenerate region (Y)10 at the 3 prime end comprising ten, for example, randomly selected pyrimidine bases C and T. R-primers have a 5' known sequence RU comprised of G and A bases and a degenerate region (R)10 at the 3 prime end comprising ten, for example, randomly selected purine bases G and A. M-primers have a 5' known sequence MU comprised of A and C bases and a degenerate region (M)10 at the 3 prime end comprising ten, for example, randomly selected bases A and C. Finally, K-primers have a 5' known sequence KU comprised of G and T bases and a degenerate region (K)10 at the 3 prime end comprising ten, for example, randomly selected bases G and T. Primers of the described design will not self-prime and thus will not form primer dimers. However, they will prime at target sites containing the corresponding Watson-Crick base partners, albeit with reduced overall frequency compared to completely random primers. In specific embodiments, these primers are capable of forming primer dimers under specific conditions but at a greatly reduced level compared to primers lacking such structure.

Facilitating primers, selectively targeting bisulfate-converted DNA, comprise a 5' known sequence RU, comprised of G and A bases, or YU, comprised of C and T bases, and a homopolymeric sequence comprised of A or T, respectively. These primers are combined at different ratios with their respective degenerate counterparts. For example, a primer with a known sequence of RU and a homopolymeric region comprised of A is combined with a degenerate primer with a known sequence of RU and a degenerate sequence of G and A. Similarly, a primer with a known sequence of YU and a homopolymeric region comprised of T is combined with a degenerate primer with a known sequence of YU and a degenerate sequence of C and T.

In some embodiments, these primers are supplemented with a completely random (i.e. comprising any of the four bases) short nucleotide sequence at their 3' end. If a limited number of completely random bases are present at the 3' end of the Y, R, M or K primers, that will increase their priming frequency yet maintain limited ability for self-priming. By using a different number of completely random bases at the 3' end of the degenerate Y, R, M or K primers, and by carefully optimizing the reaction conditions, one can precisely control the outcome of the polymerization reaction in favor of the desired DNA product with minimum primer-dimer formation.

Thus, in the first step referred to as "library synthesis," primers of the described design are randomly incorporated in an extension/polymerization reaction with a DNA polymerase possessing strand-displacement activity. The resulting branching process creates DNA molecules having known (universal) self complementary sequences at both ends. In a second step referred to as the "amplification" step, these molecules are amplified exponentially by polymerase chain reaction using Taq DNA polymerase and a single primer corresponding to the known 5'-tail of the random primers. FIG. 1 presents a schematic outline of the method of the invention. The invention overcomes major problems known in the art for DNA amplification by random primers.

1. Sources of DNA

Figure 4:
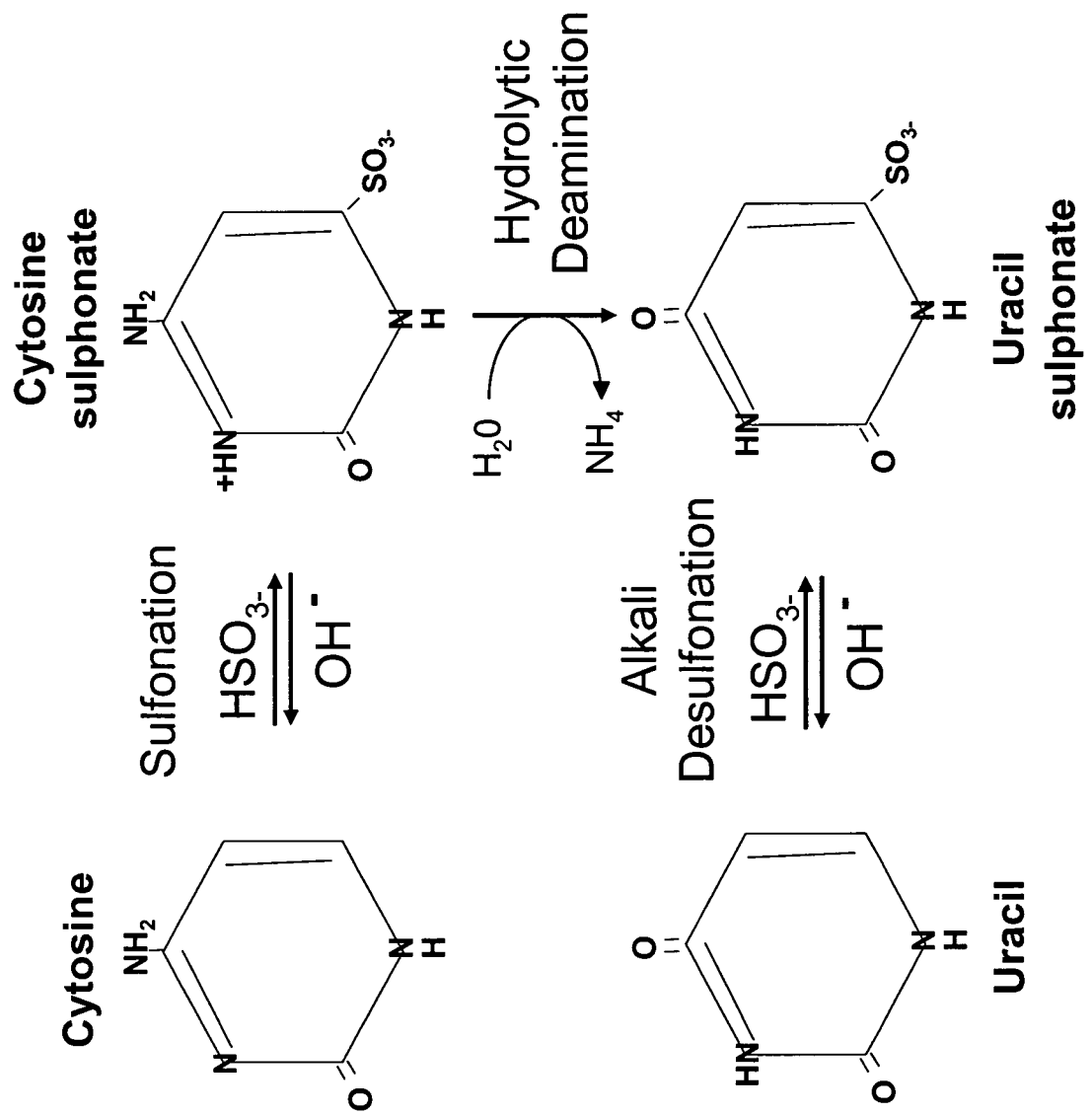
FIG. 4 depicts the principle steps in the reaction of chemical conversion of cytosine to uracil by sodium bisulfite and alkali treatment.

DNA of any source or complexity, or fragments thereof, can be amplified by the method described in the invention before or after conversion with bisulfite. In specific embodiments dsDNA is denatured with heat, chemical treatment (such as alkaline pH), mechanical manipulation, or a combination thereof to generate ss DNA, wherein the ssDNA is subjected to the methods described herein. Single-stranded DNA prepared by alkaline denaturation is treated with sodium bisulfite to chemically convert substantially all cytosine bases to uracil using established protocols well known in the art (Frommer et al., 1992; Grunau et al., 2001). Methylated cytosines are resistant to this chemical reaction and thus are not converted to uracil as illustrated in FIG. 3 and FIG. 4. In specific embodiments ds DNA is denatured with heat, chemical treatment (such as alkaline pH), mechanical manipulation, or a combination thereof to generate ssDNA, wherein the ss DNA is subjected to the methods described herein.

2. Design of Degenerate Primers

FIG. 2 illustrates the design of self-inert degenerate primers utilized in this aspect of the invention. In principle, the oligonucleotide primers comprise a constant known sequence at their 5' end and a degenerate nucleotide sequence 3' to it, each comprised of any of at least four possible base combinations known not to participate in Watson-Crick base pairing. The possible primer compositions include pyrimidines only (C and T), purines only (A and G), or non-pairing purines and pyrimidines (A and C or G and T). The last combination (G and T) is known in the art to permit non-canonical Watson-Crick base-pairing. In a preferred embodiment, the G and T pair is utilized in the invention. In a specific embodiment, the primers comprise a constant part of about 18 base sequence comprised of C and T, G and A, A and C, or G and T bases at the 5' end, followed by an about 10 random Y, R, M or K bases, respectively, and between 0 and about 6 completely random bases N at the 3' end (FIG. 2, SEQ ID NO: 1-7). Examples 1 and 2 show that Y and YN primers form only a limited amount of primer-dimers, and this is proportional to the number of completely random bases (N) at their 3' termini. In contrast, a primer of similar design but comprised of bases that can participate in Watson-Crick base-pairing generates an excessive amount of primer-dimers, which greatly reduces the efficiency of DNA amplification.

The choice of primers will depend on the base composition, complexity, and the presence and abundance of repetitive elements in the target DNA. By combining the products of individual amplification reactions with degenerate primers comprising different non-Watson-Crick pairs, but having the same known sequence at the ends, one can achieve the highest possible level of representative and uniform DNA amplification. A skilled artisan recognizes how to select the optimal primers and reaction conditions to achieve the desired result.

3. Design of Primers Targeting Sodium Bisulfite-Converted DNA

To specifically target DNA strands with chemically changed base composition after bisulfate conversion, self-inert degenerate primers comprised of A and G or C and T bases are mixed with primers having the same constant 18 base sequence at the 5' end, followed by about 10 bases of homo-polymeric sequence comprised of A or T, respectively, and between 0 and about 6 completely random bases (N) at the 3' end (FIG. 1 and SEQ ID NO: 18 and SEQ ID NO:19), herein referred to as "facilitating primers". Thus, the primer composition is specifically enriched for bases that will target converted DNA strands with reduced G/C and increased A/T content.

4. Choice of DNA Polymerases

In a preferred embodiment, a DNA polymerase is utilized that possesses strand-displacement activity. Preferred strand-displacement DNA polymerases are as follows: Klenow fragment of *E. coli* DNA polymerase I; exo– DNA polymerases of the T7 family, i.e. polymerases that require host thioredoxin subunit as co-factor, such as: T7, T3, fI, fII, W31, H, Y, gh-1, SP6, or All22 (Studier, 1979); exo– Bst large fragment; Bca DNA polymerase; 9oNm polymerase; M-MuLV Reverse Transcriptase; phage f29 polymerase; phage M2 polymerase; phage fPRD1 polymerase; exo– VENT polymerase; and phage T5 exo– DNA polymerase.

Klenow fragment of DNA polymerase I and phage T7 DNA polymerase with reduced or eliminated 3'-5' exonuclease activities are most preferred in the present invention. Thus, in a preferred embodiment the Klenow fragment of DNA polymerase I or Sequenase version 2 is used as the polymerase (Example 2).

5. Reaction Conditions

In general, factors increasing priming efficiency, such as reduced temperature or elevated salt and/or $Mg^{2+}$ ion concentration, inhibit the strand-displacement activity and the nucleotide incorporation rate of DNA polymerases, and elevated temperatures and low $Mg^{2+}$ ion or salt concentrations increase the efficiency of polymerization/strand-displacement but reduce the priming efficiency. On the other hand, factors promoting efficient priming also increase the chances of primer-dimer formation. Strand-displacement activity can be facilitated by several protein factors. Any polymerase that can perform strand-displacement replication in the presence or in the absence of such strand-displacement or processivity enhancing factors is suitable for use in the disclosed invention, even if the polymerase does not perform strand-displacement replication in the absence of such factors. Factors useful in strand-displacement replication are (i) any of a number of single-stranded DNA binding proteins (SSB proteins) of bacterial, viral, or eukaryotic origin, such as SSB protein of *E. coli*, phage T4 gene 32 product, phage T7 gene 2.5 protein, phage Pf3 SSB, replication protein A RPA32 and RPA14 subunits (Wold, 1997); (ii) other DNA binding proteins, such as adenovirus DNA-binding protein, herpes simplex protein ICP8, BMRF1 polymerase accessory subunit, herpes virus UL29 SSB-like protein; (iii) any of a number of replication complex proteins known to participate in DNA replication such as phage T7 helicase/primase, phage T4 gene 41 helicase, *E. coli* Rep helicase, *E. coli* recBCD helicase, *E. coli* and eukaryotic topoisomerases (Champoux, 2001).

The exact parameters of the polymerization reaction will depend on the choice of polymerase and degenerate primers, and a skilled artisan recognizes, based on the teachings provided herein, how to modify such parameters. By varying the number of random bases at the 3' end of the degenerate primers and by carefully optimizing the reaction conditions, formation of primer-dimers can be kept to a minimum, while at the same time the amplification efficiency and representation can be maximized.

Random fragmentation of DNA can be performed by mechanical, chemical, or enzymatic treatment. In a preferred embodiment, DNA is fragmented by heating at about 95° C. in low salt buffers such as TE (10 mM Tris-HCl, 1 mM EDTA, having pH between 7.5 and 8.5) or TE-L (10 mM Tris-HCl, 0.1 mM EDTA, having pH between 7.5 and 8.5) for between about 1 and about 10 minutes (for example, see U.S. patent application Ser. No. 10/293,048, filed Nov. 13, 2002, now U.S. Pat. No. 7,655,791, incorporated by reference herein in its entirety).

A typical library synthesis reaction of the present invention is performed in a reaction mixture having a volume ranging between about 10 and about 25 µl. The reaction mixture preferably comprises about 0.5 to about 100 ng of thermally or mechanically fragmented DNA, or in particular embodiments less than about 0.5 ng DNA, about 0.5 to about 30 µM of degenerate primer, about 0 to about 200 nM of known sequence primer (i.e., primer corresponding to the known 5' end of the respective degenerate primer), between about 2 to about 10 units of Klenow Exo⁻ (New England Biolabs) or Sequenase version 2 (USB Corporation), between 0 and about 360 ng SSB protein, and between about 5 to 10 mM $MgCl_2$, and between 0 and about 100 mM NaCl. The reaction buffer preferably has a buffering capacity that is operational at physiological pH between about 6.5 and about 9. Preferably, the incubation time of the reaction is between about 10 minutes to about 180 minutes, and the incubation temperature is between about 12° C. to 37° C. Incubation is performed by cycling between about 12° C. and about 37° C. for a total of 3 to 5 min per cycle, or preferably by a single isothermal step between about 12° C. to 30° C. or sequential isothermal steps between about 12° C. to 37° C. The reaction is terminated by addition of a sufficient amount of EDTA to chelate $Mg^{2+}$ or, preferably, by heat-inactivation of the polymerase, or both.

In a preferred embodiment of the present invention, the library synthesis reaction is performed in a volume of about 15 µl. The reaction mixture comprises about 5 ng or less of non-converted or sodium bisulfite converted fragmented DNA, about 1 µM of degenerate primer K(N)$_2$ primer, (SEQ ID NO:14) containing G and T bases at the known and degenerate regions and 2 completely random 3' bases for amplification of non-converted DNA or about 0.5 µM degenerate primers Y(N)$_2$ and R(N)$_2$ (FIG. 1 and SEQ ID NO:3 and SEQ ID NO:10) comprised of A and G or C and T bases at the known and degenerate regions and 2 completely random 3' bases (FIG. 1 and SEQ ID NO:3 and SEQ ID NO:10) and about 0.5 µM facilitating primers $R_U(A)_{10}(N)_2$ and $Y_U(T)_{10}(N)_2$ (FIG. 1 and SEQ ID NO:18 and SEQ ID NO:19) having the same constant 18 base sequence at the 5' end as the respective degenerate primers, followed by 10 bases of homo-polymeric sequence comprised of A or T respectively and 2 completely random bases N at the 3' end for amplification of bisulfite-converted DNA, between about 2 units and about 10 units of Klenow Exo– DNA polymerase (NEB), between about 5 mM and about 10 mM $MgCl_2$, about 100 mM NaCl, about 10 mM Tris-HCl buffer having pH of about 7.5, and about 7.5 mM dithiothreitol. Preferably, the incubation time of the reaction is between about 60 and about 120 minutes and the incubation temperature is about 24° C. in an isothermal mode or in another preferred embodiment by sequential isothermal steps at between about 16° C. and about 37° C.

A typical amplification step with known sequence primer comprises between about 1 and about 10 ng of library synthesis products and between about 0.3 and about 2 µM of known sequence primer in standard PCR reaction well known in the art, under conditions optimal for a thermostable DNA polymerases, such as Taq DNA polymerase, Pfu polymerase, or derivatives and mixtures thereof

TABLE I

OLIGONUCLEOTIDE SEQUENCES

| No | Code | Sequence 5'-3'* | |
|---|---|---|---|
| 1. | Y | CCTTTCTCTCCCTTCTCTYYYYYYYYYY | (SEQ ID NO: 1) |
| 2. | YN | CCTTTCTCTCCCTTCTCTYYYYYYYYYYN | (SEQ ID NO: 2) |
| 3. | Y(N)$_2$ | CCTTTCTCTCCCTTCTCTYYYYYYYYYYNN | (SEQ ID NO: 3) |
| 4. | Y(N)$_3$ | CCTTTCTCTCCCTTCTCTYYYYYYYYYYNNN | (SEQ ID NO: 4) |
| 5. | Y(N)$_4$ | CCTTTCTCTCCCTTCTCTYYYYYYYYYYNNNN | (SEQ ID NO: 5) |
| 6. | Y(N)$_5$ | CCTTTCTCTCCCTTCTCTYYYYYYYYYYNNNNN | (SEQ ID NO: 6) |
| 7. | Y(N)$_6$ | CCTTTCTCTCCCTTCTCTYYYYYYYYYYNNNNNN | (SEQ ID NO: 7) |
| 8 | Y$_U$ | CCTTTCTCTCCCTTCTCT | (SEQ ID NO: 8) |
| 9. | Template | GTAATACGACTCACTATAGGRRRRRRRRRR | (SEQ ID NO: 9) |
| 10. | R(N)$_2$ | AGAGAAGGGAGAGAAAGGRRRRRRRRRRNN | (SEQ ID NO: 10) |
| 11. | R$_U$ | AGAGAAGGGAGAGAAAGG | (SEQ ID NO: 11) |
| 12. | M(N)$_2$ | CCAAACACACCCAACACAMMMMMMMMMMNN | (SEQ ID NO: 12) |
| 13. | M$_U$ | CCAAACACACCCAACACA | (SEQ ID NO: 13) |
| 14. | K(N)$_2$ | TGTGTTGGGTGTGTTTGGKKKKKKKKKKNN | (SEQ ID NO: 14) |
| 15. | K$_U$ | TGTGTTGGGTGTGTTTGG | (SEQ ID NO: 15) |
| 16 | T7(N)$_6$ | GTAATACGACTCACTATAGGNNNNNN | (SEQ ID NO: 16) |
| 17. | T7 | GTAATACGACTCACTATAGG | (SEQ ID NO: 17) |
| 18. | R$_U$(A)$_{10}$(N)$_2$ | AGAGAAGGGAGAGAAAGGAAAAAAAAAANN | (SEQ ID NO: 18) |
| 19. | Y$_U$(T)$_{10}$(N)$_2$ | CCTTTCTCTCCCTTCTCTTTTTTTTTTTNN | (SEQ ID NO: 19) |
| 20. | RH93704 F | GTACTCCCATTCCTGCCAAA** | (SEQ ID NO: 20) |
| 21. | RH93704 B | TAAACATAGCACCAAGGGGC** | (SEQ ID NO: 21) |
| 22. | Met RH93704 F | ATACTCCCATTCCTACCAAA | (SEQ ID NO: 22) |
| 23. | Met RH93704 B | TAAATATAGTATTAAGGGGT | (SEQ ID NO: 23) |
| 24. | p15 Neg F | CCTCTGCTCCGCCTACTGG | (SEQ ID NO: 24) |
| 25. | p15 Neg B | CACCGTTGGCCGTAAACTTAAC | (SEQ ID NO: 25) |
| 26. | p16 Neg F | CAGAGGGTGGGGCGGACCGC | (SEQ ID NO: 26) |
| 27. | p16 Neg B | CCGCACCTCCTCTACCCGACCC | (SEQ ID NO: 27) |
| 28. | E-Cad Neg F | GCTAGAGGGTCACCGCGT | (SEQ ID NO: 28) |
| 29. | E-Cad Neg B | CTGAACTGACTTCCGCAAGCTC | (SEQ ID NO: 29) |
| 30. | GSTP-1 Neg F | GTGAAGCGGGTGTGCAAGCTC | (SEQ ID NO: 30) |
| 31. | GSTP1 Neg B | CGAAGACTGCGGCGGCGAAAC | (SEQ ID NO: 31) |
| 32. | T7GG | AGTAATACGACTCACTATAGG | (SEQ ID NO: 32) |
| 33. | T7GGN | AGTAATACGACTCACTATAGGN | (SEQ ID NO: 33) |
| 34. | T7SH | CCTATAGTGAGT/3AmMC7/*** | (SEQ ID NO: 34) |
| 35. | T7NSH | NCCTATAGTGAGT/3AmMC7/*** | (SEQ ID NO: 35) |

TABLE I-continued

OLIGONUCLEOTIDE SEQUENCES

| No | Code | Sequence 5'-3'* | |
|---|---|---|---|
| 36. | T7-C$_{10}$ | CCCCCCCCCCGTAATACGACTCACTATAGG | (SEQ ID NO: 36) |
| 37. | T7 | GTAATACGACTCACTATA | (SEQ ID NO: 37) |
| 38. | C$_{10}$ | CCCCCCCCCC | (SEQ ID NO: 38) |
| 39. | p15 5'-Flank | TGCCACTCTCAATCTCGAACTA | (SEQ ID NO: 39) |
| 40. | p16 3'-Flank | GCGCTACCTGATTCCAATTCCCC | (SEQ ID NO: 40) |
| 41. | E-cad 5'-Flank | CATAGGTTTGGGTGAACTCTAA | (SEQ ID NO: 41) |
| 42. | E-cad 3'-Flank | GGCCTTTCTTCTAACAATCAG | (SEQ ID NO: 42) |
| 43. | Adapt Backbone | TGAGGTTGTTGAAGCGTTUACCCAAUTCGATUAGGCAA/3AmMC7/*** | (SEQ ID NO: 43) |
| 44. | Adapt Biot | Biot-TTGCCTAATCGAATTGGGTAAACG | (SEQ ID NO: 44) |
| 45. | Adapt Nick | CTTCAACAACCTCA/3AmMC7/*** | (SEQ ID NO: 45) |
| 46. | p15 Nick F | AGGTGCAGAGCTGTCGCTTTC | (SEQ ID NO: 46) |
| 47. | p15 Nick B | CACTGCCCTCAGCTCCTAATC | (SEQ ID NO: 47) |
| 48. | p16 Nick F | GGTAGGGGACACTTTCTAGTC | (SEQ ID NO: 48) |
| 49. | p16 Nick B | AGGCGTGTTTGAGTGCGTTC | (SEQ ID NO: 49) |
| 50. | E-Cad Nick F | CCAAGGCAGGAGGATCGC | (SEQ ID NO: 50) |
| 51. | E-Cad Nick B | TCAGAAAGGGCTTTTACACTTG | (SEQ ID NO: 51) |
| 52. | E-Cad Add | GTGAGCTGTGATCGCACCA | (SEQ ID NO: 52) |
| 53. | E-Cad Add | GCGGTGACCCTCTAGCCT | (SEQ ID NO: 53) |
| 54. | GT short | CCAAACACACCC/3AmMC7/*** | (SEQ ID NO: 54) |
| 55. | T7SH-2N | NNCCTATAGTGAGT/3AmMC7/*** | (SEQ ID NO: 55) |
| 56. | T7SH-3N | NNNCCTATAGTGAGT/3AmMC7/*** | (SEQ ID NO: 56) |
| 57. | T7SH-4N | NNNNCCTATAGTGAGT/3AmMC7/*** | (SEQ ID NO: 57) |
| 58. | T7SH-5N | NNNNNCCTATAGTGAGT/3AmMC7/*** | (SEQ ID NO: 58) |
| 59. | T7SH-6N | NNNNNNCCTATAGTGAGT/3AmMC7/*** | (SEQ ID NO: 59) |
| 60. | GTSH-6N | NNNNNNCCAAACACAC/3AmMC7/*** | (SEQ ID NO: 60) |
| 61. | p16 SH-F | GGTAGGGGACACTTTCTAGTC | (SEQ ID NO: 61) |
| 62. | p16 SH-B | AGGCGTGTTTGAGTGCGTTC | (SEQ ID NO: 62) |
| 63. | p15 SF | GCGCGCGATCCAGGTAGC | (SEQ ID NO: 63) |
| 64. | p15 SB | TAGGTTCCAGCCCCGATCCG | (SEQ ID NO: 64) |
| 65. | p16 LF | GGTGCCACATTCGCTAAGTGC | (SEQ ID NO: 65) |
| 66. | p16 LB | GCTGCAGACCCTCTACCCAC | (SEQ ID NO: 66) |
| 67. | E-Cad LB | CAGCAGCAGCGCCGAGAGG | (SEQ ID NO: 67) |
| 68. | GSTP1 Neg B2 | CCTGGAGTCCCCGGAGTCG | (SEQ ID NO: 68) |

*Random bases definitions:
N = A, C, G, or T; Y = C or T; R = A or G; M = A or C; K = G or T
**Primers to STS marker sequence RH93704 are from the UniSTS database at the National Center for Biotechnology Information's website.
***/3AmMC7/ = amino C7 modifier B. Analysis of DNA Methylation Following Cleavage with McrBC Endonuclease Methylation of cytosines in the 5' position of the pyrimidine ring is the most important epigenetic alteration in eukaryotic organisms. In animals and humans, methylcytosine is predominantly found in cytosine-guanine (CpG) dinucleotides, whereas in plants it is more frequently located in cytosine-any base-guanine trinucleotides (CpNpG) (Fraga and Esteller, 2002). Two alternative groups of methods are currently used to study the degree of methylation in DNA samples: non-bisulfite and bisulfite conversion. The first relies on the use of methylation-sensitive restriction endonucleases combined with, for example, Southern blot or PCR detection. The second utilizes PCR amplification of bisulfite-converted DNA. Both methods suffer from significant drawbacks. Whereas the former is limited by the availability of suitable restriction sites, and the specificity of methylation-sensitive enzymes, the latter is limited by the amount of DNA left after chemical conversion, incomplete denaturation, and/or incomplete desulfonation. In addition, bisulfite conversion is tedious, time-consuming, and requires a great deal of empirical optimization of specific primers and PCR conditions for the converted DNA.

In the present invention, there is a novel use of the unique properties of the exemplary $E.$ $coli$ endonuclease McrBC and its utility in the analysis of methylation in specific genomic regions.

In embodiments of the present invention there is a novel use of McrBC DNA endonuclease comprising digestion of genomic DNA to produce a plurality of ends originating from cleavage between $DC^m$ ($A/GC^m$) recognition sites separated by about 35 and about 3000 bases. In specific embodiments, digestion with McrBC is incomplete and results in predominant cleavage of a subset of sites separated by about 35 and about 200 bases. In other specific embodiments, cleavage is complete and results in digestion of substantially all possible cleavage sites.

In a specific embodiment of the invention, PCR amplification with primers flanking a region analyzed for methylation is performed following McrBC cleavage. The presence of methylation sites recognized by the McrBC endonuclease results in at least one cleavage event between the priming sites and thus results in a lack of amplification products. The sensitivity of detection decreases in this McrBC-mediated direct promoter methylation assay if a mixture of methylated and non-methylated DNA is analyzed, as is often the case with clinical samples containing a few malignant cells amidst a large number of non-malignant cells. Thus, there is a necessity for developing a DNA methylation assay for methylation analysis of samples containing a mixture of different cells.

In embodiments of the present invention, the present inventors take advantage of the frequency of McrBC recognition sites and the kinetic differences between hypermethylated sites and sites with low levels of methylation or a lack of methylation.

In a specific embodiment, DNA termini produced by cleavage with McrBC are modified by ligation of universal adaptor sequences followed by incorporation of short homopolymeric sequence that allow multiplexed asymmetric one-sided PCR amplification between the universal terminal sequence and sites internal to, or flanking, the hypermethylated region.

In another specific embodiment of the invention, DNA termini produced by cleavage with McrBC are modified by ligation of biotinylated nick-attaching adaptor sequences. The nicks are propagated to a controlled distance from the adaptor, and the uniformly sized nick-translation products are immobilized on a solid phase and analyzed for the presence of sequences internal to, or flanking, a methylation site. The McrBC libraries of this type can be used for discovery of unknown hypermethylated promoters or imprinted genes by sequencing or by hybridization to microarrays.

In another specific embodiment, 3' recessed ends of McrBC cleavage sites are extended in the presence of a biotin-comprising nucleotide analog, followed by DNA fragmentation, immobilization on solid support, and/or analysis for sequences internal to, or flanking, a methylation site. McrBC libraries of this type can also be used for discovery of unknown hypermethylated sites by sequencing or by hybridization to microarrays.

In a preferred embodiment of the invention, libraries comprising short amplifiable DNA sequences generated by McrBC cleavage from promoter sites are utilized. These short sequences will be present only if a particular promoter is methylated, and thus comparative hybridization and/or amplification can be used for genome-wide analysis and quantification of the methylation pattern at promoter CpG sites. First, genomic DNA from test and control samples is cleaved with McrBC endonuclease. Universal adaptor sequences are then ligated to the overhangs produced by the enzyme, and short fragments are amplified either prior to, or following, size separation of the DNA. The method of size separation could be any of a number of physical DNA fractionation methods well known in the art, such as gel electrophoresis, size exclusion chromatography, or membrane micro-filtration, for example. In a specific embodiment of the invention, the size fractionation is achieved by a membrane micro-filtration process. In another specific embodiment, separation is carried out by size-selective DNA amplification. Analysis and quantification of promoter-specific short fragments in the amplified libraries are conducted by comparative hybridization and/or amplification. The magnitude of the signal will be proportional to the level of methylation of the promoter site being investigated. An added advantage to the quantitative aspect of the method described in this embodiment is the potential of physical mapping of methylation patterns by hybridization to, for example, a microarray comprising a tiled path of short promoter sequences.

1. Sources of DNA

Genomic DNA of any source or complexity, or fragments thereof, can be analyzed by the methods described in the invention. Clinical samples representing biopsy materials, pap smears, DNA from blood cells, serum, plasma, or other body fluids, or DNA isolated from cultured primary or immortalized tissue cultures, for example, can be used as a source for methylation analysis.

2. McrBC Cleavage

In embodiments of the present invention DNA is digested with McrBC endonuclease in the presence of GTP as the energy source for subunit translocation. A typical digestion with McrBC endonuclease is performed in a volume ranging from about 5 µl to about 50 µl in buffer containing about 50 mM NaCl, about 10 mM Tris-HCl having pH of about 7.5 to about 8.5, about 100 µg/ml of bovine serum albumin, about 0.5 to about 2 mM GTP, and about 0.2 to about 20 units of McrBC endonuclease. The temperature of incubation is between about 16° C. and about 42° C. and the duration is between about 10 minutes and about 16 hours. The quanitity of DNA in the reaction is between 50 pg and 10 µg. It should be noted that McrBC makes one cut between each pair of half-sites, cutting close to one half-site or the other, but cleavage positions are distributed over several base pairs approximately 30 base pairs from the methylated base (Panne et al., 1999) resulting in a smeared pattern instead of defined bands. In specific embodiments, digestion with McrBC is incomplete and results in predominant cleavage of a subset of sites separated by about 35 and about 250 bases. In other specific embodiments, cleavage is complete and results in digestion of substantially all possible cleavage sites. Example 3 describes the optimization of the cleavage of human genomic DNA and analysis of the termini produced by McrBC. It should be noted that from the existing literature the nature of the ends produced by McrBC digestion is not understood. Example 9 also details the analysis of the nature of the ends produced by McrBC cleavage.

3. Direct Analysis of DNA Methylation by PCR Following McrBC Cleavage

In a preferred embodiment, following McrBC cleavage of genomic DNA, aliquots of digested DNA or control non-digested DNA, are amplified by PCR using primers specific to known methylation sites within promoter CpG islands involved in epigenetic control of carcinogenesis. A typical reaction mixture comprises 1× Titanium Taq reaction buffer (Clontech), about 200 µM of each dNTP, about 4% DMSO, about 200 nM of primers specific for CpG regions of a methylation site of interest, and about 2 units of Titanium Taq polymerase (Clontech) in a reaction volume of between about 20 and about 50 µl. Cycling conditions vary depending on the melting temperatures of the primers and the length of the amplified product. Control samples of non-digested DNA are included in parallel with the analyzed samples, along with positive controls of genomic DNA that is fully methylated with SssI CpG methylase. Aliquots of the PCR reactions are analyzed on a 1% agarose gel after staining with ethidium bromide. If at least one cleavage event occurs between priming sites that flank McrBC recognition half-sites, no PCR product will be amplified. The assay is thus reducing the signal, or is producing a negative signal, that correlates with methylation of cytosines (see Example 5 and FIG. 12).

4. Analysis of DNA Methylation by One-Sided PCR from McrBc Cleavage Sites

Example 6 provides a description of another aspect of the present invention regarding development of McrBC-mediated library assays for DNA methylation based on ligation of a universal adaptor to McrBC cleavage sites, followed by incorporation of a poly-C tail allowing one-sided PCR between the homopolymeric sequence and a specific site flanking the methylated region. The McrBC libraries of this type can be used for cancer diagnostics, gene imprinting, and developmental research studies, as well as for discovery of unknown hypermethylated genomic regions, for example.

In a typical reaction about 100 ng or less of McrBC digested DNA is treated with Klenow fragment of DNA polymerase I to produce blunt ends in about 10 to about 100 µl of 1×T4 Ligase buffer (NEB) containing about 2 to about 20 nM of each dNTP, at about 25° C., for about 15 minutes to overnight. The ligation reaction comprises 1×T4 Ligase buffer (NEB), 100 ng or less of blunt-end template DNA, 3.75 µM final concentration of universal T7 adaptors (see Example 6), and 2,000-2,000,000 units of T4 DNA Ligase at about 16° C. to about 25° C. for about 1 hour to overnight. Homo-polymeric extensions are next incorporated at the ends of the ligated fragments using a T7-$C_{10}$ (SEQ ID NO:36) comprising ten 5' cytosine bases and a 3' T7 promoter sequence. A critical feature of this sequence is that it allows asymmetric one-sided PCR amplification due to the strong suppression effect of the terminal poly-G/poly-C duplex making the amplification between the terminal inverted repeats substantially inefficient (U.S. patent application Ser. No. 10/293,048, filed Nov. 13, 2002, now U.S. Pat. No. 7,655,791; U.S. patent application Ser. No. 10/797,333, filed Mar. 8, 2004, published as U.S. Patent Application Publication No.: 2004/0209299 and is now abandoned; U.S. patent application Ser. No. 10/795,667, filed Mar. 8, 2004, now U.S. Pat. No. 7,718,403). The amplification reaction comprises about 1 to about 5 ng of McrBC library DNA with ligated universal T7 adaptors, about 1×Taq polymerase, about 200 µM of each dNTP, and about 1 µM universal T7-$C_{10}$ primer (SEQ ID NO: 36). In addition, fluorescein calibration dye (FCD) and SYBR Green I (SGI) may be added to the reaction to allow monitoring of the amplification using real-time PCR by methods well known in the art. PCR is carried out at 72° C. for 15 minutes to "fill-in" the 3'-recessed ends of the T7 adaptor sequence, followed by a 2-step cycling protocol of 94° C. for 15 seconds, 65° C. for 2 minutes for the optimal number of cycles. Optimal cycle number is determined by analysis of DNA production using either real-time PCR or optical density. Typically, about 3 to 5 µg of amplified DNA can be obtained from a 25 µl reaction using optimized conditions.

To analyze the methylation status of promoter CpG islands, one-sided PCR is performed using about 20 to about 50 ng of purified McrBC library DNA prepared as described above from control and test cells, a universal $C_{10}$ primer comprising ten C bases (SEQ ID NO: 38), and primers specific for regions flanking the CpG islands of different promoters implicated in epigenetic control of carcinogenesis. The amplification reaction comprises about 20 to about 50 ng of McrBC library DNA, about 1×Taq polymerase, about 200 µM of each dNTP, about 4% DMSO, and about 1 uM universal $C_{10}$ primer (SEQ ID NO: 38). In addition, fluorescein calibration dye (FCD) and SYBR Green I (SGI) may be added to the reaction to allow monitoring of the amplification using real-time PCR by methods well known in the art. PCR is carried out under optimal conditions for annealing temperature, extension time, and cycle number depending on the melting temperature and length of the amplified product.

Since the amplification involves the boundaries of hypermethylated genomic regions, a skilled artisan will recognize that flanking regions of different promoters will have different levels of methylation. This fact should be taken into consideration when designing primers for one-sided PCR. For example, the transcribed regions adjacent to the 3' end of most CpG islands in normal cells are known to be heavily methylated, whereas for promoters involved in epigenetic control of carcinogenesis in cancer cells, these regions are largely hypomethylated (Baylin and Herman, 2000). Generally, primers located at a distance between about 300 to 700 bases from the boundary of a CpG island are well suited for analysis of methylation. Example 6 and FIG. 14 demonstrate the sensitivity limits of the McrBC-mediated library promoter methylation assay described herein. As little as 0.1% of cancer DNA can be detected in a background of 99.9% of normal DNA (see FIG. 14).

5. DNA Libraries Prepared by Nick-Translation from McrBc Cleavage Sites and their Utility for DNA Methylation Analysis In a preferred embodiment of the present invention, an McrBC-mediated library promoter methylation diagnostic assay is described utilizing ligation of nick-attaching biotinylated adaptor to McrBC cleavage sites, propagation of the nick to a controlled distance from the adaptor, immobilization of the uniformly sized nick-translation products on a solid support, and analysis of sequences internal to, or flanking, a methylation site, for example a CpG island (see Example 7). The McrBC libraries of this type can be used for cancer diagnostics, gene imprinting, and developmental research studies, as well as for discovery of unknown hypermethylated genomic regions.

In a typical library synthesis reaction, about 100 to about 1000 ng of McrBC digested DNA is treated with Klenow fragment of DNA polymerase I to produce blunt ends in about 10 to about 100 µl of 1×T4 Ligase buffer (NEB), containing about 2 to about 20 nM of each dNTP, at about 25° C. for about 15 minutes to overnight. The ligation reaction comprises 1×T4 Ligase buffer (NEB), 100 ng or less of blunt-end template DNA, 3.75 µM final concentration of biotinylated nick-attaching adaptor (see Example 7), and 2,000 to about 2,000,000 units of T4 DNA Ligase at about 16° C. to about 25° C. for about 1 hour to overnight. Samples are purified and further subjected to nick-translation in about 100 μl of 1× ThermoPol buffer (NEB) containing about 200 μM of each dNTP, and about 5 units of wild type Taq polymerase at about 45° C. to about 65° C. for about 1 to about 5 minutes. The nick-translation products are denatured and bound to streptavidin magnetic beads. After washing of the unbound material, aliquots of the beads are either directly analyzed for the presence of sequences internal to, or flanking, hypermethylated sites, or the DNA is further amplified using self-inert degenerate primers and the Klenow fragment of DNA polymerase I (see U.S. Provisional Patent Application 60/453,060, filed Mar. 7, 2003, and the U.S. Nonprovisional application claiming priority to same, filed concomitantly herewith), and then analyzed similarly. For direct methylation analysis, aliquots of the streptavidin beads suspensions are amplified in reactions comprising about 200 μM of each dNTP, about 4% DMSO, about 200 nM each forward and reverse primer, and about 5 units of Taq polymerase. In addition, fluorescein calibration dye (FCD) and SYBR Green I (SGI) may be added to the reaction to allow monitoring of the amplification using real-time PCR by methods well known in the art. PCR is carried out under optimal conditions for annealing temperature, extension time, and cycle number, depending on the annealing temperature and length of the amplified product.

In order to produce sufficient amounts of the McrBC library DNA for analysis of multiple methylation sites or for microarray analysis of unknown hypermethylation sites, aliquots of the DNA bound to the magnetic beads may be amplified in a reaction comprising about 50 to about 500 μg magnetic beads, about 0.05 to about 1 μM universal $K_U$ primer (SEQ ID NO: 15), about 4% DMSO, about 200 μM 7-deaza-dGTP (Sigma), and about 5 units of Taq polymerase. PCR is carried out using a cycling protocol of 94° C. for 15 seconds, 65° C. for 2 minutes for the optimal number of cycles. Aliquots of the amplified DNA are then analyzed for the presence of sequences internal to, or flanking, hypermethylated sites, or hybridized to microarrays for discovery of unknown methylation sites.

6. Preparation of DNA Libraries by Direct Biotin Incorporation at McrBC Cleavage Sites for DNA Methylation Analysis Example 8 describes another aspect of the present invention in which a McrBC-mediated library promoter methylation diagnostic assay is developed by extension of the 3' recessed ends of McrBC cleavage sites in the presence of a biotin-containing nucleotide analog, followed by DNA fragmentation, immobilization on a solid support, and analysis of sequences internal to, or flanking, a methylation site, such as a promoter CpG island. The McrBC libraries of this type can be used for cancer diagnostics, gene imprinting, and developmental research studies, as well as for discovery of unknown hypermethylated genomic regions.

In a typical library preparation, about 100 to about 1000 ng of McrBC digested DNA are labeled in a reaction comprising about 20 nM of each dNTP, about 20 to about 50 nM of biotin-containing nucleotide analog either completely substituting or in about equal ratio with the corresponding unlabeled nucleotide, about 5 to about 20 units of the Klenow Exo– fragment of DNA polymerase I or about 5 to about 10 units of wild type Taq polymerase at about 25° C. (in the case of Klenow) or at about 55° C. (in the case of Taq polymerase) for about 20 to about 120 minutes. After removal of the free biotin analog the labeled DNA is fragmented by heating at 95° C. in TE buffer for about 2 to about 8 minutes (see, for example, U.S. patent application Ser. No. 10/293,048, filed Nov. 13, 2002, now U.S. Pat. No. 7,655,791), snap-cooled on ice for about 5 minutes, and bound to streptavidin magnetic beads. After washing of the unbound material, aliquots of the beads are either directly analyzed for the presence of sequences internal to, or flanking, hypermethylated sites, or the DNA is further amplified using self-inert degenerate primers and the Klenow fragment of DNA polymerase I (see, for example, U.S. patent application Ser. No. 10/795,667, filed Mar. 8, 2004, now U.S. Pat. No. 7,718,403), and then analyzed similarly. For direct methylation analysis, aliquots of the streptavidin beads suspension are amplified in a reaction comprising about 200 μM of each dNTP, about 4% DMSO, about 200 nM each forward and reverse primer, and about 5 units of Taq polymerase. In addition, fluorescein calibration dye (FCD) and SYBR Green I (SGI) may be added to the reaction to allow monitoring of the amplification using real-time PCR by methods well known in the art. PCR is carried out under optimal conditions for annealing temperature, extension time, and cycle number, depending on the annealing temperature and length of the amplified product.

In order to produce sufficient amounts of the McrBC library DNA for analysis of multiple methylation sites, or for microarray analysis of unknown hypermethylation sites, aliquots of the DNA bound to magnetic beads are amplified in a reaction comprising about 50 to about 500 μg magnetic beads, about 0.05-1 μM universal $K_U$ primer (SEQ ID NO: 15), about 4% DMSO, about 200 μM 7-deaza-dGTP (Sigma), and about 5 units of Taq polymerase. PCR is carried out using cycling protocol of 94° C. for 15 seconds, 65° C. for 2 minutes for the optimal number of cycles. Aliquots of the amplified DNA are then analyzed for the presence of sequences internal to, or flanking, hypermethylated sites, or hybridized to microarrays for the discovery of unknown methylation sites.

7. Preparation of Libraries from Short DNA Fragments Produced by McrBC Cleavage for Analysis of Promoter Hypermethylation Examples 10, 11 and 12 describe the preparation of libraries comprising short amplifiable DNA sequences generated by McrBC cleavage of promoter sites. First, genomic DNA from test and control samples is cleaved with McrBC. Universal adaptor sequences are then ligated to the overhangs produced by the nuclease, and short fragments are amplified either prior to, or following, size separation of DNA.

Size separation can be achieved by any of a number of physical size fractionation methods well known in the art, such as gel electrophoresis, size exclusion chromatography, or membrane micro-filtration, for example. Alternatively, separation is achieved by size-selective DNA amplification.

Analysis and quantification of promoter-specific short fragments is accomplished by comparative hybridization and/or amplification. The magnitude of the signal is proportional to the level of methylation of the promoter site.

In a typical McrBC cleavage reaction, aliquots of about 1 to about 50 ng of test and control genomic DNA are digested with about 0.1 to about 10 units of McrBC endonuclease. After inactivation of the McrBC enzyme the products of digestion are incubated in a ligation reaction comprising T4 ligase buffer, about 200 nM to about 1 μM of universal adaptors with 5' overhangs comprising about 5 or 6 completely random bases, and about 200 to 2,500 units of T4 DNA ligase for about 1 hour to overnight at about 16° C. to about 25° C. The T4 DNA ligase is inactivated for 10 minutes at 65° C. and the resulting DNA molecules are either size-fractionated by applying any of a number of physical size fractionation methods well known in the art, such as gel electrophoresis, size exclusion chromatography, or membrane micro-filtration, or by size selective DNA amplification. In preferred embodiments, the method of size fractionation is micro-filtration through a membrane filter. The ligation reactions are supplemented with about 50 mM to about 250 mM NaCl, and DNA is passed through Microcon YM-100 filters (Millipore) at 500×g at ambient temperature. Under these ionic strength conditions the Microcon filters retain DNA fragments above approximately 250 bp.

The small fragments in the filtrate fractions are then concentrated by ethanol precipitation and used in PCR amplification reactions (see below). In other preferred embodiments size separation is achieved by selective amplification using two different universal adaptor sequences and reduced extension times (Example 12). The 3' ends of the universal adaptor are first filled in by extension and the libraries are amplified by PCR in a reaction comprising about 0.25 to about 1 µM universal adaptor primer(s), about 200 µM of each dNTP, about 4% DMSO, and about 5 units of Taq DNA polymerase. PCR is carried out using a cycling protocol of 94° C. for 15 seconds, 65° C. for 15 seconds (in the case of size-selective amplification) or 2 minutes (in the case of libraries that are size fractionated by microfiltration) for the optimal number of cycles. In addition, fluorescein calibration dye (FCD) and SYBR Green I (SGI) may be added to the reaction to allow monitoring of the amplification using real-time PCR by methods well known in the art. Aliquots of the amplified DNA are then analyzed for the presence of sequences internal to, or flanking, promoter CpG islands. This can be achieved by comparative hybridization and/or amplification. The magnitude of the signal is proportional to the level of methylation of a promoter site.

C. Amplification and Identification of Methylated Restriction Sites Using Methylation-Sensitive Restriction Enzyme Digestion of DNA, Whole Genome Amplification, Restriction Digestion with the Same Enzyme, and Site-Specific Genome Amplification In this embodiment, there are methods of preparing a library of DNA molecules in such a way as to select for molecules adjacent to methylated CpG's that are contained in a methylation-sensitive restriction enzyme recognition site. A list of exemplary methylation-sensitive restriction enzymes is presented in Table III. The choice of restriction enzyme defines the sites that will be targeted during library preparation and amplification. The presence of a specific site in the final amplified product will indicate that the adjacent CpG contained in the methylation-sensitive restriction site was methylated. Furthermore, use of control DNA that is not digested by the restriction enzyme during the initial library preparation will allow validation of the selection of each site during library preparation and amplification.

1. Digestion of Genomic DNA with a Methylation-Sensitive Restriction Endonuclease In a specific embodiment, genomic DNA is digested with a methylation-sensitive restriction endonuclease, such as Not I. The digestion reaction comprises about 50 ng to 5 µg of genomic DNA, 1× reaction buffer, and 1 to about 25 U of Not I restriction endonuclease. The mixture is incubated at 37° C. for 12 to 16 hours to ensure complete digestion. The enzyme is inactivated at 65° C. for 15 minutes and the sample is precipitated and resuspended to a final concentration of 1 to 50 ng/ul. Genomic DNA that has not been digested is used as a positive control during library preparation and analysis, for example.

2. Preparation of Randomly Fragmented DNA

Generally, a library is prepared in at least 4 steps: first, randomly fragmenting the DNA into pieces, such as with an average size between about 500 bp and about 4 kb; second, repairing the 3' ends of the fragmented pieces and generating blunt, double stranded ends; third, attaching universal adaptor sequences to the 5' ends of the fragmented pieces; and fourth, filling in of the resulting 5' adaptor extensions. In an alternative embodiment, the first step comprises obtaining DNA molecules defined as fragments of larger molecules, such as may be obtained from a tissue (for example, blood, urine, feces, and so forth), a fixed sample, and the like, and may comprise substantially fragmented DNA. Such DNA may comprise lesions including double or single stranded breaks.

A skilled artisan recognizes that random fragmentation can be achieved by at least three exemplary means: mechanical fragmentation, chemical fragmentation, and/or enzymatic fragmentation.

3. Repairing of the 3' Ends of the Fragmented Pieces and Preparation of Blunt Double Stranded Ends
a. Repair of Mechanically Fragmented DNA Mechanical fragmentation can occur by any method known in the art, including hydrodynamic shearing of DNA by passing it through a narrow capillary or orifice (Oefner et al., 1996; Thorstenson et al., 1998), sonicating the DNA, such as by ultrasound (Bankier, 1993), and/or nebulizing the DNA (Bodenteich et al., 1994). Mechanical fragmentation usually results in double strand breaks within the DNA molecule.

DNA that has been mechanically fragmented has been demonstrated to have blocked 3' ends that are incapable of being extended by Taq polymerase without a repair step. Furthermore, mechanical fragmentation utilizing a hydrodynamic shearing device (such as HydroShear; GeneMachines, Palo Alto, Calif.) results in at least three types of ends: 3' overhangs, 5' overhangs, and blunt ends. In order to effectively ligate the adaptors to these molecules and extend these molecules across the region of the known adaptor sequence, the 3' ends need to be repaired so that preferably the majority of ends are blunt. This procedure is carried out by incubating the DNA fragments with a DNA polymerase having both 3' exonuclease activity and 3' polymerase activity, such as Klenow or T4 DNA polymerase (see, for example, U.S. patent application Ser. No. 10/293,048, filed Nov. 13, 2002, now U.S. Pat. No. 7,655,791), or with a mixture of enzymes that separately comprise the 3' exonuclease activity and the 3' polymerase activity. Although reaction parameters may be varied by one of skill in the art, in an exemplary embodiment incubation of the DNA fragments with Klenow in the presence of 40 nmol dNTP and 1×T4 DNA ligase buffer results in optimal production of blunt end molecules with competent 3' ends.

Alternatively, Exonuclease III and T4 DNA polymerase can be utilized to remove 3' blocked bases from recessed ends and extend them to form blunt ends (U.S. Pat. No. 6,197,557). In a specific embodiment, an additional incubation with T4 DNA polymerase or Klenow maximizes production of blunt ended fragments with 3' ends that are competent to undergo ligation to the adaptor.

In specific embodiments, the ends of the double stranded DNA molecules still comprise overhangs following such processing, and particular adaptors are utilized in subsequent steps that correspond to these overhangs.

b. Repair of Chemically Fragmented DNA

Chemical fragmentation of DNA can be achieved by any method known in the art, including acid or alkaline catalytic hydrolysis of DNA (Richards and Boyer, 1965), hydrolysis by metal ions and complexes (Komiyama and Sumaoka, 1998; Franklin, 2001; Branum et al., 2001), hydroxyl radicals (Tullius, 1991; Price and Tullius, 1992) and/or radiation treatment of DNA (Roots et al., 1989; Hayes et al., 1990). Chemical treatment could result in double or single strand breaks, or both.

In a specific embodiment, chemical fragmentation occurs by heat (see, for example, U.S. patent application Ser. No. 10/293,048, filed Nov. 13, 2002, now U.S. Pat. No. 7,655,791). In a further specific embodiment, a temperature greater than room temperature, in some embodiments at least about 40° C., is provided. In alternative embodiments, the temperature is ambient temperature. In further specific embodiments, the temperature is between about 40° C. and 120° C., between about 80° C. and 100° C., between about 90° C. and 100° C., between about 92° C. and 98° C., between about 93° C. and 97° C., or between about 94° C. and 96° C. In some embodiments, the temperature is about 95° C.

Figure 39:
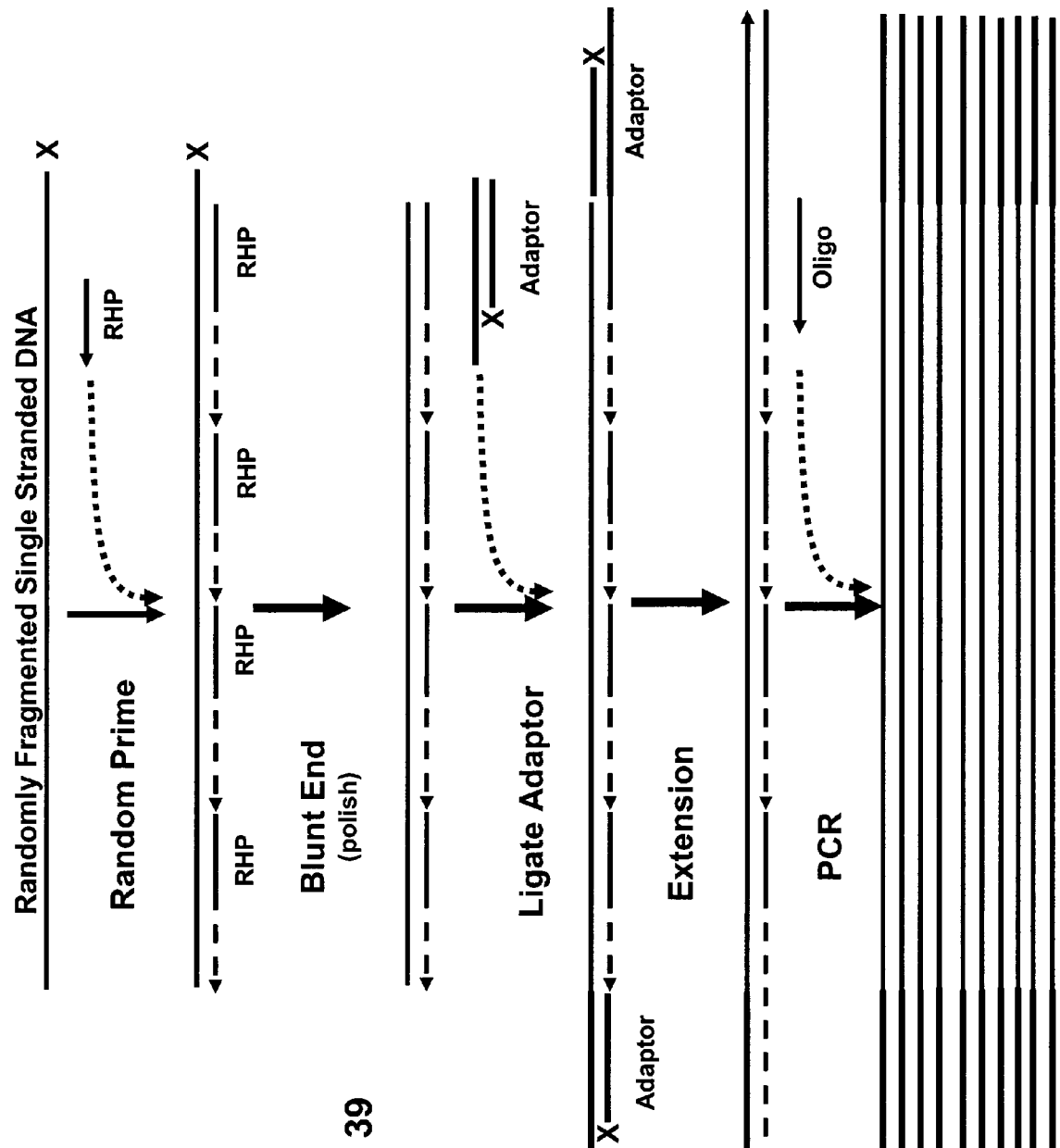
FIG. 39 illustrates preparation of a whole genome library by chemical fragmentation using a non-strand displacing polymerase. Briefly, genomic DNA is fragmented chemically resulting in the production of single stranded DNA fragments with blocked 3' ends. A fill-in reaction with a non-strand displacing polymerase is performed. The resulting dsDNA fragments have blunt or several by overhangs at each end and may contain nicks of the newly synthesized DNA strand at the points where the 3' end of an extension product meets the 5' end of a distal extension product. Adaptor sequences are ligated to the 5' ends of each side of the DNA fragment. Finally, an extension step is performed to displace the short 3' blocked adaptor and extend the DNA fragment across the ligated adaptor sequence. This process results in only one competent strand for amplification if there are nicks present in the strand created during the fill-in reaction.
Figure 40:
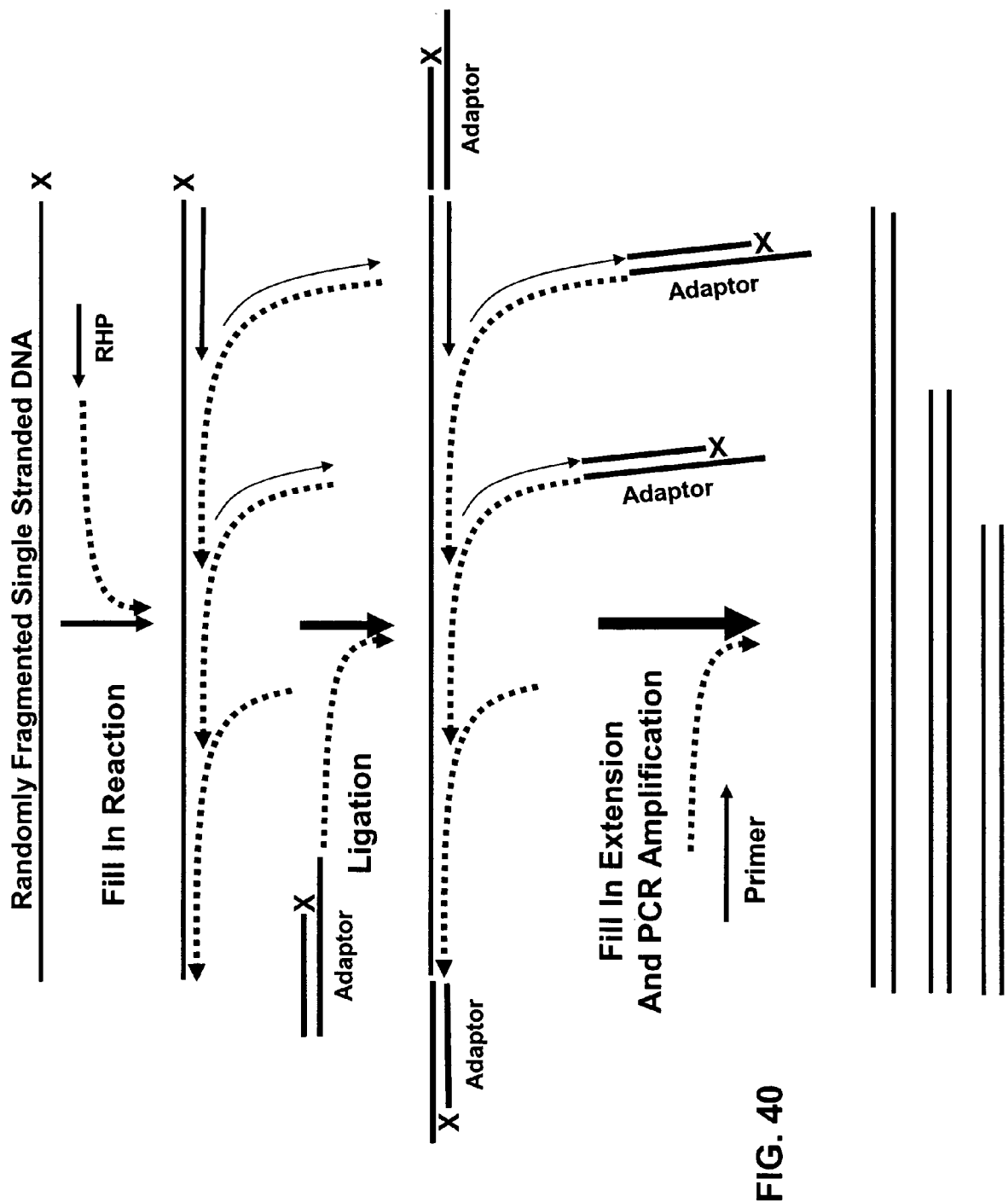
FIG. 40 represents an alternative model by which a whole genome library is prepared by chemical fragmentation using a strand-displacing polymerase. Briefly, genomic DNA is fragmented chemically resulting in the production of single stranded DNA fragments with blocked 3' ends. A fill-in reaction with a strand displacing polymerase is performed. The resulting DNA fragments have a branched structure resulting in the creation of additional ends. All ends are either blunt or have several by overhangs. Adaptor sequences are ligated to the 5' ends of each end of the DNA fragments. Finally, an extension step is performed to displace the short 3' blocked adaptor and extend the DNA fragment across the ligated adaptor sequence. This process may result in multiple strands of different sizes being competent to undergo subsequent amplification, depending on the amount of strand displacement that occurs. In the example depicted, the full-length parent strand and the most 3' distal daughter strand are competent to undergo amplification.
Figure 41:
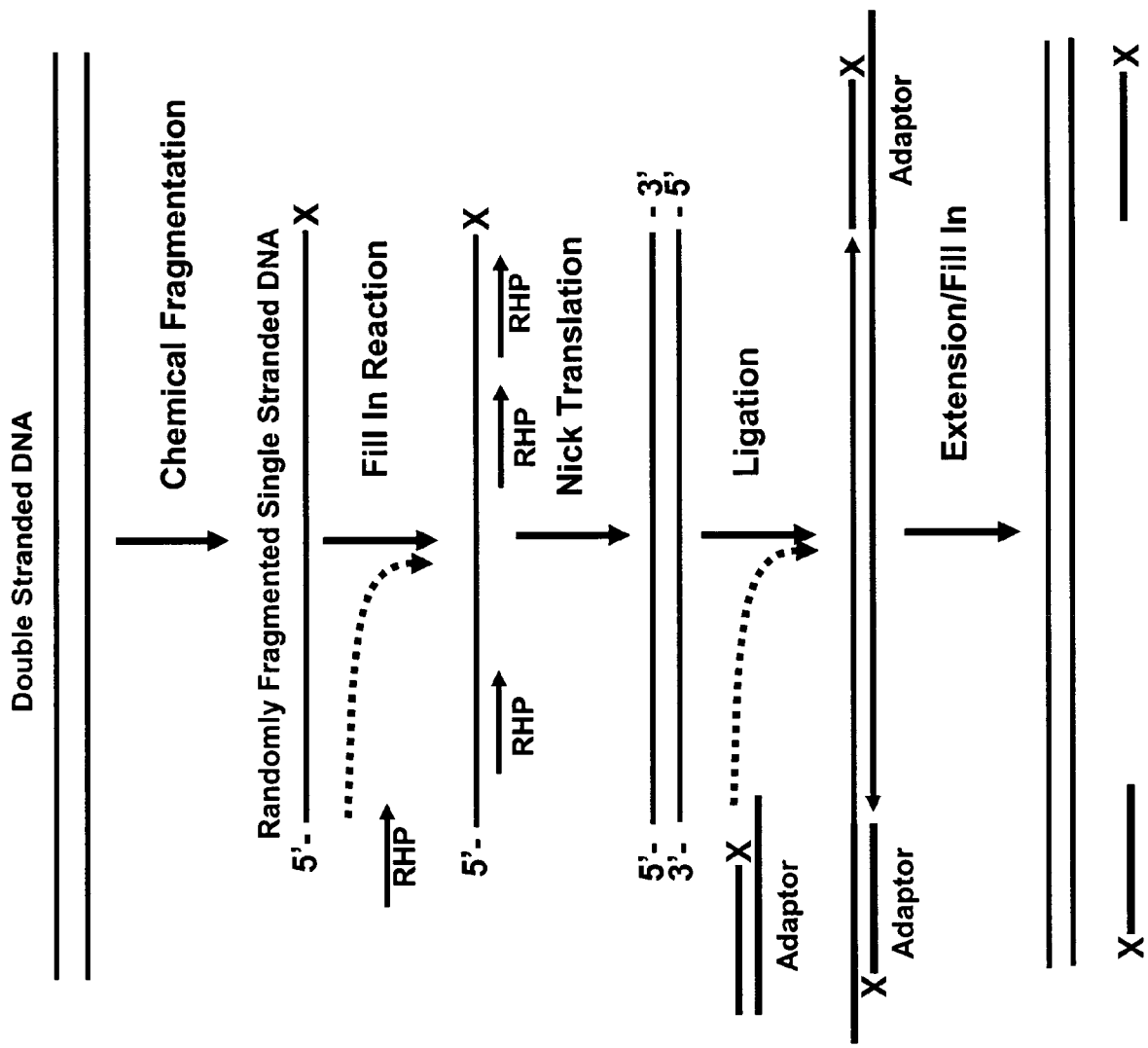
FIG. 41 represents an alternative model by which a whole genome library is prepared by chemical fragmentation using a polymerase with nick translation ability. Briefly, genomic DNA is fragmented chemically, resulting in the production of single stranded DNA fragments with blocked 3' ends. A fill-in reaction with a polymerase capable of nick translation is performed. The resulting ds DNA fragments have blunt or several by overhangs at each end and the daughter strand is one continuous fragment. Adaptor sequences are ligated to the 5' ends of each side of the DNA fragment. Finally, an extension step is performed to displace the short 3' blocked adaptor and extend the DNA fragment across the ligated adaptor sequence. Both strands of the DNA fragment are suitable for amplification due to the creation of a full-length daughter strand by nick translation during the fill-in reaction.

In a specific embodiment, DNA that has been chemically fragmented exists as single stranded DNA and has been demonstrated to have blocked 3' ends. In order to generate double stranded 3' ends that are competent to undergo ligation, a fill-in reaction with random primers and DNA polymerase that has 3'-5' exonuclease activity, such as Klenow, T4 DNA polymerase, or DNA polymerase I, is performed (see, for example U.S. patent application Ser. No. 10/797,333, filed Mar. 8, 2004, published as U.S. Patent Application Publication No.: 2004/0209299 and is now abandoned). This procedure results in several types of molecules depending on the polymerase used and the conditions of the reaction. In the presence of a non strand-displacing polymerase, such as T4 DNA polymerase, fill-in with phosphorylated random primers will result in multiple short sequences that are extended until they are stopped by the presence of a downstream random-primed fragment. This will result in two ends that are competent to undergo ligation (FIG. 39). A strand-displacing enzyme such as Klenow will result in displacement of downstream fragments that can subsequently be primed and extended. This will result in production of a branched structure that has multiple ends competent to undergo ligation in the next step (FIG. 40). Finally, use of an enzyme with nick translation ability, such as DNA polymerase I, will result in nick translation of all fragments leading to a single secondary strand capable of ligation (FIG. 41). A skilled artisan recognizes that nick translation comprises a coupled polymerization/degradation process that is characterized by coordinated 5'-3' DNA polymerase activity and 5'-3' exonuclease activity. The two enzymatic activities are usually present within one enzyme molecule (as in the case of Taq DNA polymerase or DNA polymerase I), however nick translation may also be achieved by simultaneous activity of multiple enzymes exhibiting separate polymerase and exonuclease activities. Incubation of the DNA fragments with Klenow in the presence of 0.1 to 10 pmol of phosphorylated primers in a two temperature protocol (37° C., 12° C.) results in optimal production of blunt end fragments with 3' ends that are competent to undergo ligation to the adaptor.

c. Repair of Enzymatically Fragmented DNA

Enzymatic fragmentation of DNA may be utilized by standard methods in the art, such as by partial restriction digestion by Cvi JI endonuclease (Gingrich et al., 1996), or by DNAse I (Anderson, 1981; Ausubel et al., 1987), for example. Fragmentation by DNAse I may occur in the presence of about 1 to 10 mM $Mg^{2+}$ ions (predominantly single strand breaks) or in the presence of about 1 to 10 mM $Mn^{2+}$ ions (predominantly double strand breaks).

DNA that has been enzymatically fragmented in the presence of $Mn^{2+}$ has been demonstrated to have either blunt ends or 1 to 2 bp overhangs. Thus, it is possible to omit the repair step and proceed directly to ligation of adaptors. Alternatively, the 3' ends can be repaired so that a higher plurality of ends are blunt, resulting in improved ligation efficiency. This procedure is carried out by incubating the DNA fragments with a DNA polymerase containing both 3' exonuclease activity and 3' polymerase activity, such as Klenow or T4 DNA polymerase. For example, incubation of the DNA fragments with Klenow in the presence of 40 nmol dNTP and 1×T4 DNA ligase buffer results in optimal production of blunt end molecules with competent 3' ends, although modifications of the reaction parameters by one of skill in the art are well within the scope of the invention.

Alternatively, Exonuclease III and T4 DNA polymerase can be utilized to remove 3' blocked bases from recessed ends and extend them to form blunt ends (see U.S. Pat. No. 6,197,557, incorporated by reference herein in its entirety). An additional incubation with T4 DNA polymerase or Klenow maximizes production of blunt ended fragments with 3' ends that are competent to undergo ligation to the adaptor.

DNA that has been enzymatically digested with DNAse I in the presence of $Mg^{2+}$ has been demonstrated to have single stranded nicks. Denaturation of this DNA would result in single stranded DNA fragments of random size and distribution. In order to generate double stranded 3' ends, a fill in reaction with random primers and DNA polymerase that has 3'-5' exonuclease activity, such as Klenow, T4 DNA polymerase, or DNA polymerase I, is performed. Use of these enzymes will result in the same types of products as described in item b. above—Repair of Chemically Fragmented DNA.

4. Sequence Attachment to the Ends of DNA Fragments

Figure 42:
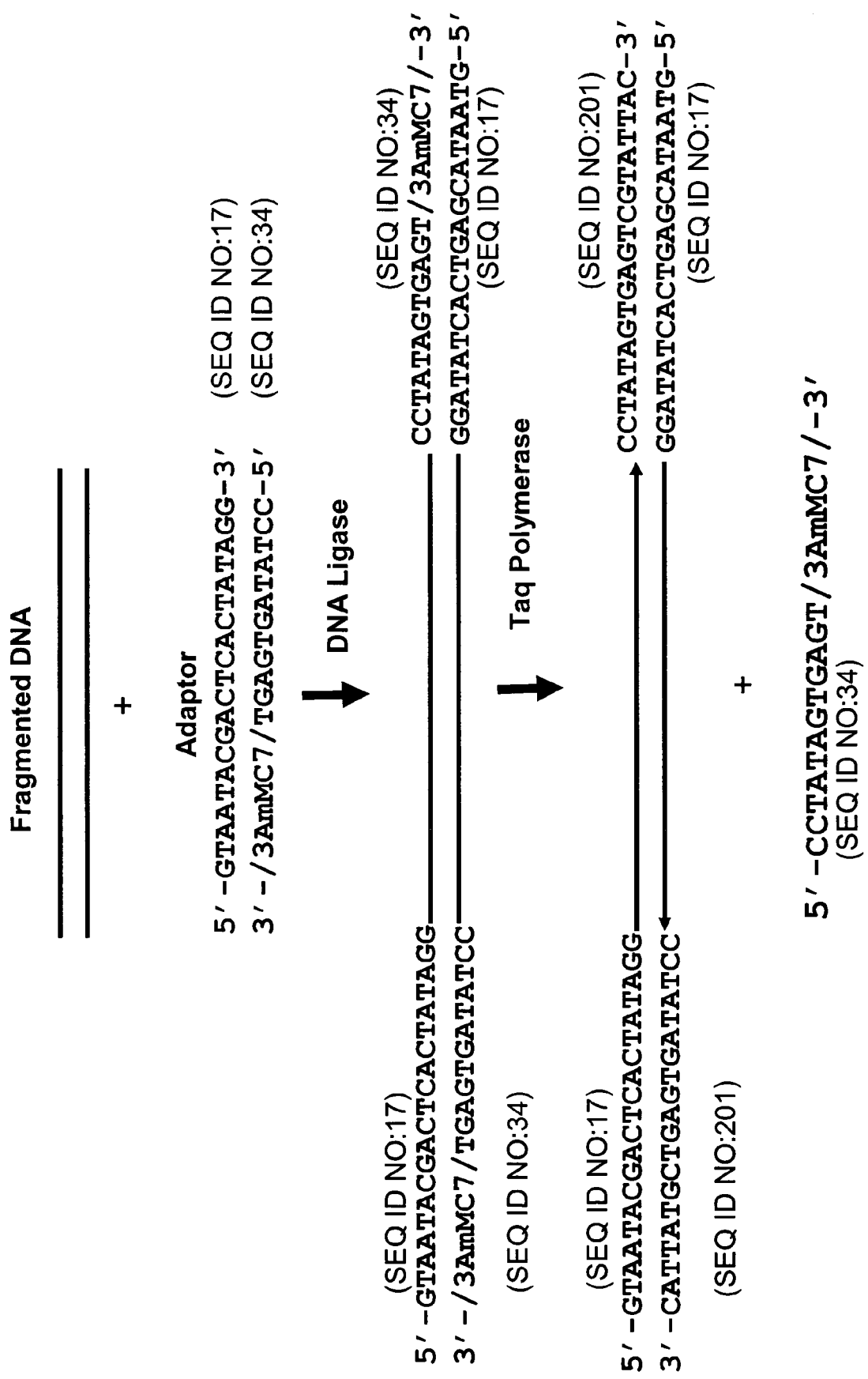
FIG. 42 shows the structure of a specific adaptor and how it is ligated to blunt-ended double stranded DNA fragments, the resulting dsDNA fragments, and the extension step following ligation used to fill in the adaptor sequence and displace the blocked short adaptor.

The following ligation procedure is designed to work with both mechanically and chemically fragmented DNA that has been successfully repaired and comprises blunt double stranded 3' ends. Under optimal conditions, the repair procedures will result in the majority of products having blunt ends. However, due to the competing 3' exonuclease activity and 3' polymerization activity, there will also be a portion of ends that have a 1 bp 5' overhang or a 1 bp 3' overhang, for example. Therefore, there are three types of adaptors that can be ligated to the resulting DNA fragments to maximize ligation efficiency, and preferably the adaptors are ligated to one strand at both ends of the DNA fragments. These three adaptors are illustrated in FIG. 32 and include the following: blunt end adaptor, 5' N overhang adaptor, and 3' N overhang adaptor. The combination of these 3 adaptors has been demonstrated to increase the ligation efficiency compared to any single adaptor. These adaptors are comprised of two oligos, 1 short and 1 long, that are hybridized to each other at some region along their length. In a specific embodiment, the long oligo is a 20-mer that will be ligated to the 5' end of fragmented DNA. In another specific embodiment, the short oligo strand is a 3' blocked 11-mer complementary to the 3' end of the long oligo. A skilled artisan recognizes that the length of the oligos that comprise the adaptor may be modified, in alternative embodiments. For example, a range of oligo length for the long oligo is about 18 bp to about 100 bp, and a range of oligo length for the short oligo is about 7 bp to about 20 bp. Furthermore, the structure of the adaptors has been developed to minimize ligation of adaptors to each other via at least one of three means: 1) lack of a 5' phosphate group necessary for ligation; 2) presence of about a 7 bp 5' overhang that prevents ligation in the opposite orientation; and/or 3) a 3' blocked base preventing fill-in of the 5' overhang. The ligation of a specific adaptor is detailed in FIG. 42.

A typical ligation procedure involves the incubation of 1 to 100 ng of DNA in 1×T4 DNA ligase buffer, 10 pmol of each adaptor, and 400 Units of T4 DNA Ligase. Ligations are performed at 16° C. for 1 hour, followed by inactivation of the ligase at 75° C. for 15 minutes. The products of ligation can be stored at −20° C. to 4° C. until amplification.

5. Extension of the 3' End of the DNA Fragment to Fill in the Universal Adaptor

Due to the absence of a phosphate group at the 5' end of the adaptor, only one strand of the adaptor (3' end) will be covalently attached to the DNA fragment. A 72° C. extension step is performed on the DNA fragments in the presence of 1×DNA polymerase, 1×PCR Buffer, 200 μM of each dNTP, and 1 uM universal primer. This step may be performed immediately prior to amplification using Taq polymerase, or may be carried out using a thermo-labile polymerase, such as if the libraries are to be stored for future use. The ligation and extension steps are detailed in FIG. 42.

6. One-Step Adaptor Attachment Method

In a specific embodiment, the amplification reaction comprises about 1 to about 5 ng of template DNA, universal primer T7-$C_{10}$ (SEQ ID NO: 36), Taq polymerase, 1× polymerase buffer, and 200 μM of each dNTP. In addition, fluorescein calibration dye (FCD) and SYBR Green I (SGI) may be added to the reaction to allow monitoring of the amplification using real-time PCR by methods well known in the art. PCR is carried out using a 2-step protocol of 94° C. 15 seconds, 65° C. 2 minutes for the optimal number of cycles. Optimal cycle number is determined by analysis of DNA production using either real-time PCR or spectrophotometric analysis. Typically, about 5 to about 15 μg of amplified DNA can be obtained from a 25 to 75 μl reaction using optimized conditions. The presence of the short oligo from the adaptor does not interfere with the amplification reaction due to its low melting temperature and the blocked 3' end that prevents extension.

7. Amplification of DNA Fragments Using the Universal Primer

In a specific embodiment, the amplified DNA from both restriction enzyme digested libraries and control libraries are digested with the same methylation-sensitive restriction endonuclease used in the first digestion, such as Not I. The digestion reaction contains 50 ng to 5 μg of amplified DNA, 1× reaction buffer, and 1 to 25 Units of Not I restriction endonuclease. The mixture is incubated at 37° C. for 12 to 16 hours to ensure complete digestion. The enzyme is inactivated at 65° C. for 15 minutes, and the sample is purified and resuspended to a final concentration of 1 to 50 ng/ul in TE-Lo.

In a specific embodiment, the amplification primer incorporates a poly-cytosine extension that functions to suppress secondary library amplification by C10 oligonucleotide alone (SEQ ID NO: 38). To incorporate the extension and provide optimal priming the library is amplified using a reaction mixture comprised of the universal primer T7-$C_{10}$ (SEQ ID NO: 36), Taq polymerase, 1× polymerase buffer, and 200 μM of each dNTP is incubated. In addition, fluorescein calibration dye (FCD) and SYBR Green I (SGI) may be added to the reaction to allow monitoring of the amplification using real-time PCR by methods well known in the art. PCR is carried out using a 2-step protocol of 94° C. 15 seconds, 65° C. 2 minutes for the optimal number of cycles. Optimal cycle number is determined by analysis of DNA production using either real-time PCR or spectrophotometric analysis. Typically, about 5 to about 15 μg of amplified DNA can be obtained from a 25 to 75 μl reaction using optimized conditions. The presence of the short oligo from the adaptor does not interfere with the amplification reaction due to its low melting temperature and the blocked 3' end that prevents extension.

8. Digestion of Amplified Fragments

In a specific embodiment, the amplified DNA from both restriction enzyme digested libraries and control libraries are digested with the same methylation-sensitive restriction endonuclease used in the first digestion, such as Not I. The digestion reaction comprises 50 ng to 5 μg of amplified DNA, 1× reaction buffer, and 1 to 25 Units of Not I restriction endonuclease. The mixture is incubated at 37° C. for 12 to 16 hours to ensure complete digestion. The enzyme is inactivated at 65° C. for 15 minutes and the sample is purified and resuspended to a final concentration of 1 to 50 ng/ul in TE-Lo.

9. Sequence Attachment to the Ends of DNA Fragments

The following ligation procedure is designed to work with DNA that has been digested with restriction endonucleases resulting in ends with either 5' overhangs, 3' overhangs, or blunt ends. Under optimal conditions, the digestion procedure will result in the majority of products having ends competent for ligation. The adaptor is comprised of two oligos, 1 short and 1 long, that are hybridized to each other at some region along their length. In a specific embodiment, the long oligo is a 16-mer that will be ligated to the 5' end of fragmented DNA. In another specific embodiment, the short oligo strand is a 3' blocked 14-mer that contains a 4 bp 5' overhang that is complementary to the 3' overhang generated by the restriction endonuclease Not I. A skilled artisan recognizes that the length of the oligos that comprise the adaptor may be modified, in alternative embodiments. For example, a range of oligo length for the long oligo is about 15 bp to about 100 bp, and a range of oligo length for the short oligo is about 7 bp to about 20 bp. In addition, the structure of the adaptor is based on the type of end generated by the restriction endonuclease. A 3' overhang on the long adaptor will be used for restriction endonucleases that result in a 5' overhang and a blunt end adaptor will be utilized with enzymes that produce blunt end molecules. The preferred method will utilize restriction enzymes that result in either 5' or 3' overhangs. Furthermore, the structure of the adaptors has been developed to minimize ligation of adaptors to each other via at least one of three means: 1) absence of a 5' phosphate group necessary for ligation; 2) presence of about a 7 bp 5' overhang that prevents ligation in the opposite orientation; and/or 3) presence of a 3' blocked base preventing fill-in of the 5' overhang. The ligation of a specific adaptor is detailed in FIG. 42.

A typical ligation procedure involves the incubation of 1 to 100 ng of DNA in 1×T4 DNA ligase buffer, 10 pmol of each adaptor, and 400 Units of T4 DNA Ligase. The ligations are performed at 16° C. for 1 hour, followed by inactivation of the ligase at 75° C. for 15 minutes. The products of ligation can be stored at −20° C. to 4° C. until amplification.

10. Extension of the 3' End of the DNA Fragment to Fill in the Universal Adaptor Due to the absence of a phosphate group at the 5' end of the adaptor, only one strand of the adaptor (3' end) will be covalently attached to the DNA fragment. A 72° C. extension step is performed on the DNA fragments in the presence of DNA polymerase, 1×PCR Buffer, 200 μM of each dNTP, and 1 uM universal primer. This step may be performed immediately prior to amplification using Taq polymerase, or may be carried out using a thermo-labile polymerase, such as if the libraries are to be stored for future use. The ligation and extension steps are detailed in FIG. 42.

11. Site-Specific Amplification of Selected Molecules

A site-specific amplification reaction is performed in order to amplify only those molecules that contain the second universal primer. Only molecules that were cut during the second restriction digest will have had the second universal adaptor attached. Furthermore, it is predicted that the majority of these molecules will have the second universal adaptor at only 1 end. In order to amplify these fragments, the second universal primer is utilized in conjunction with a poly C primer to selectively amplify those molecules comprising either the second universal priming site at both ends or the first amplification priming site at one end and the second universal priming site at the other end. The poly C primer is unable to amplify molecules that contain the first universal priming site at both ends (see, for example, U.S. patent application Ser. No. 10/293,048, filed Nov. 13, 2002, now U.S. Pat. No. 7,655,791; U.S. patent application Ser. No. 10/797,333, filed Mar. 8, 2004, published as U.S. Patent Application Publication No.: 2004/0209299 and is now abandoned; U.S. patent application Ser. No. 10/795,667, filed Mar. 8, 2004, now U.S. Pat. No. 7,718,403). In a specific embodiment, the amplification reaction comprises about 1 to 5 ng of template DNA, Taq polymerase, 1× polymerase buffer, 200 μM of each dNTP, and 1 uM each of universal primers $K_U$ and $C_{10}$ (SEQ ID NO:15 and SEQ ID NO:38, respectively). In addition, fluorescein calibration dye (FCD) and SYBR Green I (SGI) may be added to the reaction to allow monitoring of the amplification using real-time PCR by methods well known in the art. PCR is carried out using a 2-step protocol of 94° C. 15 seconds, and 65° C. 2 minutes for the optimal number of cycles. Optimal cycle number is determined by analysis of DNA production using either real-time PCR or spectrophotometric analysis. Typically, about 5 to 15 μg of amplified DNA can be obtained from a 25 to 75 μl reaction using optimized conditions. The presence of the short oligo from the adaptor does not interfere with the amplification reaction due to its low melting temperature and the blocked 3' end that prevents extension.

12. One-Step Adaptor Attachment Method

In a specific embodiment, a one-step process utilizing a dU-Hairpin Adaptor method described in Example 33, 38, and 39 can be used for attachment of the universal adaptor.

In a specific embodiment, attachment of such an adaptor comprises providing in a single reaction the following: a double stranded DNA molecule; an adaptor, which may be referred to as an oligonucleotide, comprising an inverted repeat with a non base-paired loop; DNA polymerase comprising 3'-5' exonuclease activity; DNA polymerase comprising 5'-3' polymerase activity (and these polymerase activities may be comprised on the same molecule or on different molecules); DNA ligase; dNTPs; and ATP, under conditions wherein the adaptor becomes blunt-end ligated to one strand of the DNA molecule, thereby producing an adaptor-ligated DNA molecule comprising a nick having a 3' hydroxyl group, wherein there is polymerization from the 3' hydroxyl group of at least part of the adaptor-ligated DNA molecule. Such a method may be further defined as comprising the following actions: producing blunt ends of the DNA molecule; producing blunt ends of the adaptor; and ligating the blunt end of the adaptor to a blunt end of the DNA molecule, thereby generating a nick in the adaptor-ligated DNA molecule.

In a specific aspect of this embodiment, polymerization of the adaptor-ligated DNA molecule excluding at least part of the inverted repeat is further defined as subjecting the adaptor-ligated DNA molecule to nick translation.

The adaptor may further comprise a non-replicable base or region and wherein polymerization ceases at said non-replicable base or region, and the non-replicable base or region may be present in the loop of the adaptor. In specific embodiments, the non-replicable base or region comprises deoxyuracil (dU) or hexaethylene glycol.

In some aspects of this embodiment, the polymerization of the adaptor-ligated DNA molecule generates an endonuclease site, such as a site-specific restriction endonuclease site and wherein at least part of the inverted repeat is removed by cleavage with said restriction endonuclease, for example. In specific embodiments, the restriction endonuclease is Eco NI or Bst UI. In another specific embodiment, the loop of the adaptor comprises about 3 dU nucleotides and wherein the endonuclease is apurunic/apyrimidinic endonuclease (APE-endonuclease).

In further specific embodiments, the single reaction is further defined as occurring at one temperature. In other specific embodiments, the adaptor is removed by 5' exonuclease. In specific embodiments, a 5' end of the adaptor lacks a phosphate.

In further embodiments, the prepared molecule is subjected to amplification and may comprise polymerase chain reaction, for example. The prepared molecule may be subjected to cloning.

In another specific aspect of this embodiment, attaching the adaptor comprises the step of providing in a single reaction the following: a double stranded DNA molecule; an adaptor comprising an inverted repeat and a loop, said loop comprising about 6-10 nucleotides; DNA polymerase comprising 3'-5' exonuclease activity; DNA polymerase comprising 5' endonuclease activity (activities that may or may not be on the same molecule); DNA ligase; dNTPs; and ATP, under conditions wherein the adaptor becomes blunt-end ligated to one strand of the DNA molecule, thereby producing an adaptor-ligated DNA molecule comprising a nick having a 3' hydroxyl group, wherein there is polymerization from the 3' hydroxyl group of at least part of the adaptor-ligated DNA molecule.

In a specific embodiment, the DNA molecule comprises two or more abasic sites, such as wherein the DNA molecule is subjected to apurinization with low pH and high temperature. In other specific embodiments, the method comprises subjecting the adaptor-ligated DNA molecule to polymerase chain reaction, wherein the polymerase chain reaction utilizes said adaptor as a primer.

13. Site-Specific Amplification of Selected Molecules

A site-specific amplification reaction is performed in order to amplify only those molecules that comprise the second universal primer. Only molecules that were cut during the second restriction digest will have had the second universal adaptor attached. Furthermore, it is predicted that the majority of these molecules will have the second universal adaptor at only 1 end. In order to amplify these fragments, the second universal primer is utilized in conjunction with a poly C primer to selectively amplify those molecules comprising either the second universal priming site at both ends or the first amplification priming site at one end and the second universal priming site at the other end. The poly C primer is unable to amplify molecules that comprise the first universal priming site at both ends (see, for example, U.S. patent application Ser. No. 10/293,048, now U.S. Pat. No. 7,655,791; U.S. patent application Ser. No. 10/795,667, filed Mar. 8, 2004; now U.S. Pat. No. 7,718,403, U.S. patent application Ser. No. 10/797,333, filed Mar. 8, 2004, published as U.S. Patent Application Publication No.: 2004/0209299 and is now abandoned). In a specific embodiment, the amplification reaction comprises about 1 to 5 ng of template DNA, Taq polymerase, 1× polymerase buffer, 200 μM of each dNTP, and 1 uM each of universal primers $K_U$ and $C_{10}$ (SEQ ID NO:15 and SEQ ID NO:38, respectively). In addition, fluorescein calibration dye (FCD) and SYBR Green I (SGI) may be added to the reaction to allow monitoring of the amplification using real-time PCR by methods well known in the art. PCR is carried out using a 2-step protocol of 94° C. 15 seconds, and 65° C. 2 minutes for the optimal number of cycles. Optimal cycle number is determined by analysis of DNA production using either real-time PCR or spectrophotometric analysis. Typically, about 5 to 15 μg of amplified DNA can be obtained from a 25 to 75 μl reaction using optimized conditions. The presence of the short oligo from the adaptor does not interfere with the amplification reaction due to its low melting temperature and the blocked 3' end that prevents extension.

14. Analysis of Amplified Products to Determine Methylation Status

The amplified DNA products are analyzed using real-time, quantitative PCR using markers that are adjacent to Not I restriction sites. A panel of 14 typical and exemplary markers is listed in Table II. In a specific embodiment, 25 μl reactions were amplified for 40 cycles at 94° C. for 15 seconds and 65° C. for 1 minute. Standards corresponding to 10, 1, and 0.2 ng of fragmented DNA were used for each marker while samples are tested at multiple dilutions, typically 1:10 to 1:1000, to ensure that they amplify within the boundaries of the standard curve. Quantities are calculated by standard curve fit for each marker and are plotted as histograms. All markers should be successfully amplified in the control DNA. Markers that are present in the restriction enzyme digested sample are considered to be sites that were methylated in the original molecule.

TABLE II

HUMAN MARKERS USED FOR METHYLATION ANALYSIS BY QUANTITATIVE REAL-TIME PCR

| #* | Accession #** | Forward Primer | Reverse Primer |
|---|---|---|---|
| 21 | AJ322533 | GAAACCCCTCAGCAACCTACC (SEQ ID NO: 69) | GCCCTTCATCCCGTATCACTT (SEQ ID NO: 70) |
| 22 | AJ322546 | CATCAGGAATGTGGAAGTCGG (SEQ ID NO: 71) | TGCTGCGGTGACAGTGTGA (SEQ ID NO: 72) |
| 23 | AJ322610 | AGCCTGACGGAGAACATCTGG (SEQ ID NO: 73) | GCCTGAGGTCACTGAGGTTGG (SEQ ID NO: 74) |
| 26 | AJ322559 | TGGCTCCTGAAATCAGACCTG (SEQ ID NO: 75) | GATTGTGTGGGTGTGAGTGGG (SEQ ID NO: 76) |
| 27 | AJ322568 | CGTCCACACCCTCCAACCAC (SEQ ID NO: 77) | CGCAGGAAACACAGACCAAAC (SEQ ID NO: 78) |
| 28 | AJ322570 | CTGGTCGCAGATTGGTGACAT (SEQ ID NO: 79) | GGCAAAAATGCAGCATCCTA (SEQ ID NO: 80) |
| 29 | AJ322572 | CCTTGTCAGGATGGCACATTG (SEQ ID NO: 81) | CCGTCTCACACGCACCCTCT (SEQ ID NO: 82) |
| 31 | AJ322623 | GCAATACGCTCGGCAATGAC (SEQ ID NO: 83) | CGGGTAAGGAGGTGGGAACAC (SEQ ID NO: 84) |
| 35 | AJ322781 | GTCAACCCAGCCTGTGTCTGA (SEQ ID NO: 85) | GGATGGTCACCCTGTTGGAG (SEQ ID NO: 86) |
| 36 | AJ322715 | GCTGAGGTTCGGCAAGTCTCC (SEQ ID NO: 87) | AGCCCCCAGTTCCTTTCAATC (SEQ ID NO: 88) |
| 37 | AJ322747 | ACCAGGCACATGAGACAAGGA (SEQ ID NO: 89) | GGGCACCTGCTGTGACTTCT (SEQ ID NO: 90) |
| 38 | AJ322801 | CGAGAAATTCCCGAAACGAGA (SEQ ID NO: 91) | GCCCCTTGAGAATACCTTGCT (SEQ ID NO: 92) |
| 44 | AJ322670 | GCAGAGCAAATTCGGGATTC (SEQ ID NO: 93) | CGGCTGAACTGATTCGGAAGT (SEQ ID NO: 94) |
| 46 | AJ322761 | GCGTTCTCAACTGCGATTCC (SEQ ID NO: 95) | TGCCCTTCCTGTGAAAGCACT (SEQ ID NO: 96) |

*Omitted sequential numbers indicate dropped sequences that did not amplify well in quantitative RT-PCR.
**Accession number of marker sequences from GENBANK ®. Sequences of the regions from which the primers were designed can be found in the nucleotide database at the National Center for Biotechnology Information's website.

TABLE III

METHYLATION-SENSITIVE RESTRICTION ENZYMES WHERE CLEAVAGE IS BLOCKED AT ALL METHYLATED SITES. POTENTIAL METHYLATION SITES (CG) ARE IN BOLD CAPITALS

| Enzyme | Sequence |
|---|---|
| Aat II | gaCGtc |
| Aci I | cCGc |
| Acl I | aaCGtt |
| Afe I | agCGct |
| Age I | acCGgt |

TABLE III-continued

METHYLATION-SENSITIVE RESTRICTION ENZYMES WHERE CLEAVAGE IS BLOCKED AT ALL METHYLATED SITES. POTENTIAL METHYLATION SITES (CG) ARE IN BOLD CAPITALS

| Enzyme | Sequence |
| --- | --- |
| Asc I | ggCGCGcc |
| AsiS I | gCGatCGc |
| Ava I | cyCGrg |
| BceA I | aCGgc |
| BmgB I | caCGtc |
| BsaA I | yaCGtr |
| BsaH I | grCGyc |
| BsiE I | CGryCG |
| BsiW I | CGtaCG |
| BsmB I | CGtctc |
| BspD I | atCGat |
| BspE I1 | tcCGga |
| BsrB I1 | cCGctc |
| BsrF I | rcCGgy |
| BssH II | gCGCGc |
| BstB I | ttCGaa |
| BstU I | CGCG |
| Cla I | atCGat |
| Eag I | CGgcCG |
| Fau I | ccCGc |
| Fse I | ggCCGgcc |
| Fsp I | tgCGca |
| Hae II | rgCGcy |
| Hga I | gaCGc |
| Hha I | gCGc |
| HinP1 I | gCGc |
| Hpa II | cCGg |
| Hpy99 I | CGwCG |
| HpyCH4 IV | aCGt |
| Kas I | ggCGcc |
| Mlu I | aCGCGt |
| Nae I | gcCGgc |
| Nar I | ggCGcc |
| NgoM IV | gcCGgc |
| Not I | gCGgcCGc |
| Nru I | tCGCGa |
| PaeR7 I1 | ctCGag |
| Pml I | caCGtg |
| Pvu I | CGatCG |
| Rsr II | CGgwcCG |
| Sac II | cCGCGg |
| Sal I | gtCGac |
| Sfo I | ggCGcc |
| SgrA I | crcCGgyg |
| Sma I | ccCGgg |
| SnaB I | taCGta |
| Til I1 | ctCGag |
| Xho I1 | ctCGag |

Figure 33A:
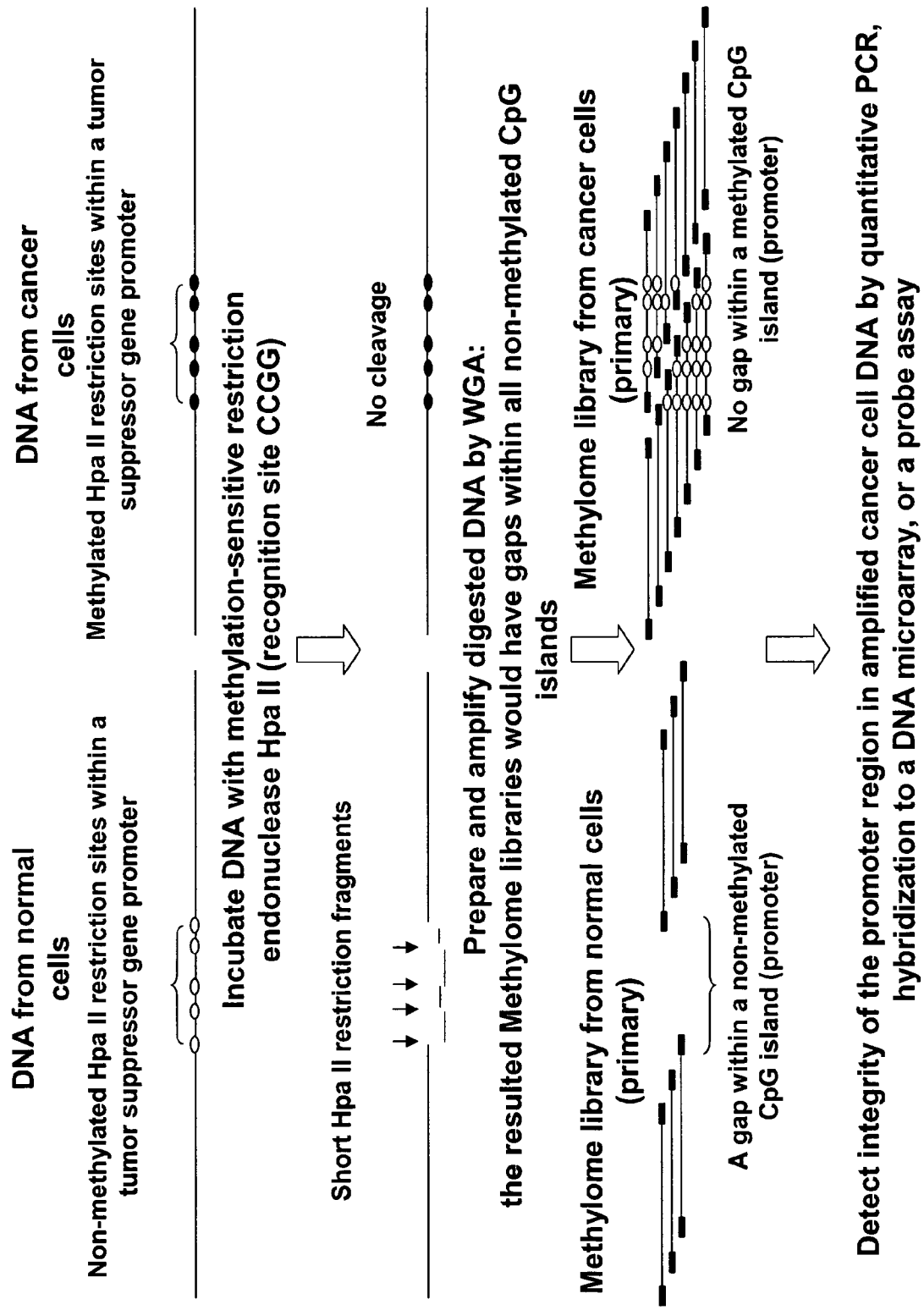
FIG. 33A depicts a method for detecting DNA methylation in cancer cells using methylation-sensitive restriction endonucleases and whole genome amplification. DNA from cancer and normal cells is incubated in the presence of a methylation-sensitive restriction endonuclease, such as, for example, Hpa II. This results in the cleavage of DNA from normal cells containing the Hpa II recognition sites, but not the DNA from cancer cells that is methylated. Primary Methylome libraries are prepared and amplified resulting in all sequences amplified in the cancer cells, while the promoter sequences containing the Hpa II restriction sites in the normal cells are not amplified due to the fact that they are cleaved during the digestion step. Analysis of the resulting DNA products allows the determination of which samples contained methylated restriction sites, as only those sites are detectable.
Figure 33B:
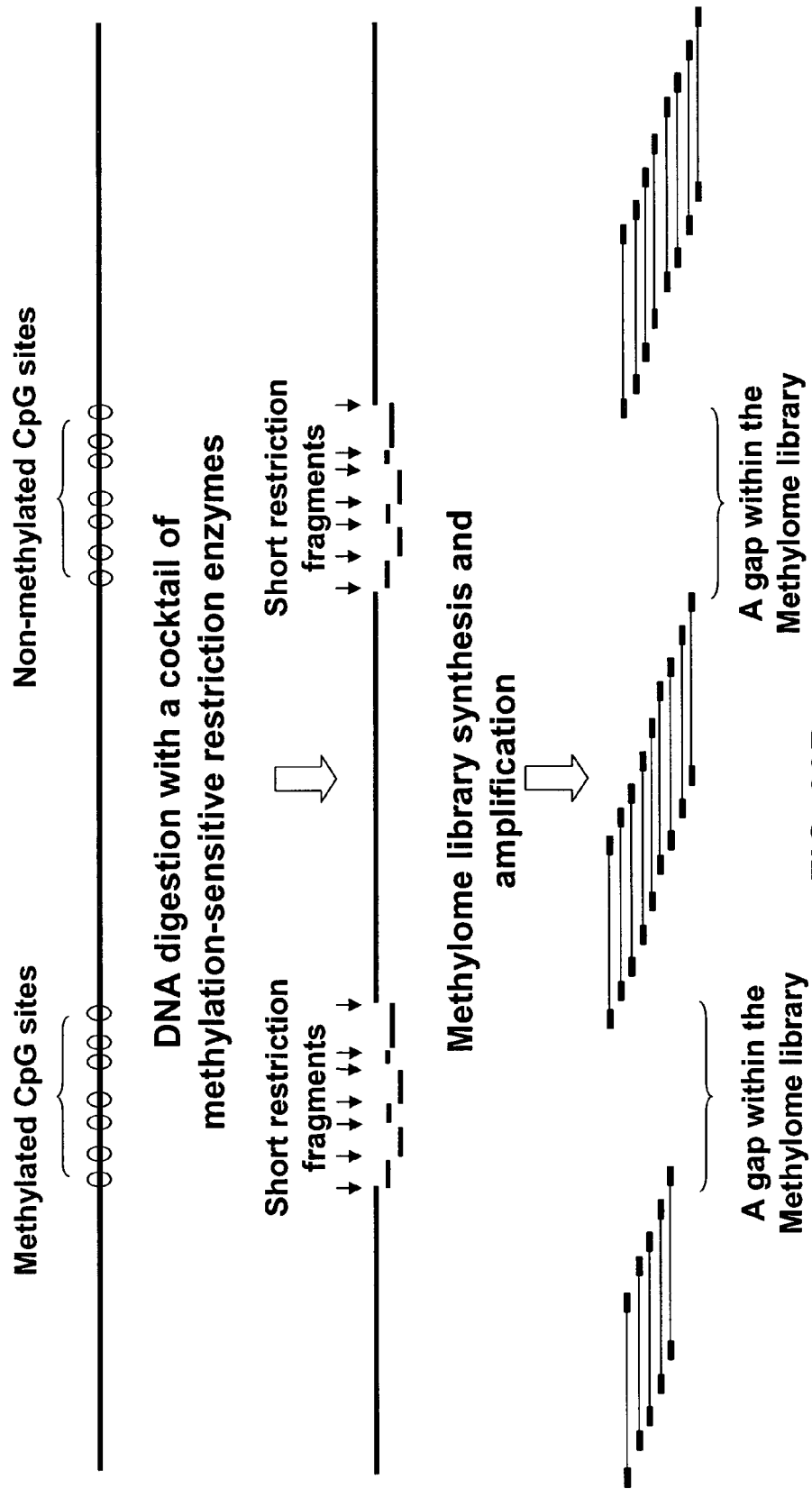
FIGS. 33B and 33C illustrate the method of synthesis of Methylome library similar to that shown on FIG. 33A with the only major difference that being instead of one enzyme a mix of multiple methylation-sensitive restriction enzymes is used in one reaction to efficiently cleave all non-methylated CpG-rich regions (islands) within the DNA. A nuclease cocktail converts such regions into very short DNA fragments that fail to amplify efficiently by the implemented whole methylome amplification (WMA) method.
Figure 33:
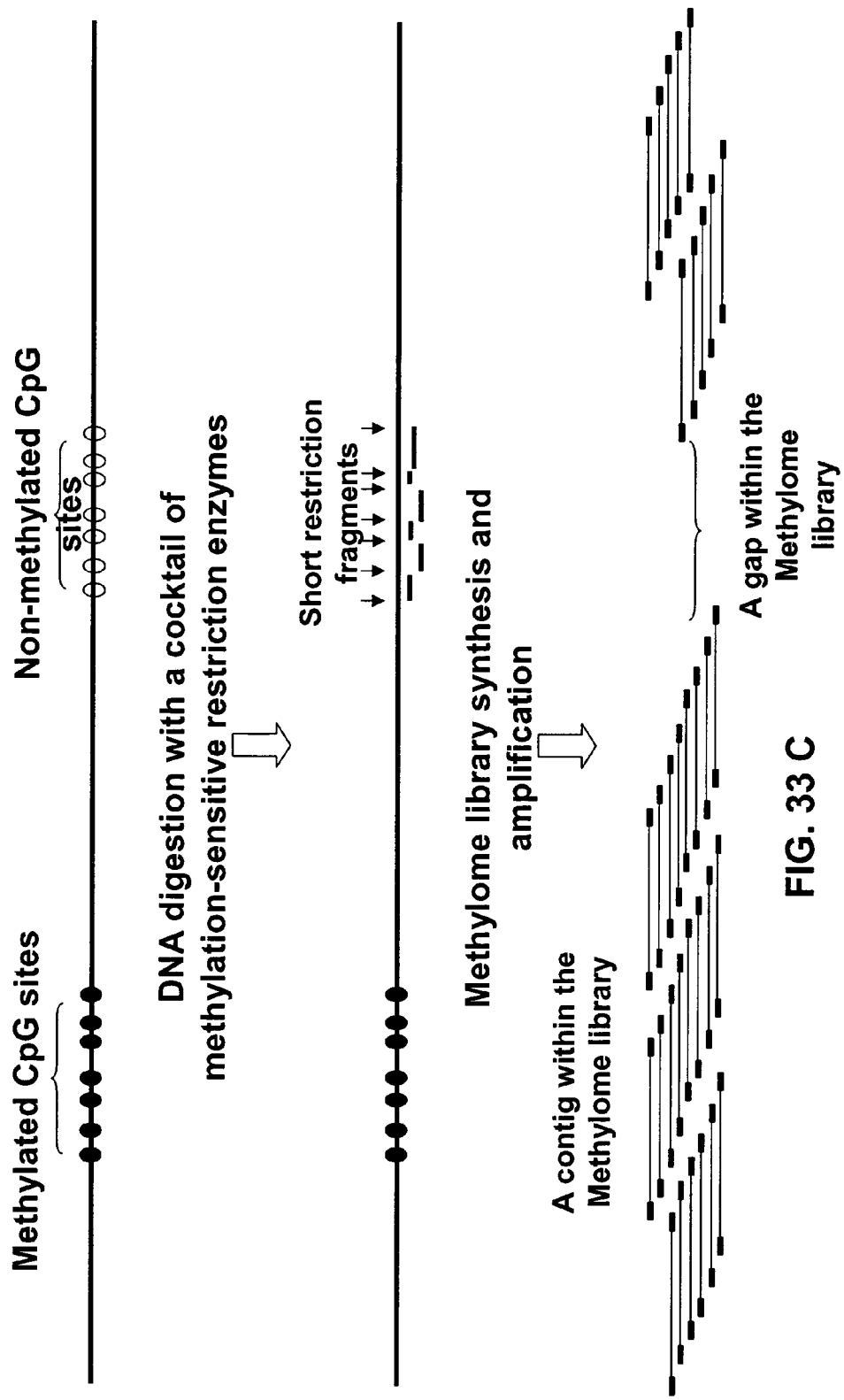
FIGS. 33D and 33E illustrate similarity in distribution of the density of CpG dinucleotides and restriction sites for more than one restriction endonuclease, such as from the following, for example: 11 restriction nucleases (Aci I, BstU I, Hha I, HinP1 I, Hpa II, Hpy 99I, Ava I, Bce AI, Bsa HI, Bsi E1, and Hga I) that can be used in one reaction cocktail for preparation of Methylome libraries.
Figure 35:
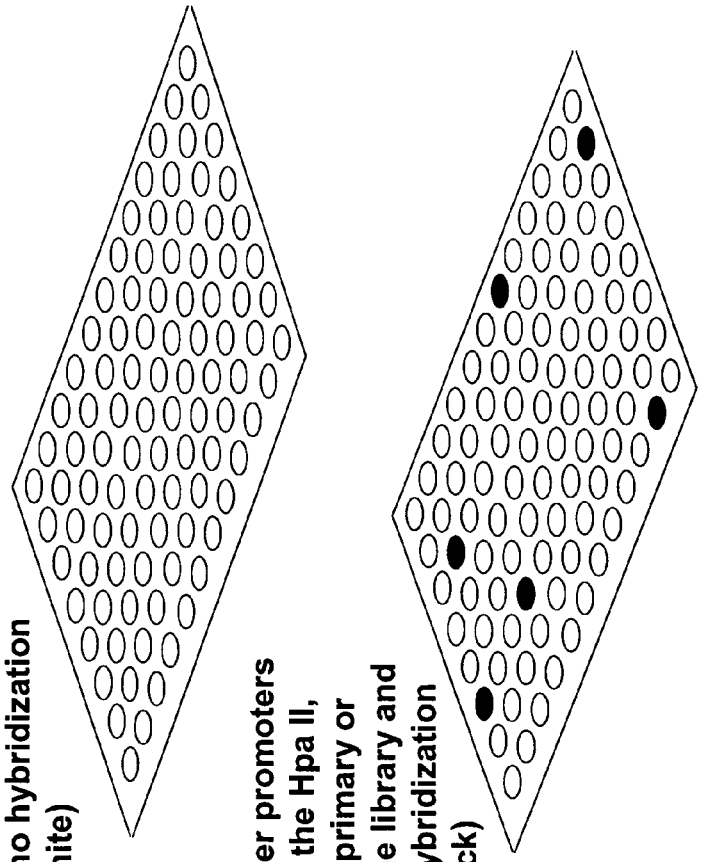
FIG. 35 demonstrates the use of DNA array hybridization for the analysis of the products produced in FIG. 33. Promoter sites of interest can be spotted on an array and hybridized with amplified products from normal or cancer cells. Normal cells, which exhibit low levels of methylation, will have very few, if any, sites that can be detected. In contrast, the detection of methylated promoters in cancer samples will result in a strong hybridization signal. Control hybridizations, such as using undigested genomic DNA, will validate the detection of all promoter sites.
Figure 51:
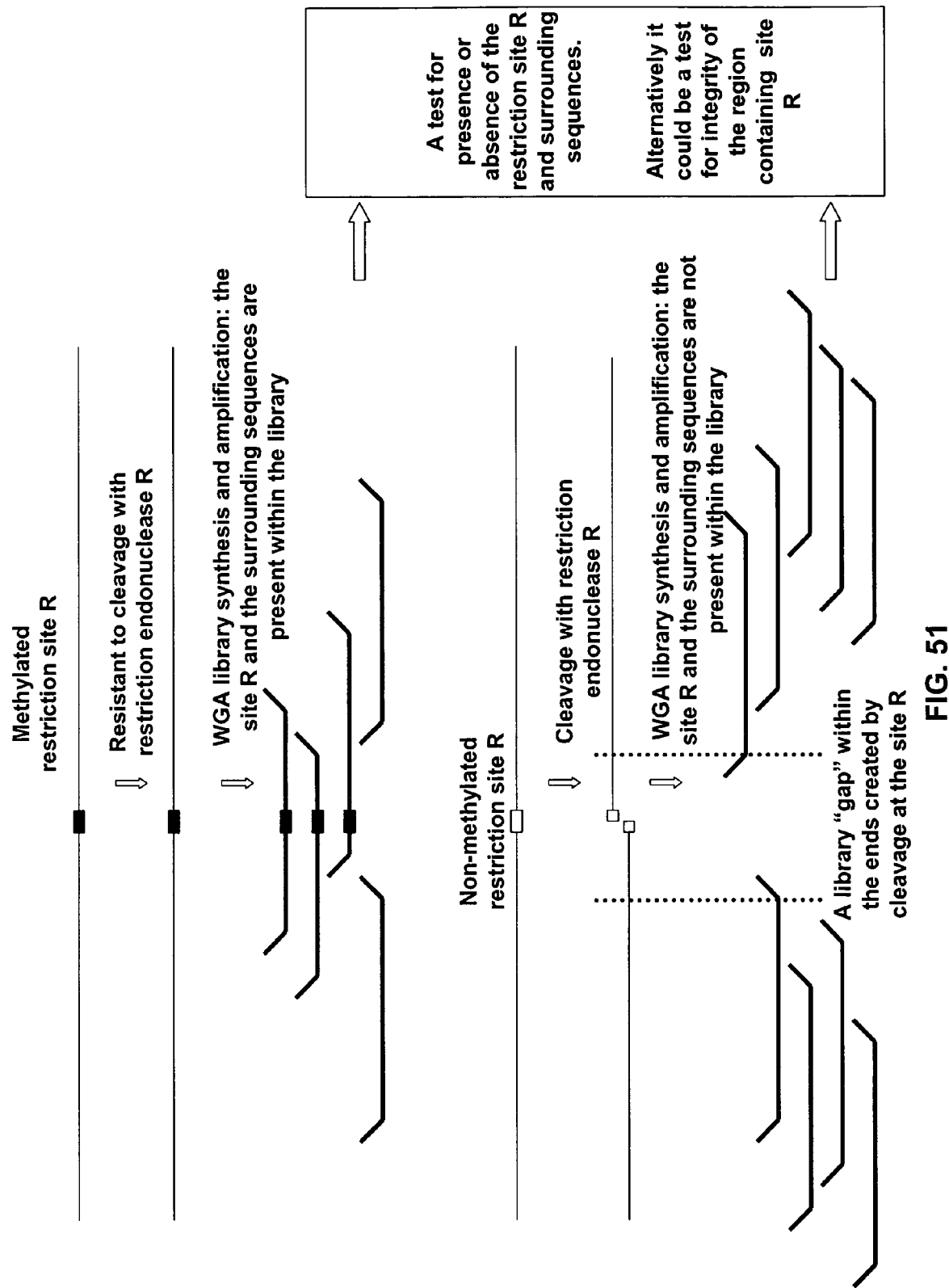
FIG. 51 depicts a comparison of the results of amplification of DNA wherein a single methylated site is not cleaved by a methylation-sensitive restriction endonuclease versus a single unmethylated site that is cleaved by a methylation-sensitive restriction endonuclease. In this example, the methylated site is amplified in the WGA libraries and can be detected by methods sensitive to the presence of both the site of interest and the surrounding sequences. In contrast, the non-methylated site is not incorporated into the library preparation or amplification steps and is not detectable by methods sensitive to the presence of the site of interest. Furthermore, the nature of the library synthesis reaction will produce, in the majority of instances, the exclusion of the sequences surrounding the site of interest. This gap is due to the random nature of the priming reaction used during library synthesis and the statistical improbability of priming directly adjacent to the site of cleavage.

D. Methylation Analysis Method Using Methylome Libraries Constructed from DNA Digested with Frequently Cutting Methylation-Sensitive Restriction Enzymes or Libraries Subjected to Similar Digestion after Construction In this embodiment, there are methods of preparing a library of DNA molecules to select for sequences that comprise recognition sites for methylation-sensitive restriction enzymes in regions of high GC content such as promoter CpG islands (FIGS. 33A, 33B, and 33C). After digestion of DNA with one (FIG. 33A) or a mixture of several, for example, 5 or more (FIGS. 33B and 33C) frequently cutting (4-5 base recognition site) methylation-sensitive restriction enzymes, a Methylome library is prepared by incorporating a universal sequence using primers comprising a universal sequence at their 5'-end and a degenerate non-self-complementary sequence at their 3'-end in the presence of DNA polymerase with strand-displacement activity (U.S. patent application Ser. No. 10/795,667, filed Mar. 8, 2004, now U.S. Pat. No. 7,718,403). The enzymes used for the DNA cleavage may include (but are not limited to) such commercially available restriction endonucleases as Aci I, Bst UI, Hha I, HinP1, Hpa II, Hpy 99I, Ava I, Bce AI, Bsa HI, Bsi E1, and Hga I, for example. The spatial distribution of recognition sites for these 11 nucleases in the human genome closely mimics the distribution of the CpG dinucleotides, with their density being especially high in many CpG-rich promoter regions (FIGS. 33D and 33E). As a result of cleavage, non-methylated CpG-rich regions such as gene promoters in normal cells are digested to very short fragments (FIG. 33B) while methylated CpG regions such as hypermethylated gene promoters in cancer cells remain intact (FIG. 33C). The Methylome DNA library may next be amplified in a PCR reaction with a primer comprising the universal sequence and a thermo-stable DNA polymerase. In the process of Methylome library synthesis and subsequent amplification, only those DNA molecules protected from cleavage by CpG methylation will amplify, whereas non-methylated DNA molecules are efficiently cleaved into small fragments that fail to be efficiently primed or converted into library amplicons. The digestion of non-methylated CpG regions results in a gap or loss of representation of these sequences in primary Methylome libraries, FIGS. 33A and 33B, and FIG. 51, Example 18). The presence of a specific DNA region encompassing a site or a group of sites in the final amplified Methylome libarary indicates that the CpG contained in the methylation-sensitive restriction site or a group of sites was methylated in the DNA template. The methylation status of any particular CpG site may be analyzed by any of a number of specific analytical methods known in the art, such as quantitative real-time PCR, LCR, ligation-mediated PCR, probe hybridization, probe amplification, microarray hybridization, a combination thereof, or other suitable methods in the art (FIG. 34 and FIG. 35, for example). Furthermore, use of control DNA that is not digested by the restriction enzyme during the initial library preparation (Whole Genome library) will allow validation of the selection of each site during library preparation and amplification.

In one specific embodiment (such as is described in Example 28), there is a method for improving the restriction enzyme cleavage efficiency by pre-heating genomic DNA at 85° C., and specifically as it pertains to cleavage by the restriction enzyme AciI within the GC-rich promoter regions. GC-rich DNA sequences, through interactions with proteins, may form alternative (non-Watson-Crick) DNA conformation(s) that are stable even after protein removal and DNA purification. These putative DNA structures could be resistant to restriction endonuclease cleavage and affect the performance of the methylation assay. Heating DNA at an elevated temperature (but not too high to melt the DNA) reduces the energetic barrier and accelerates the transition of DNA from a non-canonical form to a classical Watson-Crick structure.

Figure 43A:
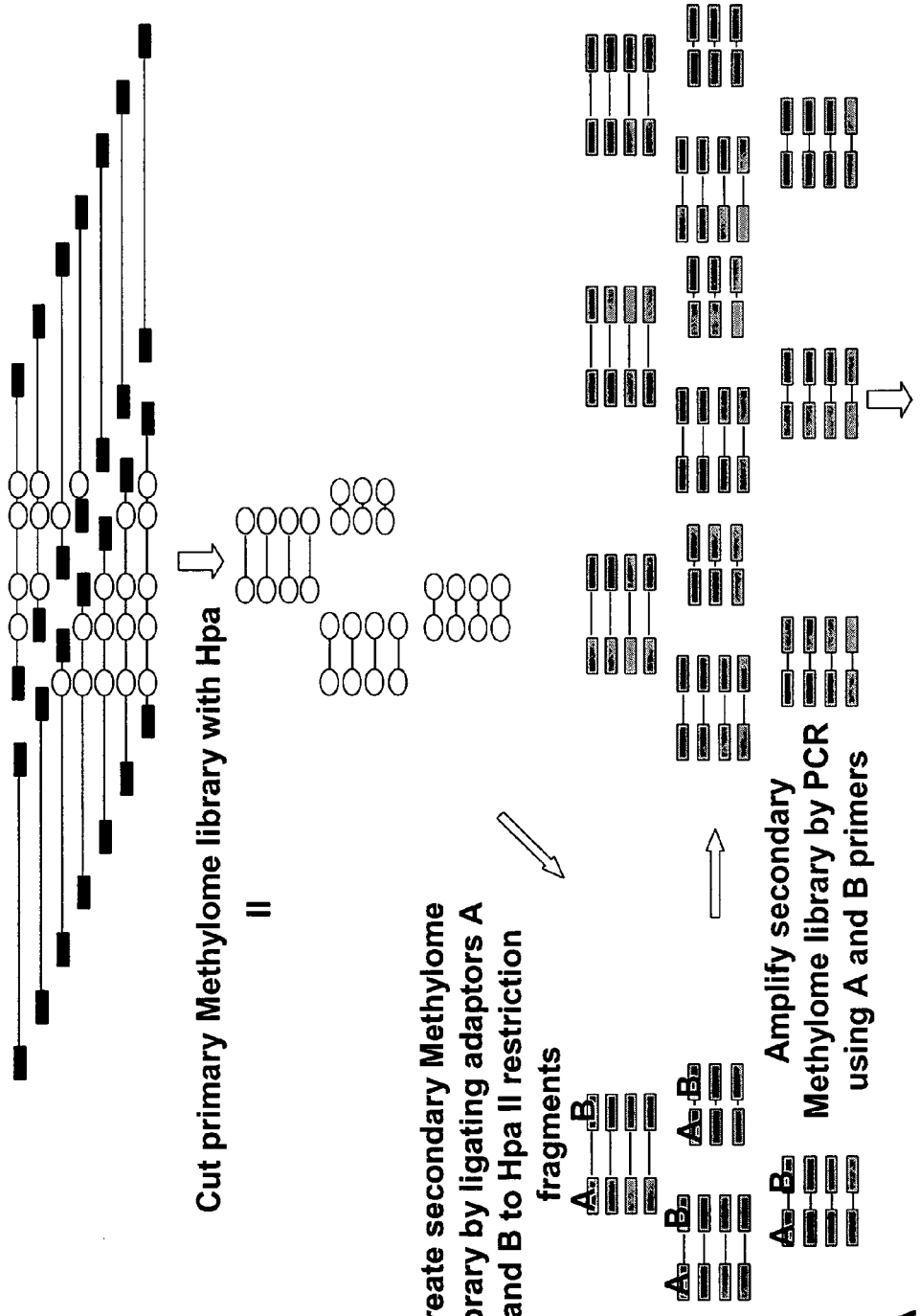
FIG. 43A illustrates a method for the preparation and analysis of a secondary Methylome library from a primary Methylome library prepared by using only one methylation sensitive restriction enzyme (Hpa II). Briefly, amplicons from a primary Methylome library are digested with the same restriction endonuclease utilized in the creation of the primary library. A mixture of two adaptors (A and B) is ligated to the resulting cleaved ends to create the secondary Methylome library. PCR is then performed to amplify only those molecules that have adaptors A and B on either end. These amplified products are highly enriched for methylated promoter sequences and can be analyzed by microarray hybridization, PCR, capillary electrophoresis, or other methods known in the art.
Figure 43B:
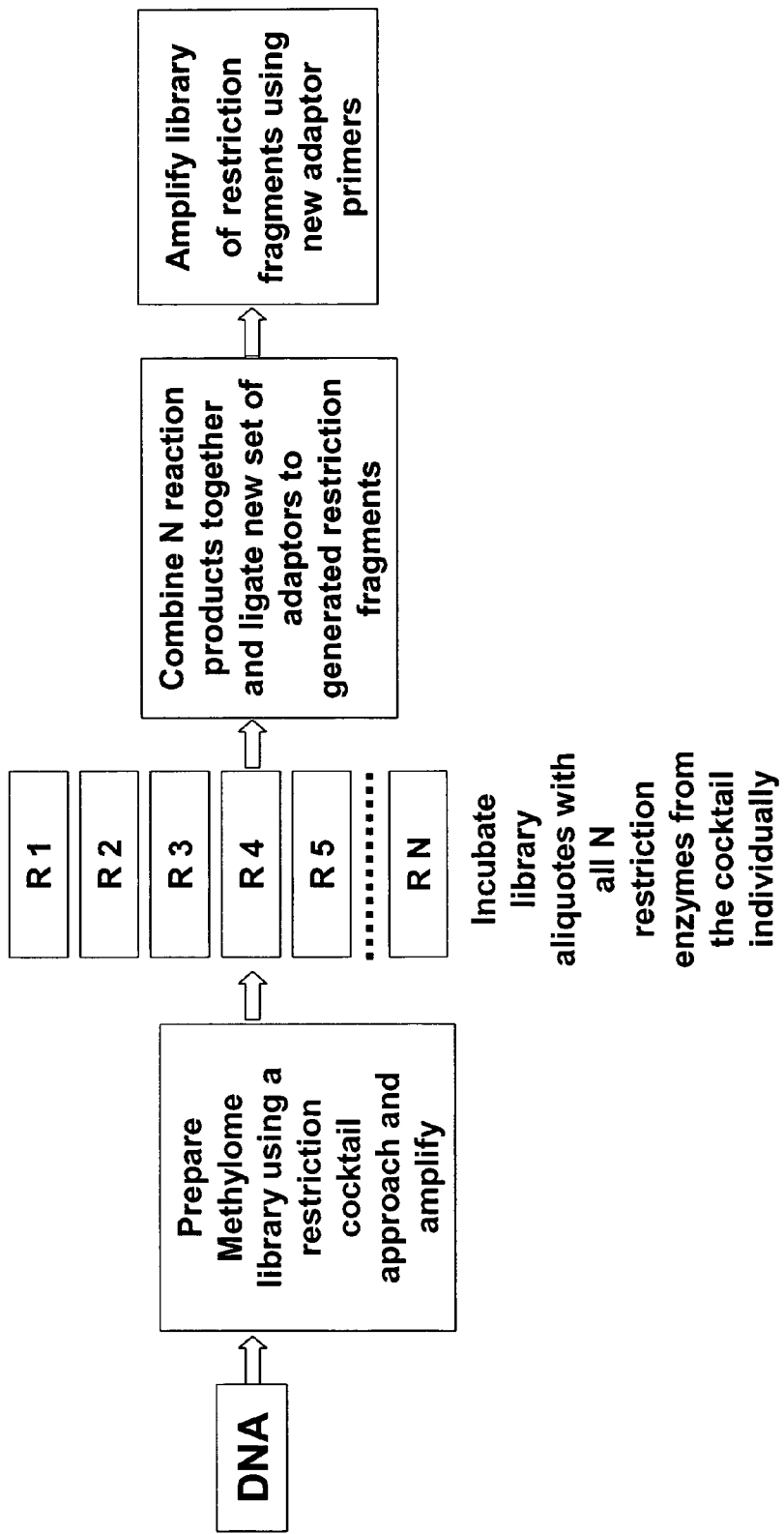
FIG. 43B illustrates a method for the preparation and analysis of a secondary Methylome library from a primary Methylome library prepared by using a restriction enzyme cocktail of 5 or more methylation-sensitive restriction enzymes. Briefly, DNA aliquots from a primary Methylome library are digested separately with the restriction endonucleases $R_1, R_2, R_3, \ldots, R_N$ utilized in the synthesis of the primary library. Products of digestion are combined together and a mixture of two adaptors (A and B) is ligated to the resulting cleaved ends to create the secondary Methylome library. PCR is then performed to amplify only those molecules that have adaptors A and B on either end. These amplified products are highly enriched for methylated promoter sequences and can be analyzed by microarray hybridization, PCR, capillary electrophoresis, or other methods known in the art. It should also be noted that within this library the same genomic region is usually represented by many different restrtiction fragments, thus creating a redundancy and improved representation that is critical for many downstream applications of secondary library including microarray analysis, for example.

In a second specific embodiment, there are methods for preparing a secondary library of DNA molecules from the amplification products of the primary Methylome library in such a way as to enrich for only those sequences that are between methylated restriction endonuclease sites present in the primary library. An outline of this method is detailed in Example 22 and is depicted in FIG. 43A 43B. Following amplification of the primary methylation library, all of the previously methylated restriction endonuclease recognition sites are converted to unmethylated sites. Digestion of these molecules with the same restriction endonuclease utilized in construction of the primary library will result in cleavage of these sites (FIG. 43A). Following cleavage, a mixture of 2 or more secondary adaptors may be ligated to the resulting newly cleaved ends. Two or more secondary adaptors are utilized to allow amplification of small molecules that would not be amplified, due to PCR suppression, if the same adaptor sequence was present at both ends. Amplification with primers complementary to these secondary adaptors will only amplify those molecules that contain the secondary adaptors at both ends. These amplimers will correspond to sequences between recognition sites that were originally methylated in the starting material (secondary Methylome library). In a preferred embodiment (Example 29), there is a demonstration of the utility of the Methylome library prepared from DNA digested with a mixture of several methylation-sensitive restriction enzymes for analysis of the methylation status of promoter regions for 24 exemplary genes in leukemia cell line DNA. The invention employs the use of five exemplary methylation-sensitive restriction enzymes, specifically, Aci I, Bst UI, Hha I, HinP1 I, and Hpa II, to convert intact non-methylated CpG-rich promoter regions into restriction fragments that fall below the minimum length competent for amplification by degenerate primary Methylome library. Secondary Methylome libraries are subsequently prepared using a mixture of several (5 or more) methylation-sensitive restriction enzymes, the secondary library can be prepared by mixing together the products of several individual restriction digests of the primary Methylome library (using individually the same restriction endonucleases that have been utilized in the primary library nuclease cocktail), ligating secondary adaptors, and amplifying with universal primer whole genome amplification (WGA) method (see, for example, U.S. patent application Ser. No. 10/293,048, filed Nov. 13, 2002, now U.S. Pat. No. 7,655,791), while methylated CpG-rich promoter regions resistant to digestion are efficiently amplified specific to the secondary adaptors (FIG. 43B). Analysis of these amplicons can be carried out by PCR, microarray hybridization, probe assay, capillary electrophoresis, sequencing, or other methods known in the art (Example 18, FIG. 34 and FIG. 35), for example. Sequencing of these products can provide a tool for discovering regions of methylation not previously characterized, as no a priori knowledge of the sequences is required and the reduced complexity of the enriched secondary library allows analysis of a small number of methylated regions.

The importance of implementation of multiple methylation-sensitive restriction enzymes in methylome library preparation stems from the analysis of promoter regions in the human genome. The spatial distribution of methylation-sensitive restriction sites that include restriction endonucleases with 4 and 5 base recognition sites such as Aci I, Bst UI, Hha I, HinP1 I, Hpa II, Hpy 99I, Hpy CH4 IV, Ava I, Bce AI, Bsa HI, Bsi E1. A specific method for the analysis of this reduced complexity secondary methylation library is presented in Example 23 and FIG. 44. Briefly, the number of molecules present in the secondary library is a function of the number of methylated CpG islands in the genome, and the average number of methylation-specific restriction endonuclease sites within each island. For example, if 1% of the approximately 30,000 CpG islands are hypermethylated, and there are 5 Hpa II restriction sites per CpG island, then there would be approximately 1,200 amplified fragments present in the secondary library. Amplification of this library with a mixture of 4 (A) primers and Hga I closely mimics the distribution of the CpG dinucleotides in these regions. When DNA is incubated with a single methylation sensitive enzyme the resulting digestion is incomplete with many restriction sites remaining uncut. Factors contributing to this phenomenon are likely the extremely high GC-content and potential for alternative secondary structure. As a result, DNA pre-treated with one restriction enzyme may still contain substantial amounts of uncut non-methylated sites. Co-digestion of DNA with a cocktail of 5 or more methylation-sensitive restriction enzymes results in efficient conversion of all non-methylated CpG island into very small DNA fragments while leaving completely methylated CpG regions intact. Subsequently, whole genome amplification (WGA) of DNA pre-treated with the restriction enzyme cocktail using universal $K_U$ primer (SEQ ID NO: 15) results in amplification of all DNA regions except the CpG- and restriction site-rich regions that were not methylated in the original DNA. These regions are digested into fragments that fail to amplify using the random-primed WGA method. Multiple-enzyme-mediated depletion of non-methylated promoter regions in the amplified methylome library is so efficient that non-methylated CpG-rich regions can not be detected by PCR. Those regions encompassing densely methylated CpG islands are not affected by the enzyme cocktail treatment and are efficiently amplified by the WGA process and can be later easily detected and quantified by real-time PCR.

The presence of methylated DNA within 24 cancer gene promoters was analyzed by quantitative real-time PCR using amplified libraries and a panel of 40 specific primer pairs. Primers were designed to test the libraries for amplicons spanning CpG-rich regions within promoters. The presence or absence of amplification for specific sequences that display a high frequency of potential cleavage sites was indicative of the methylation status of the promoter. Initially a set of 24 promoters frequently implicated in different types of cancer were evaluated. The exemplary primer pairs used in the PCR assays are listed in Table IV.

Figure 65:
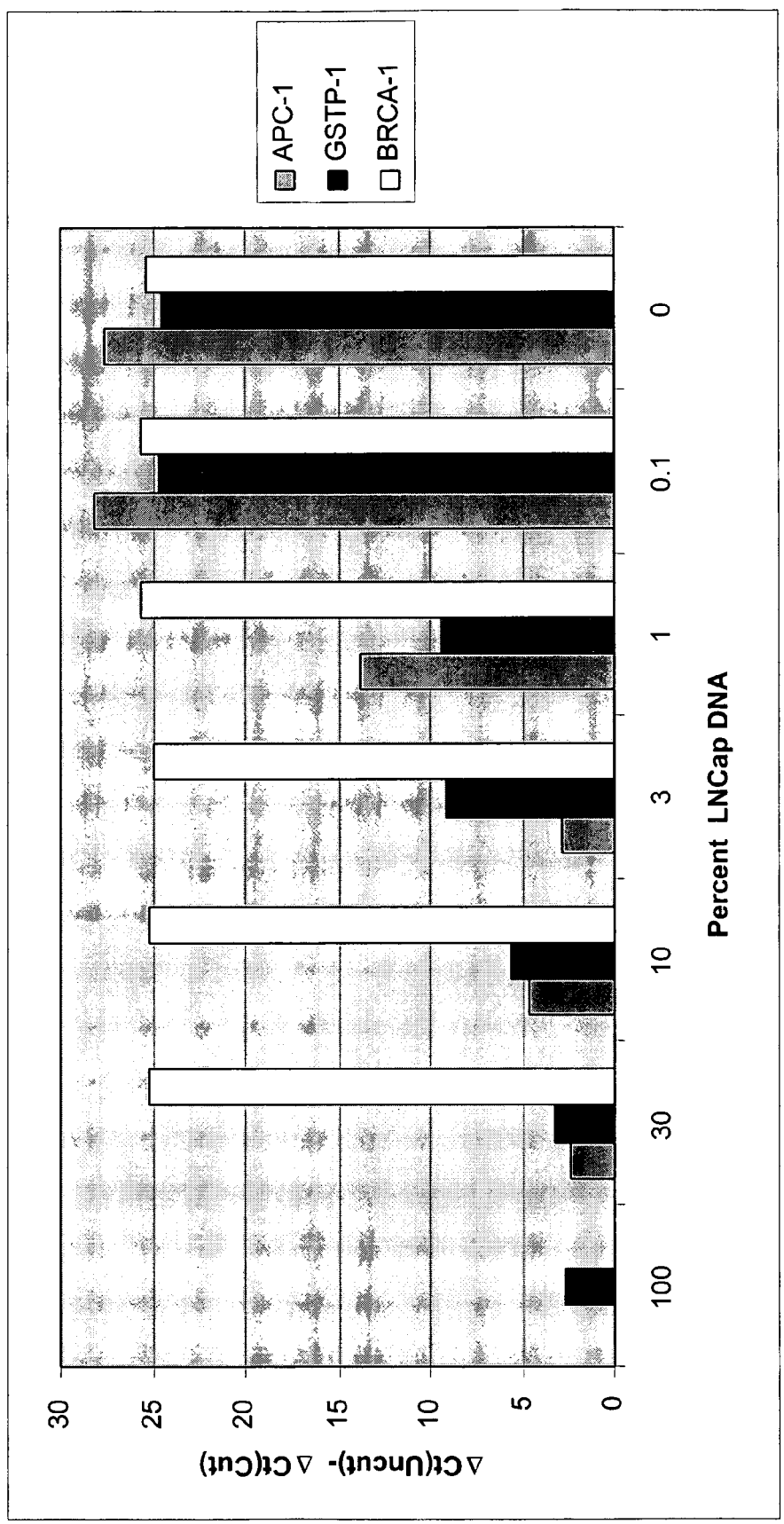
FIG. 65 shows the threshold cycle (Ct) difference between cut and uncut mixtures of LNCaP prostate cancer DNA and normal non-methylated DNA calculated from real time PCR curves for three primer pairs amplifying promoter sites in methylome libraries prepared by incorporation of universal sequence by self-inert primers. Detection sensitivity of at least 99% is evident.

In a third specific embodiment (such as is described in Example 40), there is an analysis of sensitivity of the methylation assay that involves preparation of Methylome libraries by multiple (five) methylation-sensitive restriction enzyme cleavage. The analysis uses libraries prepared by incorporation of universal sequence and amplification with self-inert $K_U$ primer (SEQ ID NO: 15) of DNA from prostate cancer cell line LNCaP mixed with normal non-methylated DNA in different ratios. FIG. 65 shows the threshold cycle (Ct) difference between cut and uncut methylome libraries from real time PCR for three promoter primer pairs with various percentages of prostate cell line (LNCaP) DNA in the libraries. Both the APC1-3 and GSTP1-1 gene promoter region primers demonstrated the presence of target promoter DNA, and thus protection from methylation-sensitive restriction enzymes cutting with as little as 1% or less of cancer cell line DNA present suggesting a sensitivity detection limit of at least 99%.

In another embodiment, there are methods for preparing a secondary library of DNA molecules from the amplification products of the primary Methylome library in such a way as to enrich for only those sequences that are between methylated restriction endonuclease sites present in the primary library. An outline of this method is detailed in Example 22 and is depicted in FIGS. 43A and 43B. Following amplification of the primary methylation library, all of the previously methylated restriction endonuclease recognition sites are converted to unmethylated sites. Digestion of these molecules with the same restriction endonuclease utilized in construction of the primary library will result in cleavage of these sites (FIG. 43A). Following cleavage, a mixture of 2 or more secondary adaptors is ligated to the resulting cleaved ends. Two or more secondary adaptors are utilized to allow amplification of small molecules that would not be amplified, due to suppression, if the same adaptor sequence was present at both ends. Amplification with primers complementary to these secondary adaptors will only amplify those molecules that contain the secondary adaptors at both ends. These amplimers will correspond to sequences between recognition sites that were originally methylated in the starting material (secondary Methylome library).

In a preferable situation a one-step library preparation process utilizing a dU-Hairpin Adaptor method described in Example 33, 38, and 39 can be used for preparation of secondary Methylome libraries. In this case, two hairpin oligonucleotides with different sequence should be used to avoid the PCR suppression effect that is known to inhibit amplification of very short DNA amplicons with one universal sequence at the end.

In a preferable case when primary Methylome library is prepared by using a mixture of several (5 or more) methylation-sensitive restriction enzymes the secondary library can be prepared by mixing together, ligating adaptors, and amplifying the products of several individual restriction digests of the primary Methylome library using the same restriction endonucleases that have been utilized in the nuclease cocktail (FIG. 43B). Analysis of these amplicons can be carried out by PCR, microarray hybridization, probe assay, capillary electrophoresis, sequencing, or other methods known in the art (Example 18, FIG. 34 and FIG. 35), for example. Sequencing of these products can provide a tool for discovering regions of methylation not previously characterized, as no a priori knowledge of the sequences is required and the reduced complexity of the enriched secondary library allows analysis of a small number of methylated regions.

In one specific embodiment (Example 30), there is a preparation and labeling of secondary Methylome library for microarray analysis and a demonstration of its 16-128-fold enrichment in the copy number for several methylated CpG promoters compared to the primary Methylome library. Libraies were prepared from the prostate cancer cell line LNCaP (Coriell Institute for Medical Research) and from DNA isolated from peripheral blood of a healthy donor. The Methylome library was prepared by using five methylation-sensitive restriction enzymes, specifically, Aci I, Bst UI, Hha I, HinP1 I, and Hpa II, for example, and degenerate primer whole genome amplification (WGA) method (see, for example, U.S. patent application Ser. No. 10/293,048, filed Nov. 13, 2002, now U.S. Pat. No. 7,655,791), and amplified using universal $K_U$ primer (SEQ ID NO:15).

The distribution of promoter sites and the level of their enrichment in amplified secondary methylome libraries from cancer DNA was analyzed by quantitative PCR using primer pairs amplifying short amplicons that do not contain recognition sites for at least two of the methylation-sensitive restriction enzymes employed in the present example (Table V, SEQ ID NOS:190 through SEQ ID NO:197). Mechanically fragmented genomic DNA from the peripheral blood of a healthy donor was used as a control for relative copy number evaluation.

FIG. 66 shows typical amplification curves of four promoter sites, three of which, GSTP-1, RASSF-1, and CD44 are methylated, and one, p16, is not methylated in LNCaP cell line DNA. For methylated promoters, between a 4 and 7 cycle leftward shift (enrichment of between 16 and 128-fold) of the amplification curves is observed from the secondary methylome library relative to the curve corresponding to control non-amplified genomic DNA. For the non-methylated p16 promoter, a curve delayed approximately 4 cycles relative to the control appeared. However, this curve did not correspond to the correct size amplicon and was most likely a product of mis-priming A specific method for the analysis of this reduced complexity secondary methylation library is presented in Example 23 and FIG. 44. Briefly, the number of molecules present in the secondary library is a function of the number of methylated CpG islands in the genome, and the average number of specific methylation-specific restriction endonuclease sites within each island. For example, if 1% of the approximately 30,000 CpG islands are hypermethylated, and there are 5 Hpa II restriction sites per CpG island, then there would be approximately 1,200 amplified fragments present in the secondary library. Amplification of this library with a mixture of 4 A primers and 4 B primers, each containing a 3' selector nucleotide, would result in 16 possible combinations of primers for amplification. Thus, the 1,200 amplified fragments would be divided between 16 reactions, resulting in approximately 75 fragments per reaction. Capillary electrophoresis of each reaction would allow for the resolution of these 75 products and the patterns of methylated CpG islands could be resolved. Additional sequencing reactions could be performed to identify the specific bands of interest from within each mixture.

1. Choice of Restriction Enzymes

Methylation-sensitive restriction enzymes with recognition sites comprising the CpG dinucleotide and no adenine or thymine are expected to cut genomic DNA with much lower frequency as compared to their counterparts having recognition sites with normal GC to AT ratios. There are two reasons for this. First, due to the high rate of methyl-cytosine to thymine transition mutations, the CpG dinucleotide is severely under-represented and unequally distributed across the human genome. Large stretches of DNA are depleted of CpG's and thus do not contain these restriction sites. Second, most methylated cytosine residues are found in CpG dinucleotides that are located outside of CpG islands, primarily in repetitive sequences. Due to methylation, these sequences will also be protected from cleavage. On the other hand, about 50 to 60% of the known genes contain CpG islands in their promoter regions and they are maintained largely unmethylated, except in the cases of normal developmental gene expression control, gene imprinting, X chromosome silencing, or aberrant methylation in cancer and some other pathological conditions. These CpG islands are digested by the methylation-sensitive restriction enzymes in normal gene promoter sites but not in aberrantly methylated promoters. Four base GC recognition restriction enzymes as exemplified by Aci I, BstU I, Hha I, HinP1 I, and Hpa II with recognition sites CCGC, CGCG, GCGC, and CCGG, respectively (Table III), are particularly useful since they will frequently cut non-methylated DNA in CpG islands, but not methylated DNA, and as exemplified herein, can be used as a 5-enzyme mix using optimized buffer conditions. Restriction endonucleases Hpy 99I, Ava I, Bce AI, Bsa HI, Bsi E1, and Hga I with 5-base recognition sites can also be used under these buffer conditions thus extending the potential number of restriction enzymes in the reaction mix (up to 11) and increasing the effective depletion of non-methylated CpG-rich DNA template. The spatial distribution of recognition sites for these nucleases in the human genome closely follows the distribution of the CpG dinucleotides (FIGS. 33D and 33E), with particularly high density in CpG-rich gene promoter regions (CpG islands). A current list of known methylation-sensitive restriction endonucleases is presented in Table III. As yet undiscovered but potentially useful enzymes for Methylome library construction would be methylation-sensitive restriction nucleases having 4-base recognition sites with two CpG dinucleotides that are separated by one, two, three, or more random bases, such as CGNCG, CGNNCG, CGNNNCG, with a general formula $CG(N)_mCG$.

2. Restriction Digestion of Target DNA

In a specific embodiment, target DNA is digested with a mix of methylation-sensitive restriction endonucleases, such as Aci I, BstU I, Hha I, HinP1 I, and Hpa II, or a compatible combination thereof. The digestion reaction usually comprises from 10 ng to 1 µg of genomic DNA in 25-100/µl of 1× NEBuffer (NEB), and about 1 to about 25 units of each restriction endonuclease. The mixture is incubated at 37° C. for 2-18 h followed by 2 h at 60° C. to insure complete digestion. When appropriate, the enzyme is inactivated at 65° C. to 70° C. for 15 minutes and the sample is precipitated and resuspended to a final concentration of 1 to 50 ng/µl. In a preferred embodiment digested DNA is directly used for library preparation. Genomic DNA that has not been digested by the methylation-sensitive enzyme mix may serve as positive control during library preparation and analysis, for example.

3. Library Preparation and Amplification

The described invention utilizes an oligonucleotide primer comprising at least as the majority of its sequence only two types of nucleotide bases that can not participate in stable Watson-Crick pairing with each other, and thus can not self-prime (see, for example, U.S. patent application Ser. No. 10/795,667, filed Mar. 8, 2004, now U.S. Pat. No. 7,718,403). The primers comprise a constant known sequence at their 5' end and a degenerate nucleotide sequence located 3' to the constant known sequence. There are four possible two-base combinations known not to participate in Watson-Crick base pairing: C-T, G-A, A-C and G-T. They suggest four different types of degenerate primers that should not form a single Watson-Crick base pair or create primer-dimers in the presence of DNA polymerase and dNTPs. These primers are illustrated in FIG. 2 and are referred to as primers Y, R, M and K, respectively, in accordance with common nomenclature for degenerate nucleotides: Y=C or T, R=G or A, M=A or C and K=G or T.

For example, Y-primers have a 5' known sequence $Y_U$ comprised of C and T bases and a degenerate region $(Y)_{10}$ at the 3 prime end comprising ten, for example, randomly selected pyrimidine bases C and T. R-primers have a 5' known sequence Ru comprised of G and A bases and a degenerate region $(R)_{10}$ at the 3 prime end comprising ten, for example, randomly selected purine bases G and A. M-primers have a 5' known sequence $M_U$ comprised of A and C bases and a degenerate region $(M)_{10}$ at the 3 prime end comprising ten, for example, randomly selected bases A and C. Finally, K-primers have a 5' known sequence $K_U$ comprised of G and T bases and a degenerate region $(K)_{10}$ at the 3 prime end comprising ten, for example, randomly selected bases G and T. Primers of the described design will not self-prime and thus will not form primer dimers. However, they will prime at target sites comprising the corresponding Watson-Crick base partners, albeit with reduced overall frequency compared to completely random primers. In specific embodiments, these primers under specific conditions are capable of forming primer dimers, but at a greatly reduced level compared to primers lacking such structure.

In some embodiments, these primers are supplemented with a completely random (i.e. containing any of the four bases) short nucleotide sequence at their 3' end. A limited number of completely random bases present at the 3' end of the Y, R, M or K primers, increases their priming frequency, yet maintains limited ability for self-priming. By using a different number of completely random bases at the 3' end of the degenerate Y, R, M or K primers, and by carefully optimizing the reaction conditions, one can precisely control the outcome of the polymerization reaction in favor of the desired DNA product with minimum primer-dimer formation.

Thus, in the first step referred to as a "library synthesis" step, primers of the described design are randomly incorporated in an extension/polymerization reaction with a DNA polymerase possessing strand-displacement activity. The resulting branching process creates DNA molecules having known (universal) self-complementary sequences at both ends. In a second step referred to as the "amplification" step, these molecules are amplified exponentially by polymerase chain reaction using Taq DNA polymerase and a single primer corresponding to the known 5'-tail of the random primers. This process overcomes major problems known in the art for DNA amplification by random primers.

Random fragmentation of DNA can be performed by mechanical, chemical, or enzymatic treatment. In a preferred embodiment, DNA is fragmented by heating at about 95° C. in low salt buffers such as TE (10 mM Tris-HCl, 1 mM EDTA, having pH between 7.5 and 8.5) or TE-L (10 mM Tris-HCl, 0.1 mM EDTA, having pH between 7.5 and 8.5) for between about 1 and about 10 minutes (for example, see U.S. Patent Application 20030143599, incorporated by reference herein in its entirety).

In a preferred embodiment of the present invention, a library synthesis reaction is performed in a volume of about 10 to about 25 µl. The reaction mixture comprises about 100 ng or less of restriction digested and thermally-fragmented DNA, about 1 µM of self-inert degenerate $K(N)_2$ primer containing G and T bases at the known and degenerate regions and 2 completely random 3' bases (SEQ ID NO: 14), about 4% (v/v) of dimethylsulfoxide (DMSO), about 200 µM 7-deaza-dGTP (Sigma), between about 2 units and about 10 units of Klenow Exo– DNA polymerase (NEB), between about 5 mM and about 10 mM $MgCl_2$, about 100 mM NaCl, about 10 mM Tris-HCl buffer having pH of about 7.5, and about 7.5 mM dithiothreitol. Preferably, the incubation time of the reaction is between about 60 minutes and about 120 minutes and the incubation temperature is about 24° C. in an isothermal mode or in another preferred embodiment by sequential isothermal steps at between about 16° C. and about 37° C.

A typical amplification step with universal sequence primer $K_U$ (SEQ ID NO: 15) comprises between about 1 and about 25 ng of library products and between about 0.3 and about 2 µM of universal sequence primer, about 4% DMSO, about 200 µM 7-deaza-dGTP (Sigma), and about 0.5 M betaine (Sigma) in a standard PCR reaction well known in the art, under conditions optimal for a thermostable DNA polymerase, such as Taq DNA polymerase, Pfu polymerase, or derivatives and mixtures thereof 4. Analysis of Amplified Products to Determine the Methylation Status of Target DNA Aliquots of the amplified library DNA are analyzed for the presence of CpG sites or regions encompassing more than one such site. This can be achieved by quantitative real-time PCR amplification, comparative hybridization, ligation-mediated PCR, ligation chain reaction (LCR), fluorescent or radioactive probe hybridization, hybridization to promoter microarrays comprising oligonucleotides or PCR fragments, or by probing microarray libraries derived from multiple samples with labeled PCR or oligonucleotide probes, for example. The magnitude of the signal will be proportional to the level of methylation of a promoter site.

A typical quantitative real-time PCR-based methylation analysis reaction comprises 1×Taq polymerase reaction buffer, about 10 to about 50 ng of library DNA, about 200 to about 400 nM of each specific primer, about 4% DMSO, 0 to about 0.5 M betaine (Sigma), 1:100,000 dilutions of fluorescein calibration dye (FCD) and SYBR Green I (SGI) (Molecular Probes), and about 5 units of Taq polymerase. PCR is carried out on an I-Cycler real-time PCR system (Bio-Rad) using a cycling protocol optimized for the respective primer pair and for the size and the base composition of the analyzed amplicon.

Preparation of Secondary Methylome Libraries and their Utility for Discovery of New Methylation Markers In a specific embodiment the preparation of what may be termed a "Secondary Methylome" library derived from the amplified primary Methylome library is described. Secondary libraries are derived by cleavage of the primary library with the same set of methylation-sensitive restriction endonucleases used in preparation of primary library and subsequent amplification of the excised short DNA fragments. Restriction sites originally methylated in the DNA sample were refractory to cleavage in the primary library, however amplification substituting the 5'-methyl cytosines of the starting template DNA with non-methylated cytosines conveys cleavage sensitivity to these previously protected restriction sites. Incubation of the amplified primary library with the restriction endonuclease set (Aci I, Hha I, HinP1 I, or Hpa II) would have no effect for amplicons lacking those restriction sites, produce a single break for amplicons with one site, and release one or more restriction fragments from CpG-rich amplicons with two or more corresponding restriction sites. Selective ligation of adaptors (containing 5'-CG-overhangs complementary to the ends of Aci I, Hha I, HinP1 I, and Hpa II restriction fragments, or blunt-end adaptors compatible with the ends of fragments produced by Bst UI) and subsequent amplification of the ligation products by PCR results in amplification of only those DNA fragments that were originally flanked by two methylated restriction sites. Secondary Methylome libraries generated by different restriction enzymes can be mixed together to produce a redundant secondary Methylome library containing overlapping DNA restriction fragments originating from the methylated CpG islands present in the sample. These libraries are highly enriched for methylated sequences and can be analyzed by hybridization to a promoter microarray or by real-time PCR using very short PCR amplicons.

5. Restriction Digestion of Amplification Products from the Primary Methylome Library In specific embodiments, amplified library DNA is digested with the same methylation-sensitive restriction endonuclease(s) utilized to generate a primary Methylome library, such as Aci I, BstU I, Hha I, HinP1 I, and Hpa II or a combination thereof. The digestion reaction contains about 0.1 ng to about 10 µg of genomic DNA, 1× reaction buffer, and about 1 to about 25 units of restriction endonuclease(s). The mixture(s) is incubated at 37° C. or at the optimal temperature of the respective endonuclease for about 1 hour to about 16 hours to insure complete digestion. The enzyme(s) is inactivated at 65° C. to 70° C. for 15 minutes and the sample is precipitated with ethanol and resuspended to a final concentration of 1 ng/µl to 50 ng/µl.

In a specific embodiment described in Example 30 primary methylome libraries prepared from DNA isolated from the prostate cancer cell line LNCaP or from control peripheral blood DNA of a healthy donor are pre-heated at 80° C. and digested in three separate tubes with the methylation-sensitive enzymes AciI, HpaII, and a mixture of HhaI and Hinp1I. Digestion products are pooled, size-fractionated by ultrafiltration to select for short products of the secondary cleavage and concentrated by ethanol precipitation.

6. Attachment of Secondary Adaptors

The following ligation procedure is designed to work with DNA that has been digested with restriction endonucleases resulting in ends with either 5' overhangs, 3' overhangs, or blunt ends. Under optimal conditions, the digestion procedure will result in the majority of products having ends competent for ligation. The adaptor is composed of two oligonucleotides, 1 short and 1 long, which are hybridized to each other at some region along their length. A range of length for the short oligonucleotide is about 7 bp to about 20 bp. In addition, the structure of the adaptor is based on the type of ends generated by the restriction endonuclease. A 3' overhang on the long adaptor will be used for restriction endonucleases that result in a 5' overhang and a blunt end adaptor will be utilized with enzymes that produce blunt end molecules. The structure of the adaptors has been developed to minimize ligation of adaptors to each other via at least one of three means: 1) lack of a 5' phosphate group necessary for ligation; 2) presence of about a 7 bp 5' overhang that prevents ligation in the opposite orientation; and/or 3) a 3' blocked base preventing fill-in of the 5' overhang.

A typical ligation procedure involves the incubation of about 1 to about 100 ng of DNA in 1×T4 DNA ligase buffer, about 10-about 100 pmol of each adaptor, and about 400-about 2,000 Units of T4 DNA Ligase. Ligations are performed at 16° C.-37° C. for 1 hour, followed by inactivation of the ligase at 75° C. for 15 minutes. The products of ligation can be stored at −20° C. to 4° C. until amplification.

In a specific embodiment described in example 30, conversion of short restriction fragments, the products of secondary restriction cleavage, to amplifiable libraries is achieved by ligation of Y1 and Y2 universal adaptors (Table V) comprising unique sequences containing only C and T (non-Watson-Crick pairing bases) on one strand and having a CG 5' overhang on the opposite (A and G) strand to the GC overhangs of the restriction fragments produced by digestion with methylation-sensitive restriction enzymes. Digested and filtered library DNA is incubated with Y1 and Y2 adaptors each present at 0.6 µM and 1,200 units of T4 DNA ligase in 45 µl of 1×T4 DNA ligase buffer (NEB) for 50 min at 16° C. followed by 10 min at 25° C.

7. Extension of the 3' End of the DNA Fragment to Fill in the Secondary Adaptors Due to the lack of a phosphate group at the 5' end of the adaptor, only one strand of the adaptor (3' end) will be covalently attached to the DNA fragment. A 72° C. extension step is performed on the DNA fragments in the presence of 1×DNA polymerase, 1×PCR Buffer, 200 µM of each dNTP, and 1 uM universal primer. This step may be performed immediately prior to amplification using Taq polymerase, or may be carried out using a thermo-labile polymerase, such as if the libraries are to be stored for future use.

8. One-Step Attachment of Secondary Adaptors

In a preferred embodiment, a one-step process utilizing a dU-Hairpin Adaptor method described in Examples 33, 38, and 39 is used for preparation of secondary Methylome libraries. In this case, a mixture of hairpin oligonucleotides comprising two different known sequences should be used to avoid the PCR suppression effect which is known to inhibit amplification of very short DNA amplicons when identical sequence attached to both ends is used.

9. Amplification of the Secondary Methylation Library

The amplification of secondary methylation libraries involves use of universal primers complementary to the secondary adaptors. Two or more secondary adaptors are utilized to allow amplification of small molecules that would otherwise fail to amplify with a single adaptor sequence resulting from PCR suppression. A typical amplification step comprises between about 1 and about 25 ng of library products and between about 0.3 and about 1 µM of each secondary adaptor sequence primer in a standard PCR reaction well known in the art, under conditions optimal for a thermostable DNA polymerase, such as Taq DNA polymerase, Pfu polymerase, or derivatives and mixtures thereof.

In a specific embodiment described in example 30 libraries are prepared for micro-array analysis by amplification with PCR and monitored in real time using a reaction mixture containing final concentrations of: 1× Titanium Taq reaction buffer (Clontech), 200 µM of each dNTP, fluorescein calibration dye (1:100,000) and SYBR Green I (1:100,000), 0.25 µM each of universal primers (Table V, SEQ ID NO: 168 and SEQ ID NO: 170), 4% DMSO, 200 µM 7-deaza-dGTP (Sigma), and 5 units of Titanium Taq polymerase (Clontech) in a final volume of 75 µl. After an initial incubation at 75° C. for 10 min to fill-in the recessed 3' ends of the ligated restriction fragments, amplifications were carried out at 95° C. for 3 min, followed by 13 cycles of 94° C. for 15 sec and 65° C. for 1.5 min on an I-Cycler real-time PCR instrument (Bio-Rad).

Amplified libraries from cancer or normal DNA were pooled and used as template in PCR labeling for subsequent microarray hybridizations.

10. Analysis of the Amplified Products to Determine the Methylation Status of Target DNA Aliquots of the amplified library DNA are analyzed for the presence of sequence adjacent to CpG sites. This can be achieved by quantitative real-time PCR amplification, comparative hybridization, ligation-mediated PCR, ligation chain reaction (LCR), fluorescent or radioactive probe hybridization, probe amplification, hybridization to promoter microarrays comprising oligonucleotides or PCR fragments, or by probing microarray libraries derived from multiple samples with labeled PCR or oligonucleotide probes. The magnitude of the signal will be proportional to the level of methylation of a promoter site.

A typical quantitative real-time PCR-based methylation analysis reaction comprises 1×Taq polymerase reaction buffer, about 10 to about 50 ng of library DNA, about 200 to about 400 nM of each specific primer, about 4% DMSO, 0 to about 0.5 M betaine (Sigma), 1:100,000 dilutions of fluorescein calibration dye (FCD) and SYBR Green I (SGI) (Molecular Probes), and about 5 units of Taq polymerase. PCR is carried out on an I-Cycler real-time PCR system (BioRad) using a cycling protocol optimized for the respective primer pair and for the size and the base composition of the analyzed amplicon.

Figure 44:
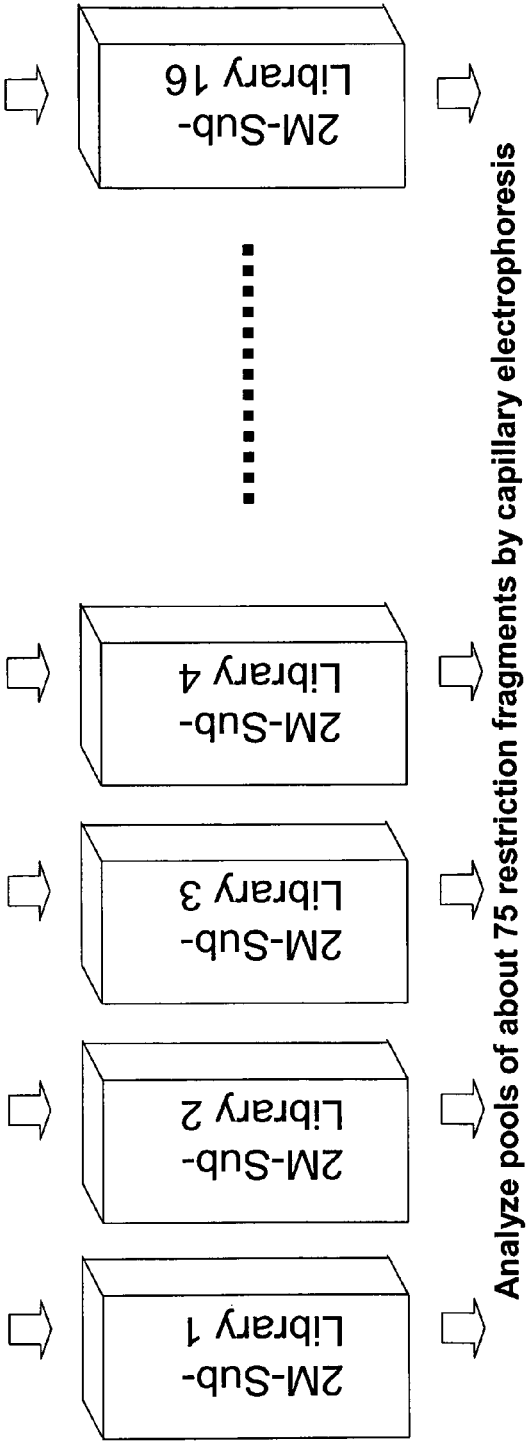
FIG. 44 is a depiction of how capillary electrophoresis can be utilized for analysis of secondary Methylome libraries. The complexity (N) of the secondary Methylome library is a function of the number of methylated CpG islands in the genome (n), and the average number of times a specific restriction endonuclease occurs in the CpG islands (m). An example is illustrated where 1% of CpG islands are methylated and the Hpa II restriction site is present 5 times/CpG island. This results in approximately 1,200 restriction fragments within the secondary library. Re-amplification of this library using 16 combinations of A and B oligos with a single 3' selecting nucleotide would result in approximately 75 specific sequences/well. This level of complexity can be analyzed by capillary electrophoresis, allowing determination of the patterns of methylation in different samples without a priori knowledge of which CpG islands are important. Sequencing of the resulting products would allow the determination of the CpG islands that were methylated in the original sample.

Alternatively, a method for analyzing all of the sequences at one time is presented in FIG. 44. The reduced complexity of the secondary methylome library allows amplification of subsets of these libraries through use of a single 3' nucleotide used as a selector. A combination of 4 A adaptors and 4 B adaptors will result in 16 amplification reactions, containing a greatly reduced number of sequences. These amplified products can be analyzed by capillary electrophoresis which allows the resolution of the different fragments without a priori knowledge of the identity of the sequences. Finally, the amplification products of the secondary methylation library can be analyzed by sequencing to allow the identification of the specific fragments of interest identified during capillary electrophoresis.

In a specific embodiment described in Example 30 the distribution of promoter sites and the level of their enrichment in amplified secondary methylome libraries from cancer DNA are analyzed by quantitative PCR using primer pairs amplifying short amplicons that do not contain recognition sites for at least two of the methylation-sensitive restriction enzymes employed in the present example (Table V, SEQ ID NOs: 190-197). Methylated promoters are enriched between 16 and 128-fold (FIG. 66) relative to a control non-amplified genomic DNA. For a non-methylated promoter no detectable product is amplified (see FIG. 66)

11. Sources of DNA for Methylation Analysis

Genomic DNA of any source or complexity, or fragments thereof, can be analyzed by the methods described in the invention. Clinical samples representing biopsy materials, pap smears, DNA from blood cells, serum, plasma, urine, feces, cheek scrapings, nipple aspirate, saliva, or other body fluids, DNA isolated from apoptotic cells, or cultured primary or immortalized tissue cultures can be used as a source for methylation analysis.

E. Methylation Analysis of Substantially Fragmented DNA Using Libraries Digested with Methylation-Sensitive Restriction Endonucleases that have Recognition Sites Comprising CpG Dinucleotides In this embodiment, there are methods for preparing libraries from substantially fragmented DNA molecules in such a way as to select for sequences that comprise recognition sites for methylation-sensitive restriction endonucleases in regions with high GC content, such as promoter CpG islands. In a preferred embodiment, serum, plasma or urine DNA, for example, is the source of the starting material. DNA isolated from serum, plasma, and urine has a typical size range of approximately 200 bp to 3 kb, based on gel analysis. Furthermore, this material can be converted into libraries and amplified by whole genome amplification methodologies (see, for example, U.S. patent application Ser. No. 10/797,333, filed Mar. 8, 2004, published as U.S. Patent Application Publication No.: 2004/0209299 and is now abandoned; and citations herein). The synthesis of these libraries involves techniques that do not affect the methylation status of the starting DNA. It is apparent to those skilled in the art that the starting material can be obtained from any source of tissue and/or procedure that yields DNA with characteristics similar to those obtained from serum, plasma, and urine DNA (for example, DNA enzymatically degraded by one or several restriction endonucleas, DNase I, McrBC nuclease, or a combination of thereof; DNA extracted from formalin-fixed, paraffin-embedded tissues; DNA isolated from other body fluids; etc.)

Following amplification of the primary methylation library, the methylated sites in the starting DNA are converted into unmethylated sites. Thus, in a second embodiment (see Example 25), the amplification products of the primary methylation libraries are amplified with a universal primer comprising a 5' poly-C sequence. Following amplification, the resulting products are digested with the same methylation-sensitive restriction endonuclease used during creation of the primary methylation library. Subsequently, a second adaptor is ligated to the resulting fragments. Amplification is carried out using a primer complementary to the second adaptor in conjunction with a poly-C primer. The resulting amplicons will comprise only those molecules that have the second adaptor at one or both ends. Molecules that were not digested during creation of the secondary methylation library will not have the second adaptor attached and will not be amplified by the poly-C primer. This lack of amplification of molecules containing a poly-C primer at both ends has been documented, for example, in U.S. patent application Ser. No. 10/293,048, filed Nov. 13, 2002, now U.S. Pat. No. 7,655, 791; U.S. patent application Ser. No. 10/797,333, filed Mar. 8, 2004, published as U.S. Patent Application Publication No.: 2004/0209299 and is now abandoned; U.S. patent application Ser. No. 10/795,667, filed Mar. 8, 2004, now U.S. Pat. No. 7,718,403. Thus, the products of amplification of the secondary methylation library will be enriched in molecules that comprised a methylated restriction endonuclease recognition site in the starting material. These products can be analyzed by methods similar to those utilized for the analysis of the primary methylation library products, or they can be sequenced to determine sites for which there is no a priori knowledge of methylation.

In one specific embodiment (such as Examples 24 and 31), the Methylome libraries are prepared from serum DNA, digested with methylation-sensitive restriction endonucleases, amplified with universal primer, and analyzed for specific sequences that were methylated in the starting material using real-time PCR. The principle of this method is disclosed in U.S. patent application Ser. No. 10/797,333, filed Mar. 8, 2004, published as U.S. Patent Application Publication No.: 2004/0209299 and is now abandoned. Cell-free DNA is isolated from serum or urine of healthy donors or from prostate cancer patients. This DNA displays typical banding pattern characteristic of apoptotic nucleosomal size. To repair DNA and generate blunt ends, the DNA is incubated with Klenow fragment of DNA polymerase I in the presence of all four dNTPs. Ligation of universal $K_U$ adaptor (Table VI) is then performed using T4 DNA ligase. Samples are purified by ethanol precipitation and split into 2 aliquots. One aliquot is digested with a cocktail of methylation-sensitive restriction enzymes AciI, HhaI, BstUI, HpaII, and Hinp1I. The second aliquot is incubated in parallel but without restriction enzymes ("uncut" control). Libraries are amplified by quantitative real-time PCR universal primer $K_U$ (Table VI, SEQ ID NO: 15) in the presence of additives that facilitate replication through promoter regions with high GC content and excessive secondary structure. Amplified library DNA is purified, and the presence of amplifiable promoter sequences in the libraries comprising one or more CpG sites as part of the methylation-sensitive restriction enzymes recognition sequences is analyzed by quantitative PCR using specific primers flanking such sites. FIG. 55 shows typical amplification curves of promoter sites for genes implicated in cancer from Methylome libraries synthesized from the serum DNA of cancer patients as compared to healthy donor controls. As expected, the level of methylation in serum DNA from cancer patients was much lower than in tumor tissue or cancer cell lines, since cancer DNA in circulation represents only a relatively small fraction of the total cell-free DNA. The method disclosed here is very sensitive to reliably detect methylation in body fluids and can be applied as a diagnostic tool for early detection, prognosis, or monitoring of the progression of cancer disease.

In another specific embodiment (Examples 24, 31), the Methylome libraries are created from urine DNA as described above, digested with methylation-sensitive restriction endonucleases, amplified with universal primer, and analyzed for specific sequences that were methylated in the starting material using real-time PCR. FIG. 56 shows typical amplification curves of promoter sites for genes implicated in cancer from methylome libraries synthesized from urine DNA of cancer patients as compared to healthy donor controls. As expected, the level of methylation in urine DNA from cancer patients was much lower than in tumor tissue or cancer cell lines, since cancer DNA in circulation represents only a relatively small fraction of the total cell-free DNA. This trend is especially pronounced for urine DNA. The method disclosed here is very sensitive to reliably detect methylation in body fluids and can be applied as a diagnostic tool for early detection, prognosis, or monitoring of the progression of cancer disease.

The resulting products can also be analyzed by sequencing, ligation chain reaction, ligation-mediated polymerase chain reaction, probe hybridization, probe amplification microarray hybridization, a combination thereof, or other methods known in the art, for example.

In one specific embodiment, preparation of the Methylome library from cell-free urine DNA is further optimized Example 32 describes the development of a single-tube library preparation and amplification method for Methylome libraries from urine DNA and its advantages over a two-step protocol described in the Example 31. The disclosed invention allows elimination of the DNA precipitation step introduced in the Example 31 protocol after ligation reaction and directluse of the DNA sample after ligation reaction in the restriction digestion reaction. In the single tube method, the entire process takes place in a universal buffer that supports all enzymatic activities. Klenow fragment of DNA polymerase I, T4 DNA ligase, and the mix of methylation-sensitive restriction enzymes are added sequentially to the same tube. Libraries are amplified by quantitative real-time PCR with universal primer $K_U$ (Table VI, SEQ ID NO: 15) in the presence of additives that facilitate replication through promoter regions with high GC content and excessive secondary structure. Amplified library DNA is purified and the presence of amplifiable promoter sequences in the libraries comprising one or more CpG sites as part of the methylation-sensitive restriction enzymes recognition sequences is analyzed by quantitative PCR using specific primers flanking such sites. Digested samples from the single tube protocol have a greatly reduced background as compared to the two step protocol, whereas the uncut samples amplified identically (FIG. 57). This results in significant improvement of the dynamic range of the assay. Another advantage of the single tube protocol is reduced hands-on time and improved high throughput and automation capability.

In another specific embodiment (Example 34), it is demonstrated that selection of DNA polymerase is critical for the preservation of DNA methylation within the promoter regions during the Methylome library synthesis. Cell free DNA in urine or circulating in plasma and serum is likely to be excessively nicked and damaged due to their natural apoptotic source and presence of nuclease activities in blood and urine. During repair of ends using a DNA polymerase with 3'-exonuclease activity, internal nicks are expected to be extended, a process that can potentially lead to replacement of methyl-cytosine with non-methylated cytosine and loss of the methylation signature. The stronger the strand displacement (or nick-translation) activity of the polymerase, the more likely the 5'-methyl cytosine would be replaced with normal cytosine during the repair process. Example 34 compares two DNA polymerases (T4 DNA polymerase and Klenow fragment of DNA polymerase I) capable of polishing DNA termini to produce blunt ends and the ability of each to preserve the methylation signature of CpG islands prior to cleavage with methylation-sensitive restriction enzymes.

Figure 59:
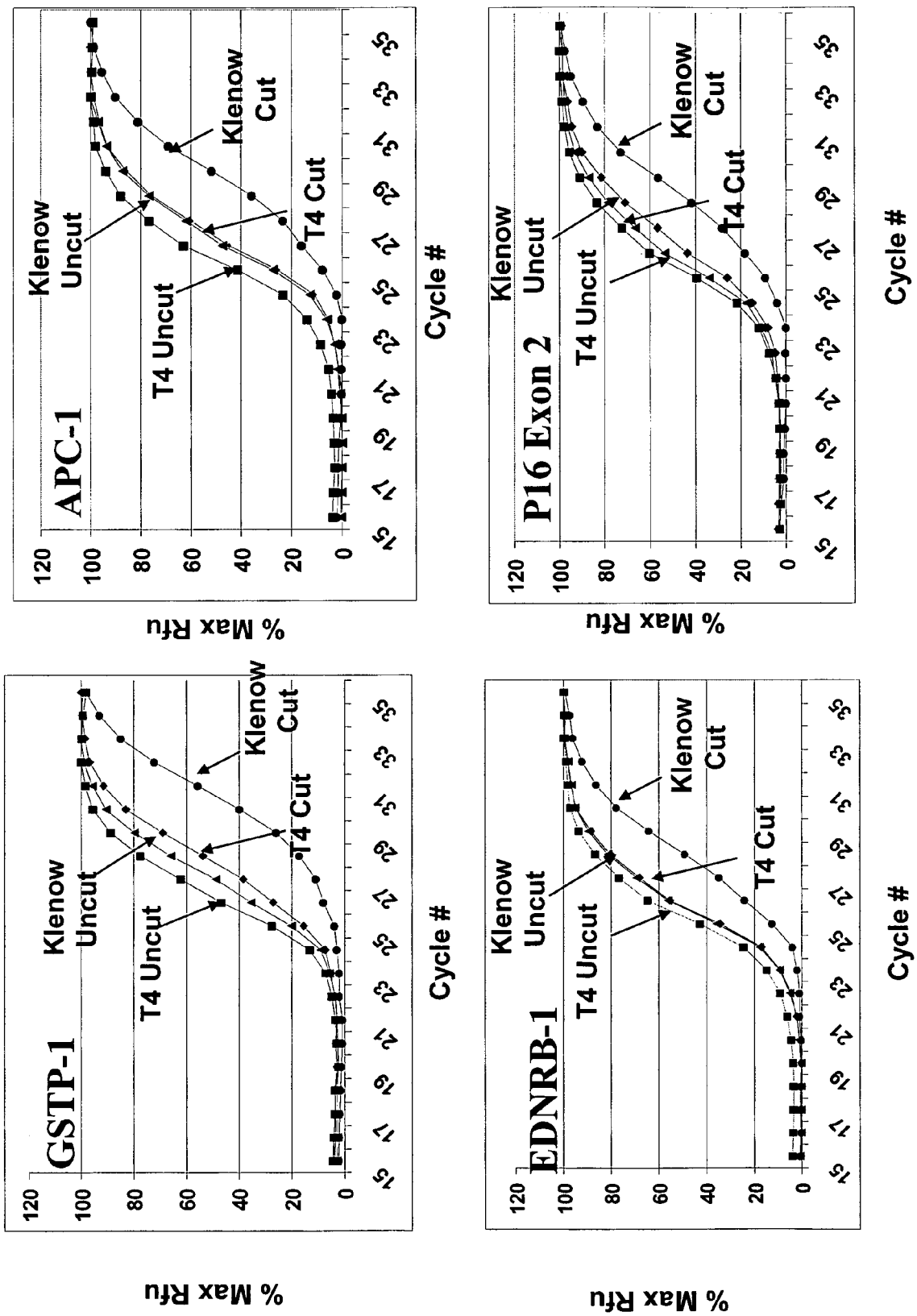
FIG. 59 shows a comparison between Klenow fragment of DNA polymerase I and T4 DNA polymerase for their ability to preserve the methylation signature of CpG islands during preparation of libraries for methylation analysis. When artificially methylated urine DNA was treated with Klenow fragment of DNA polymerase I prior to restriction cleavage a delay to threshold cycle (Ct) of 2 to 3 cycles was observed in the resulting libraries suggesting that a significant fraction (estimated 75% to 90=%) of methyl-cytosine containing fragments are lost during the Klenow enzymatic repair process. In contrast, when T4 polymerase was used for repair, the Ct shift is only one cycle or less depending on the site analyzed. This suggests that 50% or more of the methyl-cytosine was preserved when T4 DNA polymerase is used.

As shown on FIG. 59, when fully methylated urine DNA was treated with Klenow fragment of DNA polymerase I prior to restriction cleavage a 2-3 cycle shift of the amplification curves was observed, suggesting that a significant fraction (estimated 75% to 90%) of methyl-cytosine was lost during the DNA end repair. On the other hand, when T4 polymerase was used for DNA end repair, the shift was only one cycle or less depending on the site analyzed. This suggests that 50% or more of the methyl-cytosine was preserved. These results are in agreement with literature data showing that E. coli DNA polymerase I has stronger strand-displacement activity than T4 polymerase. Thus, T4 DNA polymerase is the preferable enzyme to produce blunt ends for methylome library preparation from urine or other sources of degraded or nicked DNA.

In one specific embodiment (Example 38), preparation of the Methylome libraries from cell-free DNA is further simplified to combine three processes, specifically, DNA end "polishing" reaction, adaptor ligation reaction, and "fill-in" end synthesis reaction into one single reaction. A single step preparation of the genomic library from cell-free urine DNA utilizes a special hairpin oligonucleotide adaptor containing deoxy-uridine in both its 5' stem region and in its loop (Table VI, SEQ ID NO:172). The hairpin oligonucleotide is ligated via its free 3' end to the 5' phosphates of target DNA molecules in the presence of 3 enzymatic activities: T4 DNA ligase, DNA polymerase, and Uracil-DNA glycosylase (UDG). Several reactions proceed simultaneously: T4 DNA polymerase creates blunt ends on DNA fragments and maintains blunt ends on the hairpin adaptor; UDG catalyzes the release of free uracil and creates abasic sites in the adaptor's loop region and the 5' half of the hairpin; T4 DNA ligase ligates the 3' end of the hairpin adaptor to the 5' phosphates of target DNA molecules; and the strand-displacement activity of the DNA polymerase extends the 3' end of DNA into the adaptor region until an abasic site (region) is reached that serves as a replication stop. This process results in truncated 3' ends of the library fragments such that they do not have terminal inverted repeats. The entire process takes place in a single tube in one step and is completed in just 1 hour, for example. It is followed by multiple methylation-sensitive restriction enzyme digestion with a cocktail of, for example, Aci I, Hha I, Hpa II, HinP1 I, and Bst UI enzymes, PCR amplification, and methylation analysis by real-time PCR, for example.

Figure 63:
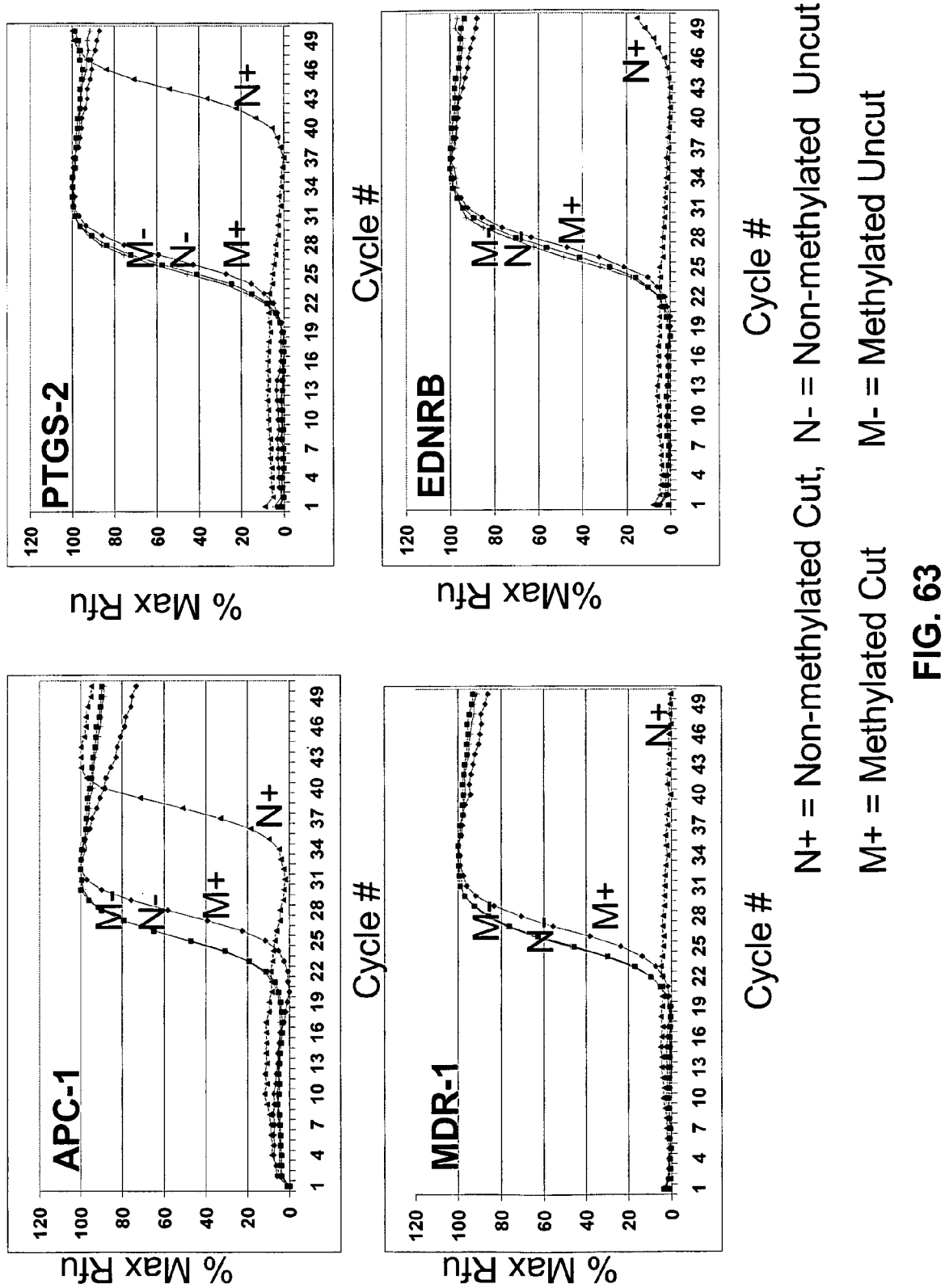
FIG. 63 shows PCR amplification curves of specific promoter sites from amplified libraries prepared from cell-free urine DNA by ligation of a degradable hairpin adaptor containing deoxy-uridine with or without subsequent cleavage with methylation-sensitive restriction enzymes. Promoter sites from non-methylated cleaved DNA amplify with significant (at least 10 cycles) delay as compared to uncut DNA for all four promoter sites tested. Methylated DNA is refractory to cleavage.

FIG. 63 shows PCR amplification curves of specific promoter sites from amplified libraries prepared from methylated or non-methylated urine DNA with or without cleavage with methylation-sensitive restriction enzymes. As expected, promoter sites from non-methylated cleaved DNA amplified with significant (at least 10 cycles) delay as compared to uncut DNA for all four promoter sites tested. On the other hand, methylated DNA is refractory to cleavage.

In another specific embodiment (Example 39), preparation of the Methylome libraries from cell-free DNA is simplified to its theoretical limit by combining all four processes, specifically, DNA end "polishing" reaction, adaptor ligation reaction, "fill-in" end synthesis reaction, and multiple methylation-sensitive restriction enzyme digestion into one single step. A single step preparation of the Methylome library from cell-free urine DNA utilizes a special hairpin oligonucleotide adaptor comprising deoxy-uridine in both its 5' stem region and in its loop (Table VI, SEQ ID NO:172). The hairpin oligonucleotide is ligated via its free 3' end to the 5' phosphates of target DNA molecules in the presence of 3 enzymatic activities: T4 DNA ligase, DNA polymerase, and Uracil-DNA glycosylase (UDG). Several reactions proceed simultaneously: T4 DNA polymerase creates blunt ends on DNA fragments and maintains blunt ends on the hairpin adaptor; UDG catalyzes the release of free uracil and creates abasic sites in the adaptor's loop region and the 5' half of the hairpin; T4 DNA ligase ligates the 3' end of the hairpin adaptor to the 5' phosphates of target DNA molecules; the strand-displacement activity of the DNA polymerase extends the 3' end of DNA into the adaptor region until an abasic site (region) is reached which serves as a replication stop; and finally, a cocktail of methylation sensitive restriction enzymes (such as the exemplary Aci I, Hha I, Hpa II, HinP1 I, and Bst UI) degrades non-methylated CpG-rich regions within the continuously prepared Methylome library. This process results in truncated 3' ends of the library fragments such that they do not have terminal inverted repeats. The entire process takes place in a single tube in one step and is completed within 1 hour. It is followed by PCR amplification and methylation analysis by real-time PCR, for example.

Figure 64:
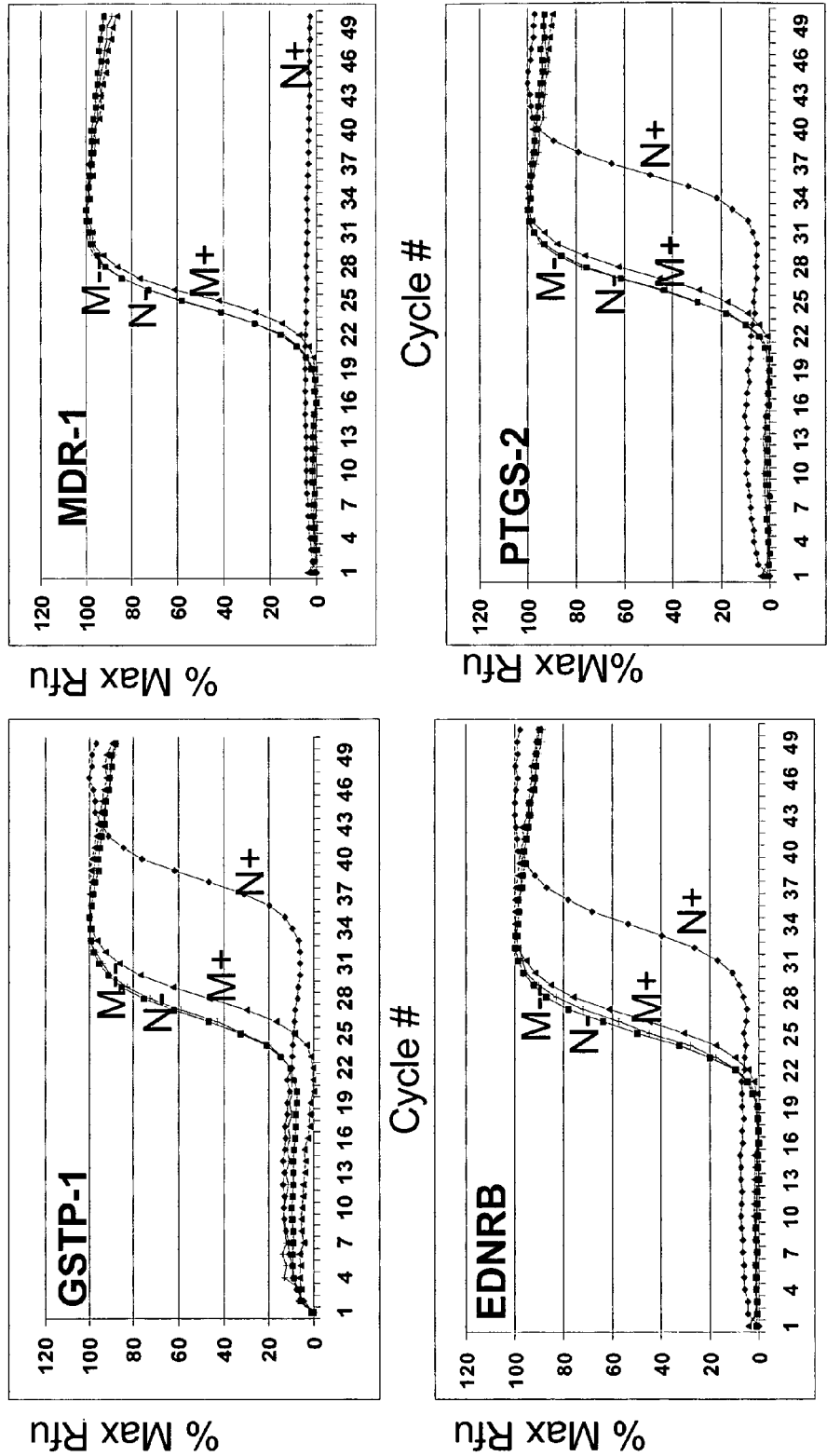
FIG. 64 shows PCR amplification curves of specific promoter sites from amplified libraries prepared from cell-free urine DNA by ligation of a degradable hairpin adaptor containing deoxy-uridine with or without simultaneous cleavage with methylation-sensitive restriction enzymes. Promoter sites from non-methylated cleaved DNA amplify with significant (at least 10 cycles) delay as compared to uncut DNA unlike methylated DNA which is refractory to cleavage.

FIG. 64 shows PCR amplification curves of specific promoter sites in amplified libraries prepared from methylated or non-methylated urine DNA in the presence or in the absence of methylation-sensitive restriction enzymes. As expected, promoter sites from non-methylated cleaved DNA amplified with significant (at least 10 cycles) delay as compared to uncut DNA for all four promoter sites tested. On the other hand, methylated DNA is completely refractory to cleavage. These results demonstrate that the unique Methylome library preparation method disclosed in the present invention can be applied as a simple one step non-invasive high-throughput diagnostic procedure for detection of aberrant methylation in cancer.

Figure 68:
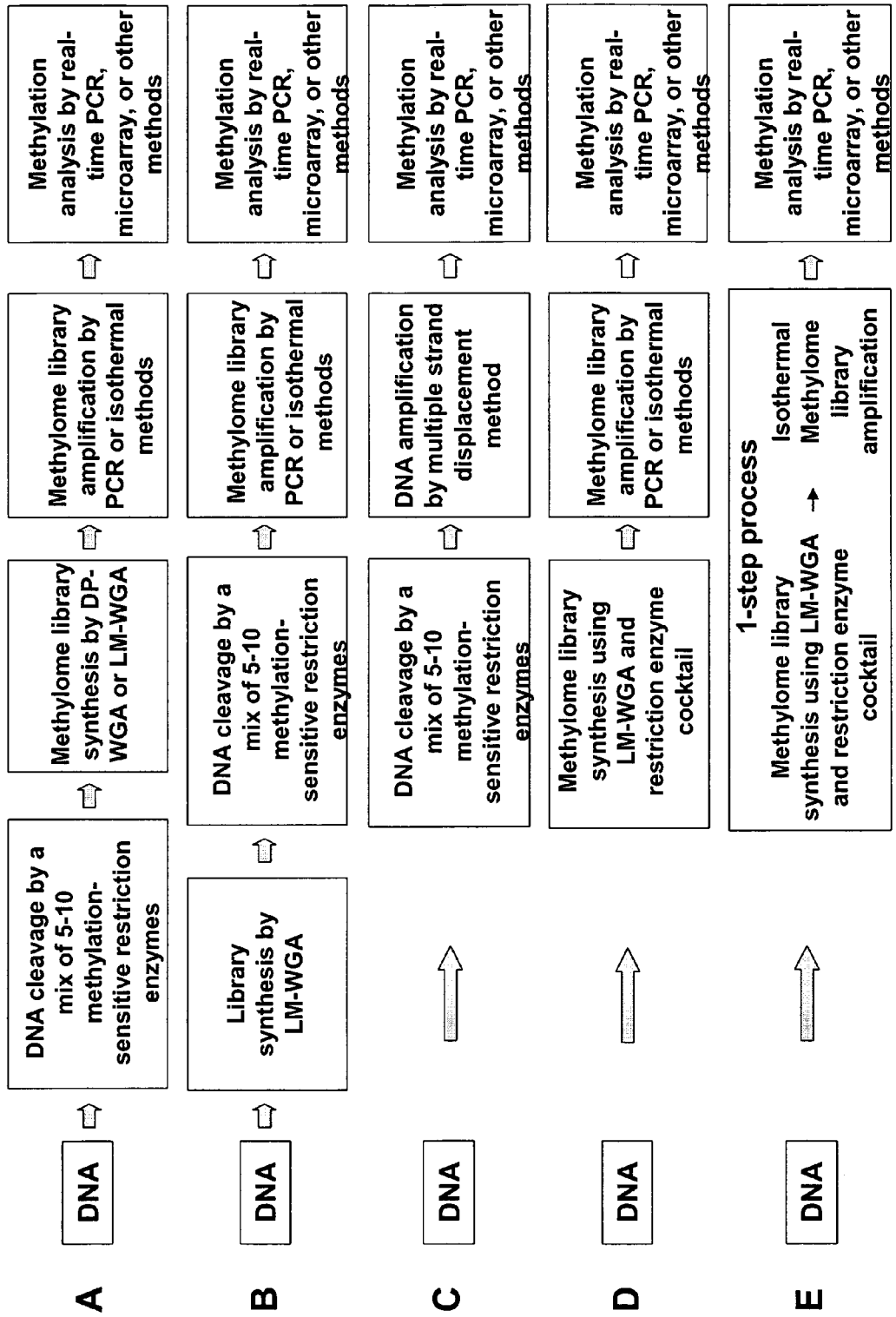
FIG. 68 shows a diagram illustrating different methods of preparing Methylome libraries that do not involve bisulfate conversion.
Figure 69:
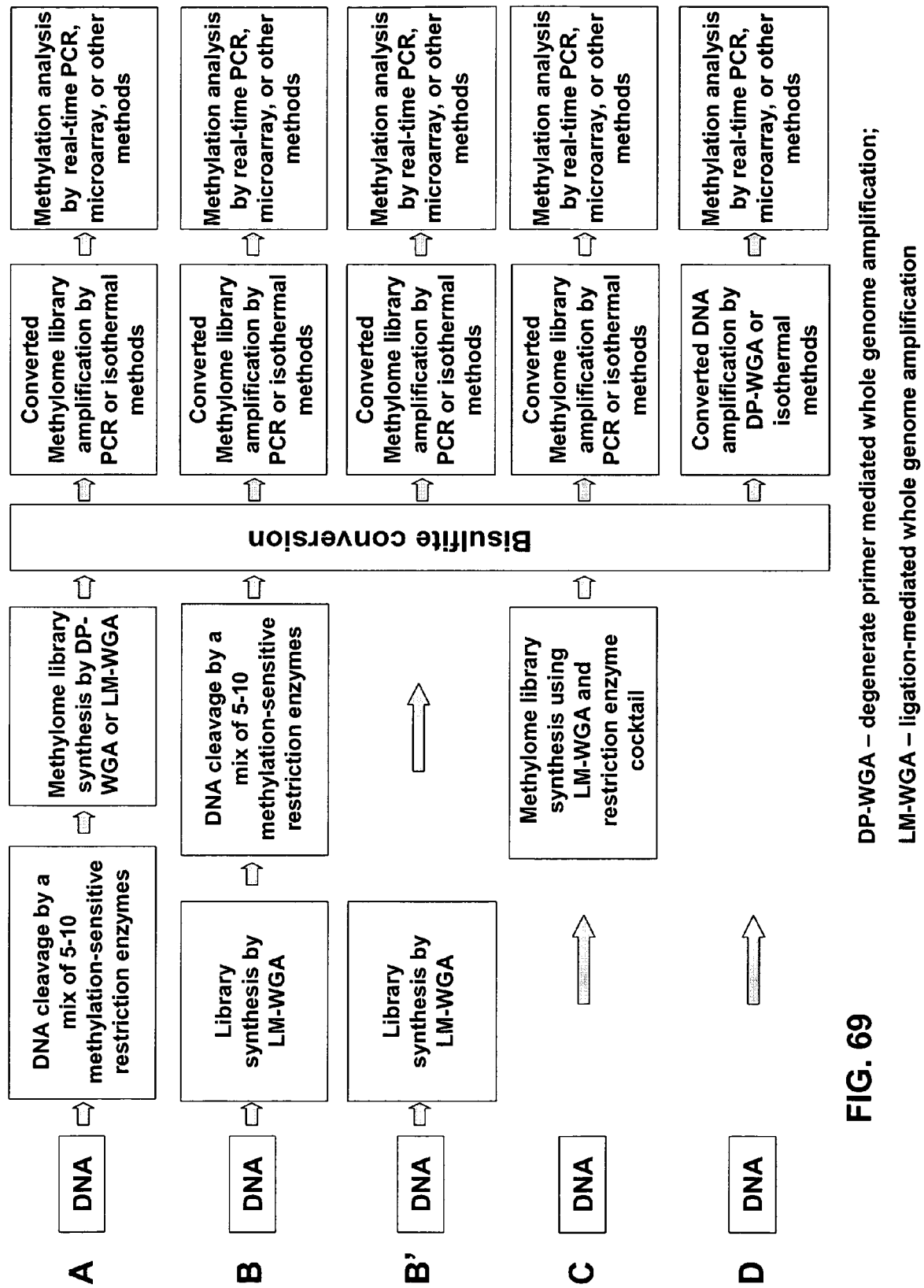
FIG. 69 shows a diagram illustrating different methods of preparing Methylome library that involves bisulfite conversion (versions of the thermo-enrichment Methylome library methods including those depicted on FIG. 69A) DNA cleavage with multiple methylation-sensitive restriction enzymes followed by the library synthesis, bisulfite conversion, amplification and analysis is provided.

In a preferred embodiment, there is a method for the preparation of Methylome libraries from substantially fragmented DNA in a multi-enzyme single step reaction that simultaneously involves DNA, DNA polymerase, DNA ligase, deoxy-uridine-comprising oligonucleotide adaptor, a mix of methylation-sensitive restriction enzymes, and a buffer system that supports all of these enzymatic activities (FIG. 68D). The DNA polymerase is preferably T4 DNA polymerase or Klenow fragment of E. coli DNA polymerase I, the DNA ligase is T4 DNA ligase, the cocktail of methylation-specific restriction enzymes comprises the following: Aci I, BstU I, Hha I, HinP1 I, HpaII, Hpy99 I, Ava I, Bce AI, Bsa HI, Bsi E1, Hga I, or a mixture thereof. The attached hairpin adaptor comprises deoxy-uridine in its loop that is converted to a replication stop comprising an abasic site, and the enzyme that converts deoxy-uridine to an abasic site is uracil-DNA glycosylase. The universal buffer that efficiently supports those enzyme activities is, for example, New England Biolabs buffer 4 (NEBuffer 4).

In some embodiments where the DNA molecule comprises nicked, partially single-stranded or otherwise damaged DNA, such as, for example, cell-free serum or urine DNA, the polymerase of choice is a DNA polymerase with reduced strand-displacement activity, such as T4 DNA polymerase.

An exemplary multi-enzyme single-step reaction that simultaneously involves DNA, DNA polymerase, DNA ligase, deoxy-uridine-comprising oligonucleotide adaptor, and a mix of methylation-sensitive restriction enzymes is performed in a reaction mixture having volume ranging from between about 10 and about 50 µl. The reaction mixture preferably comprises about 0.5 to about 100 ng of DNA, or in particular embodiments less than about 0.5 ng DNA, between 0.5-about 5 µM of deoxy-uridine containing hairpin adaptor, between 1-about 200 µM of all four dNTPs, between 0.1-about 10 mM ATP, between 0-about 0.1 mg/ml of bovine serum albumin (BSA), between 0.1-about 10 units of T4 DNA polymerase or Klenow fragment of E. coli DNA polymerase I, between 0.1-about 10 units of uracil-DNA glycosylase (UDG), between 10-about 5,000 units of T4 DNA ligase, and between about 0.1-about 50 units of a methylation-sensitive restriction endonuclease including but not limited to the following: Aci I, BstU I, Hha I, HinP1 I, HpaII, Hpy99 I, Ava I, Bce AI, Bsa HI, Bsi E1, Hga I or a mixture thereof. The reaction buffer preferably has a buffering capacity that is operative at physiological pH between about 6.5 and about 9. Preferably, the incubation time of the reaction is between about 10 to about 180 min, and the incubation temperature is between about 16° C.-about 42° C. in a buffer that efficiently supports all enzymatic activities such as the exemplary NEBuffer 4 (5 mM potassium acetate, 20 mM Tris-acetate, 10 mM magnesium acetate, 1 mM dithiothreitol, pH 7.9 at 25° C.).

In a specific embodiment (Example 33), there is analysis and determination of the dynamic range and sensitivity limits of methylation detection in cell-free urine DNA samples using mixed libraries of artificially methylated and non-methylated DNA. As shown on FIG. 58 as little as 0.01% of methylated DNA can be reliably detected in the background of 99.99% of non-methylated DNA. The figure also shows that the method disclosed in the present invention has a dynamic range of at least 3 orders of magnitude.

1. Attachment of Adaptors

There are two specific methods for the attachment of universal adaptors to the ends of DNA isolated from serum and plasma. Both of these methods have been detailed in U.S. patent application Ser. No. 10/797,333, filed Mar. 8, 2004, published as U.S. Patent Application Publication No.: 2004/0209299 and is now abandoned, and are included in their entirety by mention herein. The first method involves the polishing of the 3' ends of serum or plasma DNA to create blunt ends, followed by ligation of the universal adaptor. The second method involves ligation of universal adaptors with a combination of specific 5' and 3' overhangs to the ends of the serum or plasma DNA.

a. Polishing of Serum, Plasma, and Urine DNA and Ligation of Universal Adaptors

DNA that has been isolated from serum and plasma has been demonstrated to have at least three types of ends: 3' overhangs, 5' overhangs, and blunt ends (U.S. patent application Ser. No. 10/797,333, filed Mar. 8, 2004, published as U.S. Patent Application Publication No.: 2004/0209299 and is now abandoned; and references herein). In order to effectively ligate the adaptors to these molecules and extend these molecules across the region of the known adaptor sequence, the 3' ends need to be repaired so that preferably the majority of ends are blunt. This procedure is carried out by incubating the DNA fragments with a DNA polymerase having both 3' exonuclease activity and 3' polymerase activity, such as Klenow or T4 DNA polymerase, for example. Although reaction parameters may be varied by one of skill in the art, in an exemplary embodiment incubation of the DNA fragments with Klenow in the presence of 40 nmol dNTP and 1×T4 DNA ligase buffer results in optimal production of blunt end molecules with competent 3' ends.

Alternatively, Exonuclease III and T4 DNA polymerase can be utilized to remove 3' blocked bases from recessed ends and extend them to form blunt ends. In a specific embodiment, an additional incubation with T4 DNA polymerase or Klenow maximizes production of blunt ended fragments with 3' ends that are competent to undergo ligation to the adaptor.

In specific embodiments, the ends of the double stranded DNA molecules still comprise overhangs following such processing, and particular adaptors are utilized in subsequent steps that correspond to these overhangs.

Urine DNA is likely to be excessively nicked and damaged. During repair of ends using DNA polymerase with 3'-exonuclease activity, internal nicks are expected to be extended, a process that can potentially lead to replacement of methyl-cytosine with non-methylated cytosine. The stronger the strand displacement (or nick-translation) activity of the polymerase, the more methyl-cytosine would be lost in the process. Example 34 compares two DNA polymerases capable of polishing DNA termini to produce blunt ends competent for ligation for their ability to preserve methylation of CpG islands prior to cleavage with methylation-sensitive restriction enzymes.

Cell-free DNA isolated from urine is artificially methylated at all CpG sites by incubation with M.SssI CpG methylase in the presence of S-adenosylmethionine (SAM). Two aliquots of methylated DNA are processed for enzymatic repair of termini by incubation with Klenow fragment of DNA polymerase I or with T4 DNA Polymerase in the presence of all four dNTPs. Samples are ligated to universal $K_U$ adaptor (Table VI) with T4 DNA ligase, and split into 2 aliquots. One aliquot is digested with a cocktail of methylation-sensitive restriction enzymes AciI, HhaI, BstUI, HpaII, and Hinp1I. The second aliquot is incubated in parallel but without restriction enzymes ("uncut" control).

Libraries are amplified by PCR with universal primer $K_U$ (Table VI, SEQ ID NO: 15) and the presence of promoter sequences in the amplified libraries comprising one or more CpG sites as part of the methylation-sensitive restriction enzymes recognition sequences is analyzed by quantitative PCR using specific primers flanking such sites.

When methylated urine DNA was treated with Klenow fragment of DNA polymerase I prior to restriction cleavage this resulted in 75% to 90% loss of methyl-cytosine during the enzymatic repair. On the other hand, when T4 polymerase was used for polishing, 50% or more of the methyl-cytosine was preserved.

Thus, in a particular embodiment, the DNA polymerase used for repair of DNA prior to methylome library preparation is T4 DNA polymerase.

b. Ligation of Universal Adaptors with 5' and 3' Overhangs to Serum and Plasma DNA DNA that has been isolated from serum and plasma has been demonstrated to have at least three types of ends: 3' overhangs, 5' overhangs, and blunt ends (U.S. patent application Ser. No. 10/797,333, filed Mar. 8, 2004, published as U.S. Patent Application Publication No.: 2004/0209299 and is now abandoned; and references herein). This mixture of ends precludes the ligation of a universal adaptor with a single type of end. Thus, a specific mixture of adaptor sequences comprising both 5' overhangs of 2, 3, 4, and 5 bp, and 3' overhangs of 2, 3, 4, and 5 bp has been developed and demonstrated to yield optimal ligation to serum and plasma DNA. The characteristics of ligation of this mixture to serum and plasma DNA has been documented in U.S. patent application Ser. No. 10/795,667, filed Mar. 8, 2004, now U.S. Pat. No. 7,718,403. These adaptors are illustrated in FIG. 48. These adaptors are comprised of two oligos, 1 short and 1 long, which are hybridized to each other at some region along their length. In a specific embodiment, the long oligo is a 20-mer that will be ligated to the 5' end of fragmented DNA. In another specific embodiment, the short oligo strand is a 3' blocked 11-mer complementary to the 3' end of the long oligo. A skilled artisan recognizes that the length of the oligos that comprise the adaptor may be modified, in alternative embodiments. For example, a range of oligo length for the long oligo is about 18 bp to about 100 bp, and a range of oligo length for the short oligo is about 7 bp to about 20 bp. Furthermore, the structure of the adaptors has been developed to minimize ligation of adaptors to each other via at least one of three means: 1) absence of a 5' phosphate group necessary for ligation; 2) presence of about a 7 bp 5' overhang that prevents ligation in the opposite orientation; and/or 3) a 3' blocked base preventing fill-in of the 5' overhang.

A typical ligation procedure involves the incubation of 1 to 100 ng of DNA in 1×T4 DNA ligase buffer, 10 pmol of each adaptor, and 400 Units of T4 DNA Ligase. Ligations are performed at 16° C. for 1 hour, followed by inactivation of the ligase at 75° C. for 15 minutes. The products of ligation can be stored at −20° C. to 4° C. until amplification.

In a particular embodiment, the adaptor of choice is partially double-stranded self-inert sequence comprising non Watson-Crick bases (for example universal $K_U$ adaptor (Table VI). Ligation of universal adaptor is performed preferably in a buffer system supporting all enzymatic activities used for methylome library synthesis such as New England Biolabs Buffer 4 (NEBuffer 4).

An exemplary adaptor ligation is performed in a reaction mixture having volume ranging from between about 5 and about 50 µl, for example. The reaction mixture preferably comprises about 0.5 to about 100 ng of DNA, or in particular embodiments less than about 0.5 ng DNA, between 0.5-about 10 µM of partially double-stranded self-inert adaptor (universal $K_U$ adaptor, Table VI), between 0.1-about 10 mM ATP, and between 10-about 5,000 units of T4 DNA ligase or another suitable DNA ligase. Preferably, the incubation time of the reaction is between about 10 to about 180 min, and the incubation temperature is between about 16° C.-about 42° C. in a buffer that efficiently supports all enzymatic activities, such as the exemplary NEBuffer 4 (5 mM potassium acetate, 20 mM Tris-acetate, 10 mM magnesium acetate, 1 mM dithiothreitol, pH 7.9 at 25° C.).

2. Choice of Restriction Endonuclease

Methylation-sensitive restriction enzymes with recognition sites comprising the CpG dinucleotide and no adenine or thymine are expected to cut genomic DNA with much lower frequency as compared to their counterparts having recognition sites with normal GC to AT ratio. There are two reasons for this. First, due to the high rate of methyl-cytosine to thymine transition mutations, the CpG dinucleotide is severely under-represented and unequally distributed across the human genome. Large stretches of DNA are depleted of CpGs and thus do not contain these restriction sites. Second, most methylated cytosine residues are found in CpG dinucleotides that are located outside of CpG islands, primarily in repetitive sequences. Due to methylation, these sequences will also be protected from cleavage. On the other hand, about 50 to 60% of the known genes comprise CpG islands in their promoter regions and they are maintained largely unmethylated, except in the cases of normal developmental gene expression control, gene imprinting, X chromosome silencing, or aberrant methylation in cancer and some other pathological conditions, for example. These CpG islands will be digested by the methylation-sensitive restriction enzymes in normal gene promoter sites but not in aberrantly methylated promoters. Four base GC recognition restriction enzymes as exemplified by Aci I, BstU I, Hha I, HinP1 I, and Hpa II with recognition sites CCGC, CGCG, GCGC, and CCGG, respectively (Table III), are particularly useful since they will frequently cut non-methylated DNA in CpG islands, but not methylated DNA. A complete list of methylation-sensitive restriction endonucleases is presented in Table III.

In preferred embodiments the methylation-sensitive restriction enzymes include but are not limited to the following: Aci I, BstU I, Hha I, HinP1 I, HpaII, Hpy99 I, Ava I, Bce AI, Bsa HI, Bsi E1, Hga I or a mixture thereof 3. Restriction Digestion of Target DNA In a specific embodiment, target DNA is digested with a methylation-sensitive restriction endonuclease(s), such as Aci I, BstU I, Hha I, HinP1 I, and Hpa II or a compatible combination thereof. The digestion reaction comprises about 0.1 ng to 5 µg of genomic DNA, 1× reaction buffer, and about 1 to about 25 units of restriction endonuclease(s). The mixture is incubated at 37° C. or at the optimal temperature of the respective endonuclease for about 1 hour to about 16 hour to ensure complete digestion. When appropriate, the enzyme is inactivated at 65° C. to 70° C. for 15 minutes and the sample is precipitated and resuspended to a final concentration of 1 to 50 ng/µl. Genomic DNA that has not been digested is used as a positive control during library preparation and analysis.

In preferred embodiments the methylation-sensitive restriction enzymes include but are not limited to the following: Aci I, BstU I, Hha I, HinP1 I, HpaII, Hpy99 I, Ava I, Bce AI, Bsa HI, Bsi E1, Hga I or a mixture thereof. The buffer for restriction digestion will support all enzymatic activities, for example NEBuffer 4 or other compatible buffer system. To achieve complete digestion, the incubation times can vary between about 1 hour and about 24 hours, for example. Incubation temperatures can also vary depending on the optimal temperature of a particular enzyme or a combination of enzymes. Stepwise incubations can be performed to accommodate the optimal temperatures of multiple restriction enzymes. In an exemplary methylation-sensitive restriction digestion, a target DNA and a cocktail of enzymes comprising AciI, HhaI, BstUI, HpaII, and Hinp1I is carried out for 12-18 hours at 37° C., the optimal temperature for AciI, HhaI, HpaII, and Hinp1I, followed by 2 hours at 60° C., the optimal temperature for BstUI.

A skilled artisan recognizes that a complete cleavage of DNA is critical in the analysis of promoter hypermethylation from clinical samples where methylated cancer DNA only represents a small fraction of the total DNA. To relax any possible constraints imposed on restriction cleavage of promoter sequences by high GC content and secondary structure that can make cleavage incomplete, one can envision using specific treatments or additives that can facilitate relaxation. One such treatment is heating the DNA to temperatures that are not denaturing yet high enough to relax secondary structure and promote proper Watson-Crick base pairing. Example 28 illustrates the effect of pre-heating of genomic DNA on the efficiency of cleavage by the methylation-sensitive restriction enzyme Aci I. Genomic DNA is pre-heated for 30 minutes at 85° C., 90° C., or 95° C. and analyzed by quantitative PCR for amplification of a promoter region of the human p16 gene that is very GC-rich and comprises excessive secondary structure. Pre-heating at 85° C. reproducibly improves the cleavage by about a factor of 2 as compared to control that was not pre-heated. This improvement of cleavage by pre-heating at 85° C. was demonstrated for multiple promoter sites and restriction enzymes. Thus, in specific embodiments genomic DNA is preheated to 85° C. prior to cleavage with restriction enzymes.

4. Extension of the 3' End of the DNA Fragment to Fill in the Universal Adaptor

Due to the absence of a phosphate group at the 5' end of the adaptor, only one strand of the adaptor (3' end) will be covalently attached to the DNA fragment. A 72° C. extension step is performed on the DNA fragments in the presence of 1×DNA polymerase, 1×PCR Buffer, 200 µM of each dNTP, and 1 uM universal primer. This step may be performed immediately prior to amplification using Taq polymerase or may be carried out using a thermo-labile polymerase, such as if the libraries are to be stored for future use, for example.

5. Amplification of Primary Methylation Library

A typical amplification step with universal sequence primer comprises between about 1 and about 25 ng of library products and between about 0.3 and about 2 µM of universal sequence primer with or without the presence of a poly-C sequence at the 5' end, in a standard PCR reaction well known in the art, under conditions optimal for a thermostable DNA polymerase, such as Taq DNA polymerase, Pfu polymerase, or derivatives and mixtures thereof.

6. Analysis of the Amplified Products to Determine the Methylation Status of Target DNA Aliquots of the amplified library DNA are analyzed for the presence of CpG sites or regions encompassing more than one such site. This can be achieved by quantitative real-time PCR amplification, comparative hybridization, ligation-mediated PCR, ligation chain reaction (LCR), fluorescent or radioactive probe hybridization, probe amplification, hybridization to promoter microarrays comprising oligonucleotides or PCR fragments, or by probing microarray libraries derived from multiple samples with labeled PCR or oligonucleotide probes, for example. The magnitude of the signal will be proportional to the level of methylation of a promoter site.

A typical quantitative real-time PCR-based methylation analysis reaction comprises 1×Taq polymerase reaction buffer, about 10 to about 50 ng of library DNA, about 200 to about 400 nM of each specific primer, about 4% DMSO, 0 to about 0.5 M betaine (Sigma), 1:100,000 dilutions of fluorescein calibration dye (FCD) and SYBR Green I (SGI) (Molecular Probes), and about 5 units of Taq polymerase. PCR is carried out on an I-Cycler real-time PCR system (BioRad) using a cycling protocol optimized for the respective primer pair and for the size and the base composition of the analyzed amplicon.

3. Sources of DNA for Methylation Analysis

The source of genomic DNA in one embodiment is serum, plasma, or urine DNA. This DNA has been demonstrated to have a size distribution of approximately 200 bp to 3 kb. Furthermore, this DNA comprises 5' phosphate groups and 3' hydroxyl groups that facilitate the attachment of universal adaptors. Genomic DNA of any source or complexity with characteristics similar to those found in DNA from serum and plasma can be analyzed by the methods described in the invention. Clinical samples comprising fragmented and/or degraded DNA representing biopsy materials, pap smears, DNA from blood cells, urine, or other body fluids, or DNA isolated from apoptotic cells, and cultured primary or immortalized tissue cultures can be used as a source for methylation analysis, for example.

F. Methylation Analysis of Substantially Fragmented DNA Using Libraries Digested with the Methylation-Specific Restriction Endonuclease McrBC In this embodiment, there are methods of preparing libraries from fragmented DNA molecules in such a way as to select for sequences that comprise recognition sites for the methylation-specific restriction endonuclease McrBC. In a preferred embodiment, serum or plasma DNA is the source of the starting material. DNA isolated from serum and plasma has a typical size range of approximately 200 bp to 3 kb, based on gel analysis. Furthermore, this material can be converted into libraries and amplified by whole genome amplification methodologies cited in U.S. patent application Ser. No. 10/797,333, filed Mar. 8, 2004, published as U.S. Patent Application Publication No.: 2004/0209299 and is now abandoned, for example. The synthesis of these libraries involves techniques that do not affect the methylation status of the starting DNA. It is apparent to those skilled in the art that the starting material can be obtained from any source of tissue and/or procedure that yields DNA with characteristics similar to those obtained from serum and plasma DNA.

In one specific embodiment (Example 26, FIG. 47), primary methylation libraries are synthesized from serum and plasma DNA by ligation of an adaptor comprising a poly-C sequence, and digestion with the methylation-specific restriction endonuclease McrBC. Subsequently, a second adaptor, or mixture of adaptors, is ligated to the resulting fragments. Amplification of the methylation library is carried out using a primer complementary to the second adaptor(s) in conjunction with a poly-C primer. The resulting amplicons will comprise only those molecules that have the second adaptor at one or both ends. Molecules that were not digested by McrBC will not have the second adaptor(s) attached and will not be amplified by the poly-C primer. This lack of amplification of molecules containing a poly-C primer at both ends has been documented in U.S. patent application Ser. No. 10/293,048, filed Nov. 13, 2002, now U.S. Pat. No. 7,655,791; U.S. patent application Ser. No. 10/795,667, filed Mar. 8, 2004, now U.S. Pat. No. 7,718,403; and U.S. patent application Ser. No. 10/797,333, filed Mar. 8, 2004, published as U.S. Patent Application Publication No.: 2004/0209299 and is now abandoned. Thus, the products of amplification of the secondary methylation library will be enriched in molecules that comprised two or more methylated CpGs in the starting material. The resulting products can be analyzed by PCR, microarray hybridization, probe assay, probe hybridization, probe amplification, or other methods known in the art, for example. Alternatively, they can be sequenced to determine sites for which there is no a priori knowledge of importance. Due to the variation in where McrBC cleavage occurs between two methylated CpG sites, further analysis may be required to determine which specific CpG sites were methylated in the starting material in regions comprising three or more CpGs.

1. Attachment of Adaptors

There are two specific methods for the attachment of universal adaptors to the ends of DNA isolated from serum and plasma. Both of these methods have been detailed in U.S. patent application Ser. No. 10/797,333, filed Mar. 8, 2004, published as U.S. Patent Application Publication No.: 2004/0209299 and is now abandoned, for example. The first method involves the polishing of the 3' ends of serum or plasma DNA to create blunt ends, followed by ligation of the universal adaptor. The second method involves ligation of universal adaptors with a combination of specific 5' and 3' overhangs to the serum or plasma DNA. For this embodiment, the adaptors that are ligated to the ends of the molecules will comprise a poly-C sequence, either alone or in combination with a universal priming sequence. Alternatively, a poly-G sequence can be added to the ends of the ligated molecules by terminal transferase addition.

a. Polishing of Serum and Plasma DNA and Ligation of Universal Adaptors

DNA that has been isolated from serum and plasma has been demonstrated to have at least three types of ends: 3' overhangs, 5' overhangs, and blunt ends. In order to effectively ligate the adaptors to these molecules and extend these molecules across the region of the known adaptor sequence, the 3' ends need to be repaired so that preferably the majority of ends are blunt. This procedure is carried out by incubating the DNA fragments with a DNA polymerase having both 3' exonuclease activity and 3' polymerase activity, such as Klenow or T4 DNA polymerase, for example. Although reaction parameters may be varied by one of skill in the art, in an exemplary embodiment incubation of the DNA fragments with Klenow in the presence of 40 nmol dNTP and 1×T4 DNA ligase buffer results in optimal production of blunt end molecules with competent 3' ends.

Alternatively, Exonuclease III and T4 DNA polymerase can be utilized to remove 3' blocked bases from recessed ends and extend them to form blunt ends. In a specific embodiment, an additional incubation with T4 DNA polymerase or Klenow maximizes production of blunt ended fragments with 3' ends that are competent to undergo ligation to the adaptor.

In specific embodiments, the ends of the double stranded DNA molecules still comprise overhangs following such processing, and particular adaptors are utilized in subsequent steps that correspond to these overhangs.

b. Ligation of Universal Adaptors with 5' and 3' Overhangs to Serum and Plasma DNA DNA that has been isolated from serum and plasma has been demonstrated to have at least three types of ends: 3' overhangs, 5' overhangs, and blunt ends.

This mixture of ends precludes the ligation of a universal adaptor with a single type of end. Thus, a specific mixture of adaptor sequences containing both 5' overhangs of 2, 3, and 5 bp, and 3' overhangs of 2, 3, and 5 bp has been developed and demonstrated to yield optimal ligation to serum and plasma DNA. The characteristics of ligation of this mixture to serum and plasma DNA has been documented in U.S. Patent Application No. Ser. No. 10/797,333, filed Mar. 8, 2004, published as U.S. Patent Application Publication No.: 2004/0209299 and is now abandoned. These exemplary adaptors are illustrated in FIG. 48. These adaptors are comprised of two oligos, 1 short and 1 long, which are hybridized to each other at some region along their length. In a specific embodiment, the long oligo is a 20-mer that will be ligated to the 5' end of fragmented DNA. In another specific embodiment, the short oligo strand is a 3' blocked 11-mer complementary to the 3' end of the long oligo. A skilled artisan recognizes that the length of the oligos that comprise the adaptor may be modified, in alternative embodiments. For example, a range of oligo length for the long oligo is about 18 bp to about 100 bp, and a range of oligo length for the short oligo is about 7 bp to about 20 bp. Furthermore, the structure of the adaptors has been developed to minimize ligation of adaptors to each other via at least one of three means: 1) absence of a 5' phosphate group necessary for ligation; 2) presence of about a 7 bp 5' overhang that prevents ligation in the opposite orientation; and/or 3) presence of a 3' blocked base preventing fill-in of the 5' overhang.

A typical ligation procedure involves the incubation of 1 to 100 ng of DNA in 1×T4 DNA ligase buffer, 10 pmol of each adaptor, and 400 Units of T4 DNA Ligase. Ligations are performed at 16° C. for 1 hour, followed by inactivation of the ligase at 75° C. for 15 minutes. The products of ligation can be stored at −20° C. to 4° C. until amplification.

2. Extension of the 3' End of the DNA Fragment to Fill in the Universal Adaptor

Due to the absence of a phosphate group at the 5' end of the adaptor, only one strand of the adaptor (3' end) will be covalently attached to the DNA fragment. An extension step is performed on the DNA fragments in the presence of Klenow, 1× Buffer, and 40 nmol of each dNTP at 25° C. for 15 minutes, followed by inactivation of the enzyme at 75° C. for 10 min, and cooling to 4° C.

3. McrBC Cleavage

In embodiments of the present invention, DNA is digested with McrBC endonuclease in the presence of GTP as the energy source for subunit translocation. A typical digestion with McrBC endonuclease is performed in a volume ranging from about 5 µl to about 50 µl in buffer comprising about 50 mM NaCl, about 10 mM Tris-HCl having pH of about 7.5 to about 8.5, about 100 µg/ml of bovine serum albumin, about 0.5 to about 2 mM GTP, and about 0.2 to about 20 units of McrBC endonuclease. The temperature of incubation is between about 16° C. and about 42° C., and the duration is between about 10 min and about 16 hours. DNA amount in the reaction is between about 50 pg and about 10 µg. It should be noted that McrBC makes one cut between each pair of half-sites, cutting close to one half-site or the other, but cleavage positions are distributed over several base pairs approximately 30 base pairs from the methylated base (Panne et al., 1999) resulting in a smeared pattern instead of defined bands. In specific embodiments, digestion with McrBC is incomplete and results in predominant cleavage of subset of sites separated by about 35 and about 250 bases. In other specific embodiments cleavage is complete and results in digestion of substantially all possible cleavage sites. Example 3 describes the optimization of the cleavage of human genomic DNA and analysis of the termini produced by McrBC. It should be noted that from the existing literature the nature of the ends produced by McrBC digestion is not understood. Example 9 also details the analysis of the nature of the ends produced by McrBC cleavage.

4. Attachment of Second Adaptor(s)

Following McrBC digestion, the cleavage products are incubated in a ligation reaction comprising T4 ligase buffer, about 200 nM to about 1 µM of universal adaptors with 5' overhangs comprising about 5 or 6 completely random bases, and about 200 to 2,500 units of T4 DNA ligase for about 1 hour to overnight at about 16° C. to about 25° C. The T4 DNA ligase is inactivated for 10 minutes at 65° C., and the reaction is cooled to 4° C.

5. Extension of the 3' End of the DNA Fragment to Fill in the Second Adaptors

Due to the absence of a phosphate group at the 5' end of the adaptors, only one strand of the adaptor (3' end) will be covalently attached to the DNA fragment. A 72° C. extension step is performed on the DNA fragments in the presence of 1×DNA polymerase, 1×PCR Buffer, 200 µM of each dNTP, and 1 uM universal primer. This step may be performed immediately prior to amplification using Taq polymerase, or may be carried out using a thermo-labile polymerase, such as if the libraries are to be stored for future use, for example.

6. Amplification of the Methylation Library

The amplification of the secondary methylation library involves use of a poly-C primer, such as $C_{10}$ (SEQ ID NO:38), as well as a universal primer complementary to the second adaptor. A typical amplification step comprises between about 1 and about 25 ng of library products and between about 0.3 and about 1 µM of second universal sequence primer, and about 1 µM $C_{10}$ primer (SEQ ID NO:38), in a standard PCR reaction well known in the art, under conditions optimal for a thermostable DNA polymerase, such as Taq DNA polymerase, Pfu polymerase, or derivatives and mixtures thereof 7. Analysis of the Amplified Products to Determine the Methylation Status of Target DNA Aliquots of the amplified library DNA are analyzed for the presence of sequences adjacent to CpG sites. This can be achieved by quantitative real-time PCR amplification, comparative hybridization, ligation-mediated PCR, ligation chain reaction (LCR), fluorescent or radioactive probe hybridization, probe amplification, hybridization to promoter microarrays comprising oligonucleotides or PCR fragments, or by probing microarray libraries derived from multiple samples with labeled PCR or oligonucleotide probes, for example. The magnitude of the signal will be proportional to the level of methylation of a promoter site.

A typical quantitative real-time PCR-based methylation analysis reaction comprises 1×Taq polymerase reaction buffer, about 10 to about 50 ng of library DNA, about 200 to about 400 nM of each specific primer, about 4% DMSO, 0 to about 0.5 M betaine (Sigma), 1:100,000 dilutions of fluorescein calibration dye (FCD) and SYBR Green I (SGI) (Molecular Probes), and about 5 units of Taq polymerase. PCR is carried out on an I-Cycler real-time PCR system (Bio-Rad) using a cycling protocol optimized for the respective primer pair and for the size and the base composition of the analyzed amplicon.

In addition, the amplification products of the methylation library can be analyzed by sequencing. The variability in the site of McrBC cleavage can complicate the identification of specific methylated CpGs in CpG islands that comprise a high number of methylated sites. Therefore, sequence analysis will allow the direct determination of the specific CpG site adjacent to the cleavage site in regions of DNA that comprise multiple CpGs in close proximity.

8. Sources of DNA for Methylation Analysis

The source of genomic DNA in one embodiment is serum or plasma DNA. This DNA has been demonstrated to have a size distribution of approximately 200 bp to 3 kb. Furthermore, this DNA comprises 5' phosphate groups and 3' hydroxyl groups, which facilitate the attachment of universal adaptors. Genomic DNA of any source or complexity with characteristics similar to those found in DNA from serum and plasma can be analyzed by the methods described in the invention. Clinical samples comprising substantially fragmented and/or degraded DNA representing biopsy materials, pap smears, DNA from blood cells, urine, or other body fluids, or DNA isolated from apoptotic cells, and cultured primary or immortalized tissue cultures can be used as a source for methylation analysis.

Figure 49:
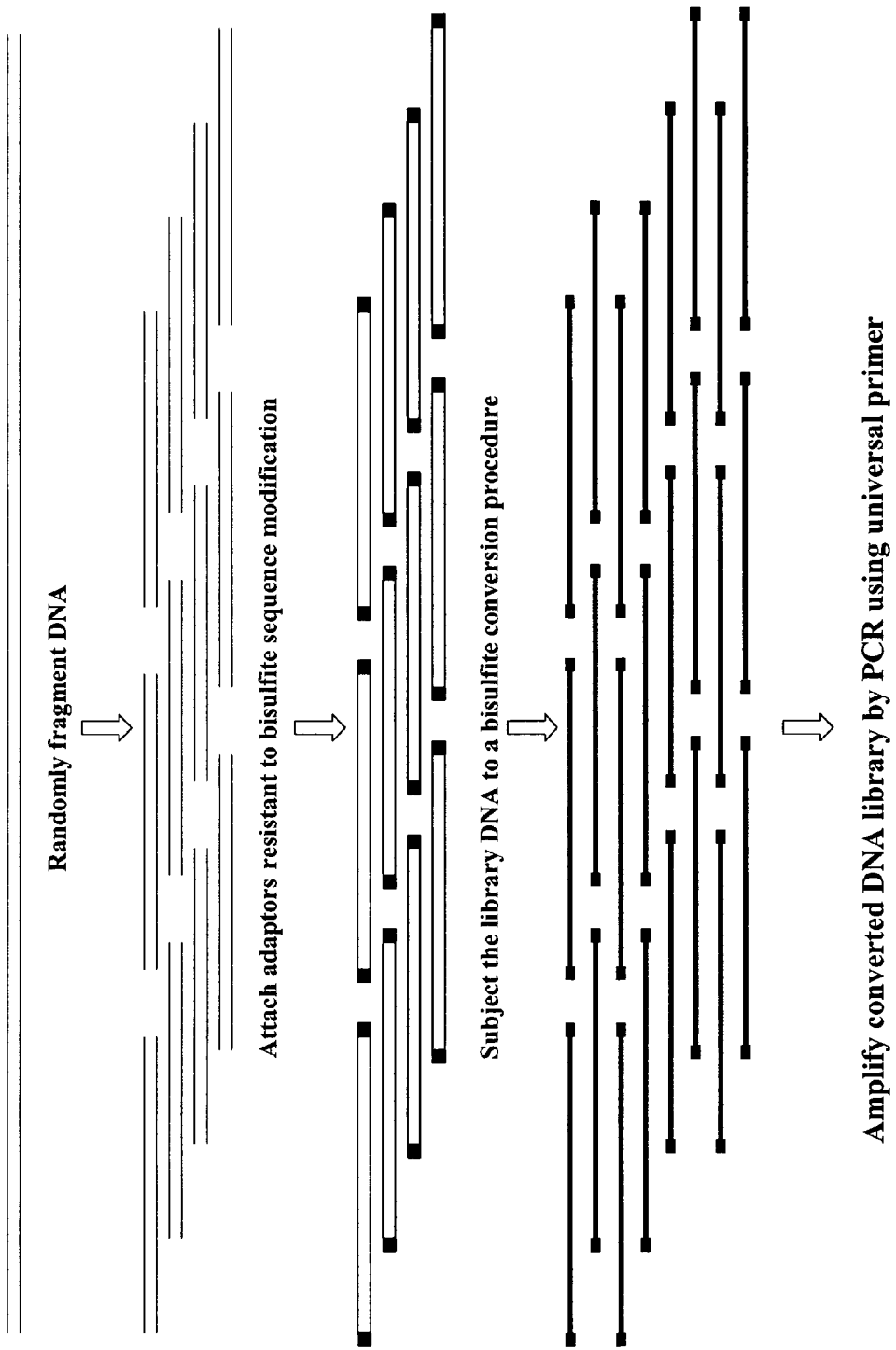
FIG. 49 depicts a method for preparation and amplification of whole genome libraries prior to bisulfite conversion. In this method, genomic DNA is randomly fragmented and adaptors are subsequently attached to the ends of the DNA fragments. These adaptors are resistant to bisulfite conversion and will maintain their sequence following bisulfite treatment (See FIG. 50). The DNA library undergoes bisulfite conversion and the products of this conversion are amplified using primers complementary to the adaptor sequence.
Figure 50:
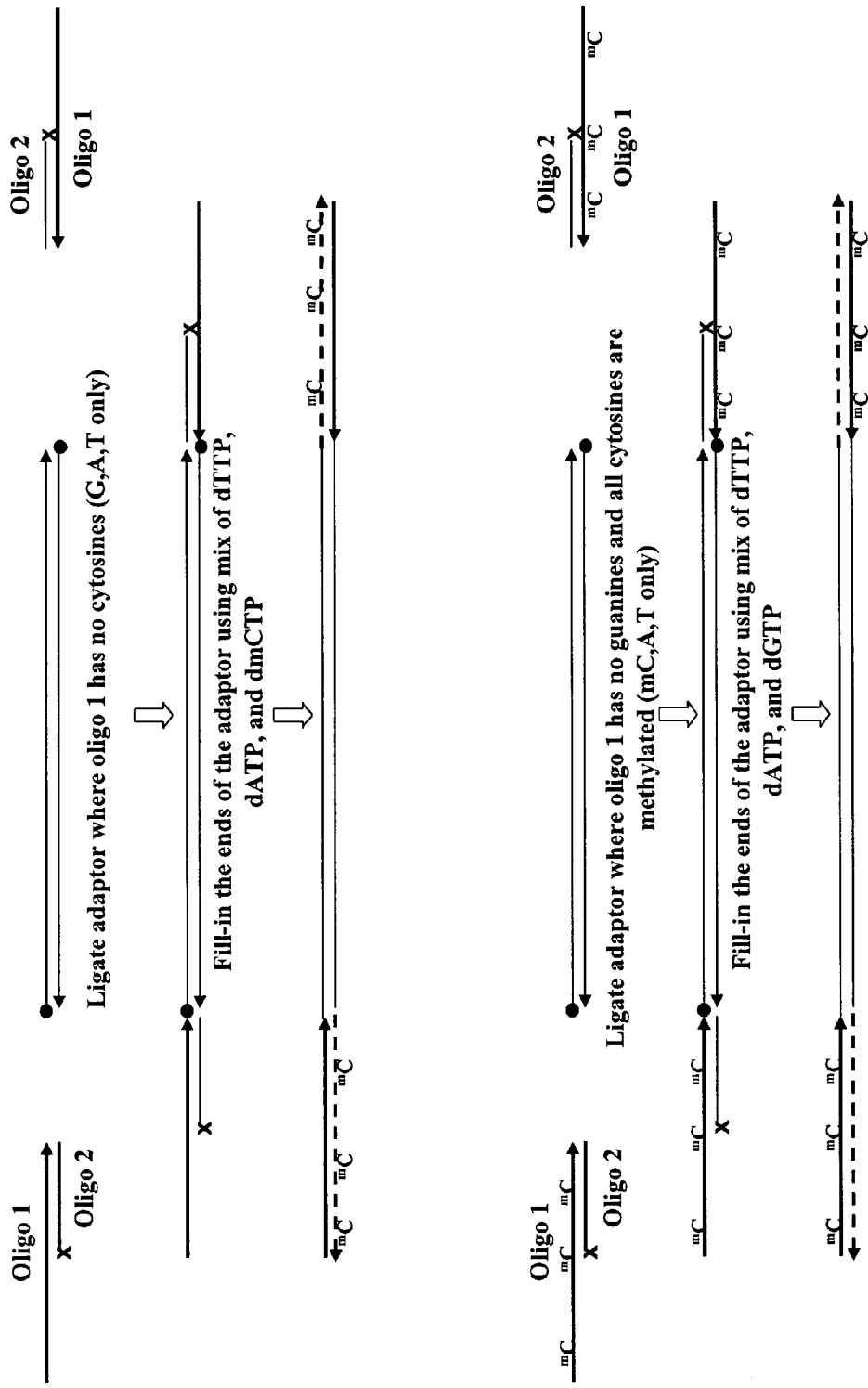
FIG. 50 illustrates attachment of two types of adaptor sequences that are resistant to bisulfite conversion used in FIG. 49. In the first case, oligo 1 does not contain any cytosines and is therefore resistant to conversion. Following attachement of the adaptor, the ends of the molecules are extended in the presence of dTTP, dATP, and dmCTP, but not dCTP or dGTP. Therefore, the filled in ends only contain methylated cytosines resistant to bisulfite conversion. In the second case, oligo 1 contains methylated cytosine, but no guanine. Thus, oligo 1 is resistant to bisulfite cleavage. Extension of the 3' ends of the molecules occurs in the presence of dGTP, dATP, and dTTP, but not dCTP. Thus, the filled-in ends do not contain any cytosines and they are not affected by bisulfite conversion. In both cases, a primer complementary to the adaptor sequence can be utilized without concern for the effects of bisulfite conversion.
Figure 60A:
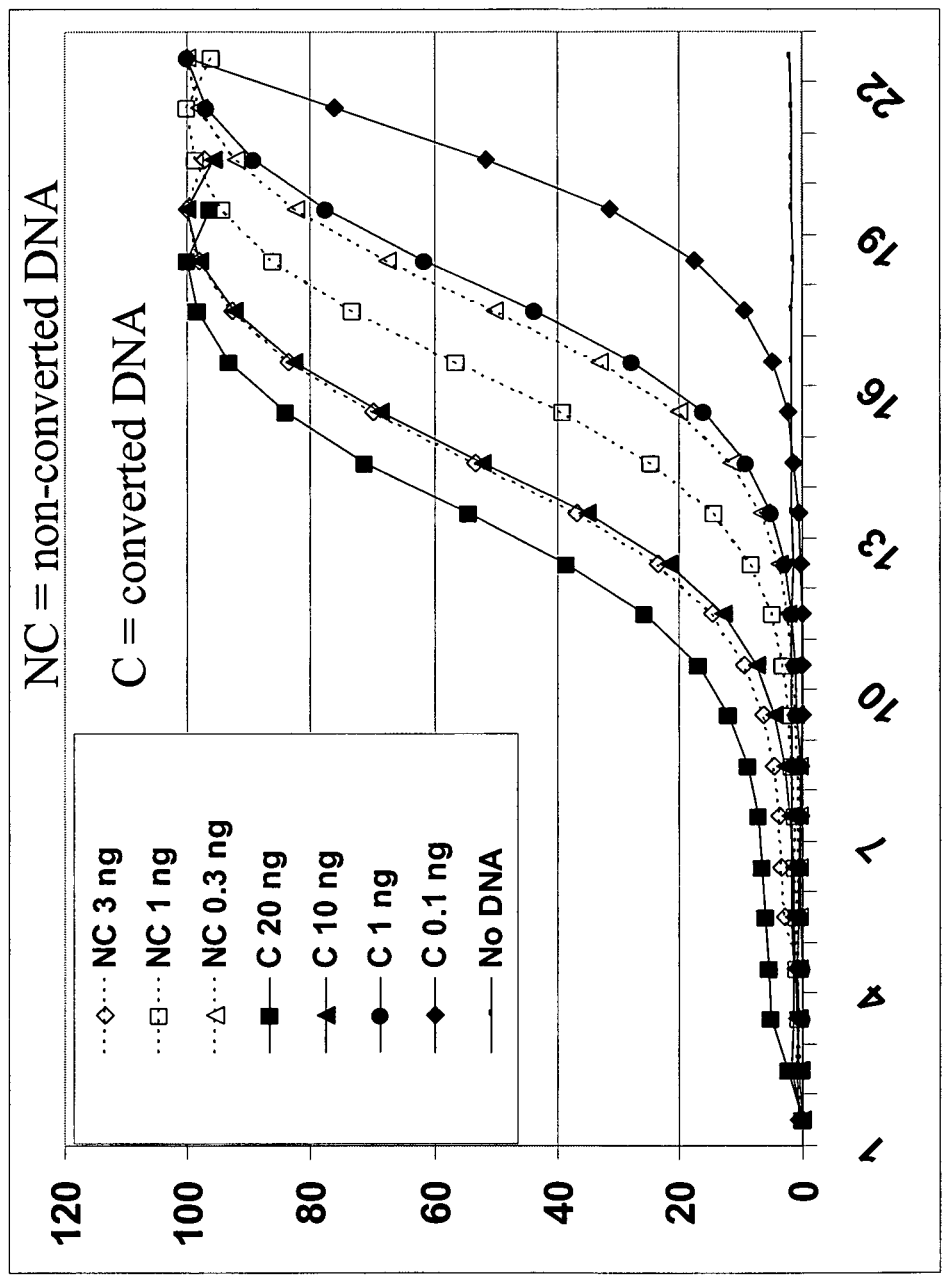
FIG. 60A shows real-time PCR amplification curves for a range of input DNA from libraries of bisulfite converted and non-converted DNA.

G. Methylation Analysis of Substantially Fragmented DNA Using Methylome Libraries Subjected to Bisulfite Conversion In this embodiment, there are methods for analyzing methylation by preparing libraries of fragmented DNA molecules in such a way that both bisulfate-converted library molecules and unconverted library molecules can be amplified with the same universal primer (FIGS. 49 and 50). The fragmented DNA molecules may be obtained in an already substantially fragmented form, such as purified from serum, plasma, or urine, or generated by random fragmentation by enzymatic, mechanical, or chemical means that do not change the methylation status of the original DNA, for example Libraries are prepared from the fragmented DNA molecules by attaching adaptors resistant to bisulfite conversion. The resistant adaptors have specific sequence requirements and may have a non-hairpin structure, as described in U.S. patent application Ser. No. 10/797,333, filed Mar. 8, 2004, published as U.S. Patent Application Publication No.: 2004/0209299 and is now abandoned, or preferably may have a dU-Hairpin structure, as described in Table VI and Examples 33, 38, and 39. Non-hairpin adaptors can comprise two different kinds of sequences, one in which the strand that is attached to the DNA fragment does not comprise cytosines, and a second in which the strand that is attached to the DNA fragment does not comprise guanines, and all cytosines in that strand are methylated. Similarly, hairpin adaptors can comprise two different kinds of sequences, one in which the 3' stem region that is attached to the DNA fragment does not comprise cytosines, and a second in which the 3' stem region does not comprise guanines, and any cytosines are methylated. The adaptors are attached according to methods as described in U.S. patent application Ser. No. 10/797,333, filed Mar. 8, 2004, published as U.S. Patent Application Publication No.: 2004/0209299 and is now abandoned, or preferably as described in Examples 33, 35, 38, and 39. To further protect the adaptor sequences from bisulfite conversion, dCTP in the nucleotide mix is substituted with methyl-dCTP during fill-in of 3' library ends. These methylome libraries are subjected to bisulfite conversion, and the converted libraries are amplified in a PCR reaction with a primer comprising the universal sequence and a thermostable polymerase. The amplified libraries may be analyzed by any of a number of specific analytical methods for bisulfite-converted DNA known in the art, such as methylation-specific PCR, sequencing, and quantitative PCR (MethyLight). The amplification of bisulfite-converted methylome libraries allows genomewide analysis of nanogram starting quantities of bisulfite-converted DNA In one specific embodiment (Example 35), there is a demonstration of the amplification of whole methylome libraries subjected to bisulfite conversion. Libraries are prepared from unmethylated urine DNA by attachment of bisulfite-resistant adaptor Ku (Table VI), and an aliquot of that library is amplified using the universal Ku primer (SEQ ID NO:15). A separate aliquot of that library is amplified using the universal Ku primer. FIG. 60A shows that approximately 30% of library molecules are amplifiable after bisulfite conversion, based upon a comparison with unconverted library molecules. The bisulfite conversion of library molecules is confirmed by detecting converted DNA sequences in the amplified, converted methylome library but not the untreated methylome library (FIG. 60B).

In a preferred embodiment, high sensitivity and specificity methylation analysis is achieved by bisulfite conversion and amplification of libraries enriched for methylated gene promoter regions by methylationsensitive restriction digestion (such as in Examples 38 and 39). For samples from sources such as serum, plasma, or urine where a major fraction of DNA may originate from normal cells and cancer DNA constitutes only a very small fraction (less than 1%, for example), amplification of enriched converted library molecules allows methylation analyses, such as MethylLight, that are not possible with converted but non-enriched DNA. The bisulfite treatment can also increase the specificity for detecting methylated gene promoter regions in the enriched libraries by greatly reducing or even completely eliminating non-methylated DNA from the library that may be present due to incomplete digestion.

H. Methylation Analysis of Substantially Fragmented DNA Using Methylome Libraries Enriched for CpG-Rich DNA by Heating In this embodiment, Methylome library synthesis employs methods for additional enrichment of CpG-rich genomic DNA from substantially fragmented DNA. Methylome libraries as described in this application are very powerful tools that permit the analysis of DNA methylation from very limited amounts and substantially fragmented samples such as cell-free DNA recovered from blood and urine, DNA isolated from biopsies, and DNA isolated from formalin fixed paraffin embedded tissues. When combined with real-time PCR analysis, as few as 2 or 3 methylated DNA molecules can be detected in a blood or urine sample. This level of robustness and sensitivity presents opportunities for multiple non-invasive diagnostic applications of the Methylome library method. Methylome libraries are characterized by a high degree of complexity and the analysis of global methylation patterns may best be resolved by hybridization to high resolution DNA microarrays. To maximize the specificity and sensitivity of Methylome analysis an efficient enrichment method may be employed to increase the relative copy number of CpG-rich DNA within the Methylome library. Previously, the present inventors described a novel enrichment method that applied secondary Methylome libraries and demonstrated that resulted in a 16-128-fold enrichment level for the various methylated promoter regions. Secondary Methylome libraries demonstrate an increased efficiency in identifying methylated CpG regions, however the complex synthesis process may limit their application. Here we introduce an alternative approach of Methylome library enrichment for the CpG-rich genomic regions which is much easier and faster than the secondary Methylome library method, specifically, the thermo-enrichment method.

Figure 71:
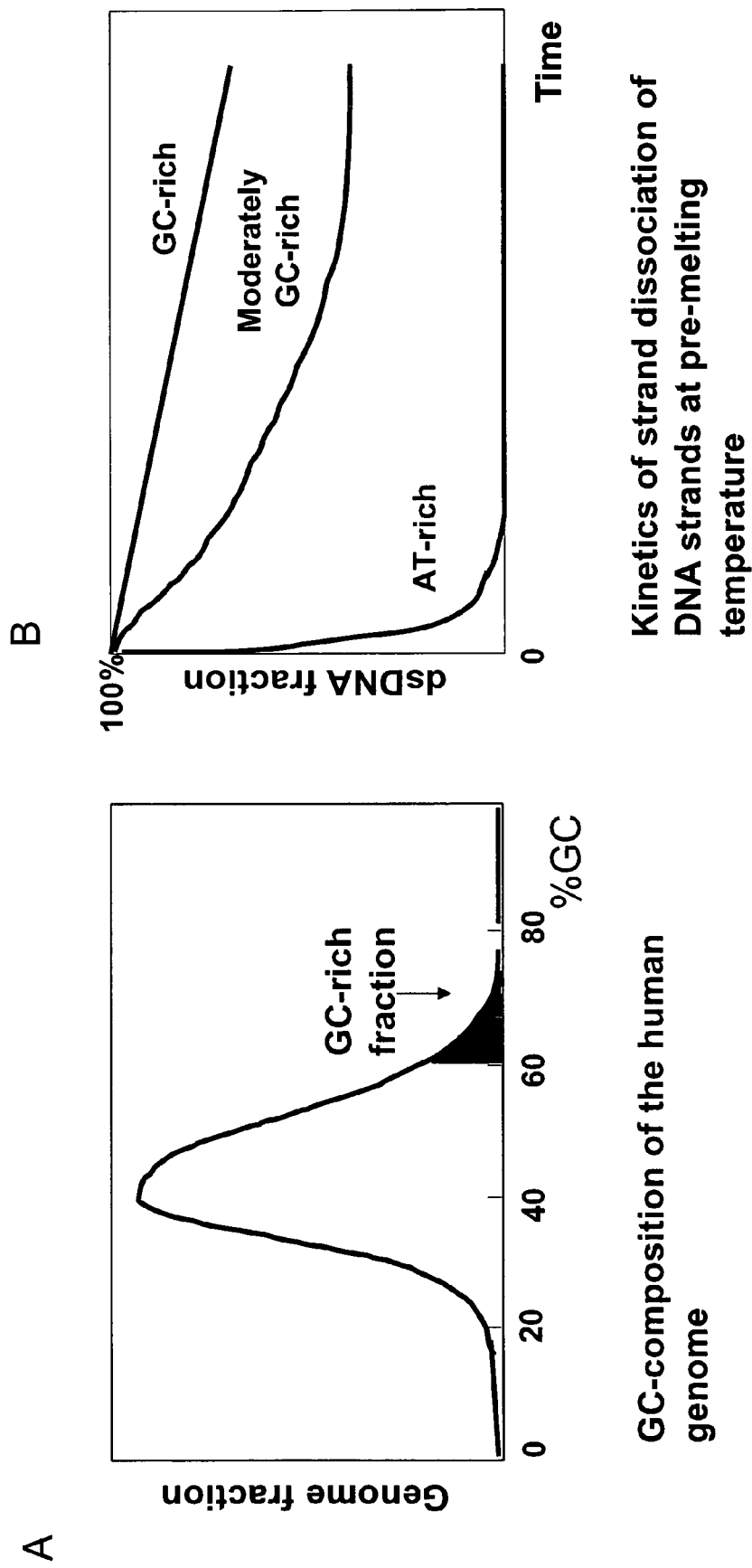
FIG. 71A shows a base composition distribution of the human genome with a peak at 42% GC.
FIG. 71B shows expected kinetics of strand dissociation for double-stranded DNA molecules with different base composition at pre-melting conditions.

The Human genome has a broad distribution of base composition with most sequences having around 42% GC (FIG. 71A). CpG-rich promoters are usually characterized by significantly higher GC content ranging from 60 to 90% GC. The Thermo-enrichment method is based on differences in the thermo-stability of DNA fragments with different base composition. At high temperature all DNA molecules undergo a conformational transition called denaturation or melting, which is characterized by unwinding of double-stranded DNA structure and separation of DNA strands. It is well known in the art that DNA molecules with high GC content have higher melting temperature than molecules with low GC content. The melting temperature also depends on length of DNA fragments, concentration of ions in a buffer (characterized by ionic strength), pH, and the presence or absence of additives such as dimethylsulfoxide, betaine, or formamide, for example.

When a heterogeneous but equimolar mixture of DNA fragments with different base composition is exposed to increasing temperature the fragments with low GC content will denature before the fragments with high GC content. This results in different amounts of double-stranded molecules for different DNA fractions, namely, practically the same amount of double-stranded for highly GC-rich fragments, an intermediate amount of double-stranded for moderately GC-rich fragments, and a very low low amount of double-stranded for highly AT-rich DNA (FIG. 71B). When a thermally-treated mixture of DNA blunt ended restriction fragments is cooled back down to 37° C. and incubated with T4 DNA ligase in the presence of the blunt-end DNA adaptor and ATP, the adaptor is ligated efficiently to only those DNA molecules that retained a double-stranded conformation during thermal selection, specifically, the molecules with high GC content. The higher the temperature that is used for thermo-treatment, the smaller the DNA fraction of sufficiently high GC content that remains double stranded and accepts adaptor in the blunt end ligation reaction. The selectivity of this method relies on kinetic differences of the DNA denaturation process for molecules with different GC content and the ligation reaction preference for double-stranded DNA ends.

Figure 70A:
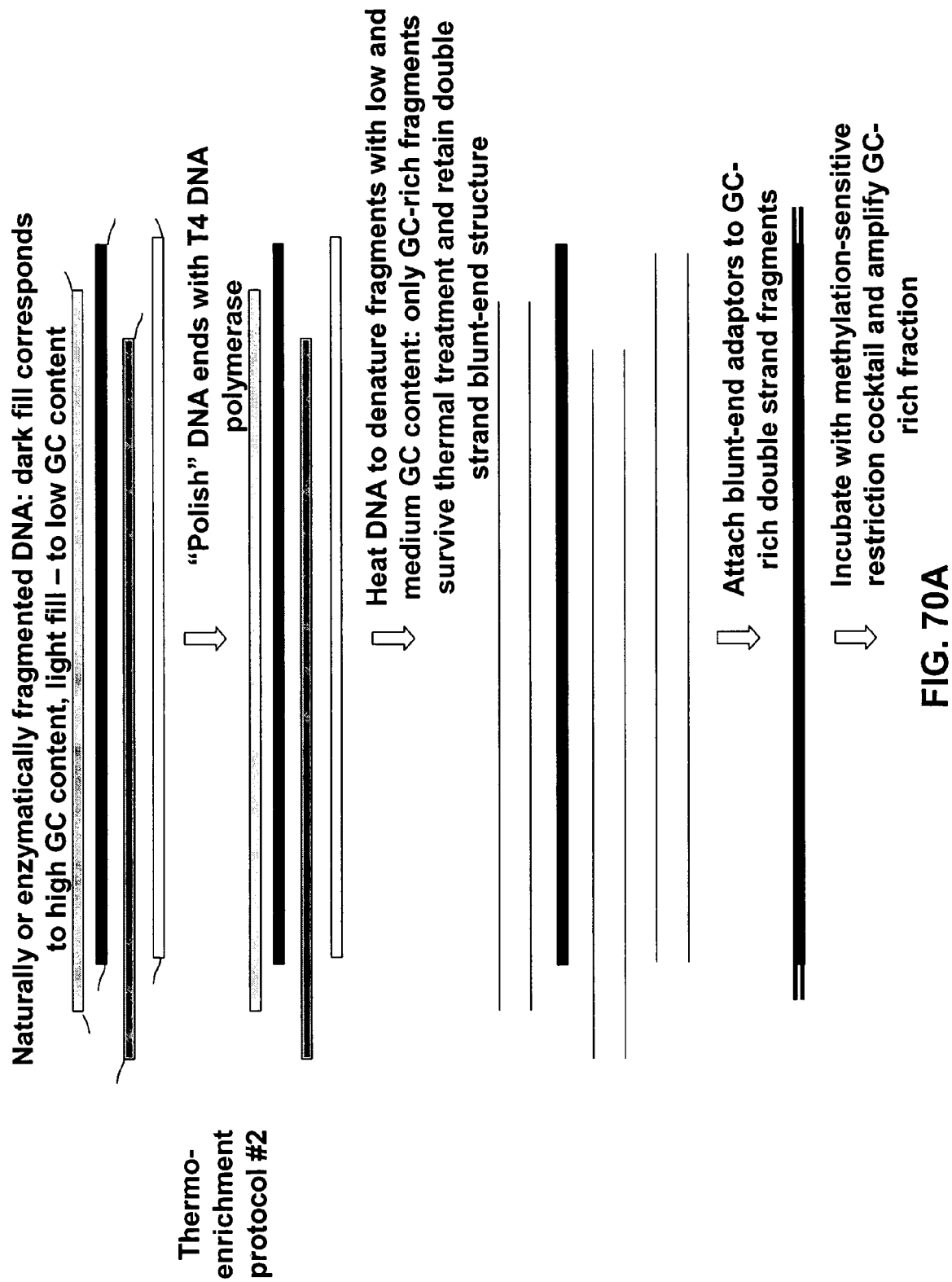
FIG. 70A illustrates a principle of the Methylome library thermo-enrichment method that utilizes a heating-selection step after the DNA end "polishing" step but prior to the adaptor ligation reaction. Only GC-rich DNA fragments would retain double stranded structure upon heating and remain competent for ligation to the blunt end adaptor.
Figure 70B:
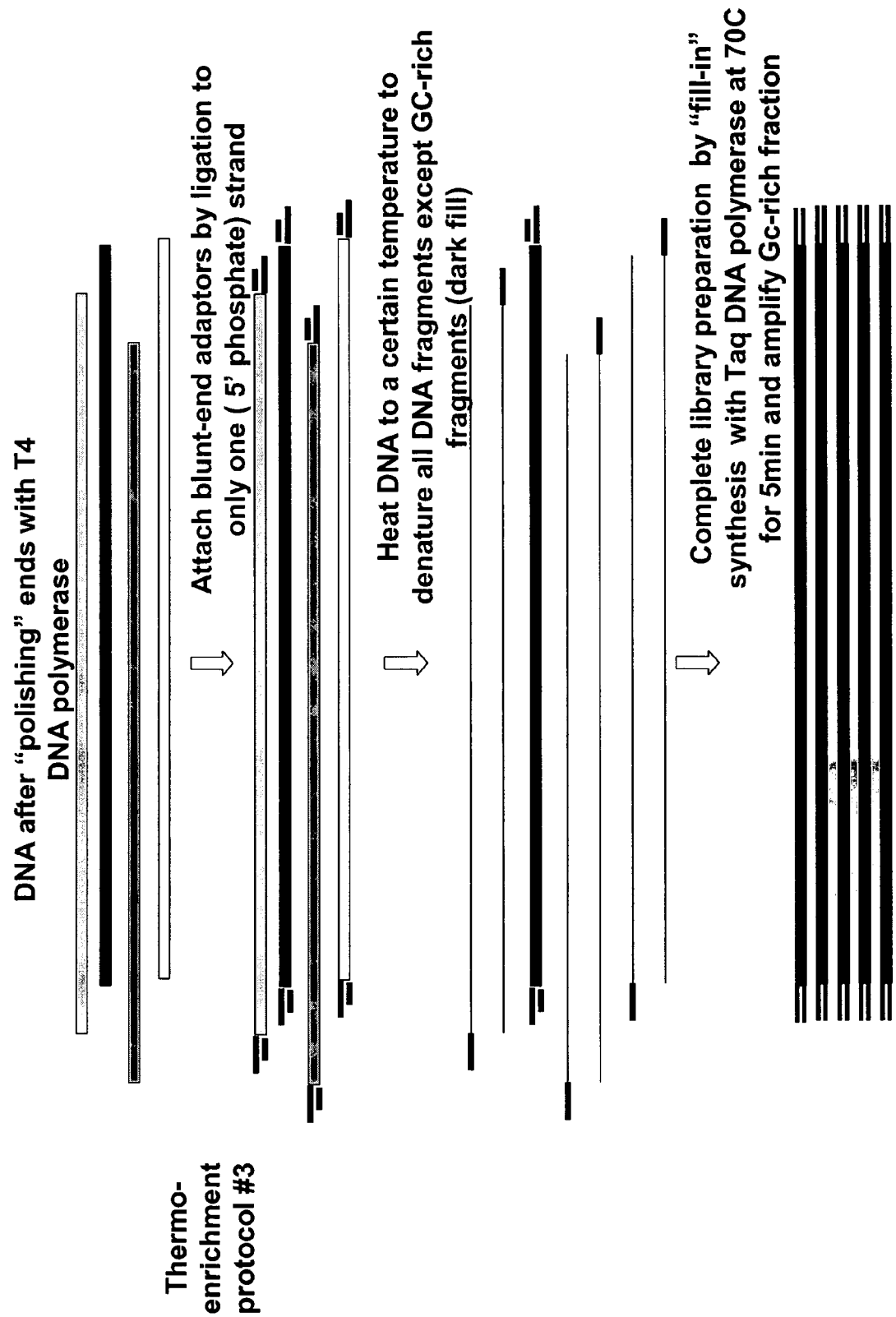
FIG. 70 B illustrates a principle of the Methylome library thermo-enrichment method that utilizes a heating-selection step after the adaptor ligation step (when only 5' DNA ends become covalently attached to the adaptor) but prior to "fill-in" polymerization step that completes formation of the Methylome library amplicons. Only GC-rich DNA fragments would retain double stranded structure upon heating and remain competent for the "fill-in" polymerization reaction.

In one specific embodiment (Example 36 and FIG. 70B, FIG. 72A), aliquots of blunt-end DNA fragments produced by Alu I digestion of human DNA were pre-heated for 10 min in 1× NEBuffer 4 at 75° C. (control), 83° C., 84.1° C., 85.3° C., 87° C., 89.1° C., 91.4° C., 93.5° C., 94.9° C., 96° C., or 97° C., snap-cooled on ice, and incubated with T4 DNA ligase, $K_U$ adaptor and ATP. After completion of the fill-in synthesis at the recessed 3' ends (15 min at 75° C.), whole genome libraries were amplified and then quantitatively analyzed using real-time PCR and primer pairs for different promoter regions. It was found that pre-heating DNA at temperatures between 89° C. and 94° C. resulted in 4 to 128-fold (median about 60-fold) enrichment of the amplified WGA library for all tested promoter regions.

In another specific embodiment (Example 37 and FIG. 70A, FIG. 72B), aliquots of cell-free DNA isolated from urine, and "polished" by Klenow fragment of DNA polymerase I, underwent thermo enrichment for 10 min in 1× NEBuffer 4 at 75° C. (control), 89° C., 91° C., or 93° C., snap-cooled on ice, and incubated with T4 DNA ligase, $K_U$ adaptor and ATP. Libraries were subsequently digested with the cocktail of methylation-sensitive restriction enzymes Aci I, HhaI, Hpa II, HinP1 I, and Bst UI, filled-in to replicate the sequence of the non-ligated adaptor strand, and amplified by PCR. Real-time PCR analysis of two CpG islands within the amplified libraries revealed a significant enrichment for the thermo-enriched Methylome libraries with a maximum enrichment level for these promoters observed in libraries prepared with pre-heating at 89° C. and 91° C.

A skilled artisan recognizes that selection for the GC-rich double-stranded DNA fraction after pre-heating step can be done not only before library amplification but also after library amplification, assuming that the universal PCR primer (primer $K_U$ in the Example described above) has a phosphate group at the 5' end generating ligation competent products. In this case (see FIG. 72D), enrichment can be achieved by heating the synthesized library amplification products to a desired melting temperature, cooling, ligating a new adaptor (or a pair of adaptors), and re-amplifying with primer(s) corresponding to the second adaptor(s). The fraction of amplified library that remained double stranded during the thermo-enrichment process will accept the second adaptor(s)

and represent the fragments corresponding to the melting temperature selected for enrichment.

Figure 72:
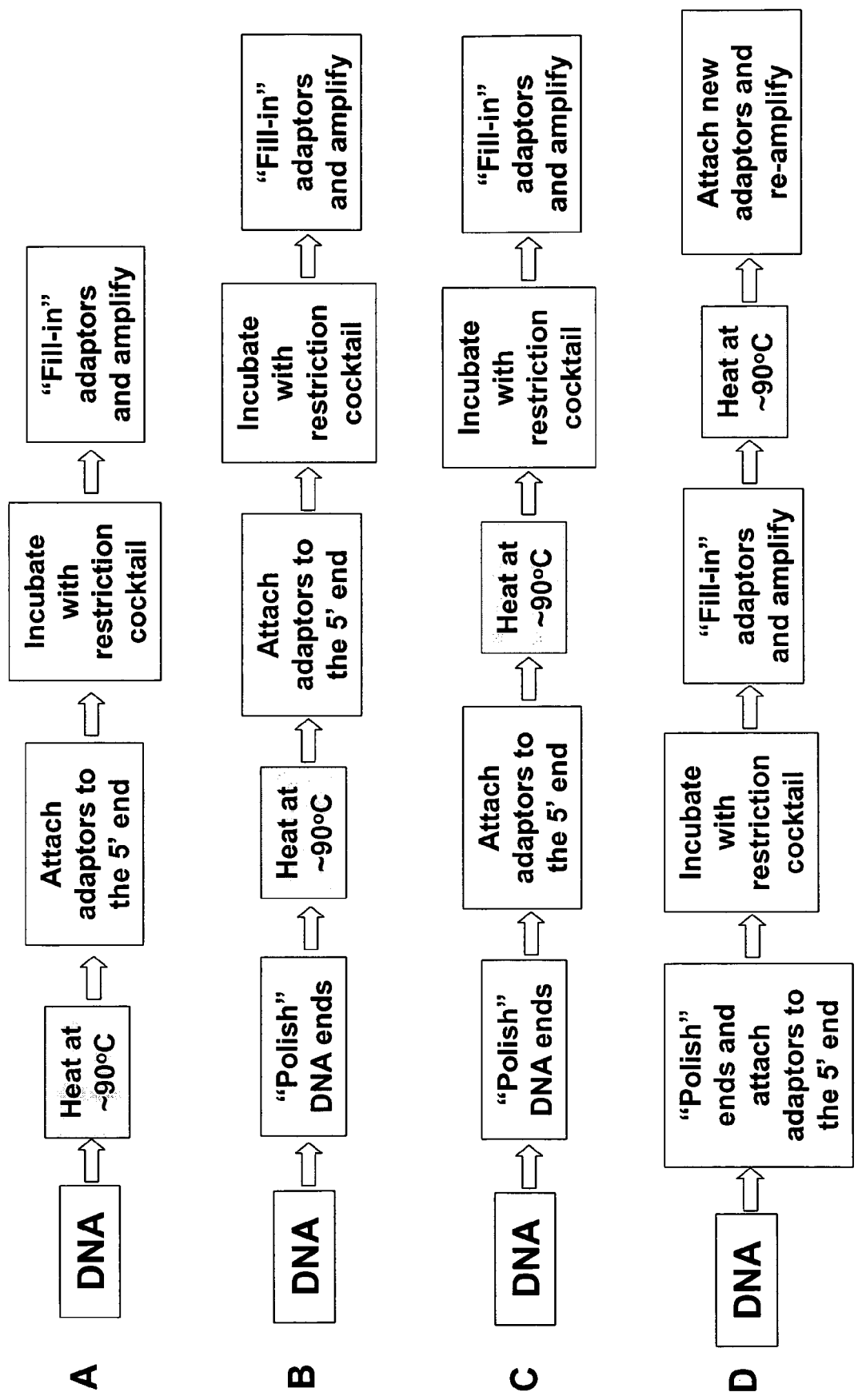
FIG. 72 illustrates and compares several envisioned versions of the thermo-enrichment Methylome library method including those depicted on FIG. 70.
Figure 73:
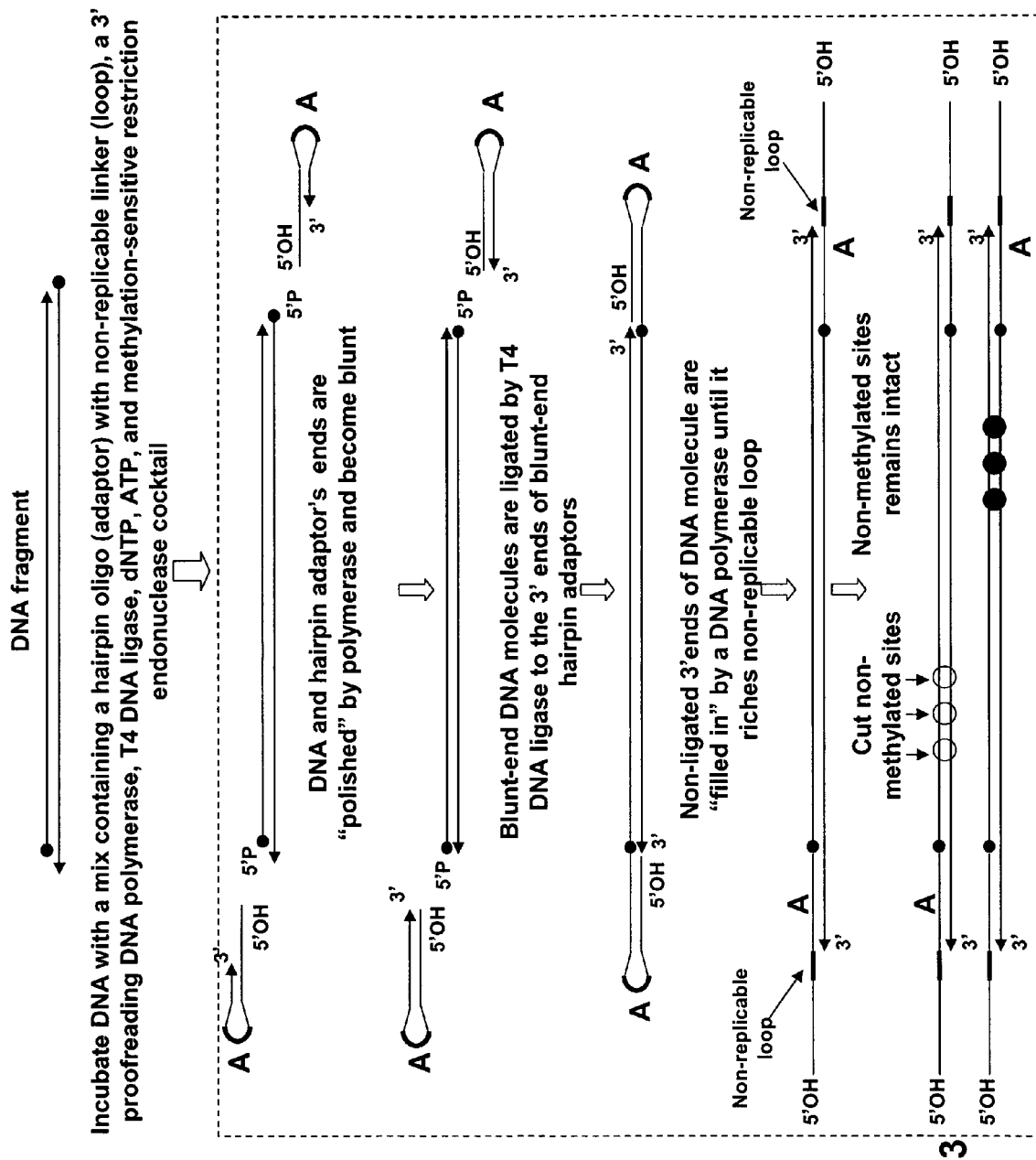
FIG. 73 illustrates the principle of the one-step Methylome library synthesis method that involves a hairpin oligonucleotide adaptor and provides the exemplary reactions including end polishing, hairpin oligonucleotide processing, oligonucleotide ligation, "fill-in" DNA end synthesis, and cleavage with multiple methylation-sensitive restriction enzymes to occur simultaneously in one complex reaction mix.
Figure 74:
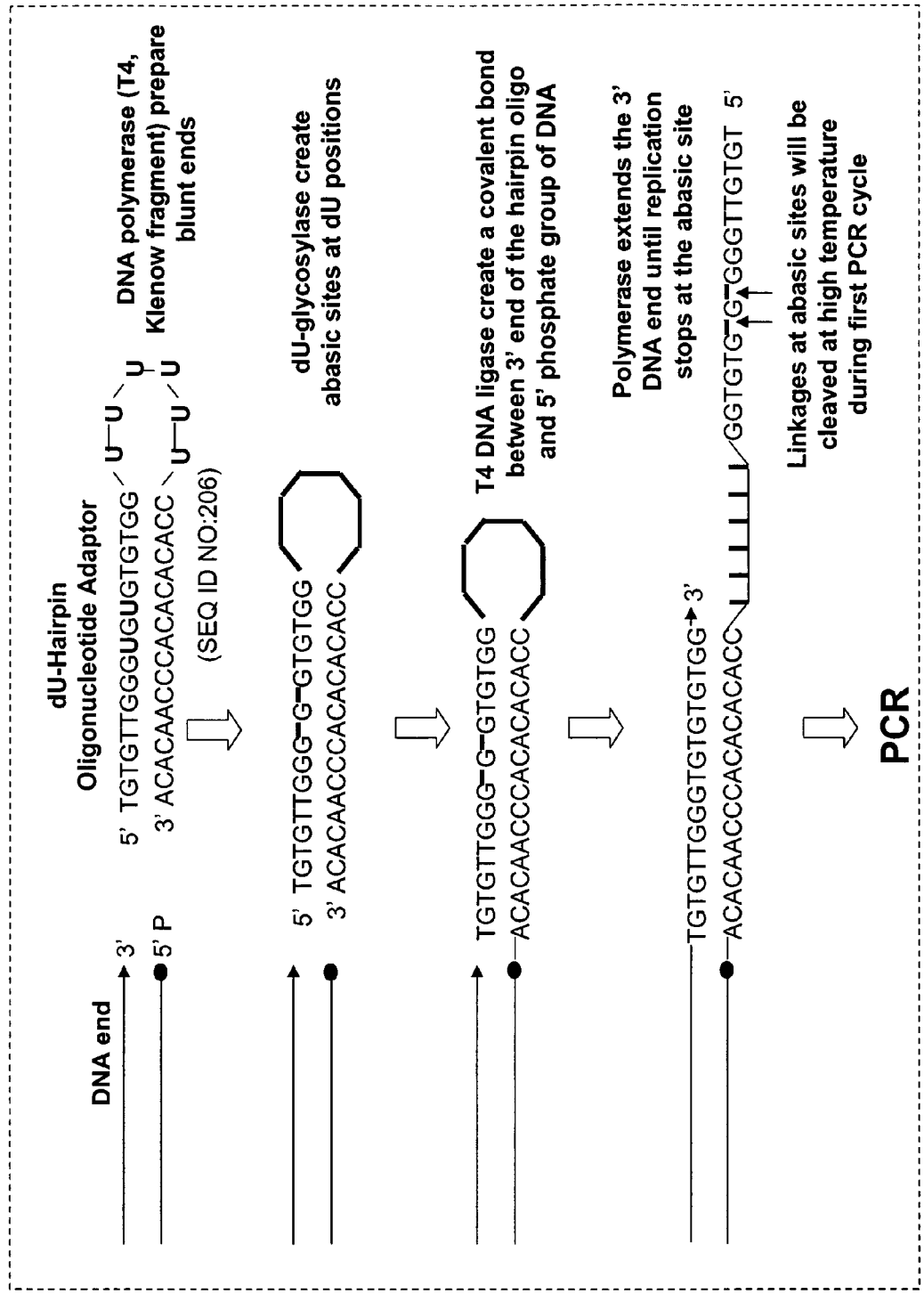
FIG. 74 shows the ligation and structural modification of the dU-Hairpin Oligonucleotide adaptor during a "One-step" methylome synthesis reaction. For simplicity a single DNA fragment end is shown accepting the adaptor through blunt-end ligation of the 3' end of the adaptor to the 5' end of the DNA fragment. Simultaneously, dUTP bases are cleaved by Uracil DNA glycosylase to abasic sites. Once ligated the 3' end of the DNA fragment is extended by DNA polymerase activity displacing the hairpin sequence and extending into the hairpin adaptor up to the first template abasic site. In addition to showing a portion of SEQ ID NO:206 (TGTGT-TGGGUGUGTGTG), FIG. 7 also shows the same sequence replaced with T residues in place of the U residues (TGTGT-TGGGTGTGTGTG; SEQ ID NO:211).

A skilled artisan recognizes that selection for the GC-rich double-stranded DNA fraction using a thermo-enrichment step can be done not only by using a ligation reaction but also by using a "fill-in" polymerization reaction of the recessed adaptor ends. In this case the heating step occurs after the ligation step but preceeds the fill-in step. Only double-stranded DNA fragments with adaptor attached to the 5' ends of DNA are competent templates for the extension reaction (FIG. 72 C).

Thermo-enrichment of GC-rich DNA is a simple and rapid method for increasing the sensitivity and specificity of Methylome libraries. When used in combination with the One-step Methylome library synthesis, it can easily be implemented for high through-put methylation analysis of clinical DNA samples for cancer diagnostics, and many other research and medical areas. Thermo-enriched Methylome libraries may be used as the method of choice for preparing enriched libraries for genome-wide methylation analysis.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention Example 1

Design of Degenerate Pyrimidine Primers and Analysis of Self-Priming and Extension This example describes the comparison between primers of different base composition for their ability to prime a model DNA template and for their propensity to self-prime.

Figure 5:
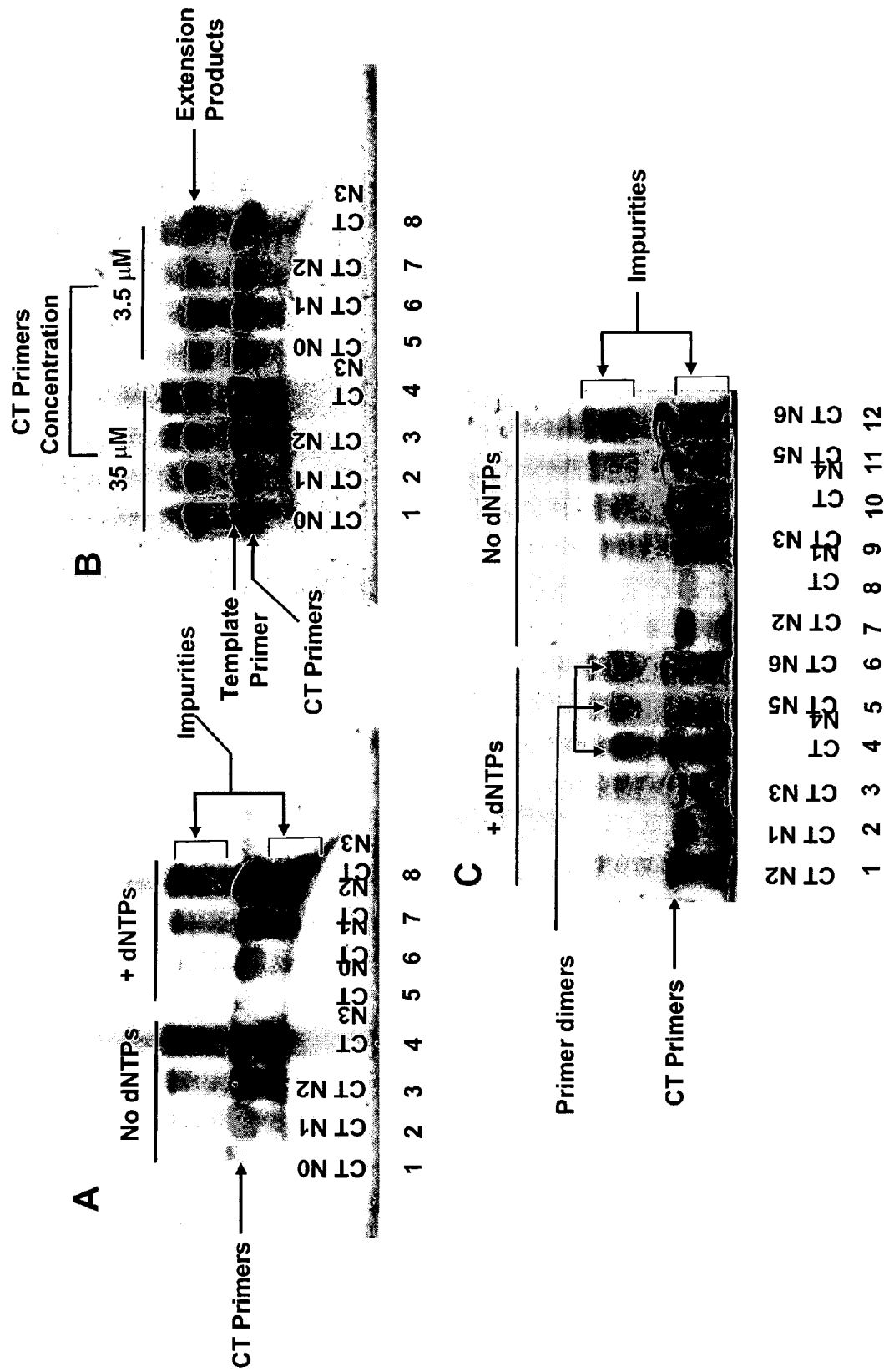
FIGS. 5A through 5C provide an analysis of self-priming and extension of degenerate YN-primers (primers containing from 0 to 6 completely random bases (N) at the 3' end, 10 degenerate pyrimidine bases Y, and the known pyrimidine sequence YU at the 5' end (FIG. 2)).

The model template oligonucleotide (SEQ ID NO:9) was comprised of the T7 promoter sequence followed by 10 random purine bases at its 3'-terminus. The reaction mixture contained 1× ThermoPol reaction buffer (NEB), 4 units of Bst DNA polymerase Large Fragment (NEB), 200 uM dNTPs, 350 nM template primer 9, and 3.5 or 35 µM of self-inert degenerate pyrimidine Y and YN primers (SEQ ID NO:1 through SEQ ID NO:7) in a final volume of 25 µl. Controls comprising no dNTPs are also included for each Y or YN primer. Samples were incubated for 5 min or 15 min at 45° C. and stopped by adding 2 µl of 0.5 M EDTA. Aliquots of the reactions were analyzed on 10% TB-urea denaturing polyacrylamide gels (Invitrogen) after staining with SYBR Gold dye (Molecular Probes). FIG. 5 shows the result of the comparison experiment. No evidence of self-priming was found with primers having up to 3 random bases at their 3'-end when applied at 35 µM concentration after 5 min incubation with Bst polymerase and dNTPs at 45° C. (FIG. 5A). In contrast, in the samples comprising template primer, a new band corresponding to extension products was observed at both 35 µM and 3.5 µM primers concentration (FIG. 5B). In a separate analysis, degenerate pyrimidine primers having up to six random bases at the 3'-end were analyzed for their ability to self-prime (FIG. 5C). After 15 min of incubation with Bst polymerase, no extension products were observed with primers having 3 random bases or less (FIG. 5C, lanes 1-3), whereas the primers with higher complexity (N3 and above) showed progressively increasing amount of extension products (FIG. 5C, lanes 4-6). Control samples incubated with Bst polymerase but no dNTPs showed no extension products band (FIG. 5C, lanes 7-12). See also U.S. patent application Ser. No. 10/795,667, filed Mar. 8, 2004, now U.S. Pat. No. 7,718,403.

Example 2

Whole Genome Amplification of Sodium Bisulfite-Converted Human DNA with Klenow Fragment of DNA Polymerase I Human genomic DNA isolated by standard methods was treated with sodium bisulfite using a modified procedure by Grunau et al (2001). One microgram of genomic DNA in 20 µl of TE-L buffer (10 mM Tris-HCl, 0.1 mM EDTA, pH 7.5), with or without 5 µg of carrier tRNA (Ambion), was mixed with 2.2 µl of 3.0 M NaOH and incubated at 42° C. for 20 minutes. Two hundred and forty microliters of freshly prepared sodium bisulfite reagent (5.41 g of $NaHSO_3$ dissolved in 8 ml distilled water and titrated to pH 5.0 with 10 N NaOH was mixed with 500 µl of 10 mM hydroquinone and filtered through a 0.2 µm membrane filter) was added to the denatured DNA samples and incubated for 4 hours at 55° C. The DNA was desalted using QIAEX II® (Qiagen) kit, recovered in 110 µl of TE-L buffer and desulfonated with 12.1 µl of 3 M NaOH at 37° C. for 30 min. After desulfonation the DNA was neutralized with 78 µl of 7.5 M ammonium acetate, precipitated with 550 µl of absolute ethanol, washed twice with 700 µl of 70% ethanol and air dried. The DNA was dissolved in 30 µl of TE-L buffer and stored at −20° C. until use.

Sodium bisulfite-converted DNA was randomly fragmented in TE-L buffer by heating at 95° C. for 3 minutes. The reaction mixture contained 60 ng of fragmented converted DNA in 1× EcoPol buffer (NEB), 200 µM of each dNTP, 360 ng of Single Stranded DNA Binding Protein (USB), and either 0.5 µM each of degenerate $R(N)_2$ and facilitating $R_U(A)_{10}(N)_2$ primers (SEQ ID NO:10 and SEQ ID NO:18) or 0.5 µM each of degenerate $Y(N)_2$ and selector $Y_U(T)_{10}(N)_2$ primers (SEQ ID NO:3 and SEQ ID NO:19) in a final volume of 14 µl. After denaturation for 2 min at 95° C., the samples were cooled to 24° C., and the reaction was initiated by adding 5 units of the Klenow fragment of DNA polymerase I that lacks 3'-5' exonuclease activity (NEB). Library synthesis with converted DNA was carried out at 24° C. for 1 hour. Control reactions containing 1 µM of $K(N)_2$ primer (SEQ ID NO: 14) were also included with either 60 ng of converted or 5 ng of non-converted (wild type) genomic DNA. Reactions were stopped with 1 µl of 83 mM EDTA (pH 8.0), and samples were heated for 5 min at 75° C. The samples were further amplified by quantitative real-time PCR by transferring the entire reaction mixture of the library synthesis reaction into a PCR reaction mixture containing a final concentration of the following: 1× Titanium Taq reaction buffer (Clontech), 200 µM of each dNTP, 100,000× dilutions of fluorescein calibration dye and SYBR Green I (Molecular Probes), 1 µM of universal Ru, $Y_U$, or $K_U$ primer (SEQ ID NO:11, SEQ ID NO:8, and SEQ ID NO:15) with sequences identical to the known 5' portion of the respective degenerate and facilitating primer, and 5 units of Titanium Taq polymerase (Clontech) in a final volume of 75 µl. Amplifications were carried out for 13 cycles at 94° C. for 15 sec and 65° C. for 2 min on an I-Cycler real-time PCR instrument (Bio-Rad).

Figure 6:
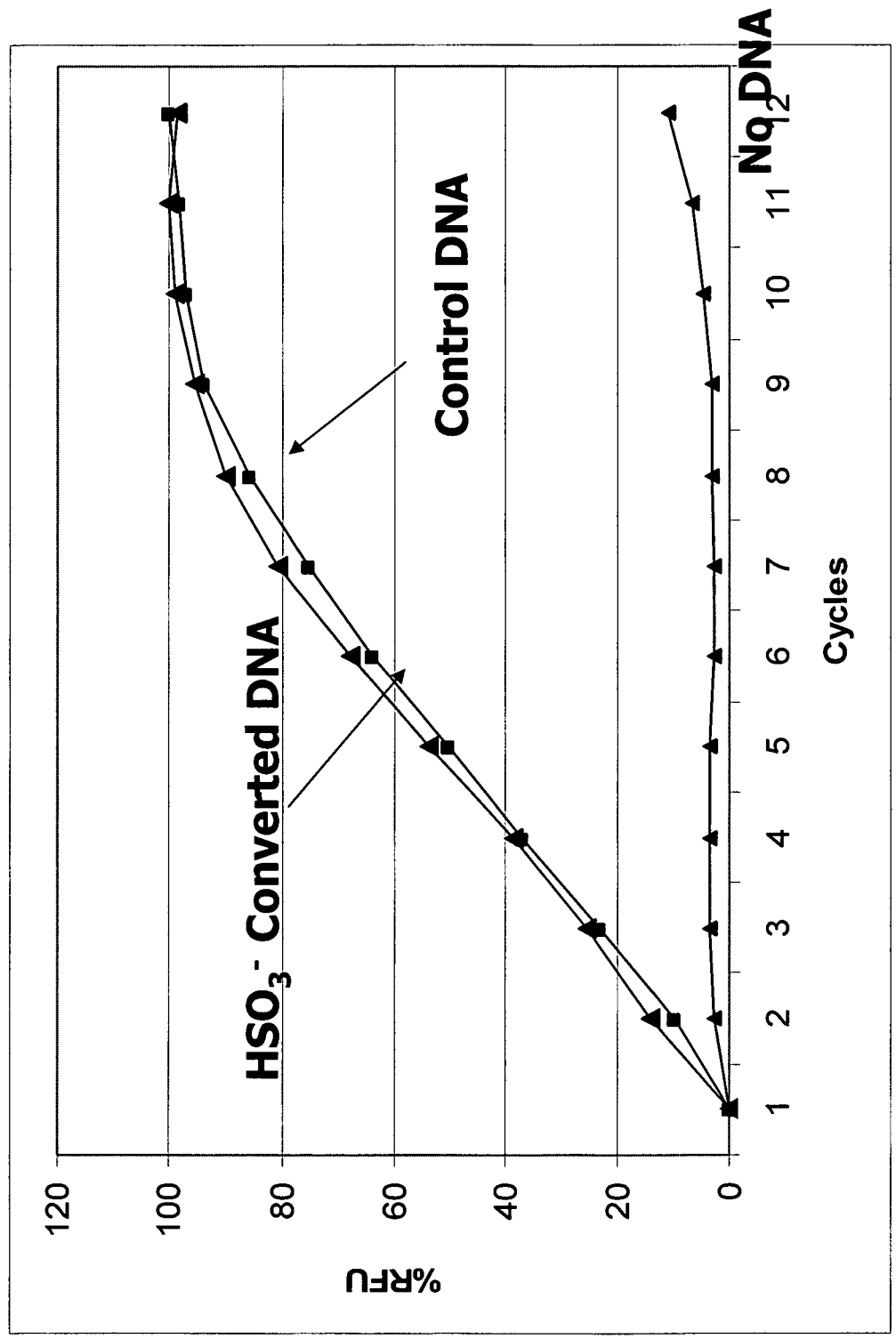
FIG. 6 shows a comparison of whole genome amplification of DNA libraries prepared from 60 ng of bisulfite converted DNA or from 5 ng of non-converted DNA using the Klenow Exo⁻ fragment of DNA polymerase I and a combination of the self-inert degenerate primer $R(N)_2$ with the facilitating primer $R_U(A)_{10}(N)_2$ (exemplary SEQ ID NO: 10 and 18) in the first case, and with the self-inert degenerate primer $K(N)_2$ (exemplary SEQ ID NO: 14) in the second case. The flat line represents a blank control without genomic DNA for the reaction with $K(N)_2$ primers.
Figure 7:
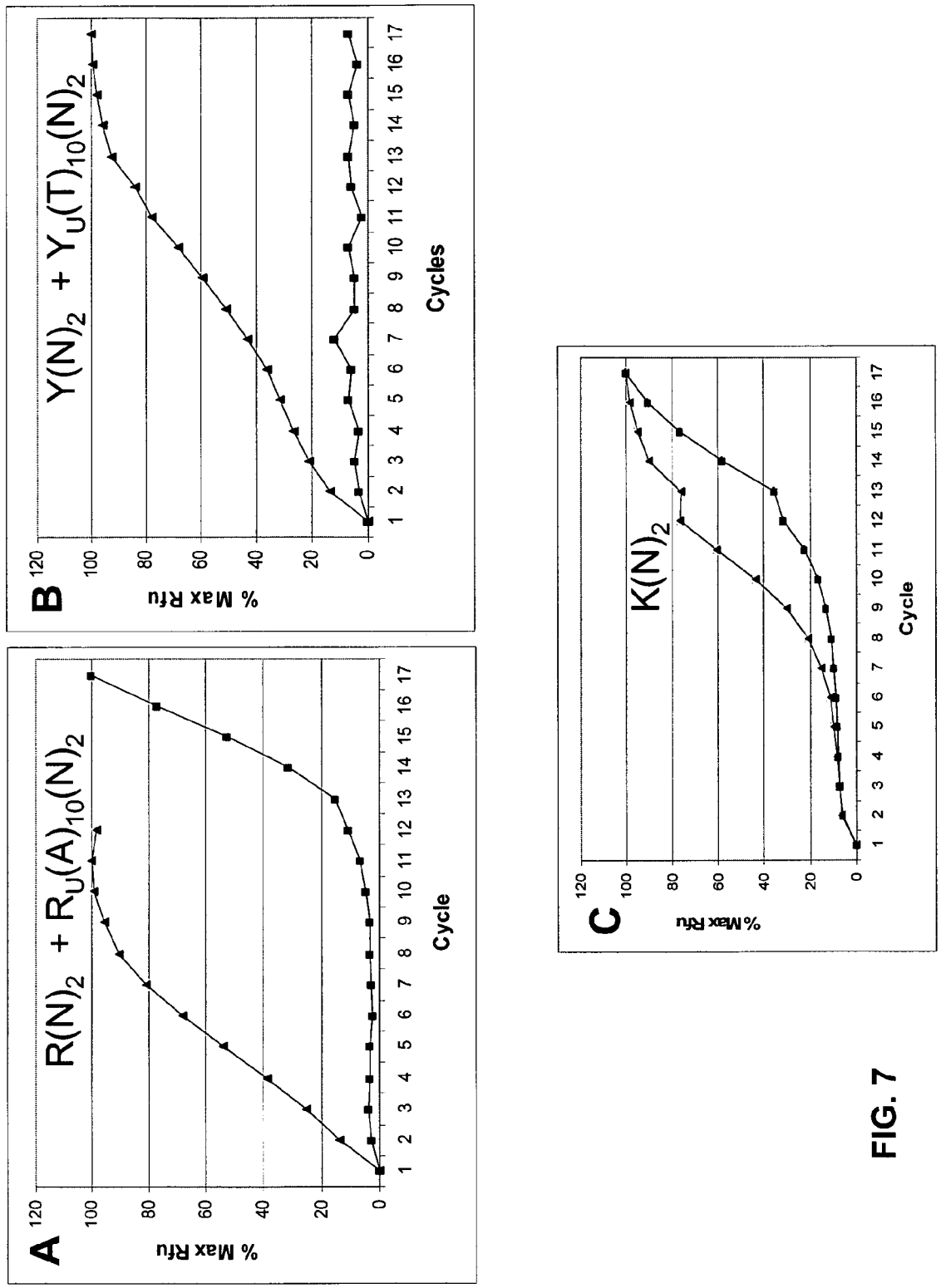
FIGS. 7A through 7C show comparison between different self-inert degenerate primer sequences supplemented with additional facilitating primers (added to facilitate priming of both strands of converted DNA) in their ability to support the library synthesis from bisulfite-converted DNA and subsequent efficient amplification by PCR. The identities of the degenerate and facilitating primers used for each reaction are shown in the top right corner of each panel. Experimental details are described in Example 2 and primer sequences are listed in Table I.

FIG. 6 demonstrates that 60 ng of bisulfite converted DNA amplifies equally to 5 ng of non-converted DNA when the former is amplified with degenerate $R(N)_2$ and facilitating $R_U(A)_{10}(N)_2$ primers and the latter with $K(N)_2$ primers, respectively. FIG. 7 shows comparison between different degenerate primer sequences supplemented with their corresponding selector sequences for their ability to amplify bisulfite converted DNA. The combination of self-inert degenerate $R(N)_2$ and facilitating $R_U(A)_{10}(N)_2$ SEQ ID NO: 18 primers was more than an order of magnitude better than the alternative combination of $Y(N)_2$ and facilitating $Y_U(T)_{10}(N)_2$ SEQ ID NO: 19 primers (FIGS. 7A and B). On the other hand, control $K(N)_2$ degenerate primer designed to target non-converted DNA, amplified bisulfite converted DNA approximately one additional order of magnitude less efficiently (FIG. 7C).

Figure 8:
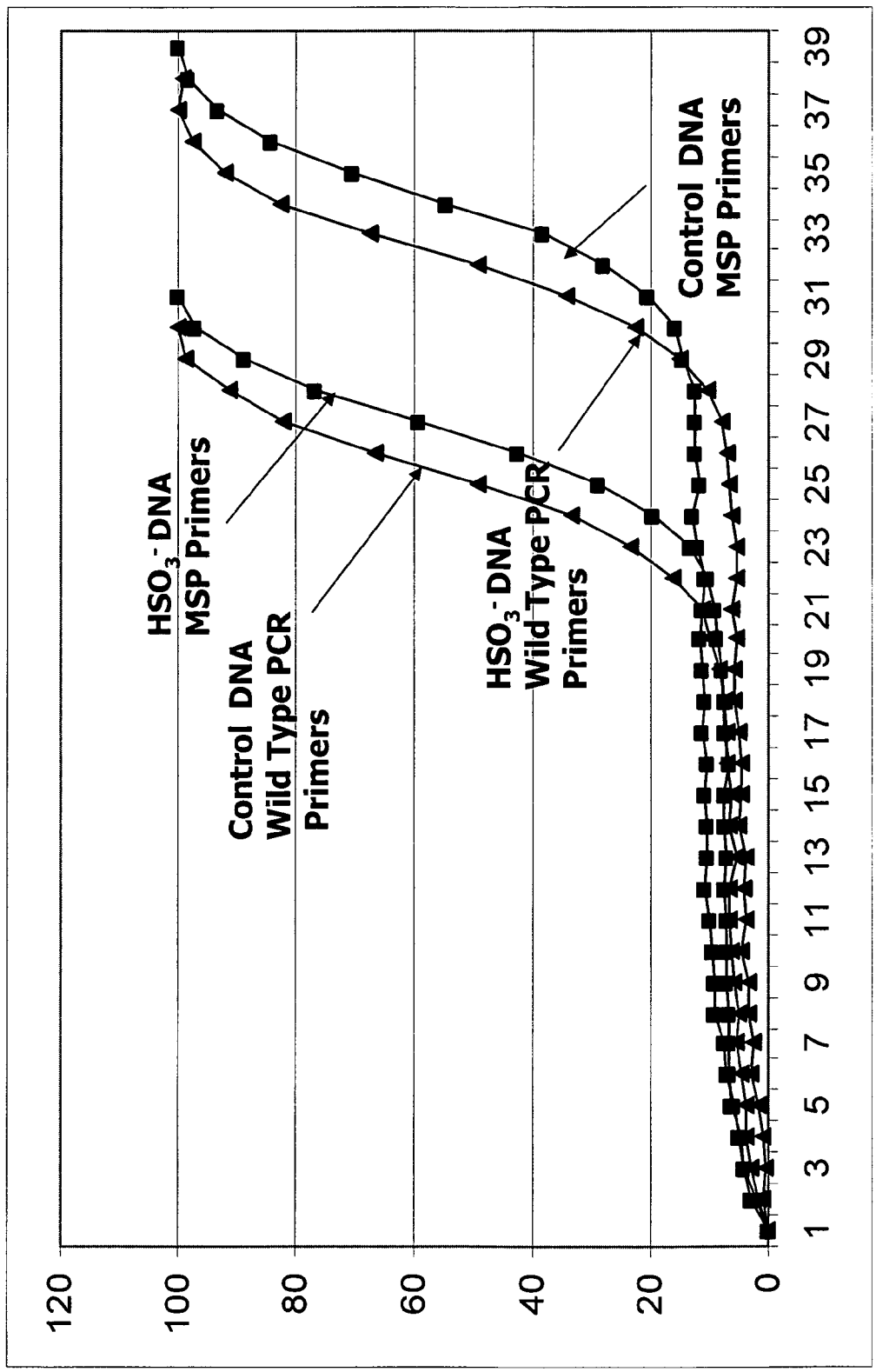
FIG. 8 demonstrates amplification of a genomic STS marker (STS sequence RH93704, UniSTS database, National Center for Biotechnology Information) with primer pairs specific for non-converted DNA (exemplary SEQ ID NO: 20 and 21) or specific for bisulfate-converted DNA (exemplary SEQ ID NO: 22 and 23) by real-time PCR using 10 ng of DNA amplified from bisulfite-converted DNA with a combination of self-inert degenerate primer $R(N)_2$ and facilitating primer R$_U$(A)$_{10}$(N)$_2$ SEQ ID NO: 18, or from non-converted DNA amplified with self-inert degenerate primer K(N)$_2$.

DNA samples amplified from bisulfite-converted DNA using degenerate $R(N)_2$ and facilitating $R_U(A)_{10}(N)_2$ SEQ ID NO: 18 primers or non-converted DNA amplified using control $K(N)_2$ degenerate primer were purified by QIAQUICK® PCR kit (Qiagen) using the manufacturer's protocol. Ten nanograms of each amplification reaction were further analyzed for a specific genomic marker (STS sequence RH93704, UniSTS database, National Center for Biotechnology Information) with primer pairs specific for non-converted DNA (SEQ ID NO:20 and SEQ ID NO:21) or specific for bisulfite-converted DNA (SEQ ID NO:22 and SEQ ID NO:23) by quantitative real-time PCR. The PCR reaction mixture comprised the following: 1× Titanium Taq reaction buffer (Clontech), 200 µM of each dNTP, fluorescein calibration dye (1:100,000) and SYBR Green I (1:100,000), 200 nM of each forward and reverse primer, 5 units of Titanium Taq polymerase (Clontech), and 10 ng Template DNA in a final volume of 50 µl. Reactions were carried out for 40 cycles at 94° C. for 15 sec and 65° C. for 1 min on an I-Cycler real-time PCR instrument (BioRad). FIG. 8 shows that approximately two orders of magnitude difference exists in the amplification of the genomic marker using PCR primers specific for converted or non-converted DNA with matched versus mismatched WGA amplified DNA as the template.

Example 3

Optimization of the Cleavage of Human Genomic DNA with McrBc Nuclease

This example describes the optimization of conditions for McRBC cleavage necessary to generate various levels of digestion of human genomic DNA.

In order to generate partially digested McRBC libraries, the rate of McRBC cleavage was investigated by varying the amount of McRBC utilized for digestion. DNA (100 ng) in 7 ul TE-Lo (10 mM Tris, 0.1 mM EDTA, pH 7.5) was added to a master mix containing 1 mM GTP, 100 µg/ml BSA, 1×T4 DNA Ligase Buffer, and $H_2O$, Subsequently, 1 µl of the appropriate amount of McRBC (0, 0.02, 0.04, 0.06, 0.08, 0.10 U) was added to each tube and incubated at 37° C. for 1 hour, followed by inactivation of the enzyme at 75° C. for 15 minutes and cooling to 4 C.

Universal GT adaptor was assembled in 10 mM KCl containing 20 µM Ku (SEQ ID NO:15) and 20 µM GT short (SEQ ID NO:54) (Table I) to form a blunt end adaptor. The adaptor was ligated to the 5' ends of the DNA using T4 DNA ligase by addition of 0.6 ul 10×T4 DNA ligase buffer, 2.4 ul $H_2O$, 2 µl GT adaptor (10 pmol) and 1 µl T4 DNA Ligase (2,000 U). The reaction was carried out for 30 minutes at 16° C., the enzyme was inactivated at 75° C. for 10 minutes, and the samples were held at 4° C. until use. Alternatively, the libraries can be stored at −20° C. for extended periods prior to use.

Figure 9:
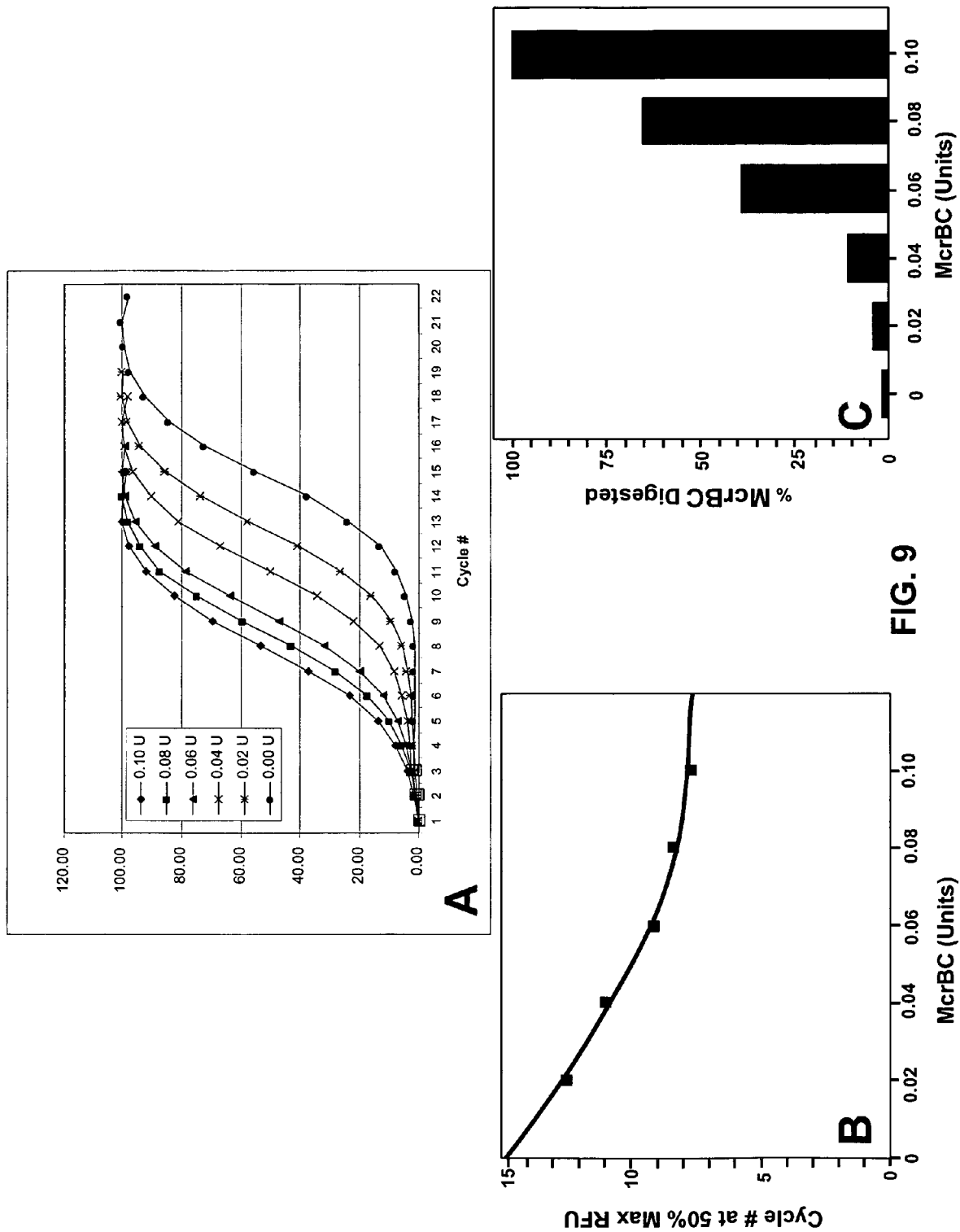
FIGS. 9A through 9C illustrate the optimization of the cleavage of human genomic DNA with McrBC nuclease.

Extension of the 3' end to fill in the universal adaptor and subsequent amplification of the library were carried out under the same conditions. Five nanograms of library or $H_2O$ (No DNA control) was added to a 25 µl reaction comprising 25 pmol T7-$C_{10}$ universal primer (SEQ ID NO:36), 200 µM of each dNTP, 1×PCR Buffer (Clontech), 1× Titanium Taq. Fluorescein calibration dye (1:100,000) and SYBR Green I (1:100,000) are also added to allow monitoring of the reaction using an I-Cycler Real-Time PCR Detection System (Bio-Rad). The samples are initially heated to 75° C. for 15 minutes to allow extension of the 3' end of the fragments to fill in the universal adaptor sequence and displace the short blocked fragment of the universal adaptor. Subsequently, amplification is carried out by heating the samples to 95° C. for 3 minutes 30 seconds, followed by 18 cycles of 94° C. 15 seconds, 65° C. 2 minutes. The amplification curves for all 3 samples are depicted in FIG. 9A. The amplification curves indicate decreased library generation and amplification with decreasing amounts of McRBC. Amplification of the No McRBC control indicates that a subset (<1%) of molecules in the genomic prep were of the appropriate size for library preparation. Plotting the cycle # at 50% of the max RFU versus McRBC quantity results in a sigmoid relationship (FIG. 9B). It should be noted that addition of greater than 0.1 U McRBC does not result in any increase in library generation or amplification. If the difference in cycles between the 0.1 U McRBC library and the other libraries is assumed to represent 1 doubling/cycle, then the effective % of McRBC digestion can be calculated. The resulting graph (FIG. 9C) indicates that small changes in the concentration of McRBC result in significant decreases in the amount of cleavage that occurs. Specifically, 0.07 U of McRBC are required to generate a 50% cleavage rate. Additional experiments have indicated that shortening the duration of McRBC incubation can also reduce the level of cleavage, although this reaction is less reproducible and more difficult to control.

In order to investigate and optimize further the conditions for McRBC digestion, additional experiments were performed using different amounts of enzyme as well as different temperatures of incubation and the resulting fragments were analyzed by field inversion gel electrophoresis.

Genomic DNA purchased from the Coriell Institute for Medical Research (repository # NA14657) was used as template for McRBC cleavage. Aliquots of 500 ng of DNA were cleaved with McRBC in 15 µl of 1× NEBuffer 2 containing 100 µg/ml BSA, 1 mM GTP, and 0, 2, 5, or 10 units of McRBC nuclease (NEB) at 37° C. for 90 min, followed by incubation at 65° C. for 20 minutes to inactivate the enzyme. In another set of samples, 10 units of McRBC were used as described above, but the incubation was at 16° C., 25° C., or 37° C.

Figure 10:
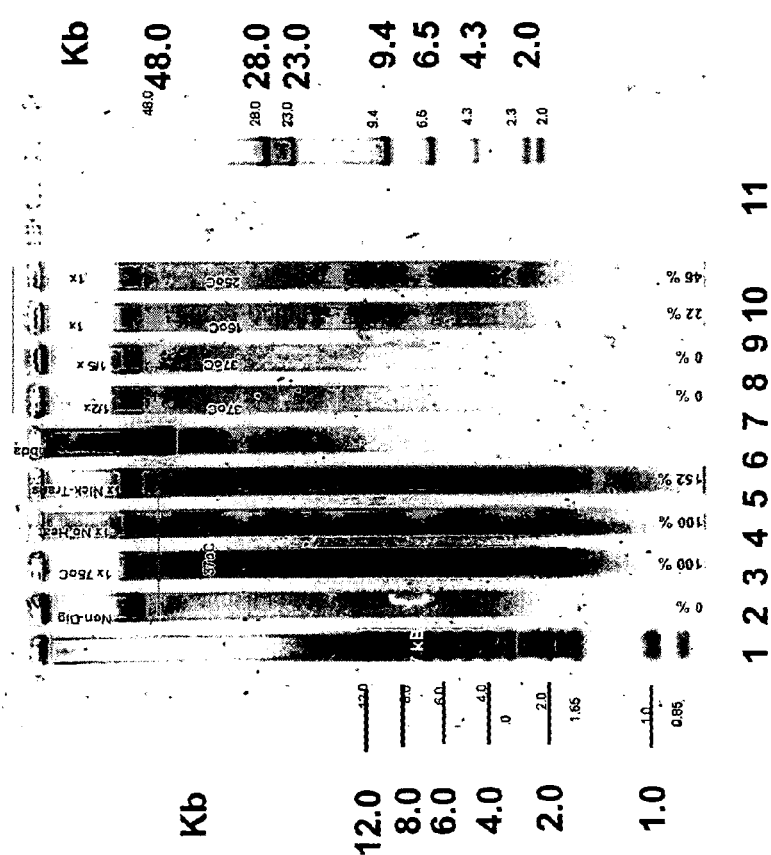
FIG. 10 shows the distribution of fragments obtained after McrBC cleavage of human genomic DNA. Lane 1, molecular weight markers; Lane 2, undigested gDNA; Lane 3, DNA digested with 10 units of McrBC at 37° C.; Lane 4, DNA digested with 10 units of McrBC at 37° C. but not heated at 75° C. before loading; Lane 5, DNA digested with 10 units of McrBC at 37° C. and treated with Taq polymerase in the presence of dNTPs to fill-in 3' recessed ends; Lane 6, Lambda genomic DNA; Lane 7, DNA digested with 5 units of McrBC at 37° C.; Lane 8, DNA digested with 2 units of McrBC at 37° C.; Lane 9, DNA digested with 10 units of McrBC at 16° C.; Lane 10, DNA digested with 10 units of McrBC at 25° C.; Lane 11, molecular weight markers.

To prevent potential gel retardation due to rehybridization of overhangs, samples cleaved with different amounts of McRBC were either left untreated or incubated with 5 units of Taq polymerase and 200 µM of each dNTP at 65° C. for 1 minute to fill-in any recessed 3' ends. Samples were then heated at 75° C. for 1 minute and analyzed on a 1% pulse-field agarose gel using Field Inversion Gel electrophoresis System (BioRad) preset program 2 for 14 hours in 0.5×TBE buffer. The gel was stained with SYBR Gold (Molecular Probes). FIG. 10 shows the distribution of fragments obtained after McRBC cleavage. After digestion using 10 units of McRBC at 37° C., the average apparent size of fragments generated from human genomic DNA was approximately 7 Kb and the range was from less than 1 Kb to about 30 Kb. Reducing the temperature or reducing the amount of enzyme resulted in less complete cleavage but the size distribution of fragments was similar. As evident from the figure, changing the temperature of incubation is a more efficient way of controlling the level of cleavage as compared to changing the amount of enzyme. The present inventors attribute this, in specific embodiments, to the necessity to maintain certain stoicheometry between the subunits of the nuclease and the template.

Example 4

Gel Fractionation of McrBc Cleavage Products and Analysis of the Segregation of Sites Internal to, or Flanking, Promoter CpG Islands This example describes the analysis of the segregation of McrBC cleavage products along an agarose gel as a function of CpG methylation.

One microgram of exemplary control genomic DNA (Coriell repository # NA14657) or exemplary KG1-A leukemia cell DNA was subjected to complete digestion with McrBC nuclease in 25 µl of 1× NEBuffer 2 (NEB) containing 100 µg/ml BSA, 1 mM GTP, and 10 units of McrBC nuclease (NEB) at 37° C. for 90 minutes, followed by incubation at 65° C. for 20 minutes to inactivate the enzyme. Samples were extracted with phenol:chloroform:isoamyl alcohol (25:24:1) to prevent gel retardation, precipitated with ethanol, and dissolved in 15 µl of TE-L buffer.

Samples were loaded on a 15 cm long 1% agarose gel, electrophoresed at 5V per cm in a modified TAE buffer (containing 0.5 mM EDTA), and stained with SYBR Gold (Molecular Probes). Gel lanes were sliced into segments of 0.75 cm, each corresponding approximately to the following sizes based on molecular weight markers: 7.5 to 12 Kb, 4.5 to 7.5 Kb, 3.0 to 4.5 Kb, 2.0 to 3.0 Kb, 1.5 to 2.0 Kb, 1.0 to 1.5 Kb, 0.65 to 1.0 Kb, 0.4 to 0.65 Kb, 0.25 to 0.4 Kb, and 0.05 to 0.25 Kb. DNA was extracted with Ultrafree DA centrifugal devices (Millipore) at 5,000×g for 10 minutes and 10 µl was used as template for amplification using primers specific for sites internal to, or flanking, promoter CpG islands. Primer pairs were used as follows: p15 promoter (SEQ ID NO:24 forward and SEQ ID NO:25 reverse), p16 promoter (SEQ ID NO:26 forward and SEQ ID NO:27 reverse), E-Cadherin promoter (SEQ ID NO:28 forward and SEQ ID NO:29 reverse) for sites internal to CpG islands, and p15 promoter (SEQ ID NO:46 forward and SEQ ID NO:47 reverse), p16 promoter (SEQ ID NO:48 forward and SEQ ID NO:49 reverse), or E-Cadherin promoter (SEQ ID NO:52 forward and SEQ ID NO:53 reverse) for sites flanking the CpG islands. PCR amplification was carried out in a reaction mixture comprising 1× Titanium Taq reaction buffer (Clontech), 200 µM of each dNTP, 4% DMSO, fluorescein calibration dye (1:100,000), SYBR Green I (1:100,000), 200 nM each forward and reverse primer, and 5 units of Titanium Taq polymerase (Clontech) in a final volume of 50 µl at 94° C. for 15 seconds and 68° C. for 1 minute for a varying number of cycles until a plateau was reached in the amplification curves. Ten microliters of each PCR reaction were analyzed on 1% agarose gel stained with ethidium bromide.

Figure 11:
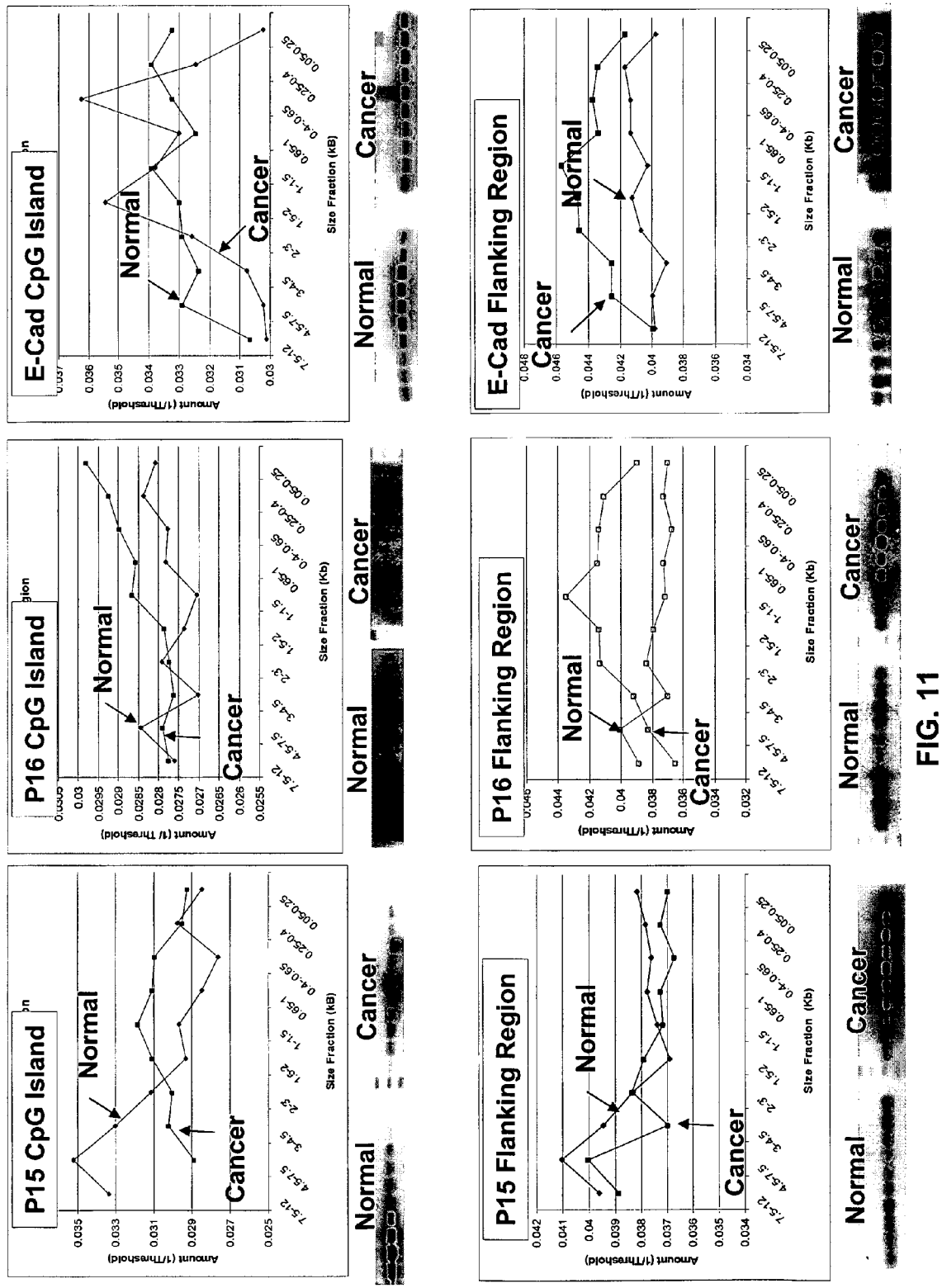
FIG. 11 represents distribution plots of gel fractions obtained after McrBC cleavage of genomic DNA isolated from KG1-A leukemia cells or control genomic DNA (Coriell repository # NA16028) followed by separation on agarose gel and elution of DNA from gel slices. Aliquots of each eluted fraction were amplified by PCR using the following primers: p15 promoter (SEQ ID NO:24 forward and SEQ ID NO:25 reverse), p16 promoter (SEQ ID NO:26 forward and SEQ ID NO:27 reverse), E-Cadherin promoter (SEQ ID NO:28 forward and SEQ ID NO:29 reverse) for sites internal to CpG islands, and p15 promoter (SEQ ID NO:46 forward and SEQ ID NO:47 reverse), p16 promoter (SEQ ID NO:48 forward and SEQ ID NO:49 reverse), or E-Cadherin promoter (SEQ ID NO:52 forward and 53 reverse) for sites flanking the CpG islands, respectively. The following size fractions were analyzed: 7.5-12 Kb, 4.5-7.5 Kb, 3.0-4.5 Kb, 2.0-3.0 Kb, 1.5-2.0 Kb, 1.0-1.5 Kb, 0.65-1.0 Kb, 0.4-0.65 Kb, 0.25-0.4 Kb, and 0.05-0.25 Kb. The size of the fractions was plotted against the reciprocal of the threshold amplification cycle for each real-time PCR curve. Shown at the bottom of each panel are the PCR products separated on agarose gel. Fractions follow the same order as on the respective curve plots.

FIG. 11 shows distribution plots of the gel fractions against the reciprocal of the threshold amplification cycle for each real-time PCR curve as well as the PCR products separated on agarose gel. All of the amplified sites were shifted toward lower molecular weight fractions in cancer versus normal cells indicating that hypermethylated regions in cancer cells are digested extensively by McrBC nuclease. On the other hand, the methylation signal of the E-Cadherin promoter was found in the intermediate size fractions indicating that the regions flanking this promoter in normal cells are heavily methylated and thus are cleaved by McrBC nuclease, thereby generating more background as compared to the other two gene promoters studied. The broad size distribution of the smaller products in DNA from cancer cells can be explained by trapping of DNA in agarose gels causing retardation and trailing of the peaks toward an apparent higher molecular weight (E. Kamberov, unpublished observation).

Example 5

Analysis of the Methylation Status of Promoter CpG Islands by Cleavage with McrBc Nuclease Followed by PCR Amplification This example describes a simple McrBC-mediated direct assay for methylation of CpG promoter islands based on the ability of the McrBC nuclease to cleave between two methylated cytosines. The cleavage reaction between sites flanking multiple methylated cytosines results in a lack of PCR amplification from the priming sites and generates a negative signal for methylation.

Genomic DNA purchased from the Coriell Institute for Medical Research (repository # NA16028) was used as a negative control for CpG island methylation. The same source of DNA was also fully methylated using SssI CpG Methylase to serve as a positive control. Genomic DNA from exemplary KG1-A leukemia cells purified by a standard procedure was used as a test sample for CpG island promoter hypermethylation. Coriell NA16028 gDNA was methylated with 4 units of SssI CpG Methylase (NEB) in 50 µl, according to the manufacturer's protocol, to serve as a positive control for methylation.

McrBC cleavage of control DNA, SssI methylated DNA, or KG1-A test DNA was performed in 50 µl of 1× NEBuffer 2 containing 5 µg of DNA, 100 µg/ml BSA, 1 mM GTP, and 35 units of McrBC nuclease (NEB) at 37° C. for 90 minutes, followed by incubation at 65° C. for 20 minutes to inactivate the enzyme.

Five nanogram aliquots of each McrBC digested sample or control non-digested DNA were amplified by quantitative real-time PCR in reaction mixture containing 1× Titanium Taq reaction buffer (Clontech), 200 µM of each dNTP, fluorescein calibration dye (1:100,000) and SYBR Green I (1:100,000), 200 nM of primers specific for CpG regions of the following promoters: p15 (Accession # AF513858) p16 (Accession #AF527803), E-Cadherin (Accession # AC099314), and GSTP-1 (Accession # M24485) (SEQ ID NO:24+SEQ ID NO:25, SEQ ID NO:26+SEQ ID NO:27, SEQ ID NO:28+SEQ ID NO:29, and SEQ ID NO:30+SEQ ID NO:31 respectively), 4% DMSO, and 2 units of Titanium Taq polymerase (Clontech) in a final volume of 30 µl. Amplifications were carried out at 94° C. for 15 seconds and 65° C. for 1 minute on an I-Cycler real-time PCR instrument (Bio-Rad) for a varying number of cycles until a plateau was reached on the amplification curves of the negative controls. Ten microliters of each PCR reaction were analyzed on 1% agarose gel after staining with ethidium bromide.

Figure 12:
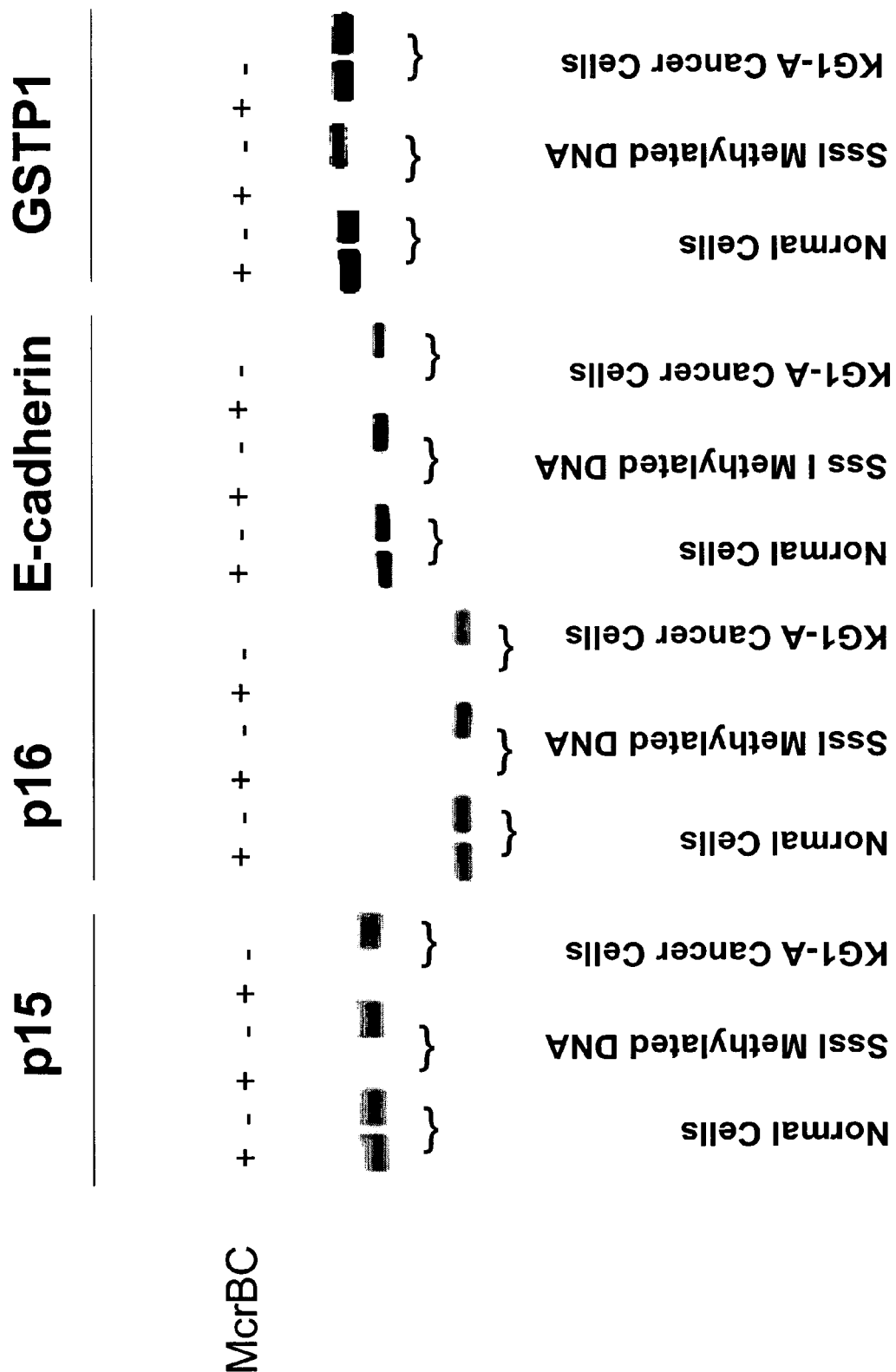
FIG. 12 shows an ethidium bromide-stained gel of amplified products from the McrBC-mediated direct promoter methylation assay. After cleavage of genomic DNA from normal cells or from leukemia KG1-A cells with McrBC nuclease, sites internal to the CpG islands of p15 (GENBANK® Accession No. AF513858) p16 (GENBANK® Accession No. AF527803), E-Cadherin (GENBANK® Accession No. AC099314), or GSTP-1 (GENBANK® Accession No. M24485) promoters were amplified using specific PCR primers (SEQ ID NO: 24+SEQ ID NO:25, SEQ ID NO:26+SEQ ID NO:27, SEQ ID NO:28+SEQ ID NO:29, and SEQ ID NO:30+SEQ ID NO:31, respectively). DNA fully methylated with SssI CpG methylase was used as a positive control. Cleavage between methylated cytosines by McrBC results in lack of amplification and correlates with the methylation status of the promoters.

FIG. 12 shows the result of the promoter methylation analysis. After digestion with McrBC, fully methylated control DNA displayed complete lack of amplification for all four promoter sites, whereas control DNA amplified normally with or without McrBC cleavage. The test cancer DNA from KG1-A leukemia cells showed strong hypermethylation in three out of the four analyzed promoters.

Example 6

Analysis of DNA Methylation by One-Sided PCR from McrBc Cleavage Sites

This example describes development of a McrBC-mediated library diagnostic assay for promoter CpG island hypermethylation based on ligation of a universal adaptor to McrBC cleavage sites followed by incorporation of a poly-C tail allowing one-sided PCR between the homopolymeric sequence and a specific site flanking the CpG island.

Five micrograms of control genomic DNA (Coriell repository # NA16028) or genomic DNA from exemplary KG1-A leukemia cells were digested with McrBC nuclease in 50 µl of 1× NEBuffer 2 containing 100 µg/ml BSA, 1 mM GTP, and 35 units of McrBC nuclease (NEB) at 37° C. for 90 min, followed by incubation at 65° C. for 20 min to inactivate the enzyme.

In the next step, a universal T7 promoter sequence was ligated to McrBC cleavage fragments that were polished, following cleavage, to produce blunt ends. Aliquots of 100 ng of each sample were blunt-ended with Klenow fragment of DNA polymerase I (USB) in 10 µl of 1×T4 Ligase buffer (NEB) containing 2 nM of each dNTP at 25° C. for 15 minutes. Universal T7 adaptors were assembled in 10 mM KCl containing 10 µM 20 µM T7GG (SEQ ID NO:32) and 20 µM T7SH (SEQ ID NO:34) to form a blunt end adaptor; 20 µM T7GG (SEQ ID NO:32) and 40 µM of T7NSH (SEQ ID NO:35) to form a 5' N overhang adaptor; and 20 µM T7GGN (SEQ ID:33) and 40 µM of T7SH (SEQ ID NO:34) to form a 3' N overhang adaptor (see Table I for exemplary oligonucleotide sequences). Adaptor mixtures were heated at 65° C. for 1 minute, cooled to room temperature and incubated for 5 min on ice. The tubes were combined in 2:1:1 ratio (blunt end:5' N overhang:3' N overhang) and kept on ice prior to use. Ligation reactions were performed in 16 µl of 1×T4 Ligase buffer (NEB), containing 100 ng of blunt-end template DNA, 3.75 µM final concentration of T7 adaptors, and 2,000 units of T4 DNA Ligase (NEB) at 16° C. for 1 hour, followed by incubation at 75° C. for 10 minutes to inactivate the ligase.

Next, homo-polymeric extensions were incorporated at the ends of the fragments using a primer T7-C10 (SEQ ID NO:36) comprising ten C bases at the 5' end followed by a 3' T7 promoter sequence. This sequence allows asymmetric one-sided PCR amplification due to the strong suppression effect of the terminal poly-G/poly-C duplex making the amplification between the terminal inverted repeats very inefficient (U.S. patent application Ser. No. 10/293,048, filed Nov. 13, 2002, now U.S. Pat. No. 7,655,791; U.S. patent application Ser. No. 10/797,333, filed Mar. 8, 2004, published as U.S. Patent Application Publication No.: 2004/0209299 and is now abandoned; and U.S. patent application Ser. No. 10/795,667, filed Mar. 8, 2004, now U.S. Pat. No. 7,718,403). PCR amplification was carried out by quantitative real-time PCR in reaction mixture comprising 1× Titanium Taq reaction buffer (Clontech), 5 ng of McrBC library DNA with ligated universal T7 adaptors, 200 µM of each dNTP, 200 µM of 7-deaza-dGTP (Sigma), 4% DMSO, 1:100,000 dilutions of fluorescein and SYBR Green I (Molecular Probes), 1 µM T7-$C_{10}$ primer (SEQ ID NO: 36), and 5 units of Titanium Taq polymerase (Clontech) in a final volume of 50 µl. Amplification was carried out at 72° C. for 10 min to fill-in the 3'-recessed ends, followed by 18 cycles at 94° C. for 15 sec and 65° C. for 2 min on an I-Cycler real-time PCR instrument (Bio-Rad). Samples were purified on Quiaquick PCR purification filters (Qiagen).

To analyze the methylation status of promoters CpG islands, one-sided PCR was performed using 50 ng of purified McrBC library DNA from normal or cancer cells, a universal $C_{10}$ SEQ ID NO: 38 primer comprising ten C bases, and primers specific for regions flanking the CpG islands of different exemplary promoters implicated in epigenetic control of carcinogenesis. PCR amplification was carried by quantitative real-time PCR in a reaction mixture comprising 1× Titanium Taq reaction buffer (Clontech), 200 µM of each dNTP, 4% DMSO, 1:100,000 dilutions of fluorescein calibration dye and SYBR Green I (Molecular Probes), 200 nM $C_{10}$ primer (SEQ ID NO:38), 200 nM of primer specific for p15 promoter (SEQ ID NO:39), p16 promoter (SEQ ID NO:40), or E-Cadherin promoter (SEQ ID NO:41 or SEQ ID NO:42), and 3.5 units of Titanium Taq polymerase (Clontech) in a final volume of 35 µl. Amplification was at 94° C. for 15 seconds and 68° C. for 1 minute on an I-Cycler real-time PCR instrument (Bio-Rad) for different number of cycles until a plateau was reached for the cancer DNA samples. Ten microliters of each PCR reaction were analyzed on 1% agarose gel after staining with ethidium bromide.

Figure 13:
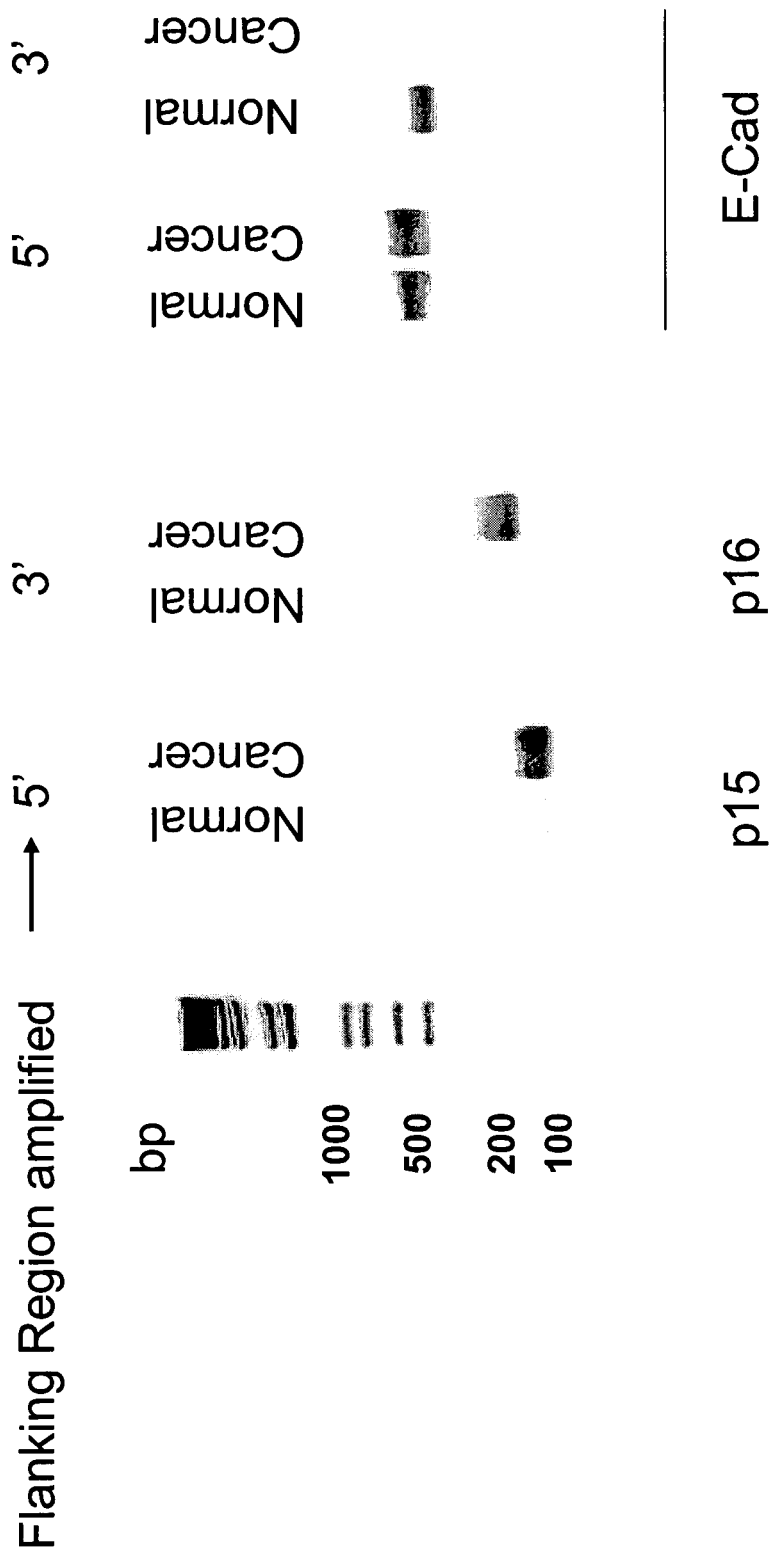
FIG. 13 shows an ethidium bromide stained gel of amplified products from the McrBC-mediated library promoter methylation assay based on the attachment of a modular adaptor to McrBC cleavage sites allowing one-sided PCR between the adaptor and specific sites flanking the CpG island. In the first amplification step, a proximal T7 promoter sequence is ligated and used to amplify all fragments, followed by incorporation of a 5' tail comprising 10 cytosines. This distal sequence allows asymmetric one-sided PCR amplification due to the strong suppression effect of the terminal poly-G/poly-C duplex. One-sided PCR was performed with C$_{10}$ primer (SEQ ID NO:38), and primers specific for the human p15 promoter (SEQ ID NO:39), p16 promoter (SEQ ID NO:40), or E-Cadherin promoter (SEQ ID NO:41 and SEQ ID NO:42).

FIG. 13 shows that a positive signal was generated from the hypermethylated cancer DNA CpG islands. Among the promoters studied, the p15 promoter had the highest ratio of cancer vs. normal signal, followed by the p16 promoter. The E-Cadherin gene promoter on the other hand, showed a very slight difference between cancer and normal DNA and when a primer specific for a region flanking the E-Cadherin CpG island on its 3' end was used, the assay produced an inverse signal (i.e. positive for normal and negative for cancer) that the present inventors in specific embodiments interpret as interference coming from methylated regions flanking the CpG islands in the 3' direction. The transcribed regions adjacent to the 3' end of most CpG islands in normal cells are known to be heavily methylated, whereas, for promoters involved in epigenetic control of carcinogenesis in cancer cells, these regions are largely hypomethylated (Baylin and Herman, 2000).

Figure 14:
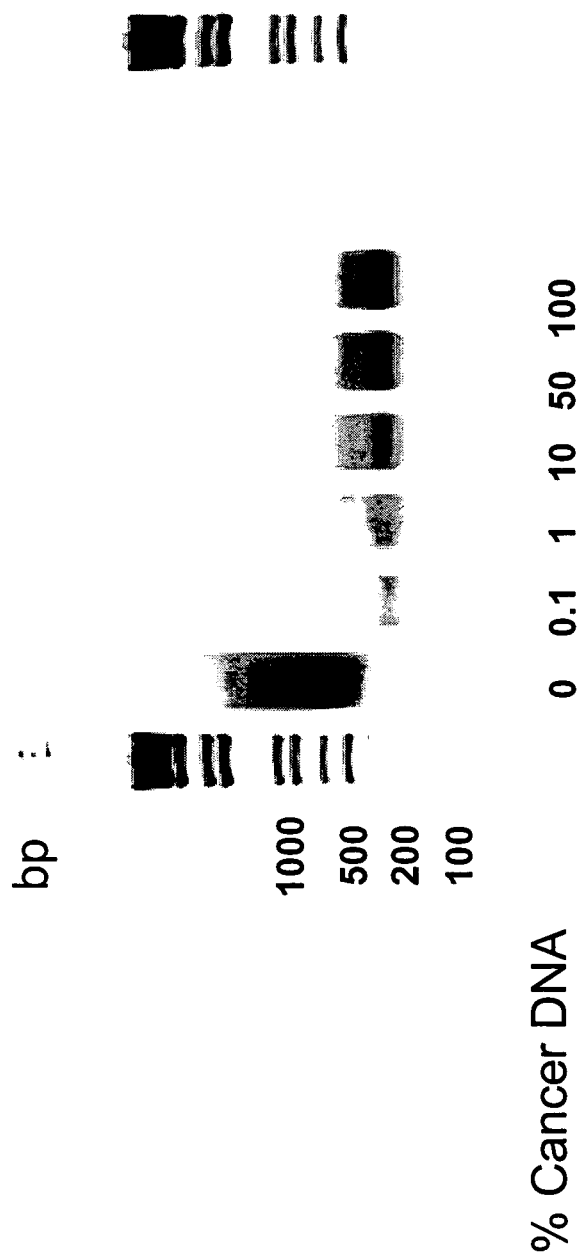
FIG. 14 demonstrates the sensitivity limits of the library methylation assay described in Example 6 and FIG. 13. Different ratios of McrBC libraries prepared from normal or cancer cells were mixed and then amplified with the universal C$_{10}$ primer (SEQ ID NO:38) and a primer specific for the p15 promoter 5' flanking region (SEQ ID NO:39). The total amount of DNA was 50 ng per amplification reaction, containing 0, 0.1, 1.0, 10, 50, or 100% of cancer DNA.

To determine the sensitivity limits of the assay, different ratios of McrBC libraries prepared from normal or cancer cells as described above were mixed and then amplified with the universal $C_{10}$ primer (SEQ ID NO:38) and a primer specific for the p15 promoter 5' flanking region (SEQ ID NO: 39). The total amount of DNA was 50 ng per amplification reaction containing 0, 0.1, 1.0, 10, 50, or 100% of cancer DNA. One-sided PCR amplification was done as described above. The result of this experiment showed that as little as 0.1% of cancer DNA can be detected in a background of 99.9% normal DNA corresponding to 1 cancer cell in about 1000 normal cells (FIG. 14).

Example 7

Preparation of Nick-Translation DNA Libraries from Fragments Originating at McrBc Cleavage Sites for Analysis of DNA Methylation In this example, a McrBC-mediated library diagnostic assay is described in which a nick-attaching biotinylated adaptor is ligated to McrBC cleavage sites, the nick is propagated to a controlled distance from the adaptor and the uniformly sized nick-translation products are immobilized on a solid phase and analyzed for the presence of sequences internal to, or flanking, a CpG island. The McrBC libraries of this type can also be used for discovery of unknown hypermethylated promoters by sequencing or by hybridization to micro arrays.

One microgram of control genomic DNA (Coriell repository # NA16028) or KG1-A leukemia cells DNA was subjected to limited digestion with McrBC nuclease in 25 µl of 1× NEBuffer 2 (NEB) containing 100 µg/ml BSA, 1 mM GTP, and 2 units of McrBC nuclease (NEB) at 37° C. for 1 hour, followed by incubation at 65° C. for 20 minutes to inactivate the enzyme.

The ends of the digested fragments were blunt-ended with the Klenow fragment of DNA polymerase I (USB) in 100 µl of 1×T4 Ligase buffer (NEB) with 2 nM of each dNTP at 25° C. for 15 minutes followed by blunt-end ligation of biotinylated nick-attaching adaptor. The adaptor was assembled in 10 mM KCl containing 18 µM Adapt Backbone (SEQ ID NO:43), 15 µM Adapt Biot (SEQ ID NO:44), and 15 µM Adapt Nick (SEQ ID NO:45) (Table I) by heating at 95° C. for 1 minute, cooling to room temperature, and incubation for 5 min on ice. Ligation reactions were performed in 160 µl of 1×T4 Ligase buffer (NEB), containing 1 µg of blunt-end template DNA, 3.75 µM of biotinylated nick-attaching adaptor, and 20,000 units of T4 DNA Ligase (NEB) at 16° C. for 1 hour, followed by incubation at 75° C. for 10 minutes to inactivate the ligase. Samples were purified on Quiaquick PCR filters (Qiagen) and reconstituted in 70 µl of TE-L buffer.

Samples were further subjected to nick-translation in total of 100 µl of 1× ThermoPol buffer (NEB) containing 200 µM of each dNTP and 5 units of Taq polymerase (NEB) at 50° C. for 5 minutes. Reactions were stopped by adding 5 µl of 0.5 M EDTA, pH 8.0.

Nick-translation products were denatured at 100° C. for 5 minutes, snap-cooled on ice and mixed with 300 µM-280 streptavidin paramagnetic beads (Dynal) in equal volume of 2× binding buffer containing 20 mM Tris-HCl, pH 8.0, 1 M LiCl, and 2 mM EDTA. After rotating the tubes for 30 minutes at room temperature, the beads were washed 4 times with 70 µl of TE-L buffer, 2 times with 70 µl of freshly prepared 0.1 N KOH, and 4 times with 80 µl of TE-L buffer. The beads were resuspended in 50 µl of TE-L buffer and stored at 4° C. prior to use.

Two microliters of streptavidin beads suspension were used to amplify specific regions flanking promoter CpG islands from libraries prepared from DNA of normal or cancer cells. To prevent fluorescence quenching, PCR library synthesis was carried out in a reaction mixture containing 1× Titanium Taq reaction buffer (Clontech), 200 µM of each dNTP, 4% DMSO, 200 nM each forward and reverse primer specific for p15 promoter (SEQ ID NO:46 forward and SEQ ID NO:47 reverse), p16 promoter (SEQ ID NO:48 forward and SEQ ID NO:49 reverse), or E-Cadherin promoter (SEQ ID NO:50 forward and SEQ ID NO:51 reverse), and 5 units of Titanium Taq polymerase (Clontech) in a final volume of 50 µl at 95° C. for 3 minutes followed by 10 cycles at 94° C. for 15 seconds and 68° C. for 1 minute. After removal of beads and addition of 1:100,000 dilutions of fluorescein calibration dye and SYBR Green I (Molecular Probes), amplification was continued at 94° C. for 15 seconds and 68° C. for 1 minute on an I-Cycler real-time PCR instrument (Bio-Rad) for varying number of cycles until a plateau was reached for the cancer DNA samples. Ten microliters of each PCR reaction were analyzed on 1% agarose gel stained with ethidium bromide.

Figure 15:
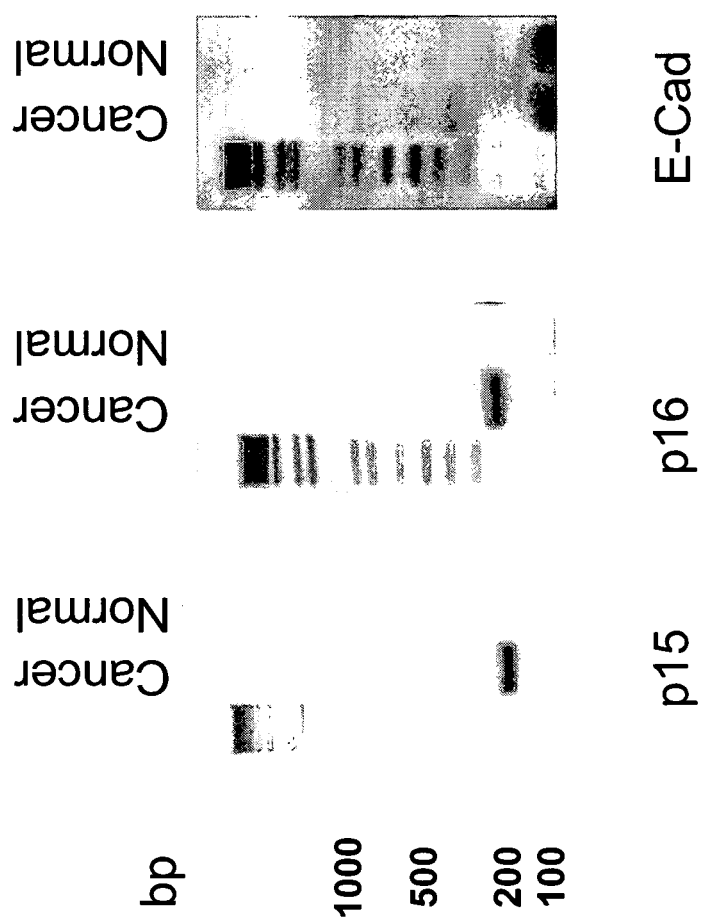
FIG. 15 shows an ethidium bromide-stained gel of amplified products from the McrBC-mediated library promoter methylation assay based on ligation of nick-attaching biotinylated adaptor to McrBC cleavage sites, propagation of the nick to a controlled distance, and immobilization of the nick-translation products on streptavidin beads. Aliquots of the streptavidin beads containing immobilized nick-translation products from normal or cancer cells were used to amplify specific regions flanking promoter CpG islands using primer pairs specific for the human p15 promoter (SEQ ID NO:46 forward and SEQ ID NO:47 reverse), p16 promoter (SEQ ID NO:48 forward and SEQ ID NO:49 reverse), or E-Cadherin promoter (SEQ ID NO:50 forward and SEQ ID NO:51 reverse).

FIG. 15 shows the results of the methylation analysis. The positive signal generated from hypermethylated p15 and p16 promoters in KG1-A cancer cells was equally strong, while the signal for E-Cadherin was weaker, but still clearly distinguishable from the signal amplified from normal cells.

In order to produce a sufficient amount of DNA for analysis of multiple promoter sites and for micro-array hybridization the present inventors studied the possibility of amplification of the McrBC libraries described above using a method for whole genome amplification with self-inert degenerate primers as described (U.S. patent application Ser. No. 10/795,667, filed Mar. 8, 2004, now U.S. Pat. No. 7,718,403). Seventeen microliters of streptavidin beads suspension of each library were resuspended in 14 µl of 1× EcoPol buffer (NEB), 200 µM of each dNTP, 1 uM degenerate K(N)$_2$ primer (SEQ ID NO:14), 15 ng/µl, and 4% DMSO. After a denaturing step of 2 minutes at 95° C., the samples were cooled to 24° C., and the reaction was initiated by adding 5 units of Klenow Exo– (NEB). The library synthesis reactions were carried out at 24° C. for 1 hr. Reactions were stopped with 1 µl of 83 mM EDTA (pH 8.0), and the samples were heated for 5 minutes at 75° C. The entire reaction mixture was further amplified by real-time PCR in a 75 µl volume containing 1× Titanium Taq reaction buffer (Clontech), 200 µM of each dNTP, fluorescein calibration dye (1:100,000) and SYBR Green I (1:100,000), 1 µM universal K$_U$ primer (SEQ ID NO:15), 4% DMSO, 200 µM 7-deaza-dGTP (Sigma), and 5 units of Titanium Taq polymerase (Clontech). Reactions were carried at 94° C. for 15 seconds and 65° C. for 2 minutes on an I-Cycler real-time PCR instrument (Bio-Rad) for different number of cycles until reaching a plateau. After cleaning the samples by QIAQUICK® PCR filters (Qiagen) 10 ng of amplified normal or cancer DNA were used to amplify specific regions flanking promoter CpG islands. PCR amplification was carried in reaction mixture containing 1× Titanium Taq reaction buffer (Clontech), 200 µM of each dNTP, 4% DMSO, fluorescein calibration dye (1:100,000) and SYBR Green I (1:100,000), 200 nM each forward and reverse primer specific for p15 promoter (SEQ ID NO:46 forward and SEQ ID NO:47 reverse), and 5 units of Titanium Taq polymerase (Clontech) in a final volume of 50 µl at 95° C. for 3 minutes followed by 94° C. for 15 sec and 68° C. for 1 minute for different number of cycles until a plateau was reached for the cancer samples. Ten microliters of each PCR reaction were analyzed on 1% agarose gel after staining with ethidium bromide.

Figure 16:
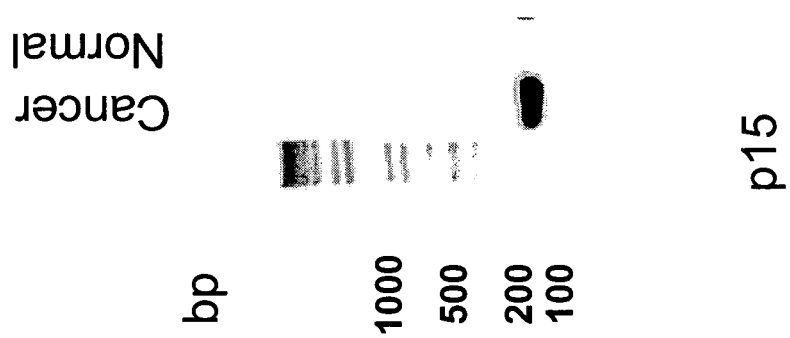
FIG. 16 shows the products of amplification of a sequence flanking the CpG island of the p15 promoter in normal and cancer cells using DNA amplified with universal K$_U$ primer (SEQ ID NO:15) from immobilized nick-translation libraries described in FIG. 15. The products amplified with primers specific for the human p15 promoter (SEQ ID NO:46 forward and SEQ ID NO:47 reverse) are illustrated.

FIG. 16 shows the amplification of a sequence flanking the CpG island of the p15 promoter in normal and cancer cells. The difference in methylation between the two samples was similar to that found in non-amplified libraries (see FIG. 15). This demonstrates that sufficient amounts of DNA can be generated for analysis of methylation in multiple promoters as well as for discovery of unknown hypermethylated promoters.

Example 8

Preparation of DNA Libraries from Fragments Originating at McrBc Cleavage Sites by Direct Biotin Incorporation for Analysis of DNA Methylation In this example a McrBC-mediated library diagnostic assay is described in which 3' recessed ends of McrBC cleavage sites are extended in the presence of a biotin-comprising nucleotide analog, followed by DNA fragmentation, immobilization on a solid support, and analysis of sequences internal to, or flanking, a CpG island. The McrBC libraries of this type can also be used for discovery of unknown hypermethylated promoters by sequencing or by hybridization to microarrays, for example.

One microgram of control genomic DNA (Coriell repository # NA16028) or KG1-A leukemia cells DNA was subjected to limited digestion with McrBC in 25 µl of 1× NEBuffer 2 (NEB) containing 100 µg/ml BSA, 1 mM GTP, and 2 units of McrBC nuclease (NEB) at 37° C. for 1 hour, followed by incubation at 65° C. for 20 minutes to inactivate the enzyme.

The 3' recessed ends of the DNA fragments were extended with Klenow fragment of DNA polymerase I in 100 µl of 1×T4 Ligase buffer (NEB) with 20 nM each of dATP, dCTP, and dGTP, 25 nM Biotin-21-dUTP (Clontech), and 6 units of the Klenow Exo− (USB) at 25° C. for 20 minutes followed by 75° C. for 10 minutes. After QIAQUICK® clean-up (Qiagen) the samples were recovered in 70 µl of TE-L buffer.

The labeled DNA was fragmented by heating at 95° C. for 4 minutes, snap-cooled on ice for 2 minutes, and mixed with 300 µg M-280 streptavidin paramagnetic beads (Dynal) in equal volume of 2× binding buffer containing 20 mM Tris-HCl, pH 8.0, 1 M LiCl, and 2 mM EDTA. After rotating the tubes for 1 hour at room temperature, the beads were washed 3 times with 80 µl of TE-L buffer, 1 time with 70 µl of freshly prepared 0.1 N KOH, and 4 times with 80 µl of TE-L buffer. The beads were resuspended in 50 µl of TE-L buffer and stored at 4° C. prior to use.

Two microliters of streptavidin beads suspension were used to amplify specific regions flanking promoter CpG islands from libraries prepared from DNA of normal or cancer cells. To prevent fluorescence quenching, PCR library synthesis was carried out in a reaction mixture comprising 1× Titanium Taq reaction buffer (Clontech), 200 µM of each dNTP, 4% DMSO, 200 nM each forward and reverse primer specific for the human p15 promoter (SEQ ID NO:46 forward and SEQ ID NO:47 reverse), and 5 units of Titanium Taq polymerase (Clontech) in a final volume of 50 µl at 95° C. for 3 minutes followed by 10 cycles at 94° C. for 15 sec and 68° C. for 1 minute. After removal of beads and addition of 1:100,000 dilutions of fluorescein calibration dye and SBYR Green I (Molecular Probes), amplification was continued at 94° C. for 15 seconds and 68° C. for 1 min on an I-Cycler real-time PCR instrument (Bio-Rad) for different number of cycles until a plateau was reached for the cancer DNA samples. Ten microliters of each PCR reaction were analyzed on 1% agarose gel after staining with ethidium bromide.

Figure 17:
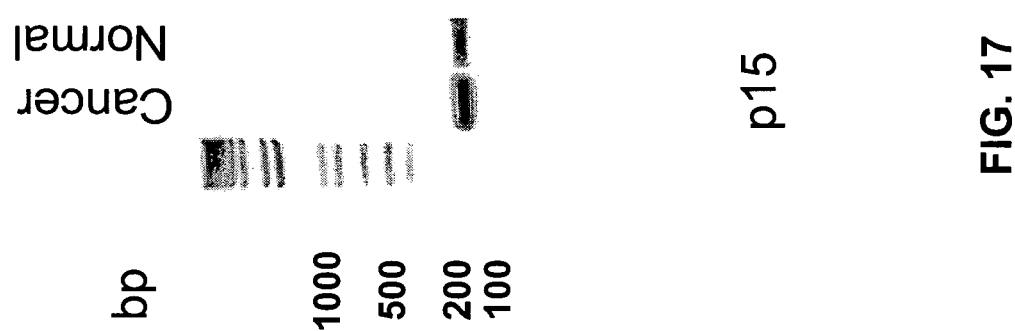
FIG. 17 shows the products of amplification of a sequence flanking the CpG island of the p15 promoter in normal and cancer cells using the McrBC-mediated library promoter methylation assay based on extension of 3' recessed ends of McrBC cleavage sites in the presence of a biotin-containing nucleotide analog, followed by DNA fragmentation and immobilization on streptavidin magnetic beads. Aliquots of the streptavidin beads and a primer pair specific for a region flanking the CpG island of the human p15 promoter were used for PCR amplification (SEQ ID NO: 46 forward and SEQ ID NO:47 reverse)

FIG. 17 shows the results of the methylation analysis. A strong positive signal was generated from hypermethylated p15 promoters in KG1-A cancer cells, but not from control cells.

In order to produce sufficient DNA for analysis of multiple promoter sites and for micro-array hybridization, we tested the possibility of amplification of the McrBC libraries described above using our patented method for whole genome amplification with self-inert degenerate primers (U.S. patent application Ser. No. 10/795,667, filed Mar. 8, 2004, now U.S. Pat. No. 7,718,403). Seventeen microliters of streptavidin beads suspension of each library were resuspended in 14 µl of 1× EcoPol buffer (NEB), 200 µM of each dNTP, 1 uM degenerate K(N)$_2$ primer (SEQ ID NO:14), 15 ng/µl, and 4% DMSO. After a denaturing step of 2 minutes at 95° C., the samples were cooled to 24° C., and the reaction was initiated by adding 5 units of Klenow Exo− (NEB). The library synthesis reactions were done at 24° C. for 1 hour. Reactions were stopped with 1 µl of 83 mM EDTA (pH 8.0), and samples were heated for 5 minutes at 75° C. The entire reaction mixture was further amplified by quantitative real-time PCR in 75 µl volume containing 1× Titanium Taq reaction buffer (Clontech), 200 µM of each dNTP, fluorescein calibration dye (1:100,000) and SYBR Green I (1:100,000), 1 µM universal K$_U$ primer (SEQ ID NO:15), 4% DMSO, and 5 units of Titanium Taq polymerase (Clontech). Reactions were carried at 94° C. for 15 sec and 65° C. for 2 min on an I-Cycler real-time PCR instrument (BioRad) for various number of cycles until reaching a plateau. After cleaning the samples by QIAQUICK® PCR filters (Qiagen) 10 ng of amplified normal or cancer DNA were used to amplify specific regions flanking promoter CpG islands. PCR amplification was carried in reaction mixture containing 1× Titanium Taq reaction buffer (Clontech), 200 µM of each dNTP, 4% DMSO, fluorescein calibration dye (1:100,000) and SYBR Green I (1:100,000), 200 nM each of forward and reverse primer specific for p15 promoter (SEQ ID NO:46 forward and SEQ ID NO:47 reverse), p16 promoter (SEQ ID NO:48 forward and SEQ ID NO:49 reverse), or E-Cadherin promoter (SEQ ID NO:50 forward and SEQ ID NO:51 reverse), and 5 units of Titanium Taq polymerase (Clontech) in a final volume of 50 µl at 95° C. for 3 min followed by 94° C. for 15 sec and 68° C. for 1 min for different number of cycles until a plateau was reached for the cancer samples. Ten microliters of each PCR reaction were analyzed on 1% agarose gel after staining with ethidium bromide.

Figure 18:
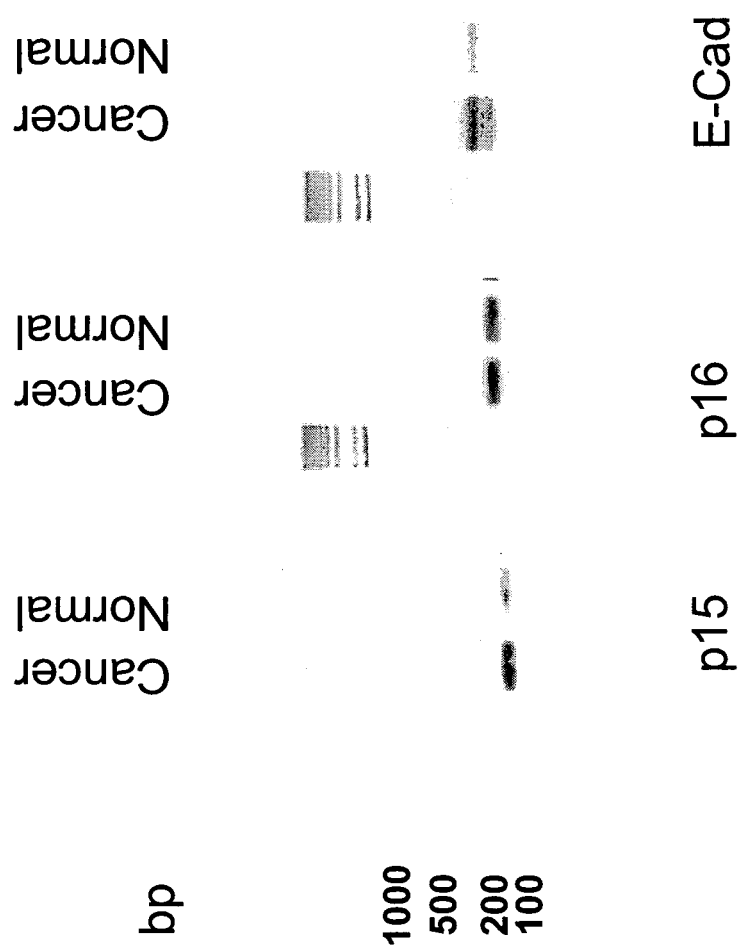
FIG. 18 shows the products of amplification of sequences flanking the CpG islands of p15, p16, and E-Cadherin promoters in normal and cancer cells using DNA amplified with universal K$_U$ primer (SEQ ID NO:15) from immobilized fill-in libraries described in FIG. 17. The products amplified with primers specific for the human p15 promoter (SEQ ID NO:46 forward and SEQ ID NO:47 reverse), p16 promoter (SEQ ID NO:48 forward and SEQ ID NO:49 reverse), or E-Cadherin promoter (SEQ ID NO:50 forward and SEQ ID NO:51 reverse) are depicted.

FIG. 18 shows the amplification of sequences flanking the CpG island of p15, p16, and E-Cadherin promoters in normal and cancer cells. The difference in methylation between the cancer and control samples was similar to that found in non-amplified libraries (see FIG. 17). This demonstrates that sufficient amounts of DNA can be generated for analysis of methylation in multiple promoters as well as for discovery of unknown hypermethylated promoters.

Example 9

Analysis of the Termini Produced by McrBc and Direct Ligation of Adaptors with 5'-Overhangs to McrBc Cleavage Sites without Prior Enzymatic Repair This example describes the analysis of the nature of the DNA ends produced by McrBC nuclease digestion. It also shows that the ends produced by McrBC cleavage are directly competent for ligation to adaptors having random 5'-overhangs without any further enzymatic repair to adaptors and defines the minimum length of these overhangs.

In order to investigate the characteristics of McrBC cleavage, several experiments were conducted to determine the types of ends that are generated. Initial experiments compared the ability of McrBC digested DNA to have universal adaptors ligated to the resulting ends and be amplified. Specifically, 1 µg of genomic DNA was digested in the presence of 0.1 U of McrBC overnight at 37° C.

The requirement of polishing for ligation to the resulting 3' ends of the digested DNA was investigated by comparing polishing with Klenow and Exo−, and No Polishing. Specifically, 1.1 µl 10×T4 DNA ligase buffer, 0.02 µl dNTP (200 nM FC) and 0.84 µl H$_2$O were added to 8 µl of fragmented DNA (100 ng). Finally, 0.04 µl of H$_2$O, Klenow (2.3 U, NEB) or Klenow Exo− (2.3 U, NEB) were added to the appropriate tubes. The reaction was carried out at 25° C. for 15 minutes, and the polymerase was inactivated at 75° C. for 15 minutes and then chilled to 4° C.

Universal T7 adaptors were assembled in 10 mM KCl containing 10 µM T7GG (SEQ ID NO:32) and 20 µM T7SH (SEQ ID NO:34) to form a blunt end adaptor; 20 µM T7GG (SEQ ID NO:32) and 40 µM of T7NSH (SEQ ID NO:35) to form a 5' N overhang adaptor; and 20 µM T7GG (SEQ ID NO:33) and 40 µM of T7GGN (SEQ ID NO:34) to form a 3' N overhang adaptor (see Table I for oligonucleotide sequences). Adaptor mixtures were heated at 65° C. for 1 minute, cooled to room temperature and incubated for 5 min on ice prior to use. T7 adaptors were ligated to the 5' ends of the DNA using T4 DNA ligase by addition of 0.5 ul 10×T4 DNA ligase buffer, 0.5 ul H₂O, 4 µl T7 adaptors (10 pmol each of the blunt end, 5' N overhang, and 3' N overhang adaptors) and 1 µl T4 DNA Ligase (2,000 U). The reaction was carried out for 1 hour at 16° C., the enzyme was inactivated at 65° C. for 10 minutes, and the samples were held at 4° C. until use. Alternatively, the libraries can be stored at −20° C. for extended periods prior to use.

Figure 19:
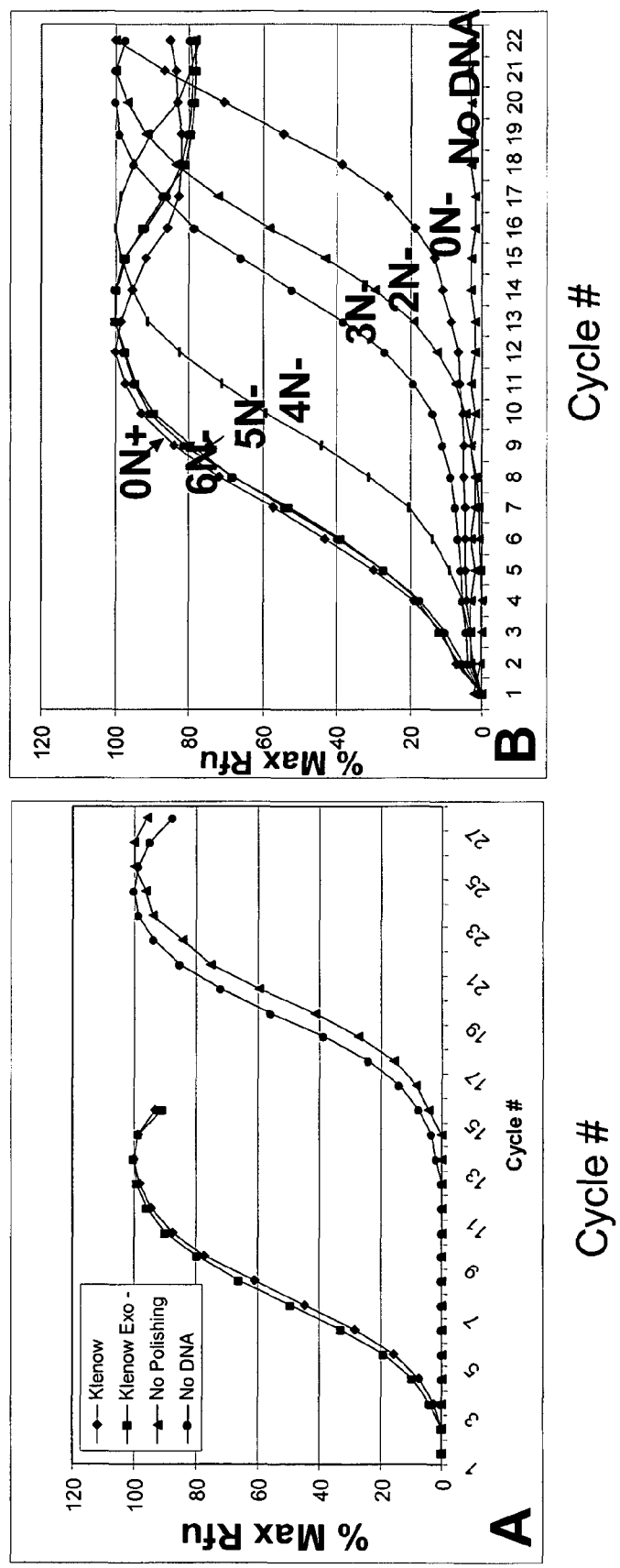
FIGS. 19A and 19B illustrate the analysis of the nature of the ends produced by McrBC cleavage as well as direct ligation of adaptors with 5'-overhangs to McrBC cleavage sites without any prior enzymatic repair.

Extension of the 3' end to fill in the universal adaptor and subsequent amplification of the library were carried out under the same conditions. Five ng of library or H₂O (No DNA control) is added to a 25 µl reaction comprising 25 pmol T7-C₁₀ (SEQ ID NO:36) universal primer, 120 nmol dNTP, 1×PCR Buffer (Clontech), 1× Titanium Taq. Fluorescein calibration dye (1:100,000) and SYBR Green I (1:100,000) were also added to allow monitoring of the reaction using the I-Cycler Real-Time Detection System (Bio-Rad). The samples are initially heated to 75° C. for 15 minutes to allow extension of the 3' end of the fragments to fill in the universal adaptor sequence and displace the short, blocked fragment of the universal adaptor. Subsequently, amplification is carried out by heating the samples to 95° C. for 3 minutes 30 seconds, followed by 18 cycles of 94° C. for 15 seconds, and 65° C. for 2 minutes. The amplification curves for all 3 samples are depicted in FIG. 19A. The amplification of the sample without polishing was identical to the no DNA control, indicating that McrBC cleavage does not result in the production of blunt ends. However, both Klenow and Klenow Exo− libraries amplified with identical kinetics, indicating that although polishing is required, the DNA termini resulting from McrBC cleavage consist of 5' overhangs with competent 3' ends.

In order to further explore the possibility that the ends produced by McrBC cleavage are directly competent for ligation without any further enzymatic repair, adaptors comprising universal T7 promoter sequence and different numbers of random base 5'-overhangs were compared for their ligation efficiency in direct ligation reaction with genomic DNA digested with McrBC. A sample of McrBC-digested DNA that was rendered blunt-ended with Klenow fragment of DNA polymerase I and ligated to a blunt end adaptor was used as a positive control to assess ligation efficiency.

One hundred nanograms of genomic DNA (Coriell repository # NA16028) was digested with McrBC nuclease in 10 µl of 1× NEBuffer 2 containing 100 µg/ml BSA, 1 mM GTP, and 10 units of McrBC nuclease (NEB) at 37° C. for 90 min, followed by incubation at 65° C. for 20 minutes to inactivate the enzyme. An aliquot of 12.5 ng of digested DNA was blunt-ended with Klenow fragment of DNA polymerase I (USB) in 10 µl of 1×T4 Ligase buffer (NEB) containing 2 nM of each dNTP at 25° C. for 15 min.

Adaptors comprising universal T7 promoter sequence with 5' overhangs comprising from 0 to 6 completely random bases were assembled in 1×T4 Ligase buffer (New England Biolabs) containing 15 µM T7GG (SEQ ID NO:32) and 30 µM T7SH (SEQ ID NO:34) to form a blunt end adaptor; or 15 µM T7GG (SEQ ID NO:32) and 30 µM of T7SH-2N, T7SH-3N, T7SH-4N, T7SH-5N, or T7SH-6N (SEQ ID:55, SEQ ID NO:56, SEQ ID NO:57, SEQ ID NO:58, and SEQ ID NO:59, respectively) to form 5' N overhang adaptors with 2, 3, 4, 5, or 6 bases respectively (see Table I for oligonucleotide sequences). Adaptor mixtures were heated at 95° C. for 1 min, cooled to room temperature and incubated for 5 min on ice prior to use.

T7 adaptors with 0, 2, 3, 4, 5 or 6 random base overhangs were then ligated to 12.5 ng (10 µl) aliquots of the McrBC digested DNA by adding 0.5 ul of 10×T4 DNA ligase buffer, 0.5 ul H2O, 4 µl T7 adaptors (15 pmol), and 1 µl T4 DNA Ligase (2,000 U). The reactions were carried out for 1 hour at 16° C. and the enzyme was inactivated at 65° C. for 10 minutes. A control blunt-end ligation reaction with 12.5 ng of polished DNA (see above) and blunt-end T7 adaptor (0 overhang) was run in parallel under the same conditions.

In the next step, extension of the 3' ends to fill in the universal adaptors and subsequent amplification of the libraries was performed. Five nanograms of DNA from each sample (or ligation buffer used as negative control) were added to 50 µl reactions comprising 1 µM T7 universal primer (SEQ ID NO: 37), 200 µM of each dNTP, 4% DMSO, 1×PCR Buffer (Clontech), 1× Titanium Taq, fluorescein calibration dye (1:100,000), and SYBR Green I (1:100,000). The extension and amplification were carried out using I-Cycler Real-Time Detection System (Bio-Rad). The samples were initially heated to 72° C. for 15 minutes to allow extension of the 3' end of the fragments to fill in the universal adaptor sequence and displace the short, blocked fragments of the universal adaptors. After denaturation at 95° C. for 3.5 minutes, library DNA was amplified for 23 cycles at 94° C. for 15 seconds, and 65° C. for 2 minutes. The amplification curves for all 7 samples and the negative control are depicted in FIG. 19B. The amplification of non-polished samples ligated to adaptors with 5 or 6 base overhangs was virtually identical to the control polished sample ligated to the blunt-end (0 overhang) adaptor, indicating that the 5' overhangs produced by McrBC cleavage are at least 6 bases long. Adaptor with overhangs shorter than 5 bases were much less efficient. This result indicates that a minimum of 5 bases are required to support efficient hybridization and subsequent ligation of adaptors to McrBC overhangs under the conditions of the ligation reaction.

Figure 20:
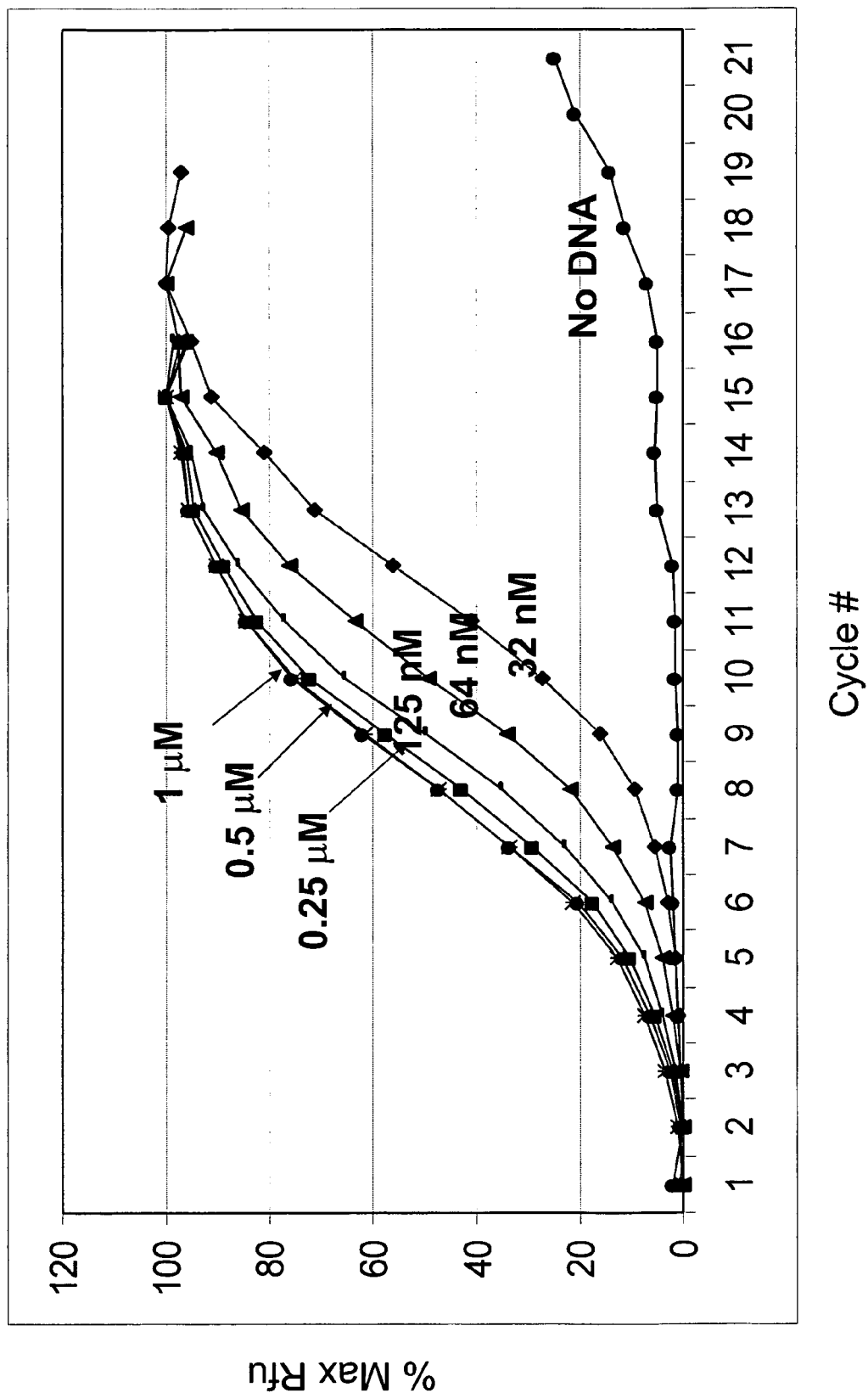
FIG. 20 illustrates library amplification aimed at determining the optimal amount of T7 adaptor with a 6-base overhang for efficient ligation to McrBC ends. Ligation of adaptor to 10 ng of McrBC digested DNA was with 1000 units of T4 ligase and 0, 0.032, 0.064, 0.125, 0.25, 0.5, or 1 µM final adaptor concentration.

To determine the optimal amount of 5' 6 base overhang T7 adaptor for efficient ligation to McrBC ends, 10 ng aliquots of McrBC-digested DNA were incubated with 1000 units of T4 ligase (New England Biolabs) in 1×T4 ligase buffer with 0, 0.032, 0.064, 0.125, 0.25, 0.5, or 1 µM final adaptor concentration. Ligation was carried out at 16° C. for 1 hour in a final volume of 30 µl. Two nanogram aliquots of the ligation reactions were amplified by real-time PCR following extension of the 3' ends to fill in the universal adaptor. Six microliters of library DNA from each ligation reaction or H₂O (no DNA control) were added to a 75 µl reaction comprising 1 µM T7 universal primer (SEQ ID NO: 37), 200 µM of each dNTP, 4% DMSO, 1×PCR Buffer (Clontech), 1× Titanium Taq, Fluorescein calibration dye (1:100,000), and SYBR Green I (1:100,000). The samples were initially heated to 72° C. for 15 minutes to fill in the universal adaptor sequence. Subsequently, amplification was carried out for 22 cycles at 94° C. for 15 seconds and 65° C. for 2 min, following denaturation for 3.5 minutes at 95° C. using an I-Cycler Real-Time Detection System (Bio-Rad). As shown in FIG. 20, adaptor concentrations of 0.25 µM and above resulted in complete ligation under the conditions tested.

Example 10

Preparation of Short Libraries for Analysis of DNA Methylation by Microcon Size Fractionation from McrBc Cleaved DNA This example describes the utility of libraries comprising short DNA sequences obtained by membrane microfiltration, which originate at McrBC cleavage sites and are rendered amplifiable by ligation of universal adaptor sequence, for the analysis of the methylation status of promoter CpG sites.

Aliquots of 50 ng or 10 ng of genomic DNA isolated from exemplary KG1-A leukemia cells or control genomic DNA (Coriell repository # NA16028) were digested with McrBC nuclease in 10 µl of 1× NEBuffer 2 containing 100 µg/ml BSA, 1 mM GTP, and 1 unit of McrBC nuclease (NEB) at 37° C. for 35 minutes, followed by 65° C. for 10 min to inactivate the enzyme. T7 adaptor with 6 random 5'-base overhang (T7-N6) consisting of T7GG and T7SH-6N (SEQ ID NO:32 and SEQ ID NO:59, respectively) (Table I) was assembled as described in Example 9.

T7-N6 adaptor was ligated to the McrBC digested DNA samples in a final volume of 30 µl containing 1×T4 DNA ligase buffer, 1 µM T7 adaptor, 2,500 U of T4 DNA Ligase (New England Biolabs), and the entire 10 µl of the McrBC digestion samples. Ligation reactions were carried out for 1 hour at 16° C. and the enzyme was inactivated at 65° C. for 10 minutes.

The ligation reactions were next supplemented with 80 µl of filtration buffer containing 10 mM Tris-HCl, pH 7.5, 0.1 mM EDTA, and 100 mM NaCl, and the DNA was size fractionated by passing the samples through Microcon YM-100 filters (Millipore) at 500×g at ambient temperature. Under these buffer conditions the Microcon filters retain DNA fragments above approximately 250 bp. The small fragments in the filtrate fractions were concentrated by ethanol precipitation and reconstituted in 15 µl of TE-L buffer.

In the next step, the 3' ends of the universal adaptor are filled in by extension and the libraries are amplified by PCR. The samples from the previous step were supplemented with PCR reaction buffer comprising 1× Titanium Taq buffer (BD Clontech), 1 µM T7 universal primer (SEQ ID NO: 37), 200 µM of each dNTP, 4% DMSO, 1× Titanium Taq polymerase (BD Clontech), fluorescein calibration dye (1:100,000) and SYBR Green I (1:100,000) in a final volume of 75 µl. Extension of the 3' ends and subsequent amplification were performed on an I-Cycler Real-Time Detection System (Bio-Rad). After initial denaturation at 95° C. for 3.5 minutes the samples were heated to 72° C. for 15 minutes and then cycled at 94° C. for 15 seconds, and 65° C. for 2 minutes until a plateau was reached by the real-time amplification curves.

To quantify the short DNA fragments released by McrBC digestion from the p16 promoter CpG island, 5 ng of library material were used in PCR reaction with a primer pair specific for a short internal promoter region. Amplification was carried in reaction mixture containing 1× Titanium Taq reaction buffer (Clontech), 200 µM of each dNTP, 4% DMSO, fluorescein calibration dye (1:100,000) and SYBR Green I (1:100,000), 200 nM each forward and reverse primer specific for p16 promoter (SEQ ID NO: 61 forward and 62 reverse), and 5 units of Titanium Taq polymerase (Clontech) in a final volume of 50 µl at 95° C. for 3 minutes followed by 94° C. for 15 seconds and 68° C. for 1 minute until a plateau was reached for the cancer samples by the real time amplification curves.

Figure 21:
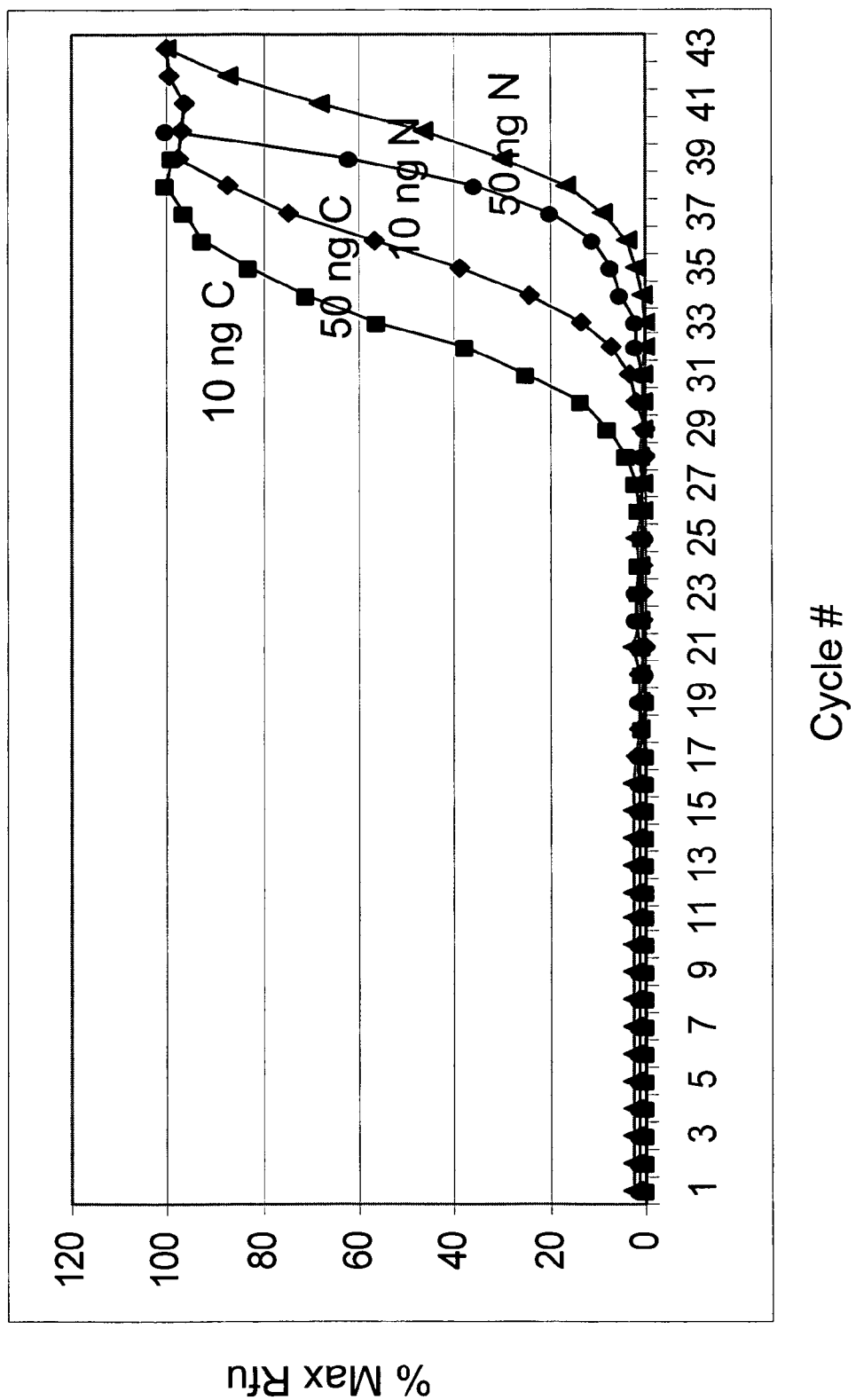
FIG. 21 shows the amplification of a short sequence from the CpG island of the p16 promoter in normal and cancer cells from libraries comprising short amplifiable DNA sequences generated by McrBC cleavage of 10 ng and 50 ng of genomic DNA, ligation of universal adaptor T7-N6 (SEQ ID NO: 32 and SEQ ID NO:59), size fractionation through Microcon YM-100 membrane filter, and amplification with universal T7 primer (SEQ ID NO:37). C=cancer DNA, N=normal DNA FIG. 22 demonstrates amplification of libraries comprising short amplifiable DNA sequences generated by McrBC cleavage of 10 ng, 1 ng, or 0.1 ng of genomic DNA after ligation of universal adaptor T7-N6 (SEQ ID NO:32 and SEQ ID NO:59)

FIG. 21 shows the amplification of short sequence in the CpG island of the p16 promoter in normal and cancer cells from the libraries prepared by Microcon filtration. A difference of 7 cycles and 5 cycles between cancer and normal cells was obtained for libraries prepared from 10 ng and 50 ng of genomic DNA respectively. This demonstrates that sufficient amounts of DNA can be generated for analysis of methylation in multiple promoters as well as for discovery of unknown hypermethylated promoters from small amount of starting material.

Example 11

Titration of the Input Amount of Genomic DNA for Preparation of Short Libraries for Analysis of Methylation by Microcon Size Fractionation from McrBc Cleaved DNA In this example, the effect of the amount of input DNA on preparation of libraries described in Example 10 was studied. To increase the sensitivity of the assay, the libraries were first amplified following ligation of universal T7-N6 adaptor, subjected to size fractionation by Microcon filters, and re-amplified.

Aliquots of 10 ng, 1 ng and 0.1 ng of genomic DNA isolated from exemplary KG1-A leukemia cells or control genomic DNA (Coriell repository # NA16028) were digested with McrBC nuclease in 10 µl of 1× NEBuffer 2 comprising 100 µg/ml BSA, 1 mM GTP, and 0.5 units of McrBC nuclease (or 1 unit of McrBC in the case of 10 ng input DNA) at 37° C. for 35 minutes, followed by incubation at 65° C. for 10 minutes to inactivate the enzyme.

Universal T7-N6 adaptor with 6 random base 5' overhang was ligated to the McrBC-digested DNA samples in a final volume of 30 µl containing 1×T4 DNA ligase buffer, 1 µM T7-N6 adaptor, 2,500 U of T4 DNA Ligase (New England Biolabs), and the entire 10 µl of the McrBC-digested samples. Ligation reactions were carried out for 1 hour at 16° C. and the enzyme was inactivated at 65° C. for 10 minutes.

Next, the 3' ends of the universal adaptors were filled in by extension and the libraries were amplified by PCR. The samples were supplemented with PCR reaction buffer comprising 1× Titanium Taq buffer (BD Clontech), 1 µM T7 universal primer (SEQ ID NO: 37), 200 µM of each dNTP, 4% DMSO, 1× Titanium Taq polymerase (BD Clontech), fluorescein calibration dye (1:100,000) and SYBR Green I (1:100,000) in a final volume of 75 µl. Extension of the 3' ends to fill in the universal adaptor sequence and subsequent amplification were performed on an I-Cycler Real-Time Detection System (Bio-Rad). After initial denaturation at 95° C. for 3.5 minutes the samples were heated to 72° C. for 15 minutes and then cycled at 94° C. 15 seconds and 65° C. for 2 minutes until a plateau was reached by the real-time amplification curves. Samples were precipitated with ethanol and reconstituted in 15 µl of TE-L buffer.

The samples were then supplemented with 80 µl of filtration buffer containing 10 mM Tris-HCl, pH 7.5, 0.1 mM EDTA, and 100 mM NaCl, and DNA was size fractionated by passing through Microcon YM-100 filters (Millipore) for 10 to 12 minutes at 500×g at ambient temperature. The filtrate fractions were concentrated by ethanol precipitation and reconstituted in 15 µl of TE-L buffer. Five nanograms of each library were then used in re-amplification reaction with the T7 primer under the conditions described in the previous paragraph.

To quantify the short DNA fragments released by McrBC digestion from the p16 promoter CpG island, 5 ng of library material were used in PCR reaction with primer pair specific for a short internal promoter region. Amplification was carried out in a reaction mixture comprising 1× Titanium Taq reaction buffer (Clontech), 200 µM of each dNTP, 4% DMSO, fluorescein calibration dye (1:100,000) and SYBR Green I (1:100,000), 200 nM each forward and reverse primer specific for p16 promoter (SEQ ID NO:61 forward and SEQ ID NO:62 reverse), and 5 units of Titanium Taq polymerase (Clontech) in a final volume of 50 µl at 95° C. for 3 minutes followed by 94° C. for 15 sec and 68° C. for 1 minute until a plateau was reached for the cancer samples by the real time amplification curves. Aliquots of the amplified material were analyzed on 1% agarose gel stained with ethidium bromide.

Figure 22:
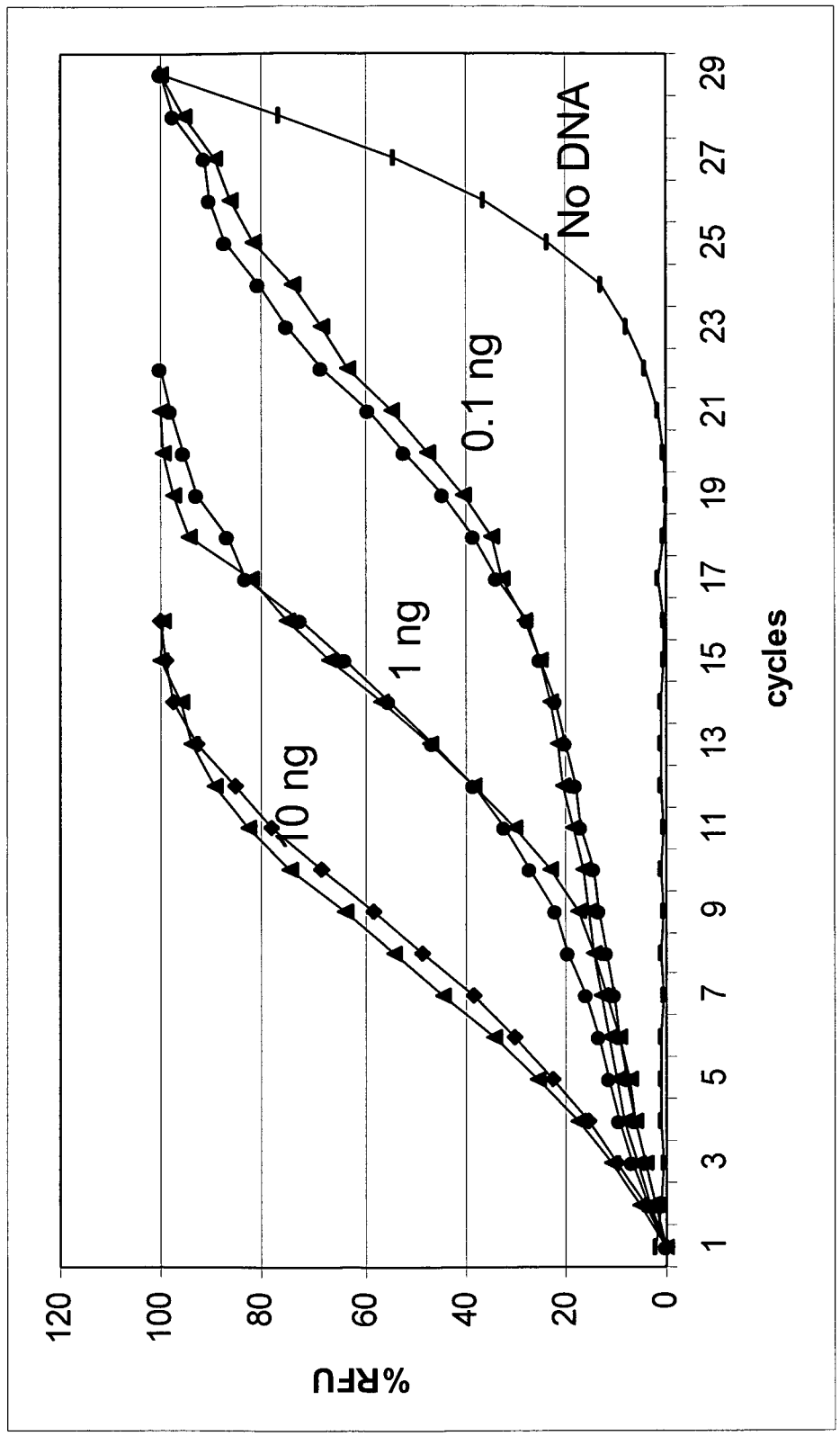
Figure 23:
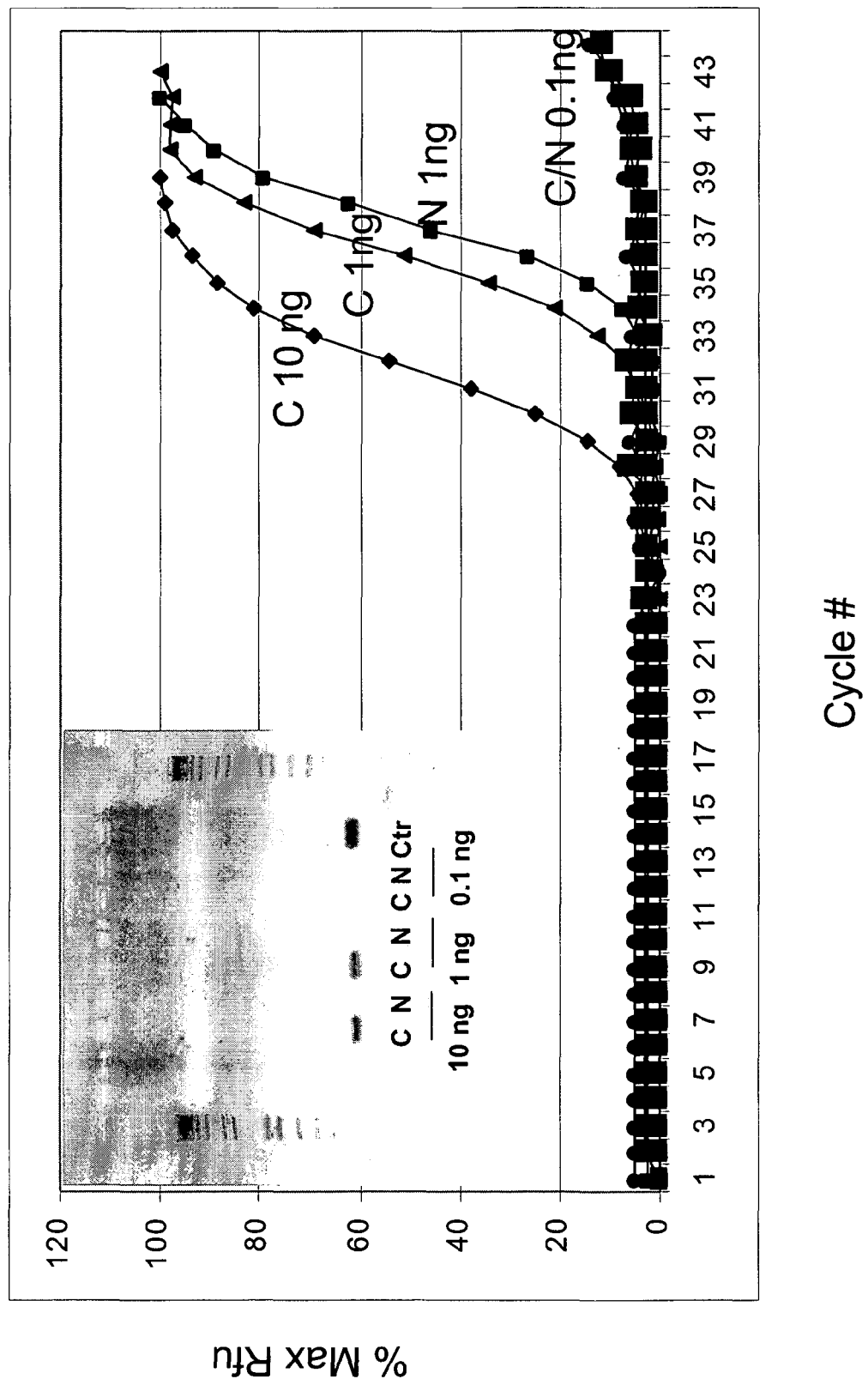
FIG. 23 illustrates amplification of short sequence from the CpG island of the p16 promoter in normal and cancer cells from libraries comprising short amplifiable DNA sequences generated by McrBC cleavage of 10 ng, 1 ng, or 0.1 ng of genomic DNA, ligation of universal adaptor T7-N6 (SEQ ID NO:32 and SEQ ID NO:59), amplification with universal T7 primer (shown in FIG. 22), size fractionation through Microcon YM-100 membrane filter, and re-amplification with universal T7 primer (SEQ ID NO:37). The insert to FIG. 23 shows analysis of the short p16 amplicon on 1% agarose gel after staining with ethidium bromide. C=cancer DNA, N=normal DNA

FIG. 22 illustrates the amplification of libraries derived from different input amounts of DNA. As shown, the libraries prepared from cancer and normal cells amplified with equal efficiencies. FIG. 23 shows amplification of short sequence in the CpG island of the p16 promoter in normal and cancer cells from libraries re-amplified after Microcon filtration. The insert to FIG. 23 represents gel analysis of the short p16 amplicon. As little as 1 ng of input material proved adequate for analysis of hypermethylation of the p16 promoter CpG island resulting in over 10 cycles difference between cancer and normal DNA. The present inventors were unable to detect the specific p16 sequence in libraries prepared from 0.1 ng of DNA.

This example demonstrates that the sensitivity of the assay in the present invention is significantly higher than methods known in the art for analysis of genome wide methylation of promoter CpG islands.

Example 12

Preparation of Short Libraries for Analysis of Methylation by Size-Selective Amplification from McrBc Cleaved DNA This example describes the preparation of libraries comprising short DNA sequences obtained by selective amplification of short fragments derived by McrBC cleavage and rendered amplifiable by ligation of two different universal adaptor sequences, for analysis of the methylation status of promoter CpG sites.

Aliquots of 10 ng of genomic DNA isolated from KG1-A leukemia cells or control genomic DNA (Coriell repository # NA16028) were digested with McrBC nuclease in 10 μl of 1× NEBuffer 2 containing 100 μg/ml BSA, 1 mM GTP, and 1 unit of McrBC nuclease (NEB) at 37° C. for 35 minutes, followed by incubation at 65° C. for 10 minutes to inactivate the enzyme. T7-N6 and GT-N6 adaptors with 6 random 5'-base overhangs consisting of T7GG and T7SH-6N oligos (SEQ ID NO:32 and SEQ ID NO:59), and Ku and GTSH-6N oligos (SEQ ID NO:15 and SEQ ID NO:60), respectively (Table I) were assembled as described in Example 9.

T7-N6 and GT-N6 adaptors were ligated to the McrBC-digested DNA samples in a reaction mixture containing 1×T4 DNA ligase buffer, 300 nM each adaptor, 760 U of T4 DNA Ligase (New England Biolabs), and the entire 10 μl of the McrBC digestion samples in a final volume of 30 μl. Ligation reactions were carried out for 1 hour at 16° C. and the enzyme was inactivated at 65° C. for 10 minutes.

The 3' ends of the universal adaptors were then filled in by extension and the libraries were amplified by PCR with T7 (SEQ ID NO:37) and Ku (SEQ ID:15) primers using reduced extension time to allow only short sequences receiving adaptors at both ends to be amplified. Five nanogram aliquots of the ligation reactions were supplemented with PCR reaction buffer comprising 1× Titanium Taq buffer (BD Clontech), 250 nM each T7 or GT primer (SEQ ID NO: 37 and SEQ ID NO:15), 200 μM of each dNTP, 4% DMSO, 1× Titanium Taq polymerase (BD Clontech), fluorescein calibration dye (1:100,000) and SYBR Green I (1:100,000) in a final volume of 75 μl. Extension of the 3' ends to fill in the universal adaptor sequence and subsequent amplification were performed on an I-Cycler Real-Time Detection System (Bio-Rad) by incubating the reactions at 72° C. for 15 minutes. After initial denaturation at 95° C. for 2.5 minutes the samples were heated to 72° C. for 15 minutes and then cycled at 94° C. 15 seconds, and 65° C. for 15 seconds until a plateau was reached by the real-time amplification curves.

Aliquots of 4 ng or 20 ng of amplified library material were then used to quantify, by PCR, the short DNA fragments released by McrBC digestion from the p16 promoter CpG island. Amplification was carried in reaction mixture containing 1× Titanium Taq reaction buffer (Clontech), 200 μM of each dNTP, 4% DMSO, fluorescein calibration dye (1:100, 000) and SYBR Green I (1:100,000), 200 nM each forward and reverse primer specific for p16 promoter (SEQ ID NO:61 forward and SEQ ID NO:62 reverse), and 5 units of Titanium Taq polymerase (Clontech) in a final volume of 50 μl at 95° C. for 3 minutes followed by a various number of cycles of 94° C. for 15 seconds and 68° C. for 1 minute until a plateau was reached for the cancer samples, as evidenced by the real time amplification curves.

Figure 24:
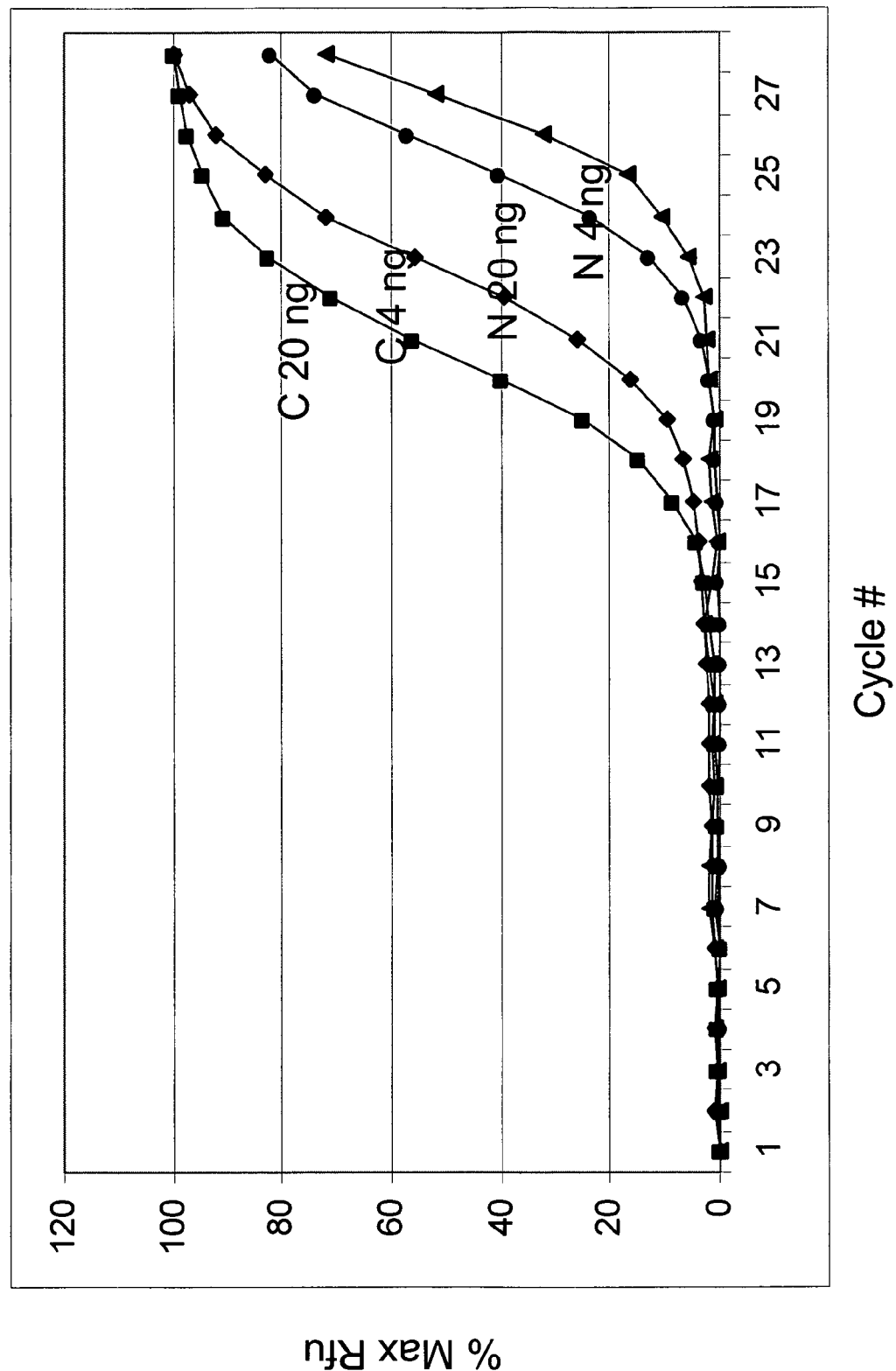
FIG. 24 depicts amplification of short sequence from the CpG island of the p16 promoter in normal and cancer cells from 4 ng or 20 ng of libraries comprising short amplifiable DNA sequences generated by McrBC cleavage of 10 ng or 50 ng, of genomic DNA, ligation of universal adaptors T7-N6 and GT-N6 (SEQ ID NO:32 and SEQ ID NO:59, and SEQ ID NO:15 and SEQ ID NO:60, respectively), and amplification with universal T7 and Ku primers (SEQ ID NO:37 and SEQ ID NO:15). C=cancer DNA, N=normal DNA

FIG. 24 shows the amplification of short sequence in the CpG island of p16 promoter in normal and cancer cells from 20 ng or 4 ng of library DNA. As shown, between 5 and 6 cycles difference could be detected between methylated cancer DNA and unmethylated control DNA.

Figure 25:
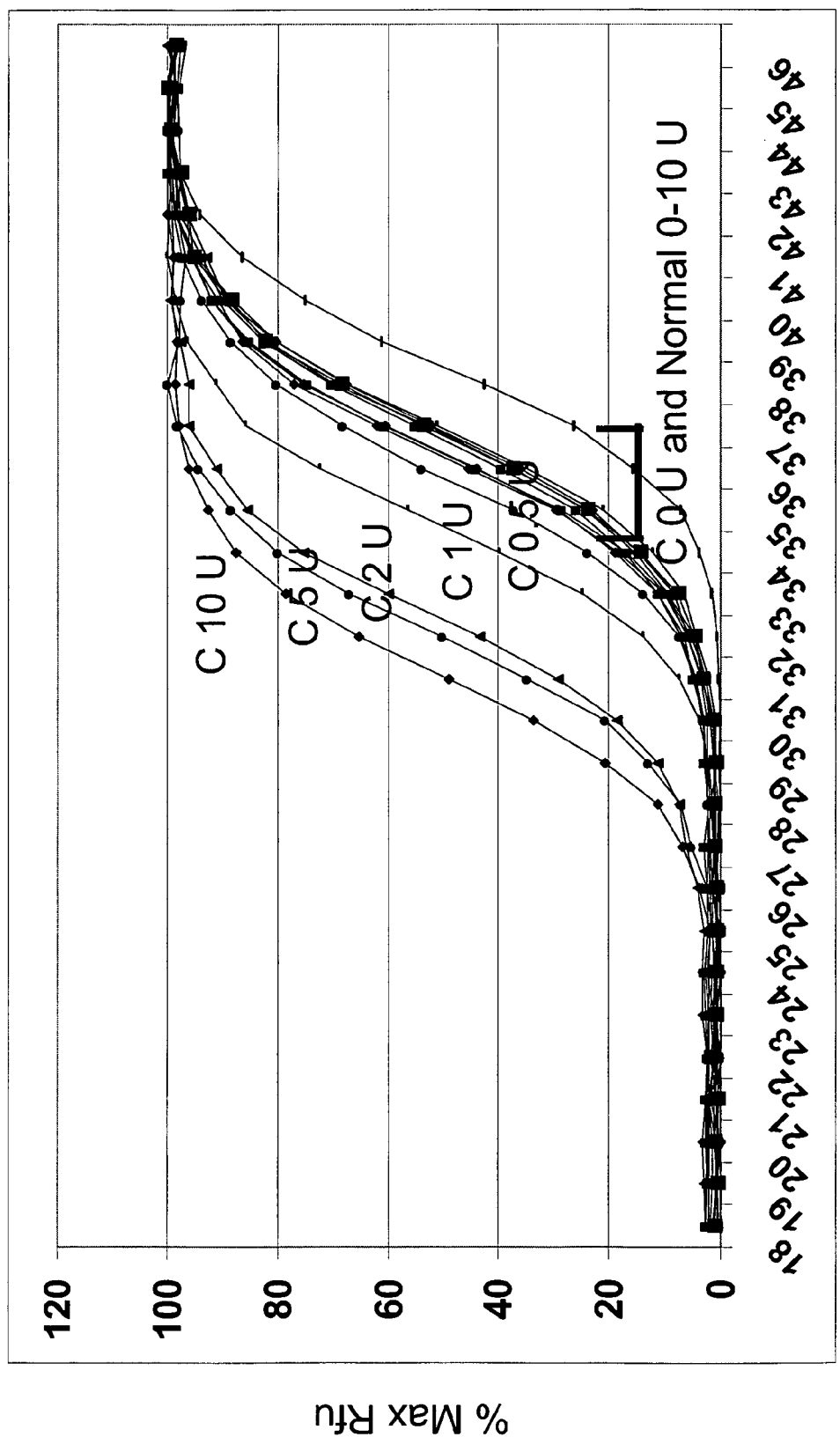
FIG. 25 shows amplification of short sequence from the CpG island of the p16 promoter in normal and cancer cells from 4 ng of libraries comprising short amplifiable DNA sequences generated by cleavage of 10 ng of genomic DNA with 0, 0.5, 1, 2, 5, or 10 units of McrBC, ligation of universal adaptors T7-N6 and GT-N6 (SEQ ID NO:32 and SEQ ID NO:59, and SEQ ID NO:15 and SEQ ID NO:60, respectively), and amplification with universal T7 and Ku primers (SEQ ID NO:37 and SEQ ID NO:15). C=cancer DNA, N=normal DNA.

To establish the optimal concentration of McrBC for library preparation, the present inventors carried out titration of the enzyme in a range of 0 to 10 units in digestion reaction comprising 10 ng of genomic DNA. McrBC digestion, ligation of universal adaptors T7-N6 and GT-N6, amplification of libraries, and analysis of p16 promoter sequence was as described above. FIG. 25 depicts the result of the McrBC titration experiment. As shown, in contrast to non-methylated control DNA, increasing the amount of enzyme incubated with methylated (cancer) DNA resulted in a proportional increase in the amplification signal for the short p16 promoter sequence. Due to the increased percentage of glycerol, it was impractical to test amounts of McrBC enzyme above 10 units per reaction. The results of the previous experiment using different ratios of enzyme to template DNA, combined with the present results, indicate that the level of McrBC degradation depends mostly on the absolute amount of, or the concentration of, McrBC, and not on the ratio of enzyme to DNA template (E. Kamberov personal observation). Thus, dimerization of McRBC plays a critical role in the process of cleavage of methylated DNA.

Example 13

Utilization of the Methylation-Sensitive Restriction enzyme not I and whole genome amplification by Mechanical Fragmentation to Create a Library of Methylated Restriction Sites This example, illustrated in FIG. 26, describes the amplification of methylated genomic DNA sites from DNA that has been digested with the methylation-sensitive restriction enzyme Not I, amplified by whole genome amplification relying on mechanical fragmentation, digested again with Not I, and amplified to select only sites that were methylated in the original intact DNA sample. A control library is also generated by omitting the first Not I digestion, which will result in all Not I sites being amplified in the final product.

Aliquots of genomic DNA (2.5 μg) were digested overnight at 37° C. with Not I restriction enzyme (25 U) in the presence of 1× buffer H (NEB). The enzyme was heat inactivated at 65° C. for 10 minutes and then cooled to 4° C. The digested DNA was precipitated with pellet paint according to the manufacturer's instructions and quantified by optical density.

Aliquots of 110 µl of genomic and Not I-digested DNA preps comprising 100 ng of DNA were heated to 65° C. for 2 minutes, vortexed for 15" and incubated for an additional 2 minutes at 65° C. The samples were spun at 12 min at ambient temperature at 16,000×G. One hundred µl of sample was transferred to a new tube and subjected to mechanical fragmentation on a HydroShear device (Gene Machines) for 20 passes at a speed code of 3, following the manufacturer's protocol. The sheared DNA has an average size of 1.5 kb as predicted by the manufacturer and confirmed by gel electrophoresis. To prevent carry-over contamination, the shearing assembly of the HydroShear was washed 3 times each with 0.2 M HCl, and 0.2 M NaOH, and 5 times with TE-L buffer prior to and following fragmentation. All solutions were 0.2 µm filtered prior to use.

Fragmented DNA samples may be used immediately for library preparation or stored at −20° C. prior to use. The first step of this embodiment of library preparation is to repair the 3' end of all DNA fragments and to produce blunt ends. This step comprises incubation with at least one polymerase. Specifically, 11.5 µl 10×T4 DNA ligase buffer, 0.38 µl dNTP (33 µM FC), 0.46 µl Klenow (2.3 U, USB) and 2.66 µl $H_2O$ were added to the 100 µl of fragmented DNA. The reaction was carried out at 25° C. for 15 minutes, and the polymerase was inactivated at 75° C. for 15 minutes and then chilled to 4° C.

Universal adaptors were ligated to the 5' ends of the DNA using T4 DNA ligase by addition of 4 µl T7 adaptors (10 pmol each of the blunt end, 5' N overhang, and 3' N overhang adaptors, SEQ ID NO: 32 and SEQ ID NO:34, SEQ ID NO:32 and SEQ ID NO:35, SEQ ID NO:33 and SEQ ID NO:34) and 1 µl T4 DNA Ligase (2,000 U). The reaction was carried out for 1 hour at 16° C., the enzyme was inactivated at 65° C. for 10', and the samples were held at 4° C. until use. Alternatively, the libraries can be stored at −20° C. for extended periods prior to use.

Extension of the 3' end to fill in the universal adaptor and subsequent amplification of the library were carried out under the same conditions. Five ng of library is added to a 25 µl reaction comprising 25 pmol T7-$C_{10}$ primer (SEQ ID NO:36), 120 nmol dNTP, 1×PCR Buffer (Clontech), 1× Titanium Taq. Fluorescein calibration dye (1:100,000) and SYBR Green I (1:100,000) are also added to allow monitoring of the reaction using the I-Cycler Real-Time Detection System (Bio-Rad). The samples are initially heated to 75° C. for 15' to allow extension of the 3' end of the fragments to fill in the universal adaptor sequence and displace the short, blocked fragment of the universal adaptor. Subsequently, amplification is carried out by heating the samples to 95° C. for 3 minutes 30 seconds, followed by 18 cycles of 94° C. 15 seconds, 65° C. 2 minutes. Following amplification, the DNA samples were purified using the QIAQUICK® kit (Qiagen) and quantified by optical density.

Aliquots of genomic and Not I digested amplified DNA was digested by Not I restriction enzyme by incubating 1 to 2 µg DNA in 1× Buffer H and 10 Units of Not I in a 30 ul reaction volume overnight at 37° C. The enzyme was heat inactivate at 65° C. for 10' and then cooled to 4° C. The digested DNA was precipitated with pellet paint according to the manufacturer's instructions and quantified by optical density.

GT adaptors were ligated to the 5' ends of DNA (50 ng) using T4 DNA ligase by addition of 2 µl GT adaptors (10 pmol, SEQ ID NO:15 and SEQ ID NO:54), 2 µl 10×DNA ligase buffer and 1 µl T4 DNA Ligase (2,000 U) in a final volume of 20 µl. The reaction was carried out for 1 h at 16° C. and then held at 4° C. until use. Alternatively, the libraries can be stored at −20° C. for extended periods prior to use.

Extension of the 3' end to fill in the GT adaptor and subsequent amplification of the library were carried out under the same conditions. Five ng of library is added to a 25 µl reaction comprising 25 pmol $C_{10}$ universal primer (SEQ ID NO:38), 25 pmol Ku primer (SEQ ID NO:15), 120 nmol dNTP, 1×PCR Buffer (Clontech), 1× Titanium Taq. Fluorescein calibration dye (1:100,000) and SYBR Green I (1:100,000) are also added to allow monitoring of the reaction using the I-Cycler Real-Time Detection System (Bio-Rad). The samples are initially heated to 75° C. for 15' to allow extension of the 3' end of the fragments to fill in the universal adaptor sequence and displace the short, blocked fragment of the universal adaptor. Subsequently, amplification is carried out by heating the samples to 95° C. for 3 minutes 30 seconds, followed by 23 cycles of 94° C. 15 seconds, 65° C. 2 minutes. Following amplification, the DNA samples were purified using the QIAQUICK® kit (Qiagen) and quantified by optical density.

Figure 27:
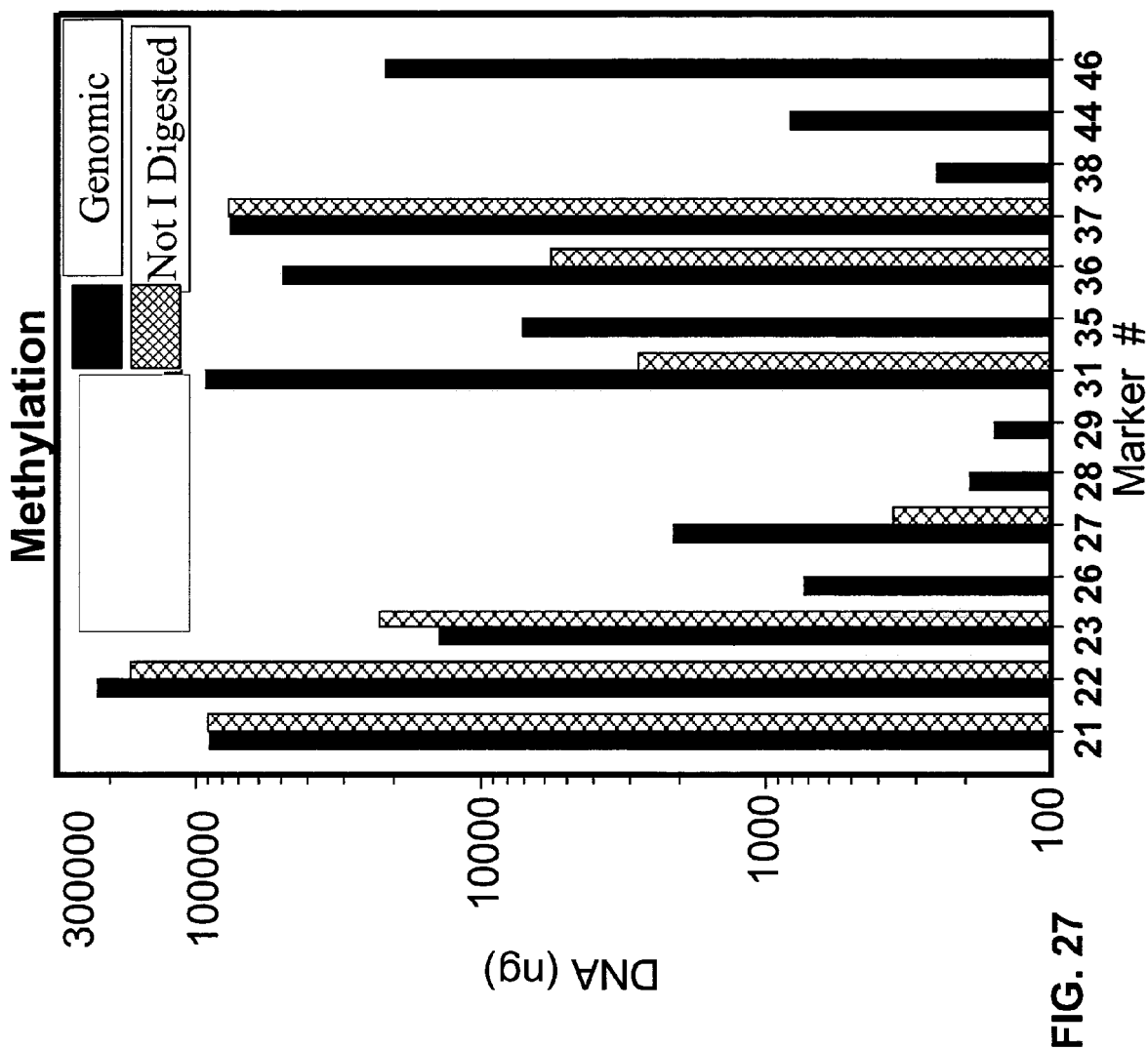
FIG. 27 illustrates the results of real-time PCR analysis of 14 markers corresponding to sites adjacent to known Not I restriction sites. Both control and Not I-digested DNA samples were analyzed. All 14 sites were detected in the control DNA, indicating that all sites wee efficiently cleaved and amplified when there is no methylation present. In contrast, only 7 of the 14 sites were detected in Not I-digested DNA, indicating that half of the 14 sites were methylated in the starting DNA.

The amplified DNA was analyzed using real-time, quantitative PCR using a panel of 14 human genomic markers adjacent to known Not I restriction sites. The markers that make up the panel are listed in Table II. Quantitative Real-Time PCR was performed using an I-Cycler Real-Time Detection System (Bio-Rad), as per the manufacturer's directions. Briefly, 25 µl reactions were amplified for 40 cycles at 94° C. for 15 seconds and 68° C. for 1 minute. Standards corresponding to 10, 1, and 0.2 ng of fragmented DNA were used for each marker. A standard curve was created for each marker and used for quantification of each sample (I-Cycler software, Bio-Rad). The resulting quantities were compared between the genomic and Not I-digested samples to determine whether each site was methylated. FIG. 27 indicates that all 14 markers were detected in the genomic control sample, indicating that all sites were successfully digested and amplified. The Not I-digested DNA sample comprised 7 of the 14 sites, indicating that half of the sites in the genomic DNA were originally methylated.

Example 14

Utilization of the Methylation-Sensitive Restriction Enzyme Not I and Whole Genome Amplification by Chemical Fragmentation to Create a Library of Methylated Restriction Sites This example, illustrated in FIG. 26, describes the amplification of methylated genomic DNA sites from DNA that has been digested with the methylation-sensitive restriction enzyme Not I, amplified by whole genome amplification relying on chemical fragmentation, digested again with Not I, and amplified to select only sites that were methylated in the original intact DNA sample. A control library is also generated by omitting the first Not I digestion, which will result in all Not I sites being amplified in the final product.

Aliquots of genomic DNA (2.5 ng) were digested overnight at 37° C. with Not I restriction enzyme (25 U) in the presence of 1× buffer H. The enzyme was heat inactivate at 65° C. for 10 minutes and then cooled to 4° C. The digested DNA was precipitated with pellet paint according to the manufacturer's instructions and quantified by optical density.

Aliquots of restriction endonuclease digested and control DNA (50 ng) were diluted in TE to a final volume of 10 µl. The DNA was subsequently heated to 95° C. for 4 minutes, and then cooled to 4° C. Two µl of 10×T4 DNA Ligase buffer was added to the DNA, and the mixture was heated to 95° C. for 2 minutes and then cooled to 4° C.

In order to generate competent ends for ligation, 40 nmol dNTP (Clontech), 0.1 pmol phosphorylated random hexamer primers (Genelink), and 5 U Klenow (NEB) were added, and the resulting 15 µl reaction was incubated at 37° C. for 30 minutes and 12° C. for 1 hour. Following incubation, the reaction was heated to 65° C. for 10' to destroy the polymerase activity and then cooled to 4° C.

GT adaptors were ligated to the 5' ends of the DNA using T4 DNA ligase by addition of 4 µl adaptors (10 pmol each of the blunt end, 5' N overhang, and 3' N overhang adaptors, SEQ ID NO:32 and SEQ ID NO:34, SEQ ID NO:32 and SEQ ID NO:35, SEQ ID NO:33 and SEQ ID NO:34) and 1 µl T4 DNA Ligase (2,000 U). The reaction was carried out for 1 hour at 16° C., the enzyme was inactivated at 65° C. for 10 minutes, and the samples were held at 4° C. until use. Alternatively, the libraries can be stored at −20° C. for extended periods prior to use.

Extension of the 3' end to fill in the universal adaptor and subsequent amplification of the library were carried out under the same conditions. Five ng of library is added to a 25 µl reaction comprising 25 pmol T7-$C_{10}$ primer (SEQ ID NO:36), 120 nmol dNTP, 1×PCR Buffer (Clontech), 1× Titanium Taq. Fluorescein calibration dye (1:100,000) and SYBR Green I (1:100,000) are also added to allow monitoring of the reaction using the I-Cycler Real-Time Detection System (Bio-Rad). The samples are initially heated to 75° C. for 15 minutes to allow extension of the 3' end of the fragments to fill in the universal adaptor sequence and displace the short blocked fragment of the universal adaptor. Subsequently, amplification is carried out by heating the samples to 95° C. for 3 minutes 30 seconds, followed by 18 cycles of 94° C. 15 seconds, 65° C. 2 minutes. Following amplification, the DNA samples were purified using the QIAQUICK® kit (Qiagen) and quantified by optical density.

Aliquots of genomic and Not I-digested amplified DNA was digested by Not I restriction enzyme by incubating 1-2 µg DNA in 1× Buffer H and 10 Units of Not 1 in a 30 µl reaction volume overnight at 37° C. The enzyme was heat inactivated at 65° C. for 10 minutes and then cooled to 4° C. The digested DNA was precipitated with pellet paint according to the manufacturer's instructions and quantified optical density.

GT adaptors were ligated to the 5' ends of DNA (50 ng) using T4 DNA ligase by addition of 2 µl of GT adaptor (10 pmol, SEQ ID NO:15 and SEQ ID NO:54), 2 µl 10×DNA ligase buffer and 1 µl T4 DNA Ligase (2,000 U) in a final volume of 20 µl. The reaction was carried out for 1 hour at 16° C. and then held at 4° C. until use. Alternatively, the libraries can be stored at −20° C. for extended periods prior to use.

Extension of the 3' end to fill in the GT universal adaptor and subsequent amplification of the library were carried out under the same conditions. Five ng of library is added to a 25 µl reaction comprising 25 pmol $C_{10}$ primer (SEQ ID NO:38), 25 pmol Ku primer (SEQ ID NO:15), 120 nmol dNTP, 1×PCR Buffer (Clontech), 1× Titanium Taq. Fluorescein calibration dye (1:100,000) and SYBR Green I (1:100,000) are also added to allow monitoring of the reaction using the I-Cycler Real-Time Detection System (Bio-Rad). The samples are initially heated to 75° C. for 15' to allow extension of the 3' end of the fragments to fill in the universal adaptor sequence and displace the short, blocked fragment of the universal adaptor. Subsequently, amplification is carried out by heating the samples to 95° C. for 3 minutes 30 seconds, followed by 23 cycles of 94° C. 15 seconds, 65° C. 2 minutes. Following amplification, the DNA samples were purified using the QIAQUICK® kit (Qiagen) and quantified optical density.

Figure 28:
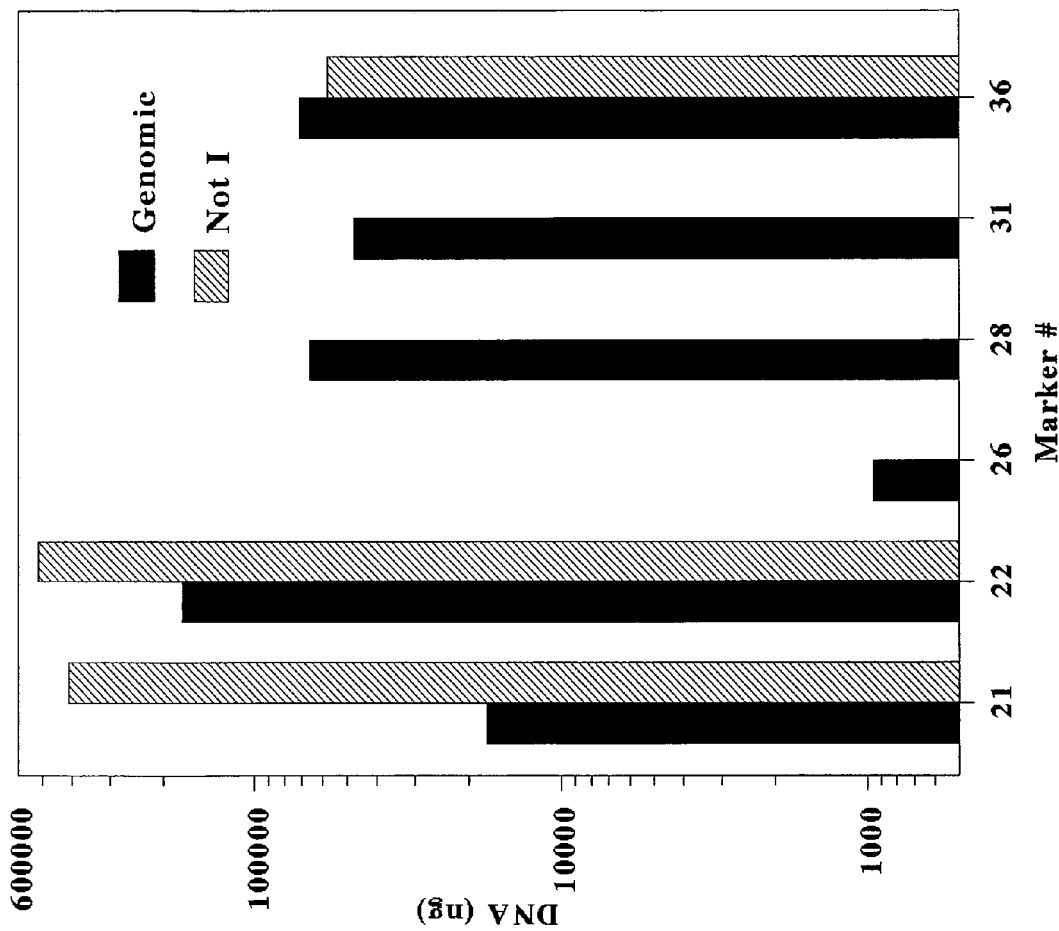
FIG. 28 illustrates the results of real-time PCR analysis of 6 markers corresponding to sites adjacent to known Not I restriction sites. Both control and Not I-digested DNA samples were analyzed. All 6 sites were detected in genomic DNA, indicating that all sites were efficiently cleaved and amplified when there is no methylation present. In contrast, only 3 of the 6 sites were detected in Not I-digested DNA, indicating that half of the sites were methylated in the starting DNA.

The amplified DNA was analyzed using real-time, quantitative PCR using a panel of 6 exemplary human genomic markers adjacent to known Not I restriction sites. The markers that make up the panel are listed in Table II. Quantitative Real-Time PCR was performed using an I-Cycler Real-Time Detection System (Bio-Rad), as per the manufacturer's directions. Briefly, 25 ul reactions were amplified for 40 cycles at 94° C. for 15 seconds and 68° C. for 1 minute. Standards corresponding to 10, 1, and 0.2 ng of fragmented DNA were used for each marker. A standard curve was created for each marker and used for quantification of each sample (I-Cycler software, Bio-Rad). The resulting quantities were compared between the genomic and Not I-digested samples to determine whether each site was methylated. FIG. 28 indicates that all 6 markers were detected in the genomic control sample, indicating that all sites were successfully digested and amplified. The Not I-digested DNA sample contained 3 of the 6 sites, indicating that half of the sites in the genomic DNA were originally methylated.

Example 15

Figure 29:
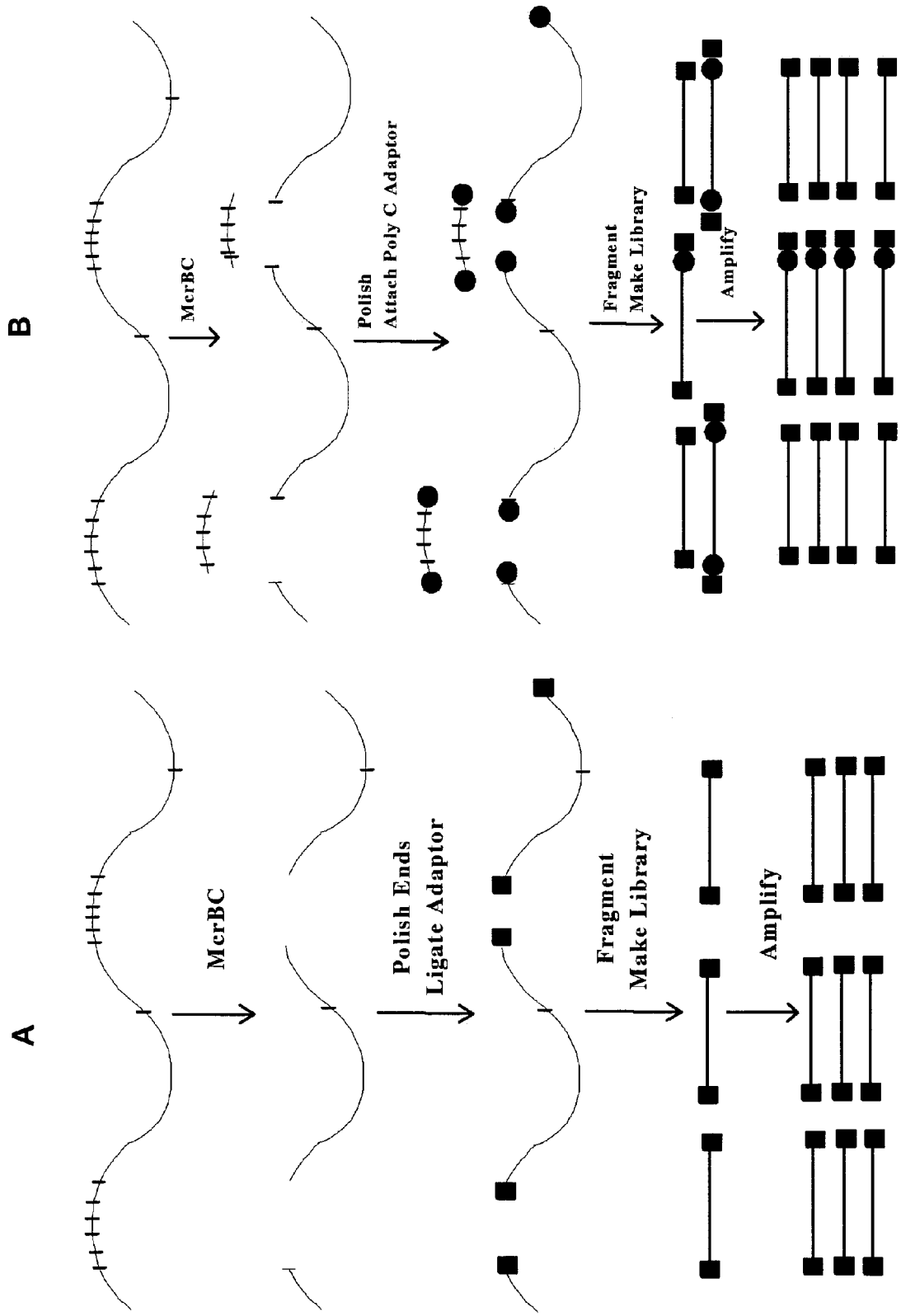
FIG. 29 depicts two methods for library preparation and amplification of hypomethylated regions of DNA based on use of the methylation-specific endonuclease McrBC.

Utilization of the Methylation-Specific Enzyme McrBc and Sub Genome Amplification to Detect Regions of Hypomethylation One important aspect of progression of many cancers and diseases is the hypomethylation of certain regions of DNA leading to the over-expression of tumor promoters. It is important to be able to detect areas where methylation inhibition has been lost in order to understand cancer and disease progression, and to develop diagnostic tools for the identification of this progression as well as treatment options for these patients, for example. FIG. 29A depicts a method for creating and amplifying libraries that are specific for hypomethylation. Test and control DNA samples are digested with McrBC to generate cleavage of hypermethylated regions. Following cleavage, random fragmentation is performed by chemical or mechanical means and libraries are created as previously described in Examples 13 and 14. The resulting amplicons from hypomethylated DNA regions are amplified and the resulting amplification products can be analyzed by PCR to detect specific sequences of interest or by hybridization to large numbers of sequences, for instance on a microarray, for discovery or diagnostic purposes, for example.

In an alternative embodiment (FIG. 29B), an additional step involving the polishing of the ends of the DNA following McrBC cleavage and ligation of adaptors comprising a Poly C sequence (10-40 bp) is performed. A universal adaptor sequence is ligated during library preparation following random fragmentation. This step allows the blockage of amplification of DNA fragments from hypermethylated regions that comprise the Poly C adaptor at both ends of the amplicons.

Example 16

Figure 30:
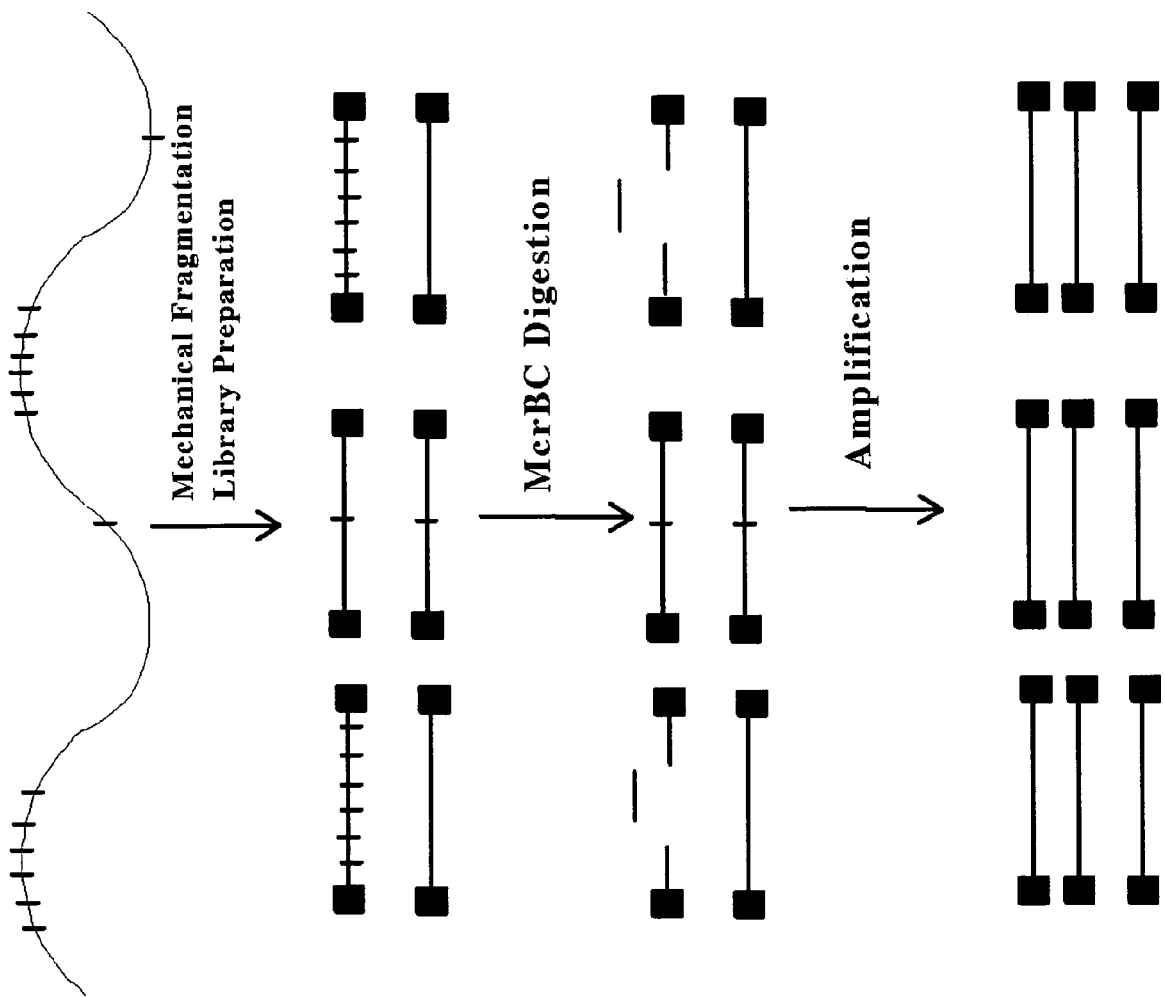
FIG. 30 demonstrates a second method for the amplification of hypomethylated regions of DNA through use of the methylation-specific endonuclease McrBC. Genomic DNA is randomly fragmented by mechanical means, and the resulting products are polished to produce blunt ends. Following polishing, universal adaptors are ligated to both ends of the molecules resulting in generation of an amplifiable library. The library is digested with McrBC, which results in cleavage of all amplicons that contain 2 or more methylated cytosines. The intact amplicons within the library are then amplified with the universal primer. The resulting products represent regions of hypomethylation within the genome and can be analyzed by PCR amplification for specific sequences, or by genome-wide hybridization for discovery and/or diagnostic purposes.

Utilization of Library Generation by Mechanical Fragmentation, the Methylation-Specific Enzyme McrBc, and Sub Genome Amplification to Detect Regions of Hypomethylation A second method for the preparation of hypomethylation-specific libraries involves the use of McrBC to cleave library amplicons that are methylated (FIG. 30). In a specific embodiment, DNA is fragmented mechanically and libraries are created by polishing the ends and attaching universal adaptors. Following library preparation, methylated amplicons is digested with the methylation-specific restriction endonuclease McrBC. This digestion cleaves all library molecules that contain 2 or more methylated cytosines, and this digestion will result in the loss of the ability to amplify these amplicons. Amplification of the remaining molecules will result in selection of only those amplicons that are hypomethylated. The resulting amplification products can be analyzed by PCR to detect specific sequences of interest or by hybridization to large numbers of sequences, for instance on a microarray, for discovery or diagnostic purposes.

Example 17

Figure 31:
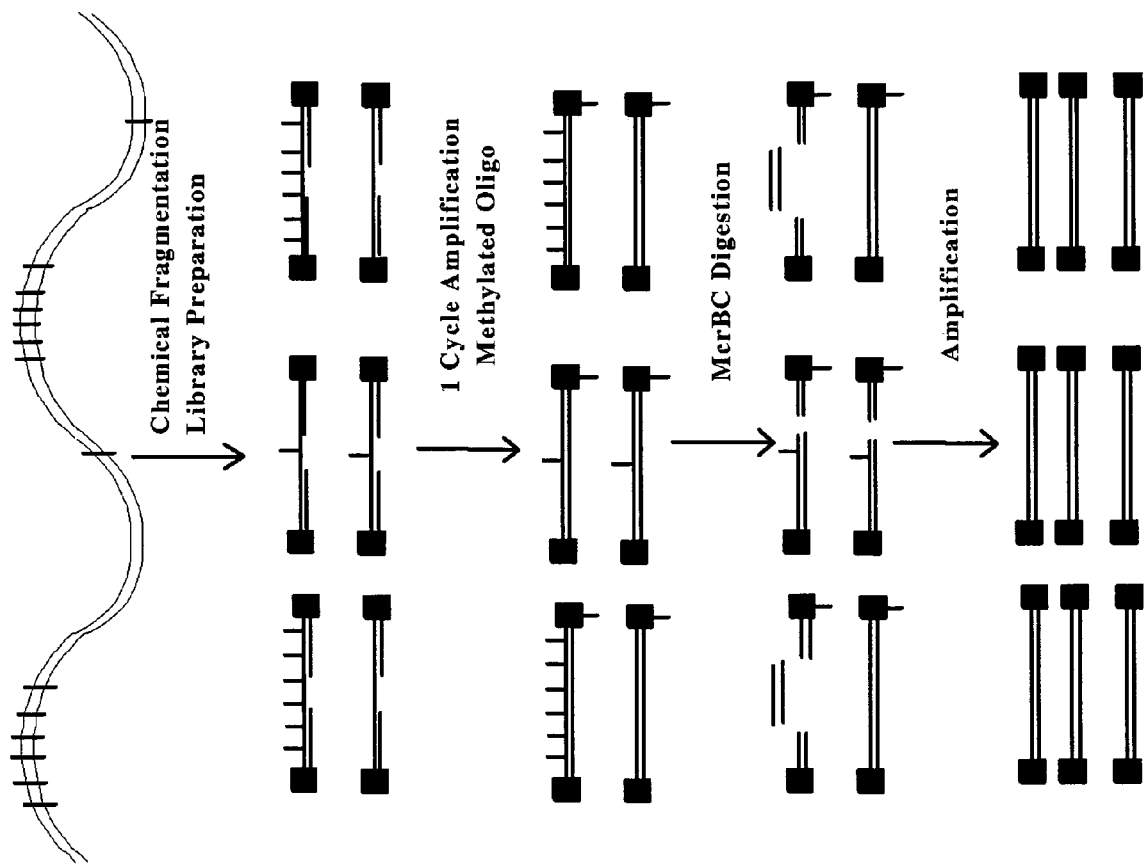
FIG. 31 demonstrates another method for the amplification of hypomethylated regions of DNA through use of the methylation-specific endonuclease McrBC. Genomic DNA is randomly fragmented by chemical means and the resulting single-stranded DNA fragments are converted into fragments with double-stranded blunt ends by a combination fill-in and polishing reaction. Universal adaptors are attached to the ends of the fragments. Following ligation, a single cycle of PCR with a thermolabile DNA polymerase is performed with a universal oligo containing a single methyl group. The resulting amplicons are digested with the methylation-specific endonuclease McrBC that will result in cleavage of all amplicons containing one or more methyl cytosines on the original parent strand. After digestion, intact strands are amplified using universal primers. The resulting products represent regions of hypomethylation within the genome and can be analyzed by PCR amplification for specific sequences, or by genome-wide hybridization for discovery or diagnostic purposes. A methylated oligo is utilized for the single amplification cycle if McrBC is only able to cleave molecules that have methyl groups in a trans orientation. An alternative method utilizing a non-methylated oligo for the single PCR step can be used if McrBC is able to cleave molecules that are methylated only in a cis orientation.

Utilization of Library Preparation by Chemical Fragmentation, the Methylation-Specific Enzyme McrBc, and Sub Genome Amplification to Detect Regions of Hypomethylation A third method for the generation of hypomethylation-specific libraries involves library preparation following chemical fragmentation and digestion with McrBC followed by a single cycle of PCR. In a specific embodiment, DNA is fragmented chemically and libraries are created by a fill-in reaction, polishing of the resulting ends, and attaching universal adaptors. One cycle of PCR is performed with either a methylated or non-methylated primer to create a double stranded intact molecule. It is unclear at this time whether McrBC requires 2 methyl groups on opposite strands (trans), or if 2 methyl groups on the same strand (cis) are capable of inducing cleavage. If methyl groups are required to be in trans, then a methylated oligo will be used for the 1 cycle PCR reaction. However, a non-methylated oligo is used if the cis orientation is sufficient for McrBC-induced cleavage. Following library preparation, methylated amplicons are digested with the methylation-specific restriction endonuclease McrBC. This digestion will cleave all library molecules that contain either 1 (trans) or more than 2 (cis) methylated cytosines and results in the loss of the ability to amplify these amplicons. Amplification of the remaining molecules results in selection of only those amplicons that are hypomethylated. The resulting amplification products can be analyzed by PCR to detect specific sequences of interest or by hybridization to large numbers of sequences, for instance on a microarray, for discovery or diagnostic purposes. A figure depicting use of a methylated oligo for the single cycle PCR reaction is illustrated in FIG. 31.

Example 18

Detection of DNA Methylation in Cancer Cells Using Methylation-Sensitive Restriction Endonucleases and Whole Genome Amplification (WGA)

This example describes a method for the preparation of libraries where only methylated promoters are present in the amplified material. An outline of this procedure is depicted in FIGS. 33A, 33B, and 33C. DNA comprising a promoter CpG island is digested with a methylation-sensitive restriction endonuclease (FIG. 33A) or a mixture of several (5 or more) methylation-sensitive restriction endonucleases such as Aci I, Bst UI, Hha I, HinP 1, Hpa II, Hpy 99I, Ava I, Bce AI, Bsa HI, Bsi E1, and Hga I (FIGS. 33B and 33C). The spatial distribution of recognition sites for these nucleases in the human genome closely mimics the distribution of the CpG dinucleotides. Their density is very high in the CpG-rich promoter regions (FIGS. 33D and 33E) and some other CpG-rich regions (CpG islands) with unknown function.

The non-methylated CpG-rich regions, such as gene promoters in normal cells, are digested into small pieces, while the methylated CpG-rich regions, such as some gene promoters in cancer cells, is maintained intact. Following digestion, the DNA is converted into a library and amplified using the random priming strand displacement method described in U.S. patent application Ser. No. 10/795,667, filed Mar. 8, 2004, now U.S. Pat. No. 7,718,403. The promoter region is present within the amplified material only if it was methylated and protected from cleavage. The small fragments produced by digestion of a non-methylated promoter region are too small to serve as suitable template in the whole genome amplification protocol and are not amplified. Analysis of the products of amplification by PCR, microarray hybridization, probe hybridization and/or probe amplification will allow the determination of whether specific regions are methylated. Thus, a determination of the state of methylation of a specific promoter region can be determined by comparing a test sample, a negative control sample that is unmethylated, and a positive control sample that is heavily methylated.

There are several potential ways for assaying the amplified material for methylation status and a couple of these are depicted in FIGS. 34 and 35. A high throughput quantitative PCR method is illustrated in FIG. 34. Briefly, amplified material from control and test samples are each placed into 48 wells of a 96 well plate containing primer pairs for 48 specific promoter regions. Quantitative real-time PCR is performed, and the difference in the number of amplification cycles is indicative of methylation in the test sample. FIG. 35 illustrates how control and test samples can be hybridized to a microarray comprising promoter regions of interest. The control and test samples can be compared directly using a two color system. Control samples should have few or no spots, allowing the methylation status of the test sample to be determined based on the strength of the signal.

Example 19

Digestion of Genomic DNA with Methylation-Sensitive Restriction Enzymes Containing CpG Dinucleotide in their Four-Base Recognition Site This example describes the analysis of the average size of DNA fragments obtained after overnight digestion of genomic DNA with methylation-sensitive restriction enzymes with recognition sites comprising the CpG dinucleotide and no adenine or thymine Aliquots of 300 ng of pooled genomic DNA isolated by standard procedures from the peripheral blood of 20 healthy male donors were digested for 15 hours with Aci I, BstUI, HinP1 I, or Hpa II restriction endonucleases (New England Biolabs). Digestion reactions were carried out in 20 μl volumes containing 1× of the respective optimal reaction buffer for each enzyme (New England Biolabs), 300 ng of genomic DNA, and 10 units of restriction enzyme, for 15 hours at 37° C., or in the case of BstU I for 15 hours at 60° C. A blank control containing no restriction enzyme was also incubated for 15 hours at 60° C.

Figure 36:
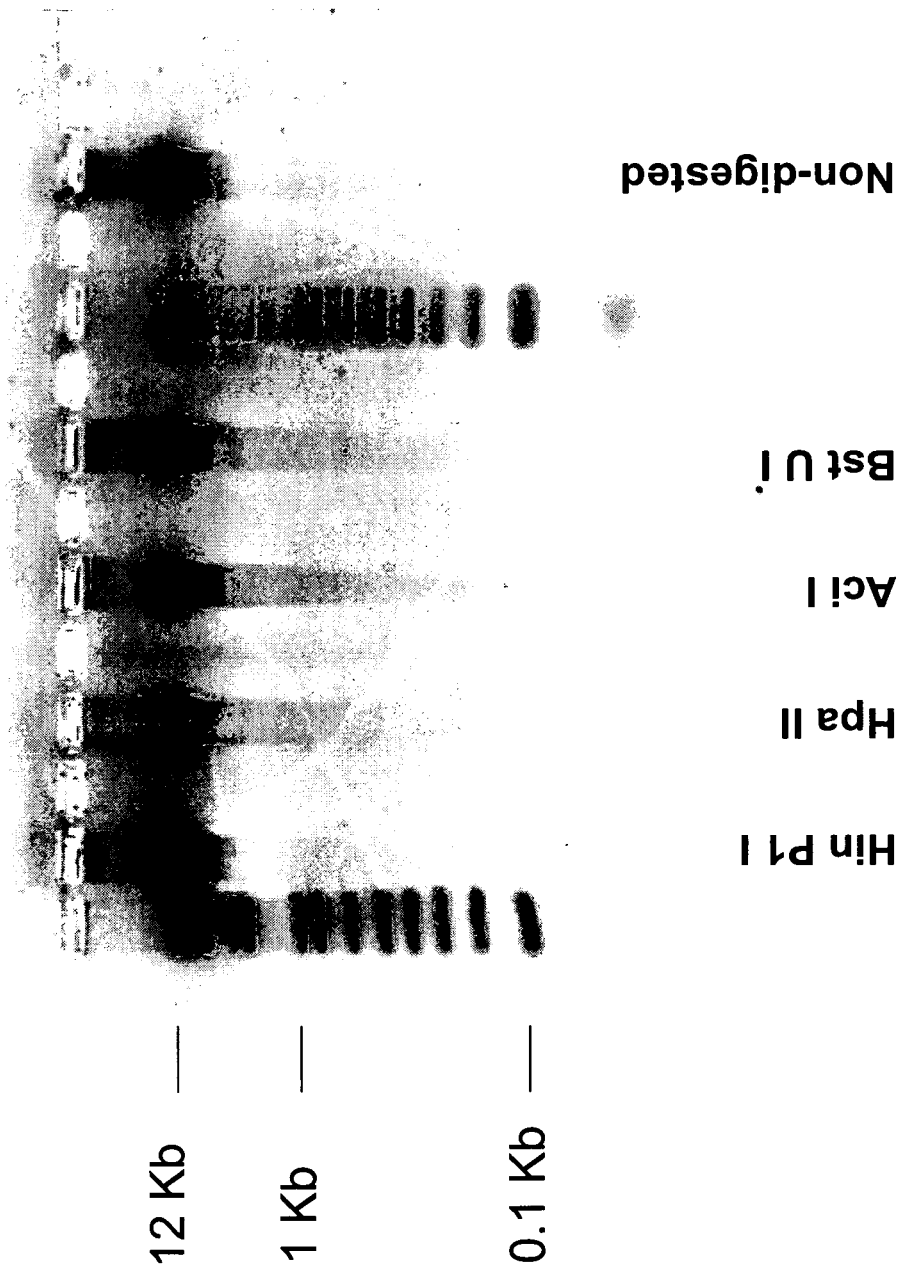
FIG. 36 illustrates the analysis of the average size of DNA fragments obtained after overnight digestion of genomic DNA with four methylation-sensitive restriction enzymes with 4-base recognition sites containing at least one CpG dinucleotide. Aliquots of 165 ng of digestion reactions are analyzed on 1% agarose gel after staining with SYBR Gold. Lanes 1 and 10 contain 1 Kb Plus DNA ladder (Invitrogen); Lanes: 3, 5, 7, 9, 11, 13, and 14 are blank; Lanes: 2, 4, 6, 8, and 12 are DNA digested with HinP1 I, HpaII, Aci I, BstUI, and non-digested control respectively.

FIG. 36 shows 165 ng aliquots of the digestion reactions analyzed on a 1% agarose gel after staining with SYBR Gold (Molecular Probes). As shown, even after overnight digestion the majority of the gDNA is still in the compression zone above 12 Kb. In several follow-up experiments, almost complete cleavage at CpG sites was demonstrated for all four enzymes, as is evident by the loss of amplification by primers flanking one or more CpG sites at different promoter regions after only 1 to 2 hours of cleavage (see Examples below). These results demonstrate that cleavage by restriction enzymes with four-base recognition sites that do not contain A or T is strongly biased due to (i) depletion of the CpG dinucleotide in the human genome, and (ii) methylation of non-island CpG sites known to be located mostly in repetitive DNA sequences.

Example 20

Methylation Analysis of P15, P16, and E-Cadherin Promoters Using Libraries Prepared by BstU I Digestion This example demonstrates the utility of libraries prepared from DNA digested with BstU I restriction enzyme by incorporating universal sequence using primers comprising the universal sequence at their 5'-end and a degenerate non-self-complementary sequence at their 3'-end in the presence of DNA polymerase with strand-displacement activity for the analysis of the methylation status of the exemplary promoter regions of p15, p16, and E-Cadherin genes.

Genomic DNA was isolated by standard procedures from the exemplary KG1-A leukemia cell line or from the peripheral blood of a pool of 20 healthy male donors. Digestion reactions were carried out in 50 µl volume containing 1× NEBuffer 2 (NEB), 50 ng DNA, and 10 units of BstU I (NEB), for 1 hour and 15 minutes at 60° C. Blank controls containing no restriction enzyme were also run in parallel. The DNA was precipitated with ethanol in the presence of 1.5 M ammonium acetate, washed with 75% ethanol, air dried, and resuspended in 50 µl of TE-L buffer.

Aliquots of 10 ng of each digested or non-digested DNA sample were randomly fragmented in TE-L buffer by heating at 95° C. for 4 minutes and subjecting them to the library synthesis protocol. The reaction mixtures contained 10 ng of fragmented DNA in 1× EcoPol buffer (NEB), 200 µM of each dNTP, 200 µM of 7-deaza-dGTP (Sigma), 4% DMSO, 360 ng of Single Stranded DNA Binding Protein (USB), and 1 µM of K(N)$_2$ primer (SEQ ID NO: 14) in a final volume of 14 µl. After denaturing for 2 minutes at 95° C., the samples were cooled to 24° C., and the reaction was initiated by adding 5 units of Klenow Exo– DNA polymerase (NEB). Samples were incubated at 24° C. for 1 hour. Reactions were then stopped by heating for 5 minutes at 75° C. The samples were further amplified by quantitative real-time PCR by transferring the entire reaction mixture of the library synthesis into a PCR reaction mixture containing final concentration of: 1× Titanium Taq reaction buffer (Clontech), 200 µM of each dNTP, 200 µM of 7-deaza-dGTP (Sigma) or 0.5 M betaine (See BRIEF DESCRIPTION OF THE DRAWINGS, FIGS. 37A, 37B, and 37C), 4% DMSO, 1: 100,000 dilutions of fluorescein calibration dye and SYBR Green I (Molecular Probes), and 5 units of Titanium Taq polymerase (Clontech) in a final volume of 75 ul. Amplifications were carried out for 15 cycles at 94° C. for 15 sec and 65° C. for 2 min on I-Cycler real-time PCR instrument (Bio-Rad). Amplified libraries were purified using the QIAQUICK® kit (Qiagen) and quantified by optical density.

Next, the presence of amplifiable promoter sequences containing one or more CpG sites as part of the BstU I recognition site in the amplified libraries was analyzed by quantitative real-time PCR using specific primers flanking such sites. The primer pairs were used as follows: p15 promoter—Primer pair #1—p15 SF upstream (SEQ ID NO:63) and p15 SB downstream (SEQ ID NO:64) amplifying a 73 bp fragment with 4 BstU I restriction sites, Primer pair #2—p15 Neg F upstream (SEQ ID NO:24), and p15 Neg B downstream (SEQ ID NO:25) amplifying a 595 bp fragment with 5 BstU I restriction sites; p16 promoter—Primer pair #1—p16 Nick F upstream (SEQ ID NO:48) and p16 Nick B downstream (SEQ ID NO:49) amplifying a 211 bp fragment with 1 BstU I restriction site, Primer pair #2—p16 LF upstream (SEQ ID NO:65), and p16 LB downstream (SEQ ID NO:66) amplifying a 399 bp fragment with 3 BstU I restriction sites; E-Cadherin promoter—Primer pair #1-E-Cad Neg F upstream (SEQ ID NO:28) and E-Cad Neg B downstream (SEQ ID NO:29) amplifying a 223 bp fragment with 2 BstU I restriction sites, Primer pair #2-E-Cad Neg F upstream (SEQ ID NO:28), and E-Cad LB downstream (SEQ ID NO:67) amplifying a 336 bp fragment with 2 BstU I restriction sites. Aliquots of 20 ng of amplified library material were used in reaction mixtures containing 1× Titanium Taq reaction buffer (Clontech), 200 µM of each dNTP, 4% DMSO, 0.5 M betaine (Sigma), fluorescein calibration dye (1:100,000) and SYBR Green I (1:100,000), 200 nM each forward and reverse primer, and 5 units of Titanium Taq polymerase (Clontech) in a final volume of 30 µl at 95° C. for 2 minute followed by 50 cycles at 94° C. for 20 seconds, and 68° C. for 1 minute.

Figure 37A:
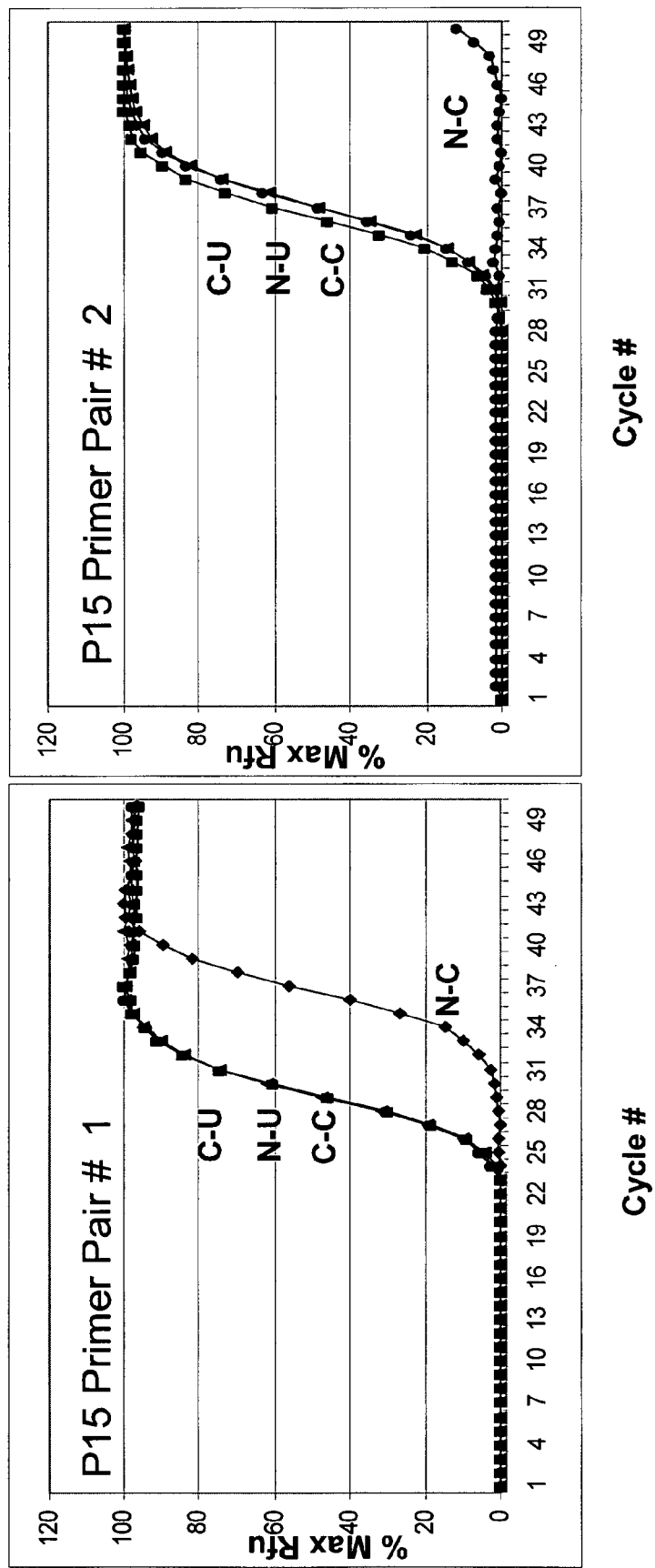
FIGS. 37A, 37B, and 37C demonstrate the real-time PCR amplification of specific promoter sequences from the CpG islands of the exemplary p15, p16, and E-Cadherin promoters in normal and cancer cells from libraries prepared by restriction digestion with BstU I (or control undigested DNA) followed by incorporation of universal sequence and subsequent amplification. The following exemplary primer pairs were used: p15 promoter region—primer pair #1—p15 SF upstream (SEQ ID NO:63) and p15 SB downstream (SEQ ID NO:64), primer pair #2—p15 Neg F upstream (SEQ ID NO:24), and p15 Neg B downstream (SEQ ID NO:25); p16 promoter region-primer pair #1—p16 Nick F upstream (SEQ ID NO:48) and p16 Nick B downstream (SEQ ID NO:49), primer pair #2—p16 LF upstream (SEQ ID NO:65), and p16 LB downstream (SEQ ID NO:66); E-Cadherin promoter region—primer pair #1-E-Cad Neg F upstream (SEQ ID NO:28) and E-Cad Neg B downstream (SEQ ID NO:29), and primer pair #2-E-Cad Neg F upstream (SEQ ID NO:28), and E-Cad LB downstream (SEQ ID NO:67). Four percent of dimethyl sulfoxide (DMSO) was included in all steps of the protocol. In addition, 7-deaza-dGTP was added at a final concentration of 200 µM in the library preparation (incorporation of universal sequence) step of all samples as well as in the library amplification step of all samples except the subset amplified with primer pair #1 of the p16 promoter (FIG. 37B). This set was supplemented with 0.5 M betaine instead. The specific sequence amplification of the p16 promoter with primer pair #2 (FIG. 34 B) and of the E-Cadherin promoter with both primer pairs (FIG. 37C) was done in the presence of an additional 0.5 M betaine. The exemplary PCR conditions are detailed in Example 20.
Figure 37B:
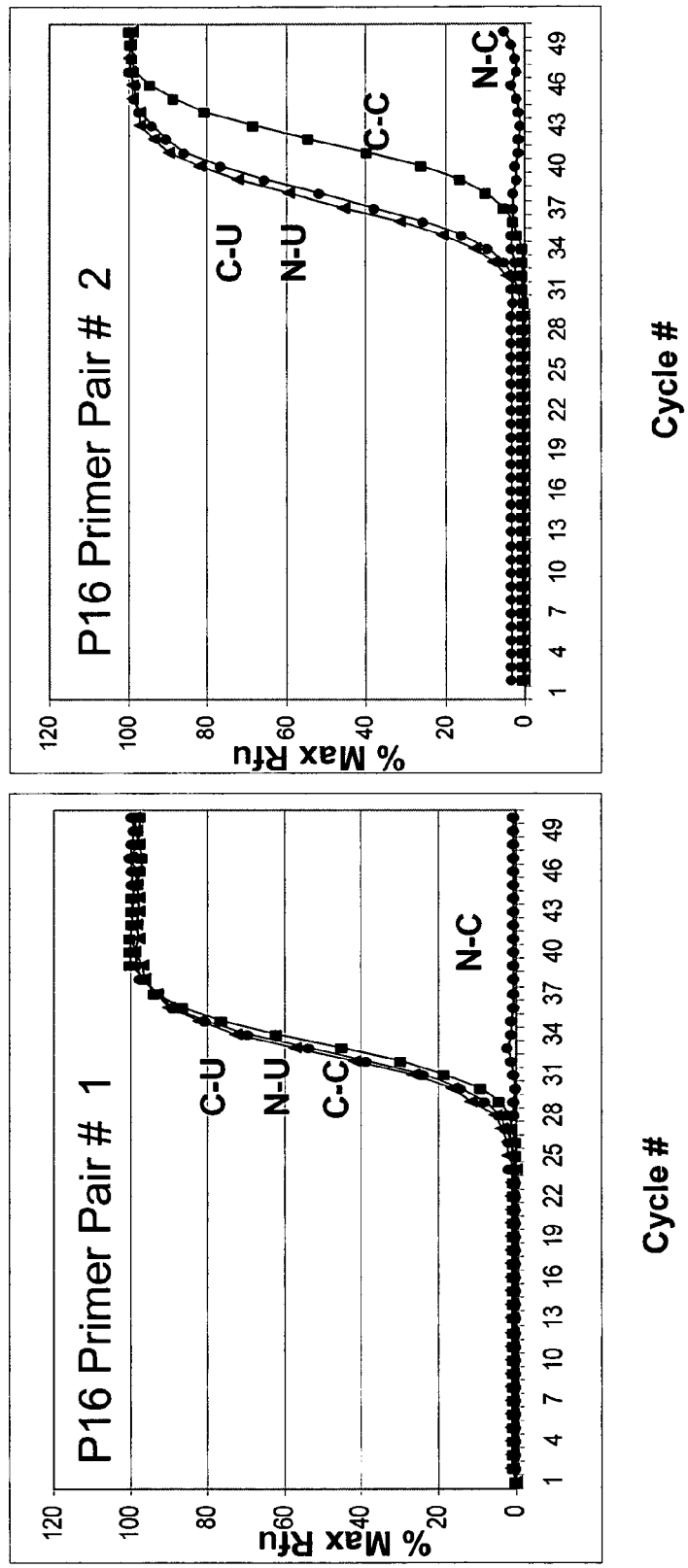
Figure 37C:
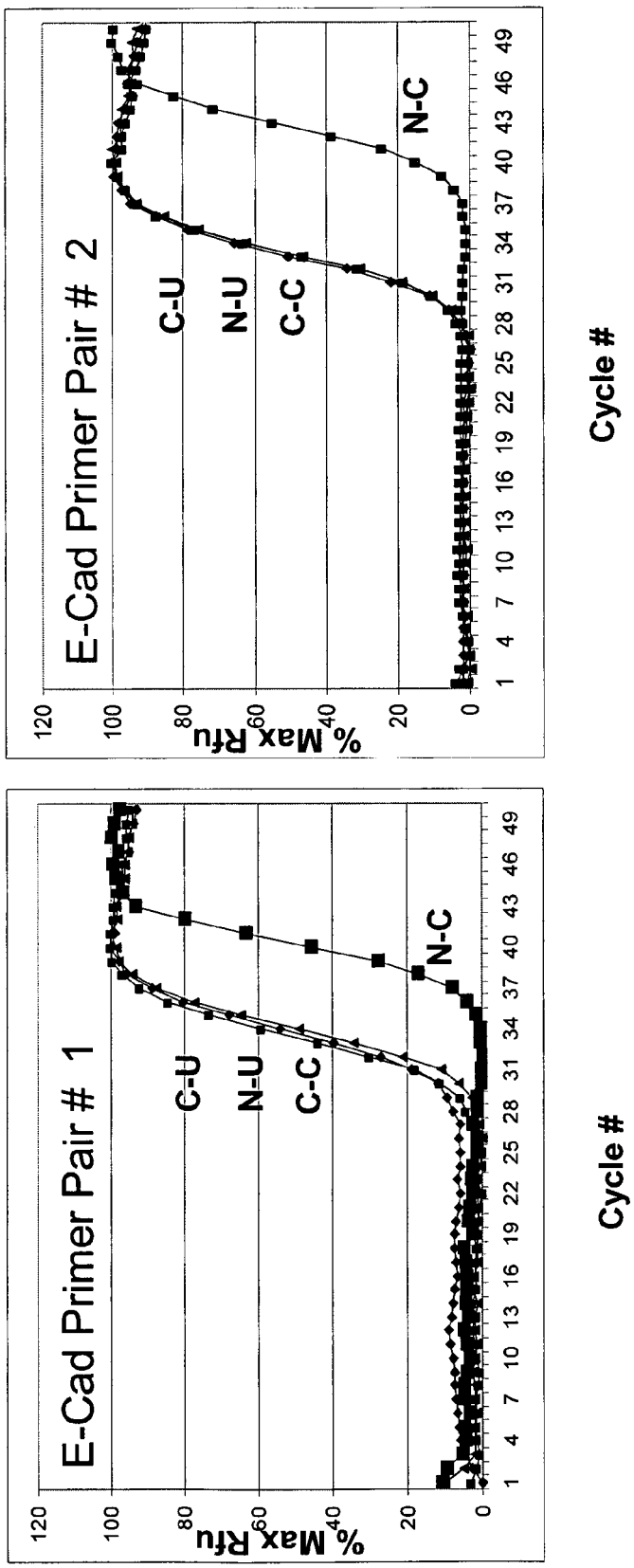

FIGS. 37A, 37B, and 37C show the amplification of promoter sequences from the CpG islands of p15, p16, and E-Cadherin promoters in normal and cancer cells from 20 ng of library DNA. For both primer pairs, in all three promoter sites tested, a shift of between 7 and over 20 cycles was observed between libraries prepared from digested versus non-digested non-methylated control DNA. On the other hand, for all primer pairs except one (p16 promoter, primer pair #2, FIG. 37B), there was no difference between libraries made from digested and non-digested cancer DNA. However, as compared to non-methylated DNA this difference was at least an order of magnitude (more than 10 cycles) smaller. The reason for the shift in the cancer DNA sample is not clear, but in a specific embodiment it is due to methylation pattern heterogeneity of the cancer cell line as a result of delayed methylation in actively replicating non-synchronous cell population. The background amplification from digested control (non-methylated) DNA in some primer sets is due to primer-dimer formation as verified by agarose gel analysis but in other cases corresponds to the expected amplicon that can be attributed to incomplete restriction digestion. Overall, in all three promoters the difference between methylated and non-methylated DNA is more than sufficient to clearly distinguish methylated from non-methylated sequences.

This example demonstrates that, as predicted, during the process of library preparation and subsequent amplification only those DNA molecules that are protected by methylation will amplify, whereas DNA molecules that are non-methylated will be digested into small fragments, will not be efficiently primed, and thus will not be present in the library. Therefore, the presence of a specific site in the final amplified product will indicate that the CpG comprised in the methylation-sensitive restriction site was methylated in the original DNA molecule. In addition to real-time PCR, analysis of the presence of specific methylated sites can be done by LCR, ligation-mediated PCR, probe hybridization, probe amplification, microarray hybridization, any suitable method in the art, or a combination thereof, for example.

Example 21

Methylation Analysis of GSTP-1 Promoter Using Libraries Prepared by Aci I or BstU I Digestion This example demonstrates the utility of libraries prepared from DNA digested with Aci I restriction enzyme for the analysis of the methylation status of the exemplary promoter region of the GSTP-1 gene in prostate cancer cell line and clinical samples from patients having prostate adenocarcinoma.

Genomic DNA was isolated by standard procedures from the exemplary RWPE prostate cancer cell line, or from 3 clinical isolates of prostate adenocarcinoma. Digestion reactions were carried out in 50 μl volume containing 1× NEBuffer 3 (NEB), 50 ng DNA, and 10 units of Aci I (NEB), for 4 hours at 37° C. Blank controls containing no restriction enzyme were also run in parallel. The DNA was precipitated with ethanol in the presence of 1.5 M ammonium acetate, washed with 75% ethanol, air dried, and resuspended in 20 μl of TE-L buffer.

Aliquots of 25 ng of each digested or non-digested DNA sample were randomly fragmented in TE-L buffer by heating at 95° C. for 4 minutes and subjected to library preparation protocol. The reaction mixtures comprised 25 ng of fragmented DNA in 1× EcoPol buffer (NEB), 200 μM of each dNTP, 200 μM of 7-deaza-dGTP (Sigma), 4% DMSO, 360 ng of Single Stranded DNA Binding Protein (USB), and 1 μM of $K(N)_2$ primer (SEQ ID NO: 14) in a final volume of 14 μl. After denaturing for 2 minutes at 95° C., the samples were cooled to 24° C., and the reaction was initiated by adding 5 units of Klenow Exo– DNA polymerase (NEB). Samples were incubated at 24° C. for 1 hour. Reactions were then stopped by heating for 5 minutes at 75° C. Aliquots representing 10 ng of genomic DNA were further amplified by quantitative real-time PCR in a reaction mixtures containing final concentration of: 1× Titanium Taq reaction buffer (Clontech), 200 μM of each dNTP, 200 μM of 7-deaza-dGTP, 4% DMSO, 1:100,000× dilutions of fluorescein calibration dye and SYBR Green I (Molecular Probes), and 5 units of Titanium Taq polymerase (Clontech) in a final volume of 75 ul. Amplifications were carried out for 15 cycles at 94° C. for 15 seconds, and 65° C. for 2 minutes on an I-Cycler real-time PCR instrument (Bio-Rad). Amplified libraries were purified using the QIAQUICK® kit (Qiagen) and quantified by optical density.

Next, the presence of a specific but exemplary GSTP-1 promoter sequence comprising two CpG sites as part of Aci I recognition site was analyzed in the amplified libraries by quantitative real-time PCR using specific primers flanking the CpG sites. The primers were GSTP-1 Neg F upstream (SEQ ID NO: 30) and GSTP1 Neg B2 downstream (SEQ ID NO: 68), amplifying a 200 bp promoter region. Aliquots of 20 ng of amplified library material were used in reaction mixtures comprising 1× Titanium Taq reaction buffer (Clontech), 200 μM of each dNTP, 4% DMSO, 0.5 M betaine (Sigma), fluorescein calibration dye (1:100,000) and SYBR Green I (1:100,000), 200 nM each forward and reverse primer, and 5 units of Titanium Taq polymerase (Clontech) in a final volume of 30 μl at 95° C. for 2 minutes followed by 50 cycles at 94° C. for 15 seconds and 68° C. for 1 minute.

Figure 38:
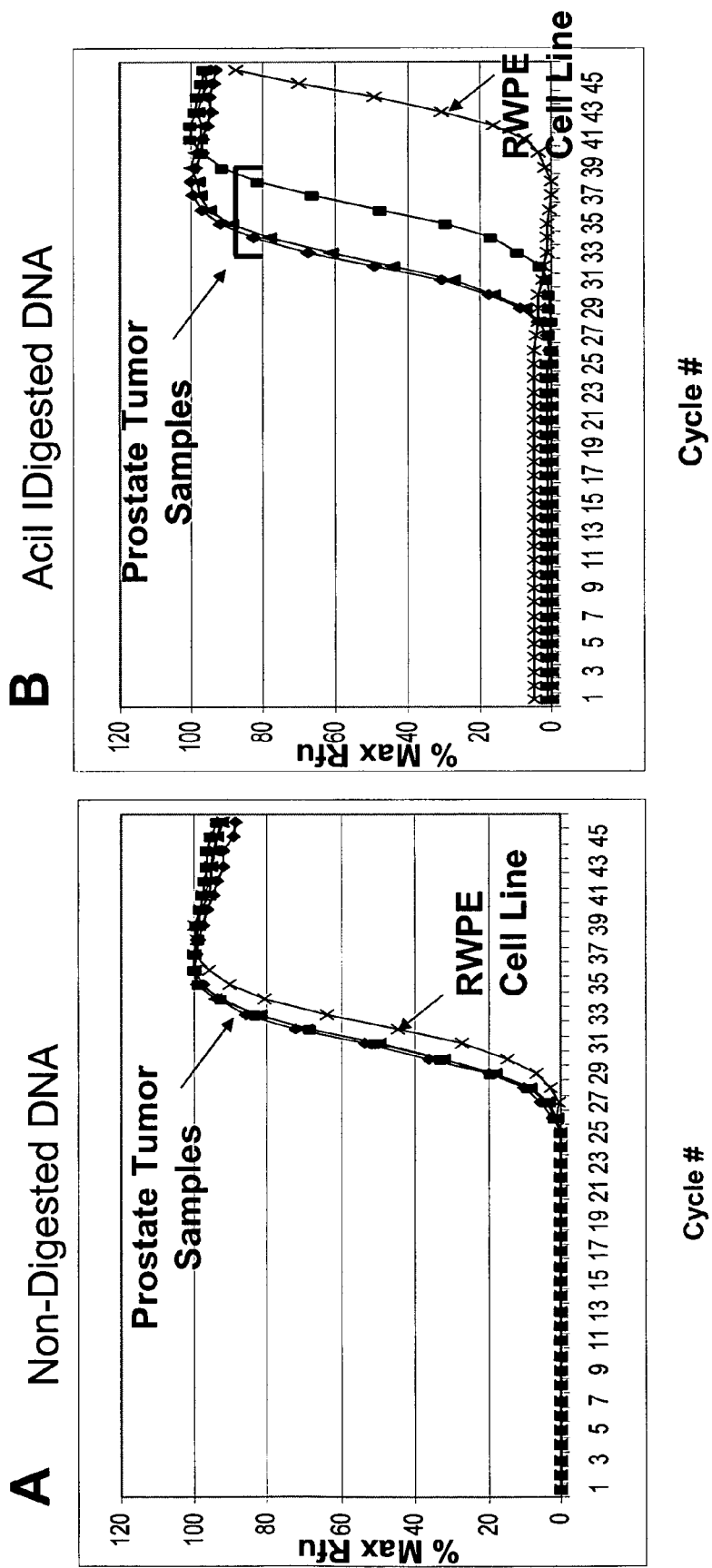
FIGS. 38A and 38B show the amplification by real-time PCR of a specific promoter sequence from the CpG island of the GSTP-1 gene of 3 clinical isolates of prostate adenocarcinoma and from RWPE prostate cancer cell line in primary whole Methylome libraries prepared from control undigested DNA (FIG. 38A), or from DNA digested with Aci I (FIG. 38B), followed by incorporation of universal sequence and subsequent amplification, as described in FIG. 33. The primers were: GSTP-1 Neg F upstream (SEQ ID NO:30) and GSTP1 Neg B2 downstream (SEQ ID NO:68) amplifying a 200 bp promoter region. Details of the PCR conditions are described in Example 21.

FIG. 38 shows the real-time PCR methylation analysis of the studied GSTP-1 promoter region in prostate samples. Two of the clinical samples showed complete methylation of the GSTP-1 promoter site, as evident by the virtually identical amplification curves from libraries of Aci I-digested and undigested DNA. The third clinical sample had a shift of about 4 cycles that in a specific embodiment the present inventors attribute to contamination with non-malignant cells. On the other hand, the RPWE prostate cell was completely unmethylated for this promoter region as evidenced by a shift of over 12 cycles (>4,000 fold difference) between digested and undigested DNA. A similar difference was found in a separate experiment for libraries prepared from control unmethylated DNA from the peripheral blood of healthy donors (results not shown).

Example 22

Creation of a Secondary Methylome Library Enriched in Methylated Promoter Regions by Cleavage of a Primary Methylome Library with Restriction Endonucleases and Ligation of Multiple Adaptors A method for the generation of secondary methylome libraries that are enriched in methylated promoter regions involves restriction endonuclease cleavage of the amplification products from primary methylome libraries followed by ligation of multiple adaptors and amplification of the resulting products. This method is illustrated in FIGS. 43A and 43B. Following amplification of a primary Methylome library, all methylation-sensitive restriction endonuclease sites that were methylated in the original DNA are converted to unmethylated DNA in the amplified products. These sites can be subsequently cleaved with the same enzyme used during library creation (FIG. 43A). When a primary Methylome library is prepared by using a mixture of several (5 or more) methylation-sensitive restriction enzymes, the secondary library can be prepared by mixing components together, ligating adaptors, and amplifying the products of several individual restriction digests of the primary Methylome library using the same restriction endonucleases that have been utilized in the nuclease cocktail (FIG. 43B).

Ligation of two or more adaptors comprising overhangs complementary to the resulting cleavage fragments can be ligated with high efficiency. Subsequent amplification of the ligation products results in amplification of only fragments of DNA between two methylated cleavage sites. These molecules can be analyzed by microarray hybridization, PCR analysis, probe amplification, probe hybridization, or other methods known in the art in order to determine the methylation status of the original DNA molecule (Example 18, FIG. 34 and FIG. 35), for example. Sequencing of these products can provide a tool for discovering regions of methylation not previously characterized, as no a priori knowledge of the sequences is required and the reduced complexity of the enriched secondary library allows analysis of a small number of methylated regions.

In a particular embodiment, a one-step library preparation process utilizing a dU-Hairpin Adaptor method described in Example 33, 38, and 39 can be used for preparation of secondary Methylome libraries. In this case, two hairpin oligonucleotides with different sequence should be used to avoid the PCR suppression effect that is known to inhibit amplification of very short DNA amplicons with one universal sequence at the end.

Example 23

Analysis of Secondary Methylome Libraries by Capillary Electrophoresis

A method for the analysis of secondary methylome libraries is based on the reduced complexity of these libraries and involves the utilization of capillary electrophoresis. This method is illustrated in FIG. 44. Due to the fact that methylation-sensitive restriction endonucleases are mostly localized in CpG islands, the number of these sites in the genome is significantly lower than would be expected statistically. Thus, the complexity of the secondary methylome library is dependent on the number of methylated CpG islands present in the genome and the number of Hpa II restriction fragments present within these CpG islands. The number of restriction fragments in the secondary methylome library can be calculated by the formula $N=n \times (m-1)$, where n is the number of methylated CpG islands and m is the average number of restriction sites per CpG island. For example, if 1% of the 30,000 CpG islands in the genome are methylated in a particular sample, and there is an average of 5 Hpa II sites per CpG island, then there would be 1,200 restriction fragments contained in the secondary methylome library. If the amplification of the secondary methylome library is performed with the 16 combinations of 4 possible A and B oligos containing a single selecting 3'-nucleotide, then each amplification would contain 75 fragments. These 75 fragments can be resolved by capillary electrophoresis. Further simplification could be achieved by using 64 amplifications, wherein one of the oligos contains two selecting 3'-nucleotides instead of one, resulting in 19 fragments per amplification. This analysis technique allows a genome-wide screening of CpG Islands for methylation status without the development of specific tests for each CpG Island contained in the genome. Sequencing of specific fragments produced within each amplification reaction will result in the identification of important regions of methylation without a priori knowledge of the importance of those regions.

Example 24

Figure 45A:
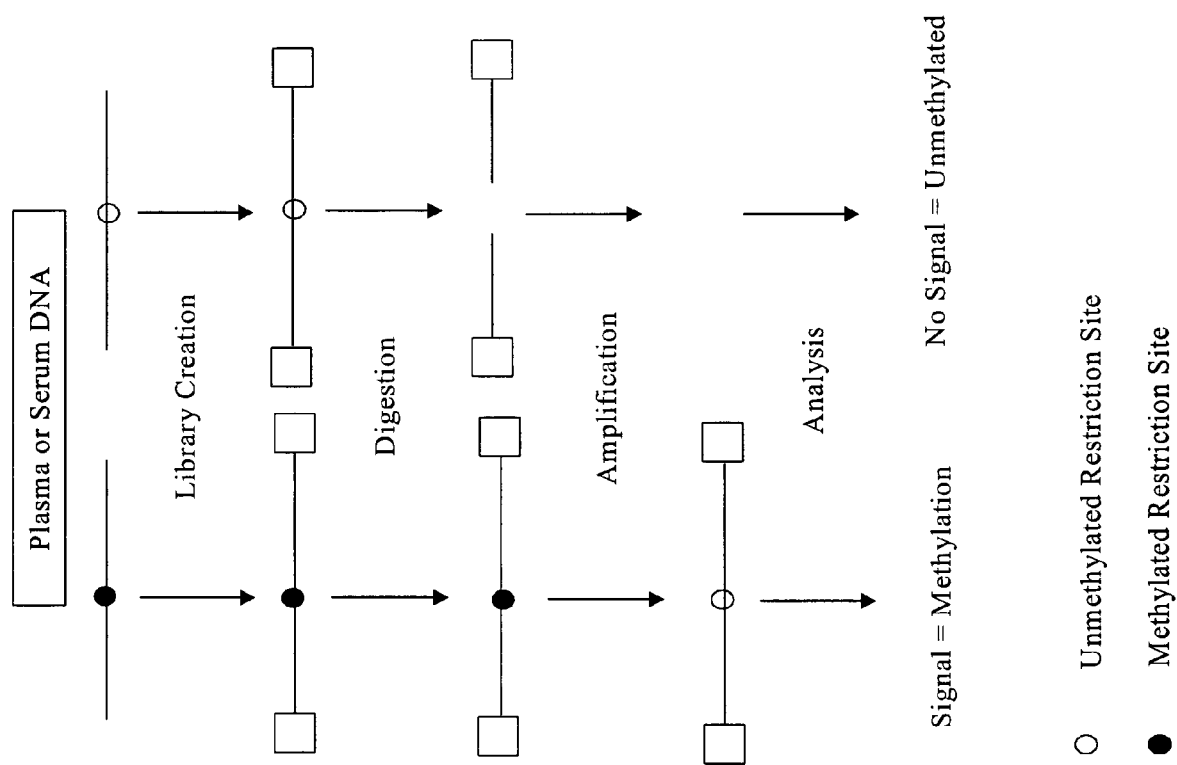
FIGS. 45A, 45B, and 45C demonstrate a method for the synthesis and amplification of methylation specific libraries from the exemplary serum and plasma DNA. The small size (200 bp-3 kb) of DNA extracted from serum and plasma allows the direct attachment of adaptors to these molecules (U.S. patent application Ser. No. 10/797,333, filed Mar. 8, 2004, published as U.S. Patent Application Publication No.: 2004/0209299 and is now abandoned incorporated by reference herein in its entirety). Digestion of the resulting library with a methylation-sensitive restriction endonuclease (FIG. 45A) results in cleavage of all molecules that contain an unmethylated restriction site. PCR amplification following digestion results in amplification of those molecules containing a methylated restriction site (resistant to cleavage), as well as molecules that do not contain the restriction site. The digested molecules that contained an unmethylated restriction site will not be able to serve as a template during PCR with universal primer. Digestion of the resulting library with a mixture of multiple restriction enzymes (such as, for example, 5 or more) (FIGS. 45B and 45C) yields increased cleavage efficiency of molecules that contain several unmethylated CpG sites that coincide with restriction sites. The density of such restriction sites within the CpG-rich promoter regions is extremely high (see FIGS. 33D 33E) and can exceed 50 sites per 100 base pairs. PCR library amplification following digestion results in amplification of only those molecules that contain methylated restriction sites, as well as molecules that do not contain the restriction site. The digested molecules that contained an unmethylated restriction site or especially a group of unmethylated restriction sites will not survive the cleavage step in tact and will not serve as a template during amplification. The resulting products can be analyzed by PCR, microarray hybridization, probe assay, or other methods known to the art, for example. Positive detection of signal indicates methylation in the starting sample.
Figure 45B:
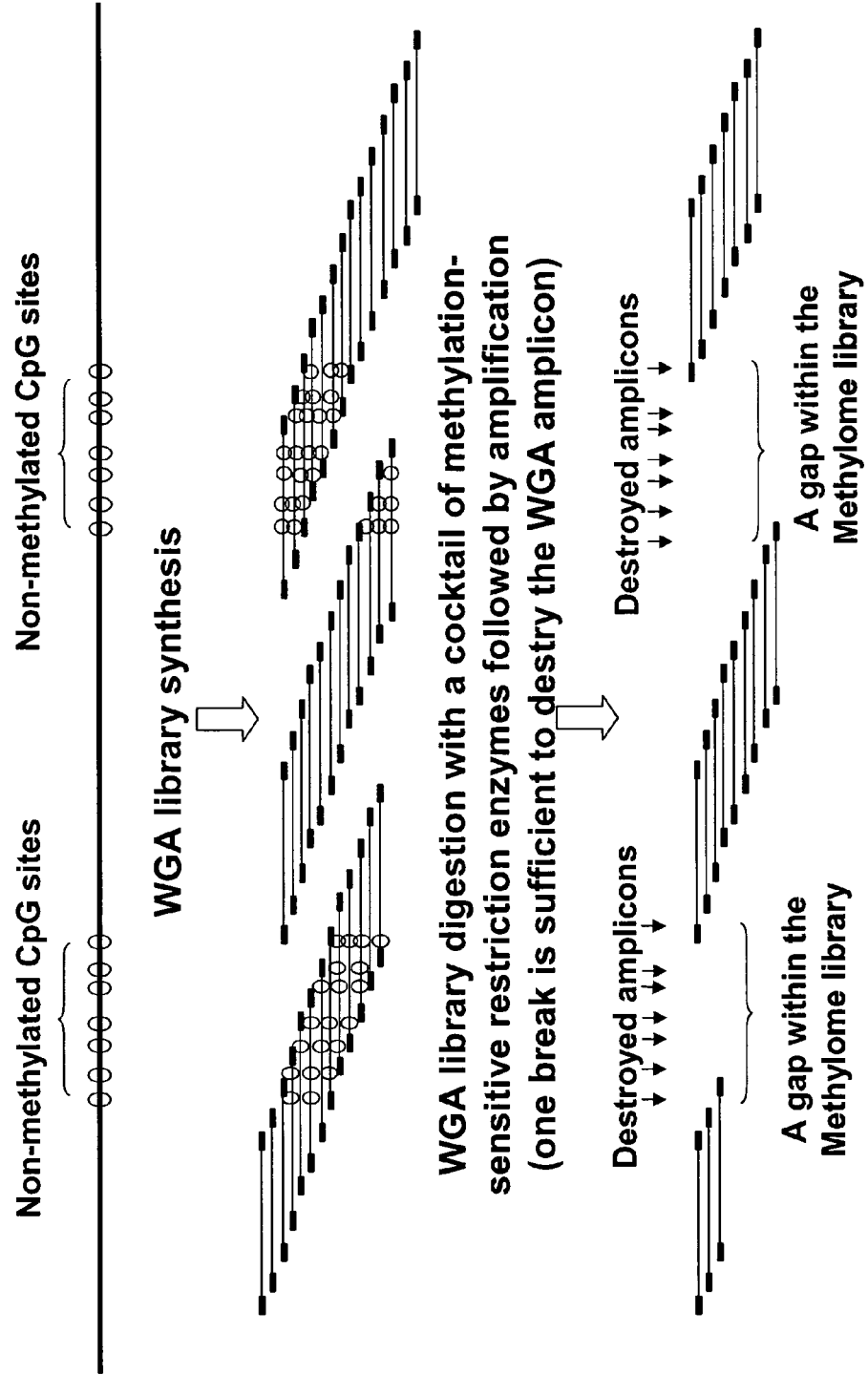
Figure 45C:
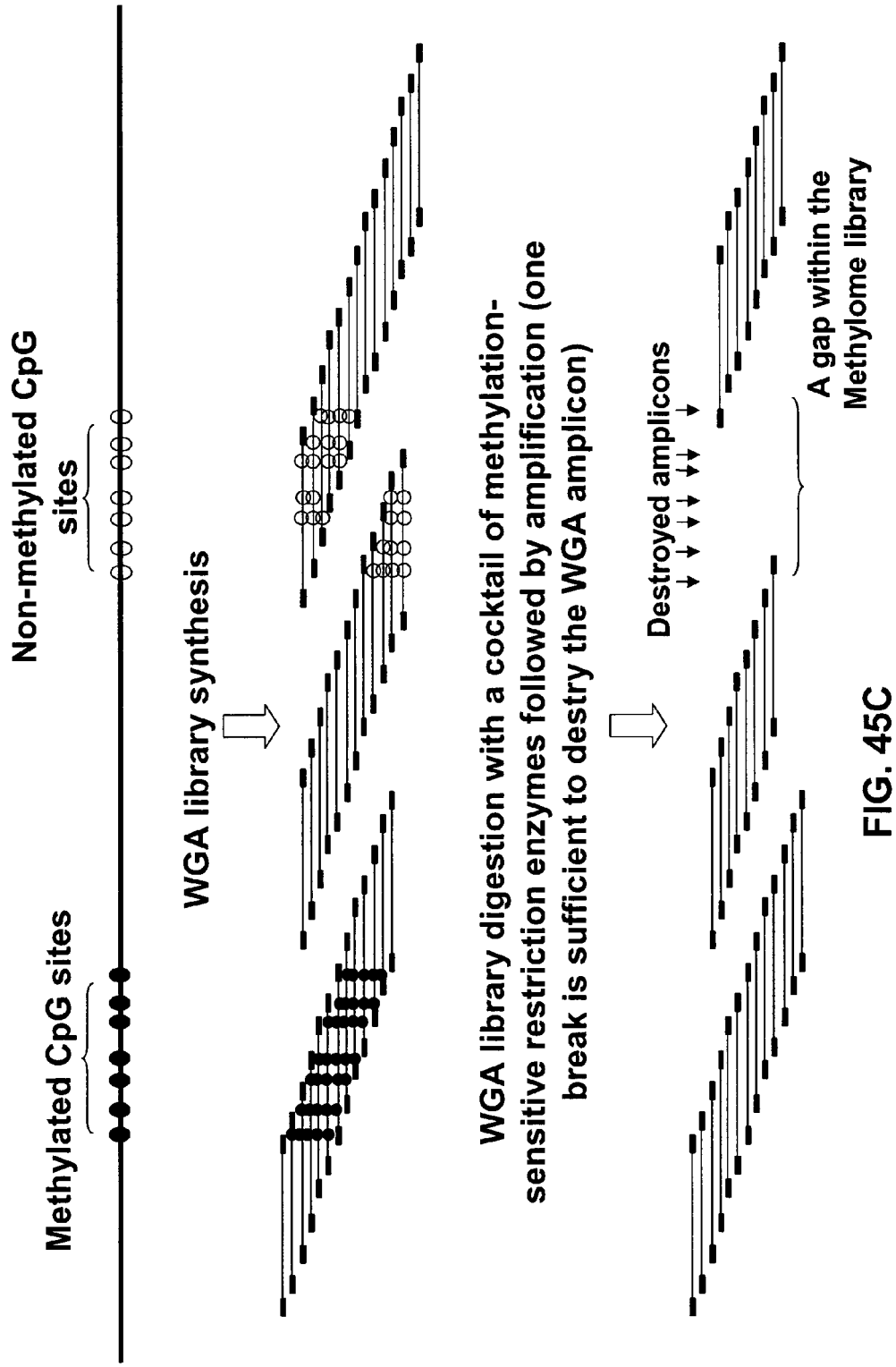

Creation of Methylation Specific Libraries from Serum, Plasma and Urine DNA by Cleavage with Methylation-Sensitive Restriction Endonucleases This method describes how a primary methylome library can be created from serum, plasma and urine DNA. An outline of this method is illustrated in FIG. 45. DNA isolated from serum, plasma and urine can be converted into an amplifiable library by ligation of adaptors (U.S. patent application Ser. No. 10/797,333, filed Mar. 8, 2004, published as U.S. Patent Application Publication No.: 2004/0209299 and is now abandoned). The molecules in this library range in size from 200 bp up to 1 to 2 kb, which are readily amplified by PCR. Furthermore, ligation of the adaptors does not result in any changes in the methylation pattern of the original DNA. Thus, the library molecules can be digested with a methylation sensitive restriction endonuclease (FIG. 45A) or a mixture of several (5 and more) methylation sensitive restriction endonucleases (FIGS. 45B and 45C). Any sites and groups of sites that are methylated, for example, hypermethylated gene promoter regions in cancer cells, will not be cleaved (FIG. 45C). Restriction site clusters that are usually non-methylated in the gene promoter regions of normal cells are cleaved at multiple sites such that the corresponding amplicons are not amplified (FIG. 45B). Amplification of the resulting library using PCR and universal primer will result in products that either comprise a methylated restriction site or a group of sites, or lack a restriction site. The resulting molecules can be analyzed by PCR, microarray hybridization, probe hybridization, probe amplification, or other methods known in the art, for example. Only those sites that were methylated in the original starting material are detected in the amplified library.

Example 25

Figure 46:
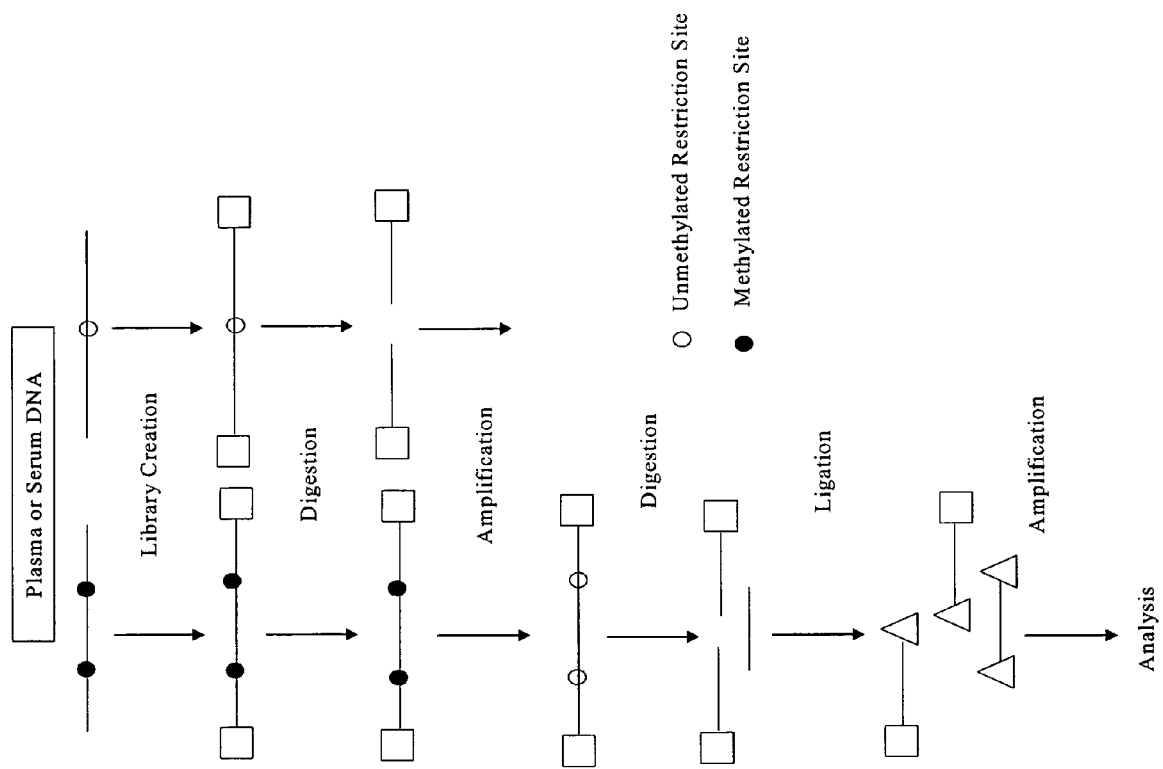
FIG. 46 illustrates a method for the synthesis and amplification of a secondary methylation library from serum and plasma DNA. The primary library is created in the same manner as illustrated in Example 24 and FIGS. 45A and 45B. Following amplification of the primary library with a primer containing a 5' $C_{10}$ sequence (SEQ ID NO: 38), all methylated sites from the original library are converted to unmethylated sites. These sites can then be digested with the same restriction endonuclease(s) utilized in the generation of the primary methylation library (see FIGS. 43A and 43B). Ligation of a second adaptor to the ends of the resulting cleavage fragments generates the secondary library. Amplification of this library with the $C_{10}$ oligo (SEQ ID NO: 38) and the second adaptor results in amplification of those molecules that contained a methylated restriction site in the original material. The molecules that did not contain a restriction site are not digested, ligated, or amplified in the secondary library. This results in enrichment of the specific methylated sequences in the secondary library, resulting in improved analysis of the amplification products.

Creation of Secondary Methylation Specific Libraries by Cleavage with the Same Methylation-Sensitive Restriction Endonucleases and Ligation of Additional Adaptors This example describes a method of generating a secondary methylome library from serum, plasma and urine DNA that comprises only those sequences adjacent to methylated restriction sites. Because methylated CpG islands usually have the largest concentration of such sites, they would be a major source for the secondary Methylome library amplicons. This library will not contain any fragments present in the amplified products from the primary library in Example 24 that lack the restriction site. An outline of this example is depicted in FIG. 46.

The primary library is created and amplified as in example 24 using PCR and a universal primer, and in a special case with the $T7-C_{10}$ primer (SEQ ID NO:36). This amplification results in the loss of methylation patterns from the original DNA. The previously methylated restriction sites are now susceptible to cleavage by the restriction endonuclease. Following digestion with the same restriction endonuclease, one or more adaptors can be ligated to the resulting fragments. When primary Methylome library is prepared by using a mixture of several (5 or more) methylation-sensitive restriction enzymes, the secondary library can be prepared by mixing together components, ligating adaptors, and amplifying the products of several individual restriction digests of the primary Methylome library using the same restriction endonucleases that have been utilized in the nuclease cocktail (FIG. 43B).

Ligation of two or more adaptors comprising overhangs complementary to the resulting cleavage fragments can be ligated with high efficiency. Subsequent amplification of the ligation products results in amplification of only fragments of DNA between two methylated cleavage sites. These molecules can be analyzed by microarray hybridization, PCR analysis, probe amplification, probe hybridization, or other methods known in the art in order to determine the methylation status of the original DNA molecule (Example 18, FIG. 34 and FIG. 35). Sequencing of these products can provide a tool for discovering regions of methylation not previously characterized, as no a priori knowledge of the sequences is required and the reduced complexity of the enriched secondary library allows analysis of a small number of methylated regions.

PCR amplification of this secondary methylome library with oligos based on these adaptors and the $C_{10}$ primer (SEQ ID NO:38) will lead to amplification of only those molecules that comprised a restriction endonuclease site that was methylated in the original material. The $C_{10}$ primer (SEQ ID NO:38) has previously been demonstrated to inhibit amplification of molecules that contain this sequence at both ends (U.S. patent application Ser. No. 10/293,048, filed Nov. 13, 2002, now U.S. Pat. No. 7,655,791; U.S. patent application Ser. No. 10/795,667, now U.S. Pat. No. 7,718,403, filed Mar. 8, 2004; and U.S. patent application Ser. No. 10/797,333, filed Mar. 8, 2004, published as U.S. Patent Application Publication No.: 2004/0209299 and is now abandoned). The use of a single adaptor during preparation of the secondary library will result in amplification of only those sequences between the original adaptor and the first cut within the amplicon. Ligation of multiple adaptors will also allow the amplification of any fragments produced by multiple cleavage events in the same amplimer that are not expressed due to suppression by ligation of a single adaptor to both ends.

Example 26

Creation of Methylation Specific Libraries from Serum and Plasma DNA Libraries by Cleavage with the Methylation Specific Endonuclease McrBc This example describes a method for amplifying methylated CpG sites from DNA isolated from plasma and serum and is illustrated in FIG. 47. DNA isolated from serum and plasma can be converted into an amplifiable library by ligation of poly-C containing adaptors (U.S. patent application Ser. No. 10/797,333, filed Mar. 8, 2004, published as U.S. Patent Application Publication No.: 2004/0209299 and is now abandoned). The molecules in this library range in size from 200 bp up to 1 to 2 kb, which are readily amplified by PCR. Furthermore, ligation of the adaptors does not result in any changes in the methylation pattern of the original DNA. The resulting library molecules can be digested with the methylation-specific endonuclease McrBC. Any molecules that comprise two or more methylated CpG sites that are more than 30 bp apart will be cleaved between the two sites. A second adaptor can be ligated to the ends resulting from McrBC cleavage. The resulting products can be amplified using the second adaptor and the poly-C primer attached during ligation. Any products that do not have the second adaptor will be suppressed by the presence of poly-C sequence at each end (U.S. patent application Ser. No. 10/293,048, filed Nov. 12, 2002, now U.S. Pat. No. 7,655,791; U.S. patent application Ser. No. 10/795,667, filed Mar. 8, 2004; now U.S. Pat. No. 7,718,403 and U.S. patent application Ser. No. 10/797,333, filed Mar. 8, 2004, published as U.S. Patent Application Publication No.: 2004/0209299 and is now abandoned). The only products that will be amplified will be those comprising either a combination of the poly-C sequence and the second adaptor (2 methylated CpGs in the original library molecule), or the second adaptor at both ends (internal fragments generated from 3 or more CpGs in the original library molecule). Analysis of the resulting products allows the determination of methylation patterns of CpGs of interest. Alternatively, the amplicons can be analyzed on a microarray or by sequencing to isolate novel CpG sequences that are methylated, for example.

Example 27

Preparation and Amplification of Whole Genome Libraries from Bisulfite-Converted DNA Using 'Resistant' Adaptors and a Ligation Reaction This example describes a method for the creation of a whole genome library prior to bisulfite conversion. Amplification of the converted library is performed following bisulfite conversion using universal priming sequences attached during library preparation. This method is outlined in FIG. 49. Genomic DNA is randomly fragmented, and adaptors that are resistant to bisulfite modification are attached to the ends of the DNA fragments. There are two types of bisulfite-resistant adaptors that can be utilized during ligation, and these are illustrated in FIG. 50. The first type of adaptor comprises an oligo that is ligated to the fragmented DNA (oligo 1) that has no cytosines present, but only guanine, adenine, and thymine. Following ligation, an extension reaction is performed using dTTP, dATP, and dmCTP, resulting in incorporation of bisulfite-resistant methylated cytosines complementary to the guanines in oligo 1. Thus, the attached adaptor sequence is resistant to bisulfite modification due to the absence of unmethylated cytosines. The second type of adaptor comprises methylated cytosines in oligo 1, along with adenine and thymine, but no guanine. Fill-in of the 3' ends of the ligated adaptor results in incorporation of thymine, guanine and adenine, but no cytosine. Thus, these ligated adaptors are also resistant to bisulfite conversion as they do not contain any unmethylated cytosines. Bisulfite conversion is carried out on the resulting libraries. The library molecules are subsequently amplified using the universal primer. The products of amplification can be analyzed by any traditional means of methylation-specific analysis, including MS-PCR and sequencing.

Example 28

Optimization of the Cleavage of Genomic DNA by the Methylation-Sensitive Restriction Enzyme AciI This example illustrates the increased restriction enzyme cleavage efficiency observed after pre-heating genomic DNA, and specifically as it pertains to cleavage by the restriction enzyme Aci-I within the GC-rich promoter regions. GC-rich DNA sequences, through interactions with proteins, may form alternative (non-Watson-Crick) DNA conformation(s) that are stable even after protein removal and DNA purification. These putative DNA structures could be resistant to restriction endonuclease cleavage and affect the performance of the methylation assay. Heating DNA to sub-melting temperatures reduces the energetic barrier and accelerates the transition of DNA from a non-canonical form to a classical Watson-Crick structure.

Aliquots of 200 ng of purified genomic DNA purchased from the Coriell Institute for Medical Research (repository # NA14657) were pre-heated for 30 minutes at 85° C., 90° C., or 95° C. in 50 µl of 1× NEBuffer 3 (50 mM Tris-HCl, 10 mM $MgCl_2$, 100 mM NaCl, 1 mM Dithiothreitol, pH 7.9 at 25° C.). Samples were cooled to 37° C. and digested with 10 units of Aci-I (NEB) for 18 hours at 37° C. Control non-digested DNA and DNA that has not been pre-heated were also run in parallel.

The effect of pre-heating genomic DNA on cleavage efficiency was evaluated using a PCR assay with primers flanking three Aci-I enzyme recognition sites within the CpG rich promoter region of the human p16 gene. Aliquots of 20 ng of each DNA sample were analyzed by quantitative real-time PCR in reaction mixtures containing: 1× Titanium Taq reaction buffer (Clontech), 200 µM of each dNTP, 4% DMSO, Fluorescein (1:100,000) and SYBR Green I (1:100,000), 200 nM each p16 forward and reverse primer (SEQ ID NO: 48 and SEQ ID NO: 49), and 5 units of Titanium Taq polymerase (Clontech) in a final volume of 50 µl. Reactions were initiated at 95° C. for 3 min followed by 40 cycles at 94° C. for 15 sec and 68° C. for 1 min.

Figure 52:
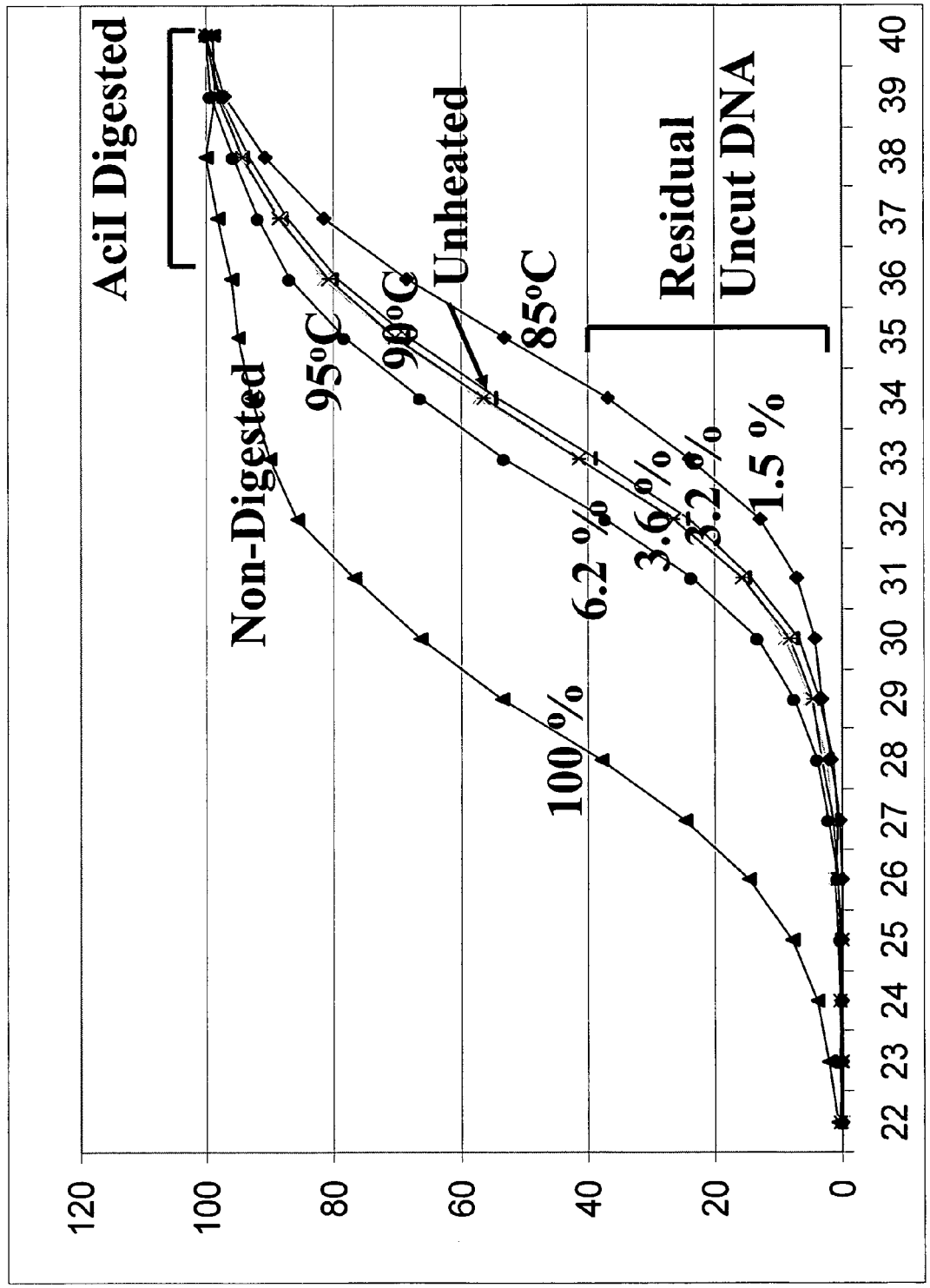
FIG. 52 illustrates the effect of pre-heating of genomic DNA on the efficiency of cleavage by the Aci I restriction enzyme. Preheating at 85° C. results in improved efficiency of cleavage.

As shown on FIG. 52, pre-heating genomic DNA at 95° C. prior to Aci-I digest resulted in reduced cleavage shown as a left shifted amplification profile indicative of a greater starting concentration of template. Heating at 90° C. had almost no effect on cleavage, whereas pre-heating at 85° C. improved the cleavage by about a factor of 2 compared to control that was not pre-heated. This improvement of cleavage by pre-heating at 85° C. was confirmed for multiple sites and multiple restriction enzymes (results are not shown) and is routinely used in our protocols for optimal digestion of genomic DNA with methylation-sensitive restriction enzymes.

The improved digestion following heat pre-treatment of genomic DNA suggests that a substantial fraction of DNA after purification may contain non-canonical nuclease-resistant structures. Upon heating, these structures may be converted into standard restriction enzyme cleavable form. Heating should not exceed the melting temperature that could cause DNA denaturation and a complete or partial loss of DNA cleavability by the restriction enzymes. In the experiment presented in FIG. 52, the reduced DNA cleavage after pre-heating at 90° C. and 95° C. is most likely a consequence of thermally-induced partial DNA denaturation.

Example 29

Methylation Analysis of 24 Promoter Regions in Random-Primed Libraries Prepared from KG1-A Leukemia Cell Line DNA after Simultaneous Cleavage with 5 Methylation-Sensitive Restriction Enzymes (Methylome Libraries)

This example demonstrates the utility of the Methylome libraries prepared from DNA digested with a mixture of 5 methylation-sensitive restriction enzymes. The libraries were prepared by incorporating universal sequence using primers comprising the universal sequence at their 5'-end and a degenerate non-self-complementary sequence at their 3'-end in the presence of DNA polymerase with strand-displacement activity. The Methylome libraries were amplified by PCR and used for analysis of the methylation status of promoter regions for 24 genes implicated in cancer.

The invention employs the use of several ($\geqq 5$) methylation-sensitive restriction enzymes to convert intact non-methylated CpG-rich DNA regions into restriction fragments that fall below the minimum length competent for amplification by random-primed whole genome amplification (WGA) (U.S. patent application Ser. No. 10/293,048, filed Nov. 13, 2002, now U.S. Pat. No. 7,655,791), while methylated CpG-rich regions resistant to digestion are efficiently amplified. The invention relies on the simultaneous use of all 5 or more restriction enzymes in one optimized reaction buffer described below. Although many restriction enzymes are predicted to follow a one-dimensional diffusion mechanism after binding DNA, the buffer conditions and methylation sensitive enzyme mix specified in the invention show no detectable interference between different restriction endonucleases.

The importance of implementation of multiple methylation-sensitive restriction enzymes in methylome library preparation stems from the analysis of promoter regions in the human genome. The spatial distribution of methylation sensitive restriction sites that include restriction endonucleases with 4 and 5 base recognition sites such as, for example, Aci I, Bst UI, Hha I, HinP1 I, Hpa II, Hpy 99I, Hpy CH4 IV, Ava I, Bce AI, Bsa HI, Bsi E1, and Hga I closely mimics the distribution of the CpG dinucleotides in these regions. When DNA is incubated with a single methylation sensitive enzyme, the resulting digestion is incomplete with many restriction sites remaining uncut. Factors contributing to this phenomenon are likely the extremely high GC-content and potential for alternative secondary structure. As a result, DNA pre-treated with one restriction enzyme may still contain substantial amounts of uncut non-methylated sites. Co-digestion of DNA with a cocktail of 5 or more methylation-sensitive restriction enzymes results in efficient conversion of all non-methylated CpG island into very small DNA fragments while leaving completely methylated CpG regions intact. Subsequently, whole genome amplification (WGA) of DNA pre-treated with the restriction enzyme cocktail results in amplification of all DNA regions except the CpG- and restriction site-rich regions that were not methylated in the original DNA. These regions are digested into fragments that fail to amplify using the random-primed WGA method. Multiple-enzyme-mediated depletion of non-methylated promoter regions in the amplified methylome library is so efficient that non-methylated CpG-rich regions can not be detected by PCR. Those regions encompassing densely methylated CpG islands are not affected by the enzyme cocktail treatment and are efficiently amplified by the WGA process and can be later easily detected and quantified by real-time PCR.

To synthesize whole methylome libraries, genomic DNA isolated by standard procedures from the exemplary KG1-A leukemia cell line or control genomic DNA (Coriell repository # NA16028) was preheated at 80° C. for 20 min (see Example 28) in 50 μl reactions containing 1× NEBuffer 4 (NEB) and 500 ng DNA. Samples were cooled to 37° C. for 2 min and 6.6 units each of AciI and HhaI, and 3.3 units each of BstUI, HpaII, and Hinp1I (NEB) were added. Sample digestions were incubated for 18 hours at 37° C., followed by 2 hours at 60° C. Blank controls containing no restriction enzymes were also run in parallel. The DNA was precipitated with ethanol in the presence of 1.5 M ammonium acetate and 50 μg/ml of glycogen, washed with 75% ethanol, air dried, and resuspended in 50 μl of TE-L buffer.

Aliquots of 30 ng of each digested or non-digested DNA sample were randomly fragmented in TE-L buffer by heating at 95° C. for 4 minutes and subjecting them to library synthesis. The reaction mixtures comprised 30 ng of fragmented DNA in 1× EcoPol buffer (NEB), 200 μM of each dNTP, 200 μM of 7-deaza-dGTP (Sigma), 4% DMSO, 360 ng of Single Stranded DNA Binding Protein (USB), and 1 μM of K(N)$_2$ primer (SEQ ID NO:14) in a final volume of 14 μl. After denaturing for 2 minutes at 95° C., the samples were cooled to 24° C., and the reactions were initiated by adding 2.5 units of Klenow Exo– DNA polymerase (NEB). Samples were incubated at 24° C. for 1 hour and terminated by heating for 5 minutes at 75° C. Aliquots of 10 ng of each sample were amplified by quantitative real-time PCR in a reaction mixture comprising the following final concentrations: 1× Titanium Taq reaction buffer (Clontech), 200 μM of each dNTP, fluorescein calibration dye (1:100,000) and SYBR Green I (1:100,000), 1 μM universal $K_U$ primer (SEQ ID NO: 15), 4% DMSO, 200 μM 7-deaza-dGTP (Sigma), and 5 units of Titanium Taq polymerase (Clontech) in a final volume of 50 ul. Reactions were carried out at 95° C. for 1 min, followed by 14 cycles of 94° C. for 15 seconds and 65° C. for 2 minutes on an I-Cycler real-time PCR instrument (Bio-Rad). Amplified libraries were purified using the QIAQUICK® kit (Qiagen) and quantified by optical density reading.

The presence of methylated DNA within 24 exemplary cancer gene promoters was analyzed by quantitative real-time PCR using amplified libraries and a panel of 40 specific primer pairs. Primers were designed to test the libraries for amplicons spanning CpG-rich regions within promoters. The presence or absence of amplification for specific sequences that display a high frequency of potential cleavage sites was indicative of the methylation status of the promoter. Initially, a set of 24 exemplary promoters frequently implicated in different types of cancer were evaluated. The primer pairs used in the PCR assays are listed in Table IV.

TABLE IV

METHYLATION PROFILE OF EXEMPLARY KG1-A LEUKEMIA CELL LINE

| Promoter | Sequence (5'-3')* | | Position** | Methylation*** |
|---|---|---|---|---|
| P16 | F GGTAGGGGGACACTTTCTAGTC | (SEQ ID NO: 48) | Upstream | + |
| (CDKN2A) | R AGGCGTGTTTGAGTGCGTTC | (SEQ ID NO: 49) | | |
| | F GGTGCCACATTCGCTAAGTGC | (SEQ ID NO: 65) | Downstream | − |
| | R GCTGCAGACCCTCTACCCAC | (SEQ ID NO: 66) | | |
| P15 | F CCTCTGCTCCGCCTACTGG | (SEQ ID NO: 97) | Flanking | + |
| (CDKN2B) | R CACCGTTGGCCGTAAACTTAAC | (SEQ ID NO: 98) | | |
| E-Cadherin | F GCTAGAGGGTCACCGCGT | (SEQ ID NO: 28) | Upstream | + |
| | R CTGAACTGACTTCCGCAAGCTC | (SEQ ID NO: 29) | | |
| | F GCTAGAGGGTCACCGCGT | (SEQ ID NO: 28) | Flanking | + |
| | R CAGCAGCAGCGCCGAGAGG | (SEQ ID NO: 67) | | |
| GSTP-1 | F GTGAAGCGGGTGTGCAAGCTC | (SEQ ID NO: 30) | Upstream | − |
| | R GAAGACTGCGGCGGCGAAAC | (SEQ ID NO: 31) | | |
| MGMT | F GCACGCCCGCGGACTA | (SEQ ID NO: 99) | Upstream | + |
| | R CCTGAGGCAGTCTGCGCATC | (SEQ ID NO: 100) | | |
| | F GCCCGCGCCCCTAGAACG | (SEQ ID NO: 101) | Downstream | +/− |
| | R CACACCCGACGGCGAAGTGAG | (SEQ ID NO: 102) | | |
| RASSF-1 | F GCCCAAAGCCAGCGAAGCAC | (SEQ ID NO: 103) | Flanking | − |
| | R CGCCACAGAGGTCGCACCA | (SEQ ID NO: 104) | | |
| hMLH-1 | F TCCGCCACATACCGCTCGTAG | (SEQ ID NO: 105) | Upstream | − |
| | R CTTGTGGCCTCCCGCAGAA | (SEQ ID NO: 106) | | |
| BRCA-1 | F CCCTTGGTTTCCGTGGCAAC | (SEQ ID NO: 107) | Flanking | − |
| | R CTCCCCAGGGTTCACAACGC | (SEQ ID NO: 108) | | |
| VHL | F CTAGCCTCGCCTCCGTTACAAC | (SEQ ID NO: 109) | Upstream | − |
| | R GCTCGGTAGAGGATGGAACGC | (SEQ ID NO: 110) | | |
| APC-A1 | F GGTACGGGGCTAGGGCTAGG | (SEQ ID NO: 111) | Flanking | − |
| | R GCGGGCTGCACCAATACAG | (SEQ ID NO: 112) | | |
| | F CGGGTCGGGAAGCGGAGAG | (SEQ ID NO: 113) | Downstream | − |
| | R TGGCGGGCTGCACCAATACAG | (SEQ ID NO: 114) | | |
| DAPK-1 | F GTGAGGAGGACAGCCGGACC | (SEQ ID NO: 115) | Downstream | + |
| | R GGCGGGAACACAGCTAGGGA | (SEQ ID NO: 116) | | |
| TIMP-3 | F AGGGGCACGAGGGCTCCGCT | (SEQ ID NO: 117) | Flanking | + |
| | R GGGCAAGGGGTAACGGGGC | (SEQ ID NO: 118) | | |
| | F CAGCTCCTGCTCCTTCGCC | (SEQ ID NO: 119) | Downstream | + |
| | R GCTGCCCTCCGAGTGCCC | (SEQ ID NO: 120) | | |
| ESR-1 | F CTGGATCCGTCTTTCGCGTTTA | (SEQ ID NO: 121) | Upstream | + |
| | R TTGTCGTCGCTGCTGGATAGAG | (SEQ ID NO: 122) | | |
| | F GGCGGAGGGCGTTCGTC | (SEQ ID NO: 123) | Downstream | + |
| | R AGCACAGCCCGAGGTTAGAGG | (SEQ ID NO: 124) | | |

TABLE IV-continued

METHYLATION PROFILE OF EXEMPLARY KG1-A LEUKEMIA CELL LINE

| Promoter | | Sequence (5'-3')* | | Position** | Methylation*** |
|---|---|---|---|---|---|
| MYOD-1 | F | CCTGATTTCTACAGCCGCTCTAC | (SEQ ID NO: 125) | Upstream | + |
| | R | TCCAAACCTCTCCAACACCCGACT | (SEQ ID NO: 126) | | |
| | F | CCTGGCCGAGAAGCTAGGG | (SEQ ID NO: 127) | Flanking | + |
| | R | CGGCCTGATTTGTGGTTAAGGA | (SEQ ID NO: 128) | | |
| CALCA | F | AGTTGGAAGAGTCCCTACAATCCTG | (SEQ ID NO: 129) | Upstream | + |
| | R | CGTCCCACTTGTATTTGCATTGAG | (SEQ ID NO: 130) | | |
| | F | CTGGCGCTGGGAGGCATCAG | (SEQ ID NO: 131) | Flanking | + |
| | R | GCGGGAGGTGGCTTGGATCA | (SEQ ID NO: 132) | | |
| CHFR | F | CGTGATCCGCAGGCGACGAA | (SEQ ID NO: 133) | Upstream | − |
| | R | TCACCAAGAGCGGCAGCTAAAG | (SEQ ID NO: 134) | | |
| | F | GAAGTCGCCTGGTCAGGATCAAA | (SEQ ID NO: 135) | Flanking | − |
| | R | GCCGCTGTCAAGAGACATTGC | (SEQ ID NO: 136) | | |
| PTGS-2 | F | CGGTATCCCATCCAAGGCGA | (SEQ ID NO: 137) | Upstream | − |
| | R | CTCTCCTCCCCGAGTTCCAC | (SEQ ID NO: 138) | | |
| MDR-1 | F | GTGGAGATGCTGGAGACCCCG | (SEQ ID NO: 139) | Downstream | − |
| | R | CTCTAGTCCCCCGTCGAAGCC | (SEQ ID NO: 140) | | |
| EDNRB | F | CGGGAGGAGTCTTTCGAGTTCAA | (SEQ ID NO: 141) | Upstream | + |
| | R | CGGGAGGAATACAGACACGTCTT | (SEQ ID NO: 142) | | |
| | F | GGGCATCAGGAAGGAGTTTCGAC | (SEQ ID NO: 143) | Downstream | + |
| | R | TCGCCAGTATCCACGCTCAA | (SEQ ID NO: 144) | | |
| RARβ-2 | F | AAAGAAAACGCCGGCTTGTG | (SEQ ID NO: 145) | Upstream | + |
| | R | CTACCCGGGCTGCTAACCTTCA | (SEQ ID NO: 146) | | |
| | F | GGACTGGGATGCCGAGAAC | (SEQ ID NO: 147) | Flanking | + |
| | R | TTTACCATTTTCCAGGCTTGCTC | (SEQ ID NO: 148) | | |
| RUNX-3 | F | GGGGCTCCGCCGATTG | (SEQ ID NO: 149) | Upstream | − |
| | R | CGCAGCCCCAGAACAAATCCT | (SEQ ID NO: 150) | | |
| | F | GGCCCCGCCACTTGATTCT | (SEQ ID NO: 151) | Flanking | − |
| | R | CGGCCGCCCCTCGTG | (SEQ ID NO: 152) | | |
| | F | CCGGGACAGCCACGAGGG | (SEQ ID NO: 153) | Downstream | − |
| | R | GCGAGAAGCGGGAAAGCAGAAGC | (SEQ ID NO: 154) | | |
| TIG-1 | F | CCAACTTTCCTGCGTCCATGC | (SEQ ID NO: 155) | Flanking | + |
| | R | AGGCTGCCCAGGGTCGTC | (SEQ ID NO: 156) | | |
| | F | CTCGCGCTGCTGCTGTTGCTC | (SEQ ID NO: 157) | Downstream | + |
| | R | TGAGGCTGCCCAGGGTCGTCGG | (SEQ ID NO: 158) | | |
| CAV-1 | F | GGGACGCCTCTCGGTGGTT | (SEQ ID NO: 159) | Upstream | − |
| | R | GGCCCGGACGTGTGCT | (SEQ ID NO: 160) | | |
| | F | CCTGCTGGGGGTTCGAAGA | (SEQ ID NO: 161) | Downstream | + |

TABLE IV-continued

METHYLATION PROFILE OF EXEMPLARY KG1-A LEUKEMIA CELL LINE

| Promoter | Sequence (5'-3')* | | Position** | Methyla-tion*** |
|---|---|---|---|---|
| | R CCCCTGCCAGACGCCAAGAT | (SEQ ID NO: 162) | | |
| CD44 | F TCGGTCATCCTCTGTCCTGACGC | (SEQ ID NO: 163) | Upstream | – |
| | R GGGGAACCTGGAGTGTCGC | (SEQ ID NO: 164) | | |
| | F CCTCTGCCAGGTTCGGTCC | (SEQ ID NO: 165) | Downstream | – |
| | R GCTGCGTGCCACCAAAACTTGTC | (SEQ ID NO: 166) | | |

Figure 53:
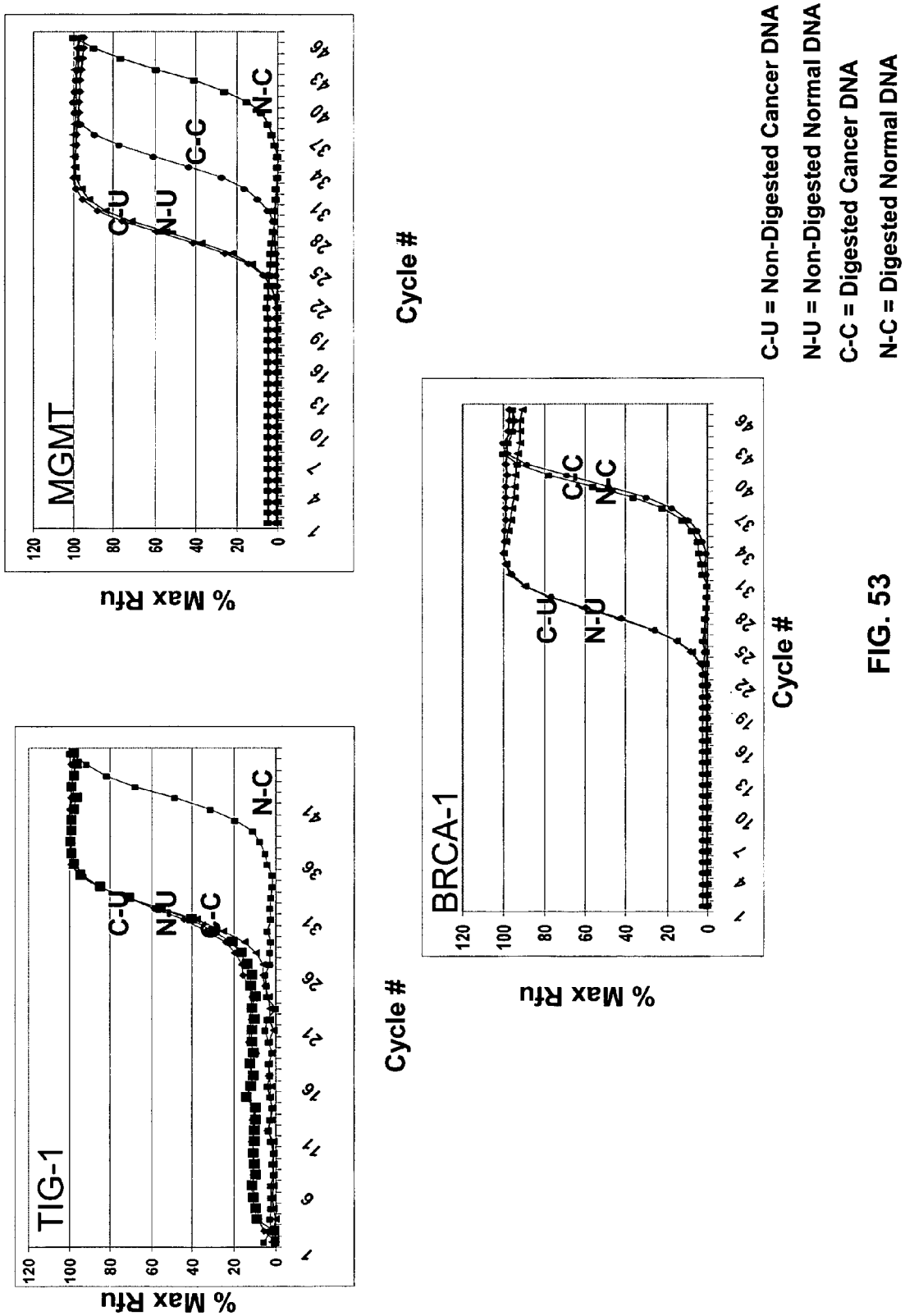
FIG. 53 shows exemplary amplification of completely methylated, partially methylated, and non-methylated promoter sites in KG1-A cell line for the human TIG-1, MGMT, and BRCA-1 genes respectively.

*F = Forward Primer, R = Reverse Primer
**Position of amplicon relative to the gene transcription start
***Methylation status of promoter sites as determined by the relative positions of amplification curves of libraries from digested cancer DNA (C-C, Cancer Cut) and normal DNA (N-C, Normal Cut) as illustrated in FIG. 53.
"+" designates a complete curve shift (complete methylation), "+/–" designates a partial shift (partial methylation), and "–" designates no shift (no methylation)

50 ng DNA aliquots from the amplified libraries were analyzed by quantitative real-time PCR in reaction mixtures comprising the following: 1× Titanium Taq reaction buffer (Clontech), 200 µM of each dNTP, 4% DMSO, 0.5 M betaine, FCD (1:100,000) and SYBR Green I (1:100,000), 200 nM each forward and reverse primer (Table IV), and 5 units of Titanium Taq polymerase (Clontech) in a final volume of 50 µl at 95° C. for 3 min followed by 45 cycles at 94° C. for 15 sec and 68° C. for 1 min.

FIG. 53 shows typical amplification curves of completely methylated, partially methylated, and non-methylated promoter sites in KG1-A cell line as exemplified by the promoters for the human TIG-1, MGMT, and BRCA-1 genes respectively.

Example 30

Preparation and Labeling of Secondary Methylome Libraries Enriched in Methylated CpG-Islands for Microarray Hybridization This example demonstrates preparation of what may be termed a "Secondary Methylome" library derived from the amplified primary Methylome library. Secondary libraries are derived by cleavage of the primary library with the same set of methylation-sensitive restriction endonucleases used in preparation of primary library and subsequent amplification of the excised short DNA fragments. Restriction sites originally methylated in the DNA sample were refractory to cleavage in the primary library, however after amplification substituting the 5'-methyl cytosines of the starting template DNA with non-methylated cytosines of the primary libarary DNA conveys cleavage sensitivity to these previously protected restriction sites. Incubation of the amplified primary library with the exemplary restriction endonuclease set (Aci I, Hha I, HinP1 I, or Hpa II) would have no effect for amplicons lacking those restriction sites, produce a single break for amplicons with one site, and release one or more restriction fragments from CpG-rich amplicons with two or more corresponding restriction sites. Selective ligation of adaptors (comprising 5'-CG-overhangs complementary to the ends of Aci I, Hha I, HinP1 I, and Hpa II restriction fragments, or blunt-end adaptors compatible with the ends of fragments produced by Bst UI) and subsequent amplification of the ligation products by PCR results in amplification of only those DNA fragments that were originally flanked by two methylated restriction sites. Secondary Methylome libraries generated by different restriction enzymes can be mixed together to produce a redundant secondary Methylome library containing overlapping DNA restriction fragments originating from the methylated CpG islands present in the sample. These libraries are highly enriched for methylated sequences and can be analyzed by hybridization to a promoter microarray or by real-time PCR using very short PCR amplicons.

An example of the process and resulting data are presented here in detail. Primary Methylome libraries were prepared from genomic DNA isolated by standard procedure from the LNCaP prostate cancer cell line (Coriell Institute for Medical Research) or from normal "non-methylated" DNA isolated from the peripheral blood of a healthy male donor. Sixty nanogram aliquots of cancer or normal DNA were pre-heated at 80° C. for 20 min in 25 µl reactions comprising 1× NEB-uffer 4 (NEB). Samples were cooled to 37° C. for 2 min and 3.3 units each of AciI and HhaI+1.67 units each of BstUI, HpaII, and Hinp1I (NEB) were added. Samples were then incubated for 14 hours at 37° C., followed by 2 hours at 60° C. The DNA was precipitated with ethanol in the presence of 0.3 M sodium acetate and 2 µl of PelletPaint (Novagen), washed with 75% ethanol, air dried, and resuspended in 20 µl of TE-L buffer. Aliquots of 30 ng of each digested DNA sample were randomly fragmented in TE-L buffer by heating at 95° C. for 4 minutes and subjected to library synthesis. The reaction mixtures comprised 30 ng of fragmented DNA in 1× EcoPol buffer (NEB), 200 µM of each dNTP, 200 µM of 7-deaza-dGTP (Sigma), 4% DMSO, 360 ng of Single Stranded DNA Binding Protein (USB), and 1 µM of K(N)$_2$ primer (SEQ ID NO: 14) in a final volume of 14 µl. After denaturing for 2 minutes at 95° C., the samples were cooled to 24° C., and the synthesis reactions were initiated by adding 2.5 units of Klenow Exo– DNA polymerase (NEB). Samples were incubated at 24° C. for 1 hour and reactions were terminated by heating for 5 minutes at 75° C. Ten nanograms aliquots of the libraries were then amplified by PCR with the universal primer ($K_U$) and product accumulation was monitored in real-time with Sybr-green I. The amplification reaction mixture comprised the following final concentrations: 1× Titanium Taq reaction buffer (Clontech), 200 µM of each dNTP, fluorescein calibration dye (1:100,000) and SYBR Green I (1:100,000), 1 µM universal $K_U$ primer (SEQ ID NO: 15), 4% DMSO, 200 µM 7-deaza-dGTP (Sigma), and 5 units of Titanium Taq polymerase (Clontech) in a final volume of 75 µl. Reactions were carried out at 95° C. for 1 min, followed by 12 cycles of 94° C. for 15 seconds and 65° C. for 2 minutes on an I-Cycler real-time PCR instrument (Bio-Rad). Amplified libraries from cancer or normal DNA were pooled and purified using MultiScreen PCR cleanup (Millipore) and quantified by optical density.

For preparation of secondary methylome libraries, 1.8 µg aliquots of cancer and 1.8 µg aliquots of normal primary methylome library DNA were digested in three separate tubes each in a final volume of 90 µl with 22.5 units of AciI in NEBuffer 3, 15 units of HpaII in NEBuffer 4, or 30 units of HhaI+15 units of Hinp1I in NEBuffer 4. Following pre-heating at 80° C. for 20 min, the samples were cooled to 37° C. for 2 min and the restriction enzymes were added at the amounts specified above. Samples were incubated for 16 hours at 37° C. and the enzymes were inactivated for 10 min at 65° C. To size fractionate, the products of the three digestion reactions of cancer DNA and the products of the three digestion reactions of normal DNA were combined, diluted to 1.32 ml with dilution buffer (10 mM Tris-HCL, pH 8.0, 0.1 mM EDTA, and 150 mM NaCl), and aliquots of 440 µl were loaded on Microcon YM-100 filters (Millipore) that had been pre-washed with the above dilution buffer. Filters were centrifuged at 500×g for 20 minutes and the flow-through fractions of cancer or normal samples were combined, precipitated with ethanol in the presence of 0.3 M sodium acetate and 2 µl of PelletPaint (Novagen), washed with 75% ethanol, air dried, and resuspended in 36 µl of TE-L buffer. To convert the filtered fragments to an amplifiable secondary library, Y1 and Y2 universal adaptors (Table V) comprising unique sequences comprising only C and T (non-Watson-Crick pairing bases) on one strand and having a CG 5' overhang on the opposite (A and G) strand were annealed and ligated to the overhangs of the restriction fragments produced as described above. Digested and filtered library DNA from the previous step was incubated with Y1 and Y2 adaptors (Table V) each present at 0.6 µM and 1,200 units of T4 DNA ligase in 45 µl of 1×T4 DNA ligase buffer (NEB) for 50 min at 16° C. followed by 10 min at 25° C. Libraries were then split into 3 aliquots of 15 µl each and amplified by PCR and monitored in real time using a reaction mixture containing final concentrations of: 1× Titanium Taq reaction buffer (Clontech), 200 µM of each dNTP, fluorescein calibration dye (1:100,000) and SYBR Green I (1:100,000), 0.25 µM each of universal primers (Table V, SEQ ID NO: 168 and SEQ ID NO: 170), 4% DMSO, 200 µM 7-deaza-dGTP (Sigma), and 5 units of Titanium Taq polymerase (Clontech) in a final volume of 75 µl. After an initial incubation at 75° C. for 10 min to fill-in the recessed 3' ends of the ligated restriction fragments, amplifications were carried out at 95° C. for 3 min, followed by 13 cycles of 94° C. for 15 sec and 65° C. for 1.5 min on an I-Cycler real-time PCR instrument (Bio-Rad). Amplified libraries from cancer or normal DNA were pooled and used as template in PCR labeling for subsequent microarray hybridizations.

TABLE V

OLIGONUCLEOTIDES AND ADAPTORS USED FOR SECONDARY METHYLOME LIBRARIES PREPARATION AND ANALYSIS

| Code Name | Sequence* (5'-3' unless otherwise indicated) | |
|---|---|---|
| Y1 Adaptor | 5'-CGAGAGAAGGGAx ** TCTCTTCCCTCTCTTTCC-5' | (SEQ ID NO: 167) (SEQ ID NO: 168) |
| Y2 Adaptor | 5'-CGAAGAGAGAGGGx TTCTCTCTCCCTTCCTTC-5' | (SEQ ID NO: 169) (SEQ ID NO: 170) |

TABLE V-continued

OLIGONUCLEOTIDES AND ADAPTORS USED FOR SECONDARY METHYLOME LIBRARIES PREPARATION AND ANALYSIS

| Code Name | Sequence* (5'-3' unless otherwise indicated) | |
|---|---|---|
| GSTP-1 (SH) | F AGTTCGCTGCGCACACTT R CGGGGCCTAGGGAGTAAACA | (SEQ ID NO: 190) (SEQ ID NO: 191) |
| RASSF-1 (SH) | F CCCAAAGCCAGCGAAGCACG R TCAGGCTCCCCCGACAT | (SEQ ID NO: 192) (SEQ ID NO: 193) |
| CD44 (SH) | F CTGGGGGACTGGAGTCAAGTG R CCAACGGTTTAGCGCAAATC | (SEQ ID NO: 194) (SEQ ID NO: 195) |
| P16(SH) | F CTCGGCGGCTGCGGAGA R CGCCGCCCGCTGCCT | (SEQ ID NO: 196) (SEQ ID NO: 197) |

*F = Forward Primer, R = Reverse Primer
**x = amino C7 modifier

Libraries were labeled during PCR by incorporation of universal primers containing 5' cyanine fluorophores. Labeling reactions were as follows: 1× Titanium Taq reaction buffer (Clontech), 200 µM of each dNTP, fluorescein calibration dye (1:100,000) and SYBR Green I (1:100,000), 0.25 µM each of Cy5 or Cy3 5'-labeled universal primers (Table V, SEQ ID NO: 168 and SEQ ID NO: 170), 4% DMSO, 200 µM 7-deaza-dGTP (Sigma), 5 units of Titanium Taq polymerase (Clontech), and 1.5 µl of library DNA from the previous step in a final volume of 75 µl. Reactions were carried out at 95° C. for 3 min, followed by 8 cycles of 94° C. for 15 sec and 65° C. for 1.5 min on an I-Cycler real-time PCR instrument (Bio-Rad). Cancer DNA was labeled with Cy3 and normal with Cy5. Multiple labeling reactions were pooled, diluted with 4 volumes of TE-L buffer and purified using MultiScreen PCR cleanup (Millipore). The purified labeled DNA was quantified by optical density.

The distribution of promoter sites and the level of their enrichment in amplified secondary methylome libraries from cancer DNA was analyzed by quantitative PCR using primer pairs amplifying short amplicons that do not contain recognition sites for at least two of the methylation-sensitive restriction enzymes employed in the present example (Table V, SEQ ID NOS:190 through SEQ ID NO:197). Mechanically fragmented genomic DNA from the peripheral blood of a healthy donor was used as a control for relative copy number evaluation.

Aliquots of 50 ng of amplified secondary methylome libraries prepared from LNCaP cell line or control genomic DNA fragmented to an average size of 1.5 Kb on a HydroShear device (Gene Machines) for 20 passes at a speed code of 3 were analyzed by quantitative real-time PCR in reaction mixtures containing: 1× Titanium Taq reaction buffer (Clontech), 200 µM of each dNTP, 4% DMSO, FCD (1:100,000) and SYBR Green I (1:100,000), 200 nM each forward and reverse primer (Table V, SEQ ID NO:190 and SEQ ID NO:191 for GSTP-1 promoter, SEQ ID NO:192 and SEQ ID NO:193 for RASSF-1 promoter, SEQ ID NO:194 and SEQ ID NO:195 for CD44 promoter, and SEQ ID NO:196 and SEQ ID NO:197 for p16 promoter), and 3 units of Titanium Taq polymerase (Clontech) in a final volume of 30 µl at 95° C. for 3 min followed by 47 cycles at 94° C. for 15 sec and 68° C. for 1 min.

FIG. 66 shows typical amplification curves of four promoter sites three of which (GSTP-1, RASSF-1, and CD44) are methylated, and one (p16) that is not methylated in the exemplary LNCaP cell line. For methylated promoters, between 4 and 7 cycles of left shift (enrichment of between 16 and 128-fold) of the amplification curves from methylome library was observed relative to the curve corresponding to control non-amplified genomic DNA. For the non-methylated p16 promoter a curve delayed approximately 4 cycles relative to the control appeared. However, this curve did not correspond to the correct size amplicon and was most likely a product of mis-priming Example 31

Preparation of Libraries from Cell-Free DNA Isolated from Serum and Urine and their Utility for Detection of Promoter Hypermethylation This example describes a method for preparation of libraries from the cell-free DNA fraction of serum or urine and their utility for detection of promoter hypermethylation. The principle of this method is described in U.S. patent application Ser. No. 10/797,333, filed Mar. 8, 2004, published as U.S. Patent Application Publication No.: 2004/0209299 and is now abandoned.

Cell-free DNA isolated from plasma, serum, and urine is typically characterized by very low amounts (nanogram quantities) of extremely short size (~200 bp). In principle, the random-prime amplification method described in Example 29 can be applied to DNA of this size but with about 10 times lower amplification efficiency compared to high molecular weight DNA isolated from tissue or cultured cells. An alternative and more efficient method of preparing Methylome libraries from very short DNA fragments utilizes elements of the invention. As in the above examples, a simultaneous digestion of DNA in one reaction buffer with multiple (five or more) methylation-sensitive restriction endonucleases is followed by whole genome amplification from universal sequences attached to DNA fragments by ligation. With this methylome library approach, DNA can be digested with the nuclease cocktail before or after library synthesis. In this detailed Example, the multi-endonuclease cleavage occurs post library synthesis, and ensures that the amplicons containing multiple non-methylated restriction sites will be efficiently eliminated by cleavage and thereby not amplified.

Blood collected from healthy donors or from prostate cancer patients was aliquoted into 6 ml Vacutainer SST Serum Separation tubes (Becton-Dickinson), incubated for 30 min at ambient temperature, and centrifuged at 1,000×g for 10 min. The upper serum phase was collected and stored at −20° C. until use. DNA was isolated using Charge Switch Kit (DRI cat #11000) and a modified protocol for DNA from blood. One ml of serum was incubated with 700 ul of lysis buffer provided with the kit, 30 µl of proteinase K (20 mg/ml), and 5 µl of RNase A/T1 cocktail (Ambion cat #2288) by incubation at 25° C. for 20 min with gentle rotation. Two hundred and fifty µl purification buffer and 30 µl of Magnetic beads were then added to each sample followed by incubation at 25° C. for 2 min. Tubes were placed on magnetic rack for 2 min. Supernatant was removed and beads were washed 3 times with 1 ml each of washing buffer. Beads were then resuspended in 40 µl of elution buffer and incubated at 25° C. for 2 min. Samples were placed on magnetic rack for 2 min and supernatant was transferred to a new tube. DNA was quantified on fluorescent spectrophotometer using Pico Green (Molecular Probes) and λ phage DNA standards.

Another source of cell-free DNA for methylome preparation was isolated from urine of healthy donors or from prostate cancer patients collected in 50 ml Falcon tubes and stabilized for storage by adding 0.1 volume of 0.5 M EDTA. Urine samples were centrifuged at 1,800×g for 10 min at ambient temperature to sediment cells and supernatant was transferred carefully to a fresh tube. An equal volume of 6 M guanidine thiocyanate was added to each sample followed by ⅙ vol of Wizard Miniprep resin (Promega catalog #A7141). DNA was bound to the resin by rotation for 1 hour at ambient temperature. The resin was then sedimented by brief centrifugation at 500×g and loaded on Wizard minicolumns (Promega catalog #A7211)) using syringe barrel extensions after carfully decanting out the supernatant. Resin was washed with 5 ml of wash buffer (Promega catalog #A8102) using Qiagen QIAvac 24 vacuum manifold. Minicolumns were then centrifuged for 2 min at 10,000×g to remove residual wash buffer and bound DNA was eluted with 50 µl of DNAse-free water at 10,000×g for 1 min. Eluted DNA was buffered by adding 0.1 vol of 10×TE-L buffer and quantified by fluorescent spectrophotometer using Pico Green (Molecular Probes) and λ phage DNA standards. FIG. 54 A shows analysis of DNA samples isolated from serum and urine by gel electrophoresis on 1.5% agarose. A typical banding pattern characteristic of apoptotic nucleosomal size is observed.

To repair DNA ends 100 ng aliquots of purified cell-free serum or urine DNA were incubated in 1×T4 ligase buffer (NEB) with 0.8 units of Klenow fragment of DNA polymerase I (USB Corporation), 0.1 mg/ml of bovine serum albumin (BSA), and 16.7 µM dNTPs for 15 min at 25° C. followed by 10 min at 75° C. in a final volume of 24 µl.

For preparation of methylome libraries repaired DNA was incubated with universal $K_U$ adaptor (Table VI) at 1.25 µM and 800 units of T4 DNA ligase in 32 µl of 1×T4 DNA ligase buffer (NEB) for 1 hour at 25° C. followed by 15 min at 75° C. DNA was precipitated with ethanol in the presence of 0.3 M sodium acetate and 2 µl of PelletPaint (Novagen), washed with 75% ethanol, air dried, and resuspended in 34.4 µl of DNAase-free water. Samples were then supplemented with 4 µl of 10× NEBuffer 4 (NEB) and split into 2 aliquots. Following pre-heating at 70° C. for 5 min and cooling to 37° C. for 2 min, one aliquot was digested with 2.66 units each of AciI and HhaI, and 1.33 units each of BstUI, HpaII, and Hinp1I (NEB) for 12 hours at 37° C., followed by 2 hours at 60° C. in a final volume of 20 µl. The second aliquot was incubated in parallel but without restriction enzymes ("uncut" control). Libraries were amplified using real-time PCR monitoring in a reaction mixture comprising the following final concentrations: 1× Titanium Taq reaction buffer (Clontech), 200 µM of each dNTP, fluorescein calibration dye (1:100,000) and SYBR Green I (1:100,000), 1 µM universal primer $K_U$ (Table VI, SEQ ID NO:15), 4% DMSO, 200 µM 7-deaza-dGTP (Sigma), and 5 units of Titanium Taq polymerase (Clontech) in a final volume of 75 µl. After initial incubation at 75° C. for 15 min to fill in the recessed 3' ends of the ligated DNA libraries, amplifications were carried out at 95° C. for 3 min, followed by 13 cycles of 94° C. for 15 sec and 65° C. for 2 min on an I-Cycler real-time PCR instrument (Bio-Rad). Amplified libraries were purified using MultiScreen PCR cleanup (Millipore) and quantified by optical density. FIG. 54 B shows analysis of DNA from libraries prepared from urine by electrophoresis on 1.5% agarose gels.

TABLE VI

OLIGONUCLEOTIDE ADAPTORS USED FOR PREPARATION
OF METHYLOME LIBRARIES FROM SERUM AND URINE DNA

| Code | Sequence* | |
|---|---|---|
| $K_U$ Adaptor | 5'-CCAAACACACCCx-3'<br>3'-GGTTTGTGTGGGTT<br>GTGT-5' | (SEQ ID NO: 171)<br>(SEQ ID NO: 15) |
| dU-Hairpin<br>Adaptor | 5'-TGTGTTGGGdUGdUGTGT<br>GGdUdUdUdUdUCCACACA<br>CACCCAACACA-3' | (SEQ ID NO: 172)** |
| $M_U$-1 Primer | 5'-CCACACACACCCAACA<br>CA-3' | (SEQ ID NO: 173) |

*x = amino C7 modifier
**dU = deoxy-Uridine

Specific regions within the library template DNA may show resistance to digestion based on their level of methylation. Promoter sequences rich in CpG methylation are thereby quantified in the amplified Methylome libraries using quantitative real-time PCR assays with promoter specific primers described in the Table VII. Aliquots of 75 ng of each DNA sample were assayed by quantitative real-time PCR in reaction mixtures comprising the following: 1× Titanium Taq reaction buffer (Clontech), 200 µM of each dNTP, 4% DMSO, 0.5 M betaine, FCD (1:100,000) and SYBR Green I (1:100,000), 200 nM each forward and reverse primer (Table VII), and 2.5 units of Titanium Taq polymerase (Clontech) in a final volume of 25 µl at 95° C. for 3 min followed by 50 cycles at 94° C. for 15 sec and 68° C. for 1 min.

FIGS. 55 and 56 show typical amplification curves of promoter sites for genes implicated in cancer from methylome libraries synthesized from the serum and urine DNA of cancer patients as compared to healthy donor controls. As expected, the level of methylation in serum and urine DNA from cancer patients was much lower than in tumor tissue or cancer cell lines, since cancer DNA in circulation represents only a relatively small fraction of the total cell-free DNA. This trend is especially pronounced for urine DNA. Nevertheless, the method disclosed here is very sensitive to reliably detect methylation in body fluids and can be applied as a diagnostic tool for early detection, prognosis, or monitoring of the progression of cancer disease.

TABLE VII

PRIMER PAIRS USED FOR METHYLATION ANALYSIS OF
SERUM AND URINE METHYLOME LIBRARIES BY REAL-
TIME PCR

| Promoter | | Sequence (5'-3') | |
|---|---|---|---|
| APC-1 | F | CGGGTCGGGAAGCGGAGAG | (SEQ ID NO: 113) |
|  | R | TGGCGGGCTGCACCAATACAG | (SEQ ID NO: 114) |
| MDR-1 | F | GGGTGGGAGGAAGCATCGTC | (SEQ ID NO: 174) |
|  | R | GGTCTCCAGCATCTCCACGAA | (SEQ ID NO: 175) |
| BRCA-1 | F | CCCTTGGTTTCCGTGGCAAC | (SEQ ID NO: 107) |
|  | R | CTCCCCAGGGTTCACAACGC | (SEQ ID NO: 108) |
| CD44 | F | CCTCTGCCAGGTTCGGTCC | (SEQ ID NO: 165) |
|  | R | GCTGCGTGCCACCAAAACTTGTC | (SEQ ID NO: 166) |
| GSTP-1 | F | TGGGAAAGAGGGAAAGGCTTC | (SEQ ID NO: 176) |
|  | B | CCCCAGTGCTGAGTCACGG | (SEQ ID NO: 177) |
| RASSF-1 | F | GCCCAAAGCCAGCGAAGCAC | (SEQ ID NO: 103) |
|  | R | CGCCACAGAGGTCGCACCA | (SEQ ID NO: 104) |

TABLE VII-continued

PRIMER PAIRS USED FOR METHYLATION ANALYSIS OF
SERUM AND URINE METHYLOME LIBRARIES BY REAL-
TIME PCR

| Promoter | | Sequence (5'-3') | |
|---|---|---|---|
| E-Cadherin | F | GCTAGAGGGTCACCGCGT | (SEQ ID NO: 28) |
|  | R | CTGAACTGACTTCCGCAAGCTC | (SEQ ID NO: 29) |
| PTGS-2 | F | AGAACTGGCTCTCGGAAGCG | (SEQ ID NO: 178) |
|  | R | GGGAGCAGAGGGGGTAGTC | (SEQ ID NO: 179) |
| EDNRB | F | GGGCATCAGGAAGGAGTTTCGAC | (SEQ ID NO: 143) |
|  | R | TCGCCAGTATCCACGCTCAA | (SEQ ID NO: 144) |
| P16 Exon 2 | F | GCTTCCTGGACACGCTGGT | (SEQ ID NO: 180) |
|  | R | TCTATGCGGGCATGGTTACTG | (SEQ ID NO: 181) |

*F = Forward primer, R = Reverse Primer

Example 32

Optimization of Library Preparation from Cell-Free DNA Isolated from Urine

In clinical applications it is very important to have simple, fast, and reliable tests. This example describes the development of a single-tube library preparation and amplification method for methylome libraries from cell-free urine DNA and its advantages over a two-step protocol.

Cell-free DNA was isolated and quantified from urine as described in Example 31. Aliquots of the purified DNA were processed for library preparation and amplification according to two different protocols as described below.

In the two-step protocol, a 100 ng DNA aliquot was processed for enzymatic repair of termini by incubation in 1×T4 ligase buffer (NEB) with 0.8 units of Klenow fragment of DNA polymerase I (USB Corporation), 0.1 mg/ml of BSA, and 16.7 µM dNTPs for 15 min at 25° C. followed by 10 min at 75° C. in a final volume of 24 µl. For library preparation, repaired DNA was incubated with universal $K_U$ adaptor (Table VI) at 1.25 µM and 800 units of T4 DNA ligase in 32 µl of 1×T4 DNA ligase buffer (NEB) for 1 hour at 25° C. followed by 15 min at 75° C. DNA was precipitated with ethanol in the presence of 0.3 M sodium acetate and 2 µl of PelletPaint (Novagen), washed with 75% ethanol, air dried, and resuspended in 34.4 µl of DNAase-free water. The sample was then supplemented with 4 µl of 10× NEBuffer 4 (NEB) and split into 2 aliquots. Following pre-heating at 70° C. for 5 min and cooling to 37° C. for 2 min one aliquot was digested with 2.66 units each of AciI and HhaI, and 1.33 units each of BstUI, HpaII, and Hinp1I (NEB) for 12 hours at 37° C., followed by 2 hours at 60° C. in a final volume of 20 µl. The second aliquot was incubated in parallel but without restriction enzymes ("uncut" control).

In the single-tube protocol, 100 ng DNA aliquot was processed for enzymatic repair of termini by incubation in 1× NEBuffer 4 (NEB) with 0.8 units of Klenow fragment of DNA polymerase I (USB Corporation), 0.1 mg/ml of BSA, and 16.7 µM dNTPs for 15 min at 25° C. followed by 10 min at 75° C. in a final volume of 24 µl. The sample of repaired DNA was supplemented with universal $K_U$ adaptor (Table VI) at a final concentration of 1.25 µM, 800 units of T4 DNA ligase, and 1 mM ATP in 1× NEBuffer 4 (NEB) added to a final volume of 32 µl. Ligation was carried out for 1 hour at 25° C. followed by 15 min at 75° C. The sample was split into 2 aliquots of 16 µl each. Following pre-heating at 70° C. for 5 min and cooling to 37° C. for 2 min, one aliquot was digested with 2 units each of AciI and HhaI, and 1 unit each of BstUI, HpaII, and Hinp1I (NEB). Sample was incubated for 12 hours at 37° C., followed by 2 hours at 60° C. The second aliquot was incubated in parallel but without restriction enzymes ("uncut" control).

Libraries were amplified using quantitative real-time PCR monitoring by supplementing the reactions with PCR master mix adding to the following final concentrations: 1× Titanium Taq reaction buffer (Clontech), 200 µM of each dNTP, fluorescein calibration dye (1:100,000) and SYBR Green I (1:100,000), 1 µM universal primer $K_U$ (Table VI, SEQ ID NO: 15), 4% DMSO, 200 µM 7-deaza-dGTP (Sigma), and 5 units of Titanium Taq polymerase (Clontech) in a final volume of 75 µl. After initial incubation at 75° C. for 15 min to fill-in the recessed 3' ends of the ligated DNA libraries, amplifications were carried out at 95° C. for 3 min, followed by 13 cycles of 94° C. for 15 sec and 65° C. for 2 min on an I-Cycler real-time PCR instrument (Bio-Rad). Amplified libraries were purified using MultiScreen PCR cleanup (Millipore) and quantified by optical density.

The presence of methylated DNA in the sample template was exhibited by resistance to cleavage with the methylation-sensitive enzyme cocktail and representation in the resulting methylome libraries. Promoter sequences in the amplified libraries were analyzed using quantitative real-time PCR with primers to the relevant cancer genes (Table VII). Aliquots of 75 ng of each DNA sample were assayed by quantitative real-time PCR in reaction mixtures containing: 1× Titanium Taq reaction buffer (Clontech), 200 µM of each dNTP, 4% DMSO, 0.5 M betaine, FCD (1:100,000) and SYBR Green I (1:100,000), 200 nM each forward and reverse primer (Table VII), and 2.5 units of Titanium Taq polymerase (Clontech) in a final volume of 25 µl at 95° C. for 3 min followed by 50 cycles at 94° C. for 15 sec and 68° C. for 1 min.

FIG. 57 shows typical amplification curves comparing libraries prepared with the single tube protocol with the two step protocol. As shown, the cut samples from the single tube protocol had a greatly reduced background as compared to the two step protocol, whereas the uncut samples amplified identically. This results in significant improvement of the dynamic range of the assay. Another apparent advantage of the single tube protocol is reduced hands-on time and improved high throughput and automation capability.

Example 33

Establishing the Dynamic Range and Sensitivity Limits of Methylation Detection in Urine Samples Using Mixed Libraries of Artificially Methylated and Non-Methylated DNA This example demonstrates the sensitivity range of methylation detection in samples of free DNA in urine as disclosed in the present invention.

Cell-free DNA isolated from urine as described in Example 31 was artificially methylated to completion at all CpG sites by incubating 50 ng DNA in 10 µl of NEBuffer 2 (NEB) with 4 units of M.SssI CpG methylase (NEB) in the presence of 160 µM S-adenosylmethionine (SAM) for 1 hour at 37° C.

Input urine DNA shown to be essentially non-methylated across the panel of promoters analyzed (results not shown) was used as a control. Artificially methylated and untreated control DNA samples were mixed at different ratios to a final content of methylated DNA of 0%, 0.01%, 0.1%, 1%, and 10%. Aliquots of each mix containing 50 ng of total DNA were processed for library synthesis using an adaptation of the single step one tube protocol described in Example 32.

Samples were incubated in 1× NEBuffer 4 (NEB) with 0.36 units of T4 DNA polymerase (NEB), 2 µM of dU-Hairpin Adaptor (Table VI, SEQ ID NO:172), 1 unit of uracil-DNA glycosylase (UDG), 800 units of T4 DNA ligase, 40 µM dNTPs, 1 mM ATP, and 0.1 mg/ml BSA for 1 hour at 37° C. in a final volume of 15 µl. The samples were split into 2 equal aliquots and one aliquot was digested with 6.67 units each of AciI and HhaI, and 3.33 units each of BstUI, HpaII, and Hinp1I (NEB) for 12 hours at 37° C., followed by 2 hours at 60° C. in 15 µl of NEBuffer 4. The second aliquot was incubated in parallel but without restriction enzymes ("uncut" control).

Libraries were amplified using quantitative real-time PCR monitoring by supplementing the reactions with PCR master mix adding to final concentrations of: 1× Titanium Taq reaction buffer (Clontech), 200 µM of each dNTP, fluorescein calibration dye (1:100,000) and SYBR Green I (1:100,000), 1 µM universal primer $M_U$-1 (Table VI, SEQ ID NO: 173), 4% DMSO, 200 µM 7-deaza-dGTP (Sigma), and 5 units of Titanium Taq polymerase (Clontech) in a final volume of 75 µl. Amplifications were carried out at 95° C. for 5 min, followed by 15 cycles of 94° C. for 15 sec and 65° C. for 2 min on an I-Cycler real-time PCR instrument (Bio-Rad). Amplified libraries were purified using MultiScreen PCR cleanup (Millipore) and quantified by optical density.

Methylation analysis was performed using real-time PCR with primers directed to a segment of the human MDR-1 promoter. Aliquots of 75 ng of each digested or non-digested DNA sample were assayed by quantitative real-time PCR in reaction mixtures containing: 1× Titanium Taq reaction buffer (Clontech), 200 µM of each dNTP, 4% DMSO, 0.5 M betaine, FCD (1:100,000) and SYBR Green I (1:100,000), 200 nM each forward and reverse primer (Table VII, SEQ ID NO: 174 and SEQ ID NO: 175), and 2.5 units of Titanium Taq polymerase (Clontech) in a final volume of 35 µl at 95° C. for 3 min followed by 50 cycles at 94° C. for 15 sec and 68° C. for 1 min.

Figure 58:
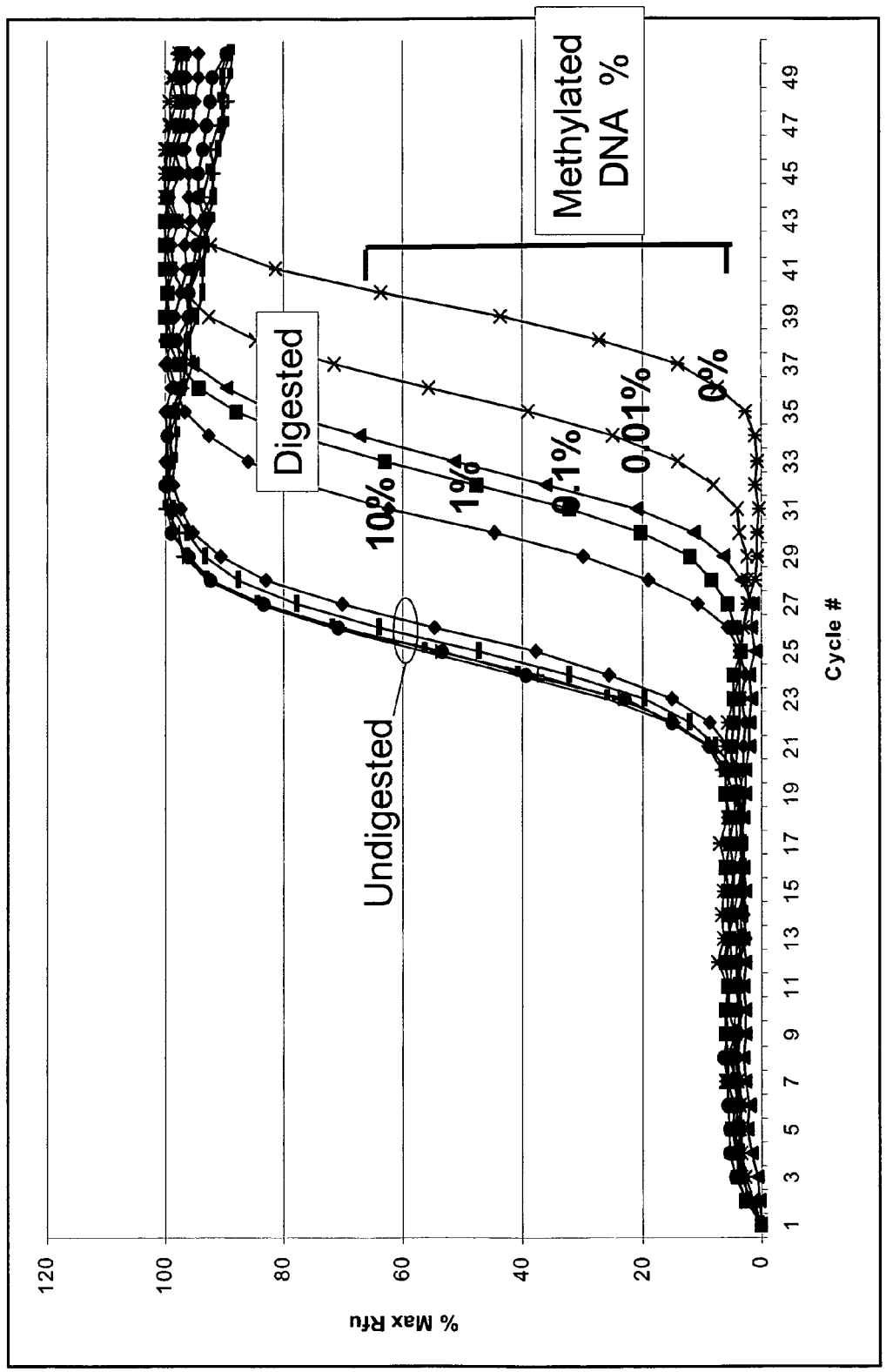
FIG. 58 shows a titration of the amount of methylated DNA in the background of bulk non-methylated DNA. As little as 0.01% of methylated DNA can be reliably detected in the background of 99.99% of non-methylated DNA.

As shown on FIG. 58, as little as 0.01% of methylated DNA can be reliably detected in the background of 99.99% of non-methylated DNA. The figure also shows that the method disclosed in the present invention has a dynamic range of at least 3 orders of magnitude.

Example 34

Comparison Between Klenow Fragment of DNA Polymerase I and T4 DNA Polymerase for their Ability to Preserve Methylation of $C_pG$ Islands During Preparation of Methylome Libraries Cell free DNA in urine or circulating in plasma and serum is likely to be excessively nicked and damaged due to their natural apoptotic source and presence of nuclease activities in blood and urine. During repair of ends using DNA polymerase with 3'-exonuclease activity internal nicks are expected to be extended, a process that can potentially lead to replacement of methyl-cytosine with non-methylated cytosine and loss of the methylation signature. The stronger the strand displacement (or nick-translation) activity of the polymerase, the more likely the 5'-methyl cytosine would be replaced with normal cytosine during the repair process. This example compares two DNA polymerases capable of polishing DNA termini to produce blunt ends and the ability of each to preserve the methylation signature of CpG islands prior to cleavage with methylation-sensitive restriction enzymes.

Cell-free DNA isolated from urine as described in Example 31 was artificially methylated at all CpG sites by incubating 100 ng DNA in 50 µl of NEBuffer 2 (NEB) with 4 units of M.SssI CpG methylase (NEB) in the presence of 160 µM S-adenosylmethionine (SAM) for 1 hour at 37° C.

Two 50 ng aliquots of methylated DNA were processed for enzymatic repair of termini by incubation in 1× NEBuffer 4 (NEB) containing either 0.8 units of Klenow fragment of DNA polymerase I (USB Corporation) or 0.48 units of T4 DNA Polymerase (NEB), 0.1 mg/ml of BSA, and 26.7 µM dNTPs for 15 min at 25° C. followed by 10 min at 75° C. in a final volume of 30 µl. Samples were supplemented with universal $K_U$ adaptor (Table VI) at a final concentration of 1.25 µM, 800 units of T4 DNA ligase, and 1 mM ATP in 1× NEBuffer 4 (NEB) added to a final volume of 38 µl. Ligation was carried out for 1 hour at 25° C. followed by 15 min at 75° C. The samples were split into 2 aliquots of 19 µl each and one aliquot was digested with 10 units each of AciI and HhaI, and 5 units each of BstUI, HpaII, and Hinp1I (NEB for 12 hours at 37° C., followed by 2 hours at 60° C. The second aliquot was incubated in parallel but without restriction enzymes ("uncut" control).

Libraries were amplified and the process was monitored by quantitative real-time PCR by supplementing the reactions with PCR master mix added to final concentrations of: 1× Titanium Taq reaction buffer (Clontech), 200 µM of each dNTP, fluorescein calibration dye (1:100,000) and SYBR Green I (1:100,000), 1 µM universal primer $K_U$ (Table VI, SEQ ID NO: 15), 4% DMSO, 200 µM 7-deaza-dGTP (Sigma), and 5 units of Titanium Taq polymerase (Clontech) in a final volume of 75 µl. After initial incubation at 75° C. for 15 min to fill-in the recessed 3' ends of the ligated DNA libraries, amplifications were carried out at 95° C. for 3 min, followed by 12-14 cycles of 94° C. for 15 sec and 65° C. for 2 min on an I-Cycler real-time PCR instrument (Bio-Rad). Amplified libraries were purified using MultiScreen PCR cleanup (Millipore) and quantified by optical density.

The preservation of methylation signature for each repair process was assessed by amplifying 4 human promoter sites from cut and uncut libraries. Aliquots of 80 ng of each DNA sample were assayed by quantitative real-time PCR in reaction mixtures containing: 1× Titanium Taq reaction buffer (Clontech), 200 µM of each dNTP, 4% DMSO, 0.5 M betaine, FCD (1:100,000) and SYBR Green I (1:100,000), 200 nM each forward and reverse primer (Table IV, SEQ ID NO:30, SEQ ID NO:31, SEQ ID NO:113, SEQ ID NO:114, SEQ ID NO:143, SEQ ID NO:144, and TABLE VII, SEQ ID NO SEQ ID NO:180 and SEQ ID NO:181), and 2.5 units of Titanium Taq polymerase (Clontech) in a final volume of 25 µl at 95° C. for 3 min followed by 50 cycles at 94° C. for 15 sec and 68° C. for 1 min.

As shown on FIG. 59, when fully methylated urine DNA was treated with Klenow fragment of DNA polymerase I prior to restriction cleavage a 2-3 cycle shift of the amplification curves was observed, suggesting that a significant fraction (estimated 75% to 90%) of methyl-cytosine was lost during the DNA end repair. On the other hand, when T4 polymerase was used for DNA end repair, the shift was only one cycle or less depending on the site analyzed. This suggests that 50% or more of the methyl-cytosine was preserved. These results are in agreement with literature data showing that E. coli DNA polymerase I has stronger strand-displacement activity than T4 polymerase. Thus, T4 DNA polymerase is the enzyme of choice, to produce blunt ends for methylome library preparation from urine or other sources of degraded or nicked DNA.

Example 35

Sodium Bisulfite Conversion and Amplification of Whole Methylome Libraries Prepared by Ligation of Universal Adaptor Sequence This example demonstrates that WGA libraries prepared by a modification of the method described in U.S. patent application Ser. No. 10/797,333, filed Mar. 8, 2004, published as U.S. Patent Application Publication No.: 2004/0209299 and is now abandoned, can be converted with sodium bisulfate and amplified to a scale suitable for genome-wide methylation studies using, for example, a methylation-specific PCR method or other available techniques. To protect the adaptor sequences from conversion, dCTP in the nucleotide mix is substituted with methyl-dCTP during fill-in of 3' library ends. The source of DNA can be urine, plasma, serum, feces, sputum, saliva, tissue biopsy, cultured cells, frozen tissue, or any other source suitable for library preparation, for example. This example demonstrates the application of bisulfite-converted DNA libraries and their utility in conjunction with methylation specific restriction digestion (as in Examples 29 and 31). Samples from sources such as serum or urine where a major fraction of DNA may originate from normal cells, and wherein cancer DNA constitutes only a very small fraction (less than 1%), may benefit from increased sensitivity. Application of the invention in this form is particularly important because it greatly reduces or may even completely eliminate non-methylated DNA from the library. As a consequence, techniques other than MSP can be used to quantitatively analyze DNA methylation.

One hundred nanograms of non-methylated cell-free DNA isolated from urine as described in Example 31 was processed for library preparation by incubation in 1× NEBuffer 4 (NEB) comprising 1.5 units of T4 DNA Polymerase (NEB), 0.1 mg/ml of BSA, and 100 µM each of dATP, dGTP, dTTP, and methyl-dCTP for 15 min at 25° C. followed by 10 min at 75° C. in a final volume of 10 µl. Samples were supplemented with universal $K_U$ adaptor (Table VI) at a final concentration of 1.43 µM, 400 units of T4 DNA ligase, and 1 mM ATP in 1× NEBuffer 4 (NEB) added to a final volume of 14 µl. Ligation was carried out for 1 hour at 25° C. followed by 15 min at 75° C. To displace the short oligonucleotide of the adaptor (Table VI, SEQ ID NO: 171) and to fill-in the 3' ends of the library molecules incorporating methyl-cytosine, 1.25 units of Titanium Taq polymerase (BD-Clontech) were added and sample was incubated for 15 min at 72° C. The sample was diluted to 20 µl with water and 18 µl (90% of the total DNA) aliquot was processed for bisulfite conversion using EZ DNA Methylation Kit (Zymo Research cat # D5001) following the manufacturer's protocol. The remaining 10% of the library was left untreated (non-converted control).

Aliquots of the converted library corresponding to 20 ng, 10 ng, 1 ng, and 0.1 ng and aliquots of the non-converted control corresponding to 3 ng, 1 ng, and 0.1 ng were amplified by quantitative real-time PCR in a reaction mixture containing the following final concentrations: 1× Titanium Taq reaction buffer (Clontech), 200 µM of each dNTP, fluorescein calibration dye (1:100,000) and SYBR Green I (1:100,000), 1 µM universal $K_U$ primer (SEQ ID NO: 15), and 5 units of Titanium Taq polymerase (Clontech) in a final volume of 50 ul. Reactions were carried out at 95° C. for 1 min, followed by 23 cycles of 94° C. for 15 seconds and 65° C. for 2 minutes on an I-Cycler real-time PCR instrument (Bio-Rad). Amplified libraries were purified using MultiScreen PCR cleanup (Millipore) and quantified by optical density.

FIG. 60A shows real-time PCR amplification curves for a range of input DNA from libraries of bisulfite converted and non-converted DNA. The calculated threshold cycle for each DNA amount was used to construct standard curves by linear regression analysis (i-Cycler software, Bio-Rad). These calculations showed that approximately 30% of the DNA was amplifiable after sodium bisulfite conversion.

To confirm the conversion of library DNA, the present inventors performed real-time PCR with modified human STS primers specific for converted DNA that do not contain the CpG dinucleotide. Reaction mixtures comprised the following: 1× Titanium Taq reaction buffer (Clontech), 50 ng of converted or non-converted library DNA, 200 µM of each dNTP, FCD (1:100,000) and SYBR Green I (1:100,000), 200 nM each forward and reverse primer (Table VIII), and 2.5 units of Titanium Taq polymerase (Clontech) in a final volume of 25 µl at 95° C. for 3 min followed by 50 cycles at 94° C. for 15 sec and 68° C. for 1 min.

TABLE VIII

PRIMER PAIRS USED FOR ANALYSIS OF BISULFITE-CONVERTED AMPLIFIED LIBRARIES

| UniSTS # | | Sequence (5'-3') | |
|---|---|---|---|
| 175841 | F | TTTGATGTTAGGATATGTTGAAA | (SEQ ID NO: 182) |
| | R | AAAAACAAAAAAAATCTCTTAAC | (SEQ ID NO: 183) |
| 170707 | F | ATTTACTACTTAATATTACCTAC | (SEQ ID NO: 184) |
| | R | TTATGTGTGGGTTATTAAGGATG | (SEQ ID NO: 185) |

As shown on FIG. 60B, real-time PCR curves from converted DNA were 8 to 10 cycles earlier. Also, only the amplification products from converted library were of the expected size (data not shown).

Example 36

Enrichment of Libraries Prepared from AluI Digested Genomic DNA for Promoter Sequences by Heat Treatment This example demonstrates that libraries prepared from AluI-digested DNA essentially as described in U.S. patent application Ser. No. 10/797,333, filed Mar. 8, 2004, published as U.S. Patent Application Publication No.: 2004/0209299 and is now abandoned, can be enriched for promoter sequences by pre-heating fragmented DNA prior to library preparation at temperatures that will selectively denature subsets of DNA fragments based on their GC content thus making a fraction of the genome incompetent for ligation.

Human genomic DNA isolated from the peripheral blood of a healthy donor by standard procedures was digested with 10 units of AluI restriction endonuclease (NEB) for 1 hour following the manufacturer's protocol. Aliquots of 70 ng were pre-heated in 15 µl of 1× NEBuffer 4 (NEB) for 10 min at 75° C. (control), 83° C., 84.1° C., 85.3° C., 87° C., 89.1° C., 91.4° C., 93.5° C., 94.9° C., 96° C., or 97° C. followed by snap-cooling at −10° C. in ice/ethanol bath.

For library preparation, the pre-heated DNA samples were incubated in a reaction mixture comprising 1× NEBuffer 4, 1.25 µM of universal $K_U$ adaptor (Table VI), 800 units of T4 DNA ligase, and 1 mM ATP in a final volume of 21 µl. Ligation was carried out for 1 hour at 25° C. followed by 15 min at 75° C.

Libraries were amplified by quantitative PCR by supplementing the reactions with PCR master mix adding to the following final concentrations: 1× Titanium Taq reaction buffer (Clontech), 200 µM of each dNTP, fluorescein calibration dye (1:100,000) and SYBR Green I (1:100,000), 1 µM universal primer $K_U$ (Table VI, SEQ ID NO: 15), 4% DMSO, 200 µM 7-deaza-dGTP (Sigma), and 5 units of Titanium Taq polymerase (Clontech) in a final volume of 75 µl. After initial incubation at 75° C. for 15 min to fill-in the recessed 3' ends of the ligated DNA libraries, amplifications were carried out at 95° C. for 3 min, followed by cycling at 94° C. for 15 sec and 65° C. for 2 min on an I-Cycler real-time PCR instrument (Bio-Rad). Amplified libraries were purified using Multi-Screen PCR cleanup system (Millipore) and quantified by optical density reading.

Forty nanograms of purified library DNA were used to analyze promoter sequences of high, intermediate, or low GC content by quantitative PCR as exemplified by the GSTP-1, MDR-1, and APC promoters, respectively. Quantitative PCR was performed in reaction mixtures comprising the following: 1× Titanium Taq reaction buffer (Clontech), 200 µM of each dNTP, 4% DMSO, 0.5 M betaine, FCD (1:100,000) and SYBR Green I (1:100,000), 200 nM each forward and reverse primer (Table VII, SEQ ID NO:176 and SEQ ID NO:177 for GSTP-1 promoter, SEQ ID NO:113 and SEQ ID NO:114 for APC-1 promoter, and SEQ ID NO:139 and SEQ ID NO:140 for MDR-1 promoter), and 1.5 units of Titanium Taq polymerase (Clontech) in a final volume of 15 µl at 95° C. for 3 min followed by 50 cycles at 94° C. for 15 sec and 68° C. for 1 min.

Figure 61A:
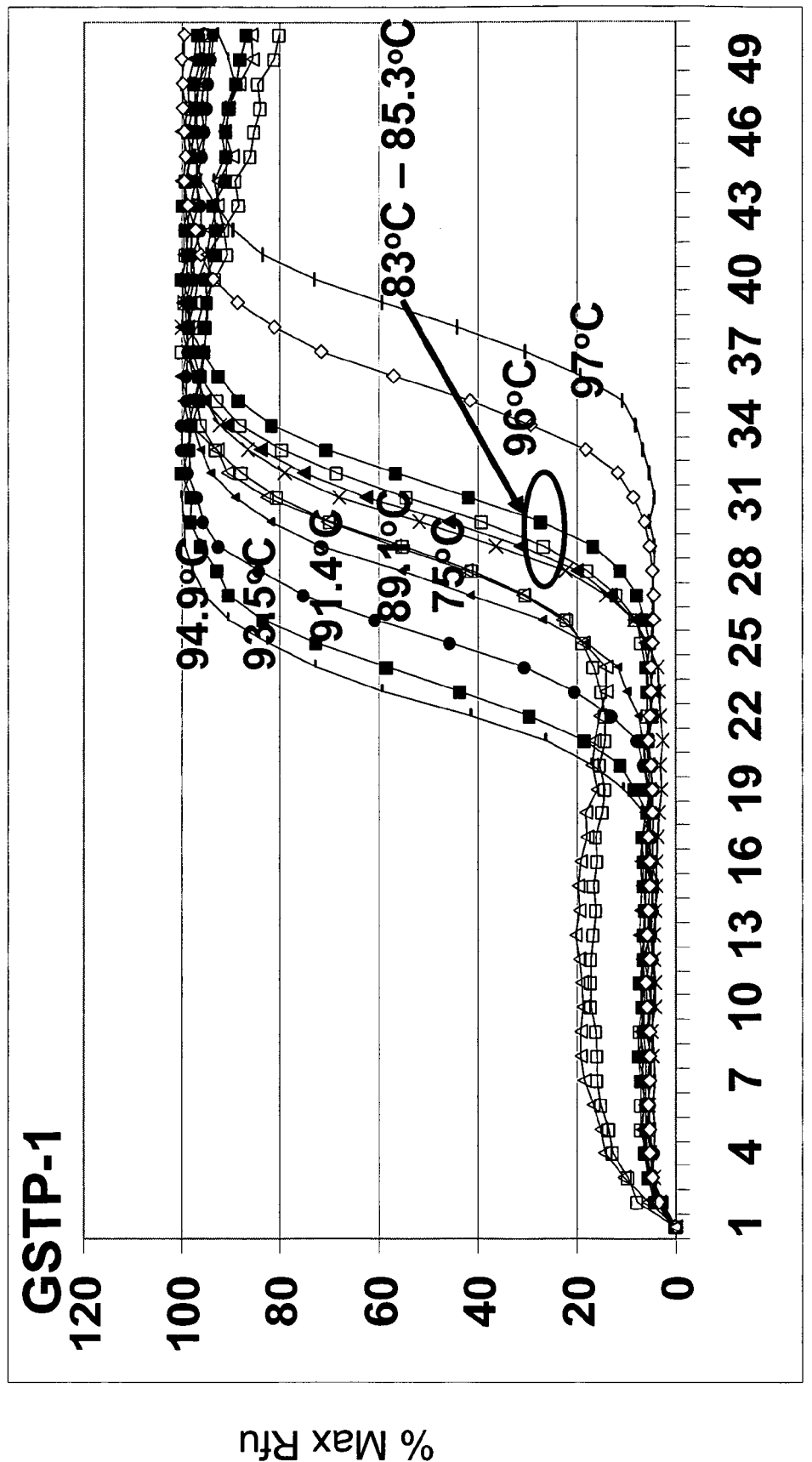
FIGS. 61A, 61B, and 61C illustrate the complex effects of pre-heating to various temperatures of Alu I restriction fragments prior to preparation of methylome libraries by ligation of universal adaptor on the relative presence of promoter sequences. Promoter sequences of high, intermediate, or low GC content are analyzed by quantitative PCR as exemplified by the GSTP-1 (FIG. 61A), MDR-1 (FIG. 61B), and APC (FIG. 61C) promoters respectively. Differential enrichment of library fragments based on their GC content is demonstrated.
Figure 61B:
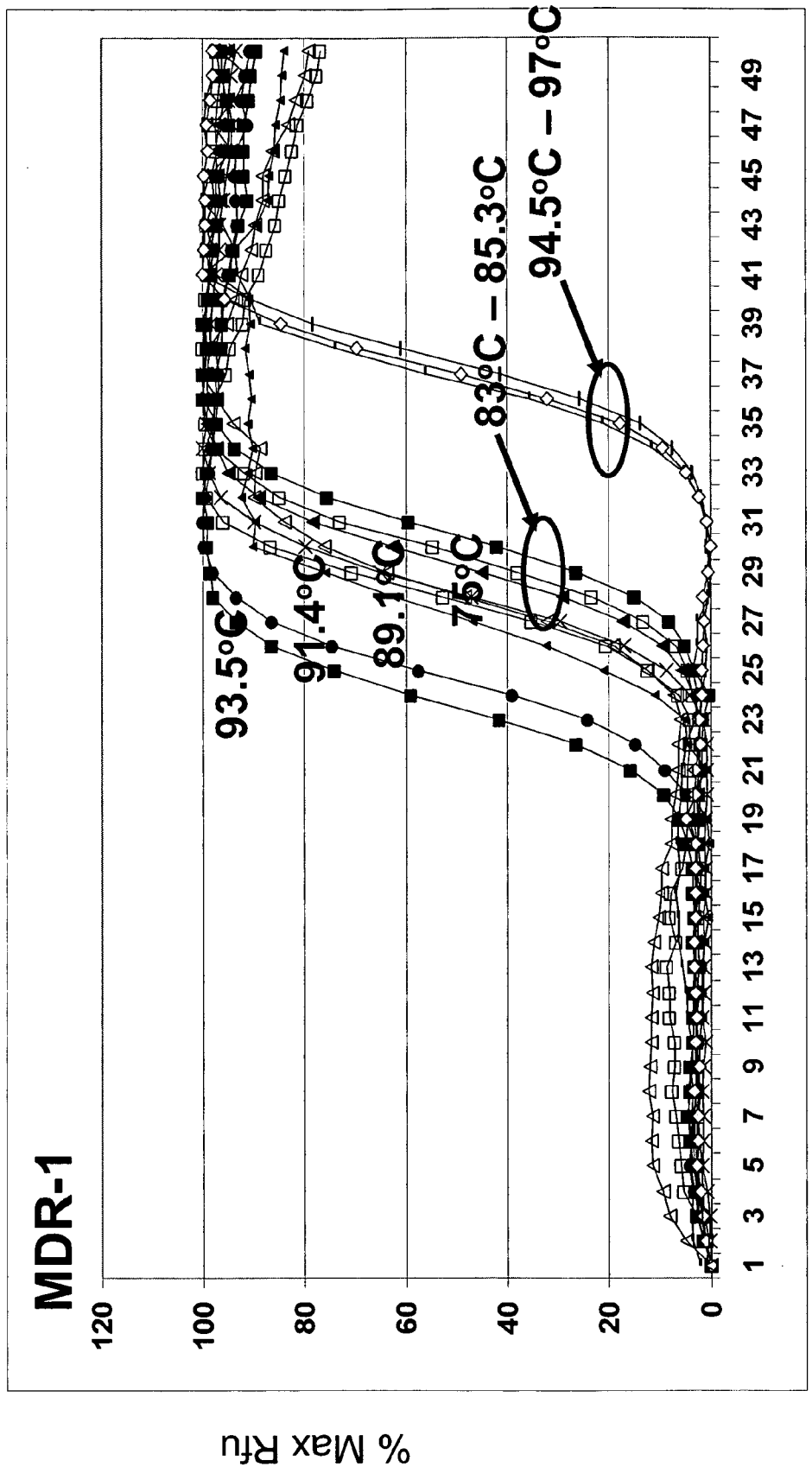
Figure 61C:
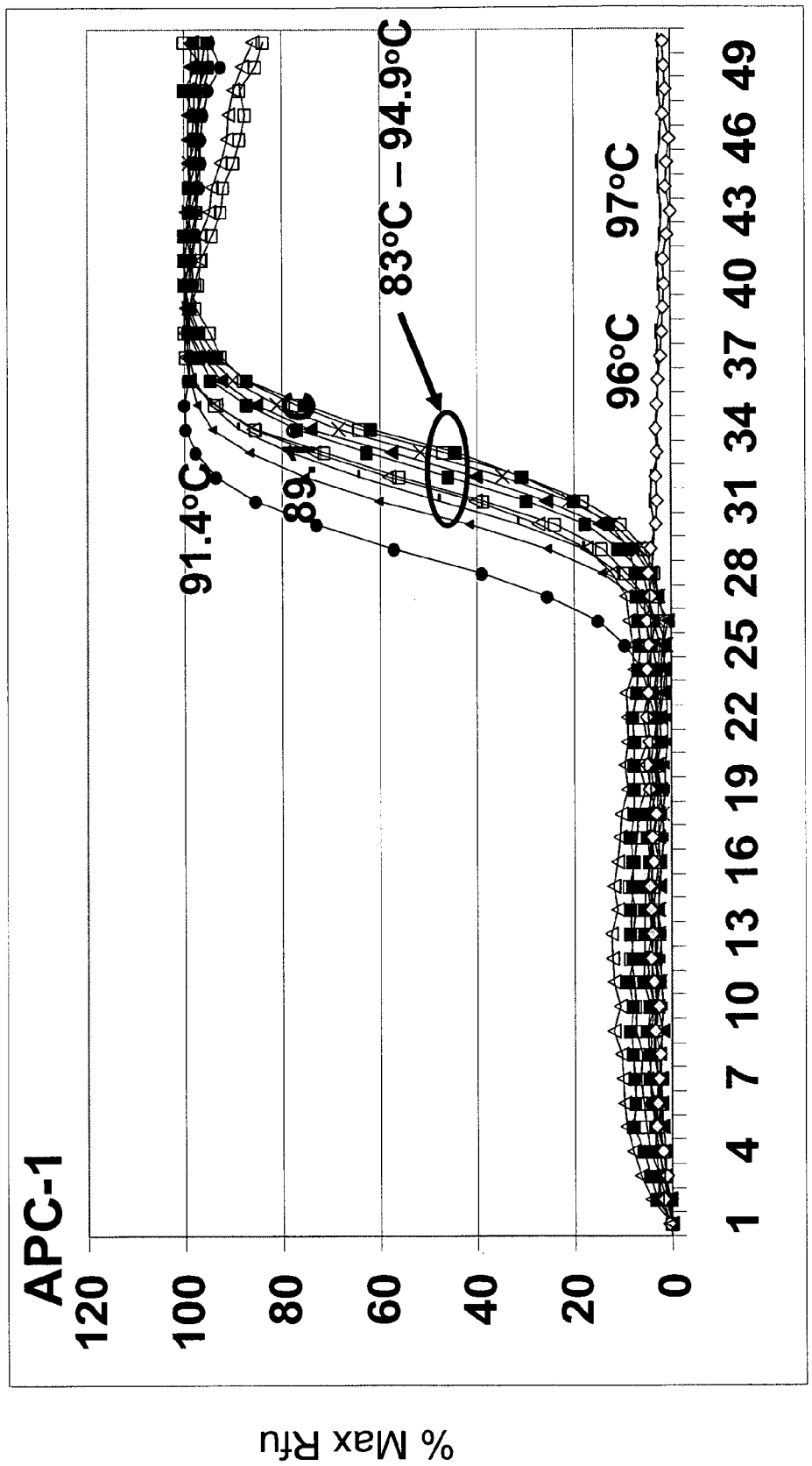

As shown on FIGS. 61A, 61B, and 61C, a complex pattern of temperature dependent shifts of the amplification curves was observed relative to the control treatment of 75° C. Temperatures of between 89° C. and 94° C. resulted in enrichment of on average 2 to 7 cycles (4 to 128 fold) for promoter sites of high to intermediate GC content (FIGS. 61A and 61B) whereas temperatures between 83° C. and 85° C. resulted in 1-2 cycles (2 to 4 times) less efficient amplification. For the lower GC content APC-1 promoter site, the optimal temperature for enrichment was 91.5° C. resulting in about 8-fold enrichment, whereas higher temperatures caused reduced amplification. For all three promoter sites, pre-heating at about 95° C. to 97° C. caused significant reduction of copy number and complete denaturing for the low GC content APC promoter site.

Example 37

Enrichment of Libraries Prepared from Cell-Free Urine DNA for Promoter Sequences by Heat Treatment This example demonstrates that methylome libraries prepared from cell-free urine DNA can be enriched for promoter sequences by pre-heating prior to library preparation at temperatures that will selectively denature the fraction of DNA having below average GC content making the more easily denatured fragments incompetent for ligation.

Cell-free DNA was isolated and quantified from the urine of a healthy donor as described in Example 31. Aliquots of 22 ng of purified DNA were either heat-treated directly or processed for enzymatic repair of termini with Klenow fragment of DNA polymerase I before heat treatment.

The first set of samples were heated in duplicate directly for 10 min at 75° C. (control), 89° C., 91° C., or 93° C. in 13 µl of NEBuffer 4 (NEB) followed by cooling on ice.

The second set of samples were first incubated in 1× NEBuffer 4 (NEB) with 0.4 units of Klenow fragment of DNA polymerase I (USB Corporation), 0.1 mg/ml of BSA, and 13.3 µM dNTPs for 15 min at 25° C. followed by 10 min at 75° C. in a final volume of 15 µl. After polishing, samples were heated for 10 min at 75° C. (control), 89° C., 91° C., or 93° C., followed by cooling on ice.

The first set was polished after heating by incubation with 0.4 units of Klenow fragment of DNA polymerase I (USB Corporation), 0.1 mg/ml of BSA, and 13.3 µM dNTPs for 15 min at 25° C. followed by 10 min at 75° C. in a final volume of 15 µl.

Both sets of samples were then ligated to universal blunt-end adaptor in a reaction mixture comprising 1.25 µM $K_U$ adaptor (Table VI), 800 units of T4 DNA ligase, and 1 mM ATP in 1× NEBuffer 4 (NEB) added to a final volume of 21 µl. Ligations were carried out for 1 hour at 25° C. followed by 15 min at 75° C.

Half of the first set of samples (treated before polishing) was subjected to digestion with a cocktail of methylation-sensitive restriction enzymes comprising 5.8 units of AciI and HhaI, and 2.9 unit of BstUI, HpaII, and Hinp1I (NEB) in 1× NEBuffer 4 for 12 hours at 37° C., followed by 2 hours at 60° C. The second half was incubated in parallel but without restriction enzymes ("uncut" controls).

Libraries were amplified by quantitative real-time PCR by supplementing the reactions with PCR master mix adding to the following final concentrations: 1× Titanium Taq reaction buffer (Clontech), 200 µM of each dNTP, fluorescein calibration dye (1:100,000) and SYBR Green I (1:100,000), 1 µM universal primer $K_U$ (Table VI, SEQ ID NO: 15), 4% DMSO, 200 µM 7-deaza-dGTP (Sigma), and 5 units of Titanium Taq polymerase (Clontech) in a final volume of 75 µl. After initial incubation at 75° C. for 15 min to fill-in the recessed 3' ends of the ligated DNA libraries, amplifications were carried out at 95° C. for 3 min, followed by cycling at 94° C. for 15 sec and 65° C. for 2 min on an I-Cycler real-time PCR instrument (Bio-Rad). Amplified libraries were purified using Multi-Screen PCR cleanup system (Millipore) and quantified by optical density reading.

Aliquots of 80 ng of each amplified library were used to analyze promoter sequences for enrichment by Q-PCR in reaction mixtures comprising: 1× Titanium Taq reaction buffer (Clontech), 200 µM of each dNTP, 4% DMSO, 0.5 M betaine, FCD (1:100,000) and SYBR Green I (1:100,000), 200 nM each forward and reverse primer (Table VII, SEQ ID NO:176 and SEQ ID NO:177 for GSTP-1 promoter, SEQ ID NO:113 and SEQ ID NO:114 for APC-1 promoter, SEQ ID NO:139 and SEQ ID NO:140 for MDR-1 promoter, SEQ ID NO:163 and SEQ ID NO:164 for CD-44, and Table IX, SEQ ID NO:186 and SEQ ID NO:187 for p16 Exon 2), and 1.5 units of Titanium Taq polymerase (Clontech) in a final volume of 15 µl at 95° C. for 3 min followed by 50 cycles at 94° C. for 15 sec and 68° C. for 1 min.

TABLE IX

PRIMERS USED FOR ANALYSIS OF p16 EXON 2

| Promoter | Sequence (5'-3')* | |
|---|---|---|
| P16 (CDKN2A) Exon 2 | F CAAGCTTCCTTTCCGTCATGCC<br>R AGCACCACCAGCGTGTCCA | (SEQ ID NO: 186)<br>(SEQ ID NO: 187) |

*F = Forward Primer, R = Reverse Primer

FIG. 62A shows the analysis of four promoter sequences in libraries prepared from samples heated after enzymatic repair (set 2 described above). Heat-treatment at 89° C. resulted in maximal enrichment in all tested promoter sites causing a shift between 4 and 7 cycles (16- to 128-fold enrichment), whereas heating at 91° C. resulted in enrichment only for the GC-rich GSTP-1 promoter but had no effect or resulted in delayed amplification for the rest of the promoters. On the other hand, treatment at 93° C. resulted in significant reduction of the copy number of all promoter sites analyzed in cell-free urine DNA libraries.

FIG. 62B shows a comparison between heat-treated samples before enzymatic repair (set 1 above) with or without subsequent cleavage with methylation-sensitive restriction enzymes for two CpG islands. As shown, significant enrichment was observed for both CpG islands for libraries pre-treated at 89° C. or 91° C. that were not cut with restriction enzymes. However, no effect of the heat-treatment was found for the samples that were digested with restriction enzymes when the GSTP promoter was analyzed indicating that the cleavage was complete for this site. On the other hand, when a different CpG site reported to be aberrantly methylated in cancer, p16 Exon 2, was analyzed, both cut and uncut samples were enriched in a similar way by the heat-treatment, suggesting that the enzymatic digestion was perhaps incomplete. In summary, maximal enrichment of promoter sites in libraries prepared from cell-free urine DNA was obtained after pre-heating at 89° C. to 91° C.

Example 38

One Step Preparation of Methylome Libraries from Cell-Free Urine DNA by Ligation of Degradable Hairpin Adaptor and their Utility for Analysis of Promoter Hyper-Methylation Following Cleavage with Methylation-Sensitive Restriction Enzymes In this example, a single step preparation of methylome libraries from cell-free urine DNA is described where a hairpin oligonucleotide adaptor containing deoxy-uridine in both its 5' stem region and in its loop (Table VI, SEQ ID NO:172) is ligated via its free 3' end to the 5' phosphates of target DNA molecules in the presence of 3 enzymatic activities: T4 DNA ligase, DNA polymerase, and Uracil-DNA glycosylase (UDG). UDG catalyses the release of free uracil and creates abasic sites in the adaptor's loop region and the 5' half of the hairpin. The strand-displacement activity of the DNA polymerase extends the free 3' end of the restriction fragments until abasic site is reached serving as a replication stop. This process results in truncated 3' ends of the library fragments such that they do not have terminal inverted repeats. The entire process takes place in a single tube in one step and is completed in just 1 hour.

Cell-free DNA isolated from urine as described in Example 31 was artificially methylated by incubating 200 ng DNA in 20 µl of NEBuffer 2 (NEB) with 4 units of M.SssI CpG methylase (NEB) in the presence of 160 µM SAM for 1 hour at 37° C.

Fifty nanograms of methylated or non-methylated DNA were incubated in 1× NEBuffer 4 (NEB) with 0.7 units of T4 DNA polymerase (NEB), 2 µM of dU-Hairpin Adaptor (Table VI, SEQ ID NO:172), 1 unit of uracil-DNA glycosylase (UDG), 800 units of T4 DNA ligase, 40 µM dNTPs, 1 mM ATP, and 0.1 mg/ml BSA for 1 hour at 37° C. in a final volume of 30 µl. The samples were split into 2 equal aliquots and one aliquot was digested with 20 units of AciI and HhaI, and 10 units of BstUI, HpaII, and Hinp1I (NEB) for 12 hours at 37° C., followed by 2 hours at 60° C. in 50 µl of NEBuffer 4. The second aliquot was incubated in parallel but without restriction enzymes ("uncut" control).

Aliquots of 5 ng were amplified by quantitative PCR in a reaction mix comprising 1× Titanium Taq reaction buffer (Clontech), 200 µM of each dNTP, fluorescein calibration dye (1:100,000) and SYBR Green I (1:100,000), 1 µM universal primer $M_U$-1 (Table VI, SEQ ID NO: 173), 4% DMSO, 200 µM 7-deaza-dGTP (Sigma), and 5 units of Titanium Taq polymerase (Clontech) in a final volume of 75 µl. Samples were pre-heated at 72° C. for 15 min followed by 95° C. for 5 min and cycling at 94° C. for 15 sec and 65° C. for 2 min on an I-Cycler real-time PCR instrument (Bio-Rad). Amplified libraries were purified using MultiScreen PCR cleanup system (Millipore) and quantified by optical density reading.

Methylation analysis of promoter sites was performed by real-time PCR using aliquots of 160 ng of each digested or non-digested amplified library DNA incubated in reaction mixtures containing: 1× Titanium Taq reaction buffer (Clontech), 200 µM of each dNTP, 4% DMSO, 0.5 M betaine, FCD (1:100,000) and SYBR Green I (1:100,000), 200 nM each forward and reverse primer (Table VII, SEQ ID NO:137 and SEQ ID NO:138 for PTGS-1 promoter, SEQ ID NO:174 and SEQ ID NO:175 for MDR-1 promoter, SEQ ID NO:141 and SEQ ID NO:142 for EDNRB promoter, and Table X, SEQ ID NO:188 and SEQ ID NO:189), and 1.5 units of Titanium Taq polymerase (Clontech) in a final volume of 15 µl at 95° C. for 3 min followed by 50 cycles at 94° C. for 15 sec and 68° C. for 1 min.

TABLE X

PRIMERS USED FOR ANALYSIS OF APC-1 PROMOTER

| Promoter | Sequence (5'-3')* | |
|---|---|---|
| APC-1 | F CTCCCTCCCACCTCCGGCATCT | (SEQ ID NO: 188) |
| | R CGCTTCCCGACCCGCACTC | (SEQ ID NO: 189) |

*F = Forward Primer, R = Reverse Primer

FIG. 63 shows PCR amplification curves of specific promoter sites from amplified libraries prepared from methylated or non-methylated urine DNA with or without cleavage with methylation-sensitive restriction enzymes. As expected, promoter sites from non-methylated cleaved DNA amplified with significant (at least 10 cycles) delay as compared to uncut DNA for all four promoter sites tested. On the other hand, methylated DNA was refractory to cleavage.

Example 39

Simplified Protocol Combining Preparation of Methylome Libraries from Cell-Free Urine DNA and Cleavage with Methylation-Sensitive Restriction Enzymes in One Step In this example the preparation of methylome libraries from cell-free urine DNA by ligation of hairpin oligonucleotide adaptor comprising deoxy-uridine as described in Example 38 is combined with the simultaneous cleavage with a mix of methylation-sensitive restriction enzymes in a single step.

Cell-free DNA isolated from urine as described in Example 31 was artificially methylated by incubating 200 ng DNA in 20 µl of NEBuffer 2 (NEB) with 4 units of M.SssI CpG methylase (NEB) in the presence of 160 µM SAM for 1 hour at 37° C.

Twenty five nanograms of methylated or non-methylated DNA were incubated in 1× NEBuffer 4 (NEB) comprising 0.35 units of T4 DNA polymerase (NEB), 1.5 µM of dU-Hairpin Adaptor (Table VI, SEQ ID NO:172), 0.5 units of UDG (NEB), 400 units of T4 DNA ligase (NEB), 30 µM dNTPs, 0.75 mM ATP, 75 µg/ml BSA, 16.7 units of AciI, 16.7 units of HhaI, 8.3 units each of BstUI, HpaII, and Hinp1I (NEB) in a final volume of 20 µl for 1 hour at 37° C. A second aliquot of 25 ng of methylated or non-methylated DNA was incubated in parallel with all the ingredients described above but without the restriction enzymes ("uncut" control).

One half of each sample (12.5 ng) was then amplified by quantitative PCR in reaction mix comprising 1× Titanium Taq reaction buffer (Clontech), 200 µM of each dNTP, fluorescein calibration dye (1:100,000) and SYBR Green I (1:100,000), 1 µM universal primer $M_U$-1 (Table VI, SEQ ID NO: 173), 4% DMSO, 200 µM 7-deaza-dGTP (Sigma), and 5 units of Titanium Taq polymerase (Clontech) in a final volume of 75 µl. Samples were pre-heated at 72° C. for 15 min followed by 95° C. for 5 min and 12 cycles at 94° C. for 15 sec and 65° C. for 2 min on an I-Cycler real-time PCR instrument (Bio-Rad). Amplified libraries were purified using MultiScreen PCR cleanup system (Millipore) and quantified by optical density reading.

Methylation analysis of promoter sites was performed by real-time PCR using aliquots of 160 ng of each digested or non-digested amplified library DNA incubated in reaction mixtures containing: 1× Titanium Taq reaction buffer (Clontech), 200 µM of each dNTP, 4% DMSO, 0.5 M betaine, FCD (1:100,000) and SYBR Green I (1:100,000), 200 nM each forward and reverse primer (Table VII, SEQ ID NO:176 and SEQ ID NO:177 for GSTP-1 promoter, SEQ ID NO:174 and SEQ ID NO:175 for MDR-1 promoter, SEQ ID NO:141 and SEQ ID NO:142 for EDNRB promoter, and SEQ ID NO:178 and SEQ ID NO:179 for PTGS-2 promoter), and approximately 1.5 units of Titanium Taq polymerase (Clontech) in a final volume of 15 µl at 95° C. for 3 min followed by 50 cycles at 94° C. for 15 sec and 68° C. for 1 min.

FIG. 64 shows PCR amplification curves of specific promoter sites in amplified libraries prepared from methylated or non-methylated urine DNA in the presence or in the absence of methylation-sensitive restriction enzymes. As expected, promoter sites from non-methylated cleaved DNA amplified with significant (at least 10 cycles) delay as compared to uncut DNA for all four promoter sites tested. On the other hand, methylated DNA was completely refractory to cleavage. These results demonstrate that the method disclosed in the present invention can be applied as a simple one-step non-invasive high-throughput diagnostic procedure for detection of aberrant methylation in cancer.

Example 40

Methylation Detection Sensitivity of Methylome Libraries Prepared from Dilutions of LNCaP Prostate Cancer Cell Line DNA in Control Non-Methylated DNA This example describes the analysis of methylation sensitivity detection using libraries prepared by incorporation of universal sequence and amplification with self-inert primers of DNA from prostate cancer cell line (LnCap) DNA diluted in normal non-methylated DNA following cleavage with methylation-sensitive restriction enzymes.

Primary Methylome libraries were prepared from 20 ng genomic DNA isolated by standard procedure from LNCaP prostate cancer cell line (Coriell Institute for Medical Research), and from normal "unmethylated" DNA, (Coriell Institute for Medical Research repository # NA07057), or from mixtures of these two DNAs (see Table 1). Twenty nanogram aliquots of DNA (0, 0.1, 1, 3, 10 and 100% LnCap mixtures) were pre-heated at 80° C. for 20 min in 92 µl reactions comprising 1× NEBuffer 4 (NEB). Samples were cooled to 37° C. for 2 min and split into two PCR tubes. Two µl of TE buffer were added to the "uncut" tube and 6.7 units each of AciI and HhaI+3.3 units each of BstUI, HpaII, and Hinp1I (NEB) were added to the "cut" tube. Samples were then incubated for 12 hours at 37° C., followed by 2 hours at 60° C. The DNA was precipitated with ethanol in the presence of 0.3 M sodium acetate and 2 µl of Pellet Paint (Novagen), washed with 75% ethanol, air dried, and resuspended in 10 µl of TE-L buffer. Each tube comprising 10 ng of uncut or cut DNA were randomly fragmented in TE-L buffer by heating at 95° C. for 4 minutes and subjected to library synthesis. The reaction mixtures comprised 10 ng of fragmented DNA in 1× EcoPol buffer (NEB), 200 µM of each dNTP (USB), 200 µM of 7-deaza-dGTP (Sigma), 4% DMSO(Sigma), 360 ng of Single Stranded DNA Binding Protein (USB), and 1 µM of $K(N)_2$ primer (SEQ ID NO:14) in a final volume of 13 µl. After denaturing for 2 minutes at 95° C., the samples were cooled to 24° C., and the reactions were initiated by adding 5 units of Klenow Exo– DNA polymerase (NEB). Samples were incubated at 24° C. for 1 hour and the reactions were terminated by heating for 5 minutes at 75° C. Libraries were then amplified by quantitative real-time PCR in a reaction mixture containing the following final concentrations: 1× Titanium Taq reaction buffer (Clontech), 200 µM of each dNTP (USB), fluorescein calibration dye (1:100,000) (Bio-rad) and SYBR Green I (1:100,000) (BioWhittaker Molecular Applications), 1 µM universal $K_U$ primer (SEQ ID NO: 15), 4% DMSO (Sigma), 200 µM 7-deaza-dGTP (Roche), and 0.5× of Titanium Taq polymerase (Clontech) in a final volume of 754 Reactions were carried out at 95° C. for 3.5 min, followed by 14 cycles of 94° C. for 15 seconds and 65° C. for 2 minutes on an I-Cycler real-time PCR instrument (Bio-Rad). Amplified libraries were purified using Multi-Screen PCR cleanup system (Millipore) and quantified by optical density reading.

TABLE XI

DILUTIONS OF LNCap DNA

| % Cancer DNA | LnCap (ng) | Control (ng) |
|---|---|---|
| 100 | 20 | 0 |
| 30 | 6 | 14 |
| 10 | 2 | 18 |
| 3 | 0.6 | 19.4 |
| 1 | 0.2 | 19.8 |
| 0.1 | 0.02 | 19.98 |
| 0 | 0 | 20 |

Aliquots of 75 ng of each DNA sample were analyzed by quantitative real-time PCR in reaction mixtures comprising the following containing 1× Titanium Taq reaction buffer (Clontech), 200 µM of each dNTP (USB), 4% DMSO (Sigma), 0.5M Betaine (Sigma), FCD (1:100,000) (Bio-Rad) and SYBR Green I (1:100,000) (BioWhittaker Molecular Applications), 200 nM each forward and reverse primer (Table IV, SEQ ID NO:113 and SEQ ID NO:114 for APC-1 promoter, SEQ ID NO:30 and SEQ ID NO:31 for GSTP-1, and SEQ ID NO:107 and SEQ ID NO:108 for BRCA-1 promoter), and 0.5× of Titanium Taq polymerase (Clontech) in a final volume of 15 µl at 95° C. for 3.5 min followed by 50 cycles at 94° C. for 15 sec and 68° C. for 1 min.

FIG. 65 shows the threshold cycle (Ct) difference between cut and uncut methylome libraries from real time PCR for three promoter primer pairs with various percentages of prostate cell line (LnCap) DNA in the libraries. If the methylation sensitive restriction enzymes (AciI, HhaI, BstUI, HpaII, and Hinp1I) failed to cut a site between the promoter primer pairs due to the presence of methylation, the target promoter site would amplify similarly to the uncut library control, and the ΔCt(Cut)-ΔCt(Uncut) would approach zero. Both the APC1-3 and GSTP1-1 gene promoter region primers demonstrated the presence of target promoter DNA, and thus protection from methylation-sensitive restriction enzymes cutting with as little as 1% or less of cancer cell line DNA present, indicating a sensitivity detection limit of at least 99%.

Example 41

Amplifiability and Cleavage of Cell-Free Urine DNA And Methylome Library Prepared from Cell-Free Urine DNA with Methylation-Sensitive Restriction Enzymes This example describes the comparison of amplifiability of promoter sites in cell-free urine DNA with that of non-amplified methylome library prepared from cell-free urine DNA with or without cleavage with methylation-sensitive restriction enzymes.

Cell-free DNA was isolated from urine as described in Example 31. A sample of 50 ng DNA was diluted to 1 ng/µl in 1× NEBuffer 4 and split into 2 equal aliquots. One aliquot was digested with 10 units of AciI and HhaI, and 5 units each of BstUI, HpaII, and Hinp1I (NEB) in a final volume of 28 µl for 12 hours at 37° C., followed by 2 hours at 60° C. in 50 µl of NEBuffer 4. The second aliquot was incubated in parallel but without restriction enzymes ("uncut" control).

Another sample of 50 ng DNA was processed for library preparation by incubation in 1× NEBuffer 4 (NEB) with 1.2 units of Klenow fragment of DNA polymerase I (USB Corporation), 2 µM of dU-Hairpin Adaptor (Table VI, SEQ ID NO:172), 1 unit of uracil-DNA glycosylase (UDG), 800 units of T4 DNA ligase, 40 µM dNTPs, 1 mM ATP, and 0.1 mg/ml BSA for 1 hour at 37° C. in a final volume of 15 µl. The library was diluted to 50 µl in 1× NEBuffer 4 and split into 2 equal aliquots. One aliquot was digested with 10 units of AciI and HhaI, and 5 units each of BstUI, HpaII, and Hinp1I (NEB) for 12 hours at 37° C., followed by 2 hours at 60° C. in 28 µl of NEBuffer 4. The second aliquot was incubated in parallel but without restriction enzymes ("uncut" control).

Aliquots of 6.25 ng of both cut and uncut urine DNA and non-amplified methylome library DNA were analyzed for promoter sequences by quantitative PCR in a reaction mix comprising 1× Titanium Taq reaction buffer (Clontech), 200 µM of each dNTP, fluorescein calibration dye (1:100,000) and SYBR Green I (1:100,000), 200 nM each forward and reverse primer (Table VII, SEQ ID NO:176 and SEQ ID NO:177 for GSTP-1 promoter and SEQ ID NO:113 and SEQ ID NO:114 for APC-1 promoter), 4% DMSO, 0.5 M betaine (Sigma), and 5 units of Titanium Taq polymerase (Clontech) in a final volume of 75 µl. Samples were pre-heated at 72° C. for 15 min followed by 95° C. for 5 min and cycling at 94° C. for 15 sec and 68° C. for 2 min on an I-Cycler real-time PCR instrument (Bio-Rad).

Figure 67:
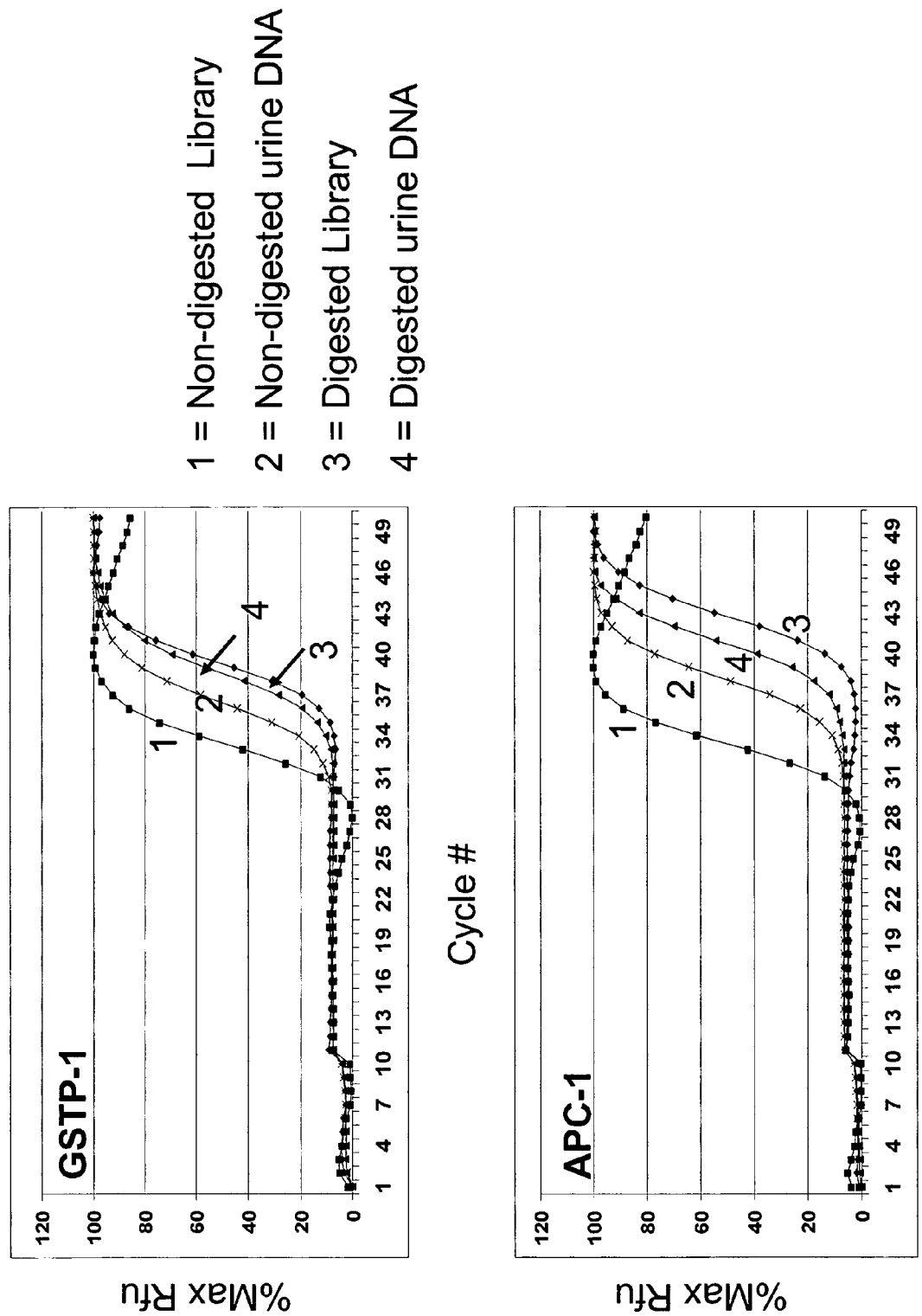
FIG. 67 shows amplification curves for two promoter sites from crude cell-free urine DNA as compared to non-amplified methylome library prepared from cell-free urine DNA with or without cleavage with methylation-sensitive restriction enzymes. Significant improvement of both PCR amplifiability and cleavage with restriction enzymes is observed after enzymatic processing of urine DNA during one-step methylome library preparation.

FIG. 67 shows amplification curves for two promoter sites. As shown, processing of cell-free DNA through the enzymatic treatments of methylome library preparation resulted in: a) improved PCR amplifiability of promoter sites and b) improved cleavage with restriction enzymes. The amplification of promoter sites improved between 4 and 6 cycles (16 to 64-fold), whereas the cleavage with a mix of restriction enzymes increased from an average of 3 cycles difference between digested and non-digested crude urine DNA to between 7 and 10 cycles difference between digested and non-digested library DNA. Thus, the fraction of cell-free urine DNA that is in double-stranded conformation after enzymatic treatment is at least 10 times greater than the DNA prior to the treatment.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference.

PATENTS

PCT WO 99/28498
PCT WO 00/50587
PCT WO 03/035860
PCT WO 03/035860A1
PCT WO 03/027259A2
PCT WO 03/025215A1
PCT WO 03/080862A1
PCT WO 03/087774 A2
U.S. Pat. No. 6,214,556
U.S. Pat. No. 6,261,782
U.S. Pat. No. 6,300,071
U.S. Pat. No. 6,383,754
U.S. Pat. No. 6,605,432
U.S. Patent Application No. 20010046669
U.S. Patent Application No. 20030099997A1
U.S. Patent Application No. 20030232371A1
U.S. Patent Application No. 20030129602A1
U.S. Patent Application No. 20050009059A1

PUBLICATIONS

Advances in Immunology, Academic Press, New York.
Annual Review of Immunology, Academic Press, New York.
Akey, D. T., Akey, J. M., Zhang, K., Jin, L. 2002. Assaying DNA methylation based on high-throughput melting curve approaches. Genomics, 80:376-384.
Akiyoshi, S., Kanada, H., Okazaki, Y., Akama, T., Nomura, K., Hayashizaki, Y., and Kitagawa, T. 2000. A genetic linkage map of the MSM Japanese wild mouse strain with restriction landmark genomic scanning (RLGS). Mamm. Genome, 11:356-359.
Anderson, S. 1981. Shotgun DNA sequencing using cloned DNase I-generated fragments. Nucleic Acids Res., 9:3015-5027.
Ausubel, F. M., Brent, R., Kingston, R. E., Moore, D. O., Seidman, J. S., Smith, J. A., and Struhl, K. 1987. Current protocols in molecular biology. Wiley, New York, N.Y.
Badal, V., Chuang, L. S. H., Tan, E. H.-H., Badal, S., VIIIa, L. L., Wheeler, C. M., Li, B. F. L., and Bernard, H.-U. 2003. CpG methylation of human papillomavirus type 16 DNA in cervical cancer cell lines and in clinical specimens: genomic hypomethylation correlates with carcinogenic progression. J Virol., 77:6227-6234.
Bankier, A. T. 1993. Generation of random fragments by sonication. Methods Mol. Biol., 23:47059.
Barbin, A., Montpellier, C., Kokalj-Vokac, N., Gibaud, A., Niveleau, A., Malfoy, B., Dutril-Laux, B., and Boureois, C. A. 1994. New sites of methylcytosine-rich DNA detected on metaphase chromosomes. Hum. Genet, 94:684-692.
Baumer, A. 2002. Analysis of the methylation status of imprinted genes based on methylation-specific polymerase chain reaction combined with denaturing high-performance liquid chromatography. Methods, 27:139-143.
Baylin, S. B., and Herman, J. G. 2000. DNA hypermethylation in tumorigenesis: epigenetics joins genetics. Trends Genet. 16:168-174.
Bodenteich, A., Chissoe, S. L., Wang, Y.-F., and Roe, B. A. 1994. Shotgun cloing or the strategy of choice to generate template for high-throughput dideoxynucleotide sequencing. In: *Automated DNA sequencing and analysis* (ed. M. D. Adams, C. Fields, and J. C. Venter), pp. 42-50. Academic Press, San Diego, Calif.
Branum, M. E., Tipton, A. K., Zhu, S., and Que, L. Jr. 2001. Double-strand hydrolysis of plasmid DNA by dicerium complexes at 37 degrees C. J. Am. Chem. Soc., 123:1898-1904.
Burri, N., and Chaubert, P. 1999. Complex methylation patterns analyzed by single-strand conformation polymorphism. Biotechniques, 26:232-234.
Cedar, H., Soage, A., Glaser, G., and Razin, A. 1979. Direct detection of methylated cytosine in DNA by use of the restriction enzyme MspI. Nucleic Acids Res., 6:2125-2132.
Champoux J. J. (2001) DNA topoisomerases: structure, function, and mechanism Annu Rev Biochem, 70:369-413.
Chen, C.-M., Chen, H.-L., Hsiau, T. H.-C., Hsiau, A. H.-A., Shi, H., Brock, G. J. R., Wei, S. H., Caldwell, C. W., Yan, P. S., and Huang, T. H.-M. 2003. Methylation Target Array for Rapid Analysis of CpG. Island Hypermethylation in Multiple Tissue Genomes. Am J Pathol, 163:3745.
Chotai, K. A. and Payne, S. J. 1998. A rapid, PCR based test for differential molecular diagnosis of Prader-Willi and Angelman syndromes. J Med Genet. 35:472-5.
Coligan, J. E., Kruisbeek A. M., Margulies, D. H., Shevach, E. M., Strober, W. 1991. Current protocols in immunology. John Wiley and Sons, Hoboken, N.J.
Collela, S., Shen, L., Baggerly, K. A., Issa, J.-P. J., and Krahe, R. 2003. Sensitive and quantitativeuniversal Pyrosequencing™ methylation analysis of CpG sites. Biotechniques, 34:146-150.
Cottrell, S. E., Distler, J., Goodman, N. S., Mooney, S. H., Kluth, A., Olek, A., Schwope, I., Tetzner, R., Ziebarth, H., and Berlin, K. 2004. A real-time PCR assay for DNA-methylation using methylation-specific Blockers. Nucleic Acids Res., 32:e10.
Dryden, D. T. F., Murray, N. E., and Rao, D. N. 2001. Nucleoside triphosphate-dependent restriction enzymes. Nucleic Acids Res., 29:3728-3741.
Dunn, B. K. 2003. Hypomethylation: one side of a larger picture. Ann. N. Y. Acad. Sci., 983:28-42.
Duthie, S. J., Narayanan, S., Blum, S., Pirie, L., and Brand, G. M. 2000. Folate deficiency in vitro induces uracil misincorporation and DNA hypomethylation and inhibits DNA excision repair in immortalized normal human colon epithelial cells. Nutr. Cancer, 37:245-251.
Eads, C. A., Danenberg, K. D., Kawakami, K., Saltz, L. B., Blake, C., Shibata, D., Danenberg, P. V., and Laird, P. W. 2000. MethyLight: a high-throughput assay to measure DNA methylation. Nucleic Acids Res., 28:E32.
Fanning, T. G., Hu, W. S., and Cardiff, R. D. 1985. Analysis of tissue-specific methylation patterns of mouse mammary tumor virus DNA by two-dimensional Southern blotting. J. Virol., 54:726-730.
Fraga, M. F. and Esteller, M. 2002. DNA Methylation: A profile of methods and applications. Biotechniques, 33:632-649.

Fraga, M. F., Rodriquez, R., and Canal, M. J. 2000. Rapid quantification of DNA methylation by high performance capillary electorphoresis. Electrophoresis, 21:2990-2994.

Franklin, S. J. 2001. Lanthanide-mediated DNA hydrolysis. Curr. Opin. Chem. Biol., 5:201-208.

Freshney, R. I. 1987. Culture of animal cells: a manual of basic technique, 2d ed., Wiley-Liss, London.

Friso, S., Choi, S. W., Dolnikowski, G. G., and Selhub, J. 2002. A method to assess genomic DNA methylation using high-performance liquid chromatography/electrospray ionization mass spectrometry. Anal. Chem., 74:4526-4531.

Frommer, M., McDonald, L. E., Millar, D. S., Collis, C. M., Watt, F., Grigg, G. W., Molloy, P. L., and Paul, C. L. 1992. A genomic sequencing protocol that yields a positive display of 5-methylcytosine residues in individual DNA strands. Proc. Natl. Acad. Sci. USA, 89:1827-1831.

Fruhwald, M. C. and Plass, C. 2002. Global and gene-specific methylation patterns in cancer: aspects of tumor biology and clinical potential. Mol Genet Metabol, 75:1-16.

Furiuchi, Y., Wataya, Y., Hayatsu, H., and Ukita, T. 1970. Chemical modification of tRNA-Tyr-yeast with bisulfate. A new method to modify isopentuladenosine residue. Biochem. Biophys. Res. Commun., 41:1185-1191.

Gait, M. 1984. Oligonucleotide Synthesis. Practical Approach Series. IRL Press, Oxford, U. K.

Gingrich, J. C., Boehrer, D. M., Basu, S. B. 1996. Partial CviJI digestion as an alternative approach to generate cosmid sublibraries for large-scale sequencing projects. Biotechniques, 21:99-104.

Gonzalgo, M. L., and Jones, P. A. 1997. Rapid quantitation of methylation differences at specific sites using methylation-sensitie single nucleotide primer extension (Ms-SNuPE). Nucleic Acids Res., 25:2529-2531.

Gonzalgo, M. L., Liang, G., Spruck, C. H. $3^{rd}$, Zingg, J. M., Rideout, W. M. $3^{rd}$, and Jones, P. A. 1997. Identification and characterization of differentially methylated regions of genomic DNA by methylation-sensitive arbitrarily primed PCR.

Guldberg, P., Worm, J., and Gronbaek, K. 2002. Profiling DNA methylation by melting analysis. Methods, 27:121-127.

Grunau, C., Clark, S. J., and Rosenthal, A. 2001. Bisulfite genomic sequencing: systematic investigation of critical experimental parameters. Nucleic Acids Res., 29:E65.

Hayashizaki, Y., Hirotsune, S., Okazaki, Y., hatada, I., Shibata, H., Kawai, J., Hirose, K., Watanabe, S., Fushiki, S., Wada, S., et al. 1993. Restriction landmark genomic scanning method and its various applications. Electrophoresis, 14:251-258.

Hayes, J. J., Kam, L., and Tullius, T. D. 1990. Footprinting protein-DNA complexes with gamma-rays. Methods Enzymol. 186:545-549.

Herman, J. G., Graff, J. R., Myohanen, S., Nelkin, B. D., and Baylin, S. B. 1996. Methylation-specific PCR: a novel PCR assay for methylation status of CpG islands. Proc. Natl. Acad. Sci. USA, 93:9821-9826.

Jain, P. K. 2003. Epigenetics: the role of methylation in the mechanism of action of tumor supressor genes. Ann. N. Y. Acad. Sci., 983:71-83.

Jones, P. A., and Baylin, S. B. 2002. The fundamental role of epigenetic events in cancer. Nat. Rev. Genet., 3:415-428.

Kaneda, A., Takai, D., Kaminishi, M., Okochi, E., and Ushijima, T. 2003. Methylation-sensitive representational difference analysis and its application to cancer research. Ann. N. Y. Acad. Sci., 983:131-141.

Komiyama, M., and Sumaoka, J. 1998. Progress towards synthetic enzymes for phosphoester hydrolysis. Curr. Opin. Chem. Biol., 2:751-757.

Lippman, Z., Gendrel, A.-V., Colot, V., and Martiensen, R. 2005. Profiling DNA methylation patterns using genomic tiling microarrays. Nature Methods 2:219-224.

Matin, M. M., Baumer, A., and Hornby, D. P. 2002. An analytical method for the detection of methylation differences at specific chromosomal loci using primer extension and ion pair reverse phase HPLC. Hum. Mutat., 20:305-311.

Matsuyama, T., Kimura, M. T., Koike, K., Abe, T., Nakano, T., Asami, T., Ebisuzaki, T., Held, W. A., Yoshida, S., and Nagase, H. 2003. Global methylation screening in the *Arabadopsis thaliana* and *Mus musculas* genome: applications of virtual image restriction landmark genomic scanning (Vi-RLGS). Nuc. Acids Res. 31:4490-4496.

Methods in Enzymology. Academic Press, New York.

Miller, J. M., and Calos, M. P. 1987. Gene Transfer Vectors for Mammalian Cells. Cold Spring Harbor Laboratory, Cold Spring Harbor.

Miller, O. J., Schnedl, W., Allen, J., and Erlander, B. F. 1974. 5-methylcytosine localized in mammalian constitutive heterochromatin. Nature, 251:636-637.

Nouzova M, Holtan N, Oshiro M M, Isett R B, Munoz-Rodriguez J L, List A F, Narro M L, Miller S J, Merchant N C, Futscher B W 2004. Epigenomic changes during leukemia cell differentiation: analysis of histone acetylation and cytosine methylation using CpG island microarrays. J Pharmacol Exp Ther 311:968-981.

Oakeley, E. J., Schmitt, F., and Jost, J. P. 1999. Quantification of 5-methylcytosine in DNA by the chloroacetaldehyde reaction. BioTechniques, 27:744-752.

Oefner, P. J., Hunicke-Smith, S. P., Chiang, L., Dietrich, F., Mulligan, J. And Davis, R. W. 1996. Efficient random subcloning of DNA sheared in a recirculating point-sink flow system. Nucleic Acids Res., 24:3879-3886.

Panne, D., Raleigh, E. A., and Bickle, T. A. 1999. The McrBC endonuclease translocates DNA in a reaction dependent on GTP hydrolysis. J. Mol. Biol., 290:49-60.

Peraza-Echeverria, S., Herrera-Valencia, V. A., and James-Kay, A. 2001. Detection of DNA methylation changes in micropropogated banana plants using methylation-sensitive amplification polymorphism (MSAP). Plant Sci., 161:359-367.

Price, M. A., and Tullius, T. D. 1992. Using hydroxyl racidal to probe DNA structure. Methods Enzymol., 212:194-219.

Pogibny, I., Ping, Y., and James, S. J. 1999. A sensitive new method for rapid detection of abnormal methylation patterns in global DNA and within CpG islands. Biochem Biophys Res Comm, 262:624-628.

Ramsahoye, B. H. 2002. Measurement of genome wide DNA methylation by reversed-phase high-performance liquid chromatography. Methods, 27:156-161.

Rand K., Qu, W., Ho, T., Clark, S. J., Molloy, P. 2002. Conversion-specific detection of DNA methylation using real-time polymerase chain reaction (ConLight-MSP), to avoid false positives. Methods, 27:114-120.

Richards, O. C., and Boyer, P. D., 1965. Chemical mechanism of sonic, acid, alkaline and enzymatic degradation of DNA. J. Mol. Biol. 11:327-340.

Roots, R., Holley, W., Chatterjee, A., Rachal, E., and Kraft, G. 1989. The influence of radiation quality on the formation of DNA breaks. Adv. Space Res., 9:45-55.

Rouillard, J. M., Erson, A. E., Kuick, R., Asakawa, J., Wimmer, K., Muleris, M., Petty, E. M., and Hannah, S. 2001.

Virtual genome scan: a tool for restriction landmark-based scanning of the human genome. Genome Res. 11:1453-1459.

Sadri, R., and Hornsby, P. J. 1996. Rapid analysis of DNA methylation using new restriction enzyme sites created by bisulfite modification. Nucleic Acids Res., 24:5058-5059.

Sambrook, J., Fritsch, E. F. and Maniatis, T. (1989) Molecular Cloning: A Laboratory Manual, second edition, Cold Spring Harbor Laboratory, Cold Spring Harbor.

Sasaki, M., Anast, J., Bassett, W., Kawakami, T., Sakuragi, N., and Dahiya, R. 2003. Bisulfite conversion-specific and methylation-specific PCR: a sensitive technique for accurate evaluation of CpG methylation. Biochem. Biophys. Res. Commun., 309:305-309.

Steigerwald, S. D., Pfeifer, G. P., and Riggs, A. D. 1990. Ligation-mediated PCR improves the sensitivity of methylation analysis by restriction enzymes and detection of specific DNA strand breaks. Nucleic Acids Res., 18:1435-1439.

Stewart, F. J., and Raleigh, E. A. 1998. Dependence of McrBC cleavage on distance between recognition elements. Biol. Chem., 379:611-616.

Studier, F. W. 1979. Relationships among different strains of T7 and among T7-related bacteriophages. Virology 95:70-84.

Sutherland, E., Coe, L., and Raleigh, E. A. 1992. McrBC: a multisubunit GTP-dependent restriction endonuclease. J. Mol. Biol., 225:327-348.

Suzuki, H., Itoh, F., Toyota, M., Kikuchi, T., Kakiuchi, H., Hinoda, Y., and Imai, K. 2000. Quantitative DNA methylation analysis by fluorescent polymerase chain reaction single strand conformation polymorphism using and automated DNA sequencer. Electrophoresis, 21:904-908.

Tawa, R., Tamura, G., Sakurai, H., Ono, T., and Kurishita, A. 1994. High-performance liquid chromatographic analysis of methylation changes of CCGG sequence in brain and liver DNA of mice during pre- and postnatal development. J. Chromatogr. B Biomed. Appl., 653:211-216.

Thorstenson, Y. R., Hunicke-Smith, S. P., Oefner, P. J., and Davis, R. W. 1998. An automated hydrodynamic process for controlled, unbiased DNA shearing. Genome Res., 8:848-855.

Tost, J., Dunker, J., and Gut, I. G. 2003. Analysis and quantification of multiple methylation variable positions in CpG islands by Pyrosequencing™. Biotechniques, 35:152-156.

Tost, J., Schatz, P., Schuster, M., Berlin, K., and Gut, I. G. 2003. Analysis and accurate quantification of CpG methylation by MALDI mass spectrometry. Nucleic Acids Res., 31:e50.

Toyota, M., and Issa, J. P. 2002. Methylated cpG island amplification for methylation analysis and cloning differentially methylated sequences. Methods Mol. Biol., 200:101-110.

Toyota, M., Ho, C., Ahuja, N., Jair, K.-W., Li, Q., Ohe-Toyota, M., Baylin, S. B., and Issa, J.-P. J. 1999. Identification of differentially methylated sequences in colorectal cancer by methylated CpG island amplification. Cancer Res., 59:2307-2312.

Tullius, T. D. 1991. DNA footprinting with the hydroxyl racidal. Free Radic. Res Commun, 12-13:521-529.

Ushijima, T., Morimura, K., Hosoya, Y., Okonogi, H., Tatematsu, M., Sugimura, T., and Nagao, M. 1997. Establishment of methylation-sensitive-representational difference analysis and isolation of hypo- and hypermethylated genomic fragments in mouse liver tumors. Proc. Natl. Acad. Sci. USA, 94:2284-2289.

Weir, D. M. 1978. Handbook of Experimental Immunology. Blackwell Scientific Publications, Oxford, U. K.

Wold, M S (1997) Replication protein A: A heterotrimeric, single-stranded DNA-binding protein required for eukaryotic DNA metabolism. Ann. Rev. Biochem. 66:61-92.

Xiong, Z., and Laird, P. W. 1997. COBRA: a sensitive and quantitative DNA methylation assay. Nucleic Acids Res. 25:2532-2534.

Yan, P. S., Chen, C-M, Shi, H., Rahmatpanah, F., Wei, S. H., Caldwell, C. W., and Huang T. H-M. 2001. Dissecting Complex Epigenetic Alterations in Breast Cancer Using CpG Island Microarrays. Cancer Research 61:8375-8380.

Yuan, Y., SanMiguel, P. J., and Bennetzen, J. L. 2002. Methylation-spanning linker libraries link gene-rich regions and identify epigenetic boundaries in Zea mays. Genome Res., 12:1345-1349.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, manufacture, composition of matter, means, methods and steps described in the specification. As one of ordinary skill in the art will readily appreciate from the disclosure of the present invention, processes, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A method of preparing a DNA molecule, comprising:
   (a) providing a DNA molecule;
   (b) digesting the DNA molecule with at least one methylation-sensitive restriction enzyme and, optionally, an additional nuclease, to provide digested DNA molecules;
   (c) incorporating a nucleic acid molecule into at least some of the digested DNA molecules to provide first modified DNA molecules, by:
       incorporating at least one primer from a plurality of primers, said primers comprising a 5' constant sequence and a 3' variable sequence that is substantially non-self-complementary and substantially non-complementary to other primers in the plurality, wherein the sequence of the constant and variable regions consists essentially of only two types of non-complementary nucleotides selected from the group consisting of adenines and guanines; adenines and cytosines; guanines and thymidines; and cytosines and thymidines, such that the primers of the population will not cross-hybridize or self-hybridize under conditions employed in step d); and
   (d) amplifying one or more of the first modified DNA molecules to provide amplified first modified DNA molecules.

2. The method of claim 1, further comprising analyzing at least part of the sequence of an amplified modified DNA molecule.

3. The method of claim 2, wherein the analyzing step comprises sequencing, quantitative real-time polymerase chain reaction, ligation chain reaction, ligation-mediated polymerase chain reaction, probe hybridization, probe amplification, microarray hybridization, restriction enzyme digestion, or a combination thereof.

4. The method of claim 1, wherein the DNA molecule that is provided is from a body fluid or tissue.

5. The method of claim 4, wherein the body fluid comprises blood, serum, urine, cerebrospinal fluid, nipple aspirate, sweat, or saliva.

6. The method of claim 4, wherein the tissue comprises biopsy, surgical sample, or cheek scrapings.

7. The method of claim 1, wherein the DNA molecule that is provided is from a sample of an individual that has a medical condition.

8. The method of claim 7, wherein the medical condition is cancer.

9. The method of claim 1, wherein the methylation-sensitive restriction enzyme has a 4-5 base pair recognition site that comprises at least one CpG dinucleotide.

10. The method of claim 1, wherein the methylation-sensitive restriction enzyme is Aci I, Bst UI, Hha I, HinP1, Hpa II, Hpy 99I, Ava I, Bce AI, Bsa HI, Bsi E1, Hga I, or a mixture thereof.

11. The method of claim 1, wherein the optional additional nuclease comprises a restriction endonuclease.

12. The method of claim 1, wherein the optional additional nuclease comprises DNAase I.

13. The method of claim 1, wherein the incorporating step is further defined as:
    fragmenting and generating single stranded nucleic acid molecules from at least some of the digested DNA molecules by heating;
    subjecting the single stranded nucleic acid molecules to a plurality of primers to form a single stranded nucleic acid molecule/primer mixture, wherein the primers comprise nucleic acid sequence that is substantially non-self-complementary and substantially non-complementary to other primers in the plurality and wherein the primers comprise a constant nucleic acid sequence and a variable nucleic acid sequence, wherein the sequence of the constant and variable regions consists essentially of only two types of non-complementary nucleotides selected from the group consisting of adenines and guanines; adenines and cytosines; guanines and thymidines; and cytosines and thymidines, such that the primers of the population will not cross-hybridize or self-hybridize; and
    subjecting said single stranded nucleic acid molecule/primer mixture to a polymerase to generate a plurality of molecules comprising the constant nucleic acid sequence at each end.

14. The method of claim 1, wherein the amplifying step comprises polymerase chain reaction.

15. The method of claim 1, further defined as determining the methylation status of at least part of the provided DNA molecule.

16. The method of claim 1, further defined as performing the method with a provided molecule from a sample of an individual with a medical condition in comparison to performing the method with a control.

17. The method of claim 16, wherein the medical condition is cancer.

18. The method of claim 1, wherein the provided DNA molecule comprises a promoter, a CpG island, or both.

19. The method of claim 1, wherein the amplifying step utilizes a primer that is complementary to the incorporated nucleic acid molecule.

20. The method of claim 1, wherein the constant and variable regions consist essentially of guanines, adenines, or both.

21. The method of claim 1, wherein the constant and variable regions consist essentially of cytosines, thymidines, or both.

22. The method of claim 1, wherein the constant and variable regions consist essentially of adenines, cytosines, or both.

23. The method of claim 1, wherein the constant and variable regions consist essentially of guanines, thymidines, or both.

24. The method of claim 1, wherein the primer is further comprised of 0 to about 3 random bases at its distal 3' end.

25. The method of claim 1, wherein the constant region and the variable region each consist of only two non-complementary nucleotides and wherein the polynucleotide comprises 0, 1, 2, or 3 random bases at its 3' end.

26. A method of preparing a DNA molecule, comprising:
(a) providing a DNA molecule;
(b) digesting the molecule with one or more methylation-specific endonucleases to provide DNA fragments;
(c) incorporating a nucleic acid molecule into the DNA fragments to provide first modified DNA molecules, by a method comprising:
incorporating at least one primer from a plurality of primers, said primer comprising a 5' constant sequence and a 3' variable sequence that is substantially non-self-complementary and substantially non-complementary to other primers in the plurality, and further wherein the sequence of the constant and variable regions consists essentially of only two types of non-complementary nucleotides selected from the group consisting of adenines and guanines; adenines and cytosines; guanines and thymidines; and cytosines and thymidines, such that the primers of the population will not cross-hybridize or self-hybridize under conditions employed in step d); and
(d) amplifying at least one first modified DNA molecule to provide amplified DNA molecules.

27. The method of claim 26, wherein the amplifying step utilizes a primer that is complementary to the incorporated nucleic acid molecule.

28. The method of claim 26, wherein the method further comprises the step of analyzing at least one of the amplified DNA molecules to determine the methylation status of the provided DNA.

29. The method of claim 26, wherein the methylation-specific endonuclease is McrBc.

30. The method of claim 26, wherein the amplifying step comprises polymerase chain reaction.

31. A method of preparing a DNA molecule, comprising:
(a) providing a bisulfite-converted DNA molecule;
(b) incorporating a nucleic acid molecule into at least some of the digested DNA molecules to provide first modified DNA molecules, by incorporating at least one primer from a plurality of primers, said primers comprising a 5' constant sequence and a 3' variable sequence that is substantially non-self-complementary and substantially non-complementary to other primers in the plurality, wherein the sequence of the constant and variable regions consists essentially of only two types of non-complementary nucleotides selected from the group consisting of adenines and guanines; adenines and cytosines; guanines and thymidines; and cytosines and thymidines, such that the primers of the population will not cross-hybridize or self-hybridize under conditions employed in step d); and
(c) amplifying one or more of the first modified DNA molecules to provide amplified first modified DNA molecules.

32. The method of claim 31, wherein the constant and variable regions consist essentially of guanines, adenines, or both.

33. The method of claim 31, wherein the constant and variable regions consist essentially of cytosines, thymidines, or both.

34. The method of claim 31, wherein the constant and variable regions consist essentially of adenines, cytosines, or both.

35. The method of claim 31, wherein the constant and variable regions consist essentially of guanines, thymidines, or both.

36. The method of claim 31, wherein the primer is further comprised of 0 to about 3 random bases at its distal 3' end.

37. The method of claim 31, wherein the constant region and the variable region each consist of only two non-complementary nucleotides wherein the polynucleotide comprises 0, 1, 2, or 3 random bases at its 3' end.

* * * * *

SEQUENCE LISTING

```
<160> NUMBER OF SEQ ID NOS: 210

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (19)..(28)
<223> OTHER INFORMATION: Y = C OR T
```

```
<400> SEQUENCE: 1
cctttctctc ccttctctyy yyyyyyy                                              28

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (19)..(28)
<223> OTHER INFORMATION: Y = C OR T
<220> FEATURE:
<221> NAME/KEY: modified_base
<222> LOCATION: (29)..(29)
<223> OTHER INFORMATION: N = A, C, G OR T/U
<220> FEATURE:
<221> NAME/KEY: misc_feature
<222> LOCATION: (29)..(29)
<223> OTHER INFORMATION: n is a, c, g, or t

<400> SEQUENCE: 2
cctttctctc ccttctctyy yyyyyyyn                                             29

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (19)..(28)
<223> OTHER INFORMATION: Y = C OR T
<220> FEATURE:
<221> NAME/KEY: modified_base
<222> LOCATION: (29)..(30)
<223> OTHER INFORMATION: N = A, C, G OR T/U
<220> FEATURE:
<221> NAME/KEY: misc_feature
<222> LOCATION: (29)..(30)
<223> OTHER INFORMATION: n is a, c, g, or t

<400> SEQUENCE: 3
cctttctctc ccttctctyy yyyyyyynn                                            30

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (19)..(28)
<223> OTHER INFORMATION: Y = C OR T
<220> FEATURE:
<221> NAME/KEY: modified_base
<222> LOCATION: (29)..(31)
<223> OTHER INFORMATION: N = A, C, G OR T/U
<220> FEATURE:
<221> NAME/KEY: misc_feature
<222> LOCATION: (29)..(31)
<223> OTHER INFORMATION: n is a, c, g, or t

<400> SEQUENCE: 4
cctttctctc ccttctctyy yyyyyyynn n                                          31
```

```
<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (19)..(28)
<223> OTHER INFORMATION: Y = C OR T
<220> FEATURE:
<221> NAME/KEY: modified_base
<222> LOCATION: (29)..(32)
<223> OTHER INFORMATION: N = A, C, G OR T/U
<220> FEATURE:
<221> NAME/KEY: misc_feature
<222> LOCATION: (29)..(32)
<223> OTHER INFORMATION: n is a, c, g, or t

<400> SEQUENCE: 5
cctttctctc ccttctctyy yyyyyyyynn nn                                    32

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (19)..(28)
<223> OTHER INFORMATION: Y = C OR T
<220> FEATURE:
<221> NAME/KEY: modified_base
<222> LOCATION: (29)..(33)
<223> OTHER INFORMATION: N = A, C, G OR T/U
<220> FEATURE:
<221> NAME/KEY: misc_feature
<222> LOCATION: (29)..(33)
<223> OTHER INFORMATION: n is a, c, g, or t

<400> SEQUENCE: 6
cctttctctc ccttctctyy yyyyyyyynn nnn                                   33

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (19)..(28)
<223> OTHER INFORMATION: Y = C OR T
<220> FEATURE:
<221> NAME/KEY: modified_base
<222> LOCATION: (29)..(34)
<223> OTHER INFORMATION: N = A, C, G OR T/U
<220> FEATURE:
<221> NAME/KEY: misc_feature
<222> LOCATION: (29)..(34)
<223> OTHER INFORMATION: n is a, c, g, or t

<400> SEQUENCE: 7
cctttctctc ccttctctyy yyyyyyyynn nnnn                                  34

<210> SEQ ID NO 8
<211> LENGTH: 18
<212> TYPE: DNA
<213> ORGANISM: Artificial Sequence
<220> FEATURE:
```

-continued

<223> OTHER INFORMATION: Description of Artificial Sequence:  Synthetic
      Primer

<400> SEQUENCE: 8
cctttctctc ccttctct                                                       18

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (21)..(30)
<223> OTHER INFORMATION: R = A OR G

<400> SEQUENCE: 9
gtaatacgac tcactatagg rrrrrrrrrr                                          30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (19)..(28)
<223> OTHER INFORMATION: R = A OR G
<220> FEATURE:
<221> NAME/KEY: modified_base
<222> LOCATION: (29)..(30)
<223> OTHER INFORMATION: N = A, C, G OR T/U
<220> FEATURE:
<221> NAME/KEY: misc_feature
<222> LOCATION: (29)..(30)
<223> OTHER INFORMATION: n is a, c, g, or t

<400> SEQUENCE: 10
agagaaggga gagaaggrr rrrrrrrrnn                                           30

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 11
agagaaggga gagaaagg                                                       18

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (19)..(28)
<223> OTHER INFORMATION: M = A OR C
<220> FEATURE:
<221> NAME/KEY: modified_base
<222> LOCATION: (29)..(30)
<223> OTHER INFORMATION: N = A, C, G OR T/U
<220> FEATURE:
<221> NAME/KEY: misc_feature

```
<222> LOCATION: (29)..(30)
<223> OTHER INFORMATION: n is a, c, g, or t

<400> SEQUENCE: 12
ccaaacacac ccaacacamm mmmmmmmmnn                                    30

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
ccaaacacac ccaacaca                                                 18

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (19)..(28)
<223> OTHER INFORMATION: K = G OR T
<220> FEATURE:
<221> NAME/KEY: modified_base
<222> LOCATION: (29)..(30)
<223> OTHER INFORMATION: N = A, C, G OR T/U
<220> FEATURE:
<221> NAME/KEY: misc_feature
<222> LOCATION: (29)..(30)
<223> OTHER INFORMATION: n is a, c, g, or t

<400> SEQUENCE: 14
tgtgttgggt gtgtttggkk kkkkkkkknn                                    30

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
tgtgttgggt gtgtttgg                                                 18

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (21)..(26)
<223> OTHER INFORMATION: N = A, C, G OR T/U
<220> FEATURE:
<221> NAME/KEY: misc_feature
<222> LOCATION: (21)..(26)
<223> OTHER INFORMATION: n is a, c, g, or t

<400> SEQUENCE: 16
gtaatacgac tcactatagg nnnnnn                                        26
```

```
<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
gtaatacgac tcactatagg                                              20

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (29)..(30)
<223> OTHER INFORMATION: N = A, C, G OR T/U
<220> FEATURE:
<221> NAME/KEY: misc_feature
<222> LOCATION: (29)..(30)
<223> OTHER INFORMATION: n is a, c, g, or t

<400> SEQUENCE: 18
agagaaggga gagaaaggaa aaaaaaaann                                   30

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (29)..(30)
<223> OTHER INFORMATION: N = A, C, G OR T/U
<220> FEATURE:
<221> NAME/KEY: misc_feature
<222> LOCATION: (29)..(30)
<223> OTHER INFORMATION: n is a, c, g, or t

<400> SEQUENCE: 19
cctttctctc ccttctcttt ttttttttnn                                   30

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
gtactcccat tcctgccaaa                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
taaacatagc accaagggge                                              20
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
atactcccat tcctaccaaa                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
taaatatagt attaaggggt                                              20

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
cctctgctcc gcctactgg                                               19

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
caccgttggc cgtaaactta ac                                           22

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
cagagggtgg ggcggaccgc                                              20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
ccgcacctcc tctacccgac cc                                           22

<210> SEQ ID NO 28

```
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
gctagagggt caccgcgt                                                 18

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
ctgaactgac ttccgcaagc tc                                            22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
gtgaagcggg tgtgcaagct c                                             21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
cgaagactgc ggcggcgaaa c                                             21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
agtaatacga ctcactatag g                                             21

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (22)..(22)
<223> OTHER INFORMATION: N = A, C, G OR T/U
<220> FEATURE:
<221> NAME/KEY: misc_feature
<222> LOCATION: (22)..(22)
<223> OTHER INFORMATION: n is a, c, g, or t
```

```
<400> SEQUENCE: 33
agtaatacga ctcactatag gn                                              22

<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
cctatagtga gt                                                         12

<210> SEQ ID NO 35
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (1)..(1)
<223> OTHER INFORMATION: N = A, C, G OR T/U
<220> FEATURE:
<221> NAME/KEY: misc_feature
<222> LOCATION: (1)..(1)
<223> OTHER INFORMATION: n is a, c, g, or t

<400> SEQUENCE: 35
ncctatagtg agt                                                        13

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 36
cccccccccc gtaatacgac tcactatagg                                      30

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 37
gtaatacgac tcactata                                                   18

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 38
cccccccccc                                                            10

<210> SEQ ID NO 39
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 39
tgccactctc aatctcgaac ta                                              22

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 40
gcgctacctg attccaattc ccc                                             23

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 41
cataggtttg ggtgaactct aa                                              22

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 42
ggcctttctt ctaacaatca g                                               21

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 43
tgaggttgtt gaagcgttua cccaautcga tuaggcaa                             38

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 44
ttgcctaatc gaattgggta aacg                                            24

<210> SEQ ID NO 45
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      Primer

<400> SEQUENCE: 45
cttcaacaac ctca                                                        14

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 46
aggtgcagag ctgtcgcttt c                                                21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47
cactgccctc agctcctaat c                                                21

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 48
ggtaggggga cactttctag tc                                               22

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 49
aggcgtgttt gagtgcgttc                                                  20

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 50
ccaaggcagg aggatcgc                                                    18

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
                        Primer

<400> SEQUENCE: 51
tcagaaaggg cttttacact tg                                              22

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 52
gtgagctgtg atcgcacca                                                  19

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 53
gcggtgaccc tctagcct                                                   18

<210> SEQ ID NO 54
<211> LENGTH: 12
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 54
ccaaacacac cc                                                         12

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (1)..(2)
<223> OTHER INFORMATION: N = A, C, G OR T/U
<220> FEATURE:
<221> NAME/KEY: misc_feature
<222> LOCATION: (1)..(2)
<223> OTHER INFORMATION: n is a, c, g, or t

<400> SEQUENCE: 55
nncctatagt gagt                                                       14

<210> SEQ ID NO 56
<211> LENGTH: 15
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (1)..(3)
<223> OTHER INFORMATION: N = A, C, G OR T/U
<220> FEATURE:
<221> NAME/KEY: misc_feature
```

-continued

```
<222> LOCATION: (1)..(3)
<223> OTHER INFORMATION: n is a, c, g, or t

<400> SEQUENCE: 56
nnncctatag tgagt                                                  15

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (1)..(4)
<220> FEATURE:
<221> NAME/KEY: misc_feature
<222> LOCATION: (1)..(4)
<223> OTHER INFORMATION: n is a, c, g, or t

<400> SEQUENCE: 57
nnnncctata gtgagt                                                 16

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (1)..(5)
<223> OTHER INFORMATION: N = A, C, G OR T/U
<220> FEATURE:
<221> NAME/KEY: misc_feature
<222> LOCATION: (1)..(5)
<223> OTHER INFORMATION: n is a, c, g, or t

<400> SEQUENCE: 58
nnnnncctat agtgagt                                                17

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (1)..(6)
<220> FEATURE:
<221> NAME/KEY: misc_feature
<222> LOCATION: (1)..(6)
<223> OTHER INFORMATION: n is a, c, g, or t

<400> SEQUENCE: 59
nnnnnnccta tagtgagt                                               18

<210> SEQ ID NO 60
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (1)..(6)
<223> OTHER INFORMATION: N = A, C, G OR T/U
```

```
<220> FEATURE:
<221> NAME/KEY: misc_feature
<222> LOCATION: (1)..(6)
<223> OTHER INFORMATION: n is a, c, g, or t

<400> SEQUENCE: 60
nnnnnnccaa acacac                                                    16

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 61
ggtaggggga cactttctag tc                                             22

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 62
aggcgtgttt gagtgcgttc                                                20

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 63
gcgcgcgatc caggtagc                                                  18

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 64
taggttccag ccccgatccg                                                20

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 65
ggtgccacat tcgctaagtg c                                              21

<210> SEQ ID NO 66
<211> LENGTH: 20
<212> TYPE: DNA
<213> ORGANISM: Artificial Sequence
<220> FEATURE:
```

<223> OTHER INFORMATION: Description of Artificial Sequence: Synthetic
      Primer

<400> SEQUENCE: 66
gctgcagacc ctctacccac                                              20

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 67
cagcagcagc gccgagagg                                               19

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 68
cctggagtcc ccggagtcg                                               19

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 69
gaaacccctc agcaacctac c                                            21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 70
gcccttcatc ccgtatcact t                                            21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 71
catcaggaat gtggaagtcg g                                            21

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 72
tgctgcggtg acagtgtga                                                    19

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 73
agcctgacgg agaacatctg g                                                 21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 74
gcctgaggtc actgaggttg g                                                 21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 75
tggctcctga aatcagacct g                                                 21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 76
gattgtgtgg gtgtgagtgg g                                                 21

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 77
cgtccacacc ctccaaccac                                                   20

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 78
cgcaggaaac acagaccaaa c        21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 79
ctggtcgcag attggtgaca t        21

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 80
ggcaaaaatg cagcatccta        20

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 81
ccttgtcagg atggcacatt g        21

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 82
ccgtctcaca cgcaccctct        20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 83
gcaatacgct cggcaatgac        20

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 84
cgggtaagga ggtgggaaca c        21

```
<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 85
gtcaacccag cctgtgtctg a                                              21

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 86
ggatggtcac cctgttggag                                                20

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 87
gctgaggttc ggcaagtctc c                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 88
agcccccagt tcctttcaat c                                              21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 89
accaggcaca tgagacaagg a                                              21

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 90
gggcacctgc tgtgacttct                                                20
```

```
<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 91
cgagaaattc ccgaaacgag a                                                 21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 92
gccccttgag aataccttgc t                                                 21

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 93
gcagagcaaa ttcgggattc                                                   20

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 94
cggctgaact gattcggaag t                                                 21

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 95
gcgttctcaa ctgcgattcc                                                   20

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 96
tgcccttcct gtgaaagcac t                                                 21

<210> SEQ ID NO 97
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 97
cctctgctcc gcctactgg                                              19

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 98
caccgttggc cgtaaactta ac                                          22

<210> SEQ ID NO 99
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 99
gcacgcccgc ggacta                                                 16

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 100
cctgaggcag tctgcgcatc                                             20

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 101
gcccgcgccc ctagaacg                                               18

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 102
cacacccgac ggcgaagtga g                                           21

<210> SEQ ID NO 103
<211> LENGTH: 20
<212> TYPE: DNA
<213> ORGANISM: Artificial Sequence
```

-continued

<220> FEATURE:
<223> OTHER INFORMATION: Description of Artificial Sequence: Synthetic
      Primer

<400> SEQUENCE: 103
gcccaaagcc agcgaagcac                                              20

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 104
cgccacagag gtcgcacca                                               19

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 105
tccgccacat accgctcgta g                                            21

<210> SEQ ID NO 106
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 106
cttgtggcct cccgcagaa                                               19

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 107
cccttggttt ccgtggcaac                                              20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 108
ctccccaggg ttcacaacgc                                              20

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic -continued

```
                            Primer

<400> SEQUENCE: 109
ctagcctcgc ctccgttaca ac                                               22

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 110
gctcggtaga ggatggaacg c                                                21

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 111
ggtacggggc tagggctagg                                                  20

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 112
gcgggctgca ccaatacag                                                   19

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 113
cgggtcggga agcggagag                                                   19

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 114
tggcgggctg caccaataca g                                                21

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer
```

-continued

<400> SEQUENCE: 115
gtgaggagga cagccggacc                                           20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 116
ggcgggaaca cagctaggga                                           20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 117
aggggcacga gggctccgct                                           20

<210> SEQ ID NO 118
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 118
gggcaagggg taacggggc                                            19

<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 119
cagctcctgc tccttcgcc                                            19

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 120
gctgccctcc gagtgccc                                             18

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 121

-continued ctggatccgt ctttcgcgtt ta                                              22

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 122
ttgtcgtcgc tgctggatag ag                                              22

<210> SEQ ID NO 123
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 123
ggcggagggc gttcgtc                                                    17

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 124
agcacagccc gaggttagag g                                               21

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 125
cctgatttct acagccgctc tac                                             23

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 126
tccaaacctc tccaacaccc gact                                            24

<210> SEQ ID NO 127
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 127
cctggccgag aagctaggg                                                  19

```
<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 128
cggcctgatt tgtggttaag ga                                              22

<210> SEQ ID NO 129
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 129
agttggaaga gtccctacaa tcctg                                           25

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 130
cgtcccactt gtatttgcat tgag                                            24

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 131
ctggcgctgg gaggcatcag                                                 20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 132
gcgggaggtg gcttggatca                                                 20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 133
cgtgatccgc aggcgacgaa                                                 20

<210> SEQ ID NO 134
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 134
tcaccaagag cggcagctaa ag                                              22

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 135
gaagtcgcct ggtcaggatc aaa                                             23

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 136
gccgctgtca agagacattg c                                               21

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 137
cggtatccca tccaaggcga                                                 20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 138
ctctcctccc cgagttccac                                                 20

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 139
gtggagatgc tggagacccc g                                               21

<210> SEQ ID NO 140
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 140
ctctagtccc ccgtcgaagc c                                              21

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 141
cgggaggagt ctttcgagtt caa                                            23

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 142
cgggaggaat acagacacgt ctt                                            23

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 143
gggcatcagg aaggagtttc gac                                            23

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 144
tcgccagtat ccacgctcaa                                                20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 145
aaagaaaacg ccggcttgtg                                                20

<210> SEQ ID NO 146
<211> LENGTH: 22
<212> TYPE: DNA
<213> ORGANISM: Artificial Sequence
<220> FEATURE:
```

-continued

<223> OTHER INFORMATION: Description of Artificial Sequence: Synthetic
      Primer

<400> SEQUENCE: 146
ctacccgggc tgctaacctt ca                                              22

<210> SEQ ID NO 147
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 147
ggactgggat gccgagaac                                                  19

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 148
tttaccattt tccaggcttg ctc                                             23

<210> SEQ ID NO 149
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 149
ggggctccgc cgattg                                                     16

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 150
cgcagcccca gaacaaatcc t                                               21

<210> SEQ ID NO 151
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 151
ggccccgcca cttgattct                                                  19

<210> SEQ ID NO 152
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 152
cggccgcccc tcgtg                                                        15

<210> SEQ ID NO 153
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 153
ccgggacagc cacgaggg                                                     18

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 154
gcgagaagcg ggaaagcaga agc                                               23

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 155
ccaactttcc tgcgtccatg c                                                 21

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 156
aggctgccca gggtcgtc                                                     18

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 157
ctcgcgctgc tgctgttgct c                                                 21

<210> SEQ ID NO 158
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 158
```

```
tgaggctgcc cagggtcgtc gg                                                  22
```

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 159

```
gggacgcctc tcggtggtt                                                      19
```

<210> SEQ ID NO 160
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 160

```
ggcccggacg tgtgct                                                         16
```

<210> SEQ ID NO 161
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 161

```
cctgctgggg gttcgaaga                                                      19
```

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 162

```
cccctgccag acgccaagat                                                     20
```

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 163

```
tcggtcatcc tctgtcctga cgc                                                 23
```

<210> SEQ ID NO 164
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 164

```
ggggaacctg gagtgtcgc                                                      19
```

```
<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 165
cctctgccag gttcggtcc                                                  19

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 166
gctgcgtgcc accaaaactt gtc                                             23

<210> SEQ ID NO 167
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 167
cgagagaagg ga                                                         12

<210> SEQ ID NO 168
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 168
tctcttccct ctctttcc                                                   18

<210> SEQ ID NO 169
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 169
cgaagagaga ggg                                                        13

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 170
ttctctctcc cttccttc                                                   18
```

```
<210> SEQ ID NO 171
<211> LENGTH: 12
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 171
ccaaacacac cc                                                          12

<210> SEQ ID NO 172
<211> LENGTH: 50
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 172
tgtgttgggd ugdugtgtgg dudududuu duccacacac acccaacaca                  50

<210> SEQ ID NO 173
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 173
ccacacacac ccaacaca                                                    18

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 174
gggtgggagg aagcatcgtc                                                  20

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 175
ggtctccagc atctccacga a                                                21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 176
tgggaaagag ggaaaggctt c                                                21

<210> SEQ ID NO 177
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 177
ccccagtgct gagtcacgg                                                      19

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 178
agaactggct ctcggaagcg                                                     20

<210> SEQ ID NO 179
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 179
gggagcagag ggggtagtc                                                      19

<210> SEQ ID NO 180
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 180
gcttcctgga cacgctggt                                                      19

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 181
tctatgcggg catggttact g                                                   21

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 182
tttgatgtta ggatatgttg aaa                                                 23

<210> SEQ ID NO 183
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      Primer

<400> SEQUENCE: 183
aaaaacaaaa aaaatctctt aac                                              23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 184
atttactact taatattacc tac                                              23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 185
ttatgtgtgg gttattaagg atg                                              23

<210> SEQ ID NO 186
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 186
caagcttcct ttccgtcatg cc                                               22

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 187
agcaccacca gcgtgtcca                                                   19

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 188
ctccctccca cctccggcat ct                                               22

<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic
```

Primer

<400> SEQUENCE: 189
cgcttcccga cccgcactc                                                19

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 190
agttcgctgc gcacactt                                                 18

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 191
cggggcctag ggagtaaaca                                               20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 192
cccaaagcca gcgaagcacg                                               20

<210> SEQ ID NO 193
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 193
tcaggctccc ccgacat                                                  17

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 194
ctgggggact ggagtcaagt g                                             21

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer -continued

```
<400> SEQUENCE: 195
ccaacggttt agcgcaaatc                                                   20

<210> SEQ ID NO 196
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 196
ctcggcggct gcggaga                                                      17

<210> SEQ ID NO 197
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 197
cgccgcccgc tgcct                                                        15

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (21)..(21)
<223> OTHER INFORMATION: n = a, c, g and/or t/u
<220> FEATURE:
<221> NAME/KEY: misc_feature
<222> LOCATION: (21)..(21)
<223> OTHER INFORMATION: n is a, c, g, or t

<400> SEQUENCE: 198
gtaatacgac tcactatagg n                                                 21

<210> SEQ ID NO 199
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 199
tgtgttgggt gtgttt                                                       16

<210> SEQ ID NO 200
<211> LENGTH: 14
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 200
ggccaaacac accc                                                         14

<210> SEQ ID NO 201
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 201
cctatagtga gtcgtattac                                                     20

<210> SEQ ID NO 202
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (21)..(22)
<223> OTHER INFORMATION: n = a, c, g and/or t/u
<220> FEATURE:
<221> NAME/KEY: misc_feature
<222> LOCATION: (21)..(22)
<223> OTHER INFORMATION: n is a, c, g, or t

<400> SEQUENCE: 202
gtaatacgac tcactatagg nn                                                  22

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (21)..(23)
<223> OTHER INFORMATION: n = a, c, g and/or t/u
<220> FEATURE:
<221> NAME/KEY: misc_feature
<222> LOCATION: (21)..(23)
<223> OTHER INFORMATION: n is a, c, g, or t

<400> SEQUENCE: 203
gtaatacgac tcactatagg nnn                                                 23

<210> SEQ ID NO 204
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (21)..(24)
<223> OTHER INFORMATION: n = a, c, g and/or t/u
<220> FEATURE:
<221> NAME/KEY: misc_feature
<222> LOCATION: (21)..(24)
<223> OTHER INFORMATION: n is a, c, g, or t

<400> SEQUENCE: 204
gtaatacgac tcactatagg nnnn                                                24

<210> SEQ ID NO 205
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
          Primer
<220> FEATURE:
<221> NAME/KEY: modified_base
<222> LOCATION: (21)..(25)
<223> OTHER INFORMATION: n = a, c, g and/or t/u
<220> FEATURE:
<221> NAME/KEY: misc_feature
<222> LOCATION: (21)..(25)
<223> OTHER INFORMATION: n is a, c, g, or t

<400> SEQUENCE: 205
gtaatacgac tcactatagg nnnnn                                          25

<210> SEQ ID NO 206
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 206
tgtgttgggu gugtgtgguu uuuuccacac acacccaaca ca                       42

<210> SEQ ID NO 207
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 207
ggggcggacc gcg                                                       13

<210> SEQ ID NO 208
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 208
gggguggauu gug                                                       13

<210> SEQ ID NO 209
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: c
<222> LOCATION: (5)..(5)
<223> OTHER INFORMATION: c is m5c
<220> FEATURE:
<221> NAME/KEY: c
<222> LOCATION: (10)..(10)
<223> OTHER INFORMATION: c is m5c
<220> FEATURE:
<221> NAME/KEY: c
<222> LOCATION: (12)..(12)
<223> OTHER INFORMATION: c is m5c

<400> SEQUENCE: 209
ggggcggacc gcg                                                       13

<210> SEQ ID NO 210
```

```
-continued
<211> LENGTH: 13
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: c
<222> LOCATION: (5)..(5)
<223> OTHER INFORMATION: c is m5c
<220> FEATURE:
<221> NAME/KEY: c
<222> LOCATION: (10)..(10)
<223> OTHER INFORMATION: c is m5c
<220> FEATURE:
<221> NAME/KEY: c
<222> LOCATION: (12)..(12)
<223> OTHER INFORMATION: c is m5c

<400> SEQUENCE: 210
ggggcggauc gcg                                                        13
```